US008825587B2

(12) United States Patent
Rosenberg et al.

(10) Patent No.: US 8,825,587 B2

(45) Date of Patent: Sep. 2, 2014

(54) PREDICTIVE MODELS AND METHOD FOR ASSESSING AGE

(75) Inventors: Steve Rosenberg, Oakland, CA (US); Whittemore G. Tingley, San Francisco, CA (US); Michael R. Elashoff, Redwood City, CA (US); James A. Winrove, Sunnyvale, CA (US)

(73) Assignee: Cardiodx, Inc., Redwood City, CA (US)

( * ) Notice: Subject to any disclaimer, the term of this patent is extended or adjusted under 35 U.S.C. 154(b) by 367 days.

(21) Appl. No.: 13/264,360

(22) PCT Filed: Apr. 14, 2010

(86) PCT No.: PCT/US2010/031076

§ 371 (c)(1), (2), (4) Date: Oct. 13, 2011

(87) PCT Pub. No.: WO2010/120914

PCT Pub. Date: Oct. 21, 2010

(65) Prior Publication Data

US 2012/0036101 A1 Feb. 9, 2012

Related U.S. Application Data

(60) Provisional application No. 61/169,241, filed on Apr. 14, 2009.

(51) Int. Cl.

| | |
|---|---|
| ***G06F 15/18*** | (2006.01) |
| ***G06F 17/15*** | (2006.01) |
| ***G06F 17/16*** | (2006.01) |
| ***C12Q 1/68*** | (2006.01) |
| ***G06Q 10/04*** | (2012.01) |
| ***G06Q 30/02*** | (2012.01) |

(52) U.S. Cl.

CPC .............. *C12Q 1/6883* (2013.01); *G06Q 10/04* (2013.01); *G06Q 30/02* (2013.01); *C12Q 2600/158* (2013.01); *C12Q 1/6809* (2013.01)

USPC ................................ 706/52; 706/20; 706/21

(58) Field of Classification Search

USPC ........................................................ 706/52

See application file for complete search history.

(56) References Cited

U.S. PATENT DOCUMENTS

2005/0142555 A1 6/2005 Anh et al.
2007/0161022 A1 7/2007 Kim et al.

FOREIGN PATENT DOCUMENTS

JP 2011092100 A * 5/2012 ............... C12Q 1/68

OTHER PUBLICATIONS

Hong et al. (Hong), "Transcriptome-Wide Assessment of Human Brain and Lymphocyte Senescence", 2008.*

(Continued)

*Primary Examiner* — Alan Chen

*Assistant Examiner* — Nathan Brown, Jr.

(74) *Attorney, Agent, or Firm* — Fenwick & West LLP

(57) ABSTRACT

Biomarkers useful for diagnosing and assessing physiological age are provided, along with kits for measuring their expression. The invention also provides predictive models, based on the biomarkers, as well as computer systems, and software embodiments of the models for scoring and optionally classifying samples. In a preferred embodiment, the biomarkers include a group of biomarkers whose expression levels are highly correlated to each other. In a preferred embodiment, expression levels of CD248; CD248 and SLC 1A7; CD248 and one, two, three or four of the group consisting of CCR7, B3GAT1, VSIG4 and LRRN3; or CD248, SLC1A7 and one, two, three or four of the group consisting of CCR7, B3GAT1, VSIG4 and LRRN3 are determined.

24 Claims, 6 Drawing Sheets

(56) References Cited

OTHER PUBLICATIONS

Abo, et al., "Postnatal Expansion of the Natural Killer and Killer Cell Population in Humans Identified by the Monoclonal HNK-1 Antibody," J. Exp. Med., Jan. 1982, pp. 321-326, vol. 155, No. 1.

Aziz, H. et al., "Peripheral Blood Gene Expression Profiling for Cardiovascular Disease Assessment," Genomic Medicine, 2007, pp. 105-112, vol. 1, No. 3.

Bijnens, A.P.J.J. et al., "Genome-Wide Expression Studies of Atherosclerosis: Critical Issues in Methodology, Analysis, Interpretation of Transcriptomics Data," Arterioscler Thromb Vasc Biol., 2006, pp. 1226-1235, vol. 6.

Heiss, C. et al., "Impaired Progenitor Cell Activity in Age-Related Endothelial Dysfunction," Journal of the American College of Cardiology Foundation, 2005; pp. 1441-1448, vol. 45.

Hong, M-G. et al., "Transcriptome-Wide Assessment of Human Brain and Lymphocyte Senescence," PLoS ONE, Aug. 2008, pp. 1-13, e3024, vol. 3, No. 8.

Melk, A. et al., "Transcriptional Analysis of the Molecular Basis of Human Kidney Aging Using cDNA Microarray Profiling," Kidney International, 2005, pp. 2667-2679, vol. 68, No. 6.

Mo, et al., "T Cell Chemokine Receptor Expression in Aging," The Journal of Immunology, 2003, pp. 895-904, vol. 70, No. 2.

PCT International Search Report and Written Opinion, PCT Application No. PCT/US10/31076, Jul. 2, 2010, 10 pages.

Sprecher, et al., 1 page Abstract of "Effect of Aging on Epidermal Dendritic Cell Populations in C57BL/6J Mice," J. Invest. Dermatol., Feb. 1990, pp. 247-253, vol. 2.

Wingrove, J.A. et al., "Correlation of Peripheral-Blood Gene Expression with the Extent of Coronary Artery Stenosis," Circulation Cardiovascular Genetetics, 2008,pp. 31-38, vol. 1.

Zahn, J.M. et al., "Transcriptional Profiling of Aging in Human Muscle Receives a Common Aging Signature," PLoS Genetics, Jul. 2006, pp. 1058-1069, e115, vol. 2, No. 7.

European Extended Search Report, European Application No. 10765112.7, Sep. 6, 2012, 4 pages.

Klement, H. et al., "Atherosclerosis and Vascular Aging as Modifiers of Tumor Progression, Angiogenesis, and Responsiveness to Therapy," The American Journal of Pathology, Oct. 2007, pp. 1342-1351, vol. 171, No. 4.

* cited by examiner

PREDICTIVE MODELS AND METHOD FOR ASSESSING AGE

CROSS-REFERENCE TO RELATED APPLICATIONS

This application is the 35 USC §371 national stage entry of PCT/US10/31076 and claims the benefit of U.S. Provisional Application 61/169,241 filed on Apr. 14, 2009, which is hereby incorporated by reference in its entirety for all purposes.

BACKGROUND OF THE INVENTION

1. Field of the Invention

The invention relates to predictive models for assessing age based on gene expression measurements, to their methods of use, and to computer systems and software for their implementation.

2. Description of the Related Art

The aging process results in a multi-tiered decline in physiological function, ranging from deficiencies at the molecular level, such as increases in DNA damage, to alterations at the cellular level, including changes in metabolism and increased cellular senescence, to system-level changes including a decline in the immune response and increased muscle atrophy. It is generally thought that such changes in function correlate with chronological age, however increasing evidence suggests that such alterations may become manifest in a chronological age-independent fashion. Numerous lines of evidence suggest that a lack of concordance between chronological age and physiological age can exist. A striking example of this is seen in premature aging syndromes such as Hutchinson-Gilford progeria and Werner's syndrome where chronologically young subjects display symptoms often associated with old age such as hair loss, wrinkles, and an increased incidence of heart disease and stroke (for a review see Kudlow et al. *Nat. Rev. Mol. Cell Biol.* 2007. 8(5):394-404).

As age is an important risk-factor in many diseases including cardiovascular disease, chronologically young subjects that are "physiologically" old may be at increased risk for age-related diseases, and might benefit from early intervention. Currently many routine screenings are recommended in whole or in part based on a subject's chronological age. If it were known that a subject's physiological age is older than his or her chronological age, the subject's physician could start certain routine screenings earlier. This benefits the subject and saves costs associated with aging-related conditions that appear unexpectedly because the subject is "too young" for that condition. For subjects who are "physiologically" young, it may be appropriate to postpone certain screenings or do them less frequently.

Methods for distinguishing physiological age from chronological age in humans have been historically limited to measuring gross physiological changes, such as assessing auditory threshold, near-point vision, and muscle tone. Recent work has suggested that it may be possible to determine physiological age at the molecular level. The ends of chromosomes, called telomeres, shorten by 50-200 base pairs with every cell division; thus cells in chronologically older individuals tend to have shorter telomeres than cells from younger individuals. Studies have shown that subjects with premature myocardial infarctions ("MI") (age <50 yrs) have significantly shorter telomeres than an age-matched control population, suggesting that telomere length might be a surrogate for physiological age, and that subjects that are physiologically older may have an increased risk for MI (Brouilette et al. *Arterioscler. Thromb. Vasc. Biol.* 2003. 23(5):842-6).

In addition to telomere length, gene expression profiling has been recently employed as a method to measure age at the molecular level. A number of studies in various tissues (brain, muscle, kidney) have recently demonstrated that changes in gene expression correlate with age (Hong et al. *PLoS ONE* 3(8):e3024; Zahn et al. *PLoS Genet.* 2006, 2(7):e115; and Melk et al. *Kidney Int.* 2005, 68(6):2667-79); however these tissues are not easily obtainable from subjects. Measuring changes in gene expression in circulating blood cells has proven to be a relatively simple, non-invasive method to assess disease status in a number of etiologies including coronary artery disease (Wingrove et al. *Circ. Cardiovasc. Genet.* 2008, 1:31-38; Aziz et al. *Genomic Medicine* 2007, 1(3):105-112; Bijnens et al. *Arterioscler Thromb Vasc Biol.* 2006, 6:1226-35). Lymphocyte senescence can be measured by assessing changes in gene expression; however this study was limited to a subset of circulating cells due to the collection methodology (Hong et al.).

Unmet Clinical and Scientific Need

A major advancement in tailoring medical care to individual subjects would be obtaining information about a subject's "physiological" age through a non-invasive diagnostic test that can guide physicians and other healthcare professionals to choose the types of routine screenings for age-related conditions would be appropriate for the subject.

SUMMARY OF THE INVENTION

This invention provides predictive models and methods of their use for scoring a sample obtained from a mammalian subject. The score can be used to identify subjects who are "physiologically" old and as such might be at higher risk for age-related disorders. This method is non-invasive, and the changes in expression levels can be assessed using established technologies such as microarrays and/or RT-PCR. In one embodiment the models are derived using expression data associated with a subset of genes. In another embodiment, samples are scored by inputting into a model expression data for the same genes used to construct the model, obtaining the score by operation of a model-derived interpretation function on the input data, and outputting the score. In another embodiment, the scores are used to classify the samples. In one embodiment the group of genes is SLC1A7, CD248, CCR7, B3GAT1, VSIG4 and LRRN3. These genes are grouped together because their expression levels in samples are highly correlated with the age of the subjects from which the samples are drawn. Accordingly, in one embodiment, a model is generated using expression data for a single gene. In another embodiment, a model is generated using expression data for two genes. In a third embodiment, a model is generated using a subset of genes within a selected group. In yet another embodiment, a model is generated using expression data for a plurality of genes within a selected group. In one embodiment, the plurality comprises all genes identified as belonging to the selected group.

In one embodiment, the model provides an interpretation function which operates upon the gene expression data to generate a score which can be outputted. In one embodiment the score is used to classify a sample associated with the gene expression data. In various embodiments of the invention, the predictive model may be (by way of example but not limitation) a partial least squares model, linear regression model, a linear discriminant analysis model, or a tree-based recursive partitioning model. In yet other embodiments, samples are scored by inputting into a model expression data for the same genes used to construct the model, obtaining the score by operation of the model-derived interpretation function on the input data, and outputting the score. In still other embodiments, a sample is classified according to the score. In one embodiment the classification predicts a "physiological" (cf. a chronological) age of a subject.

In certain embodiments, a model is constructed using expression data for CD248.

In other embodiments a model is constructed using expression data for CD248 and one of the group consisting of CCR7, B3GAT1, VSIG4 and LRRN3.

In other embodiments a model is constructed using expression data for CD248 and two of the group consisting of CCR7, B3GAT1, VSIG4 and LRRN3.

In other embodiments a model is constructed using expression data for CD248 and three of the group consisting of CCR7, B3GAT1, VSIG4 and LRRN3.

In other embodiments a model is constructed using expression data for CD248, CCR7, B3GAT1, VSIG4 and LRRN3.

In other embodiments, a model is constructed using expression data for CD248 and SLC1A7.

In other embodiments, a model is constructed using expression data for CD248, SLC1A7 and one of the group consisting of CCR7, B3GAT1, VSIG4 and LRRN3.

In other embodiments, a model is constructed using expression data for CD248, SLC1A7 and two of the group consisting of CCR7, B3GAT1, VSIG4 and LRRN3.

In other embodiments, a model is constructed using expression data for CD248, SLC1A7 and three of the group consisting of CCR7, B3GAT1, VSIG4 and LRRN3.

In other embodiments, a model is constructed using expression data for CD248, SLC1A7, CCR7, B3GAT1, VSIG4 and LRRN3.

In certain embodiments the gene expression data is derived from a blood sample.

In another embodiment, the gene expression data is derived from RNA extracted from cells in a blood sample.

In one embodiment, the gene expression data is derived using microarray hybridization analysis. In another embodiment, the gene expression data is derived using polymerase chain reaction analysis.

In one embodiment, a model for scoring a sample is carried out by a computer processor configured to execute the model.

BRIEF DESCRIPTION OF THE DRAWINGS AND TABLES

Figure 1:
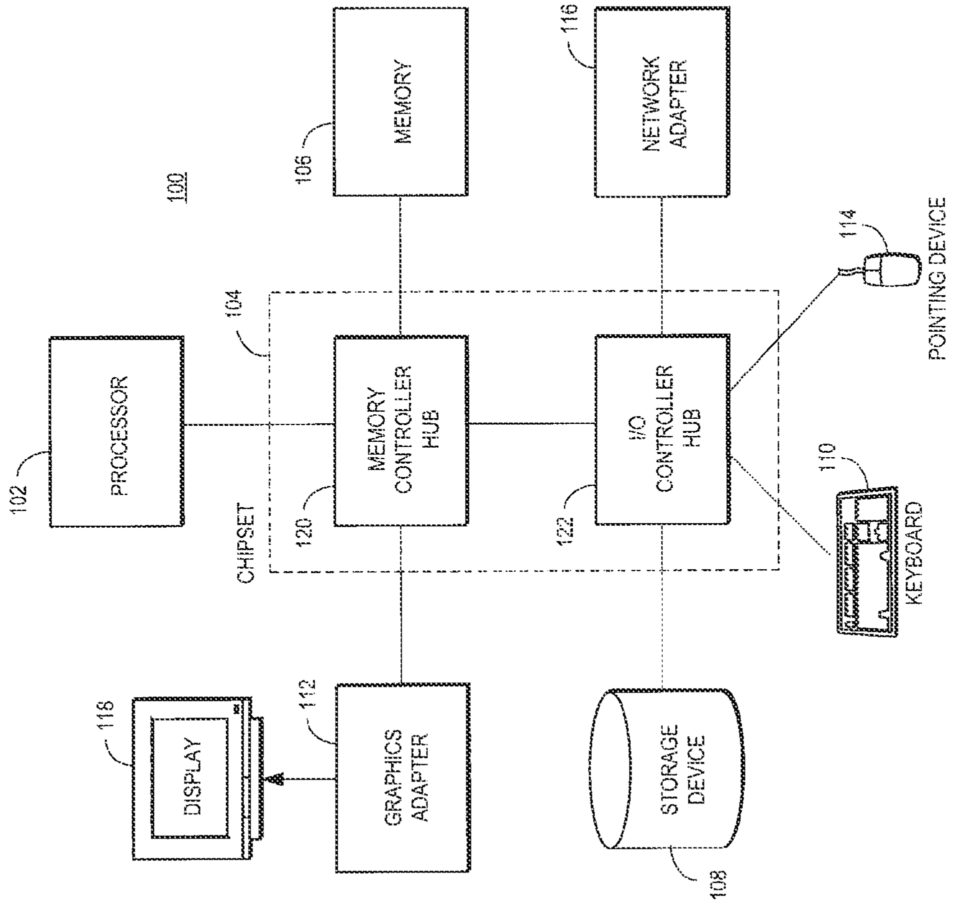
FIG. 1 depicts a computer according to one embodiment.

Table 1 lists clinical demographics (age and sex) for samples from the Cathgen Registry, where 1 corresponds to male and 0 corresponds to female, and age is the subject's chronological age of the subject associated with the sample.

Table 2 lists clinical demographics (age and sex) for samples from the prospective clinical trial (PREDICT), where 1 corresponds to male and 0 corresponds to female, and age is the subject's chronological age of the subject associated with the sample.

Table 3 lists 888 significant genes identified from analysis of the Cathgen Registry samples and the PREDICT samples.

Table 4 is an ANOVA table illustrating the relationship between CD248 and SLC1A7 average expression level and delta score of average gene expression level of CD248 minus average gene expression level of SLC1A7 and the age group by decade.

Table 5 contains data obtained from RT-PCR validation study of the genes identified in Example 1.

Table 6 shows the five-gene model coefficients and intercept from data of the PREDICT cohort.

Table 7 is an ANOVA table illustrating the relationship between CD248 average expression and age group by decade when the CD248 expression is measured both by array and by PCR.

Table 8 shows the one-gene model coefficient and intercept from data of the PREDICT cohort.

Table 9 shows the two-gene model coefficients and intercept from data of the PREDICT cohort.

Table 10 shows the three-gene model coefficients and intercept from data of the PREDICT cohort.

Table 11 shows the four-gene model coefficients and intercept from data of the PREDICT cohort.

DETAILED DESCRIPTION OF THE INVENTION

Definitions

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

The term "$C_t$" refers to cycle threshold and is defined as the PCR cycle number where the fluorescent value is above a set threshold. Therefore, a low $C_t$ value corresponds to a high level of expression, and a high $C_t$ value corresponds to a low level of expression.

The term "FDR" means to false discovery rate. FDR can be estimated by analyzing randomly-permuted datasets and tabulating the average number of genes at a given p-value threshold.

The term "highly correlated gene expression" refers to gene expression values that have a sufficient degree of correlation to allow their interchangeable use in a predictive model of age. For example, if gene x having expression value X is used to construct a predictive model, highly correlated gene y having expression value Y can be substituted into the predictive model in a straightforward way readily apparent to those having ordinary skill in the art and the benefit of the instant disclosure. Assuming an approximately linear relationship between the expression values of genes x and y such that $Y=a+bX$, then X can be substituted into the predictive model with $(Y-a)/b$. For non-linear correlations, similar mathematical transformations can be used that effectively convert the expression value of gene y into the corresponding expression value for gene x.

The term "mammal" encompasses both humans and non-humans and includes but is not limited to humans, non-human primates, canines, felines, murines, bovines, equines, and porcines.

The term "obtaining a dataset associated with a sample" encompasses obtaining a set of data determined from at least one sample. Obtaining a dataset encompasses obtaining a sample, and processing the sample to experimentally determine the data. The phrase also encompasses receiving a set of data, e.g., from a third party that has processed the sample to experimentally determine the dataset. Additionally, the phrase encompasses mining data from at least one database or at least one publication or a combination of databases and publications.

FIG. 1 is a high-level block diagram of a computer 100. Illustrated are at least one processor 102 coupled to a chipset 104. Also coupled to the chipset 104 are a memory 106, a storage device 108, a keyboard 110, a graphics adapter 112, a pointing device 114, and a network adapter 116. A display 118 is coupled to the graphics adapter 112. In one embodiment, the functionality of the chipset 104 is provided by a memory controller hub 120 and an I/O controller hub 122. In another embodiment, the memory 106 is coupled directly to the processor 102 instead of the chipset 104.

The storage device 108 is any device capable of holding data, like a hard drive, compact disk read-only memory (CD-ROM), DVD, or a solid-state memory device. The memory 106 holds instructions and data used by the processor 102. The pointing device 114 may be a mouse, track ball, or other type of pointing device, and is used in combination with the keyboard 110 to input data into the computer system 100. The graphics adapter 112 displays images and other information on the display 118. The network adapter 116 couples the computer system 100 to a local or wide area network.

As is known in the art, a computer 100 can have different and/or other components than those shown in FIG. 1. In addition, the computer 100 can lack certain illustrated components. Moreover, the storage device 108 can be local and/or remote from the computer 100 (such as embodied within a storage area network (SAN)).

As is known in the art, the computer 100 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 108, loaded into the memory 106, and executed by the processor 102.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Informative Genes

The predictive models of the present invention and their methods of use are based on the discovery of six informative genes. Those are CD248, SLC1A7, CCR7, B3GAT1, VSIG4 and LRRN3. CCR7, B3GAT1, VSIG4 and LRRN3 can be grouped and used interchangeably as the expression of each one is highly correlated with the expression of the others, and the expression level of this group of genes has been shown to correlate with chronological age of human subjects. The predictive models can be developed and used based on the expression value of gene(s) chosen from the six genes or a gene whose expression is highly correlated with that of an exemplified gene. When using one gene, the model can be used based on the expression value of CD248. When using two genes, the model can be used based on the expression value of CD248 and SLC1A7 or CD248 and one of the group consisting of CCR7, B3GAT1, VSIG4 and LRRN3. When using three genes, the model can be used based on the expression value of CD248, SLC1A7 and one of the group consisting of CCR7, B3GAT1, VSIG4 and LRRN3 or CD248 and two of the group consisting of CCR7, B3GAT1, VSIG4 and LRRN3. When using four genes, the model can be used based on the expression value of CD248, SLC1A7 and two of the group consisting of CCR7, B3GAT1, VSIG4 and LRRN3 or CD248 and three of the group consisting of CCR7, B3GAT1, VSIG4 and LRRN3. When using five genes, the model can be used based on the expression value of CD248, SLC1A7 and three of the group consisting of CCR7, B3GAT1, VSIG4 and LRRN3 or CD248, CCR7, B3GAT1, VSIG4 and LRRN3. When using six genes, the model can be used based on the expression value of CD248, SLC1A7, CCR7, B3GAT1, VSIG4 and LRRN3. Predictive models wholly or partially based on these combinations are expressly contemplated to be within the scope of the present invention.

In addition to the specific, exemplary genes or sequences identified in this application by name, accession number, or sequence, included within the scope of the invention are all operable predictive models of age and methods for their use to score and optionally classify samples using expression values of variant sequences having at least 90% or at least 95% or at least 97% or greater identity to the exemplified sequences or that encode proteins having sequences with at least 90% or at least 95% or at least 97% or greater identity to those encoded by the exemplified genes or sequences. The percentage of sequence identity may be determined using algorithms well known to those of ordinary skill in the art, including, e.g., BLASTn, and BLASTp, as described in Stephen F. Altschul et al., *J. Mol. Biol.* 215:403-410 (1990) and available at the National Center for Biotechnology Information website maintained by the National Institutes of Health. As described below, in accordance with an embodiment of the present invention, are all operable predictive models and methods for their use in scoring and optionally classifying samples that use a gene expression measurement that is now known or later discovered to be highly correlated with the expression of an exemplary gene expression value in addition to or in lieu of that exemplary gene expression value. For the purposes of the present invention, such highly correlated genes are contemplated to be within the literal scope of the claimed inventions or alternatively encompassed as equivalents to the exemplary genes. Identification of genes having expression values that are highly correlated to those of the exemplary genes, and their use as a component of a predictive model is well within the level of ordinary skill in the art.

In certain embodiments the gene expression data is derived from a blood sample. In another embodiment, the gene expression data is derived from RNA extracted from cells in a blood sample.

Alternatively, gene expression data is derived by measuring the levels of the proteins expressed by the genes. In one embodiment the levels of secreted proteins is determined. In another embodiment the levels of membrane-bound proteins are determined.

In yet another embodiment, microRNA's (miRNA's) which show age-dependent changes in expression levels are determined. Recent evidence suggests that miRNAs can serve as master regulators, with a single miRNA governing the levels of multiple miRNAs. (Hayden, *Nature.* 2008, 454(7204):562 and Selbach et al., *Nature.* 2008, 455(7209): 58-63)

In a further embodiment, genetic polymorphisms which contribute to the levels of expression for the genes are identified.

EXAMPLES

Example 1

Identification of Candidate Genes

Genes were identified in two cohorts. The first cohort of 204 samples was derived from the Cathgen Registry collected at Duke University ("Cathgen cohort"). The clinical demographics for the Cathgen cohort are shown in Table 1. The second cohort of 232 samples was collected in a prospective clinical trial designed to identify gene expression signatures that correlate with coronary artery disease ("PREDICT cohort"). The clinical demographics for the PREDICT cohort are shown in Table 2.

The subjects in both cohorts had undergone cardiac catheterization and blood samples from these subjects had been prepared for RNA extraction. The samples were collected in PAXGENE™ tubes. RNA was isolated using standard methodology (PAXGENE™ Blood RNA Kit, cat. no. 762164; available from PreAnalytiX in Hombrechtikon, Switzerland) and quantified using RIBOGREEN™ RNA Quantitation Reagent and Kit (available from Invitrogen in Carlsbad, Calif., USA). RNA was labeled with a fluorescent cyanine dye, Cy3, using methods recommended by the manufacturer (Agilent, Santa Clara, Calif., USA) and hybridized to whole genome arrays (41K whole genome array, part no. G4112A Agilent, Santa Clara, Calif., USA). Array feature data was extracted using Agilent Feature Extraction software and normalized using mean normalization followed by log transformation.

To identify genes whose expression levels correlated with age, a robust linear model was used (Huber P J. *Robust Statistics*. New York: Wiley; 1981.), with age as the dependant variable and gene as the independent variable. Table 3 contains the 888 genes which showed significant ($p<0.05$) correlation with age in both sets of data. 2678 probes, representing 2352 genes were significantly associated with age in the Cathgen cohort, whereas 7049 probes, representing 5720 genes showed significance in the PREDICT cohort. In both sets more genes were down-regulated than up-regulated. 59% were down-regulated in PREDICT and 64% down-regulated in Cathgen. The significant genes in the 2 datasets showed a large degree of overlap, with 38% of Cathgen genes also showing significance in the PREDICT cohort, roughly an 8-fold increase over what would be expected by chance ($p>0.05$). Of the 888 significant in both cohorts, 98.8% agreed in direction.

Example 2

Figure 2:
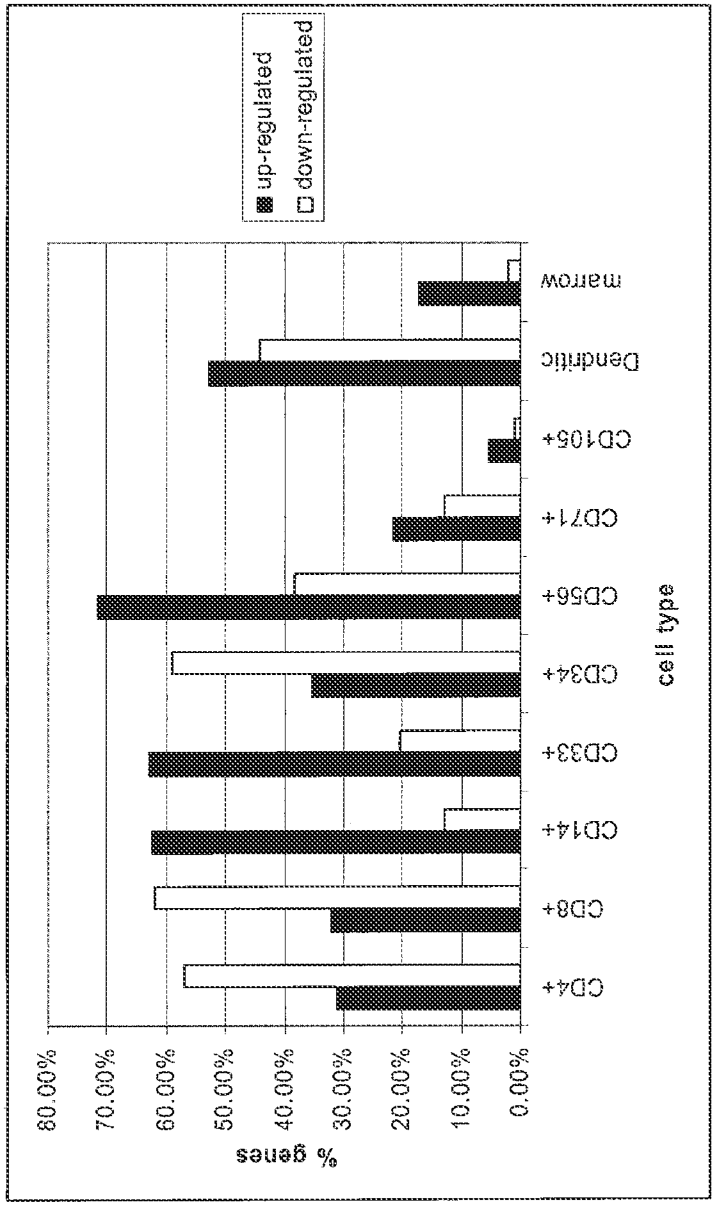
FIG. 2 is a graph depicting for different cell types the percentage of 208 genes whose up-regulation correlates with age and the percentage of the 680 genes whose down-regulation correlates with age.

Determination of Expression Levels of Genes Identified Example 1 in Various Types of Cells By querying a publicly available gene expression database (GNF Atlas v1.2.4, available from the Genomics Institute of the Novartis Research Foundation) it was determined that the up-regulated genes are found in a different population of cells than the genes being down-regulated. The cell types queried were CD4+, CD8+, CD14+, CD33+, CD34+, CD56+, CD71+, CD105+, dendritic and bone marrow. The results are illustrated in FIG. 2 where cell type is shown on the x-axis and the percentage of genes either up-regulated or down-regulated is shown on the y-axis. Of the 680 down-regulated genes common to both sets and agreeing in direction, 202 (30%) showed expression levels >10-fold over the median tissue expression calculated by GNF (across 79 tissues) in at least one of the 10 cell types queried. This number was 45% for the up-regulated genes. A higher percentage of the down-regulated gene were found in CD4+, CD8+ and CD34+ cells, whereas a higher percentage of the up-regulated genes were found in CD14+, CD33+, CD71+ and CD56+ cells, as well as bone-marrow. Roughly equal percentages were found in cells of dendritic origin.

Searches of the literature revealed that the gene whose expression showed the most significant correlation with age, CD248, is highly expressed in endothelial precursor cells (EPCs). It is interesting to note that recent evidence suggests that levels of EPCs decline with increased chronological age, suggesting a possible mechanism for the age-dependent decreases in levels of CD248 expression (Heiss et al. *J Am Coll Cardiol*. 2005; 45:1441-1448).

Example 3

Validation of Genes Identified in Example 1

Figure 3:
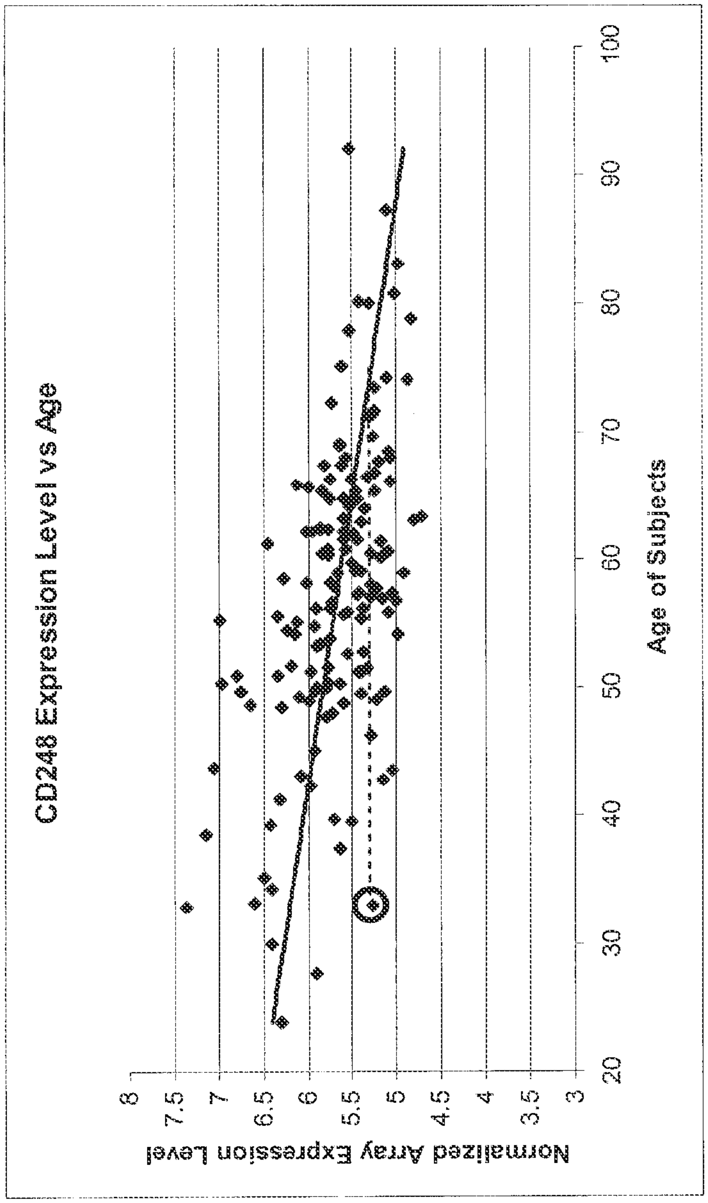
FIG. 3 is a graph plotting CD248 expression levels versus chronological age.
Figure 4:
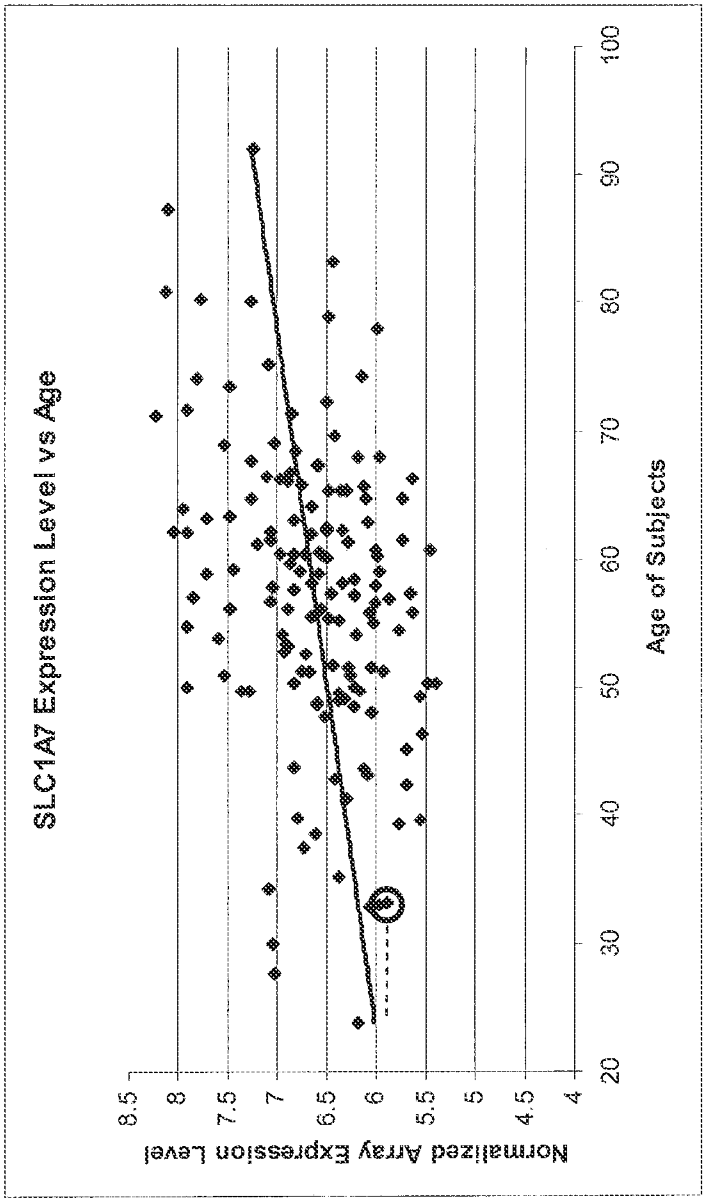
FIG. 4 is a graph plotting SLC1A7 expression levels versus chronological age.
Figure 5:
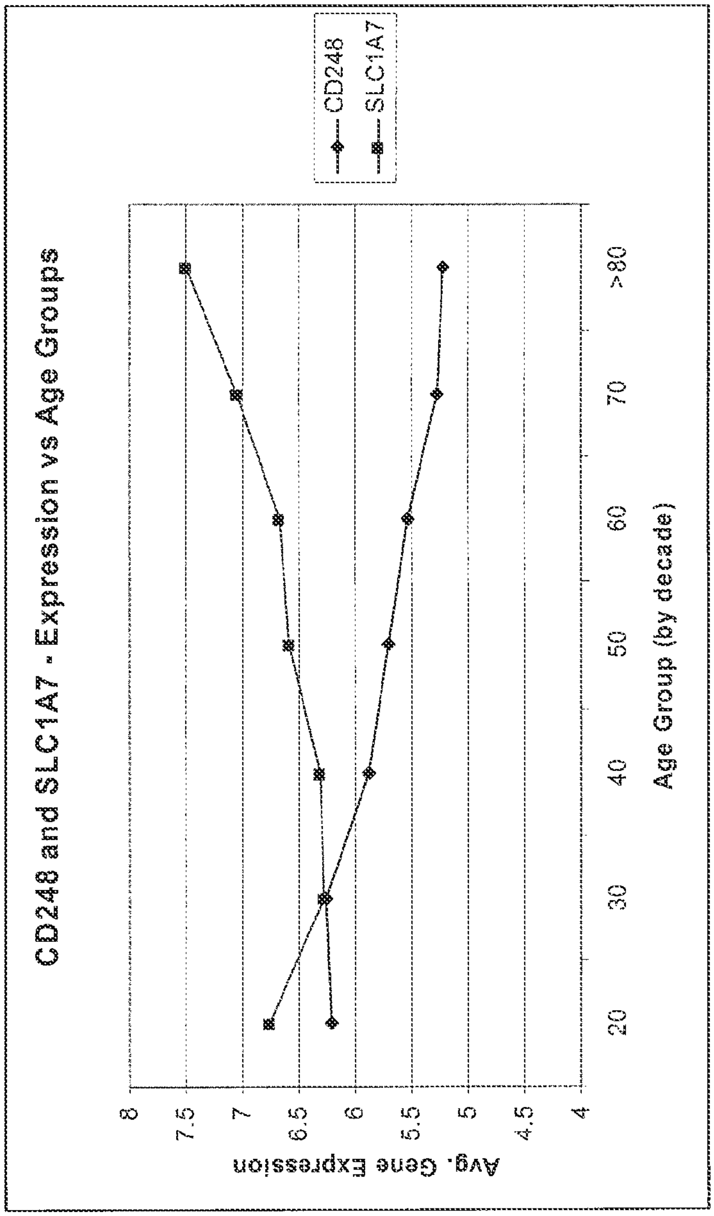
FIG. 5 is a graph plotting both CD248 and SLC1A7 average expression levels plotted versus age group by decade.
Figure 6:
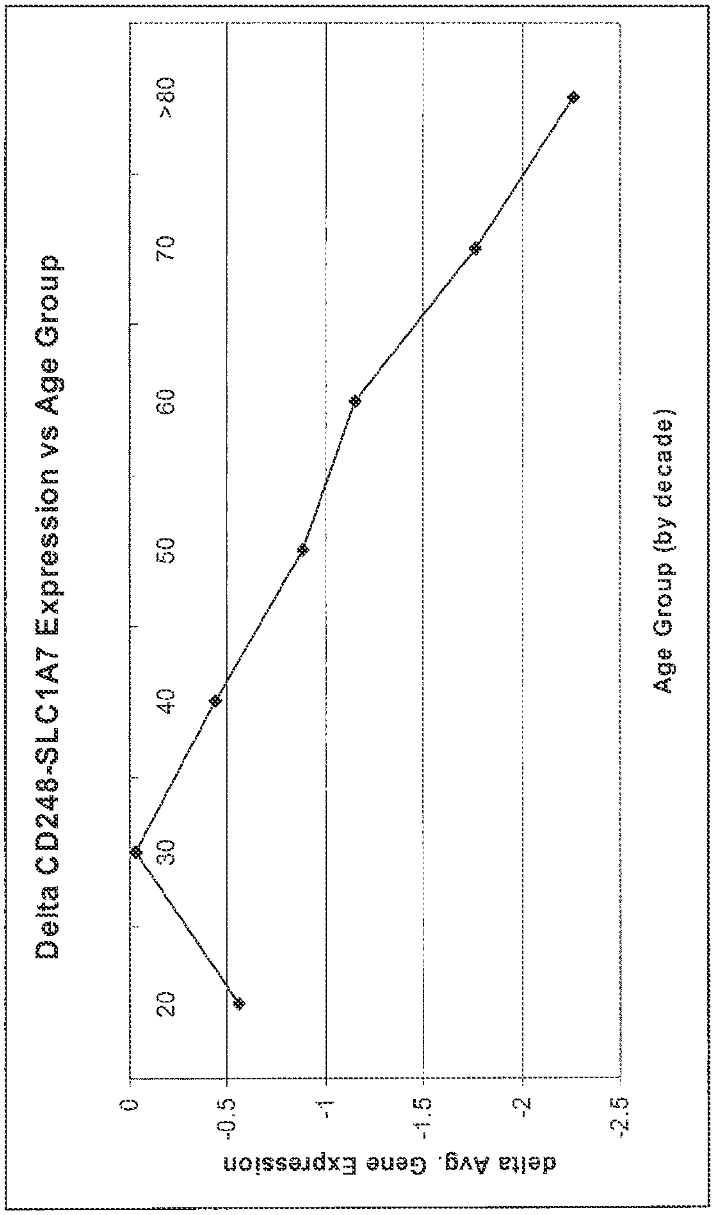
FIG. 6 is a graph plotting the delta score of average gene expression level of CD248 minus average gene expression level of SLC1A7 versus age group by decade.

FIG. 3 plots CD248 expression levels versus age. It is apparent that individuals exist that appear to be physiologically older than their chronological age. The subject whose data is circled in FIG. 3 is 33 yrs old, yet has the physiological age equivalent to a 75.8 yr old, using a simple linear model. However, plotting the predicted age for the same subject using the up-regulated gene SLC1A7 (as shown in FIG. 4, the subjects predicted age is now 20.8 yrs, suggesting that using a single gene to predict physiological age may not be accurate in all instances, and that creating a model in which multiple orthogonal signals are used can result in models having greater accuracy. To investigate this, subjects were grouped in age by decade and the average expression levels of CD248 and SLC1A7 determined for each group. In addition, a delta score (avg. CD248 minus avg. SLC1A7) was determined. FIG. 5 is a graph plotting both CD248 and SLC1A7 average expression levels versus age group by decade. FIG. 6 is a graph plotting the delta score of average gene expression level of CD248 minus average gene expression level of SLC1A7 versus age group by decade.

As shown in the ANOVA table at Table 4, the correlation of average expression level to decade of life was significant for both CD248 and SLC1A7 (ANOVA p 0.000155 and 0.000189 respectively), however combining the two terms resulted in a stronger correlation with age (ANOVA p 4.3E-05), supporting the idea that orthogonal terms can provide a more robust model.

TABLE 4

| Age Group | CD248 Avg. Expression Level on Array | SLC1A7 Avg. Expression Level on Array | Delta CD248 and SLC1A7 |
|---|---|---|---|
| 20 | 6.203277 | 6.755609 | −0.55233 |
| 30 | 6.25925 | 6.284284 | −0.02503 |
| 40 | 5.8717 | 6.305427 | −0.43373 |
| 50 | 5.706564 | 6.586082 | −0.87952 |
| 60 | 5.529029 | 6.67716 | −1.14813 |
| 70 | 5.278777 | 7.046635 | −1.76786 |
| >80 | 5.229388 | 7.492656 | −2.26327 |
| ANOVA p | 0.000155 | 0.000189 | 4.3E−05 |

Example 4

RT-PCR Validation of Genes Identified in Example 1

An RT-PCR validation of the genes identified in Example 1 was carried out on the PREDICT cohort. In 122 subjects, four of the five genes, CD248, LRRN3, B3GAT1, and VSIG4 were significant in splitting the subjects in half by age. The data from the RT-PCR validation is presented in Table 5.

Example 5

A Five-Gene Model for Predicting Age

Using the genes validated in Example 4, a predictive model was developed utilizing five genes, B3GAT1, CCR7, CD248, LRRN3 and VSIG4. The model was built using a forward selection linear regression approach.

Table 6 shows the five-gene model coefficients and intercept from data of the PREDICT cohort. The CDXR prefix in the table prior to the gene name is used to identify the assay used to obtain the data.

TABLE 6

| Estimate | Coefficient | Pr(>\|t\|) |
|---|---|---|
| (Intercept) | 62.8746 | 0.001197 |
| CDXR0685.B3GAT1 | −2.9126 | 0.0006 |
| CDXR0603.CCR7 | −8.6575 | 0.000354 |
| CDXR0771.CD248 | 5.6576 | 1.34E−06 |
| CDXR0725.LRRN3 | 3.8656 | 0.004688 |
| CDXR0119.VSIG4 | −2.8279 | 0.002258 |

Using the data from Table 6, the model is an interpretation function as follows: Age=(−2.9126)[B3GAT1]+(−8.6575)[CCR7]+(5.6576)[CD248]+(3.8656)[LRRN3]+(−2.8279)[VSIG4]+62.8746

Example 6

A One-Gene Model for Predicting Age

As shown in the ANOVA table at Table 7, the correlation of average expression level to decade of life was significant for CD248 alone when the expression level was measured on either microarray or PCR.

TABLE 7

| Age Group | CD248 Avg. Expression Level on Array | CD248 Avg. Expression CT Level on PCR |
|---|---|---|
| 20 | 6.20 | 8.77 |
| 30 | 6.26 | 9.20 |
| 40 | 5.87 | 9.84 |
| 50 | 5.71 | 9.84 |
| 60 | 5.53 | 10.20 |
| 70 | 5.28 | 10.74 |
| >80 | 5.23 | 11.03 |
| ANOVA p | 0.000155 | 1.8E−07 |

Table 8 shows the one-gene model coefficient and intercept from data of the PREDICT cohort.

TABLE 8

| Estimate | Coefficient | Pr(>\|t\|) |
|---|---|---|
| (Intercept) | −8.6389 | 0.349 |
| CDXR0771.CD248 | 6.6422 | 1.56e−11 |

Using the data from Table 8, the model is an interpretation function as follows: Age=(6.6422)[CD248]+(−8.6389)

Example 7

A Two-Gene Model for Predicting Age

Using the genes validated in Example 4, a predictive model was developed utilizing two genes, CD248 and VSIG4. The model was built using a forward selection linear regression approach.

Table 9 shows coefficients and intercept for a two-gene model from data of the PREDICT cohort.

TABLE 9

| Estimate | Coefficient | Pr(>\|t\|) |
|---|---|---|
| (Intercept) | 29.21 | 0.0804 |
| CDXR0771.CD248 | 5.82 | 5.9E−09 |
| CDXR0119.VSIG4 | −2.59 | 0.0074 |

Using the data from Table 9, the model is an interpretation function as follows: Age=(5.82)[CD248]+(−2.59)[VSIG4]+29.21

Example 8

A Three-Gene Model for Predicting Age

Using the genes validated in Example 4, a predictive model was developed utilizing three genes, CD248, B3GAT1 and VSIG4. The model was built using a forward selection linear regression approach.

Table 10 shows coefficients and intercept for a three-gene model from data of the PREDICT cohort.

TABLE 10

| Estimate | Coefficient | Pr(>\|t\|) |
|---|---|---|
| (Intercept) | 36.25 | .0118 |
| CDXR0685.B3GAT1 | −3.29 | .0002 |
| CDXR0603.CCR7 | −5.08 | .0237 |
| CDXR0771.CD248 | 7.26 | 4.5E−10 |

Using the data from Table 10, the model is an interpretation function as follows: Age=(−3.29)[B3GAT1]+(−5.08)[CCR7]+(7.26)[CD248]+36.25

Example 9

A Four-Gene Model for Predicting Age

Using the genes validated in Example 4, a predictive model was developed utilizing four genes, CD248, CCR7, B3GAT1 and VSIG4. The model was built using a forward selection linear regression approach.

Table 11 shows coefficients and intercept for a four-gene model from data of the PREDICT cohort.

TABLE 11

| Estimate | Coefficient | Pr(>\|t\|) |
|---|---|---|
| (Intercept) | 24.23 | .1040 |
| CDXR0685.B3GAT1 | −3.14 | .0003 |
| CDXR0603.CCR7 | −7.56 | .0020 |
| CDXR0771.CD248 | 6.38 | 7.6E−08 |
| CDXR0725.LRRN3 | 3.41 | .0143 |

Using the data from Table 11, the model is an interpretation function as follows: Age=(−3.14)[B3GAT1]+(−7.56)[CCR7]+(6.38)[CD248]+(3.41)[LRRN3]+24.23

Example 10

An Exemplary Computer-Implemented Method for Predicting Age

Referring to the computer of FIG. 1, dataset of gene expression levels for B3GAT1, CCR7, CD248, LRRN3 and VSIG4 are received by the processor 102. In one embodiment, the dataset is received via the keyboard 110. In yet another embodiment, the dataset is received from the storage device 108. The processor 102 determines a score that is predictive of age from the dataset by inputting the dataset into an interpretive function. The processor 102 then outputs the score. In one embodiment, the score is output to the display 118 and displayed to a user. Alternatively, the score is output to the storage device 108. In another embodiment, the score is output to a remote location on the network via the network adapter 116.

TABLE 1

Clinical Demographics for Cathgen Registry samples

| ID | SEX (1 = male; 0 = female) | AGE |
|---|---|---|
| T1005951 | 1 | 82 |
| T1005520 | 0 | 57 |
| T1005586 | 1 | 60 |
| T1006817 | 0 | 61 |
| T1005741 | 1 | 57 |
| T1005761 | 0 | 68 |
| T1001459 | 1 | 57 |
| T1005550 | 0 | 68 |
| T1005858 | 1 | 56 |
| T1005911 | 0 | 69 |
| T1005534 | 1 | 59 |
| T1006837 | 1 | 54 |
| T1005880 | 1 | 54 |
| T1005945 | 0 | 58 |
| T1001512 | 0 | 69 |
| T1006045 | 0 | 76 |
| T1005882 | 1 | 41 |
| T1006032 | 0 | 77 |
| T1006046 | 1 | 67 |
| T1005548 | 1 | 43 |
| T1005861 | 0 | 56 |
| T1005711 | 1 | 53 |
| T1005572 | 0 | 77 |
| T1005733 | 1 | 58 |
| T1005791 | 0 | 52 |
| T1001489 | 0 | 41 |
| T1005616 | 0 | 60 |
| T1006056 | 1 | 67 |
| T1005618 | 1 | 71 |
| T1005788 | 0 | 66 |
| T1005612 | 1 | 54 |
| T1006051 | 1 | 52 |
| T1005844 | 0 | 64 |
| T1001444 | 1 | 62 |
| T1001497 | 0 | 45 |
| T1006811 | 1 | 46 |
| T1005636 | 1 | 56 |
| T1005996 | 1 | 39 |
| T1006844 | 0 | 77 |
| T1006054 | 0 | 70 |
| T1005726 | 0 | 59 |
| T1005829 | 0 | 55 |
| T1005870 | 0 | 75 |
| T1006076 | 1 | 65 |
| T1006017 | 1 | 67 |

TABLE 1-continued

Clinical Demographics for Cathgen Registry samples

| ID | SEX (1 = male; 0 = female) | AGE |
|---|---|---|
| T1006075 | 0 | 66 |
| T1005757 | 1 | 56 |
| T1005856 | 1 | 61 |
| T1006804 | 1 | 71 |
| T1005570 | 1 | 68 |
| T1006077 | 1 | 52 |
| T1001061 | 1 | 63 |
| T1001066 | 1 | 64 |
| T1001073 | 1 | 51 |
| T1001503 | 1 | 65 |
| T1001504 | 1 | 49 |
| T1006049 | 1 | 66 |
| T1005567 | 1 | 58 |
| T1006806 | 0 | 63 |
| T1006018 | 0 | 76 |
| T1005966 | 1 | 66 |
| T1005819 | 0 | 42 |
| T1005765 | 1 | 63 |
| T1005731 | 0 | 51 |
| T1005801 | 0 | 53 |
| T1006818 | 1 | 73 |
| T1005837 | 0 | 63 |
| T1006050 | 1 | 51 |
| T1005637 | 1 | 63 |
| T1005737 | 0 | 83 |
| T1005584 | 0 | 23 |
| T1001443 | 1 | 63 |
| T1005903 | 0 | 53 |
| T1005760 | 1 | 50 |
| T1005694 | 0 | 74 |
| T1006061 | 0 | 58 |
| T1005660 | 0 | 78 |
| T1006815 | 1 | 61 |
| T1005968 | 1 | 48 |
| T1006026 | 1 | 61 |
| T1001069 | 1 | 55 |
| T1001468 | 0 | 57 |
| T1001471 | 1 | 67 |
| T1005568 | 0 | 72 |
| T1006087 | 0 | 53 |
| T1005689 | 0 | 40 |
| T1005710 | 0 | 55 |
| T1005720 | 1 | 33 |
| T1005852 | 0 | 73 |
| T1006020 | 0 | 46 |
| T1006000 | 1 | 81 |
| T1006826 | 1 | 63 |
| T1005601 | 1 | 78 |
| T1005997 | 1 | 51 |
| T1005857 | 0 | 77 |
| T1005905 | 0 | 35 |
| T1005774 | 0 | 45 |
| T1001490 | 0 | 85 |
| T1005874 | 1 | 76 |
| T1005934 | 1 | 57 |
| T1005826 | 0 | 59 |
| T1005717 | 1 | 66 |
| T1005846 | 1 | 62 |
| T1006088 | 1 | 40 |
| T1005776 | 1 | 72 |
| T1005641 | 0 | 36 |
| T1006827 | 0 | 66 |
| T1005799 | 1 | 56 |
| T1000765 | 1 | 51 |
| T1000766 | 1 | 80 |
| T1000769 | 0 | 61 |
| T1000770 | 0 | 51 |
| T1000773 | 1 | 51 |
| T1000774 | 1 | 62 |
| T1000775 | 0 | 72 |
| T1000778 | 0 | 35 |
| T1000779 | 1 | 62 |
| T1000784 | 1 | 57 |
| T1000786 | 1 | 73 |

TABLE 1-continued

| Clinical Demographics for Cathgen Registry samples | | |
|---|---|---|
| ID | SEX (1 = male; 0 = female) | AGE |
| T1000787 | 1 | 62 |
| T1000788 | 0 | 71 |
| T1000794 | 0 | 55 |
| T1000795 | 0 | 80 |
| T1000800 | 0 | 78 |
| T1000802 | 1 | 61 |
| T1000803 | 1 | 60 |
| T1000809 | 0 | 52 |
| T1000815 | 0 | 38 |
| T1000817 | 0 | 40 |
| T1000818 | 1 | 53 |
| T1000819 | 0 | 59 |
| T1000821 | 0 | 51 |
| T1000823 | 0 | 58 |
| T1000824 | 0 | 54 |
| T1000832 | 0 | 57 |
| T1000837 | 1 | 55 |
| T1000849 | 1 | 40 |
| T1000854 | 1 | 48 |
| T1000857 | 1 | 65 |
| T1000859 | 0 | 79 |
| T1000864 | 1 | 65 |
| T1000866 | 1 | 59 |
| T1000870 | 1 | 63 |
| T1000871 | 0 | 68 |
| T1000876 | 0 | 80 |
| T1000879 | 1 | 72 |
| T1000880 | 1 | 54 |
| T1000883 | 0 | 60 |
| T1000896 | 1 | 60 |
| T1000898 | 0 | 50 |
| T1000899 | 0 | 45 |
| T1000900 | 0 | 61 |
| T1000907 | 1 | 56 |
| T1000911 | 0 | 48 |
| T1000913 | 0 | 45 |
| T1000924 | 0 | 72 |
| T1000931 | 0 | 66 |
| T1000934 | 1 | 47 |
| T1000937 | 1 | 51 |
| T1000939 | 1 | 50 |
| T1000940 | 1 | 66 |
| T1000946 | 1 | 62 |
| T1000948 | 1 | 55 |
| T1000949 | 0 | 72 |
| T1000952 | 0 | 45 |
| T1000955 | 1 | 61 |
| T1000958 | 0 | 29 |
| T1000959 | 0 | 47 |
| T1000960 | 0 | 52 |
| T1000962 | 0 | 55 |
| T1000966 | 1 | 64 |
| T1000967 | 1 | 59 |
| T1000968 | 1 | 56 |
| T1000969 | 0 | 66 |
| T1000971 | 0 | 60 |
| T1000972 | 1 | 75 |
| T1000975 | 1 | 70 |
| T1000976 | 1 | 65 |
| T1000977 | 1 | 61 |
| T1000979 | 1 | 57 |
| T1000980 | 0 | 66 |
| T1000981 | 1 | 76 |
| T1000982 | 0 | 50 |
| T1000983 | 0 | 45 |
| T1000984 | 1 | 68 |
| T1000985 | 0 | 49 |
| T1000987 | 1 | 34 |
| T1000988 | 0 | 61 |
| T1000990 | 1 | 59 |
| T1000992 | 0 | 42 |
| T1000994 | 0 | 53 |
| T1000997 | 0 | 64 |
| T1000998 | 1 | 56 |

TABLE 1-continued

| Clinical Demographics for Cathgen Registry samples | | |
|---|---|---|
| ID | SEX (1 = male; 0 = female) | AGE |
| T1000999 | 0 | 56 |
| T1001000 | 1 | 62 |
| T1001001 | 0 | 38 |
| T1001002 | 0 | 45 |
| T1001003 | 1 | 62 |
| T1001004 | 1 | 57 |
| T1001005 | 1 | 47 |
| T1001006 | 1 | 58 |
| T1001007 | 1 | 63 |
| T1001008 | 1 | 68 |
| T1001009 | 0 | 53 |

TABLE 2

| Clinical Demographics for PREDICT samples | | |
|---|---|---|
| ID | SEX (1 = male; 0 = female) | AGE |
| C003\|PREDICT\|00400042 | 0 | 67.88775 |
| C005\|PREDICT\|00400047 | 1 | 43.72895 |
| C002\|PREDICT\|00400012 | 1 | 50.03696 |
| C001\|PREDICT\|00400032 | 0 | 62.01232 |
| C005\|PREDICT\|00400034 | 0 | 67.31828 |
| C002\|PREDICT\|00400065 | 1 | 64.00548 |
| C009\|PREDICT\|00400014 | 1 | 51.26352 |
| C006\|PREDICT\|00400004 | 0 | 73.52225 |
| C005\|PREDICT\|00400027 | 1 | 62.17112 |
| C002\|PREDICT\|00400077 | 0 | 62.31896 |
| C003\|PREDICT\|00400023 | 0 | 57.79603 |
| C009\|PREDICT\|00400007 | 1 | 59.07734 |
| C005\|PREDICT\|00400061 | 1 | 57.06229 |
| C001\|PREDICT\|00400007 | 0 | 80.13415 |
| C001\|PREDICT\|00400053 | 1 | 66.66393 |
| C002\|PREDICT\|00400074 | 1 | 69.74675 |
| C005\|PREDICT\|00400026 | 1 | 53.3963 |
| C009\|PREDICT\|00400012 | 1 | 34.34086 |
| C001\|PREDICT\|00400013 | 1 | 60.48734 |
| C005\|PREDICT\|00400019 | 1 | 49.08966 |
| C003\|PREDICT\|00400073 | 0 | 61.35524 |
| C009\|PREDICT\|00400004 | 0 | 78.88296 |
| C002\|PREDICT\|00400007 | 1 | 27.73443 |
| C003\|PREDICT\|00400024 | 0 | 35.09103 |
| C005\|PREDICT\|00400028 | 0 | 55.7974 |
| C001\|PREDICT\|00400019 | 1 | 65.71663 |
| C003\|PREDICT\|00400079 | 1 | 53.19097 |
| C002\|PREDICT\|00400058 | 1 | 33.15811 |
| C003\|PREDICT\|00400007 | 0 | 49.58522 |
| C009\|PREDICT\|00400019 | 1 | 92.11773 |
| C001\|PREDICT\|00400039 | 1 | 72.34497 |
| C005\|PREDICT\|00400046 | 0 | 63.03901 |
| C003\|PREDICT\|00400048 | 0 | 55.10746 |
| C001\|PREDICT\|00400018 | 1 | 80.33402 |
| C005\|PREDICT\|00400006 | 1 | 54.19576 |
| C006\|PREDICT\|00400013 | 1 | 48.46543 |
| C006\|PREDICT\|00400011 | 1 | 67.436 |
| C001\|PREDICT\|00400025 | 0 | 65.94114 |
| C002\|PREDICT\|00400072 | 1 | 58.16016 |
| C005\|PREDICT\|00400029 | 1 | 71.70157 |
| C002\|PREDICT\|00400085 | 0 | 75.08008 |
| C002\|PREDICT\|00400009 | 0 | 59.73169 |
| C009\|PREDICT\|00400005 | 1 | 55.6386 |
| C003\|PREDICT\|00400013 | 0 | 71.21971 |
| C009\|PREDICT\|00400003 | 1 | 55.7399 |
| C001\|PREDICT\|00400030 | 1 | 58.11636 |
| C002\|PREDICT\|00400069 | 0 | 67.68789 |
| C005\|PREDICT\|00400018 | 0 | 63.16222 |
| C001\|PREDICT\|00400001 | 0 | 78.03149 |
| C002\|PREDICT\|00400088 | 1 | 60.49281 |
| C001\|PREDICT\|00400009 | 1 | 56.07392 |

TABLE 2-continued

Clinical Demographics for PREDICT samples

| ID | SEX (1 = male; 0 = female) | AGE |
|---|---|---|
| C006|PREDICT|00400007 | 1 | 68.95277 |
| C003|PREDICT|00400033 | 1 | 29.89733 |
| C002|PREDICT|00400063 | 1 | 52.75565 |
| C050|PREDICT|00400007 | 0 | 32.78303 |
| C003|PREDICT|00400061 | 1 | 51.75907 |
| C006|PREDICT|00400005 | 0 | 42.37645 |
| C005|PREDICT|00400056 | 1 | 60.74196 |
| C002|PREDICT|00400093 | 1 | 48.57769 |
| C005|PREDICT|00400057 | 1 | 48.04928 |
| C006|PREDICT|00400001 | 1 | 49.29227 |
| C001|PREDICT|00400033 | 1 | 61.34976 |
| C001|PREDICT|00400029 | 0 | 56.79671 |
| C002|PREDICT|00400076 | 0 | 66.40383 |
| C003|PREDICT|00400080 | 0 | 65.3963 |
| C002|PREDICT|00400062 | 1 | 39.82204 |
| C006|PREDICT|00400006 | 1 | 60.45448 |
| C002|PREDICT|00400089 | 1 | 59.0527 |
| C002|PREDICT|00400086 | 1 | 58.45585 |
| C009|PREDICT|00400017 | 1 | 54.49692 |
| C003|PREDICT|00400057 | 1 | 58.00684 |
| C003|PREDICT|00400067 | 0 | 45.18549 |
| C003|PREDICT|00400041 | 0 | 61.60438 |
| C005|PREDICT|00400052 | 0 | 42.81999 |
| C001|PREDICT|00400014 | 0 | 55.39493 |
| C003|PREDICT|00400060 | 1 | 65.30322 |
| C001|PREDICT|00400027 | 0 | 64.0794 |
| C009|PREDICT|00400002 | 1 | 57.28405 |
| C005|PREDICT|00400043 | 1 | 58.96235 |
| C005|PREDICT|00400035 | 0 | 63.40041 |
| C001|PREDICT|00400017 | 1 | 55.86311 |
| C009|PREDICT|00400010 | 0 | 56.65708 |
| C003|PREDICT|00400066 | 1 | 51.20876 |
| C002|PREDICT|00400082 | 1 | 74.17933 |
| C002|PREDICT|00400073 | 0 | 50.31896 |
| C005|PREDICT|00400023 | 1 | 64.77207 |
| C009|PREDICT|00400015 | 1 | 57.40452 |
| C009|PREDICT|00400016 | 1 | 62.9295 |
| C005|PREDICT|00400021 | 0 | 57.3744 |
| C003|PREDICT|00400040 | 1 | 49.03765 |
| C006|PREDICT|00400014 | 1 | 68.94182 |
| C009|PREDICT|00400009 | 1 | 50.94319 |
| C005|PREDICT|00400044 | 1 | 39.26626 |
| C001|PREDICT|00400031 | 1 | 37.36071 |
| C003|PREDICT|00400038 | 0 | 39.63313 |
| C003|PREDICT|00400011 | 1 | 50.26146 |
| C050|PREDICT|00400004 | 1 | 47.80561 |
| C002|PREDICT|00400068 | 0 | 64.82683 |
| C003|PREDICT|00400090 | 0 | 50.93224 |
| C003|PREDICT|00400052 | 1 | 55.16222 |
| C001|PREDICT|00400008 | 0 | 50.11636 |
| C050|PREDICT|00400005 | 0 | 56.09582 |
| C003|PREDICT|00400032 | 1 | 62.33265 |
| C002|PREDICT|00400071 | 0 | 68.45175 |
| C005|PREDICT|00400004 | 1 | 53.7577 |
| C001|PREDICT|00400046 | 1 | 43.60027 |
| C001|PREDICT|00400021 | 1 | 43.17317 |
| C003|PREDICT|00400037 | 1 | 66.27789 |
| C005|PREDICT|00400053 | 1 | 51.55099 |
| C005|PREDICT|00400045 | 0 | 65.4319 |
| C001|PREDICT|00400005 | 1 | 60.31759 |
| C005|PREDICT|00400041 | 0 | 59.28268 |
| C009|PREDICT|00400013 | 0 | 87.29637 |
| C005|PREDICT|00400051 | 1 | 71.32375 |
| C005|PREDICT|00400030 | 0 | 60.38604 |
| C002|PREDICT|00400078 | 1 | 62.46407 |
| C005|PREDICT|00400054 | 1 | 41.34155 |
| C006|PREDICT|00400003 | 1 | 38.46407 |
| C001|PREDICT|00400003 | 0 | 80.85147 |
| C005|PREDICT|00400042 | 1 | 58.85558 |
| C003|PREDICT|00400091 | 0 | 62.21492 |
| C005|PREDICT|00400032 | 1 | 51.60027 |
| C003|PREDICT|00400019 | 1 | 61.56605 |
| C003|PREDICT|00400043 | 0 | 54.21218 |
| C003|PREDICT|00400036 | 1 | 74.11636 |

TABLE 2-continued

Clinical Demographics for PREDICT samples

| ID | SEX (1 = male; 0 = female) | AGE |
|---|---|---|
| C001|PREDICT|00400006 | 1 | 49.72758 |
| C006|PREDICT|00400009 | 0 | 33.04586 |
| C005|PREDICT|00400037 | 1 | 57.72485 |
| C002|PREDICT|00400064 | 1 | 49.70294 |
| C005|PREDICT|00400005 | 1 | 48.76112 |
| C003|PREDICT|00400015 | 1 | 46.4011 |
| C001|PREDICT|00400026 | 1 | 54.78166 |
| C001|PREDICT|00400035 | 1 | 51.34839 |
| C001|PREDICT|00400022 | 1 | 52.63792 |
| C002|PREDICT|00400066 | 1 | 64.80219 |
| C003|PREDICT|00400085 | 0 | 60.65982 |
| C009|PREDICT|00400018 | 0 | 83.23066 |
| C002|PREDICT|00400042 | 0 | 23.90144 |
| C003|PREDICT|00400030 | 1 | 66.06982 |
| C005|PREDICT|00400063 | 1 | 60.2245 |
| C003|PREDICT|00400058 | 0 | 62.16564 |
| C002|PREDICT|00400087 | 1 | 56.15058 |
| C003|PREDICT|00400082 | 1 | 68.00548 |
| C001|PREDICT|00400051 | 1 | 60.62697 |
| C003|PREDICT|00400075 | 1 | 56.99932 |
| C002|PREDICT|00400080 | 1 | 66.26694 |
| C005|PREDICT|00400039 | 0 | 50.38193 |
| C005|PREDICT|00400040 | 0 | 49.68104 |
| C002|PREDICT|00400083 | 0 | 41.16085 |
| C005|PREDICT|00400048 | 1 | 83.79466 |
| C050|PREDICT|00400010 | 1 | 74.2204 |
| C005|PREDICT|00400038 | 0 | 65.39904 |
| C050|PREDICT|00400002 | 0 | 72.02464 |
| C050|PREDICT|00400001 | 0 | 83.99179 |
| C005|PREDICT|00400050 | 1 | 64.09856 |
| C003|PREDICT|00400028 | 1 | 68.69815 |
| C006|PREDICT|00400012 | 0 | 46.1629 |
| C006|PREDICT|00400008 | 1 | 51.8412 |
| C003|PREDICT|00400084 | 0 | 69.19097 |
| C003|PREDICT|00400039 | 1 | 51.72895 |
| C002|PREDICT|00400075 | 0 | 58.141 |
| C001|PREDICT|00400028 | 0 | 58.60643 |
| C002|PREDICT|00400057 | 1 | 51.14305 |
| C001|PREDICT|00400040 | 1 | 55.36208 |
| C003|PREDICT|00400031 | 0 | 58.22587 |
| C005|PREDICT|00400025 | 0 | 77.51951 |
| C006|PREDICT|00400002 | 1 | 60.19165 |
| C001|PREDICT|00400023 | 0 | 43.37851 |
| C003|PREDICT|00400051 | 1 | 48.06571 |
| C001|PREDICT|00400012 | 1 | 65.19918 |
| C002|PREDICT|00400084 | 0 | 48.14511 |
| C005|PREDICT|00400049 | 0 | 67.47433 |
| C003|PREDICT|00400017 | 0 | 56.17522 |
| C007|PREDICT|00400018 | 0 | 48.12047 |
| C002|PREDICT|00400053 | 1 | 47.12936 |
| C002|PREDICT|00400015 | 1 | 75.76454 |
| C001|PREDICT|00400052 | 1 | 54.75975 |
| C002|PREDICT|00400022 | 0 | 70.59274 |
| C007|PREDICT|00400012 | 1 | 48.63792 |
| C007|PREDICT|00400009 | 0 | 50.94045 |
| C050|PREDICT|00400008 | 0 | 53.71937 |
| C002|PREDICT|00400013 | 0 | 73.45106 |
| C007|PREDICT|00400022 | 1 | 61.78234 |
| C007|PREDICT|00400023 | 1 | 66.71595 |
| C007|PREDICT|00400015 | 0 | 75.09103 |
| C002|PREDICT|00400048 | 0 | 64.12594 |
| C002|PREDICT|00400005 | 1 | 69.06502 |
| C002|PREDICT|00400044 | 0 | 73.25667 |
| C001|PREDICT|00400044 | 1 | 71.85763 |
| C002|PREDICT|00400056 | 0 | 52.54757 |
| C007|PREDICT|00400001 | 0 | 68.20534 |
| C002|PREDICT|00400032 | 0 | 64.21903 |
| C002|PREDICT|00400067 | 1 | 65.29774 |
| C007|PREDICT|00400021 | 0 | 63.52361 |
| C007|PREDICT|00400005 | 1 | 49.61259 |
| C002|PREDICT|00400018 | 0 | 50.12183 |
| C007|PREDICT|00400010 | 1 | 54.02053 |
| C007|PREDICT|00400004 | 0 | 84.67351 |
| C007|PREDICT|00400013 | 0 | 79.5154 |

TABLE 2-continued

| Clinical Demographics for PREDICT samples | | |
|---|---|---|
| ID | SEX (1 = male; 0 = female) | AGE |
| C002\|PREDICT\|00400035 | 1 | 58.89117 |
| C002\|PREDICT\|00400045 | 1 | 68.89802 |
| C002\|PREDICT\|00400004 | 1 | 66.37645 |
| C002\|PREDICT\|00400017 | 1 | 50.75428 |
| C002\|PREDICT\|00400016 | 1 | 73.49213 |
| C002\|PREDICT\|00400006 | 0 | 45.08145 |
| C002\|PREDICT\|00400047 | 0 | 40.80219 |
| C007\|PREDICT\|00400014 | 1 | 53.34155 |
| C002\|PREDICT\|00400041 | 0 | 61.88638 |
| C002\|PREDICT\|00400011 | 1 | 51.07461 |
| C001\|PREDICT\|00400042 | 1 | 61.31143 |
| C002\|PREDICT\|00400008 | 0 | 44.77207 |
| C002\|PREDICT\|00400033 | 0 | 59.94798 |
| C007\|PREDICT\|00400003 | 1 | 50.1629 |
| C002\|PREDICT\|00400025 | 1 | 43.88501 |
| C007\|PREDICT\|00400006 | 0 | 65.90281 |
| C002\|PREDICT\|00400028 | 0 | 59.47981 |

TABLE 2-continued

| Clinical Demographics for PREDICT samples | | |
|---|---|---|
| ID | SEX (1 = male; 0 = female) | AGE |
| C002\|PREDICT\|00400038 | 0 | 65.0705 |
| C002\|PREDICT\|00400002 | 1 | 42.59274 |
| C002\|PREDICT\|00400052 | 0 | 62.89938 |
| C001\|PREDICT\|00400041 | 1 | 56.53388 |
| C002\|PREDICT\|00400014 | 1 | 68.59959 |
| C002\|PREDICT\|00400001 | 0 | 76.88706 |
| C007\|PREDICT\|00400007 | 1 | 51.87406 |
| C007\|PREDICT\|00400019 | 0 | 61.78234 |
| C007\|PREDICT\|00400017 | 0 | 64.21629 |
| C007\|PREDICT\|00400011 | 0 | 75.93429 |
| C007\|PREDICT\|00400008 | 0 | 61.64819 |
| C002\|PREDICT\|00400019 | 1 | 48.7447 |
| C007\|PREDICT\|00400002 | 1 | 40.61602 |
| C002\|PREDICT\|00400031 | 0 | 56.52841 |
| C007\|PREDICT\|00400024 | 0 | 46.35729 |
| C002\|PREDICT\|00400026 | 0 | 79.2909 |

TABLE 3

| 888 Significant Genes Identifed from Cathgen Registry and PREDICT Samples | | | | |
|---|---|---|---|---|
| a.probe | a.symbol | PREDICT slope | PREDICT Age P | Cath 12 direction |
| A_23_P103720 | AGMAT | -0.008803937 | 2.07E-07 | -1.00 |
| A_23_P1833 | B3GAT1 | 0.013902215 | 0.001057164 | 1.00 |
| A_23_P343398 | CCR7 | -0.013211538 | 0.001028078 | -1.00 |
| A_23_P52697 | CD248 | -0.020288957 | 1.29E-10 | -1.00 |
| A_32_P221958 | CTGLF1 | -0.007522506 | 0.001821048 | -1.00 |
| A_32_P230196 | CTGLF1 | -0.006064753 | 0.045698146 | -1.00 |
| A_23_P206284 | GPR56 | 0.012416219 | 0.0059667 | 1.00 |
| A_23_P206280 | GPR56 | 0.012328918 | 0.010882326 | 1.00 |
| A_23_P404494 | IL7R | -0.011824829 | 0.005276568 | -1.00 |
| A_23_P31376 | LRRN3 | -0.024900328 | 1.93E-08 | -1.00 |
| A_24_P187766 | LRRN3 | -0.003318136 | 6.80E-07 | -1.00 |
| A_23_P107959 | NOSIP | -0.005976111 | 0.042625066 | -1.00 |
| A_24_P194017 | NOSIP | -0.004745901 | 0.046117051 | -1.00 |
| A_24_P65864 | NSFL1C | 0.004189195 | 0.038779554 | 1.00 |
| A_24_P937405 | PRSS23 | 0.003620002 | 0.031966115 | 1.00 |
| A_23_P150789 | PRSS23 | 0.013715164 | 0.000354823 | 1.00 |
| A_23_P7582 | TCF7 | -0.007399509 | 0.025751108 | -1.00 |
| A_23_P7582 | TCF7 | -0.007195589 | 0.030875098 | -1.00 |
| A_23_P7582 | TCF7 | -0.006768292 | 0.043008266 | -1.00 |
| A_23_P7582 | TCF7 | -0.006927223 | 0.043671908 | -1.00 |
| A_23_P7582 | TCF7 | -0.006748277 | 0.046458031 | -1.00 |
| A_23_P7582 | TCF7 | -0.006632438 | 0.049101883 | -1.00 |
| A_23_P389588 | TCF7L2 | 0.001118378 | 0.005868735 | 1.00 |

TABLE 3-continued

888 Significant Genes Identifed from Cathgen Registry and PREDICT Samples

| | | | | |
|---|---|---|---|---|
| A_23_P217269 | VSIG4 | 0.009950452 | 1.70E-05 | 1.00 |
| A_23_P348636 | FOXJ1 | -0.001601641 | 0.003537539 | -1.00 |
| A_32_P34920 | FOXD1 | 0.001687678 | 0.000239026 | 1.00 |
| A_23_P338919 | SPEG | -0.010435852 | 0.001015979 | -1.00 |
| A_32_P90346 | THC2313103 | -0.006632925 | 6.08E-07 | -1.00 |
| A_24_P213788 | LOC641518 | -0.0057745 | 0.000952581 | -1.00 |
| A_23_P103486 | CYP2J2 | -0.00266472 | 0.000348678 | -1.00 |
| A_23_P56433 | ECRG4 | -0.001564424 | 0.0300671 | -1.00 |
| A_23_P143981 | FBLN2 | -0.003687408 | 1.37E-05 | -1.00 |
| A_23_P66881 | RGS9 | 0.008481249 | 0.004435714 | 1.00 |
| A_23_P32444 | MXRA8 | -0.003187591 | 0.043817518 | -1.00 |
| A_24_P162319 | SCML1 | -0.002593311 | 0.006667324 | -1.00 |
| A_23_P254512 | EFNA1 | -0.007469334 | 0.000136555 | -1.00 |
| A_23_P325562 | SLC1A7 | 0.017809387 | 0.000372758 | 1.00 |
| A_23_P143068 | IQCA | -0.00229614 | 3.20E-08 | -1.00 |
| A_23_P417951 | TSPYL5 | -0.003998797 | 0.012160305 | -1.00 |
| A_23_P204751 | ACCN2 | -0.002020837 | 0.000210068 | -1.00 |
| A_23_P43484 | CDKN2A | 0.002250026 | 0.000915078 | 1.00 |
| A_23_P43484 | CDKN2A | 0.001812571 | 0.006061248 | 1.00 |
| A_23_P43484 | CDKN2A | 0.001784398 | 0.011818184 | 1.00 |
| A_23_P43484 | CDKN2A | 0.001652225 | 0.017373446 | 1.00 |
| A_23_P43484 | CDKN2A | 0.001549463 | 0.018531677 | 1.00 |
| A_23_P43484 | CDKN2A | 0.001603705 | 0.020496291 | 1.00 |
| A_23_P43484 | CDKN2A | 0.001613222 | 0.023726035 | 1.00 |
| A_23_P18493 | PTPN13 | -0.003548137 | 4.40E-05 | -1.00 |
| A_32_P4985 | CAMTA1 | -0.001390559 | 0.000893093 | -1.00 |
| A_23_P10025 | NELL2 | -0.01246328 | 0.000120655 | -1.00 |
| A_32_P133072 | SPON1 | -0.006138694 | 5.08E-07 | -1.00 |
| A_32_P34220 | BU633484 | -0.000664017 | 0.018989929 | -1.00 |
| A_23_P60499 | ZNF462 | -0.001388643 | 0.034067892 | -1.00 |
| A_23_P259741 | SATB1 | -0.006132903 | 0.012550079 | -1.00 |
| A_23_P13232 | A_23_P13232 | 0.010901489 | 0.000101753 | 1.00 |
| A_23_P300600 | NEFH | -0.00845308 | 0.000118487 | -1.00 |
| A_23_P411723 | PLAG1 | -0.008281744 | 0.000230663 | -1.00 |
| A_23_P107744 | EDG8 | 0.009423681 | 0.026283651 | 1.00 |
| A_23_P215956 | MYC | -0.010202804 | 0.000192472 | -1.00 |
| A_23_P215956 | MYC | -0.009516793 | 0.000223 | -1.00 |
| A_23_P215956 | MYC | -0.009320475 | 0.00028325 | -1.00 |
| A_23_P215956 | MYC | -0.00921947 | 0.000357617 | -1.00 |

TABLE 3-continued

888 Significant Genes Identifed from Cathgen Registry and PREDICT Samples

| | | | | |
|---|---|---|---|---|
| A_23_P215956 | MYC | -0.00911906 | 0.000395827 | -1.00 |
| A_23_P215956 | MYC | -0.009016196 | 0.000541279 | -1.00 |
| A_23_P215956 | MYC | -0.008791042 | 0.00060702 | -1.00 |
| A_23_P215956 | MYC | -0.00875603 | 0.000607169 | -1.00 |
| A_23_P215956 | MYC | -0.008923727 | 0.000774153 | -1.00 |
| A_23_P215956 | MYC | -0.009073476 | 0.000963406 | -1.00 |
| A_23_P309207 | ZNF577 | -0.002659207 | 0.000406441 | -1.00 |
| A_23_P324107 | RORC | -0.004121289 | 4.84E-07 | -1.00 |
| A_23_P25060 | FLJ13769 | -0.003933812 | 0.014107406 | -1.00 |
| A_24_P680704 | LENG10 | -0.006952134 | 0.000409466 | -1.00 |
| A_23_P75915 | RIC3 | -0.005946941 | 0.010164885 | -1.00 |
| A_23_P253221 | ARHGEF4 | -0.004327116 | 0.010745532 | -1.00 |
| A_32_P52227 | THC2314457 | -0.003603094 | 0.003204 | -1.00 |
| A_32_P118568 | RFPL1S | -0.001184477 | 1.38E-06 | -1.00 |
| A_23_P41528 | KSP37 | 0.012035829 | 0.032771254 | 1.00 |
| A_23_P82738 | RAD54B | -0.004155325 | 4.04E-09 | -1.00 |
| A_23_P82738 | RAD54B | -0.004349022 | 1.94E-08 | -1.00 |
| A_23_P82738 | RAD54B | -0.003972477 | 6.48E-08 | -1.00 |
| A_23_P82738 | RAD54B | -0.003706821 | 3.64E-07 | -1.00 |
| A_23_P82738 | RAD54B | -0.003391834 | 5.71E-07 | -1.00 |
| A_23_P82738 | RAD54B | -0.004197272 | 1.84E-06 | -1.00 |
| A_23_P82738 | RAD54B | -0.003538416 | 3.36E-06 | -1.00 |
| A_23_P82738 | RAD54B | -0.003310807 | 6.19E-06 | -1.00 |
| A_23_P82738 | RAD54B | -0.003485288 | 1.54E-05 | -1.00 |
| A_23_P82738 | RAD54B | -0.002760063 | 0.000130117 | -1.00 |
| A_23_P65278 | NBEA | -0.001797613 | 7.83E-05 | -1.00 |
| A_24_P314786 | SLC4A10 | -0.003216671 | 0.00016461 | -1.00 |
| A_32_P68504 | KIAA1571 | -0.001771877 | 0.004174818 | -1.00 |
| A_32_P137826 | THC2298931 | -0.00119604 | 0.023657092 | -1.00 |
| A_24_P354715 | NT5E | -0.009077484 | 1.84E-05 | -1.00 |
| A_23_P128613 | KDELC1 | -0.001006531 | 0.001344132 | -1.00 |
| A_23_P128613 | KDELC1 | -0.00084489 | 0.00366957 | -1.00 |
| A_23_P128613 | KDELC1 | -0.000664396 | 0.006097691 | -1.00 |
| A_23_P128613 | KDELC1 | -0.000650187 | 0.006416025 | -1.00 |
| A_23_P128613 | KDELC1 | -0.000589418 | 0.00912583 | -1.00 |
| A_23_P128613 | KDELC1 | -0.000584867 | 0.020461019 | -1.00 |
| A_23_P128613 | KDELC1 | -0.000577096 | 0.026169985 | -1.00 |
| A_23_P128613 | KDELC1 | -0.000932694 | 0.049190963 | -1.00 |
| A_23_P391228 | MANEAL | 0.00270094 | 0.003436366 | 1.00 |

TABLE 3-continued

| 888 Significant Genes Identifed from Cathgen Registry and PREDICT Samples | | | | |
|---|---|---|---|---|
| A_23_P155688 | SPINK2 | -0.003291652 | 0.000461777 | -1.00 |
| A_32_P230398 | THC2440435 | 0.004357137 | 0.020996952 | 1.00 |
| A_32_P146659 | LOC401431 | -0.006257345 | 0.003313684 | -1.00 |
| A_32_P18475 | THC2340539 | -0.002789708 | 0.000567034 | -1.00 |
| A_24_P77432 | ROBO1 | -0.00055596 | 0.013742967 | -1.00 |
| A_23_P167599 | FLJ20152 | -0.010800307 | 2.68E-05 | -1.00 |
| A_23_P53081 | OSBPL5 | 0.00999006 | 0.002800858 | 1.00 |
| A_23_P348992 | MYSM1 | -0.003746391 | 8.42E-05 | -1.00 |
| A_23_P85783 | PHGDH | -0.004587792 | 0.000132389 | -1.00 |
| A_32_P203728 | THC2280735 | -0.007702796 | 3.31E-05 | -1.00 |
| A_24_P595460 | NUCB2 | -0.003211855 | 0.000283957 | -1.00 |
| A_23_P346900 | CACNA2D2 | 0.004271691 | 0.024559504 | 1.00 |
| A_23_P128993 | GZMH | 0.016392662 | 0.027412134 | 1.00 |
| A_23_P89871 | ZNF415 | -0.001103312 | 0.003938465 | -1.00 |
| A_24_P766716 | AK126405 | 0.008842402 | 0.008136227 | 1.00 |
| A_24_P313210 | AMN | -0.002093613 | 0.001780653 | -1.00 |
| A_23_P73747 | ARMCX2 | -0.004501117 | 0.001470338 | -1.00 |
| A_24_P111242 | DKFZp313A2432 | -0.001796199 | 0.010337054 | -1.00 |
| A_23_P14853 | LTK | -0.010705661 | 4.25E-05 | -1.00 |
| A_32_P133926 | A_32_P133926 | -0.003386493 | 0.000377658 | -1.00 |
| A_23_P87421 | BC063022 | 0.00254589 | 0.000929459 | 1.00 |
| A_23_P119042 | NKG7 | 0.009707677 | 0.016664843 | 1.00 |
| A_23_P109171 | BFSP1 | 0.005507897 | 0.049323251 | 1.00 |
| A_23_P117602 | GZMB | 0.013545277 | 0.001370499 | 1.00 |
| A_32_P31021 | A_32_P31021 | -0.000702812 | 0.005191414 | -1.00 |
| A_23_P1473 | PRF1 | 0.009344548 | 0.035979258 | 1.00 |
| A_32_P151823 | LOC346887 | -0.003370821 | 0.016720527 | -1.00 |
| A_23_P348257 | NUAK1 | 0.006261501 | 0.002133297 | 1.00 |
| A_23_P14957 | CDR2 | -0.00695312 | 0.001135618 | -1.00 |
| A_23_P327156 | LOC645431 | -0.001602897 | 0.011756463 | -1.00 |
| A_23_P23834 | LGR6 | 0.003552967 | 0.021992261 | 1.00 |
| A_23_P101093 | COPZ2 | 0.003728992 | 2.95E-05 | 1.00 |
| A_24_P173754 | C1orf21 | 0.003875663 | 0.02642982 | 1.00 |
| A_23_P86171 | FOXD2 | 0.002667478 | 0.019458367 | 1.00 |
| A_32_P71744 | BG695979 | -0.012882185 | 3.81E-05 | -1.00 |
| A_24_P89080 | DCK | -0.007252942 | 2.60E-05 | -1.00 |
| A_23_P250347 | CAMK4 | -0.007842621 | 1.85E-05 | -1.00 |
| A_24_P306355 | A_24_P306355 | 0.007341652 | 0.001537039 | 1.00 |
| A_23_P428887 | RP11-450P7.3 | -0.004950968 | 0.00243352 | -1.00 |

TABLE 3-continued

| 888 Significant Genes Identifed from Cathgen Registry and PREDICT Samples | | | | |
|---|---|---|---|---|
| A_23_P313828 | PRR6 | -0.001460273 | 0.007661607 | -1.00 |
| A_23_P91991 | OXNAD1 | -0.009633469 | 0.000764144 | -1.00 |
| A_24_P341058 | A_24_P341058 | 0.00564887 | 0.007892069 | 1.00 |
| A_23_P47788 | METTL1 | -0.00451683 | 0.003649043 | -1.00 |
| A_23_P107750 | EDG8 | 0.005565189 | 0.007932664 | 1.00 |
| A_23_P253921 | ZNF167 | -0.003523236 | 0.002129447 | -1.00 |
| A_24_P124349 | PDGFD | 0.002211945 | 0.009759272 | 1.00 |
| A_23_P7503 | TIMD4 | -0.001334845 | 0.033326273 | -1.00 |
| A_24_P20630 | LEF1 | -0.011671283 | 0.002174739 | -1.00 |
| A_23_P421513 | LOC220594 | -0.004509799 | 0.046987882 | -1.00 |
| A_23_P393051 | C1orf172 | -0.003602793 | 0.016386606 | -1.00 |
| A_24_P301186 | WDR89 | -0.002943361 | 0.001380683 | -1.00 |
| A_24_P92823 | A_24_P92823 | 0.00720175 | 0.016268711 | 1.00 |
| A_23_P258612 | ATP8A2 | -0.000611917 | 0.021112858 | -1.00 |
| A_23_P29384 | ZNF502 | -0.007862375 | 0.000462432 | -1.00 |
| A_23_P209360 | ENST00000288548 | -0.00369573 | 0.001445755 | -1.00 |
| A_24_P285501 | ZNF650 | -0.002860308 | 0.003548616 | -1.00 |
| A_23_P502520 | IL4I1 | -0.008678192 | 0.003289217 | -1.00 |
| A_23_P126844 | TNFRSF25 | -0.010567125 | 0.001834734 | -1.00 |
| A_23_P318296 | PLEKHA8 | -0.001853968 | 0.026143636 | -1.00 |
| A_32_P11673 | A_32_P11673 | 0.00134248 | 0.010259114 | 1.00 |
| A_32_P128399 | A_32_P128399 | -0.004809276 | 0.005858046 | -1.00 |
| A_23_P35082 | SESN2 | 0.004153586 | 0.006925038 | 1.00 |
| A_23_P35205 | ENST00000374395 | -0.006644003 | 0.003550049 | -1.00 |
| A_23_P158925 | GPR125 | -0.005277311 | 3.40E-06 | -1.00 |
| A_32_P154473 | KIF5C | -0.005685137 | 0.000162155 | -1.00 |
| A_23_P76078 | IL23A | -0.009545748 | 0.010597317 | -1.00 |
| A_23_P133543 | KLHL3 | -0.007754954 | 6.82E-05 | -1.00 |
| A_24_P168398 | ZNF177 | -0.001841177 | 0.005496611 | -1.00 |
| A_24_P944714 | ENST00000381655 | -0.001823844 | 0.038390752 | -1.00 |
| A_24_P392022 | FAM86A | -0.002151477 | 0.021313138 | -1.00 |
| A_32_P60687 | AI278811 | -0.001743227 | 0.001147482 | -1.00 |
| A_24_P108863 | SCML1 | -0.004663696 | 8.53E-05 | -1.00 |
| A_23_P86731 | ZNF239 | -0.00434379 | 0.000836965 | -1.00 |
| A_32_P171061 | ASCL2 | 0.008197959 | 0.008980625 | 1.00 |
| A_24_P813520 | CR626222 | -0.002715565 | 0.007577283 | -1.00 |
| A_32_P149060 | C21orf71 | -0.000447506 | 0.00256037 | -1.00 |
| A_23_P91095 | CD28 | -0.011638884 | 0.000158727 | -1.00 |
| A_23_P344281 | ZIK1 | -0.004385142 | 2.14E-06 | -1.00 |

TABLE 3-continued

888 Significant Genes Identifed from Cathgen Registry and PREDICT Samples

| | | | | |
|---|---|---|---|---|
| A_23_P341938 | NOG | -0.005537143 | 0.00055328 | -1.00 |
| A_23_P202520 | ABLIM1 | -0.011173189 | 0.000298139 | -1.00 |
| A_24_P273014 | A_24_P273014 | -0.001132638 | 0.033131837 | -1.00 |
| A_32_P542318 | AK026718 | -0.00137017 | 0.001165876 | -1.00 |
| A_23_P1352 | SFRP5 | -0.000431237 | 0.019182606 | -1.00 |
| A_23_P93787 | HGF | 0.000831791 | 0.02940223 | 1.00 |
| A_23_P93787 | HGF | 0.000771948 | 0.040546653 | 1.00 |
| A_23_P14165 | GPR18 | -0.009894763 | 0.000168885 | -1.00 |
| A_24_P546003 | CR609843 | -0.00910398 | 0.000284484 | -1.00 |
| A_32_P129540 | A_32_P129540 | -0.002218562 | 0.047424077 | -1.00 |
| A_23_P16022 | ZNF256 | -0.006071078 | 0.000160019 | -1.00 |
| A_23_P129458 | ENST00000328945 | -0.001885674 | 0.002530303 | -1.00 |
| A_23_P112531 | FAM102A | -0.008911963 | 0.003259879 | -1.00 |
| A_32_P205329 | AF088007 | -0.004626384 | 0.048648597 | -1.00 |
| A_24_P923934 | AF085846 | -0.006076958 | 0.000645136 | -1.00 |
| A_24_P413791 | BX538272 | -0.001558556 | 0.033425071 | -1.00 |
| A_24_P772147 | CR618720 | -0.005000087 | 0.00398557 | -1.00 |
| A_24_P126931 | A_24_P126931 | -0.005196316 | 0.033613869 | -1.00 |
| A_32_P156851 | DSCR1L1 | 0.003926759 | 2.08E-05 | 1.00 |
| A_24_P927189 | OXNAD1 | -0.004770028 | 0.012802487 | -1.00 |
| A_24_P320970 | ENST00000376834 | -0.005739619 | 0.000105739 | -1.00 |
| A_32_P130522 | THC2311764 | -0.005814519 | 0.011006006 | -1.00 |
| A_32_P40463 | NUDT9P1 | -0.007008234 | 0.000480657 | -1.00 |
| A_23_P93348 | LTB | -0.007578393 | 0.015203122 | -1.00 |
| A_23_P168788 | PLOD3 | 0.004682873 | 0.017675886 | 1.00 |
| A_23_P216396 | EXOSC2 | -0.002367906 | 0.003838783 | -1.00 |
| A_23_P326204 | MGC26963 | 0.001143063 | 0.021808319 | 1.00 |
| A_23_P420269 | INTS2 | -0.001950693 | 0.004082561 | -1.00 |
| A_23_P8834 | EPHX2 | -0.008304983 | 0.011383457 | -1.00 |
| A_24_P153207 | CR627133 | -0.003830879 | 0.048738177 | -1.00 |
| A_23_P138635 | BNIP3 | -0.008613933 | 5.94E-05 | -1.00 |
| A_32_P119604 | THC2300570 | -0.007390494 | 0.01772733 | -1.00 |
| A_24_P239664 | BCKDHB | -0.003753785 | 5.39E-05 | -1.00 |
| A_23_P105251 | GLI1 | -0.001617437 | 0.00747978 | -1.00 |
| A_32_P38782 | THC2449916 | 0.0050094 | 0.000721605 | 1.00 |
| A_24_P164815 | A_24_P164815 | -0.003786335 | 0.001929985 | -1.00 |
| A_24_P266880 | UBC | 0.002512013 | 0.023940532 | 1.00 |
| A_24_P266880 | UBC | 0.002502741 | 0.036597392 | 1.00 |
| A_24_P266880 | UBC | 0.002455984 | 0.039936657 | 1.00 |

TABLE 3-continued

888 Significant Genes Identifed from Cathgen Registry and PREDICT Samples

| | | | | |
|---|---|---|---|---|
| A_24_P266880 | UBC | 0.002516897 | 0.040898483 | 1.00 |
| A_24_P266880 | UBC | 0.002409749 | 0.041319945 | 1.00 |
| A_23_P212649 | FLJ36868 | -0.006336707 | 2.37E-05 | -1.00 |
| A_32_P232559 | LOC439949 | -0.008013554 | 0.018362318 | -1.00 |
| A_32_P100830 | A_32_P100830 | 0.009564446 | 0.002905201 | 1.00 |
| A_23_P215070 | TSGA14 | -0.002972859 | 0.000702013 | -1.00 |
| A_23_P101319 | ZNF285 | -0.002433266 | 0.000211312 | -1.00 |
| A_24_P289178 | C16orf74 | -0.007583546 | 0.001416765 | -1.00 |
| A_23_P122531 | C6orf48 | -0.008584304 | 0.003867546 | -1.00 |
| A_24_P234921 | CCR6 | -0.012170822 | 2.75E-08 | -1.00 |
| A_23_P209954 | GNLY | 0.014173425 | 0.025315851 | 1.00 |
| A_24_P139665 | HPCAL4 | -0.001403082 | 0.006733827 | -1.00 |
| A_32_P147622 | BC064982 | -0.004779695 | 0.001628048 | -1.00 |
| A_23_P301360 | ZNF572 | -0.003109018 | 0.001871685 | -1.00 |
| A_24_P136387 | ENST00000368491 | -0.003001204 | 4.44E-05 | -1.00 |
| A_24_P848714 | THC2403056 | -0.002555979 | 0.003053093 | -1.00 |
| A_23_P502312 | CD97 | 0.006989993 | 0.021228902 | 1.00 |
| A_23_P124542 | CR2 | -0.006220892 | 0.014099562 | -1.00 |
| A_32_P103474 | BE144057 | -0.000542795 | 0.013931705 | -1.00 |
| A_23_P208208 | ZNF649 | -0.001798322 | 0.000421168 | -1.00 |
| A_23_P105066 | ILK | 0.004353868 | 0.021041697 | 1.00 |
| A_24_P737451 | MTERFD2 | -0.005218406 | 0.041140027 | -1.00 |
| A_24_P943802 | SEC31L1 | -0.004202 | 0.026640501 | -1.00 |
| A_23_P502314 | CD97 | 0.007638893 | 0.021489662 | 1.00 |
| A_32_P518489 | BTBD4 | 0.000387796 | 0.029700804 | 1.00 |
| A_23_P321160 | ZNF594 | -0.002551454 | 4.05E-05 | -1.00 |
| A_23_P157215 | BZW2 | -0.007572585 | 7.21E-05 | -1.00 |
| A_24_P220921 | CAMTA1 | -0.001398509 | 0.013293962 | -1.00 |
| A_23_P144165 | DZIP3 | -0.008185313 | 1.74E-05 | -1.00 |
| A_24_P295633 | FLJ14213 | 0.002308594 | 0.015038821 | 1.00 |
| A_23_P214156 | SENP6 | -0.002992086 | 0.003903834 | -1.00 |
| A_24_P291826 | SYTL3 | 0.007885165 | 0.000617109 | 1.00 |
| A_32_P155811 | THC2276639 | -0.002554825 | 0.028150945 | -1.00 |
| A_23_P6963 | UBE2E1 | -0.000452586 | 0.049176095 | -1.00 |
| A_24_P298587 | C8ORFK29 | 0.000853758 | 0.024553033 | 1.00 |
| A_24_P920319 | ZBED5 | -0.006357042 | 0.022671129 | -1.00 |
| A_24_P339071 | CDR2 | -0.004879661 | 0.010095093 | -1.00 |
| A_23_P401076 | SUSD3 | -0.008088848 | 0.001009347 | -1.00 |
| A_24_P29445 | TMEM14B | -0.00841769 | 0.000597105 | -1.00 |

TABLE 3-continued

| 888 Significant Genes Identifed from Cathgen Registry and PREDICT Samples | | | | |
|---|---|---|---|---|
| A_23_P74088 | MMP23B | 0.006721068 | 0.004904725 | 1.00 |
| A_23_P53476 | LDHB | -0.009472271 | 0.007452212 | -1.00 |
| A_32_P159023 | THC2285720 | -0.00072918 | 0.013083408 | -1.00 |
| A_23_P142407 | ZNF101 | -0.004467223 | 0.049571214 | -1.00 |
| A_24_P32735 | A_24_P32735 | 0.003952204 | 0.030860186 | 1.00 |
| A_24_P406006 | AYTL2 | 0.004965676 | 0.021410704 | 1.00 |
| A_23_P41280 | PAICS | -0.008113749 | 0.000119648 | -1.00 |
| A_23_P97481 | TTLL7 | 0.000508732 | 0.015003924 | 1.00 |
| A_23_P31765 | PKIA | -0.01078472 | 1.78E-06 | -1.00 |
| A_23_P107724 | ZNF228 | -0.000568725 | 0.001846742 | -1.00 |
| A_23_P365149 | BCKDK | 0.004250422 | 0.021899422 | 1.00 |
| A_24_P160466 | KIAA1893 | 0.000818996 | 0.018620599 | 1.00 |
| A_32_P56434 | AW079854 | 0.006393467 | 0.046306837 | -1.00 |
| A_23_P125107 | HLA-B | 0.004315434 | 0.021372471 | 1.00 |
| A_23_P30163 | FLJ13197 | -0.004667071 | 0.026169317 | -1.00 |
| A_32_P135243 | MTHFD1L | -0.001713741 | 0.012496536 | -1.00 |
| A_24_P372608 | RPS13 | -0.00912154 | 0.001132334 | -1.00 |
| A_24_P187874 | FLJ40712 | -0.00054393 | 0.002519038 | -1.00 |
| A_24_P258073 | PEO1 | -0.00618278 | 0.001520667 | -1.00 |
| A_23_P410613 | C12orf23 | -0.012998883 | 0.000165185 | -1.00 |
| A_23_P501849 | RPL13 | -0.010683117 | 0.000832027 | -1.00 |
| A_23_P120557 | TASP1 | -0.006280021 | 9.38E-06 | -1.00 |
| A_23_P68198 | SH3YL1 | -0.005451635 | 0.03477475 | -1.00 |
| A_24_P4877 | ZCRB1 | -0.002491639 | 0.012762867 | -1.00 |
| A_23_P157299 | AEBP1 | -0.003549059 | 0.011742507 | -1.00 |
| A_32_P231493 | AF339771 | -0.005139435 | 0.021357303 | -1.00 |
| A_23_P123478 | PDE7A | -0.005806672 | 0.045007901 | -1.00 |
| A_24_P376483 | HLA-A | 0.008554895 | 0.006583323 | 1.00 |
| A_23_P80752 | PLXND1 | 0.002021686 | 0.002825381 | 1.00 |
| A_24_P266048 | FLJ20152 | -0.004211407 | 0.000109965 | -1.00 |
| A_32_P210252 | RPL22 | -0.006842628 | 0.010246718 | -1.00 |
| A_23_P96590 | GPRASP1 | -0.008103922 | 0.001230943 | -1.00 |
| A_24_P15586 | ENST00000313516 | -0.002562336 | 0.002326533 | -1.00 |
| A_23_P396842 | C6orf89 | 0.003571228 | 0.022915875 | 1.00 |
| A_23_P29096 | PDE9A | -0.004563919 | 0.006100366 | -1.00 |
| A_23_P70539 | HLA-C | 0.009784158 | 0.00190711 | 1.00 |
| A_32_P132477 | BQ337821 | 0.001882123 | 0.021634632 | 1.00 |
| A_24_P873757 | THC2432550 | -0.001790209 | 0.005351262 | -1.00 |
| A_32_P145447 | BU566406 | -0.002669211 | 0.044299433 | -1.00 |

TABLE 3-continued

| 888 Significant Genes Identifed from Cathgen Registry and PREDICT Samples | | | | |
|---|---|---|---|---|
| A_32_P542928 | LOC285989 | -0.003312281 | 0.00515469 | -1.00 |
| A_23_P210829 | PCMTD2 | -0.009401051 | 2.41E-05 | -1.00 |
| A_23_P74138 | TAGLN2 | 0.00626902 | 0.037864611 | 1.00 |
| A_23_P9152 | RCL1 | -0.006353658 | 0.000856631 | -1.00 |
| A_32_P200901 | CXXC5 | -0.003348085 | 0.004324898 | -1.00 |
| A_24_P239309 | LOC197322 | -0.001643031 | 0.018496256 | -1.00 |
| A_24_P69654 | KLF6 | 0.006465551 | 0.014315754 | 1.00 |
| A_24_P88763 | LOXL3 | 0.004273784 | 0.033121279 | 1.00 |
| A_23_P387585 | CXorf50 | -0.004492569 | 0.000350389 | -1.00 |
| A_32_P353072 | TMEM106B | -0.010147656 | 9.90E-05 | -1.00 |
| A_24_P942370 | GALNT4 | -0.001144756 | 0.03900214 | -1.00 |
| A_23_P90696 | TRIB2 | -0.009242177 | 0.0002956 | -1.00 |
| A_23_P155556 | CLDND1 | -0.008906832 | 0.002786039 | -1.00 |
| A_32_P7916 | BX096603 | -0.008152387 | 0.033423621 | -1.00 |
| A_32_P111394 | THC2441040 | -0.006034788 | 0.02803674 | -1.00 |
| A_24_P208998 | TRIM23 | -0.002657669 | 0.032701565 | -1.00 |
| A_24_P48408 | RNMT | -0.002196582 | 0.029709123 | -1.00 |
| A_24_P193295 | RAB15 | -0.005397798 | 0.02973202 | -1.00 |
| A_23_P112482 | AQP3 | -0.005875592 | 0.048765691 | -1.00 |
| A_23_P90790 | MAP1D | -0.002174622 | 0.009469348 | -1.00 |
| A_24_P50437 | BC065737 | -0.015783764 | 0.006873164 | -1.00 |
| A_24_P360529 | PDE7A | -0.005454285 | 0.002839295 | -1.00 |
| A_24_P98047 | SLC16A10 | -0.000553549 | 0.000418787 | -1.00 |
| A_24_P264685 | A_24_P264685 | 0.00657084 | 0.002281239 | 1.00 |
| A_24_P137997 | ZNF34 | -0.001709781 | 0.02352105 | 1.00 |
| A_32_P165340 | SRP9 | -0.007144542 | 0.024218608 | -1.00 |
| A_23_P253405 | SLC31A1 | 0.002694079 | 0.038858158 | 1.00 |
| A_32_P797019 | NPEPL1 | -0.001987128 | 0.033833207 | -1.00 |
| A_23_P204208 | KLRD1 | 0.008930421 | 0.002593241 | 1.00 |
| A_24_P450596 | CR627133 | -0.000934435 | 0.009224427 | -1.00 |
| A_32_P101334 | AK130366 | -0.00280519 | 0.001791823 | -1.00 |
| A_24_P233256 | ZNF649 | -0.001289168 | 6.31E-05 | -1.00 |
| A_24_P517901 | HNRPA1 | -0.006308877 | 0.012368938 | -1.00 |
| A_23_P377888 | KIAA1018 | -0.005088735 | 0.048412261 | -1.00 |
| A_23_P423543 | ENST00000298249 | -0.00526031 | 0.004936452 | -1.00 |
| A_23_P105465 | CMKLR1 | 0.002425028 | 0.002449084 | 1.00 |
| A_32_P34516 | AK056119 | -0.005575006 | 0.001479516 | -1.00 |
| A_32_P26017 | DB380193 | -0.000908258 | 0.031724202 | -1.00 |
| A_23_P157527 | LRRCC1 | -0.000945222 | 0.042153387 | -1.00 |

TABLE 3-continued

| 888 Significant Genes Identifed from Cathgen Registry and PREDICT Samples | | | | |
|---|---|---|---|---|
| A_23_P76918 | TIMM9 | -0.007061741 | 0.000834114 | -1.00 |
| A_23_P161194 | VIM | 0.006999861 | 0.000769074 | 1.00 |
| A_24_P96505 | GFRA2 | 0.000965651 | 0.019139935 | 1.00 |
| A_23_P105461 | CMKLR1 | 0.004061643 | 0.023202104 | 1.00 |
| A_32_P138432 | THC2386572 | -0.002434662 | 3.56E-08 | -1.00 |
| A_32_P128258 | SIGLECP3 | 0.010994627 | 0.006649296 | 1.00 |
| A_23_P254997 | C6orf149 | -0.00460986 | 0.02191434 | -1.00 |
| A_24_P76358 | A_24_P76358 | -0.012998263 | 0.036549565 | -1.00 |
| A_23_P27947 | PDCD2L | -0.004575389 | 0.004124008 | -1.00 |
| A_24_P137434 | DCBLD2 | -0.001806521 | 0.001337144 | -1.00 |
| A_23_P77714 | CLUAP1 | -0.00593632 | 0.004860848 | -1.00 |
| A_32_P139894 | BF514513 | -0.002430004 | 0.002957734 | -1.00 |
| A_23_P343250 | ZNF554 | -0.002831034 | 0.005974154 | -1.00 |
| A_23_P67785 | SPAG16 | -0.002331567 | 0.001135344 | -1.00 |
| A_23_P1691 | MMP1 | 0.001291111 | 0.032899192 | 1.00 |
| A_32_P53558 | ENST00000341569 | -0.003758342 | 0.034316123 | -1.00 |
| A_32_P115663 | THC2405842 | -0.000749897 | 0.045963961 | -1.00 |
| A_23_P146554 | PTGDS | 0.018399353 | 0.000776847 | 1.00 |
| A_23_P345460 | PLEKHG4 | -0.007919253 | 0.000120446 | -1.00 |
| A_24_P915300 | ENST00000234668 | -0.002008286 | 0.00161165 | -1.00 |
| A_23_P215931 | LEPROTL1 | -0.01246053 | 3.04E-05 | -1.00 |
| A_24_P325015 | BC065520 | -0.005376188 | 0.000130607 | -1.00 |
| A_24_P942112 | POLR1B | -0.001717767 | 0.006933888 | -1.00 |
| A_32_P145159 | A_32_P145159 | -0.004343601 | 0.020945272 | -1.00 |
| A_23_P48585 | SALL2 | -0.002993818 | 0.041869317 | -1.00 |
| A_32_P472968 | BC047110 | -0.001158755 | 0.003744352 | -1.00 |
| A_32_P122285 | A_32_P122285 | -0.004811413 | 0.030212186 | -1.00 |
| A_23_P138725 | MARVELD1 | 0.007287767 | 0.011495931 | 1.00 |
| A_32_P196036 | LOC643837 | -0.001277385 | 0.00613138 | -1.00 |
| A_23_P255591 | ZNF268 | -0.007931373 | 0.000956284 | -1.00 |
| A_24_P215475 | ZNF10 | -0.004190806 | 0.000192674 | -1.00 |
| A_23_P17134 | MAL | -0.007879737 | 0.024362449 | -1.00 |
| A_24_P35537 | RIC3 | -0.001775716 | 0.001657625 | -1.00 |
| A_24_P170103 | A_24_P170103 | -0.006120354 | 0.02755505 | -1.00 |
| A_23_P210176 | ITGA6 | -0.007875289 | 0.000650661 | -1.00 |
| A_24_P923190 | AK094415 | -0.001203259 | 0.035815187 | -1.00 |
| A_24_P316019 | ENST00000342829 | 0.004199775 | 0.002232366 | 1.00 |
| A_24_P252310 | KIAA0773 | 0.001238647 | 0.013022799 | 1.00 |
| A_24_P204244 | ANXA2P1 | 0.004720651 | 0.0417602 | 1.00 |

TABLE 3-continued

888 Significant Genes Identifed from Cathgen Registry and PREDICT Samples

| | | | | |
|---|---|---|---|---|
| A_23_P114814 | RHOU | 0.001225158 | 0.015201843 | 1.00 |
| A_24_P631993 | A_24_P631993 | 0.006912835 | 0.00192295 | 1.00 |
| A_23_P373724 | PPFIBP1 | -0.00236474 | 0.002586008 | -1.00 |
| A_32_P191004 | ENST00000238789 | -0.005771977 | 0.002349035 | -1.00 |
| A_24_P123347 | PPAT | -0.002391102 | 0.025317145 | -1.00 |
| A_23_P43786 | LMLN | -0.00266571 | 0.00630938 | -1.00 |
| A_24_P134727 | TFAM | -0.003140605 | 0.002644497 | -1.00 |
| A_23_P36226 | BMSC-MCP | -0.003475548 | 0.030560373 | -1.00 |
| A_32_P95015 | THC2404993 | -0.005075401 | 0.044199151 | -1.00 |
| A_23_P146187 | RRS1 | -0.005707847 | 0.002082365 | -1.00 |
| A_23_P201731 | TRAF5 | -0.009659492 | 0.001471653 | -1.00 |
| A_24_P118541 | A_24_P118541 | -0.010109766 | 0.018487045 | -1.00 |
| A_23_P415611 | LOC150159 | -0.00298718 | 0.003496604 | -1.00 |
| A_24_P24230 | A_24_P24230 | 0.003099177 | 0.033410078 | 1.00 |
| A_32_P131143 | CECR4 | -0.001740063 | 0.044960719 | -1.00 |
| A_23_P62642 | CCDC19 | 0.007346288 | 0.002262312 | 1.00 |
| A_23_P434710 | PPP1CA | 0.004041646 | 0.016538648 | 1.00 |
| A_23_P3823 | BCKDK | 0.00519061 | 0.00910995 | 1.00 |
| A_24_P813667 | THC2252199 | -0.000883095 | 0.047663234 | -1.00 |
| A_32_P63086 | BC041913 | -0.00331568 | 0.025472645 | -1.00 |
| A_24_P256654 | LOC401588 | -0.002868211 | 0.021168382 | -1.00 |
| A_24_P596406 | THC2281336 | -0.005281045 | 0.00028612 | -1.00 |
| A_32_P177955 | LOC441461 | -0.001276263 | 0.035990179 | -1.00 |
| A_32_P50066 | MAP9 | -0.004773918 | 0.000451111 | -1.00 |
| A_24_P177795 | ENST00000343149 | 0.004776072 | 0.040586494 | 1.00 |
| A_24_P325035 | AK092090 | -0.005949321 | 0.000760969 | -1.00 |
| A_24_P153643 | DOCK3 | -0.00158522 | 0.018270655 | -1.00 |
| A_23_P52058 | TARBP1 | -0.006256708 | 0.00290823 | -1.00 |
| A_23_P217886 | UBE2J2 | 0.002750852 | 0.036797476 | 1.00 |
| A_24_P40907 | PPAPDC2 | -0.004717944 | 0.015977337 | -1.00 |
| A_23_P34144 | MAGEH1 | -0.006072172 | 0.007084057 | -1.00 |
| A_23_P19313 | TBP | -0.004505809 | 0.000667498 | -1.00 |
| A_23_P19313 | TBP | -0.004044054 | 0.00161558 | -1.00 |
| A_23_P19313 | TBP | -0.0041897 | 0.00175154 | -1.00 |
| A_23_P19313 | TBP | -0.003905852 | 0.003479562 | -1.00 |
| A_23_P19313 | TBP | -0.003845252 | 0.003827178 | -1.00 |
| A_23_P19313 | TBP | -0.003715747 | 0.005006304 | -1.00 |
| A_23_P19313 | TBP | -0.003601998 | 0.005105065 | -1.00 |
| A_23_P19313 | TBP | -0.003452138 | 0.010531563 | -1.00 |

TABLE 3-continued

888 Significant Genes Identifed from Cathgen Registry and PREDICT Samples

| | | | | |
|---|---|---|---|---|
| A_23_P19313 | TBP | -0.003513599 | 0.012590108 | -1.00 |
| A_23_P19313 | TBP | -0.003278729 | 0.017633611 | -1.00 |
| A_24_P300952 | APLP2 | 0.005936733 | 0.0241682 | 1.00 |
| A_24_P418044 | BC089454 | 0.006166289 | 0.000385814 | 1.00 |
| A_24_P418044 | BC089454 | 0.005952161 | 0.000490525 | 1.00 |
| A_24_P418044 | BC089454 | 0.00609218 | 0.000536761 | 1.00 |
| A_24_P418044 | BC089454 | 0.005854278 | 0.001221721 | 1.00 |
| A_24_P418044 | BC089454 | 0.005700171 | 0.001740982 | 1.00 |
| A_24_P418044 | BC089454 | 0.005597334 | 0.001964398 | 1.00 |
| A_24_P418044 | BC089454 | 0.005303263 | 0.003470584 | 1.00 |
| A_24_P418044 | BC089454 | 0.004975564 | 0.005269663 | 1.00 |
| A_24_P418044 | BC089454 | 0.00463771 | 0.007825884 | 1.00 |
| A_24_P418044 | BC089454 | 0.004727894 | 0.009855126 | 1.00 |
| A_23_P92012 | TSEN2 | -0.005714497 | 0.006694181 | -1.00 |
| A_24_P511143 | THC2324252 | -0.00090855 | 0.015708502 | -1.00 |
| A_23_P342000 | RBM11 | -0.001238252 | 0.003787269 | -1.00 |
| A_32_P173744 | CR603215 | -0.007902555 | 0.019380285 | -1.00 |
| A_24_P205268 | KIAA0323 | 0.003844212 | 0.041753565 | 1.00 |
| A_32_P113007 | THC2415754 | -0.003212907 | 0.011801954 | -1.00 |
| A_23_P72025 | SLC25A20 | -0.004650541 | 0.032124903 | 1.00 |
| A_23_P44154 | CD96 | -0.006118557 | 0.007885787 | -1.00 |
| A_23_P22143 | PDE6B | -0.003327231 | 0.030883135 | -1.00 |
| A_23_P397341 | PAQR4 | 0.00183403 | 0.012891952 | 1.00 |
| A_32_P174214 | THC2437618 | -0.00250388 | 0.034996035 | -1.00 |
| A_32_P123966 | KIAA1005 | -0.001057684 | 0.031707011 | -1.00 |
| A_32_P211141 | LOC90624 | -0.007072365 | 0.001377952 | -1.00 |
| A_23_P407614 | PYDC1 | 0.006045947 | 0.005748753 | 1.00 |
| A_24_P225339 | MOBKL2C | 0.002327306 | 0.04463934 | 1.00 |
| A_23_P98350 | BIRC3 | -0.012284591 | 0.001082817 | -1.00 |
| A_32_P515088 | AF086045 | -0.003733934 | 0.000755454 | -1.00 |
| A_23_P8640 | GPR30 | 0.008316993 | 0.00450708 | 1.00 |
| A_23_P31006 | HLA-DRB5 | 0.006524346 | 0.036465276 | 1.00 |
| A_23_P129064 | GATM | -0.004870391 | 0.003008763 | -1.00 |
| A_23_P371215 | ICOS | -0.010125077 | 0.000693736 | -1.00 |
| A_24_P280903 | ENST00000311218 | -0.004683556 | 0.048072785 | -1.00 |
| A_32_P203430 | ZNF30 | -0.004249704 | 0.002180638 | -1.00 |
| A_23_P28625 | WDR12 | -0.003285471 | 0.018645805 | -1.00 |
| A_23_P62335 | TMLHE | 0.001939973 | 0.013630635 | 1.00 |
| A_23_P82478 | PUS7 | -0.00546973 | 0.002352776 | -1.00 |

TABLE 3-continued

| 888 Significant Genes Identifed from Cathgen Registry and PREDICT Samples | | | | |
|---|---|---|---|---|
| A_23_P4611 | SLC27A5 | -0.005391682 | 0.008838157 | -1.00 |
| A_23_P379142 | ZNF626 | -0.00392303 | 0.028535556 | -1.00 |
| A_24_P64071 | ZBTB10 | -0.000319199 | 0.046467537 | -1.00 |
| A_24_P208452 | BBS5 | -0.001292743 | 0.049622075 | -1.00 |
| A_24_P674924 | THC2303869 | -0.002946926 | 0.047533597 | -1.00 |
| A_32_P122940 | AL390181 | -0.003498886 | 0.001132472 | -1.00 |
| A_32_P6452 | A_32_P6452 | -0.002633713 | 0.04502005 | -1.00 |
| A_32_P66625 | THC2303043 | -0.005797512 | 0.000667049 | -1.00 |
| A_32_P834726 | AK055679 | -0.00225599 | 0.011623311 | -1.00 |
| A_32_P8120 | GNL3 | -0.008269841 | 0.007738958 | -1.00 |
| A_23_P160518 | TRIM45 | 0.000624096 | 0.044266224 | 1.00 |
| A_23_P42588 | GIMAP5 | -0.004359352 | 0.042724971 | -1.00 |
| A_32_P38467 | CR625561 | -0.009311836 | 0.015674225 | -1.00 |
| A_32_P200120 | THC2404892 | -0.00210273 | 0.01020644 | -1.00 |
| A_24_P535219 | ENST00000341591 | -0.004322862 | 0.000312928 | -1.00 |
| A_23_P69877 | ZFP62 | -0.010754527 | 0.000112366 | -1.00 |
| A_32_P24489 | BX538250 | -0.005573137 | 0.005949817 | -1.00 |
| A_24_P921897 | HOOK1 | -0.002552521 | 0.000884517 | -1.00 |
| A_24_P195240 | ENST00000309184 | 0.001032186 | 0.013135693 | 1.00 |
| A_24_P54000 | C1orf71 | -0.00145067 | 0.00240596 | -1.00 |
| A_23_P59528 | ACN9 | -0.005845752 | 0.000900521 | -1.00 |
| A_24_P358337 | A_24_P358337 | -0.008058995 | 0.028761567 | -1.00 |
| A_32_P28939 | ALKBH2 | -0.005764954 | 0.002866866 | -1.00 |
| A_23_P68211 | SPR | 0.001843133 | 0.014527149 | 1.00 |
| A_32_P104263 | THC2432735 | 0.006133742 | 0.005646787 | 1.00 |
| A_23_P55127 | C17orf48 | -0.005182281 | 0.002106314 | -1.00 |
| A_24_P256603 | LOC90624 | -0.00635143 | 0.001419937 | -1.00 |
| A_23_P411431 | ENST00000282366 | -0.006506147 | 0.00130477 | -1.00 |
| A_23_P44964 | C10orf38 | -0.003641751 | 0.015950058 | -1.00 |
| A_24_P376391 | PLXND1 | 0.006621422 | 0.011512989 | 1.00 |
| A_24_P602507 | LOC123688 | -0.0005677 | 0.023662909 | -1.00 |
| A_24_P263767 | ENST00000376793 | 0.008802388 | 0.001145125 | 1.00 |
| A_23_P26223 | ASL | 0.00514416 | 0.006766742 | 1.00 |
| A_32_P86028 | RPS13 | -0.009354831 | 0.001232679 | -1.00 |
| A_23_P154500 | DNMT3A | -0.00274888 | 0.043572301 | -1.00 |
| A_23_P29836 | TMEM42 | -0.006462507 | 0.016111924 | -1.00 |
| A_32_P3932 | THC2280799 | -0.002338049 | 0.012700161 | -1.00 |
| A_32_P173058 | TMEM41B | -0.004853923 | 0.011608441 | -1.00 |
| A_24_P217904 | ENST00000372922 | -0.004879337 | 0.007031842 | -1.00 |

TABLE 3-continued

888 Significant Genes Identifed from Cathgen Registry and PREDICT Samples

| | | | | |
|---|---|---|---|---|
| A_23_P136493 | NRG1 | 0.00108299 | 0.031549552 | 1.00 |
| A_24_P156113 | EHD2 | 0.001136189 | 0.011157342 | 1.00 |
| A_24_P849801 | RPL22 | -0.006101157 | 0.003494705 | -1.00 |
| A_23_P10591 | METRNL | 0.007369585 | 0.002021773 | 1.00 |
| A_24_P269853 | ACTR1A | 0.003858548 | 0.001430564 | 1.00 |
| A_24_P586264 | AK092450 | -0.008680022 | 0.003103613 | -1.00 |
| A_32_P61657 | ZNF33B | -0.001878817 | 0.021503881 | -1.00 |
| A_24_P247576 | A_24_P247576 | -0.004497089 | 0.043511583 | -1.00 |
| A_23_P49060 | SPINT1 | 0.003787613 | 0.026880379 | 1.00 |
| A_32_P189034 | THC2310027 | -0.011785306 | 0.002745109 | -1.00 |
| A_32_P220696 | TERF1 | -0.004474033 | 0.002960634 | -1.00 |
| A_23_P127467 | MGC11102 | 0.002003015 | 0.03489084 | 1.00 |
| A_23_P200047 | ENST00000263739 | -0.00198574 | 0.000901767 | -1.00 |
| A_23_P162047 | DKK3 | -0.004569896 | 0.000740336 | -1.00 |
| A_23_P66891 | CDC42EP4 | 0.002852021 | 0.002552214 | 1.00 |
| A_23_P99496 | MCF2L | -0.002221656 | 0.005333888 | -1.00 |
| A_24_P200427 | PAICS | -0.00394754 | 0.000344698 | -1.00 |
| A_24_P122524 | WDR3 | -0.005373954 | 0.000412404 | -1.00 |
| A_32_P127019 | THC2411655 | -0.002894298 | 0.047573733 | -1.00 |
| A_23_P354827 | ZNF550 | -0.012513161 | 2.18E-05 | -1.00 |
| A_23_P216610 | SUSD1 | 0.004733898 | 0.011375337 | 1.00 |
| A_24_P358328 | LOC286016 | 0.004590061 | 0.005958045 | 1.00 |
| A_24_P400690 | A_24_P400690 | 0.00177907 | 0.027403596 | 1.00 |
| A_23_P12896 | FANCF | -0.006615082 | 0.000364257 | -1.00 |
| A_32_P181271 | THC2323620 | -0.005303763 | 0.002526558 | -1.00 |
| A_23_P166453 | CDC42EP1 | 0.002018082 | 0.008676086 | 1.00 |
| A_23_P370434 | C1QBP | -0.006130143 | 0.001718174 | -1.00 |
| A_24_P910262 | ENST00000354586 | -0.004251926 | 0.013799503 | -1.00 |
| A_23_P50571 | KIR2DL2 | 0.007700385 | 0.019177586 | 1.00 |
| A_23_P253464 | CCDC98 | -0.003963631 | 0.011603956 | -1.00 |
| A_23_P253464 | CCDC98 | -0.003917377 | 0.014944051 | -1.00 |
| A_23_P253464 | CCDC98 | -0.003957431 | 0.018855677 | -1.00 |
| A_23_P253464 | CCDC98 | -0.003706102 | 0.018900818 | -1.00 |
| A_23_P253464 | CCDC98 | -0.003646707 | 0.020060149 | -1.00 |
| A_23_P253464 | CCDC98 | -0.003419351 | 0.025419145 | -1.00 |
| A_23_P253464 | CCDC98 | -0.003526304 | 0.025891723 | -1.00 |
| A_23_P253464 | CCDC98 | -0.003407301 | 0.026659291 | -1.00 |
| A_23_P253464 | CCDC98 | -0.003367595 | 0.030598375 | -1.00 |

TABLE 3-continued

| 888 Significant Genes Identifed from Cathgen Registry and PREDICT Samples | | | | |
|---|---|---|---|---|
| A_24_P298099 | A_24_P298099 | -0.006679829 | 0.014390054 | -1.00 |
| A_23_P103601 | MAN1C1 | -0.007541551 | 0.022216473 | -1.00 |
| A_24_P406870 | ILK | 0.006519753 | 0.000588023 | 1.00 |
| A_23_P55682 | ZNF447 | -0.009750487 | 0.00251877 | -1.00 |
| A_23_P253301 | PFN2 | -0.001173399 | 0.040629463 | -1.00 |
| A_23_P13822 | STYK1 | 0.003990448 | 0.000690978 | 1.00 |
| A_23_P167818 | C6orf60 | -0.003325698 | 0.001122208 | -1.00 |
| A_32_P148275 | SPIC | -0.001579831 | 0.006146739 | -1.00 |
| A_24_P156388 | FLJ20699 | 0.007539119 | 0.003876194 | 1.00 |
| A_23_P41246 | TETRAN | 0.003883299 | 0.032186012 | 1.00 |
| A_23_P168188 | SYTL3 | 0.007253532 | 0.008116932 | 1.00 |
| A_24_P217063 | THC2337363 | -0.001890393 | 0.006578244 | -1.00 |
| A_24_P323885 | A_24_P323885 | 0.002757737 | 0.032500173 | 1.00 |
| A_23_P350719 | MGC52282 | 0.008138817 | 0.003979936 | 1.00 |
| A_32_P31945 | ACADSB | -0.001730653 | 0.043178945 | -1.00 |
| A_24_P247044 | ENST00000355095 | -0.003247848 | 0.007003075 | -1.00 |
| A_23_P58538 | TIGA1 | -0.007578595 | 0.008324176 | -1.00 |
| A_23_P17152 | A_23_P17152 | -0.004644087 | 0.036193279 | -1.00 |
| A_24_P34944 | PCDHGA12 | 0.001681409 | 0.000119535 | 1.00 |
| A_23_P157283 | C7orf23 | -0.009869668 | 2.40E-05 | -1.00 |
| A_23_P250212 | ENST00000330777 | -0.00628281 | 0.022749337 | -1.00 |
| A_24_P15630 | C12orf42 | -0.002848815 | 0.000188905 | -1.00 |
| A_32_P63858 | THC2279910 | -0.00268869 | 0.020693608 | -1.00 |
| A_23_P47790 | METTL1 | -0.004363428 | 7.21E-05 | -1.00 |
| A_23_P3681 | NETO2 | -0.002320354 | 0.013248119 | -1.00 |
| A_23_P147326 | SERINC2 | 0.002046783 | 0.014829129 | 1.00 |
| A_23_P362183 | ANKS6 | -0.007996872 | 0.001447556 | -1.00 |
| A_23_P119362 | EMP3 | 0.005794394 | 0.024731695 | 1.00 |
| A_24_P144025 | ENST00000337102 | -0.010668024 | 0.030243421 | -1.00 |
| A_23_P386420 | GTF2H3 | -0.001468604 | 0.003570633 | -1.00 |
| A_24_P71021 | GNB1 | 0.004936887 | 0.037838489 | 1.00 |
| A_32_P192922 | LOC157562 | -0.005762801 | 0.002703179 | -1.00 |
| A_23_P88831 | SLC7A6 | -0.002251951 | 0.010749425 | -1.00 |
| A_24_P309415 | TMEM123 | -0.009328916 | 0.005452831 | -1.00 |
| A_24_P376139 | AK057798 | -0.003016934 | 0.018899381 | -1.00 |
| A_23_P132486 | OXSM | -0.004099093 | 0.036296002 | -1.00 |
| A_23_P73117 | CTNNA3 | 0.000698125 | 0.002176244 | 1.00 |
| A_23_P64792 | KCNMB4 | -0.004850083 | 0.003293985 | -1.00 |
| A_23_P420373 | DNMT3A | -0.004207728 | 0.018340236 | -1.00 |

TABLE 3-continued

888 Significant Genes Identifed from Cathgen Registry and PREDICT Samples

| | | | | |
|---|---|---|---|---|
| A_23_P45940 | TFB2M | -0.006121609 | 0.000508967 | -1.00 |
| A_24_P60972 | C9orf97 | -0.003531358 | 8.95E-05 | -1.00 |
| A_23_P16722 | DOCK10 | -0.006202453 | 0.013081303 | -1.00 |
| A_32_P132438 | AKAP1 | -0.004689922 | 0.024912001 | -1.00 |
| A_24_P791669 | ENST00000356555 | -0.003868142 | 0.000170982 | -1.00 |
| A_23_P167920 | DLL1 | -0.005223471 | 1.44E-07 | -1.00 |
| A_24_P13041 | PLEKHK1 | -0.003747765 | 0.029345874 | -1.00 |
| A_24_P343233 | HLA-DRB1 | 0.006988685 | 0.012902096 | 1.00 |
| A_24_P343233 | HLA-DRB1 | 0.007168224 | 0.013550431 | 1.00 |
| A_24_P343233 | HLA-DRB1 | 0.006892757 | 0.018431964 | 1.00 |
| A_24_P343233 | HLA-DRB1 | 0.006553904 | 0.018558073 | 1.00 |
| A_24_P343233 | HLA-DRB1 | 0.006624037 | 0.019600522 | 1.00 |
| A_24_P343233 | HLA-DRB1 | 0.006371012 | 0.025204299 | 1.00 |
| A_24_P343233 | HLA-DRB1 | 0.005988604 | 0.032533605 | 1.00 |
| A_24_P343233 | HLA-DRB1 | 0.005734402 | 0.035029908 | 1.00 |
| A_32_P25273 | HSPD1 | -0.005124434 | 0.045475165 | -1.00 |
| A_23_P66481 | RTN4RL1 | -0.001092994 | 0.001934906 | -1.00 |
| A_23_P348227 | ZNF135 | -0.002512869 | 0.000224882 | -1.00 |
| A_23_P12514 | RHOC | 0.007342958 | 0.016059405 | 1.00 |
| A_23_P100355 | PPP4C | 0.006147369 | 0.002983142 | 1.00 |
| A_23_P392470 | NR3C2 | -0.004225278 | 0.015721874 | -1.00 |
| A_32_P121716 | AK057443 | -0.000704049 | 0.043359576 | -1.00 |
| A_23_P86100 | KARCA1 | -0.00168514 | 0.010332368 | -1.00 |
| A_32_P167904 | CR624679 | -0.001219682 | 0.035488151 | -1.00 |
| A_23_P90014 | AX775899 | 0.004111833 | 0.03418677 | 1.00 |
| A_23_P252155 | STRBP | -0.009278922 | 0.001938048 | -1.00 |
| A_32_P18159 | LOC90624 | -0.00302219 | 0.0002939 | -1.00 |
| A_24_P481824 | AF086017 | -0.002109334 | 0.001000903 | -1.00 |
| A_23_P356484 | RPS10 | -0.010856523 | 0.00949559 | -1.00 |
| A_32_P144421 | KIAA1729 | -0.003845606 | 0.00424685 | -1.00 |
| A_32_P71476 | THC2380681 | -0.007526191 | 0.02312219 | -1.00 |
| A_24_P193257 | THC2437177 | -0.001310687 | 0.022779931 | -1.00 |
| A_23_P356581 | ROBO3 | -0.006296366 | 0.03082864 | -1.00 |
| A_24_P224526 | C17orf75 | -0.004349147 | 0.009752406 | -1.00 |
| A_23_P211878 | FLNB | -0.003377787 | 0.017598915 | -1.00 |
| A_24_P118472 | A_24_P118472 | 0.003996014 | 0.047395704 | -1.00 |
| A_24_P940166 | PAPSS2 | 0.002297091 | 0.015065592 | 1.00 |
| A_23_P201193 | TSPAN2 | 0.008996189 | 0.004384112 | 1.00 |
| A_23_P255884 | GSN | 0.007899902 | 0.007280261 | 1.00 |

TABLE 3-continued

888 Significant Genes Identifed from Cathgen Registry and PREDICT Samples

| | | | | |
|---|---|---|---|---|
| A_23_P318646 | RPS10 | -0.009811925 | 0.022369749 | -1.00 |
| A_32_P91107 | BC089156 | -0.004254711 | 0.016167163 | -1.00 |
| A_24_P170874 | BC013295 | -0.002729541 | 0.000525001 | -1.00 |
| A_24_P409521 | A_24_P409521 | -0.005854606 | 0.030187192 | -1.00 |
| A_32_P14894 | RPS10 | -0.009375106 | 0.028951318 | -1.00 |
| A_24_P573533 | CBWD2 | -0.003781033 | 0.023399218 | -1.00 |
| A_23_P89249 | ERBB2 | 0.00731545 | 0.006867083 | 1.00 |
| A_23_P89249 | ERBB2 | 0.006850384 | 0.008525821 | 1.00 |
| A_23_P89249 | ERBB2 | 0.006853348 | 0.012505237 | 1.00 |
| A_23_P89249 | ERBB2 | 0.006586321 | 0.012608906 | 1.00 |
| A_23_P89249 | ERBB2 | 0.006677219 | 0.01279926 | 1.00 |
| A_23_P89249 | ERBB2 | 0.006594554 | 0.013049003 | 1.00 |
| A_23_P89249 | ERBB2 | 0.006591935 | 0.016687512 | 1.00 |
| A_23_P89249 | ERBB2 | 0.00621982 | 0.016875846 | 1.00 |
| A_23_P89249 | ERBB2 | 0.006146739 | 0.021092964 | 1.00 |
| A_23_P89249 | ERBB2 | 0.005713559 | 0.025707906 | 1.00 |
| A_23_P88095 | TBC1D4 | -0.007686722 | 0.001579783 | -1.00 |
| A_32_P228268 | ENST00000280576 | 0.001177828 | 0.02542467 | 1.00 |
| A_23_P347468 | FZD3 | -0.001044189 | 0.01808983 | -1.00 |
| A_24_P810735 | AX721128 | -0.003396707 | 0.000579736 | -1.00 |
| A_24_P396650 | RPS6KA1 | 0.004609889 | 0.042075132 | 1.00 |
| A_32_P220671 | BE005242 | -0.002096423 | 5.78E-06 | -1.00 |
| A_32_P25972 | BE826587 | -0.001993377 | 0.012122393 | -1.00 |
| A_32_P68533 | FLJ13305 | -0.00139663 | 0.001709292 | -1.00 |
| A_24_P37441 | PDK1 | -0.006639125 | 0.000955171 | -1.00 |
| A_32_P486620 | IGSF22 | -0.002040389 | 0.006165217 | -1.00 |
| A_24_P238427 | A_24_P238427 | -0.0080632 | 0.006184449 | -1.00 |
| A_32_P57989 | BX115064 | -0.001112608 | 0.011646103 | -1.00 |
| A_23_P33643 | ENST00000381961 | -0.011427338 | 0.001428407 | -1.00 |
| A_24_P186065 | DHFRL1 | -0.003982764 | 0.006161172 | -1.00 |
| A_32_P164630 | RPS10 | -0.011497836 | 0.009006153 | -1.00 |
| A_32_P46817 | THC2280638 | -0.005246456 | 0.017847694 | -1.00 |
| A_23_P30634 | BACH2 | -0.009975778 | 9.23E-05 | -1.00 |
| A_23_P18142 | RPL32 | -0.008363888 | 0.008025905 | -1.00 |
| A_32_P127997 | LOC644656 | -0.002778821 | 0.012378582 | -1.00 |
| A_24_P750636 | THC2267012 | -0.010178203 | 0.006523118 | -1.00 |
| A_23_P207811 | PAIP1 | -0.008127533 | 0.000142345 | -1.00 |
| A_23_P58898 | CASP8AP2 | -0.005852202 | 0.001004372 | -1.00 |
| A_32_P78311 | CR590180 | -0.001117913 | 0.001716542 | -1.00 |

TABLE 3-continued

888 Significant Genes Identifed from
Cathgen Registry and PREDICT Samples

| | | | | |
|---|---|---|---|---|
| A_23_P129476 | C16orf7 | 0.005319395 | 0.044707287 | 1.00 |
| A_24_P106145 | WDR1 | 0.005014912 | 0.030965969 | 1.00 |
| A_24_P396881 | THC2403165 | -0.003133022 | 0.015291233 | -1.00 |
| A_32_P160972 | C6orf115 | -0.008156335 | 0.001398283 | -1.00 |
| A_23_P154447 | NOP5/NOP58 | -0.007333894 | 0.030579346 | -1.00 |
| A_24_P626931 | C6orf157 | -0.002028333 | 0.011749087 | -1.00 |
| A_23_P137532 | PLOD1 | 0.007525177 | 0.000664248 | 1.00 |
| A_24_P261417 | DKK3 | -0.000724261 | 0.006976922 | -1.00 |
| A_23_P143127 | EML4 | -0.008201652 | 0.003821989 | -1.00 |
| A_24_P902313 | BF129169 | -0.005746539 | 0.010802639 | -1.00 |
| A_23_P134734 | FLJ20366 | -0.001737016 | 7.86E-05 | -1.00 |
| A_24_P192627 | MLLT3 | -0.002695176 | 0.005480476 | -1.00 |
| A_32_P146844 | THC2406576 | -0.007235591 | 0.00587876 | -1.00 |
| A_32_P115277 | THC2279466 | -0.00388274 | 0.000252324 | -1.00 |
| A_23_P79732 | RPS27A | -0.008197176 | 0.026113987 | -1.00 |
| A_23_P99275 | KLRB1 | -0.017541936 | 0.000202122 | -1.00 |
| A_23_P162766 | DOCK9 | -0.004186984 | 0.031556779 | -1.00 |
| A_32_P195401 | ALS2CR13 | -0.006171381 | 0.020704506 | -1.00 |
| A_24_P398691 | ABHD13 | -0.001646061 | 0.046786453 | -1.00 |
| A_24_P127051 | A_24_P127051 | 0.005064714 | 0.030464707 | 1.00 |
| A_23_P209700 | NMUR1 | 0.014360503 | 0.000374811 | 1.00 |
| A_24_P627415 | THC2268216 | -0.003990155 | 0.033049083 | -1.00 |
| A_32_P217643 | CR594711 | -0.001009788 | 0.003811274 | -1.00 |
| A_24_P89718 | TTC26 | 0.00076442 | 0.015323989 | 1.00 |
| A_24_P15823 | ENST00000330189 | 0.003907436 | 0.035290197 | -1.00 |
| A_23_P13364 | NUCB2 | -0.00631646 | 0.020672425 | -1.00 |
| A_23_P423309 | PCDH12 | 0.000638457 | 0.044823334 | 1.00 |
| A_32_P109835 | THC2316236 | -0.004287371 | 0.00161048 | -1.00 |
| A_24_P272523 | A_24_P272523 | 0.003679714 | 0.009027308 | 1.00 |
| A_24_P854896 | CR615261 | -0.000986166 | 0.028340968 | -1.00 |
| A_32_P205913 | A_32_P205913 | -0.003623484 | 1.90E-06 | -1.00 |
| A_23_P214281 | PAQR8 | -0.004908095 | 0.0058249 | -1.00 |
| A_32_P226149 | YWHAZ | 0.003502964 | 0.030902427 | 1.00 |
| A_23_P63798 | KLF6 | 0.006546867 | 0.011794474 | 1.00 |
| A_24_P96527 | ATP5L | -0.005584391 | 0.046699683 | -1.00 |
| A_32_P139229 | ZNF543 | -0.004317982 | 3.22E-05 | -1.00 |
| A_24_P345866 | ENST00000311412 | -0.003613422 | 0.038676313 | -1.00 |
| A_23_P32328 | C6orf149 | -0.004338913 | 0.008051211 | -1.00 |
| A_24_P141520 | AK022297 | -0.004071494 | 0.003466357 | -1.00 |

TABLE 3-continued

888 Significant Genes Identifed from Cathgen Registry and PREDICT Samples

| | | | | |
|---|---|---|---|---|
| A_23_P146981 | A_23_P146981 | 0.002414712 | 0.04740421 | 1.00 |
| A_32_P835626 | FBXO34 | -0.006821715 | 0.019291061 | 1.00 |
| A_24_P336577 | C1orf183 | 0.007819251 | 0.033057704 | 1.00 |
| A_24_P108291 | IMPACT | -0.00246553 | 0.004051443 | -1.00 |
| A_23_P140848 | MPHOSPH6 | -0.003135756 | 0.00558928 | -1.00 |
| A_23_P259438 | DCK | -0.010319066 | 4.40E-06 | -1.00 |
| A_24_P174903 | ENST00000259969 | -0.0044708 | 0.010555858 | -1.00 |
| A_24_P418998 | AK095214 | -0.002554709 | 0.020201694 | -1.00 |
| A_23_P210323 | CEP68 | -0.005060339 | 0.037723859 | -1.00 |
| A_24_P769672 | AL359596 | -0.003023173 | 0.006932617 | -1.00 |
| A_23_P310956 | COL6A2 | 0.00200388 | 0.032402012 | 1.00 |
| A_23_P22672 | CXorf45 | -0.00855091 | 0.000486128 | -1.00 |
| A_23_P209032 | ZNF302 | -0.00706407 | 0.000103492 | -1.00 |
| A_24_P944519 | PDE4D | -0.001528052 | 0.001191123 | -1.00 |
| A_24_P179816 | SLC27A3 | 0.005879137 | 0.01131736 | 1.00 |
| A_24_P188941 | NPM1 | -0.010411729 | 0.001661889 | -1.00 |
| A_32_P135634 | THC2375394 | -0.000821925 | 0.035079819 | -1.00 |
| A_32_P55987 | THC2282958 | -0.005326819 | 0.025909997 | -1.00 |
| A_24_P359856 | HDAC4 | 0.004186248 | 0.012758746 | 1.00 |
| A_23_P205997 | APH1B | 0.007817623 | 0.000296531 | 1.00 |
| A_32_P93045 | AL080082 | -0.002129439 | 3.72E-05 | -1.00 |
| A_24_P74571 | PGEA1 | -0.001942473 | 0.041358177 | -1.00 |
| A_23_P421401 | PDGFRB | 0.006264296 | 0.000606682 | 1.00 |
| A_24_P914513 | BCKDHB | -0.001931914 | 0.000279628 | -1.00 |
| A_23_P120660 | RPS21 | -0.01297188 | 0.012223861 | -1.00 |
| A_23_P404091 | GRPEL2 | -0.009642424 | 0.000338221 | -1.00 |
| A_24_P942786 | AK024870 | -0.009821239 | 0.000185869 | -1.00 |
| A_24_P482189 | THC2408010 | -0.000938995 | 0.037379995 | -1.00 |
| A_24_P677525 | AF336795 | 0.005283143 | 0.02571697 | 1.00 |
| A_23_P214789 | SNX9 | -0.004025244 | 0.023667685 | -1.00 |
| A_24_P32849 | RP11-78J21.1 | -0.004672323 | 0.034873799 | -1.00 |
| A_24_P917866 | SET | -0.008972926 | 0.013522495 | -1.00 |
| A_23_P318380 | ZNF683 | 0.016851437 | 0.022172101 | 1.00 |
| A_32_P123629 | THC2373876 | -0.005842628 | 0.014539341 | -1.00 |
| A_23_P93881 | SYPL1 | -0.006185524 | 0.000670727 | -1.00 |
| A_24_P58529 | TUBA6 | 0.004996066 | 0.010888748 | 1.00 |
| A_24_P181149 | BBS10 | -0.002981752 | 0.045943942 | -1.00 |
| A_23_P399146 | ZNF549 | -0.001848832 | 0.009625066 | -1.00 |
| A_23_P359174 | BC069659 | -0.00321779 | 0.039054857 | -1.00 |

TABLE 3-continued

888 Significant Genes Identifed from Cathgen Registry and PREDICT Samples

| | | | | |
|---|---|---|---|---|
| A_24_P652502 | Y15200 | -0.001648241 | 0.003458558 | -1.00 |
| A_23_P87810 | THC2373936 | -0.004967074 | 0.005576912 | -1.00 |
| A_23_P170453 | CST5 | 0.006249905 | 0.034042404 | 1.00 |
| A_23_P55936 | FCGRT | 0.007141312 | 0.002342906 | 1.00 |
| A_23_P124837 | LRP1 | 0.004787367 | 0.00028314 | 1.00 |
| A_23_P124837 | LRP1 | 0.004795187 | 0.000443663 | 1.00 |
| A_23_P124837 | LRP1 | 0.004669961 | 0.000586161 | 1.00 |
| A_23_P124837 | LRP1 | 0.004649726 | 0.000810977 | 1.00 |
| A_23_P124837 | LRP1 | 0.00423301 | 0.001170064 | 1.00 |
| A_23_P124837 | LRP1 | 0.004334309 | 0.00120745 | 1.00 |
| A_23_P124837 | LRP1 | 0.004534556 | 0.001226914 | 1.00 |
| A_23_P124837 | LRP1 | 0.004324698 | 0.00180883 | 1.00 |
| A_23_P124837 | LRP1 | 0.003870331 | 0.005143692 | 1.00 |
| A_23_P124837 | LRP1 | 0.003229736 | 0.016327377 | 1.00 |
| A_24_P418619 | RPS10 | -0.009326712 | 0.036623855 | -1.00 |
| A_23_P405175 | C1orf71 | -0.005571481 | 0.000756685 | -1.00 |
| A_24_P48403 | YES1 | -0.002025398 | 0.012172383 | -1.00 |
| A_23_P71790 | MAMDC4 | 0.004380304 | 0.000752855 | 1.00 |
| A_23_P101811 | ZNF14 | -0.004539441 | 0.018614544 | -1.00 |
| A_24_P90022 | ENST00000327347 | -0.00722956 | 3.56E-05 | -1.00 |
| A_32_P58201 | AK021570 | -0.003941073 | 0.021884291 | -1.00 |
| A_23_P250813 | WRN | -0.003756578 | 0.00402134 | -1.00 |
| A_23_P250813 | WRN | -0.004234826 | 0.004843167 | -1.00 |
| A_23_P250813 | WRN | -0.004026633 | 0.006294694 | -1.00 |
| A_23_P250813 | WRN | -0.003960259 | 0.007374841 | -1.00 |
| A_23_P250813 | WRN | -0.003419237 | 0.010562006 | -1.00 |
| A_23_P250813 | WRN | -0.003890161 | 0.013913213 | -1.00 |
| A_23_P250813 | WRN | -0.003388837 | 0.014527006 | -1.00 |
| A_23_P250813 | WRN | -0.003387599 | 0.014533403 | -1.00 |
| A_23_P250813 | WRN | -0.003628687 | 0.016458879 | -1.00 |
| A_23_P250813 | WRN | -0.003175676 | 0.029808563 | -1.00 |
| A_23_P148015 | AXIN2 | -0.004361055 | 0.044127824 | -1.00 |
| A_32_P104432 | AK123302 | -0.002147495 | 0.049888202 | -1.00 |
| A_32_P405942 | CR620977 | -0.007313721 | 0.000752742 | -1.00 |
| A_24_P931428 | AK021980 | -0.005003552 | 0.022882438 | -1.00 |
| A_24_P912382 | ENST00000376802 | 0.008808712 | 0.004921382 | 1.00 |
| A_24_P246626 | ENST00000383097 | 0.008864125 | 0.004090172 | 1.00 |
| A_23_P207939 | C18orf1 | -0.002175552 | 0.007107985 | -1.00 |
| A_24_P878388 | ENST00000333982 | -0.010149782 | 0.012462649 | -1.00 |

TABLE 3-continued

888 Significant Genes Identifed from Cathgen Registry and PREDICT Samples

| | | | | |
|---|---|---|---|---|
| A_23_P433758 | SPN | 0.005482445 | 0.034582119 | 1.00 |
| A_23_P13899 | GAPDH | 0.004859377 | 0.013574325 | 1.00 |
| A_23_P13899 | GAPDH | 0.004724492 | 0.014550966 | 1.00 |
| A_23_P13899 | GAPDH | 0.004986148 | 0.015272334 | 1.00 |
| A_23_P13899 | GAPDH | 0.004668624 | 0.015982383 | 1.00 |
| A_23_P13899 | GAPDH | 0.004601049 | 0.017749103 | 1.00 |
| A_23_P13899 | GAPDH | 0.004754469 | 0.017945847 | 1.00 |
| A_23_P13899 | GAPDH | 0.004750905 | 0.018842488 | 1.00 |
| A_23_P13899 | GAPDH | 0.004524499 | 0.023797668 | 1.00 |
| A_23_P13899 | GAPDH | 0.004363947 | 0.029588047 | 1.00 |
| A_23_P13899 | GAPDH | 0.004351752 | 0.029706878 | 1.00 |
| A_32_P94161 | BC053353 | -0.001662628 | 0.012072182 | -1.00 |
| A_24_P199774 | TINAGL1 | 0.000870702 | 0.015517988 | 1.00 |
| A_24_P391531 | COX11 | -0.002169409 | 0.049223044 | -1.00 |
| A_24_P272761 | DENND1A | 0.005135928 | 0.000483868 | 1.00 |
| A_24_P112087 | ASF1A | -0.003085995 | 0.000992445 | -1.00 |
| A_24_P316430 | NT5E | -0.000554432 | 0.002892569 | -1.00 |
| A_23_P153086 | C18orf22 | -0.004179094 | 0.02342982 | -1.00 |
| A_32_P116813 | C6orf149 | -0.003803413 | 0.02000601 | -1.00 |
| A_23_P310911 | BLMH | -0.003973056 | 0.015411248 | -1.00 |
| A_23_P47004 | DHX32 | -0.00199379 | 0.012430932 | -1.00 |
| A_23_P501080 | ZNF92 | -0.006294937 | 0.009696595 | -1.00 |
| A_23_P160881 | SMPDL3B | 0.001898452 | 0.013747251 | 1.00 |
| A_32_P223370 | BC041401 | -0.003526186 | 0.000898423 | -1.00 |
| A_32_P215789 | FARSLB | -0.000637552 | 0.001816622 | -1.00 |
| A_23_P312752 | KCNJ13 | 0.001891238 | 0.002801833 | 1.00 |
| A_23_P171324 | L1CAM | 0.000578711 | 0.029139911 | 1.00 |
| A_23_P254193 | FLJ20699 | 0.00964319 | 0.002605216 | 1.00 |
| A_24_P288722 | CASK | -0.002071525 | 0.026394993 | -1.00 |
| A_23_P158596 | AGTRAP | 0.007748615 | 0.000134494 | 1.00 |
| A_23_P77779 | RPL19 | -0.004755946 | 0.028176835 | -1.00 |
| A_23_P99642 | SLC7A7 | 0.007539318 | 0.001358141 | 1.00 |
| A_32_P234459 | HLA-H | 0.005688304 | 0.021583625 | 1.00 |
| A_23_P14769 | FES | 0.005897214 | 0.023804795 | 1.00 |
| A_32_P540407 | ZNF320 | -0.001511548 | 0.021820408 | -1.00 |
| A_23_P166716 | RG9MTD1 | -0.008022069 | 0.005615463 | -1.00 |
| A_23_P166716 | RG9MTD1 | -0.007511977 | 0.0067771 | -1.00 |
| A_23_P166716 | RG9MTD1 | -0.007677274 | 0.007179511 | -1.00 |
| A_23_P166716 | RG9MTD1 | -0.00740081 | 0.007283821 | -1.00 |

TABLE 3-continued

888 Significant Genes Identifed from Cathgen Registry and PREDICT Samples

| | | | | |
|---|---|---|---|---|
| A_23_P166716 | RG9MTD1 | -0.00727325 | 0.008118572 | -1.00 |
| A_23_P166716 | RG9MTD1 | -0.006932883 | 0.008171234 | -1.00 |
| A_23_P166716 | RG9MTD1 | -0.00735281 | 0.009908011 | -1.00 |
| A_23_P166716 | RG9MTD1 | -0.007142782 | 0.011806579 | -1.00 |
| A_23_P166716 | RG9MTD1 | -0.007136032 | 0.012606557 | -1.00 |
| A_23_P166716 | RG9MTD1 | -0.006909192 | 0.01354537 | -1.00 |
| A_24_P153234 | A_24_P153234 | -0.003455681 | 0.025870337 | -1.00 |
| A_24_P893239 | ENST00000373335 | -0.002786904 | 0.023965053 | -1.00 |
| A_23_P8558 | ABHD11 | 0.001793008 | 0.035612395 | 1.00 |
| A_23_P501732 | FCN2 | 0.009628336 | 0.001162015 | 1.00 |
| A_24_P374427 | ZDHHC21 | -0.000408723 | 0.042016348 | -1.00 |
| A_24_P316059 | A_24_P316059 | 0.009692923 | 0.000269746 | 1.00 |
| A_23_P8522 | TMEM106B | -0.003641758 | 0.017111383 | -1.00 |
| A_24_P307869 | LLGL2 | 0.004209822 | 0.037696113 | 1.00 |
| A_23_P29851 | LRPAP1 | 0.004403644 | 0.022720104 | 1.00 |
| A_23_P255126 | GAB3 | 0.004773326 | 0.006029262 | 1.00 |
| A_23_P141606 | BLMH | -0.005514119 | 0.017041492 | -1.00 |
| A_23_P200138 | SLAMF8 | 0.007799344 | 0.002300238 | 1.00 |
| A_24_P342807 | SLC30A6 | -0.002039109 | 0.000365175 | -1.00 |
| AT_nD_3 | AT_nD_3 | 0.000623657 | 0.01745085 | 1.00 |
| AT_nD_3 | AT_nD_3 | 0.000746297 | 0.028519727 | 1.00 |
| AT_nD_3 | AT_nD_3 | 0.000449625 | 0.033614999 | 1.00 |
| A_23_P101655 | ACTN4 | 0.006702955 | 0.007621629 | 1.00 |
| A_24_P726336 | THC2304714 | -0.004716121 | 0.017207308 | -1.00 |
| A_24_P532589 | RP11-11C5.2 | -0.003822496 | 0.000177367 | -1.00 |
| A_24_P174367 | PPP1R2 | -0.007640069 | 0.003813637 | -1.00 |
| A_23_P156788 | STX11 | 0.006983473 | 0.042670421 | 1.00 |
| A_32_P331052 | C20orf151 | 0.001013838 | 0.018128762 | 1.00 |
| A_24_P346807 | HERC4 | -0.003658377 | 0.021323851 | -1.00 |
| A_23_P213045 | LEF1 | -0.004616809 | 0.031505104 | -1.00 |
| A_32_P23154 | THC2406749 | 0.000900097 | 0.026473067 | -1.00 |
| A_23_P384085 | GCC2 | -0.004650631 | 0.006984276 | -1.00 |
| A_23_P165346 | FARSLB | -0.003215672 | 0.029977343 | -1.00 |
| A_32_P42197 | HNRPA1 | -0.005276165 | 0.022541128 | -1.00 |
| A_24_P98371 | PSIP1 | -0.009430514 | 0.003211147 | -1.00 |
| A_24_P881608 | A_24_P881608 | -0.012169415 | 0.017745647 | -1.00 |
| A_23_P55666 | ZNF702 | -0.001324041 | 0.029390785 | -1.00 |
| A_24_P645765 | KLHDC5 | -0.004263101 | 0.003924622 | -1.00 |
| A_23_P65068 | EID3 | -0.005362565 | 0.002143419 | -1.00 |

TABLE 3-continued

| 888 Significant Genes Identifed from Cathgen Registry and PREDICT Samples | | | | |
|---|---|---|---|---|
| A_23_P143143 | ID2 | 0.005223094 | 0.020862883 | 1.00 |
| A_23_P121702 | OCIAD2 | -0.012560196 | 9.68E-05 | -1.00 |
| A_23_P415443 | BRRN1 | 0.002178521 | 0.012764996 | 1.00 |
| A_23_P219197 | RGS3 | 0.004392573 | 0.037368889 | 1.00 |
| A_23_P146050 | ZFAND1 | -0.007045259 | 0.018571752 | -1.00 |
| A_23_P102320 | NUP35 | -0.007281158 | 7.29E-05 | -1.00 |
| A_24_P186944 | LOC654350 | -0.016361698 | 0.026592709 | -1.00 |
| A_23_P62959 | PHLDA3 | 0.001753975 | 0.009527534 | 1.00 |
| A_23_P56703 | ENST00000335459 | -0.009227585 | 0.010512644 | -1.00 |
| A_24_P650611 | AI089783 | 0.000626913 | 0.023077645 | 1.00 |
| A_23_P11214 | NKRF | -0.003287489 | 0.019778087 | -1.00 |
| A_24_P332326 | A_24_P332326 | -0.00504837 | 0.044729046 | -1.00 |
| A_23_P350295 | ENST00000383620 | 0.005904909 | 0.003794415 | 1.00 |
| A_23_P154115 | IGFBP5 | 0.00053774 | 0.006490485 | 1.00 |
| A_23_P28953 | DNMT3B | -0.001503274 | 0.016048426 | -1.00 |
| A_32_P193939 | T05215 | -0.001793942 | 0.001316189 | -1.00 |
| A_32_P233250 | THC2404896 | -0.003137016 | 0.000952134 | -1.00 |
| A_24_P90349 | TMEM80 | 0.002824807 | 0.006025568 | 1.00 |
| A_24_P37020 | THC2282321 | -0.007566822 | 0.006530906 | -1.00 |
| A_32_P152046 | A_32_P152046 | -0.001416903 | 0.029164621 | -1.00 |
| A_24_P916266 | ZNF175 | -0.001296813 | 0.002159082 | -1.00 |
| A_32_P175042 | THC2339455 | -0.001240001 | 0.000222564 | -1.00 |
| A_24_P876408 | MGC3032 | -0.002161207 | 0.017872743 | -1.00 |
| A_24_P99984 | THC2338942 | -0.001687358 | 0.006903617 | -1.00 |
| A_23_P131308 | CYP27A1 | 0.009016595 | 0.017473647 | 1.00 |
| A_23_P23356 | CGI-115 | -0.004139964 | 0.002271005 | -1.00 |
| A_32_P32835 | TMEM99 | -0.005977783 | 0.000633548 | -1.00 |
| A_24_P916586 | BICD1 | -0.001680307 | 5.94E-05 | -1.00 |
| A_23_P139476 | CD63 | 0.006537509 | 0.004032977 | 1.00 |
| A_24_P902091 | ENST00000367146 | -0.008719 | 0.000740369 | -1.00 |
| A_32_P101799 | THC2282944 | -0.007372302 | 0.023625574 | -1.00 |
| A_32_P221452 | LOC653256 | -0.001541822 | 0.029670865 | -1.00 |
| A_32_P38404 | ENST00000374865 | -0.005222012 | 0.005528003 | -1.00 |
| A_24_P180680 | LAPTM4B | -0.003876902 | 0.039388302 | -1.00 |
| A_24_P526623 | CR606637 | -0.003836395 | 0.005242257 | -1.00 |
| A_24_P307368 | A_24_P307368 | -0.009581518 | 0.023701787 | -1.00 |
| A_23_P35645 | RBM17 | -0.004715481 | 0.000791209 | -1.00 |
| A_23_P406521 | SIRPD | 0.002157102 | 0.007188187 | 1.00 |
| A_24_P248240 | SYT11 | 0.006553715 | 0.001791158 | 1.00 |

TABLE 3-continued

888 Significant Genes Identifed from Cathgen Registry and PREDICT Samples

| | | | | |
|---|---|---|---|---|
| A_23_P402604 | PFAS | -0.00477963 | 0.001417716 | -1.00 |
| A_24_P898945 | U78519 | -0.001723112 | 0.023329657 | -1.00 |
| A_32_P57453 | THC2435128 | -0.002759127 | 0.022148279 | -1.00 |
| A_24_P298320 | A_24_P298320 | -0.009945506 | 0.019061733 | -1.00 |
| A_32_P82863 | ENST00000330692 | -0.002930569 | 0.01292114 | -1.00 |
| A_32_P215856 | A_32_P215856 | -0.001113522 | 0.01581317 | -1.00 |
| A_32_P192430 | CKS1B | -0.005114793 | 0.028281252 | -1.00 |
| A_23_P22682 | ARMCX1 | -0.002073085 | 0.006170458 | -1.00 |
| A_24_P186216 | SCC-112 | -0.001830225 | 0.010782697 | -1.00 |
| A_32_P87872 | IMMP2L | -0.002676788 | 0.007667054 | -1.00 |
| A_24_P213110 | COX11 | -0.004412847 | 0.019331795 | -1.00 |
| A_23_P157022 | DKFZp762I137 | -0.003769874 | 0.02681568 | -1.00 |
| A_32_P139196 | C13orf25 | -0.003412508 | 0.002352238 | -1.00 |
| A_23_P80891 | USP4 | 0.006020237 | 0.004368342 | 1.00 |
| A_23_P208812 | ZNF507 | -0.002086769 | 0.001419356 | -1.00 |
| A_32_P131367 | RNF13 | 0.004506149 | 0.04522578 | 1.00 |
| A_24_P312417 | ENST00000373656 | -0.00303087 | 0.003641174 | -1.00 |
| A_23_P140614 | ENST00000355788 | 0.001209831 | 0.011294209 | 1.00 |
| A_23_P37685 | C16orf30 | -0.008037006 | 0.019525692 | -1.00 |
| A_23_P78152 | MIS12 | -0.00487893 | 0.00373971 | -1.00 |
| A_23_P141315 | NLE1 | -0.003580261 | 0.024576358 | -1.00 |
| A_32_P166272 | THC2313495 | 0.006247779 | 0.003895543 | 1.00 |
| A_23_P41025 | GNL3 | -0.005651867 | 0.048957948 | -1.00 |
| A_24_P67806 | ENST00000366577 | -0.002057866 | 0.04118263 | -1.00 |
| A_32_P89837 | TRAF3 | -0.004034865 | 0.0212417 | -1.00 |
| A_32_P17635 | THC2427841 | -0.007198308 | 0.003042816 | -1.00 |
| A_23_P88439 | MTAC2D1 | -0.00722681 | 0.000514522 | -1.00 |
| A_23_P216693 | MLLT3 | -0.00381088 | 0.000577793 | -1.00 |
| A_23_P353905 | DUSP16 | -0.004116814 | 0.018228508 | -1.00 |
| A_24_P306094 | ENST00000238571 | -0.003035775 | 0.001417224 | -1.00 |
| A_23_P434040 | LOC554206 | -0.001850094 | 0.008447914 | -1.00 |
| A_24_P349869 | A_24_P349869 | 0.007776029 | 0.000485384 | 1.00 |
| A_24_P218688 | ALDH3B1 | 0.006848077 | 0.000119446 | 1.00 |
| A_24_P548354 | RPS29 | -0.011088327 | 0.042283492 | -1.00 |
| A_32_P783 | RPL37A | -0.009794094 | 0.000208449 | -1.00 |
| A_23_P104493 | PAPSS2 | 0.00342117 | 0.013713772 | 1.00 |
| A_32_P2050 | THC2373975 | -0.00088849 | 0.030594682 | -1.00 |
| A_32_P115947 | ENST00000381391 | -0.005233875 | 0.002080936 | -1.00 |
| A_23_P430411 | ENST00000320216 | 0.007462133 | 0.00644743 | 1.00 |

TABLE 3-continued

888 Significant Genes Identifed from Cathgen Registry and PREDICT Samples

| | | | | |
|---|---|---|---|---|
| A_23_P141856 | ZNF544 | -0.004754112 | 0.003503062 | -1.00 |
| A_32_P223551 | ENST00000380831 | -0.003212783 | 0.01832328 | -1.00 |
| A_32_P105110 | AK057196 | -0.004478056 | 0.000126878 | -1.00 |
| A_24_P563736 | AK024924 | 0.000816177 | 0.01141594 | 1.00 |
| A_23_P56922 | HSPE1 | -0.008988717 | 0.014288489 | -1.00 |
| A_23_P212568 | TRAT1 | -0.010798468 | 0.003985547 | -1.00 |
| A_24_P503710 | AK000038 | -0.00277868 | 0.026217723 | -1.00 |
| A_24_P738859 | AK075186 | -0.000352701 | 0.007062661 | -1.00 |
| A_24_P171041 | CLPX | -0.005210415 | 0.007178583 | -1.00 |
| A_32_P167705 | AGBL2 | -0.002233469 | 0.008950302 | -1.00 |
| A_32_P195924 | BU661610 | -0.00479004 | 0.01403371 | -1.00 |
| A_24_P912985 | A_24_P912985 | 0.006992671 | 0.002589177 | 1.00 |
| A_23_P211522 | SYNGR1 | 0.00387054 | 0.015905116 | 1.00 |
| A_32_P19135 | RAB4B | 0.002619496 | 0.033159468 | 1.00 |
| A_24_P141736 | THC2336852 | -0.001690253 | 0.016088805 | -1.00 |
| A_23_P109733 | CCDC52 | -0.001810622 | 0.007240677 | -1.00 |
| A_24_P116378 | GRINL1A | -0.005148028 | 0.001710921 | -1.00 |
| A_23_P12680 | PSAP | 0.008226841 | 0.003894754 | 1.00 |
| A_23_P142447 | MYO1F | 0.006980045 | 0.015007274 | 1.00 |
| A_23_P24763 | RPS13 | -0.007209404 | 0.001555498 | -1.00 |
| A_32_P132276 | BE091362 | -0.006452425 | 0.009792839 | -1.00 |
| A_23_P42695 | C7orf24 | -0.005411077 | 0.006645291 | -1.00 |
| A_23_P207387 | LGP1 | 0.003133302 | 0.027598073 | 1.00 |
| A_23_P566 | FOXJ3 | -0.003178851 | 0.045539379 | -1.00 |
| A_23_P123330 | RPL30 | -0.010105628 | 0.003814319 | -1.00 |
| A_23_P146284 | SQLE | -0.004747553 | 0.015006369 | -1.00 |
| A_24_P842962 | THC2379232 | -0.003857074 | 0.003276525 | -1.00 |
| A_23_P202737 | JRKL | -0.003092047 | 0.000201748 | -1.00 |
| A_24_P307486 | ENST00000340534 | 0.005699215 | 0.0109994 | -1.00 |
| A_23_P364792 | CYorf15A | -0.00708542 | 0.006621564 | -1.00 |
| A_23_P213441 | UTP15 | -0.00431273 | 0.001694978 | -1.00 |
| A_32_P14744 | RPS15A | -0.016211063 | 0.008298407 | -1.00 |
| A_23_P435051 | DZIP3 | -0.005475118 | 0.004181588 | -1.00 |
| A_23_P431638 | C20orf142 | -0.003894089 | 0.001562352 | -1.00 |
| A_23_P156355 | TMEM161B | -0.007064625 | 0.001798008 | -1.00 |
| A_23_P93780 | HGF | 0.005227787 | 0.004699633 | 1.00 |
| A_32_P3342 | THC2315555 | -0.006282516 | 0.015041897 | -1.00 |
| A_32_P27763 | U92025 | -0.001901425 | 0.009197146 | -1.00 |
| A_23_P132874 | C3orf26 | -0.005614344 | 0.016385994 | -1.00 |

TABLE 3-continued

888 Significant Genes Identifed from Cathgen Registry and PREDICT Samples

| | | | | |
|---|---|---|---|---|
| A_23_P78628 | MAP2K7 | 0.001373588 | 0.017005124 | 1.00 |
| A_24_P336137 | C22orf23 | 0.0004047 | 0.022336065 | 1.00 |
| A_23_P83159 | KLHL9 | -0.00525479 | 0.011060823 | -1.00 |
| A_23_P88470 | TRPM7 | -0.004517173 | 0.000833861 | -1.00 |
| A_24_P136441 | AK023121 | -0.000999205 | 0.008187697 | -1.00 |
| A_23_P202496 | NOC3L | -0.009152053 | 0.000351487 | -1.00 |
| A_23_P202496 | NOC3L | -0.008882894 | 0.000883848 | -1.00 |
| A_23_P202496 | NOC3L | -0.008699361 | 0.000907976 | -1.00 |
| A_23_P202496 | NOC3L | -0.008769911 | 0.00103005 | -1.00 |
| A_23_P202496 | NOC3L | -0.008410743 | 0.0010908 | -1.00 |
| A_23_P202496 | NOC3L | -0.008858461 | 0.001127381 | -1.00 |
| A_23_P202496 | NOC3L | -0.008778657 | 0.001295936 | -1.00 |
| A_23_P202496 | NOC3L | -0.008652872 | 0.001850552 | -1.00 |
| A_23_P202496 | NOC3L | -0.008003674 | 0.002811927 | -1.00 |
| A_23_P202496 | NOC3L | -0.007809125 | 0.004334336 | -1.00 |
| A_23_P97770 | RNPEP | 0.008190853 | 0.001335428 | 1.00 |
| A_23_P23443 | EFHD2 | 0.00451067 | 0.042159444 | 1.00 |
| A_24_P287503 | ZFYVE1 | 0.002301114 | 0.043115624 | 1.00 |
| A_23_P81973 | HSD17B8 | -0.005357746 | 0.002453251 | -1.00 |
| A_23_P40611 | TCN2 | 0.0023636 | 0.027032693 | 1.00 |
| A_32_P225604 | RPL5 | -0.010131283 | 0.003635995 | -1.00 |
| A_23_P85371 | RABGGTB | -0.007315387 | 0.004801922 | -1.00 |
| A_23_P93750 | LSM5 | -0.006004749 | 0.021774646 | -1.00 |
| A_24_P391868 | CPLX2 | 0.000530009 | 0.034988916 | 1.00 |
| A_23_P200015 | AK5 | -0.007044814 | 0.031503718 | -1.00 |
| A_23_P34018 | RPL39 | -0.015602618 | 0.022305912 | -1.00 |
| A_24_P583040 | C17orf67 | -0.001361447 | 0.044173634 | -1.00 |
| A_23_P214666 | RPS18 | -0.008853367 | 0.048213362 | -1.00 |
| A_23_P14432 | A_23_P14432 | -0.005892805 | 0.002857008 | -1.00 |
| A_32_P95739 | TPI1 | 0.004379804 | 0.004113439 | 1.00 |
| A_23_P150903 | MLSTD1 | 0.006118753 | 0.0052057 | 1.00 |
| A_23_P335039 | ZNF721 | -0.006909684 | 0.007419198 | -1.00 |
| A_23_P53646 | NAP1L1 | -0.007456798 | 0.005865203 | -1.00 |
| A_23_P146417 | C9orf5 | -0.006247065 | 0.003439871 | -1.00 |
| A_24_P929867 | A_24_P929867 | 0.000334609 | 0.026632776 | 1.00 |
| A_32_P61684 | PAG1 | -0.007183722 | 0.007108454 | -1.00 |
| A_23_P20752 | CCRK | -0.003103606 | 0.012681542 | -1.00 |
| A_23_P157926 | LRRN6C | 0.004808326 | 0.001396842 | 1.00 |
| A_23_P76969 | SIPA1L1 | 0.011768626 | 1.19E-05 | 1.00 |

TABLE 3-continued

888 Significant Genes Identifed from Cathgen Registry and PREDICT Samples

| | | | | |
|---|---|---|---|---|
| A_32_P134846 | C9orf123 | -0.008882803 | 0.00236814 | -1.00 |
| A_23_P78499 | USP29 | 0.000313082 | 0.032809859 | 1.00 |
| A_23_P129466 | ATF7IP2 | -0.009622706 | 0.000736601 | -1.00 |
| A_23_P99226 | SIRT4 | -0.001805363 | 0.032281686 | -1.00 |
| A_24_P76911 | RNF167 | 0.004946567 | 0.007450319 | 1.00 |
| A_23_P34093 | G6PD | 0.006050615 | 0.019575477 | 1.00 |
| A_32_P168756 | AA714039 | -0.003908375 | 0.030001135 | -1.00 |
| A_23_P54556 | MKL2 | -0.005754215 | 0.000416801 | -1.00 |
| A_23_P3651 | HBZ | -0.022371889 | 0.020834821 | 1.00 |
| A_24_P145787 | A_24_P145787 | -0.015231394 | 0.02319888 | -1.00 |
| A_23_P302654 | CEP72 | -0.004354101 | 0.000613393 | -1.00 |
| A_23_P502470 | IL6ST | -0.00284314 | 0.026006746 | -1.00 |
| A_24_P134195 | MYADM | 0.00673914 | 0.007765857 | 1.00 |
| A_24_P780052 | LOC388524 | -0.010206988 | 0.001771042 | -1.00 |
| A_23_P141405 | NME2 | -0.006718429 | 0.016081981 | -1.00 |
| A_23_P56553 | METTL8 | -0.004674168 | 0.003852741 | -1.00 |
| A_24_P565908 | A_24_P565908 | 0.001515006 | 0.028822901 | 1.00 |
| A_24_P919840 | ENST00000377156 | -0.003863508 | 0.018044274 | -1.00 |
| A_23_P325661 | ZNF134 | -0.002858194 | 0.005195058 | -1.00 |
| A_32_P49832 | C6orf204 | -0.002221668 | 0.021213483 | -1.00 |
| A_24_P198820 | THC2435239 | -0.001936255 | 0.015108269 | -1.00 |
| A_24_P161933 | CR608347 | 0.007359973 | 0.00608829 | 1.00 |
| A_24_P161933 | CR608347 | 0.007212923 | 0.0080146 | 1.00 |
| A_24_P161933 | CR608347 | 0.00713501 | 0.010138762 | 1.00 |
| A_24_P161933 | CR608347 | 0.006949369 | 0.011633297 | 1.00 |
| A_24_P161933 | CR608347 | 0.007092025 | 0.011739025 | 1.00 |
| A_24_P161933 | CR608347 | 0.007047709 | 0.011768527 | 1.00 |
| A_24_P161933 | CR608347 | 0.006817193 | 0.013599111 | 1.00 |
| A_24_P161933 | CR608347 | 0.006217419 | 0.027757392 | 1.00 |
| A_24_P161933 | CR608347 | 0.006295802 | 0.027843104 | 1.00 |
| A_24_P161933 | CR608347 | 0.006229752 | 0.033061151 | 1.00 |
| A_23_P121875 | FLJ21657 | -0.003542639 | 0.000290291 | -1.00 |
| A_24_P97785 | CR611332 | -0.003339275 | 0.002962045 | -1.00 |
| A_24_P285880 | TLOC1 | -0.004495969 | 0.006227009 | -1.00 |
| A_24_P607880 | AL832758 | -0.00280317 | 0.007645267 | -1.00 |
| A_23_P209962 | SMC6 | -0.005038412 | 0.001707446 | -1.00 |
| A_23_P209962 | SMC6 | -0.004626621 | 0.00668961 | -1.00 |
| A_23_P209962 | SMC6 | -0.004706237 | 0.011702105 | -1.00 |
| A_23_P209962 | SMC6 | -0.004467991 | 0.013555614 | -1.00 |

TABLE 3-continued

| 888 Significant Genes Identifed from Cathgen Registry and PREDICT Samples | | | | |
|---|---|---|---|---|
| A_23_P209962 | SMC6 | -0.00445344 | 0.015111739 | -1.00 |
| A_23_P209962 | SMC6 | -0.004335652 | 0.018981137 | -1.00 |
| A_23_P209962 | SMC6 | -0.003985082 | 0.019675111 | -1.00 |
| A_23_P209962 | SMC6 | -0.004001046 | 0.025287776 | -1.00 |
| A_23_P313632 | FUT8 | -0.007387957 | 0.000169101 | -1.00 |
| A_24_P221366 | RPS15A | -0.014130919 | 0.018581088 | -1.00 |
| A_23_P398005 | NME2P1 | -0.005488747 | 0.030060839 | -1.00 |
| A_32_P142128 | ENST00000374224 | -0.001515737 | 0.033835467 | -1.00 |
| A_32_P50123 | SRGAP2 | 0.00183605 | 0.023012209 | 1.00 |
| A_32_P220798 | CD34 | -0.001711824 | 1.16E-05 | -1.00 |
| A_23_P159920 | IKBKG | 0.004821733 | 0.011591766 | 1.00 |
| A_23_P336854 | ENST00000246019 | -0.007060317 | 0.005433317 | -1.00 |
| A_23_P107214 | RAB5C | 0.004458748 | 0.037505751 | 1.00 |
| A_24_P154573 | ZNF509 | -0.002993676 | 0.018436257 | -1.00 |
| A_23_P203115 | TMEM25 | -0.004723716 | 0.029935715 | -1.00 |
| A_23_P123315 | BC067244 | -0.006232416 | 0.020238877 | -1.00 |
| A_23_P123315 | BC067244 | -0.005856744 | 0.029468483 | -1.00 |
| A_23_P123315 | BC067244 | -0.00571209 | 0.033965856 | -1.00 |
| A_23_P123315 | BC067244 | -0.005639379 | 0.036118887 | -1.00 |
| A_23_P123315 | BC067244 | -0.005645134 | 0.045259321 | -1.00 |
| A_23_P123315 | BC067244 | -0.005501751 | 0.045453816 | -1.00 |
| A_24_P178224 | FLJ37549 | -0.002210411 | 6.65E-07 | -1.00 |
| A_32_P218989 | YBX1 | -0.006234502 | 0.037639495 | 1.00 |
| A_23_P85969 | ZNF326 | -0.004058718 | 0.003517997 | -1.00 |
| A_24_P329487 | FAM84B | -0.003855427 | 0.030299512 | -1.00 |
| A_32_P67036 | BC067908 | -0.005396253 | 0.006067358 | -1.00 |
| A_23_P385126 | DEPDC7 | -0.002697454 | 1.91E-06 | -1.00 |
| A_32_P17343 | THC2347909 | -0.011996792 | 0.002371419 | -1.00 |
| A_23_P109442 | HPS4 | -0.005973594 | 0.005900876 | -1.00 |
| A_24_P309317 | PSAP | 0.009463439 | 0.002158685 | 1.00 |
| A_23_P342910 | ENST00000328046 | -0.002434557 | 0.021318538 | -1.00 |
| A_24_P921801 | A_24_P921801 | 0.005142107 | 0.038586052 | 1.00 |
| A_23_P145718 | AOAH | 0.004947359 | 0.023151509 | 1.00 |
| A_24_P102283 | AK098835 | 0.006201531 | 0.020510494 | 1.00 |
| A_23_P107206 | STAT3 | 0.006829999 | 0.00468696 | 1.00 |
| A_23_P107206 | STAT3 | 0.006485116 | 0.00476179 | 1.00 |
| A_23_P107206 | STAT3 | 0.006682801 | 0.004945155 | 1.00 |
| A_23_P107206 | STAT3 | 0.006489148 | 0.00581763 | 1.00 |
| A_23_P107206 | STAT3 | 0.006386969 | 0.006464178 | 1.00 |

TABLE 3-continued

888 Significant Genes Identifed from Cathgen Registry and PREDICT Samples

| | | | | |
|---|---|---|---|---|
| A_23_P107206 | STAT3 | 0.006618583 | 0.00652241 | 1.00 |
| A_23_P107206 | STAT3 | 0.006227609 | 0.006597615 | 1.00 |
| A_23_P107206 | STAT3 | 0.00620483 | 0.011169781 | 1.00 |
| A_23_P107206 | STAT3 | 0.006094648 | 0.014225777 | 1.00 |
| A_23_P107206 | STAT3 | 0.005471426 | 0.018609699 | 1.00 |
| A_32_P135336 | LOC388242 | 0.005544024 | 0.000651442 | 1.00 |
| A_24_P812018 | LOC338805 | -0.002389492 | 0.039214267 | -1.00 |
| A_23_P328022 | SLC5A10 | 0.001620124 | 0.01774287 | 1.00 |
| A_23_P58877 | GOPC | -0.008884024 | 0.001637896 | -1.00 |
| A_23_P212655 | KLHL6 | -0.004740697 | 0.015446959 | -1.00 |
| A_23_P16694 | PRO0132 | 0.000437936 | 0.031377573 | 1.00 |
| A_24_P930926 | ENST00000287322 | -0.001857791 | 0.015593727 | -1.00 |
| A_23_P58647 | CTNNA1 | 0.005297055 | 0.004261104 | 1.00 |
| A_24_P315986 | ENST00000332649 | -0.007577766 | 0.00316128 | -1.00 |
| A_23_P57293 | ENST00000270201 | -0.002238223 | 0.009386454 | -1.00 |
| A_23_P68601 | CST7 | 0.008992643 | 0.010086607 | 1.00 |
| A_32_P189093 | AI090167 | -0.001883334 | 0.038306248 | -1.00 |
| A_24_P9285 | LMAN2 | 0.004658226 | 0.025008775 | 1.00 |
| A_24_P134488 | MGC17330 | -0.005338836 | 0.03923378 | -1.00 |
| A_23_P95612 | BBS10 | -0.003576813 | 0.029146754 | -1.00 |
| A_23_P157875 | FCN1 | 0.009731343 | 0.00029228 | 1.00 |
| A_23_P121250 | EIF4A2 | -0.010002246 | 0.001326264 | -1.00 |
| A_23_P46182 | RPS8 | -0.008523127 | 0.011250816 | -1.00 |
| A_23_P106602 | CRISPLD2 | 0.007178072 | 0.029249893 | 1.00 |
| A_24_P169645 | A_24_P169645 | -0.005582892 | 0.007603283 | -1.00 |
| A_23_P102183 | L48692 | -0.004757624 | 0.002075977 | -1.00 |
| A_23_P143484 | PIGP | -0.005661664 | 0.000122162 | -1.00 |
| A_23_P500271 | IRF5 | 0.010366309 | 0.040950947 | 1.00 |
| A_24_P134683 | BCAP31 | 0.003558162 | 0.031911941 | 1.00 |
| A_24_P232856 | RPL9 | -0.015785688 | 0.034225611 | -1.00 |

| a.probe | Cath12 Age P | Probe Sequence |
|---|---|---|
| A_23_P103720 | 1.9708E-05 | AACCGTCTGAGTCTTGTGCTCTTCAAGACAAAACA GATTGCGTCGCTGACAAGTTCTCAA |
| A_23_P1833 | 4.4434E-05 | ACTTCTTTGGGCAGATGCTAGGTCAGTTGTTTTCA CCTAATATCCTCTTTTAGCTGCATG |
| A_23_P343398 | 7.4714E-05 | AAGAGAGCAACATTTTACCCACACACAGATAAAGT TTTCCCTTGAGGAAACAACAGCTTT |
| A_23_P52697 | 4.6566E-12 | CTCTCTCAACCACTAGACTTGGCTCTCAGGAACTC TGCTTCCTGGCCCAGCGCTCGTGAC |
| A_32_P221958 | 1.0228E-02 | ATGGGAAAAATAAGGATAACTCAGAATTTCAAAAG GAAATCACAAATTCAGCTAGTAATA |

TABLE 3-continued

| 888 Significant Genes Identifed from Cathgen Registry and PREDICT Samples | | |
|---|---|---|
| A_32_P230196 | 2.1555E-02 | TCGTAAACTAAGTGAATACACAAAATGTTGATTTTT CTGACCATAAGACATATTTTATGT |
| A_23_P206284 | 9.5746E-05 | TCTGGTGACACTGGCCTAGAGCCTGACACTCTCC TAAGAGGTTCTCTCCAAGCCCCCAAA |
| A_23_P206280 | 1.5161E-04 | GCGTTCAATCTTGACCTTGAAGATGGGAAGGATGT TCTTTTTACGTACCAATTCTTTTGT |
| A_23_P404494 | 7.5357E-03 | CATCCTGCTTCTACCATGTGGATTTGGTCACAAGG TTTAAGGTGACCCAATGATTCAGCT |
| A_23_P31376 | 8.7533E-11 | GCCTCTCTCCAGAAATGAACTGTGATGGTGGACA CAGCTATGTGAGGAATTACTTACAGA |
| A_24_P187766 | 4.8847E-05 | AAATCCAATTATCAGAATCAAAGACATGAACTTTAA GCCTCTTATCAATCTTCGCAGCCT |
| A_23_P107959 | 6.9926E-04 | GCCCTCTGGGGCTGTGGTCACCCTCGAATGCGTG GAGAAGCTGATTCGGAAGGACATGGT |
| A_24_P194017 | 9.8699E-03 | ATGATGTCCAACCTGGGCCCAGTGTGGGTCCTCC AAGTAAGGACAAGGACAAAGTGCTGC |
| A_24_P65864 | 3.9201E-02 | TTGAAACTCTGGAAGAGTGGATTCAGCCTGGATAA TGGAGAACTCAGAAGCTACCAAGAC |
| A_24_P937405 | 6.6843E-05 | CAAAGTGTGCTCCTTAAACACTCATGCCTTATGAT TTTCTACCAAAAGTAAAAAGGGTTG |
| A_23_P150789 | 8.6784E-05 | GAATCACTCCTCTCAAATATGCCCAGATTTGCTATT GGATTAAAGGAAACTACCTGGATT |
| A_23_P7582 | 1.8005E-02 | CCCAGAAAACCTCCAGTAGTGGACAACAGGTTTTC ACCATAGCCTACGTTAACCCATTTT |
| A_23_P7582 | 1.8005E-02 | CCCAGAAAACCTCCAGTAGTGGACAACAGGTTTTC ACCATAGCCTACGTTAACCCATTTT |
| A_23_P7582 | 1.8005E-02 | CCCAGAAAACCTCCAGTAGTGGACAACAGGTTTTC ACCATAGCCTACGTTAACCCATTTT |
| A_23_P7582 | 1.8005E-02 | CCCAGAAAACCTCCAGTAGTGGACAACAGGTTTTC ACCATAGCCTACGTTAACCCATTTT |
| A_23_P7582 | 1.8005E-02 | CCCAGAAAACCTCCAGTAGTGGACAACAGGTTTTC ACCATAGCCTACGTTAACCCATTTT |
| A_23_P7582 | 1.8005E-02 | CCCAGAAAACCTCCAGTAGTGGACAACAGGTTTTC ACCATAGCCTACGTTAACCCATTTT |
| A_23_P389588 | 4.3814E-02 | AAGCATCAGGACTCCAAAAAGGAAGAAGAAAAGAA GAAGCCCCACATAAAGAAACCTCTT |
| A_23_P217269 | 1.1013E-04 | CTCAGAGGACCAGCTATATCCAGGATCATTTCTCT TTCTTCAGGGCCAGACAGCTTTTAA |
| A_23_P348636 | 1.3499E-08 | TAGCTGTAGCTGAGGCTTAACTGGGAGGGATGCC GAGCTTGCTGGAACTACTGGGACCAA |
| A_32_P34920 | 3.0633E-07 | CTCCCTTGACGTTTGGCAGATGAAAAACAACTAAG CCTTTTTGAGGTGTAGAGATTCTCA |
| A_23_P338919 | 5.1208E-07 | GCAGGGGGCCACTGTAGTGAGCGTGGAGAAATTT GGAAACACCTATTTCTTAACTCAAAT |
| A_32_P90346 | 7.0976E-07 | TACAGGGATTAGATCCGAGCCACATTACCCATATA TGCTCAGAATGGTCTGTCAGGAACA |
| A_24_P213788 | 7.9191E-07 | AGATTAATGCAGAACAAGGTCGTTAGTCTCATTGT TTATCCAGTTACTAGCTGCATAGAT |
| A_23_P103486 | 1.0335E-06 | CACGTGTTCTGAAACCACTGGTGTCTGCTCAGATG TGTTGGGACAAAATGAAAGTGACTT |
| A_23_P56433 | 1.5981E-06 | AGCGAAATTTGAAGATGACATCACCTATTGGCTTA ACAGAGATCGAAATGGACATGAATA |

TABLE 3-continued

| 888 Significant Genes Identifed from Cathgen Registry and PREDICT Samples | | |
|---|---|---|
| A_23_P143981 | 1.7596E-06 | CACTGCGTGGGAGGGACTGGGTCACTATTGTGGT TTTTACTATAACTTTGTAAATTAACT |
| A_23_P66881 | 2.2621E-06 | ACACACTTGCTCGAGAACCAAAGTGCATTTGGGTG ACATTTGAAGATTGGGGAGACAAGA |
| A_23_P32444 | 2.9175E-06 | GTGGCCTGTGTTGCCACTCTCAGCACCCCACATTT GCATCTGCTGGTGGACCTGCCACCA |
| A_24_P162319 | 4.8014E-06 | GAAGATTGATGTGATTCGTAGAAAGGTTTCAAAAA TCCAACGTTTCCATGCGAGATCCCT |
| A_23_P254512 | 5.3735E-06 | TAAAGGGCAGGGCCCACGTGTATAGTATCTGTATA TAAGTTGCTGTGTGTCTGTCCTGAT |
| A_23_P325562 | 7.4671E-06 | GGCCCTGGTGTCAGAACTCCCCAAAGGCCTGTGC GTCCAAGTGGAGTCAGGTTTTCTATT |
| A_23_P143068 | 8.4535E-06 | TTAACCGGGACATTTCCTGACTACCCTGACGTTGA AGAAGGAGGGTCAGCTATTATTTTT |
| A_23_P417951 | 9.7459E-06 | AGTAACTGGTTGTTCTACTTGGTAATTTGACACCC TGTTAATAACGCAATTATTTCTGTG |
| A_23_P204751 | 1.3118E-05 | TCATACCTCCCCAGAGGGAAGCAGGAATGAGGCC AAAAAGTGTGCATTGGATAGGGGAAC |
| A_23_P43484 | 1.8025E-05 | GGGTTACTGGCTTCTCTTGAGTCACACTGCTAGCA AATGGCAGAACCAAAGCTCAAATAA |
| A_23_P43484 | 1.8025E-05 | GGGTTACTGGCTTCTCTTGAGTCACACTGCTAGCA AATGGCAGAACCAAAGCTCAAATAA |
| A_23_P43484 | 1.8025E-05 | GGGTTACTGGCTTCTCTTGAGTCACACTGCTAGCA AATGGCAGAACCAAAGCTCAAATAA |
| A_23_P43484 | 1.8025E-05 | GGGTTACTGGCTTCTCTTGAGTCACACTGCTAGCA AATGGCAGAACCAAAGCTCAAATAA |
| A_23_P43484 | 1.8025E-05 | GGGTTACTGGCTTCTCTTGAGTCACACTGCTAGCA AATGGCAGAACCAAAGCTCAAATAA |
| A_23_P43484 | 1.8025E-05 | GGGTTACTGGCTTCTCTTGAGTCACACTGCTAGCA AATGGCAGAACCAAAGCTCAAATAA |
| A_23_P43484 | 1.8025E-05 | GGGTTACTGGCTTCTCTTGAGTCACACTGCTAGCA AATGGCAGAACCAAAGCTCAAATAA |
| A_23_P18493 | 1.9235E-05 | GCAGATCTTAGGGATGATTAAAGGCAGCATTTGAT GATAGCAGACATTGTTACAAGGACA |
| A_32_P4985 | 2.4518E-05 | TCTGACCGCTTTTTCTTGGTTATGAATCTTAATTTC GAATATAAGATGATAGGTAAGCGC |
| A_23_P10025 | 2.6365E-05 | ACATCACCATGTAGAAGAATGGGCGTACAGTATAT ACCGTGACATCCTGAACCCTGGATA |
| A_32_P133072 | 3.0829E-05 | ACCAGGTTAATGGCTAAGAATGGGTAACATGACTC TTGTTGGATTGTTATTTTTTGTTTG |
| A_32_P34220 | 3.1785E-05 | TATGATCCTATTTGGTGCATTTTCTACCATGGTCCA AGATCATTACATGGATACAGCCAA |
| A_23_P60499 | 4.0203E-05 | ATGACGGTAGAAGACTTCTCATTGGGGAGCAACTT TTTGACGCACAACTTTTGGTGCGTT |
| A_23_P259741 | 5.3997E-05 | TCTGTGATTATGATTTCCTCTCCTATAATTATTTCT GTAGCACTCCACACTGATCTTTGG |
| A_23_P13232 | 7.1442E-05 | CTAAGCCAAACCCCAGTTTCCATTTTTTACTGAATC ATAATCAAAATCAAAGCCAAAGAC |
| A_23_P300600 | 7.1535E-05 | ACTGAATTATGCCAGGGCGCACTTTCCACTGGAGT TCACTTTCAATTGCTTCTGTGCAAT |
| A_23_P411723 | 7.1665E-05 | TCCATTAGGAAACGGATTGCATCATACCTGAACAT AAGCTGGACTGCTGAAATTGTATTT |

TABLE 3-continued

| 888 Significant Genes Identifed from Cathgen Registry and PREDICT Samples | | |
|---|---|---|
| A_23_P107744 | 7.7287E-05 | ATAGAAGCTTCTAAGCAGAAGAGGGACTTGCCCTA ATTCAGGTGATCACAGGTGTCTTGT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P215956 | 7.7354E-05 | TTCAAATGCATGATCAAATGCAACCTCACAACCTT GGCTGAGTCTTGAGACTGAAAGATT |
| A_23_P309207 | 7.7434E-05 | TGTAGAGGCAATGGATATGGAAAACATTTTTCGTA AAATATGGGAGAATTTATAGAAAAG |
| A_23_P324107 | 7.9476E-05 | CTCAGACATAGAGTTAAAACTCAAACCTCTTATGT GCACTTTAAAGATAGACTTTAGGGG |
| A_23_P25060 | 7.9828E-05 | CAGAGTTCTTGGAGGATTCTGAGGTAGAGAGTAG CATAATCTCATTTGTGTTTTTATTCT |
| A_24_P680704 | 8.6926E-05 | ATCGTAGCTTGATGTTAGCTCTCTGTAACCTTTCA GGTATATTAATCAAAAAAGCCAAAC |
| A_23_P75915 | 9.0180E-05 | AGCCATGATTTCAGTTTCACATAAGAATGTTTACTC AATGTTTAAGTGTGTTGCCCCAAA |
| A_23_P253221 | 9.1166E-05 | TTGCACTATTCCTTCTCCAAGCCAGAAACCACATT TAATTTCATAAATAAATTTATGAAA |
| A_32_P52227 | 9.2055E-05 | TTTGGGGATAAAATCTGGCAGGATTGCTGACCTG GACTCTGTCATCTAAAGTTCTCACAC |
| A_32_P118568 | 9.3597E-05 | TACATCAGACTCAAAGGTAATAGGGGCATGCATTC CATTGAGGAAATTCTAGGGAATTTT |
| A_23_P41528 | 9.7076E-05 | CAATATGATAGGGAACAGGTGCTGATGGGCCCAA GAGTGACAAGCATACACAACTACTTA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |

TABLE 3-continued

| 888 Significant Genes Identifed from Cathgen Registry and PREDICT Samples | | |
|---|---|---|
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P82738 | 1.1028E-04 | CAAGCTACTGGCACATAGTGAAAGATTACTTCTGA CATTCCATTGCTCTTCTTTTGAAAA |
| A_23_P65278 | 1.1450E-04 | TAGCTTAGAATTGGGAGGATACTTAACATCTGGAA GACAAGTTCATTTCATCTTGAGATC |
| A_24_P314786 | 1.1796E-04 | AGGGCACAGTACAACTCCCATTGGAAGGGCACTA TAGAGATGATCCATCTGTGATCAATA |
| A_32_P68504 | 1.3580E-04 | TGTCCTGAGTTCTACAGTATGTGAACAATATCGTG TGAAGTGTGTTTTTGCATTTGTGCA |
| A_32_P137826 | 1.3666E-04 | GCTGTGGGCTAAAACAAGGTAGCCAGTTTGAGAC TGGGGATAAAGGGTGGATTTTAGTAA |
| A_24_P354715 | 1.4420E-04 | TCTGCCTCCAAATCTGAACAGTCACTGTAAATCAT TCTTAAGCCCAGATATGAGAACTTC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P128613 | 1.4811E-04 | AATCTGTGTGATTGTTTGCAGTATGAAGACACATT TCTACTTATGCAGTATTCTCATGAC |
| A_23_P391228 | 1.5221E-04 | CTCCAGAGCCTAATTTTTCCCAGATGCATATTTAG CTCTAGGGAGAGGACTAGGAGGAAA |
| A_23_P155688 | 1.5304E-04 | TTTACATGAGATTTGTTAACACACATTTTCTGAGAG CAGGTATGGAAGACAGCCATGTGT |
| A_32_P230398 | 1.5380E-04 | GTGCTGAGCAGTCAGGGACCTGTAAGGTCACATT TCTTTCAGGTATTCTTTCTAGGTGTA |
| A_32_P146659 | 1.6319E-04 | AGGTCTGATGCAGTAGCTTTTACTATTGGTGGAAA TCGATGTTTTTTCCTTGAAAGTCTA |
| A_32_P18475 | 1.6706E-04 | CTGGGGCCATTTTTGGCACAATAGTTGTTCAAATG TAGATCACTATGCTGAATGCTCATG |
| A_24_P77432 | 1.8717E-04 | TGGCCAATGTCGAAACCTACAAGATTTCCTTAAAA TCTCTAATAGAGGCATTACTTGCTT |
| A_23_P167599 | 2.0030E-04 | ACTGAAGACTTTGAACACTTGCTTTTTGTGATTGCT TATGTCATTAGTGCCTCATGACTG |
| A_23_P53081 | 2.0110E-04 | GAGGCTCAAGTTCGCCACTTTACTCAGACCGATGC ACAGTCTTCCCATTTTACACTTTTT |

TABLE 3-continued

| 888 Significant Genes Identifed from Cathgen Registry and PREDICT Samples | | |
|---|---|---|
| A_23_P348992 | 2.1613E-04 | CATGTATTTAAACCTATGAATTATAAAATAGTATTTAGATTCTAGCGTGAGTTAAATAGA |
| A_23_P85783 | 2.4020E-04 | TTGGTCCAAGGCACTACACCTGTACTGCAGGGGCTCAATGGAGCTGTCTTCAGGCCAGAA |
| A_32_P203728 | 2.4783E-04 | TGATATCAATCACTATTACTGGAATCATTATCAACATATCAATAAATATTTTTAGAACAT |
| A_24_P595460 | 2.5412E-04 | AAATTGTATGTGATATTCCAACAGCAAGTTGGATGCAATGTGTCATAAAAATGACCTCAG |
| A_23_P346900 | 2.5958E-04 | AAACAGACAAAACAATCCCCATCAGGTAGCTGTCTAACCCCCAGCTGGGTCTAATCCTTC |
| A_23_P128993 | 2.6000E-04 | TCTGGGACAGAGGCAAGAATCCCCAAGGGGTGGGCAGTCAGGGTTGCAGGACTGTAATAA |
| A_23_P89871 | 2.7468E-04 | TAACTGTGTGGCAGAGGCTTCATTTAGGTCTCACAACTCACTAGACATCAAAATGTGTAA |
| A_24_P766716 | 3.0563E-04 | GGGGTGGTATCTAGGACCAGAGAGGAATCTACTATTTCTACTGTGAAATAATTCAGCAGG |
| A_24_P313210 | 3.1018E-04 | CTGGGAATGCTATAGGACCTCCTACTATTCTCTTAAGGTCCTAGGAAAGTTTCAGGAACT |
| A_23_P73747 | 3.2049E-04 | CTGAATTGACAGTAAACCTGTCCATTATGAATGGCCTACTGTTCTATTATTTGTTTTGAC |
| A_24_P111242 | 3.3942E-04 | TATAAAAATATTAGGTAATTCTATACAATGCATAGTCATAAACCTTAACATTTTTGTTCA |
| A_23_P14853 | 3.5187E-04 | AGCTTTTGATCTTGGGGCCAGAGGCCGCCTTACACACACCCCAGGTGTCCATGGGGAGCA |
| A_32_P133926 | 3.5375E-04 | GAAAACTCTCTGAGTTCTGGAGCACTGTTCGCGGCCGGACTGAGTGGCATGTCCGCATTT |
| A_23_P87421 | 3.7543E-04 | CTGAGTTGAATGCTTCCAGGCAATCTAGGTATCTACTTTTAAACCAACCTATCGGGAGTC |
| A_23_P119042 | 3.9206E-04 | GTTTTGAGCGTTGTATTCCAAAGGCCTCATCTGGAGCCTCGGGAAAGTCTGGTCCCACAT |
| A_23_P109171 | 3.9758E-04 | GTTCCTGTTTGGATTAGACCATAGTTGACCCATCTGGCATTGCCAACGAAGCCTTCATTA |
| A_23_P117602 | 4.1290E-04 | AACCATGAAACGCTACTAACTACAGGAAGCAAACTAAGCCCCCGCTGTAATGAAACACCT |
| A_32_P31021 | 4.1701E-04 | CCTGTAACTGGAGGTGTTGCACACTTGCCAGGCATTTTGTGAGTTACAAGCATAGCTAAT |
| A_23_P1473 | 4.3303E-04 | TGTGATCAGGCTCCCAAGTCTGGTTCCCATGAGGTGAGATGCAACCTGAATCATGGCCAC |
| A_32_P151823 | 4.5725E-04 | AGGGCATGTCTTCTTATTCCATGTGACAGTGGCTGGCTGAGTTGCTAGTACGTTTTTGAA |
| A_23_P348257 | 4.8085E-04 | GCCTGCTGTCTTGAGTACAAATGTGAATGATCGACTGACTGCTTGTTGCCAAACTGGAAA |
| A_23_P14957 | 4.9580E-04 | TCTGAACTAGTTGAACTGTGACTGACAGGTAATCCTAATATATCCAAATCCAACTGAATA |
| A_23_P327156 | 5.2494E-04 | CGTATTTATTGTCAGCTCTTTAAACAAAAAGCACTCTATGAAGTGCTGTACTTTACAGTC |
| A_23_P23834 | 5.5123E-04 | TAAGCTTTGGAAGAGATTACACATGATGTCTTTTTCTTAGAGATTCACAGTGCATGTTAG |
| A_23_P101093 | 5.5311E-04 | GGTTCTTCAGTCTGCCAAGGAACAAATTAAATGGTCGTTATTGAAATGAAGGCTGTGGAT |
| A_24_P173754 | 5.5476E-04 | AAAGCCAACAAGAATTCTTCAGAATGCTGGATGAAAAAATTGAAAAGGGTCGGGATTACT |

TABLE 3-continued

| 888 Significant Genes Identifed from Cathgen Registry and PREDICT Samples | | |
| --- | --- | --- |
| A_23_P86171 | 6.1551E-04 | TGGGGAAGCTCTGTGAAATCGTCTGATGGTCTGT GTGGAAGAAAAGAAAAATCTGTCTGC |
| A_32_P71744 | 6.2150E-04 | TTTCTCCGAACGTGTTTGTGATCTTCTGTTATATTT TGGGGCATGTTACCTTTATGGTAT |
| A_24_P89080 | 6.2709E-04 | TTAACTACTTATCTCTAAACCATCTATGTGAATATT TGTAAAAATAATGAATGGACTCAT |
| A_23_P250347 | 6.4239E-04 | AGGTGCAAGCCTTAGAGAAAGTTAAAGGTGCAGA TATAAATGCTGAAGAGGCCCCCAAAA |
| A_24_P306355 | 6.6091E-04 | ATCAATAGAGATCCCATCACCATCTTCCAGGAGCT AGATTCCACCAGAATCAAATGGGGT |
| A_23_P428887 | 6.6761E-04 | GGGCGGGGGGTCAAATAGAAGGCTATATGAATCA ACTTCAGTGAGCTGGTGAAAGAAAAT |
| A_23_P313828 | 6.7569E-04 | TTTGACTGCAATTGCAGCATTTGCAAGAAGAAGCA GAATAGACACTTCATTGTTCCAGCT |
| A_23_P91991 | 6.8308E-04 | ATGTACCCAAAGAACACATTTGCTTTGAGAAGTGG TGGTAGGAGGCAGACAAAGGCAGAA |
| A_24_P341058 | 6.8613E-04 | CCAAGGTCATCCATGACAACTGTATTGTGGAGGG ACTCATGACCACATTTCATGTAGTCA |
| A_23_P47788 | 7.3844E-04 | GACTGAGATGGTCAAAGGACTTTGGACCATAGGG GATCTTTGGAAGGCTGTGGGGTCTTG |
| A_23_P107750 | 7.5166E-04 | CTTGTTCTTTTTACATAAAGGAATTTGTAGGAAATG CAGCCAAAGGTGCAGTCGGAAAAG |
| A_23_P253921 | 7.6292E-04 | CTGTATACTTTTATACCAACTTATTGTAGGCTCTTT GAGGTCAGGTATGTATTTCTTTCC |
| A_24_P124349 | 7.7101E-04 | ACTCTAACCTGAACAGCTCACAATGTAGCTGTAAA TATAAAAAATGAGAGTGTTCTACCC |
| A_23_P7503 | 7.7230E-04 | TTAGATTGAGGATGGGGGCATGACACTCCAGTGT CAAAATAAGTCTTAGTAGATTTCCTT |
| A_24_P20630 | 8.4366E-04 | GCCCAAAACTGTCATCCTAACGTTTGTCATTCCAG TTTGAGTTAATGTGCTGAGCATTTT |
| A_23_P421513 | 8.5185E-04 | GCATACTTTATAGTTCAAGATTTTCGGTATATAAAA TCTGTCCTTTCCTACCTGGACATG |
| A_23_P393051 | 8.5813E-04 | AGCTTATCTTAAATGTATTGTATTGGGGGGTGGGC AGGGCCCACTCTATGTTATGTTAAG |
| A_24_P301186 | 8.6555E-04 | CGGACTACATAAGCGTTAAAAATTGTGTTTTTCAG AATCTTTAAAATATAAGACAGTGCT |
| A_24_P92823 | 8.8438E-04 | ATCTCAATGCCTGCAAGCAGCTCGCTATGGCATTA ACACCACAGACATCCTCCAAACTGT |
| A_23_P258612 | 8.9944E-04 | ACTCGTCTGCAGTGCTTAGCCTAACTTTTGTTTAT GTCGTTATGAAGCATTCAACTGTGC |
| A_23_P29384 | 9.0987E-04 | CCCATTTTCGTTGGCTGGCAGGTTGAGATGTTTTT CTTAAACACTGCCTGTCAGTGTGAA |
| A_23_P209360 | 1.0014E-03 | ACACAGATGACATTGAAATTCGTTTCTCTCCTCATC TATCACACTGGAGCAAAACTGGCT |
| A_24_P285501 | 1.0086E-03 | CATGGTATAATGTATTCAGACTTTGATTACTACTTA TTTAAAATGGAATGTTTTATGGTT |
| A_23_P502520 | 1.0556E-03 | CCAGTTATCTCTCCAAAACACGACCCACACGAGGA CCTCGCATTAAAGTATTTTCGGAAA |
| A_23_P126844 | 1.0681E-03 | CGAGAGGGGGTGAAGACATTTCTCAACTTCTCGG CCGGAGTTTGGCTGAGATCGCGGTAT |

TABLE 3-continued

888 Significant Genes Identifed from
Cathgen Registry and PREDICT Samples

| | | |
|---|---|---|
| A_23_P318296 | 1.0794E-03 | TCAAATTTTTGAAGGGATTTTTGACAGAAGTGAAAA ATGGGGAGAAGGATATCCAGACAG |
| A_32_P11673 | 1.1497E-03 | TTAATCAGTAATTCACTTCAGATAACAACTCTAGAG ATAAAATATGCCTTAGGGGTTGGC |
| A_32_P128399 | 1.1622E-03 | TTCTACTGAGGAGGAGTTTTTCAAACAGTGGGGTG CTGTCTGCAATGTGTACAGCCTTAA |
| A_23_P35082 | 1.1990E-03 | CCTGCCGCAGATGTCTCCCAAAAAGTTGAGCCTTT CTAGATGGCTTAGGTGGCACCATGG |
| A_23_P35205 | 1.2090E-03 | CCACTGCTAGGCCTCAATGTAAATTCAGTTGAAAT TTGCAATTCTATCAGCAATTTAATG |
| A_23_P158925 | 1.2344E-03 | GTTGTCAAAGCACCAACAGGACATTTTGGGATGTG AAATGTAATTTCTTGGAATCTGTAA |
| A_32_P154473 | 1.2445E-03 | TGGTGGTTTATATCAATAACGATGCTGTACTATAG TCCATGTAACAAAAGATCTGGAAGT |
| A_23_P76078 | 1.2455E-03 | GAAGGGAAATTTGGGGATTATTTATCCTCCTGGGG ACAGTTTGGGGAGGATTATTTATTG |
| A_23_P133543 | 1.2566E-03 | TGGCTGTTAGGGACTGTATATCTTGTAAAAGAACA CTTGTCACATGCTTGATCAGTTACA |
| A_24_P168398 | 1.2587E-03 | TTCAGTTTAATTGCATTGTGAACAGAACACATGGT CTTCAATATGTAGATTCTGTGTGAC |
| A_24_P944714 | 1.2623E-03 | GAAACTTGGGGGTCAAGAGAGCTTATCAAGAGCC TTTTATAGGTAAGCTCTTCCGTGTGA |
| A_24_P392022 | 1.2880E-03 | ACGGGATTGTTAGAATCAAATCACTCTCGTGGGAA GAATTTTTATATGGGAAAGCGGATA |
| A_32_P60687 | 1.3620E-03 | TCCGTAGCTGTTCAAGTTTGTGTTTCAACTGTTCT CGTCGTTTCCGCAACAAGTCCTCTT |
| A_24_P108863 | 1.3623E-03 | CATTGTTTGCATCTCTCTATGAAGATACGTCTGTC CAAACTTTTAAAAGGCATAACTGTA |
| A_23_P86731 | 1.4035E-03 | ATGCTGTACAATGAATGGATTGTTCTTGTTTCTCA GATGGGTAGAGTAAAAGTGTCTGTA |
| A_32_P171061 | 1.4521E-03 | CTGCTGGAGGGACACTGCTGGCAAACGGAGACCT ATTTTTGTACAAAGAACCCTTGACCT |
| A_24_P813520 | 1.4773E-03 | AATGATTTGCGTGTTTTAAGAACTGGTGTATATAG GTACATCTTGAATGTTCTGCTTTCC |
| A_32_P149060 | 1.5159E-03 | TATTCTGTTTGTTTAAACTAGCTAGTGTAGATCCTG TTGTTTGTAACCAAGAGTGTTGAC |
| A_23_P91095 | 1.5377E-03 | ATTTTTGATTGTGAGCTCACCTATTTGGGTTAAGC ATGCCAATTTAAAGAGACCAAGTGT |
| A_23_P344281 | 1.5455E-03 | GCACTGGTCACTCCTATGTGCTAAGACAAGGCAG ACATCTGTGTGTTCTCTTAAGTCTTT |
| A_23_P341938 | 1.5614E-03 | GCCAGCGCTGCGGCTGGATTCCCATCCAGTACCC CATCATTTCCGAGTGCAAGTGCTCGT |
| A_23_P202520 | 1.6037E-03 | TCACTGCACTCCTTTGTCATATACTCTGCATCACT GTCATACTCACAACTTCGTGAATAA |
| A_24_P273014 | 1.6080E-03 | ACTCCTGAAGGGCTCAAGATGGTTAAAAACTTAGA GTGGGTTGCAGAGAGAGAAGAGTTG |
| A_32_P542318 | 1.6754E-03 | GGGAATTACAACAAGATAAATGTGAGTAATAGTTC ATTTTCCTGCATTTTTGATGAGGGC |
| A_23_P1352 | 1.7370E-03 | GCCCTACTGGAGGGTGTTTTCACGAATGTTGTTAC TGGCACAAGGCCTAAGGGATGGGCA |
| A_23_P93787 | 1.7401E-03 | AACACAGCTTTTTGCCTTCGAGCTATCGGGGTAAA GACCTACAGGAAAACTACTGTCGAA |

TABLE 3-continued

| 888 Significant Genes Identifed from Cathgen Registry and PREDICT Samples | | |
|---|---|---|
| A_23_P93787 | 1.7401E-03 | AACACAGCTTTTTGCCTTCGAGCTATCGGGGTAAA GACCTACAGGAAAACTACTGTCGAA |
| A_23_P14165 | 1.7699E-03 | TCAAAACAATTTCAGGCTCGAGTCATTAGTGTCAT GCTATACCGTAATTACCTTCGAAGC |
| A_24_P546003 | 1.7704E-03 | TGAAAGGATCTCTGGATCACCACAAAGTCTGGCTC AGTGACTATGGCTTTGCAAACACTA |
| A_32_P129540 | 1.7956E-03 | AACAAGATGAGATTATGCCTGAGGTTGCGGAAAA GGAAGATTATTCAGATATTATAGGGA |
| A_23_P16022 | 1.8023E-03 | GGATAAAGGTTAGGTAACACACATAGGGCTGTTAC GGACTGAGAAGTGTCCCTGCAAAAT |
| A_23_P129458 | 1.8230E-03 | CAGAAAGGATAGTATGGGAACATTACAAGGGGGA TACATTACTGTGGAAAGTTCTGCTAG |
| A_23_P112531 | 1.8866E-03 | AGTATATCAGAGATATTTTTGGAAAGGAGTTGGTC TATGCAATGTCAGTTTGGAATCTTC |
| A_32_P205329 | 1.9028E-03 | CTCATTAAAACAAACAAAACCACACCTGGATTGCC TGGTACTTAAATAAAATGCACTATG |
| A_24_P923934 | 2.0043E-03 | TGGTTAAGAGAATGTAAAAATACCATTTATTATTAT CATATCTACTAATACATTGGTGGA |
| A_24_P413791 | 2.0174E-03 | TATATAGTTCTAGTATGAAGTTTAATAGTTAAGGAG TTAGCTATTTGTTATCTTTAAGAG |
| A_24_P772147 | 2.0876E-03 | ATGAGACAATAAATGCTATAGGAATTATGGAGGAA TAATTAGCTATTTATTTTCTTGGTT |
| A_24_P126931 | 2.1219E-03 | ACCCCGTAGAAGATGGAATCACAGATGCTGCCTTT GAGCAGTTTTTGCAAGAAAGGATCA |
| A_32_P156851 | 2.1601E-03 | AATGAAGGGGAAGGGGAAGATTTCCCACCAACTG AATCATTTGTGCACGTGTATAGCTCA |
| A_24_P927189 | 2.1719E-03 | AGTGTGTTGTCGTTATTAATTTGCTATTCCTTGTCC TATTCAGAAAGGATTTCAAGAGGC |
| A_24_P320970 | 2.1761E-03 | GGAGAAGCTGTAAAAATCACAGTATAAAATTATGA AGTTTGGTAACTGTAAAATGTACTG |
| A_32_P130522 | 2.1831E-03 | ATTCACTGTAAATGATTCCATGGCTCCCTGTAGTA CTTCTACAAAGCATCTATCACAATT |
| A_32_P40463 | 2.1895E-03 | GGGAAAAGTTCAATCTCTATTTTGGTCCACAAGGA TCAAGTGCTTATGAACCAGACCAAA |
| A_23_P93348 | 2.2180E-03 | CGCGAGAGGGAAGACCTTCTTTGGGGCCGTGATG GTGGGGTGAGGGAATATGAGTGCGTG |
| A_23_P168788 | 2.2208E-03 | GGGATGGGTCTCTCTGTCTCCCCACTTCCTGAGTT CATGTTCCGCGTGCCTGAACTGAAT |
| A_23_P216396 | 2.2425E-03 | CTGGGAAAGCAAAGCTGTTTTCATCCTATAATTGA AGTAGTGTGGAGCATTAACTTGTGG |
| A_23_P326204 | 2.2600E-03 | TCGACCTGAGGAGCAAAACAAAGGCATCAGCTCTT ACACCAAAAGAGTTAACGCTGTAAC |
| A_23_P420269 | 2.2904E-03 | TTCAAATCATGAAGTGCATAGTATCACATGTGATA GAATATTTATAACTTTTTATTAGAT |
| A_23_P8834 | 2.4200E-03 | TGGCCTTACACACATCTTGCATGGATGGCAGCATT GTTCTGAAGGGGTTTGCAGAAAAAA |
| A_24_P153207 | 2.4386E-03 | AACCTTATGATTGTAAGGAATGTGGGAAGGCCTTT AGACTTCGTTTACGACTTACTCAAC |
| A_23_P138635 | 2.4583E-03 | TTCTGCTGAAGGCACCTACTCAGTATCTTTTCCTC TTTATCACTCTGCATTGGTGAATTT |

TABLE 3-continued

| 888 Significant Genes Identifed from Cathgen Registry and PREDICT Samples | | |
|---|---|---|
| A_32_P119604 | 2.5532E-03 | CAGAACTCTACTTCAGCAGACACTCAACTCAAAAA GACTGGCAAATGGACATGTATTTAC |
| A_24_P239664 | 2.5747E-03 | TTGTAACACACATGTATTGATGATTTTCATTAAGAG TTTCAGTTTAACTTTGAAAAATAT |
| A_23_P105251 | 2.6076E-03 | ATGTATAGTCTGTATACGTTTTGAGGAGAAATTTG ATAATGACACTGTTTCCTGATAATA |
| A_32_P38782 | 2.6314E-03 | CATCCTGAGTGGTAGAAGTCCAGTGCCCTTTCTCT ACCCACAGCCACTCACACCACCCAG |
| A_24_P164815 | 2.7308E-03 | CCACGTGTCAAGTAATCCTTAAAAGAATATCTTGG AAAAGGAAACAGATTTTTTCCTGTG |
| A_24_P266880 | 2.7483E-03 | TGACACCATCGAGAATGTCAAGGCAAAGATCCAAG ATAAGGAAGGCATCCCTCCTGATCA |
| A_24_P266880 | 2.7483E-03 | TGACACCATCGAGAATGTCAAGGCAAAGATCCAAG ATAAGGAAGGCATCCCTCCTGATCA |
| A_24_P266880 | 2.7483E-03 | TGACACCATCGAGAATGTCAAGGCAAAGATCCAAG ATAAGGAAGGCATCCCTCCTGATCA |
| A_24_P266880 | 2.7483E-03 | TGACACCATCGAGAATGTCAAGGCAAAGATCCAAG ATAAGGAAGGCATCCCTCCTGATCA |
| A_24_P266880 | 2.7483E-03 | TGACACCATCGAGAATGTCAAGGCAAAGATCCAAG ATAAGGAAGGCATCCCTCCTGATCA |
| A_23_P212649 | 2.8056E-03 | GTACACTCAGCTTTTTGTATCTGTAGGTTTAATATC TGTGTATGTAAGCAAACTTGGATG |
| A_32_P232559 | 2.8364E-03 | GCTTGGAGGAAACCAGTTTGCACTATTTGATGAGG AATTTGGCCACCAAACCACTGATAC |
| A_32_P100830 | 2.8653E-03 | GGGAGGGAATCTGGTTTTGTTACTTGGCAGTGGT TTTTTCTCACCCTTCCTTTTTAACAA |
| A_23_P215070 | 2.8810E-03 | AGAGCTGTTCTAATCTGCGTTTTGCATGTTAAGTG TTAATATCAAACATTCTTTACGTGC |
| A_23_P101319 | 2.8888E-03 | TCAACTGCTGTATGCTACAATGGCAAAGAGGTTAC TTTTGACAAATGGGTGGTTTGTGGT |
| A_24_P289178 | 2.8977E-03 | CCCCAGGGCTGTGCAAACACATGCCCCTGCCATA AGCACCAACAAGAACTTCTTGCAGGT |
| A_23_P122531 | 2.9166E-03 | ATTTGCTGACACAATATCTTCCGCCTGGTGCTGGG CATATCCTAAGAACTTACAACTTTC |
| A_24_P234921 | 2.9224E-03 | AAGCTTTAACTATATCTCTCTTTAAAATGCAAAATA ATGTCTTAAGATTCAAAGTCTGTA |
| A_23_P209954 | 2.9437E-03 | GTGTGTAGGACGGGGAGGTCACGATGGCGCGAC GTCTGCAGAAATTTCATGAGGAGGTAT |
| A_24_P139665 | 2.9828E-03 | CAAAAGTGAAGAAAAAGTTAGTTCATAAGTAAAGG CACTAAATCCTTTCCTGACAATGGC |
| A_32_P147622 | 3.0081E-03 | CGGCAACAATGCACCAGCATTCCAGCGTCCAACA GAGCATCCGTGTACCATTCCGGCATT |
| A_23_P301360 | 3.0977E-03 | TTGCATGGGGGTTATTTTATCTTTCATGATTGTGGT GCACCTGATGCTGGCGGGGTATTT |
| A_24_P136387 | 3.1073E-03 | AAGAGGTGTGAAATTTTGACGTGATGCTCTTTTTC CTTAGCATTGTAATGTATGTGTTAC |
| A_24_P848714 | 3.1209E-03 | AGTTGAAATAGACATCTTTTCATGAACTCTGTAATA TTTGAAATTATTGATAACTCTTAC |
| A_23_P502312 | 3.1546E-03 | TCCTGGACTTTTCCTCTCATGTCTTTGCTGCAGAA CTGAAGAGACTAGGCGCTGGGGCTC |
| A_23_P124542 | 3.1665E-03 | TTGATAGTAGCTTCCTCCTCTGGTGGTGTTAATCA TTTCATTTTTACCCTTACTGTTTGA |

TABLE 3-continued

| 888 Significant Genes Identifed from Cathgen Registry and PREDICT Samples | | |
|---|---|---|
| A_32_P103474 | 3.1897E-03 | AGTTCATGTTACTGAGTTATGACAAATTTATTATCA TGAGGGAAAACAAGAGTAGCCAGC |
| A_23_P208208 | 3.3073E-03 | CAGTCAGTCTATGGTGTATTTTTTCTAGTAGCCTG AACTGACTGAAAGAAAATCATGAAC |
| A_23_P105066 | 3.4630E-03 | CTCATGTGTGTAAGCTCATGAAGATCTGCATGAAT GAAGACCCTGCAAAGCGACCCAAAT |
| A_24_P737451 | 3.5080E-03 | GACGATGACAGGCTTCGACTCTGTGGTTTCTAAAG CATATAATATTCTCACGTACTTCTT |
| A_24_P943802 | 3.5712E-03 | GCTGACTTAATTTTCTGTTTTGTAAATATATACAAA CAAGTTGATACAAATTTTGTTTAT |
| A_23_P502314 | 3.5972E-03 | ACTGCCTGCTCAACAAGAAGGTTCGGGAAGAATA CCGGAAGTGGGCCTGCCTAGTTGCTG |
| A_32_P518489 | 3.6587E-03 | CGAAGGAAGAATCGGAAAAACAAAGAGACCGTCC GGCACATCACACAGCAGGTGGAAGAT |
| A_23_P321160 | 3.7448E-03 | CCAGATTAAAAACTAACCAATTCATCTTTGATGGA GCTTGAATCAAACTAAGGGTATTGG |
| A_23_P157215 | 3.7993E-03 | CCCCACTGGTGTCTATTACAGGCCACTTTGGTAGT TGTGTATCTGCTCATGTATGTGATT |
| A_24_P220921 | 3.8285E-03 | CAGTGGAGGGCTTAGATCATACAAAAATCTTTATT GGGTCCGTGTGTTCTCATTTCCTTC |
| A_23_P144165 | 3.8317E-03 | TTGCTTTTTGTGACAAAGTGAATACCCACTGGGCT AAGTTTCATATCTAAAGCTTGTCAC |
| A_24_P295633 | 3.8715E-03 | AAAGGACTGTTCTTTGTGGAGGAGAAGATCAAGCT GTGTGAAGGTGAAAATCGCATTGAG |
| A_23_P214156 | 4.0132E-03 | TCTATGGTAATATTTTGACCCTTTATATTTGTTCTA AAATAAGTCAAAATGTGAAAATAA |
| A_24_P291826 | 4.0389E-03 | ATACGAAGACAGCGTTCCTCAGAGTAATGGAGAG CTCACAGTCCGGGCTAAGCTGGTTCT |
| A_32_P155811 | 4.1112E-03 | AAAGCATGCTTCTCTCTCAAAAAGAAAAATTAAAG GATTTTATTGCCAGTCGTGTCAGTC |
| A_23_P6963 | 4.1254E-03 | ATATTAACAGTCAAGGTGTTATTTGCTTGGACATAT TGAAAGATAATTGGAGTCCAGCAC |
| A_24_P298587 | 4.2185E-03 | GAATACTTGGGCCGTTACATCGCCCGGAAACTCAA CATCAACTACTTCGACTACCTGGCC |
| A_24_P920319 | 4.3717E-03 | TTGCATGTCTCATGATAACCAAATGTAAGATGAAA ATAAAAGATGATTTACTTCAAAAAA |
| A_24_P339071 | 4.4434E-03 | CATTCAGACAAGTGTTTGTAGACTCTGAAGCCTAA TGTTACTCATGACGTTTGCCTCATT |
| A_23_P401076 | 4.4631E-03 | TGGCCTCCCACTAACTAGCATTCCTTTAAAGAGAC TGGGAAATGTTTTAAGCAAATCTAG |
| A_24_P29445 | 4.5442E-03 | CGTTTGGGGTTTCCTAGCCGCTACATCTGTTACTT TTGTTGGTGTTATGGGAATGAGATC |
| A_23_P74088 | 4.5598E-03 | GCTGCGGCCAGAAGATCCTCCACAAGAAAGGGAA AGTGTACTGGTACAAGGACCAGGAGC |
| A_23_P53476 | 4.5770E-03 | TGGGACATCCAGAAGGACCTAAAAGACCTGTGAC TAGTGAGCTCTAGGCTGTAGAAATTT |
| A_32_P159023 | 4.5866E-03 | TGAGACACTATGGCTCCAGAGTTCTGCTAACAACC ACCTGAAACAAACTTAGTAGGAGAA |
| A_23_P142407 | 4.6001E-03 | AATGTCAAAAATGTGCCAAAGTCTTTAGATGTCCC ACGTCCCTTCAAGCACATGAAAGAG |
| A_24_P32735 | 4.6002E-03 | ATGGGTGTGAACCATGAGAAATATGACAACAGCTC AATTATCAGCAATGCCTCCTGCACC |

TABLE 3-continued

| 888 Significant Genes Identifed from Cathgen Registry and PREDICT Samples | | |
|---|---|---|
| A_24_P406006 | 4.6184E-03 | CAGTAAGTACGGGAAAAAATGTTTACTAACTTCCT CAGAGATTCGTGATACGCGTTTCTC |
| A_23_P41280 | 4.6363E-03 | GTCTTGGCTGTTCAACCGTACTTTCTCCAGAAGGA TCAGCTCAATTTGCTGCTCAGATAT |
| A_23_P97481 | 4.7001E-03 | GCCAAGGGCTGTGGAACTGTTTCTGTGATTCAGG ATCCTCTTGGGAGAGTATATTCAATA |
| A_23_P31765 | 4.7361E-03 | AAATTCTCATTAATACTGTGTTTGATGGCCTCTGCT GTGTTTTAACATCGTGCTTCTTAT |
| A_23_P107724 | 4.7569E-03 | TGCTGCATTTCTTAACGTTTGGTCTCTATACATTAT ACCATCTGCTGAAGTTTAGCTTTG |
| A_23_P365149 | 4.7602E-03 | TGCTCAAGAATGCCATGAGAGCCACAATGGAGAG TCACCTAGACACTCCCTACAATGTCC |
| A_24_P160466 | 4.7714E-03 | GGTGTTCTTGGGTATTGGGGACAGGACAGAGAGC TCATTCTATAACCACAGTTGTCTTTT |
| A_32_P56434 | 4.7898E-03 | TAATATACAACCTGTCCAGTAGCCGAACAGTTTGT TTTTATTGTGTTTTCTAACCGTAAG |
| A_23_P125107 | 4.7945E-03 | AAGAGCAGAGATACACATGCCATGTACAGCACGA GGGGCTGCCGAAGCCCCTCACCCTGA |
| A_23_P30163 | 4.8866E-03 | AACTACTGGTAATAGCCAAGAAAATTTGGAGGTGC AGAGAACATGCTGAAACAGAATTTT |
| A_32_P135243 | 4.8881E-03 | TTACACTCAGCAGGGTTTTGGAAATTTGCCCATCT GCATGGCAAAGACCGATCTTTCTCT |
| A_24_P372608 | 4.9051E-03 | TGTAATCCTGAGAGATTCACATGGTGTTGCACAAG TACGTTTTGTGACAGGCAATAAAAT |
| A_24_P187874 | 4.9096E-03 | ACGGTAATGGATATTTGTGAATGTCTCTTTGGCCA AATGAGTCTGGAAAATGATGTGCTA |
| A_24_P258073 | 4.9309E-03 | CTGCTGGAGTCAGGACATTTTATAGAGCCTTTTCC AGTTTTACTAAAAAATTTTTCCATT |
| A_23_P410613 | 4.9341E-03 | TTGTATACACCTGGAGGCATCTGTTATTCAGCTTA TCCTTTGAGTGGGTATTTGGCACAA |
| A_23_P501849 | 4.9707E-03 | GAAAGACAGTCCAAGCCCTGGATAATGCTTTACTT TCTGTGTTGAAGCACTGTTGGTTGT |
| A_23_P120557 | 4.9896E-03 | TTGCTTCTCCGTGGATGAAATAGAAACTCCTCATT GTGTGACCAGGAATGGTTAAATCAT |
| A_23_P68198 | 5.0485E-03 | TGGAGACAGAATCACAGTTATATCAAAAACAGATT CACATTTTGATTGGTGGGAAGGAAA |
| A_24_P4877 | 5.1459E-03 | GAAAAATTAATACTATCATGTTAATACTATTATTGT CATCCCAAGAAAAAAGATATTTTA |
| A_23_P157299 | 5.2084E-03 | ACAGTAGAGACCTACACAGTGAACTTTGGGGACTT CTGAGATCAGCGTCCTACCAAGACC |
| A_32_P231493 | 5.2363E-03 | CTCTTGTTACCTTGGCTCTCTAAGCTGTATCTACTT CTATACAAGGCGAACAATTTTGTC |
| A_23_P123478 | 5.2838E-03 | GGTTTTACAGATGGCTTTGAAATGTGCTGATATTT GTAACCCATGTCGGACGTGGGAATT |
| A_24_P376483 | 5.3846E-03 | AGACTGACCGAGTGGACCTGGGGACCCTGCGCG GCTACTACAACCAGAGCGAGGCCGGTT |
| A_23_P80752 | 5.3877E-03 | CATGGCAGAGATTTATAAGTACGCCAAGAGGTATC GGCCGCAGATCATGGCCGCGCTGGA |
| A_24_P266048 | 5.4094E-03 | TGTGATCATCAGCAATAAAGATATAATAACTCTGTT TTCTTAGCCTGTATAGAGGAGAGG |
| A_32_P210252 | 5.4280E-03 | TGTCAGTTGTATCTGTTGCTTTTCTCAATGATTCAG GGATACAAGTGGGCTTCTCTCATT |

TABLE 3-continued

| 888 Significant Genes Identifed from Cathgen Registry and PREDICT Samples | | |
|---|---|---|
| A_23_P96590 | 5.4356E-03 | GAGCTGAAAACACATTTGTTGATATTTGTCTTGTC CACATTGTGATGTTCAGTATTTGAG |
| A_24_P15586 | 5.4989E-03 | GCTAAACTTTCTGTATTTATACAGTTAAACTTATAA ACCAAAAATTTTAATGAGGTTAAT |
| A_23_P396842 | 5.5260E-03 | GTGGTTCCCATTTCCTTATCCATGGAGGAGACCTC TGAACAGATCACAAATGTTACGTGA |
| A_23_P29096 | 5.5392E-03 | AGGTCCGTCCAATGGAAGTCGCAGAGCCTTGGGT GGACTGTTTATTAGAGGAATATTTTA |
| A_23_P70539 | 5.5491E-03 | AACTGCGCGGCTACTACAACCAGAGCGAGGACGG GTCTCACACCCTCCAGTGGATGTATG |
| A_32_P132477 | 5.5698E-03 | GCAGTCTTTGATCATGCCAGGGCTGATCTCCCCA GTAAAAGCCCCATTAGTCACTTTGTA |
| A_24_P873757 | 5.5882E-03 | ACAATGCTTTTTGTTTCAGATATTTTCTGTACTTGA ATTTCAAATATTTATACAGAACAG |
| A_32_P145447 | 5.6355E-03 | GGGAGGGCTGAGATGATCACTTCGTTTTCTGTTAC GGCTACTTTTATATTTTTCAACATT |
| A_32_P542928 | 5.6618E-03 | ATCACGTAATTGTTTCCATGAAAAGCAATAAATGTA ACAAAGGGTTTTTCTATGGGAGCC |
| A_23_P210829 | 5.7475E-03 | TCCTGCGCACCTTATACCAGAATTCAGTATAATAC ACTACTTTCTGTTTTCAAACAGATA |
| A_23_P74138 | 5.7486E-03 | CTGGGAGTCACTGATGCTGCCTCTGCCTTCTGAT GCTGGACTGGCCTTGCTTCTACAAGT |
| A_23_P9152 | 5.8608E-03 | TGGCTGCGGGGCTCCAAGTAAGTTATTGGGATGT TTTTTATATTCCAGGTGTGCTGTACA |
| A_32_P200901 | 5.8686E-03 | TTGCCTCTTCTTCCGCAACTGGTGCAATGAGTTTT TCCTTAAGAGTTGCCATTTTGCACA |
| A_24_P239309 | 5.8687E-03 | CCTGTCATAGTTTTATACAACTATAAAATATATACG TGCCAAAATAAATTTGATAGGAAC |
| A_24_P69654 | 5.9166E-03 | AGGCACTTCCGAAAGCACACCGGGGCCAAGCCTT TTAAATGCTCCCACTGTGACAGGTGT |
| A_24_P88763 | 5.9620E-03 | AGGAGGTCAGGATGGTCAGCTCCAGTATCTCCCC TAAGTTTAGGGGGATACAGCTTTACC |
| A_23_P387585 | 5.9816E-03 | TATAAAAAGATAAAATAAAAAGCCGGTCAGTGTCT GTTGCACAAAATTACAACCGCTCTC |
| A_32_P353072 | 6.0242E-03 | TGCTCACTTGATTGACTTGGTCAGATATTTGAATG ATGGTATTACCTAGATTCTAATCCT |
| A_24_P942370 | 6.0433E-03 | TCCCTATAACTCAAAATAACTTGTTTGTAAAAGAAA ATTTGTTTACTTACCCATTAGTAA |
| A_23_P90696 | 6.0451E-03 | ACGGCTTTTCTATTGCTGTATGATACAGAACTCTTT TGGCATAAATATTTGTGTTCCCAG |
| A_23_P155556 | 6.0743E-03 | AAAGTTCTGGCTGTCCATTAACCTCCAACTATGGT CTTTATTTCTTGTGGTAATATGATG |
| A_32_P7916 | 6.0846E-03 | TATTACGCTTCACTGGGCCCTGGAGGATATTGTCT TATACAGTCCACTGGGTTTTGGATA |
| A_32_P111394 | 6.1042E-03 | GAATACAGTGTTCCTTTTCATCCCATATTTGACTGA ACCTAAGACACATCAATTATAAGG |
| A_24_P208998 | 6.1100E-03 | ATAAATAATACTTCCGAATTAAATTATTTAATATTTG ACTGATTTCAATAACTGTGAAAA |
| A_24_P48408 | 6.1351E-03 | AACTTTTTATTAAAGTGTAACTATAGAAACACATCA ATGATTTTTCACAAGTGGAGCACG |
| A_24_P193295 | 6.1439E-03 | TCTCGGGTCCATATATGAATTGTGAGCAGGGTTCA TCTATTTTAAACACAGATGTTTACA |

TABLE 3-continued

| 888 Significant Genes Identifed from Cathgen Registry and PREDICT Samples | | |
|---|---|---|
| A_23_P112482 | 6.1847E-03 | AATTTGGGTCAATACATCCTTTTGTCTCCCAAGGG AAGAGAATGGGCAGCAGGTATGTGT |
| A_23_P90790 | 6.1966E-03 | GACAGTTACAATGATCTTTGTATCTGAACTTTGCAC GTCTGCCGAAAAATCCGAACCTGT |
| A_24_P50437 | 6.2422E-03 | TGCAGAATGATGAAGTTGCATTTAGAAAATTCCTG ATTACTGAAGATGTTCAGGGCAAAA |
| A_24_P360529 | 6.2721E-03 | TTCAGAAAGATGAAGTTTCCAGAAACTAAGAAGGT AGCACAATATGTGGCATCATACTCA |
| A_24_P98047 | 6.2982E-03 | CATGTCTGAAAGTCACATATTGTGAAAATTTGAAG CTATCTCAGTAAAAAGCAGCTTTGG |
| A_24_P264685 | 6.3146E-03 | AACTTTGGCATCATAGAAGAACTTATAACCACAGT CCATGCCATCACTGCCCAGAAGACC |
| A_24_P137997 | 6.3401E-03 | AGGCTTTACACAAAGTTCTAACCTTATCCAACATCA GAGAATTCACACTGGAGAGAAACC |
| A_32_P165340 | 6.5919E-03 | ACATTGAAATATGTTTTGTATAAATTTGTCATGTTG AACAACATTTTAGCATGGTAAGTT |
| A_23_P253405 | 6.7754E-03 | GCTCAACAGAGGTTTAGTTTACAGTCTCTGAACTA AAGTAGTAACCTCCCAAATTGTTTT |
| A_32_P797019 | 6.7894E-03 | TTCAGCATTTTTGTTTATTTGTTTGTTCTTTAACAAA AGTTGTTTTGGTTTGAGATTCAG |
| A_23_P204208 | 6.8617E-03 | ATACAAAGAACTGCATAGCGTATAATCCAAATGGA AATGCTTTAGATGAATCCTGTGAAG |
| A_24_P450596 | 6.9100E-03 | TCAGTAGGTATTCTTTTATGTGCTTTAGTAAGTCTT TATATTTTTAGCATAAAAGTGTAC |
| A_32_P101334 | 6.9613E-03 | TACTGAGAGTTTTCTGTGAAGCTACAGCATATCTA ATCAGAGAATTTCTGATTTGTTTCC |
| A_24_P233256 | 7.0056E-03 | TTATCATTCTAACTTCAAGGACATTATATCACTTAC TGTATAATAAAATAATCTTACAGT |
| A_24_P517901 | 7.0321E-03 | GAAGACACTGAAGAACATCACCTAAGAGATTATTT TGAGCAGTGTAGAAAAATTGAAGTG |
| A_23_P377888 | 7.0906E-03 | TTTAACGCTCTCTGTTCTGAAAAAGAGGTGTTTGG TTACGTGTGAGCCAACATCACGTTT |
| A_23_P423543 | 7.1071E-03 | CCTTCTAACACCTTTTAAATCTATGTACTTTAATAG TTAAGAGAAAATAAGTTTGCAGAT |
| A_23_P105465 | 7.1609E-03 | GGACACCCAAGGATATGTCTTCTGAAGATCAAGGC AAGAACCTCTTTAGCATCCACCAAT |
| A_32_P34516 | 7.2315E-03 | GTAAAAGGATGTAGTCTGCAATCATTTTCTGACTC TTGGTGTAATAAAAATTAAGTGGCC |
| A_32_P26017 | 7.3492E-03 | AAATAGGATGGAGGATGGGTCACTGTGTCCGTATT ACCAATGACAGTCACCCCAAGAAAC |
| A_23_P157527 | 7.4049E-03 | AATTCAGCAAGATATGTGATGGTTCTGAGAATGAA TTTAATTGAAATAGACCAGCAGACC |
| A_23_P76918 | 7.4081E-03 | TTGAGGCCTTATGATTCAGCAGCTTGGTCACTTGA TTAGAAAAATAAACCATTGTTTCTT |
| A_23_P161194 | 7.4968E-03 | CCAGATGCGTGAAATGGAAGAGAACTTTGCCGTT GAAGCTGCTAACTACCAAGACACTAT |
| A_24_P96505 | 7.5517E-03 | TGCTTCACAGAGCTCACGACAAATATCATCCCAGG GAGTAACAAGGTGATCAAACCTAAC |
| A_23_P105461 | 7.6203E-03 | CCTTGGACTAGCAATTTATGCTTCTTGGGAGGCCA GCCTTGACTGACTCAAAGCAAAAAA |
| A_32_P138432 | 7.6226E-03 | GGTCCTACTAGACTAGACAGAAATTTGACTCAAAA TGGTTGAGGCCATGCCAACCTGAAT |

TABLE 3-continued

| | 888 Significant Genes Identifed from Cathgen Registry and PREDICT Samples | |
|---|---|---|
| A_32_P128258 | 7.6930E-03 | ACTATGTGCCAGCATTTCCGTATGTGCAGAAGTTC ATCAATAGATATAGACTCAAAGAGC |
| A_23_P254997 | 7.7394E-03 | CAGTCATTTTTCTCTATTCTGAAGCTCTCCCACTGT TTTCAATGTTTAACCAACTGGGGA |
| A_24_P76358 | 7.7512E-03 | TTACTGAAGATGTTCAGGGCAAAAACTGCCTAACT TCCGGCATGGATCTTATTCGTGACA |
| A_23_P27947 | 7.8692E-03 | AGCATGCTCAAGAGTGCTAATTTAGGTCTTTCTGT GGAATTTGGAACAATTCTAGTTTAC |
| A_24_P137434 | 7.8954E-03 | TCATGTCACATGAAACGATTCTCTGCTTTTTGGTTC TGAACTTGAAGTCCCTAAACTGCA |
| A_23_P77714 | 7.9085E-03 | AGGGGAACATCTGGCTGTTAATCACTTGCACAGTT GAGAACATTTCCTATACATCGGCTT |
| A_32_P139894 | 7.9466E-03 | CAAACATGCGGATTCAATTCTTTAAAACTCGTTGAA CGTTTATACCAAAGGTCCCGCCCC |
| A_23_P343250 | 7.9662E-03 | TAGTACTCTGACACATACATGTGGTTATCTTTTGCC CTGTTGTGATGGATAATTTGAAAA |
| A_23_P67785 | 8.0915E-03 | TCTGCAATTTCTTGATCAAAATGGGAATGACCAGA ACTCTTGATTGCTTTCAGTCTGAAT |
| A_23_P1691 | 8.1217E-03 | ACATGTGCAGTCACTGGTGTCACCCTGGATAGGC AAGGGATAACTCTTCTAACACAAAAT |
| A_32_P53558 | 8.2052E-03 | GTTGTCCTTTGAAATGATTGACCAGGAAAAAGATC ATCCTTAAATTTTGAAGCAAGTGAG |
| A_32_P115663 | 8.2160E-03 | TCCGCATTTCAGCCAATTTAGCAGATGACTAACCA CCTTAAAACGGTCCACACAATTATC |
| A_23_P146554 | 8.2998E-03 | CCGCCAAAGCACCCCTGCCCACTCGGGCTTCATC CTGCACAATAAACTCCGGAAGCAAGT |
| A_23_P345460 | 8.3073E-03 | GACTTGATGCCTTTTGAATAACTTTCAATAGAATTG TCTAAAATTATCTTACTGGTTGTT |
| A_24_P915300 | 8.3704E-03 | GCTAAGCGTTAAGGGAACATTGAATTATATAAACA GTCCAGATAATACTCCTTCTTTGTC |
| A_23_P215931 | 8.4347E-03 | TGCTGTCTCTGATTTCTAGGCTAGTTACTTGAGAT ATGAATTTTCCATAGAATATGCACT |
| A_24_P325015 | 8.4556E-03 | CGATGCTATGTTGAATGTATTCTGATCGGATCGTT TATGGTTATTTACAATGCAGTTACT |
| A_24_P942112 | 8.4844E-03 | GATCATCTTGTATATACTTCTGCAATTATAAGATGT TTTTTGATGATGAGAGCTTTCCTA |
| A_32_P145159 | 8.5240E-03 | CATACATTGGCGTGTACATAAACGTTTGTGGAAAA CTTAGTTGTGTGATTATTCTCTTTG |
| A_23_P48585 | 8.6475E-03 | CTAGTAAAATGTCAAGAACAGACGGGAGATATTAG TGTCTTTCCCTCTATCATTAAAGGT |
| A_32_P472968 | 8.7164E-03 | GAACCATCCATGATTCTGATATTGTATTTCTTTCCA GTATTAACATGTGTATTGTGTGGC |
| A_32_P122285 | 8.7824E-03 | CATGCAGAAAGATCAGTTTGCAGCAGCAAGTACAA AAGGAGAATAGGAATATCTGTCGAA |
| A_23_P138725 | 8.8164E-03 | TGGTTGGGGAGAGGGGACCGATGTGCCTCATTGT TTAGTGGTGATTACAAATATGCTTTT |
| A_32_P196036 | 8.8397E-03 | AAAGGAATAAGAAGAGGTCGGTTAAGCTCTCTATT AAGTTGAGAAAATGGGAACTTCAGG |
| A_23_P255591 | 8.8514E-03 | TTATGAATGTACCAAATAAACCACAGCTGGACTGT TAACCTCACCTTAGAAGCTTCATTC |
| A_24_P215475 | 8.9227E-03 | CACCATGCCCACATACAACATACCTATCAGAAATG GTTTTCATTAAGGGAGTAGAATAGT |

TABLE 3-continued

| 888 Significant Genes Identifed from Cathgen Registry and PREDICT Samples | | |
|---|---|---|
| A_23_P17134 | 8.9936E-03 | GCCCCATCTTGTGCCATGTTTTAAGTCTTCATGGATGTTCTGCATGTCATGGGGACTAAA |
| A_24_P35537 | 9.0245E-03 | CTGTTAGAAGGTATGGGATCATATTAAGATAATCTGTCAGCTACTACTAGGCATTTATTG |
| A_24_P170103 | 9.1560E-03 | AACGACAACAGAAAAACAATCTTATTCCAAGTCATTCCAGTAACTTTTTTGGGTACGTAC |
| A_23_P210176 | 9.3999E-03 | ATTTCTGTAAAACAGGTTATAACAGTGTTTAAAGTCTCAGTTTCTTGCTTGGGGAACTTG |
| A_24_P923190 | 9.5102E-03 | AATCCATCCTATTATGAGTAATTAATGGGCTATATAATAGTGAGATTAACGGAGTCCCTC |
| A_24_P316019 | 9.5133E-03 | AGAAGCTTCGGCAGCTGGCCAAGCCACAGAGCGTCTTCGAGGAGCTGAACAATGAGAACA |
| A_24_P252310 | 9.6092E-03 | GGGGGGTGCACTTTCATTTTCAATTGACTTTATTAAATGAAAATCCAAATCTTCCACTCC |
| A_24_P204244 | 9.6271E-03 | TATCAGCACTTAAGTCAGCCTTATCTGGCCACCTAGATGTGGCTTTGGGCCTATTAAAGA |
| A_23_P114814 | 9.6682E-03 | ACTCCAGATAAAATGAAAAACCTCTCCAAGTCCTGGTGGAAGAAGTACTGCTGTTTCGTA |
| A_24_P631993 | 9.7215E-03 | AGAAGTATGGAAACAGCCTCAAGATTATCAGCAATGCCTCCTGCACCACCAGTTGCTTAA |
| A_23_P373724 | 9.7406E-03 | CAAATATTTTTTATTCAGGATGGTATAACCTAACTGATAATAGGTAATAAGGTTAAATTT |
| A_32_P191004 | 9.7424E-03 | GTGGGTAATTTCTTCCCTTTTTTGATTAAGTTGGTTCAGCTATGGTGCTATTCAGTAGGT |
| A_24_P123347 | 9.7814E-03 | CAAATTGGCATTTGAATAAAGCCCTGGGACCACCTCAACATGCGTAGCCTCTTGTCTTAA |
| A_23_P43786 | 9.9272E-03 | GAATTGTGTACTAATAGCAAGGTATAAGTTTGGTGTAGAGCCTATCCAGTAGCGTCCACT |
| A_24_P134727 | 9.9305E-03 | ATTATGGAAGCAGGAGTTTCCTTTTCAAAATTGTTACAAATTGTAGAAGCCACAGTGTTC |
| A_23_P36226 | 9.9609E-03 | CTTTTATAGAGGACTGTTTGCCCAGCTTATCCGGCAGATCCCAAATACTGCCATTGTGTT |
| A_32_P95015 | 9.9695E-03 | TCTGGAGCAAAAATGATTATGTTGTAAGAACTTTTGGAGGTTTTCCTCCTCGTAAAATTC |
| A_23_P146187 | 9.9832E-03 | GAATTAGGGAAATAATTTGGTGGAAACCGGGAATGAGTTCTATTCTTAAACAGCCTTTTT |
| A_23_P201731 | 1.0050E-02 | TGGTTTGCTTAGGAGTTCAGAGTTCCTTCATCATCGAAATAGTGATTAAGTGATCCCAGA |
| A_24_P118541 | 1.0225E-02 | AGCTGGCAGACAAGAATGTGCCCAACGTTCACATGAAGGCCATGCAGTCTCTGAAGTCCC |
| A_23_P415611 | 1.0226E-02 | ATGCTTACACGCCATTATGATCCAAGCAAAATAAAACTGCAGTTGTCAACATTAGAACAT |
| A_24_P24230 | 1.0244E-02 | CTTAAGAGGAGATATTACAGACAGCACTGCACTTTGCAGTCAGCTACATCAAGGACCTCT |
| A_32_P131143 | 1.0441E-02 | AAGGACACCAACGGCAGCATCAGCAAGTCCGTGTTGTCTCCCAAATAAGTGGTGTTCTCC |
| A_23_P62642 | 1.0457E-02 | TGAGCTGCGAAAAAGTCGGCTCGAACAGGTGGCTTTCAAGGAGCACGCTCTGGCTGTTCA |
| A_23_P434710 | 1.0477E-02 | CGACCTTCTGCGACTATTTGAGTATGGCGGTTTCCCTCCCGAGAGCAACTACCTCTTTCT |
| A_23_P3823 | 1.0502E-02 | CTGCTCCACACACTGCTGCATCTTGGGTCTCAGGGACCCAGACAGATGGACTTACATGGA |

TABLE 3-continued

| 888 Significant Genes Identifed from Cathgen Registry and PREDICT Samples | | |
|---|---|---|
| A_24_P813667 | 1.0565E-02 | TTCAGTTTTCATCATGATGTAGAGATATCAGTTTTA TAGATTGTATGTTTATTTGCCATA |
| A_32_P63086 | 1.0594E-02 | CCTCACGTGAAATAAATATTTTATATGGTTTTACTA AAAATAAGACTCATGTATCTGGTC |
| A_24_P256654 | 1.0634E-02 | AGTGTGAATTTTCTAATGCTGAGTAAGTTGTGATC CAGAAGTAAATGTATCTGCAAGCTG |
| A_24_P596406 | 1.0687E-02 | ATTAAATCTACAAATGACTGGCTGTACCCATGAAG TGAGTTATTCTAAAGACAATGGAAC |
| A_32_P177955 | 1.0696E-02 | CCCAGACTTCTGATCAACAAATATTGCTGCTACAT TAACTGATTCGCAACAAAGAAAGAA |
| A_32_P50066 | 1.0751E-02 | TTGAGATAGTCACTCAGAGGTTTTCACATACAGGA TTAACCTTGCTGCAGTGCGTGTGCA |
| A_24_P177795 | 1.0799E-02 | CCCCGAATCTGGCTTGGCAGAATATATCTTTAACA AGAACACCCTGGGAGACAGTGATAA |
| A_24_P325035 | 1.0804E-02 | TGGGTTATTTCTTGCTTTCCAAATTCCCTTGTCTGT AGCTATCTTTCATCACTTGCAAAA |
| A_24_P153643 | 1.0898E-02 | ATGCTGTGTATTTGTACAGGAATTTGAGCAAAAAA TGTATAGAGTGTGATGTCCAATTGG |
| A_23_P52058 | 1.0946E-02 | GTGGAACAAACTGCCAAAAGTTTAGACCTAACCCA ATATTGCTTTCCTGAGAAATCTCTG |
| A_23_P217886 | 1.0996E-02 | AAGTCTTTTGTGAATTATTTCCTGAAGTCGTGGAG GAGATTAAACAAAAACAGAAAGCAC |
| A_24_P40907 | 1.1000E-02 | TAGGCTTACCATCTGATTTGTAATTACAATTTTGGA ATTCTCTGTTTTAGTTGCTGAGGC |
| A_23_P34144 | 1.1015E-02 | ATTTCTTCATATCTGACGTTTCTGAAACCCTTTGTG TCTGCTGTTGTGTGAAGATTGACA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_23_P19313 | 1.1065E-02 | GACAAGTTGGTTTGAGGGAGAAAACTTTAAGTGTT AAAGCCACCTCTATAATTGATTGGA |
| A_24_P300952 | 1.1071E-02 | GCTCTACAAAGTACCTTATGTAGCCCAAGAAATTC AAGAGGAAATTGATGAGCTCCTTCA |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |

TABLE 3-continued

| 888 Significant Genes Identifed from Cathgen Registry and PREDICT Samples | | |
|---|---|---|
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_24_P418044 | 1.1121E-02 | ACTTCTCTTTCTGCAAAGGCATCTGAATGTGTCTG TGTCCCTATAGGCATAATGTGAGGT |
| A_23_P92012 | 1.1166E-02 | AAGCACTTTCATACGCAGGCATCTCTTGTTACCTA CATCTAAGCTGTTCCCGAAAGAGTG |
| A_24_P511143 | 1.1200E-02 | AGAGATGTAATCTGTATAATGATTCATATTTTCCCA TGTGAATACAGTCTGATAAAGATG |
| A_23_P342000 | 1.1205E-02 | ACTAAAGCTAATTGAAAGAGTCATGCAACTCAGTT GGGAATTAACCACTCAATTCAATAG |
| A_32_P173744 | 1.1208E-02 | TCACTGGAATAACTTTAAAAAAGAATTACAATACAT GGCTTTTTAGAATTTCGTTATGTA |
| A_24_P205268 | 1.1260E-02 | AATTAGGGATGACTGCATTATCAAAATACTCTCAG GGTTCCTATAAATGGCAGCTCTCCT |
| A_32_P113007 | 1.1287E-02 | GAAATCTTACTGAACCAAGAAAGTTTTGCAGAATTT CTGAAGGCCGAATATTCAGACTTA |
| A_23_P72025 | 1.1339E-02 | TGTGCATGGACTTGGTGAGACTGTTGCCTTAATGA CATCCTGCACCGTGTATAACTTAGT |
| A_23_P44154 | 1.1348E-02 | CTCAAGAAACAAATGCTAGCTTCATATGTATGGCT GTTGCTTTGCTTCATGTGTATGGCT |
| A_23_P22143 | 1.1354E-02 | ACTGAGAACATTTGCAGCCACACATGTACATATGT GTACACAGGTAGACAGATGGACACA |
| A_23_P397341 | 1.1415E-02 | GCCATGTTGCCACATGAGCAAGCTTGGGTGCTCC CAAGGTTCAAATACTTTTTATTAGAC |
| A_32_P174214 | 1.1426E-02 | GTCCAAGTGAGTTAGCCTTTTTAGGGTTGATTAAT TAAAAGAGCAGCAAGAATGGCATTT |
| A_32_P123966 | 1.1502E-02 | CCTAATCGTCCCACTAAATGGAATGCCTATGATTA GCTTCATTAAGAGTTTTATACTGTG |
| A_32_P211141 | 1.1519E-02 | GGCGTTATGCTCCATGTATTCTGCAACTTTTCATC ATACATTAGGTTTTGGCGATTTAGC |
| A_23_P407614 | 1.1528E-02 | CGAGGCCATCCTGAAGGTGCTGGAGAACCTGACA CCGGAGGAGCTCAAGAAGTTCAAGAT |
| A_24_P225339 | 1.1530E-02 | ACCTGCTACAAGCACTTCTACTACTTCATCCGCGA GTTCAGTCTGGTGGACCAGCGGGAG |
| A_23_P98350 | 1.1586E-02 | TCCTATACATCGAAGGTGTGCATATATGTTGAATG ACATTTTAGGGACATGGTGTTTTTA |
| A_32_P515088 | 1.1593E-02 | TTTACACTTGCTTGATGTGATAACTCTAAAGACTTT TTAACTGATAAAAGCGCACATGGC |
| A_23_P8640 | 1.1648E-02 | AACAGCTGGGGACAACTGCGGTGATGATGTAAAA ACCTTCCCATAAAATGTAAGAAAAGC |

TABLE 3-continued

| 888 Significant Genes Identifed from Cathgen Registry and PREDICT Samples | | |
|---|---|---|
| A_23_P31006 | 1.1649E-02 | AAGCCTGACGAGCCCTCTCACAGTGGAATGGAGA GCACGGTCTGAATCTGCACAGAGCAA |
| A_23_P129064 | 1.1699E-02 | AATATCTGATAGATACACTGCATCTTTGGTCATCTA AGATTTGTTTACAAATGTGCAAAT |
| A_23_P371215 | 1.1706E-02 | AAGCTGTGCCTCGACACATCCTCATCCCAAGCATG GGACACCTCAAGATGAATAATAATT |
| A_24_P280903 | 1.1722E-02 | AAATGCTATCAAGAAACCCCGATCACAAAGATACA AATCTCTTAAGTGGATGGACCCCAG |
| A_32_P203430 | 1.1914E-02 | GGAATTTATGCTGGTAGGAAACTTTCAAATGTGAA GAATATTGGCAGGTCTATTCTCATC |
| A_23_P28625 | 1.1937E-02 | GAGCAGACAATAAATTGTATTCCTACAGATATTCA CCTACCACTTCCCATGTTGGGGCAT |
| A_23_P62335 | 1.1942E-02 | GCCATTGAAGCATGAATATATTGAAGATGTTGGAG AATGTCACAACCACATGATTGGGAT |
| A_23_P82478 | 1.2210E-02 | CTTTGTCACCAGTGGCTTTGGTATTTCCATGTCTG GCATTGCATAAACTTCTCTGGTGTG |
| A_23_P4611 | 1.2214E-02 | CCATACCCTCAACCTCAGTGGGCTGGAAATGACA GTGGGCCCTGTAGCAGTGGCAGAATA |
| A_23_P379142 | 1.2278E-02 | TAGGAATGTGATGTTAGAGAACTACAGTAACCTGG TCTTCCTTGGTATTACTGTTTCTAA |
| A_24_P64071 | 1.2285E-02 | GATATTTGTGGAAAACTGTTTACTCGAAGAGAACA TGTAAAAAGACATTCCCTGGTGCAT |
| A_24_P208452 | 1.2354E-02 | TTATAAATGTTTATTTTGTACTTAATACCTGTAAAGT CTTAGTTTTCAGACATTAAGTGA |
| A_24_P674924 | 1.2406E-02 | GGATTTCGCAGTCATCTTTTTGGGGAAACTGAAAG TACCATCTCATTTGCATGAAGTGAC |
| A_32_P122940 | 1.2409E-02 | GCTTTGGCAAAATTTTTAAGATTTCTTTGATGTCCG ATGTGCTCATTTCTTGGTTTGTTC |
| A_32_P6452 | 1.2419E-02 | TAACTAGCCTTTACTTTGAAGAATCGTGACAGAGT AGACTCAATATTGTAGCTGACTAGA |
| A_32_P66625 | 1.2510E-02 | TTAACCAATTTCACCTGTAAATCTGTCTGTGCTTTG TAATTTTGGTGATACTGTTGACTC |
| A_32_P834726 | 1.2539E-02 | AGACAACGTTTGTTATTATTACTGCTACTATTACTA TTTGCTCCTCATGAGATCAAGGTG |
| A_32_P8120 | 1.2593E-02 | GACTGCTAAACTGTTCTCTGTATAAGTTATGGTAT GCATGAGCTGTGTAAATTTTGTGAA |
| A_23_P160518 | 1.2650E-02 | GCAGCACCACTTGAGATTTCCAGAGGACCCAGAC CTTTGTTCATTCTAAAGAGACTGATA |
| A_23_P42588 | 1.2710E-02 | TCATTGTTCTAATAATCACCAATTCAGACTCAGATC CTCGTGGTCTATGGAGCATGCTGC |
| A_32_P38467 | 1.2745E-02 | CGGCAATGGACTTATCGTAGTTGGGGAAACGGGT GTTCCGAATAATATCCTGGAAGTTAT |
| A_32_P200120 | 1.2756E-02 | CTTCCAACACACATATGCAGGCGTCTCTAAAATTC CGGAGATATGGTCACCAATTATTTT |
| A_24_P535219 | 1.2798E-02 | ACATTTAGTACAGGTACCATAACCAAGAGATTTCTT AGTTTTGATGGATTAAGAGAGAGC |
| A_23_P69877 | 1.2853E-02 | TCACTCTCTCTTTGTCATGAAAGCCAGCTCCTTGT GGCGAGGTAAAGTGGAATTCCAATA |
| A_32_P24489 | 1.2886E-02 | AGGTTGCAGGTGAACATGGCCTTGAGGTAAATCT GTCCCTTGCTGAATACAGTTTCAGTA |
| A_24_P921897 | 1.2901E-02 | AGGGAGGCTTGAGTACATATACCAATGAAGAGATA TTCAGCATTTGTCTATTTGATAAGG |

TABLE 3-continued

| 888 Significant Genes Identifed from Cathgen Registry and PREDICT Samples | | |
|---|---|---|
| A_24_P195240 | 1.2977E-02 | AAGCACTGGCTACAGTTATTCTGAAAAATCCCAAACGCAAAAGGGAGGCAAAGCTGTCTC |
| A_24_P54000 | 1.3000E-02 | GAAGACTATTTGAACAGCCTTTTAGAAGGATGTTTAAAAGATACTGAAGATTCCCTTTCC |
| A_23_P59528 | 1.3009E-02 | AATGCTATTCTCATCCAGCCATATTAGTCTTCTGGCTTTTCTTTAGCTTCATCAAATAAG |
| A_24_P358337 | 1.3042E-02 | CTTGGAAACGCTTGGTGATAGATAAAAATAAATACAACACACTCAAATACAGGATGACAG |
| A_32_P28939 | 1.3047E-02 | GCCCACGGGAGCTTACTAATGATGAACCACCCGACCAACACGCACTGGTACCACAGTCTT |
| A_23_P68211 | 1.3135E-02 | GAACACAGAAGAGAGGAGGTTGTGTCTCTTGCTCATAGCAAGCCTGTGGGTAGAGGAAAG |
| A_32_P104263 | 1.3177E-02 | TTTTTTAAAGCAGTAAGTTTATAGCATGCATTCCCAGTGGCCTTCTCATCTGGGCCTGGA |
| A_23_P55127 | 1.3417E-02 | AGTGTCTTGGGCGTGGATCAGTCTTCTCCAAAATACGAGCAGTGTATGAAGATATTGAGG |
| A_24_P256603 | 1.3473E-02 | ATGAATTCAGGTCTTTTAAGTTTTATTCCATTGTAAGAATAAACAAGTTTGTTCATTCAT |
| A_23_P411431 | 1.3490E-02 | GTCTGTCTGTAAGGAGATGCCATCTACTAACCAATTTGTATTGTGTTTCCAATAAATTCC |
| A_23_P44964 | 1.3501E-02 | ACAGTCCCTCGCTTTTTGTTGTTGTTGGTTTTCTTAACCCCTTTAATGGAACTGCCTGGA |
| A_24_P376391 | 1.3700E-02 | CGAGGCTGTAGCTGGGCTACTTGATCTTGCTGAAAGTGTTTCTAAAGATAGCACCACTTT |
| A_24_P602507 | 1.3747E-02 | CCAGAATCGAAACCGAGAGATTGTTGAGCATGTCATTCATCTGTTCAAGGAGGAAGTAAT |
| A_24_P263767 | 1.3759E-02 | CCGCTACTACAACCAGAGCGAGGCGGGGTATCACATCCTCCAGGGAATGTTTGGCTGCGA |
| A_23_P26223 | 1.3779E-02 | TGGCCACTGGCGTCATCTCTACGCTGCAGATTCACCAAGAGAACATGGGACAGGCTCTCA |
| A_32_P86028 | 1.3784E-02 | TCTAAGGGACTTGCTCCTGATCTTCCTGAAGATCTCTACCATTTAATTAAGAAAGCAGTT |
| A_23_P154500 | 1.3785E-02 | AGGGAGACGAGAACACCACACAAGACATTTTTCTACAGTATTTCAGGTGCCTACCACACA |
| A_23_P29836 | 1.3798E-02 | TGGGGCTTTCTGACAGTTCCATGCTGATGTATCAGGCCATCTGTGTCATGCTTATGTATT |
| A_32_P3932 | 1.3803E-02 | GGTGACAGTTAAACTCCTTTTTGCATGAAAAAATACAGATTCTTATTAAAACAATAATCG |
| A_32_P173058 | 1.3812E-02 | TTCTTCTCCTAAGAGAATAGACAGTTTTTCCAGATTCATCATCATTGACTGTCAAGAAAG |
| A_24_P217904 | 1.3884E-02 | ATTAGAGGAAGGTTGTAAATATTTTCTAGGAGTTCTATTGTAAAGAAAAGTATTTTTGAA |
| A_23_P136493 | 1.3901E-02 | ACCATCGTGGAATCAAACGCTACATCTACATCCACCACTGGGACAAGCCATCTTGTAAAA |
| A_24_P156113 | 1.3907E-02 | GGACCCCATGGAAAAGATGGGGAAGAGCAAAATACATGGAGACGACGCACCCTCCAGGAT |
| A_24_P849801 | 1.3949E-02 | ACGTGTAAGTAATGTTTCTACAGGTCTTTGCAACAAACTGTCACTTTCGTCTCCAGCAGA |
| A_23_P10591 | 1.4003E-02 | AGCTTCCAGCCAAGGATGCCCTGGCCGATTGGAAATGCTGTAAAATGCAAACTAAGTTAT |
| A_24_P269853 | 1.4032E-02 | TTTAAACCCACGAAAAAACCGGGAACGAGCTGCCGAAGTTTTCTTCGAGACCTTCAATGT |

TABLE 3-continued

| 888 Significant Genes Identifed from Cathgen Registry and PREDICT Samples | | |
|---|---|---|
| A_24_P586264 | 1.4033E-02 | GGATGAGACCAATTGACTCTCCCATTGGTTGTTAG ATAGTTGAAATGGTGCGTTGGTGGT |
| A_32_P61657 | 1.4097E-02 | CTTGTCAGTGTAATGAATGTGGAAAAATCTTTTACC GTAAATCAGACCTTGCTAAACATC |
| A_24_P247576 | 1.4120E-02 | ATTCTCAGAGACCAAGTGCCCACTTAGCCGTGAAA AAGATATTTGTTGGCGGCATTAAAG |
| A_23_P49060 | 1.4174E-02 | GAGAAGTCTCAGCTAAGCTCACGTCCTGAGAAAG CTCAAAGGTTTGGAAGGAGCAGAAAA |
| A_32_P189034 | 1.4181E-02 | ACCAACACCCACAGGATAGTGGACGGCAAAGTGG TGTTTGAGACCAACATCACAGACGTC |
| A_32_P220696 | 1.4208E-02 | CTTCATTTAATATATCAATATTGGGCCTAAAACAGT ATTCTGTAAAGCTTAAATTGGTAT |
| A_23_P127467 | 1.4254E-02 | TTCTCTGAAGTGGCTGAGAAACACAACAACAGGAA CAGACAAACTCAACCAGAACTCCCA |
| A_23_P200047 | 1.4255E-02 | AATTAGGAATACTAATTAATTGAATTTTCACTCATG AGTATGTTCTGAATATTTAATATT |
| A_23_P162047 | 1.4259E-02 | GTGTGAAACATGGTTGTAATATGCGACTGCGAACA CTGAACTCTACGCCACTCCACAAAT |
| A_23_P66891 | 1.4331E-02 | TGCCCCACGCAATATTTGGAACACTTATGTGAAAA ATGATTTGTTTTTCTGAAATTCACG |
| A_23_P99496 | 1.4416E-02 | GCTTTTCTAAGAATGGAGTACTCGTTTTCAAGAGA TTTGTCCTAATTATATTTTCCAGCG |
| A_24_P200427 | 1.4501E-02 | GGCCCACGTTTTTATCATTAAGACCTATTTGTTAGC TAGTAGAGCTTTATGTTCGCTGTC |
| A_24_P122524 | 1.4517E-02 | TGGCAGATGATTTGTCATTTATTTATATTAGGTTTT ACTGCCTATTGAGACAACCAGGTG |
| A_32_P127019 | 1.4667E-02 | ATTGGAGGCCATTATAAGAATGTTTGGAAATAGCT TGACCCCTGAAAGATATCTATAAAC |
| A_23_P354827 | 1.4695E-02 | TGACACTGTATTTATCTTCAGTCTCTTGTTGGTATC TAACTTTGGTTCTGAAGTTTATGG |
| A_23_P216610 | 1.4729E-02 | AATTAGTTGATATACTAATGAGAAAATATACTAGCC TGGCCATGCCAATAAGTTTCCTGC |
| A_24_P358328 | 1.4842E-02 | ACCCTATTGTGGCCTCATCCAAACTGTATCTTCCT TTACTATGTATACCTTCACCGTGTA |
| A_24_P400690 | 1.4845E-02 | AGGCGCAGGAGGCAGGAGAAGCGGAGGGCGCAG AGACAAGCGGCCCTACCCAGAGGCCGC |
| A_23_P12896 | 1.4946E-02 | ATTCTGTGGTACAACCCAGGGGTAAACTATTATTC CAGTAGTCAGTACACTTTTCTAGAT |
| A_32_P181271 | 1.4960E-02 | TGTCATTCTGAAAACATCCTATGCGATGGAATGGA GAAGGAAGTGATGACTCAGAGTGTG |
| A_23_P166453 | 1.5036E-02 | ACCTTTGAATTTGCGGATGCTGAGGAGGATGATGA GGTCAAGGTGTGAGGGGCTGGGGCA |
| A_23_P370434 | 1.5079E-02 | TCATGGCAGGCTTTGGCCAGTGAACAAATCCTACT CTGAAGCTAGACATGTGCTTTGAAA |
| A_24_P910262 | 1.5487E-02 | GAGTACAATATTAATGTAGACAAACCATGAAGTTTA TTATTTCATATAAGAACATTACAG |
| A_23_P50571 | 1.5565E-02 | ACTCACAATTCCAAACATACAAGAGGCTCCCTCTT AACGCAGCACTTAGACACGTGTTGT |
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |

TABLE 3-continued

| 888 Significant Genes Identifed from Cathgen Registry and PREDICT Samples | | |
|---|---|---|
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |
| A_23_P253464 | 1.5585E-02 | TATTAGTGGTAACGTGATAGAATTTATTCCCGATAT CTGATGTTACAAACTTTAGGGTCC |
| A_24_P298099 | 1.5597E-02 | AAGTTGTTAAGAGTAAGGCCTACTTTAAGAGATAT GTGAAATTTAGAAGACGACGAGAGG |
| A_23_P103601 | 1.5643E-02 | GGGGTTTCCCTTTGGGCCTCAGTGTTACAAATTAC TAGTGCTATTTTCATTATTATTGTA |
| A_24_P406870 | 1.5647E-02 | CTGCAAAGCGACCCAAATTTGACATGATTGTGCCT ATCCTTGAGAAGATGCAGGACAAGT |
| A_23_P55682 | 1.5655E-02 | GCAAGTGGTCACCAGCATTACACAGCAATGAAGC AGAATAAAGTAGGCCAGAATGCATCA |
| A_23_P253301 | 1.5680E-02 | CTGCAGTAGTTTGCTTTTAGTATTGTTGTTGCACTT GAGCAGAGACAAACCTTTATTCAT |
| A_23_P13822 | 1.5736E-02 | AGGCTTAGTAGCTCAGTCTTTAACAAGGGCTAGAA AAGAATGTAATCTGATATGGAAGGA |
| A_23_P167818 | 1.5751E-02 | AGGAGTGGTTTGCCCGGTACTTCACATTCTGAAAG AATTGTGTTGGCACAGCTCTGTATA |
| A_32_P148275 | 1.6049E-02 | GAAATTACCAAAATCCGGAGGAAGCTGACTTACCA GTTCAGTGAGGCCATTCTCCAAAGA |
| A_24_P156388 | 1.6156E-02 | GGACCTTTTCATTCTTTTCTTTATATTCTAGACAGT CTCTGTTGTCTCATTGTGTTGCTG |
| A_23_P41246 | 1.6212E-02 | GCTGAGCTTCCTCACACACCAGCGCTTCCAGTTCA GTAGCCTACAGCAGGGGAAGATGTT |
| A_23_P168188 | 1.6326E-02 | CTGTGTATATTTACGTTAAACACAATTATGTTACCT AAGCCTCTGGTGGGTTATCTCCTC |
| A_24_P217063 | 1.6513E-02 | ATTTAGGTCTTTCATAGCTTTTTTATTTAAAGGTAT ATGATTAAGATAAAGGAAAAGTAA |
| A_24_P323885 | 1.6516E-02 | AAGTATCCCAAGGGTTACTTTGTCCAGAACACAGA CTTTGACTTCTTCAACTACGCGGGA |
| A_23_P350719 | 1.6551E-02 | CACCCAGGTGCTAAGCTACACAGACTGGATTCAG AGAACCCTGGCTGAATCTCACTCAGG |
| A_32_P31945 | 1.6571E-02 | AATTCAGAAATTGGGTTTTGGTTCAGTGATTCTCA AGAAAAAGATCTCTTGCCCATTAAG |
| A_24_P247044 | 1.6641E-02 | TGATGCATGAGGTAGGTGTTCCGAGTAATATTCTG CATTATATTGAGAGACAAATTTTGT |
| A_23_P58538 | 1.6726E-02 | AGTTGCCTGGATCATTTGAAATTTCTGGGAGTCTG AGGAGTACTGACATAATTACCTGCT |
| A_23_P17152 | 1.6793E-02 | TATGCGTGTGTTTATGTACAGAAATTTTAGTGTTTT TGTTTGTCTGTTATTGCCCAAGGC |
| A_24_P34944 | 1.6828E-02 | TCGAGTCTCCAGCTAACTCTGAAACCTCAGACCTC ACTCTGTACCTGGTGGTAGCGGTGG |

TABLE 3-continued

| | 888 Significant Genes Identifed from Cathgen Registry and PREDICT Samples | |
|---|---|---|
| A_23_P157283 | 1.6898E-02 | CCCTCAACTACCTCCAAAACCGTTGAATATATTCTT TGCTGTCTGCATCTCTTTGAGTAG |
| A_23_P250212 | 1.6925E-02 | GAACTGAATGCAGCCTGGACACTGGCCTCAATAC CTTGTTTAGGATTTCTTCACCCTTTT |
| A_24_P15630 | 1.7103E-02 | TTGTTAGGCTTTTGTGAAGCATTTTTGAACCTAATA AATAATGTCAAAAGTCCCTAGCGC |
| A_32_P63858 | 1.7150E-02 | ACTGAGGAAAATTAATTGCCATTTGTATATTCCTTA GTACCAGATTATCGTTGATTATGT |
| A_23_P47790 | 1.7321E-02 | GGGTCTTCCCAGTTGAGACTGCTGGAGCTGAGAC ACAGTACTCTCTTAAAGAAGGTGGGG |
| A_23_P3681 | 1.7389E-02 | AGACCTTGGAAATGTGGACATAAGCTCTTTCTTTC CTTTTGTTACTGTATTTAGTTTGTG |
| A_23_P147326 | 1.7396E-02 | TCACCAACTGGTACAAGCCCGGTGAGACCCGGAA GATGATCAGCACGTGGACCGCCGTGT |
| A_23_P362183 | 1.7598E-02 | CCAGCAGTTCCTGTTCAACGTGTAAAGAGACCTGA TGTTTTCCCTAATAAAGCTGATAAC |
| A_23_P119362 | 1.7646E-02 | TGTTCATGTTCCAGCTCTACACCATGCGACGAGGA GGTCTCTTCTATGCCACCGGCCTCT |
| A_24_P144025 | 1.7650E-02 | AAGGTGGCATCGTCTCAAAGAACTTTTGACTGGAG AGAATCACAGATGTGGAATATTTGT |
| A_23_P386420 | 1.7671E-02 | GCCATACGAAATTTGAACGTAGCTTTGGAAAAAGG GACTATTTGTGGAGTAATGGCATTA |
| A_24_P71021 | 1.7759E-02 | ATGTCATGAGCCTTTCTCTTGCTCCTGACACCAGA CTGTTCGTCTCTGGTGCTTGTGATG |
| A_32_P192922 | 1.7889E-02 | AGGTATTTCATCTGTTTGTTCTGAAAATGCAGCTG CTGTCTAGATTTATGTGTGCTCTGA |
| A_23_P88831 | 1.8010E-02 | TGTATGAGCAGGACGGCTGCATTGGATTGTACAA CTGTTTTGTGATGCCCCCAGACACTG |
| A_24_P309415 | 1.8044E-02 | GTTTCCTCTGCATTGGGTTTGAAGTAGTTTAGTTAT GTCTTTTTCTCTGTATGTAAGTAG |
| A_24_P376139 | 1.8087E-02 | CCAGAGTTTTGGGGCTTTTTTAGGCTCAACTATCA TGCATTATTATTCTTTCATAAAAAA |
| A_23_P132486 | 1.8128E-02 | GGCAGCTTTTACCACATTAGCTTGTTATTATCAAAA ACTACCACCTACTTTAAACCTGGA |
| A_23_P73117 | 1.8278E-02 | GTGCCTATATGACAAAATCCTGCCTAACCACACTG CTTTATTTTACACTTAAGAAGTTCT |
| A_23_P64792 | 1.8359E-02 | CTGCTGTAGCAATGGCTAAAGGGTCAAGATCTTAG CTGTATGGAGTAACTATTTCAGAAA |
| A_23_P420373 | 1.8411E-02 | CAAAAAGTCTTCCTTCCAAGCGTGTATGATGAAAT GAGTAAATTGATTAATTGGCGTAAC |
| A_23_P45940 | 1.8453E-02 | TATGATGAAACCCTGGAAGATAGGTAGCAACTAGA CTGTCGTTTTTGGTGGAGCGGTTCA |
| A_24_P60972 | 1.8558E-02 | AGAAAGGTGTTTTCAAAAGTATTTGGCCGTAGATT TTCACATCCATCATAAGGTTGGCAT |
| A_23_P16722 | 1.8669E-02 | CCATAAGTTTGCTGTCAGTTATTGTATGGTCAGTA CCCCAGTCCTAGTACACATATTTTA |
| A_32_P132438 | 1.8688E-02 | CACACTGGACAGGTGACTGTATGGTAGAGACTGT GATCTGGGAACTTTTTGCTGTACAAA |
| A_24_P791669 | 1.8743E-02 | CTTCCTGACTACTTGTTCCAAACTCTGAGTCAGAT CTAAAGTCACTTTAAGTCACAGAAC |
| A_23_P167920 | 1.8776E-02 | ATGGGTGAACTGAATTACGCCTAAGAAGCATGCAC TGCCTGAGTGTATATTTTGGATTCT |

TABLE 3-continued

| 888 Significant Genes Identifed from Cathgen Registry and PREDICT Samples | | |
|---|---|---|
| A_24_P13041 | 1.8843E-02 | CTTTACAGAGAGAGGCCTACTAATCAATGTGCTTA GAGAAACAAACTACCTTTACATTCA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_24_P343233 | 1.9025E-02 | TTCGTGCTGGGCCTGCTCTTCCTTGGGGCCGGGC TGTTCATCTACTTCAGGAATCAGAAA |
| A_32_P25273 | 1.9038E-02 | ATTTTAGTGCTTGCCACCACCAGATGAGAAGTTAA GCAGCCTTTCTGTGGAGAGTGAGAA |
| A_23_P66481 | 1.9039E-02 | AGCATCCACAGTGTTAGTCCAAAGGGTCGGACCG TGTCGTCAGCCTAGCGTTTGGTCAGT |
| A_23_P348227 | 1.9110E-02 | TAAACAGCTGTCTTGTCTGTGTGTATATTGTTTGAT CAGGGTACATGGCAGCCAGTCACA |
| A_23_P12514 | 1.9122E-02 | ACCAGCACTTTATACACTTCTGGCTCACAGGAAAG TGTCTGCAGTAGGGGACCCAGAGTC |
| A_23_P100355 | 1.9147E-02 | TGGCCCAGTTCAACGCAGCCAATGACATTGACATG ATCTGCCGTGCCCACCAACTGGTGA |
| A_23_P392470 | 1.9262E-02 | AATACAGTCAACTTACGGTGCACAGTAATATGAAA GCCACACTTTGAAGGTAATAAATAC |
| A_32_P121716 | 1.9280E-02 | AGTCTGTGCCTGAATGTATTTACATCTGTTTGTAG CCCAAAAGCCAAAAGCATACATACG |
| A_23_P86100 | 1.9290E-02 | AAGCCTCGTTTTGTTTTGCTTTGTTGCAAACCTATA AAGCGTTATCACCAGAGCTATCTG |
| A_32_P167904 | 1.9373E-02 | CTACAGTATACTTATGCCACAATGTACGTTTCCAT GCAAAATCTTCTATTTGTAAGTGTG |
| A_23_P90014 | 1.9383E-02 | CTGTTCCGGCATTACTATGTCATGGTCATCTGCTA CGTCTACTTCACCCGCATCATCGCC |
| A_23_P252155 | 1.9412E-02 | CCAACATATCCTGTTCCCCACTACTCATTCTTTTAG CAAATGACAGAAGCTAATTCCTAT |
| A_32_P18159 | 1.9542E-02 | GGCCTTAGTAGAATTAGCTGTATTTAGACAAAGTT AGACTTTAGTGTGAAATGTAATCGG |
| A_24_P481824 | 1.9570E-02 | GGAATATATATGACAATTATTTTCTGTACATTAATG TCTAAACATTATACTTACTTTTTC |
| A_23_P356484 | 1.9592E-02 | AGCCACCTCAGTAAAATTGGAGAGGATTCTTTTGC ATTGAATAAACTTACAGCCAAAAAA |
| A_32_P144421 | 1.9611E-02 | TAATCCATCTCAGAAGTTGAAGATGTGATGTTGCT CGGCCTTTGGAATAATTTTTAAATC |
| A_32_P71476 | 1.9687E-02 | ATGCAAGCTCCTTCTCTCTTGTGGCTTGCCGAGCC TGGTTAGCTCTGAGACCGGAAGTTC |
| A_24_P193257 | 1.9701E-02 | TGATATTTGCTTGGAAATTAAGTTAGTTGAACTCTT TGAACCACAGTAGAAACCGCTTTG |

TABLE 3-continued

| 888 Significant Genes Identifed from Cathgen Registry and PREDICT Samples | | |
|---|---|---|
| A_23_P356581 | 1.9703E-02 | GGGCTAGCTGAAGCCCATTGGTTTCCACGATTTCA ATTGGCTGAGAAGGCAGAGAGCTAG |
| A_24_P224526 | 1.9724E-02 | AAGCCAAAAATGTGATAGCTGTCCTTGAAGAATTC ATGAAAGAAGCTCTTGACCAAAGTT |
| A_23_P211878 | 1.9731E-02 | GCCCCAGCCAACTTCATGGGTCACTTTTTCTGGAA AATAATGATCTGTACAGACAGGACA |
| A_24_P118472 | 1.9847E-02 | CGTGTATCTTTTGGAATCTGAGGAGGAGACTGCCA TTGAGATGTCCCAACACCTTTTTCA |
| A_24_P940166 | 1.9847E-02 | GCTATTCCAAAGATTTCAAGCTGTTCTGAGACATC TTCTGATGGCTTTACTTCCTGAGAG |
| A_23_P201193 | 1.9871E-02 | AACAGGTCCAACCTACATGCCCAAAGGAGCTTCTA GGACACAAGAATTGCATCGATGAAA |
| A_23_P255884 | 1.9962E-02 | GTGAAGCAAGGCTTTGAGCCTCCCTCCTTTGTGG GCTGGTTCCTTGGCTGGGATGATGAT |
| A_23_P318646 | 1.9966E-02 | CTTCACGTCATGAAGGCCATGCAGTCTCTCAAGTC CCGGGGCTGCGTGAAGGAACAGTTT |
| A_32_P91107 | 2.0203E-02 | ACATCAAACCTGCCCAATCAAGGTCTGCCAAAGGA AGGAGTCTGCAAATGACATTTCTCA |
| A_24_P170874 | 2.0433E-02 | CTTACCTATTGTAGCACGGCCGGAAAGTGAGCCG CCTTAGCTGCTGATTGTACTAGAGCA |
| A_24_P409521 | 2.0572E-02 | CTATGAAGTTAGGAAAGCCCTGAAACAAGAGATGG CTAGTGTTTCATCCAGACAAAGAGG |
| A_32_P14894 | 2.0691E-02 | CAAGAATGTGCCCAACCTTCATGTCATGAAAGCCA TGCAGTCTCTCTAGTCCCGAGGCTA |
| A_24_P573533 | 2.0693E-02 | ATTTATTTATTACTTTAGTTACGAATTCCAATATACT TTAAAATGGTATTTGTTTTACAG |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P89249 | 2.0750E-02 | AATGGGTGTTGTATGGGGAGGCAAGTGTGGGGG GTCCTTCTCCACACCCACTTTGTCCAT |
| A_23_P88095 | 2.0799E-02 | ATGACATTCACGCATGCTGGGTATAGGCAAGGAA AGTAATTTTCAAAGTACATTTGCAGT |
| A_32_P228268 | 2.0878E-02 | TTTTTGAAGCTGATCTCTTTACCACGAGGCACATTT CTCACTGGGTGCTGCAAGGAGTAT |
| A_23_P347468 | 2.0928E-02 | TTAGGCATGAAATCAATCAGAAGAGAAAGAAAAAT GCTGGAACATGCTTGATGTATTATG |

TABLE 3-continued

| 888 Significant Genes Identifed from Cathgen Registry and PREDICT Samples | | |
|---|---|---|
| A_24_P810735 | 2.0929E-02 | ACTGGAGAAAGGCCTTATGACTGCAGTGAATGTG GCAAATCCTTTCGCCAGGTATTATTG |
| A_24_P396650 | 2.1056E-02 | ATGGACTCTTCTCGGCTCAGGCTCTGCTGGTGGA AAGCGATTCACTGTATAAACTTTTTT |
| A_32_P220671 | 2.1208E-02 | AGCCTTGGGTGTTAGAATGGTCTGTTTCAAATTTT CAGGCATGCTATTTCGACTTACTTA |
| A_32_P25972 | 2.1257E-02 | CAGTCCGCTTGAAACACCGCTGTAAAAGTGGTAAA AAATGATTTCATTGTGATTATGTTA |
| A_32_P68533 | 2.1285E-02 | TTCTCCATCAGGGGCAAATGTTTACTTGTAATTTTC TTCCTACAGTTCGTGTTAAATTAC |
| A_24_P37441 | 2.1383E-02 | TGGACACGAAGTGATTTTTGTAACCTGAGCAGTTA ATGAATGTGCCAACATTTTCTAGGA |
| A_32_P486620 | 2.1622E-02 | AGATGATAAGTCAGTTGTAGCATCCATCACCGAGA GTCTGCAGAAGAAATCAAAGCACCT |
| A_24_P238427 | 2.1633E-02 | TGTAAGAAGGAGAAAGCCCAAGTCATCACCGAGG AGAAGAATTTCAAAGCCTTCGCTAGT |
| A_32_P57989 | 2.1638E-02 | TTCTGATCAGTTCTTTCTGGATTTTCCGGGCATTTT TGTTACCAGGTGTCTGAAAGATCC |
| A_23_P33643 | 2.1643E-02 | GCAATGAGTGAACTGACTGTGGCTACATTCTTGAA GATATACGGGAGAGACGTATTATTA |
| A_24_P186065 | 2.1650E-02 | GTTAGGATGCATTATAAACTGAAGAGGCTTTTAAA GATTACATGTATTAATATATGTATT |
| A_32_P164630 | 2.1661E-02 | ATGCAGTCTCTCAAGTCCCGAGGCTACGTGAAGG AACACTTTGCCTGGAGACATTTCTAC |
| A_32_P46817 | 2.1687E-02 | CAGCTCATACGCATTCTTTTGTGTTAGGCCACTGA GATTTCAGAGCGTGCCCTAATAAAG |
| A_23_P30634 | 2.1761E-02 | CCCTCTGTACCTCTCATAACTGGTCAACGACTGTA ACAGGTTACATCAGGTGTTTTTCTA |
| A_23_P18142 | 2.1786E-02 | CCAGGCTGCGCAGTGAAGAAAATGAGTAGGCAGC TCATGTGCACGTTTTCTGTTTAAATA |
| A_32_P127997 | 2.1848E-02 | AAAGTTGAAGGCGTCAGAAATGGTTGTCGCTACG GTCTTTTGTATGTTCTTGTGTTGCGA |
| A_24_P750636 | 2.1871E-02 | GGTTGCACCCACCCTGTAGAAGATGGAATCATGG ATGCTGCCAATTTTGAGCAAGTTTTT |
| A_23_P207811 | 2.1984E-02 | TTGGTACATCTGTGTCTGCTAATACAGTTAGCTTT CTCACTTTTCTGCTTGTTTGTTCAG |
| A_23_P58898 | 2.1991E-02 | ATCTATATTTGTTATTACTCAGTGACTCTCTAATTT CACATCAGCATGTTCAGCTTGTGC |
| A_32_P78311 | 2.2068E-02 | AGTTCCTGCAGTAATTATTAGTACCCCATTTAATGG CTAAGTAATTATAGCTAACAGTGC |
| A_23_P129476 | 2.2086E-02 | GCAGTCCAGTTTCTCTCCCCTCTGACCCCTAGAAG GGGAGTTGTAGCCCCATGAACTAGT |
| A_24_P106145 | 2.2102E-02 | GACGCCAGCAAGGTGGTCACAGTGTTCAGCGTTG CTGACGGCTACTCGGAGAACAATGTT |
| A_24_P396881 | 2.2163E-02 | AATTAAAATTCTGAAGCTCCCTAGTTAGTTAGATCC AATTGCTGGTTACATTTTGGGAAG |
| A_32_P160972 | 2.2235E-02 | TTGACATTCTGCGAAAGCAACAAGCAAACTGAAGA CCAACTCCTATGAGAAATATTATGA |
| A_23_P154447 | 2.2303E-02 | ATTAAGGAAGAACCACTTTCTGAGGAAGAACCATG TACCAGCACAGCAATTGCTAGTCCA |
| A_24_P626931 | 2.2322E-02 | AGGCAAGTGTAGAAGTTACATCTCTATTTCCCACA GAGAGGAATATTCACATATGTGCAG |

TABLE 3-continued

| 888 Significant Genes Identifed from Cathgen Registry and PREDICT Samples | | |
|---|---|---|
| A_23_P137532 | 2.2458E-02 | GGAACCCAGTCCAGCCTCCTGGCTGTTGACTTCC CATTGCTCTTGGAGCCACCAATCAAA |
| A_24_P261417 | 2.2585E-02 | GGTAATTGTAGGGCGAGGATTATAAATGAAATTTG CAAAATCACTTAGCAGCAACTGAAG |
| A_23_P143127 | 2.2609E-02 | ATGAATCCAAGTGTTTCATGTGAAGATGTTGAGCC ATTGCTATCATGCATTCCTGTCTCA |
| A_24_P902313 | 2.2766E-02 | GTAAGGTGGGCGCTGTGTCTATTGAGGTGCTTAG CAATAAAGAAAGGTAGTGAGTTGAAA |
| A_23_P134734 | 2.2974E-02 | TTGAAGAAGTCTTGAATAGCTCTTTACTGTCTTACT TGGGGTTGATAAGATTTGAGTGTT |
| A_24_P192627 | 2.2983E-02 | TTAACTTGTAGATTCAGTGGTTCAATACCTGTTTAG TTGCTTGCTAATATTTCCAGAAGG |
| A_32_P146844 | 2.3129E-02 | CCTGTGGGCTGATTCCAGACTGAGAGTTGAAGTTT TGTGTGCATCATCATGTGCCATTAA |
| A_32_P115277 | 2.3296E-02 | GAACCAGTTATATGCAAGGATCATAGCTTGTTAGC AGATCAGGGATTATAATTCAGATGT |
| A_23_P79732 | 2.3307E-02 | CTGTCCTGAAATATTATAAGGTGGATGAGAATGGC AAAATTAGTCGCCTTCGTCGAGAGT |
| A_23_P99275 | 2.3330E-02 | TCAACCCTTGGAATAACAGTCTAGCTGATTGTTCC ACCAAAGAATCCAGCCTGCTGCTTA |
| A_23_P162766 | 2.3341E-02 | AACAAAGGTGTGGTAGACACTCTTGAGCTGGACTT AGATTTTATTCTTCCTTGCAGAGTA |
| A_32_P195401 | 2.3366E-02 | TCGGTATTGTTACGCTGTACTTATGTATTCCCTGTA CCTGAACACTTGTTGCTGCCTCAC |
| A_24_P398691 | 2.3425E-02 | TTTACAATAAATTTCTTTTAAAATATACTTTCTATTT TTCTGTACTGACATATGCAATAA |
| A_24_P127051 | 2.3473E-02 | TGGCGAATTTTCCTTCAGGATATCAAGAAACCAGA CTGATGACTGGGATAGTGGGCTGAA |
| A_23_P209700 | 2.3509E-02 | GTTTTCTTTCTGTGTGTGTGTAAGCCACTGCTTA TAATAAAACCAACAATACCCTCAGA |
| A_24_P627415 | 2.3520E-02 | TCCTAATGACTTTGACCCCAAGACGTTGGTTCAGA TTACATGATGTCAGTAGTGGTGGGT |
| A_32_P217643 | 2.3522E-02 | CTTTGACCTCATAATATTATGTTGGAAATTACACGA TAGTAAACATAATGATAAATGGGG |
| A_24_P89718 | 2.3575E-02 | TACAAGTTGGATTACTATGATGTGTCTCAAGAAGT TTTGGCTGTTTACCTTCAGCAAATT |
| A_24_P15823 | 2.3738E-02 | GAAAACTTTCGTGCTCTGAGCACTGGACAAAAAGG ATTTGGTTGTAAGAGTTCCTGCTTT |
| A_23_P13364 | 2.3802E-02 | GATGAGCTTCAGAAACAAAAAGAAGAGCTACAACG TCAGCATGATCAACTGGAGGCTCAG |
| A_23_P423309 | 2.3886E-02 | GAAGAGGACCTCTCTGTGAAGCAACTGCTAGAAG AAGAGCTGTCAAGTCTGCTGGACCCC |
| A_32_P109835 | 2.3887E-02 | TCCCTTGCTCATTTAAAAAATGTTGGTGTGAATGAT TTGGGGACCCTTGGTCTATCAAAG |
| A_24_P272523 | 2.3954E-02 | CGACCAGATGCAGACCTGGGTGAGCGAAGGCTAC TTTCCTGATGGTGTTTACTGCCGGAA |
| A_24_P854896 | 2.4011E-02 | TGTTTTTCTTAGAGAACATCATTTGTCATATTTATTT GATCAAGAAGTTGAAGATTTATA |
| A_32_P205913 | 2.4013E-02 | TCTCTGGACAAGGAAACTAGCTGGTTTCTTTTGAG TGTTGTAACATTTTATACCATTGTA |
| A_23_P214281 | 2.4031E-02 | TCCTGTTAATCCTCAAATATCTGAACTTCTGTGTTA CCCAAGTGTCTTATACAAGCTTCT |

TABLE 3-continued

| 888 Significant Genes Identifed from Cathgen Registry and PREDICT Samples | | |
|---|---|---|
| A_32_P226149 | 2.4095E-02 | CTCTAAATAATGATGGGGCTAAGTTATACCCAAAG CTCACTTTACAAAATATTTCGTCAG |
| A_23_P63798 | 2.4154E-02 | GGTTGGGTTGATTGTATGTTGAGGATCTATTACTG ACCGTATGATGAGGCCAACTTTTTT |
| A_24_P96527 | 2.4164E-02 | ACACGTCTGTTTAGCCCGCAATTGGAAAGGATATA TGTGGCAATATTAACCTGGTACATG |
| A_32_P139229 | 2.4178E-02 | TCTTTACCTCTCCTTTGAGTTAGGTCCACCTCAGTT TTCTAAAGGTCAAATTAAGGCCCC |
| A_24_P345866 | 2.4413E-02 | AGGAGCTAAAGCTGAAAATTAAATTTTAGATCTTTC AATACTCTTAAATTTTATATGTAA |
| A_23_P32328 | 2.4425E-02 | CTGTTGCAGGCTTAGTGAAAAAGGACTGCTGTCTT TCCTTGGTTCAAGTGTTAGAATGGA |
| A_24_P141520 | 2.4470E-02 | AAATCCTACGGCAAGCTTTGACAATGTAACATCTT TATCTTGTGGTTAGGAAAATGGACC |
| A_23_P146981 | 2.4527E-02 | TCATTGACTGTGGCAATGCTGGCTCTTGTGAAGG GGGCAATGACCTTCCGGTGTGGGAGT |
| A_32_P835626 | 2.4536E-02 | CTCATGGCGGAATTAGAAGAACTAGAACAGGAGG AACCAGACAAGAATTTGCTGGAAGTC |
| A_24_P336577 | 2.4616E-02 | AATCCCTCTGACATCTCCACTGCCCCCAAAGACCT CCGTTGAACATTCTGTATGGAAAAG |
| A_24_P108291 | 2.4646E-02 | AGAGCCTTTCTGAAGAGAATTATATCAAACTAATTA CAACCAAGAAATAATAGTATGAAG |
| A_23_P140848 | 2.4753E-02 | TCATTTTAGAAACATGCTGTTTTTGAAACAGATGTG TGATGGATGTTGTACATCCTTTGC |
| A_23_P259438 | 2.4785E-02 | TGTTTTTGGTTTCTTATTCAAAGATGATAATTTAGT GGATTAACCAGTCCAGACGCACTG |
| A_24_P174903 | 2.4855E-02 | CTAACTGCAGCCTGTAGACAATTTGCTATTAAAGA TTCAGTGCACAAAATATAGCTAACA |
| A_24_P418998 | 2.4973E-02 | TCTGAGGTTCCTACCTGAAACTTCTAACTCTAGTC CTCTGAAAATGTTAACCAAGAATTC |
| A_23_P210323 | 2.4995E-02 | TTACTTTCTTGGCTAACCAGTTTCTTAGAAGAAAAT GTGTCAGGGACTTGGGGATCTACA |
| A_24_P769672 | 2.5121E-02 | TCCTAATTTATTGCATCAAACTACTTGTCCTTAAGC ACTTAGTCTAATGCTAACTGCAAG |
| A_23_P310956 | 2.5145E-02 | CAAGTTCGCCACCGGGGTAGAGCGGCAGGACTG GATGGAGCTGTTCATTGACACCTTTAA |
| A_23_P22672 | 2.5151E-02 | TAATACTGGATGTATGTAAGTGTTTTACTGCACTGT ATTGAATTGGTGTCTTTTGCACAG |
| A_23_P209032 | 2.5170E-02 | TCAGAAAAATGTATACTGGGGAAAAGTTGTATGAA GGTGGTGAACATGGGAGACTTTTAG |
| A_24_P944519 | 2.5223E-02 | TTTTTTCTCACCAAATGACCTTACCTGTAATACAGT CTTGTTTGTCTGTTTACAACCATG |
| A_24_P179816 | 2.5438E-02 | CCCACGCTTTGGACCTTATGCAGCTCTACACCCAC GTGTCTGAGAACTTGCCACCTTATG |
| A_24_P188941 | 2.5461E-02 | AATGTTATGATAGGACATAGTAGTAGCGGTGGTCA GACATGGAAATGGTGGGGAGACAAA |
| A_32_P135634 | 2.5496E-02 | TCGGTGTTGACAGTGTGGCATTTCTGTTATCTAAT TTCTGGTTTTGACTGAAAGCGAAGT |
| A_32_P55987 | 2.5595E-02 | GAAAAGAACCCAGTGCTGTAACGGAAGTCTAATAG CTGCTCAGTACATAGTAAATGCTAT |
| A_24_P359856 | 2.5722E-02 | GCCGAATTCAGTTGACACGAGGCACAGAAAACAA ATATCAAAGATCTAATAATACAAAAC |

TABLE 3-continued

| 888 Significant Genes Identifed from Cathgen Registry and PREDICT Samples | | |
|---|---|---|
| A_23_P205997 | 2.5807E-02 | AAGACAAGAACTTTCTTCTTTACAACCAGCGCTCC AGATAACCTCAGGGAACCAGCACTT |
| A_32_P93045 | 2.5813E-02 | TAAGCTAAATTTTGGTGCACAGCAGGTTGTACATG ATTTCATGTTTATGTAGCAAAATGC |
| A_24_P74571 | 2.5850E-02 | TGGACATCTTATTAGACATGCTTTCAGAGTCCACT GCTGAATCCCACTTAATGGAGAAGG |
| A_23_P421401 | 2.5867E-02 | ACTCACGTTAACTCACATTTATACAGCAGAAATGC TATTTTGTATGCTGTTAAGTTTTTC |
| A_24_P914513 | 2.5869E-02 | CATTTTCTGTCTGTTCTAGTCTAAGAATATTGTTAT AGATGGAAGTTAGGACCATTAGCC |
| A_23_P120660 | 2.5914E-02 | TATGCTATCTGCGGGGCCATTCGTAGGATGGGTG AGTCAGATGATTCCATTCTCCGATTG |
| A_23_P404091 | 2.6086E-02 | GCACATTGTTTTTCCTGCCTTTTTATGGCTGTCTAA AGTCTAGGGAAAAGGGAAGACTGG |
| A_24_P942786 | 2.6251E-02 | AAAGTTGAGGACTAGAGCATCGTAGTGTCTAAGTG CACCTAATAACTTAATGCATGTGCA |
| A_24_P482189 | 2.6313E-02 | TTATCATCTGCGAATACCGTTTTTCCTTTAAATGCA ATGTGTCTTTCAAAGCTGACTTGA |
| A_24_P677525 | 2.6349E-02 | ATAAGCTGAGCCGCGATTCTCCCAGCAACAAGCT GCTGTACGCAGGAGGATCTCGGTGAT |
| A_23_P214789 | 2.6466E-02 | GAACATCTTGTTCTTCAATATCACGGGTTTTTGTTA ATGTTTCATAAGTAATTCTCCCCA |
| A_24_P32849 | 2.6553E-02 | CTTTGGACGTAGTGGAAGCTACAATGATTTTGGCA ATTACAACAATCAGTCTTCAAATTT |
| A_24_P917866 | 2.6866E-02 | ATGATGCTCAGTTTTAAACATTAAAAGTGTACAAGT TGCGTTGTTACAATAAAACTAAAT |
| A_23_P318380 | 2.6972E-02 | GGGACTCCCCTGGTGATGGGGCAGGACCAGAACA ATTAAAAATGTTTCTTCTGTCAAAAA |
| A_32_P123629 | 2.6987E-02 | TGCCGTGACTTATCCAACCTGTGAACTGATTGTGA TCTGCTTGGTAACTTGGTTTGGTGT |
| A_23_P93881 | 2.7014E-02 | TTATATGTATGGGCATTACTCTTAGTGATATTTGTT TCCTGTCCTTTGTTGCTCATGCTG |
| A_24_P58529 | 2.7015E-02 | ATCTGTGACATCTGTTGTAGAAACCTCAATATCGA GCGCCCAACCTACACTAACCTTAAC |
| A_24_P181149 | 2.7208E-02 | TTGTAAGGATATGTCATGTATTTACTGGTTTTTCTT GTATCTGGTGCATAGCCAGAGTTC |
| A_23_P399146 | 2.7326E-02 | CTGGTTTTCCAAAAGGAGAGGTAGATGCATATTTT TGTGTGGAACCATTTATCTTAAAAC |
| A_23_P359174 | 2.7357E-02 | CCAGGGGTGCATACTAGGGTAAAGAAAAATTTTGT AATAGCAACAGTGGTTTGGGATTTT |
| A_24_P652502 | 2.7726E-02 | CATAACCTGTAGCCACAACAACATTGCTACAAATG ATTATATCACGTGGTACCAACAGTT |
| A_23_P87810 | 2.7784E-02 | TGGACATCAATGTCCTTGTCTTTTTGGCCCAATTG TTTTAGTCACCAGAAACTTTTTCAG |
| A_23_P170453 | 2.7788E-02 | AACTTGGACAACTGTCCCTTCAATGACCAGCCAAA ACTGAAAGAGGAAGAGTTCTGCTCT |
| A_23_P55936 | 2.7910E-02 | CTGTGGTCTGCCTCAGTTTCCCCTCCTAATACATA TGGCTGTTTTCCACCTCGATAATAT |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |

TABLE 3-continued

888 Significant Genes Identifed from
Cathgen Registry and PREDICT Samples

| | | |
|---|---|---|
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_23_P124837 | 2.7945E-02 | GTGGAGATTGGAAACCCCACCTACAAGATGTACG AAGGCGGAGAGCCTGATGATGTGGGA |
| A_24_P418619 | 2.8011E-02 | GAGGCTACGTGAAAGAACACTTTGCCTGGAGACA TTTCTACTGGTACCTTACCAATGAGT |
| A_23_P405175 | 2.8063E-02 | CCTTTCCTTATCTGAGGTGTAGTGGTCTAACATTT AGGAAGCCTTGCTTTGACTTTATCG |
| A_24_P48403 | 2.8087E-02 | CTGGTACTAAAAATTGTGGTTGTTTTTTCTGTTTAC GTAACCTGCTTAGTATTGACACTC |
| A_23_P71790 | 2.8147E-02 | CATCCTTTTCAATGCGGATGGTGTCACCCTCCCGG CATCTGTCACCAGTGATCCGTAGAC |
| A_23_P101811 | 2.8347E-02 | TATGAAAGGAGTCAGAGTGGGGTGAAAGTCTATAA ATGTAAGACATTTGGGAAAGCCTTC |
| A_24_P90022 | 2.8352E-02 | CTGAAAGTGATTGGACATTTTATAGGAATTGATAG AGATGTTGGTCCTCAAAAGCTACAA |
| A_32_P58201 | 2.8384E-02 | GAGTCCATAGCACTTTGTAAACTAATGTGAAGTTT CTTGTTGAATCATAAAAGCTACCTG |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P250813 | 2.8452E-02 | GCAATTCATGTAGTTTCTGGGTCTTCTGGGAGCCT ACGTGAGTACATCACCTAACAGAAT |
| A_23_P148015 | 2.8643E-02 | TTTTGTCTTAAAGGTCTTGAGGGTTGACCATGTTG CGTCATCATCAACATTTTGGGGGTT |

TABLE 3-continued

| 888 Significant Genes Identifed from Cathgen Registry and PREDICT Samples | | |
|---|---|---|
| A_32_P104432 | 2.8721E-02 | TGGCCAGAGAGATGTTCTTGTTTCTGGTGTTGTCA CGTCTTCTTGTTTTCTCTAAGTTTA |
| A_32_P405942 | 2.8811E-02 | GGGAAGATGATGAGTGAACAATAAGCCTTGTAATA TACATGGGTATGTATCTTAATGTAC |
| A_24_P931428 | 2.8840E-02 | CAGGCAGAATATGATCTGTGTCCAAAAGTGAACTT GAGTCAGGATTGAATCAATTTCAGC |
| A_24_P912382 | 2.8901E-02 | CTCACCCTGAGACGGGATAGAAAAGGAGGGAGTT GCTCTCAGGCTGCAAGCAGTGACAGT |
| A_24_P246626 | 2.9015E-02 | TTGACAAGTTCTTCCCACCAGTGCTGAACATCACG TGGCTGCGCAATGGGGAGCCAGTCA |
| A_23_P207939 | 2.9101E-02 | GGAAGATTAAGTTCCAGCATTTCTGACTTGTTATTT TGAGTTACTCTGCTACTCTTAGGC |
| A_24_P878388 | 2.9121E-02 | GCCACTTTGACAGGCATTATTGTGGCAAATGTTGT CTTATTGCTTCAACAAACCAGACAA |
| A_23_P433758 | 2.9217E-02 | CAGGGCAGGGCTGGCACCTCTCAACGTCTGTGGA CTGAATGAATAAACCCTCCTCATCCA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_23_P13899 | 2.9303E-02 | GCCTTCCGTGTCCCAACTGCCAACGTGTCAGTGTT GGACCTGACCTGCCGTCTAGAAAAA |
| A_32_P94161 | 2.9340E-02 | TATTCAGTTATAATTGAAGACCTCTACGCTGCACAT ATATAAAGCCGTAAGTTTGGTTTG |
| A_24_P199774 | 2.9375E-02 | GATGGGGAGAGGAGACGCTGCCAGATGGAAGGA CGCTCAAATACTGGACTGCGGCCAACT |
| A_24_P391531 | 2.9473E-02 | TACAGAGCTAAGAATCCTGCTGACAAACCACTAAT TGGAATTTCTACATACAATGTTGTT |
| A_24_P272761 | 2.9477E-02 | ATAAACCAAGTTAAAGTATGGCCCGACCATTTAAG AAAACAACCATCTGAGACACGCAGG |
| A_24_P112087 | 2.9594E-02 | CATTATTGTCCAGTGAATTCAAGACCGAATACAAT ATCGGGAGAAAATACAAACTCCCTG |
| A_24_P316430 | 2.9731E-02 | CAAATCCAGGGACAAATTTAGTGTTTGAAGATGAA ATCACTGCATTACAACCTGAAGTAG |
| A_23_P153086 | 2.9810E-02 | GCTCTTCTGCTACTTCAACATTTTCTAGCTTTTCCG TGTATCTAAACACAATTTGCTACA |
| A_32_P116813 | 2.9814E-02 | TGCAGGCTTAGTGAAAAAGGACTGCTGTCTTTCCT TGGTTCAAGTGTTAGAATGGAGAGC |

TABLE 3-continued

| 888 Significant Genes Identifed from Cathgen Registry and PREDICT Samples | | |
|---|---|---|
| A_23_P310911 | 2.9834E-02 | AAAGTTTGGTTCTGTGTCTGTGTTTTAATAAGACG AGAGGACGAGCGATTGAGGTGTATG |
| A_23_P47004 | 2.9935E-02 | TCTAAACATAAAGAAAGCTCTTCTGTCCGGTTACTT TATGCAGATTGCTCGGGATGTTGA |
| A_23_P501080 | 2.9966E-02 | GAATATTAAGTGCTACTTGAGGTACATGTTCAGAC TAACATTCTTTTGCAGTATAGTGAG |
| A_23_P160881 | 3.0012E-02 | AGGTGTCCCCATAAGCGCCATGTTCATCACACCTG GAGTCACCCCATGGAAAACCACATT |
| A_32_P223370 | 3.0016E-02 | CCTTATTTCTATGCTGAAGCAGATTCTGAACGTCTT AAAATCTGTTCATTATCAGATGCT |
| A_32_P215789 | 3.0027E-02 | ACATCGTAAACTTATAGTCTCAGAAGATAGAAAAA CTGTGCGCTATGGAAATACAACACA |
| A_23_P312752 | 3.0111E-02 | AGTAAAGGCAAGCAGGTGTGAAGAGCAGGGCTCA GCAGCAAGTCACATTTTTCTACTATT |
| A_23_P171324 | 3.0143E-02 | GAGGGCAGTCAGAGGAAGCACAGCAAGAGACATA TCCACAAAGACCATGTGGTGGTGCCC |
| A_23_P254193 | 3.0257E-02 | CACAGATGTTTTTCAAGTTCCTCAGTTTGTACTGAA ATTAGGGATTCATCAGGGCAGGAA |
| A_24_P288722 | 3.0258E-02 | TCCCTAGAGACTACCTAGTTGTAGTGTGACCTACA TTTATAATTATTGTCATGTCCGAAT |
| A_23_P158596 | 3.0261E-02 | TTTCTGGGTGGCTTGCTGGCCACAATCTTCCTGGA CATCGTGCACATCAGCATCTTCTAC |
| A_23_P77779 | 3.0312E-02 | GGAGGAAGAGACCAAGAAATAAAACCTCCCACTTT GTCTGTACATACTGGCCTCTGTGAT |
| A_23_P99642 | 3.0494E-02 | GTAATTTATTTGTTTTGCTACATACTGTTCCAGACT TTTAAAGGGGACAATGAAGGTGAC |
| A_32_P234459 | 3.0509E-02 | AACAGCACGCCTACGACGGCAAGGATTACATCGC CCTGAACGAGGACCTGCGCTCCTGGA |
| A_23_P14769 | 3.0532E-02 | TGTCCTGAAGATCAGTGACTTTGGGATGTCCCGA GAGGAAGCCGATGGGGTCTATGCAGC |
| A_32_P540407 | 3.0729E-02 | GAGTCAAATCAGCATTGACCTGAGTTTGAGTTGAC TTAACATTGATTTCAAGCATTAATC |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |
| A_23_P166716 | 3.0789E-02 | TCTTTCCCAACTGACTGTAGGGTTGTGTCTTTTCC CAATTAAATATCTGCAGAACTTTGG |

TABLE 3-continued

888 Significant Genes Identifed from
Cathgen Registry and PREDICT Samples

| | | |
|---|---|---|
| A_24_P153234 | 3.0813E-02 | GTTAACTTTGGTGACCTTTCGTGTACTTTACACGA AATACCTTATATAATAAGTACTGGG |
| A_24_P893239 | 3.0889E-02 | CATTACTTTCTTGGCTGAGAGCTGTAGTCTGTGGT AGTTGTTTTGTTTTGTTTTTTGTTT |
| A_23_P8558 | 3.1000E-02 | ACAGGTGTCTCCCACTTTGCAACCTACGTGGCAG CCATGAGGGCCATCAACATCGCAGAT |
| A_23_P501732 | 3.1290E-02 | GCTAAGTACAGATCATTCAAGGTGGCCGACGAGG CGGAGAAGTACAATCTGGTCCTGGGG |
| A_24_P374427 | 3.1322E-02 | CTCAGAAATACGAACAGAAATACAGCAGACGAACA TATTTATTGGTACTGAAAAGAGATG |
| A_24_P316059 | 3.1344E-02 | TGTATCGATTTGCCCAGGATCACTTTGACCGCAAC ATAAGCCCTACCATTGAGGTATCTT |
| A_23_P8522 | 3.1349E-02 | GTTGAAATGGTAATCATCTGCATGTTTTTGTCACTT ATTTCAGGTTAGTGATTGCCTAAC |
| A_24_P307869 | 3.1475E-02 | AGCACCCTCGAGACCCCAACCAGATCCTGATCGG CTACAGCCGAGGCCTCGTTGTCATCT |
| A_23_P29851 | 3.1647E-02 | AACCTCAATGTCATCTTGGCCAAGTATGGTCTGGA CGGAAAGAAGGACGCTCGGCAGGTG |
| A_23_P255126 | 3.1777E-02 | TCTAACCAAGGGCCTAATGTTTGTTACAGAAATGA TCCCAGAGACCTACAAGATGTGGGA |
| A_23_P141606 | 3.1899E-02 | GTTGGGTGAGAACAACCAAAATCTTATCATGGTCT CAGTCATAATCATTAGGGGGAACTC |
| A_23_P200138 | 3.1999E-02 | TGCACCAGGGCCTTGTTGAACAGATCCACACTGCT CTAATAAAGTTCCCATCCTTAATGA |
| A_24_P342807 | 3.2141E-02 | CAGAAATTTTGGAATACATTCTATCTAGCACAATTT GAATTTTTAATTATCAAGATTTTT |
| AT_nD_3 | 3.2388E-02 | #N/A |
| AT_nD_3 | 3.2388E-02 | #N/A |
| AT_nD_3 | 3.2388E-02 | #N/A |
| A_23_P101655 | 3.2397E-02 | TAAATATGTATGATGTGTTGTGCTTTTTTAACCAAG GAGGGGCCAGTGGATTCCCACAGC |
| A_24_P726336 | 3.2434E-02 | CTTAGAACATTGTTTAGCTTTCCTAAGTATATATAA ATGCATATATGTATAAAATTGGGA |
| A_24_P532589 | 3.2576E-02 | TCCTTATTTATAGCTCTGATAGCTTTAATTTTCTAA GCAGTCTGTCTATCAGATGTGCAC |
| A_24_P174367 | 3.2699E-02 | GGGTATGAACTAGTCAAAATATGAACCATTATGAT TCAAGTTAGATTTTCCTCTGGAGAG |
| A_23_P156788 | 3.2709E-02 | GGAGCTCTGCCCTGCAGGGAGTTGCCCCAACCCT TTCCGGAACTCAGTCTTTAGAAAAGA |
| A_32_P331052 | 3.3010E-02 | GAGCCTGGGGACAAAGCCTCCAAAAAGCCATCCA GAGGGAGAAGGAAACTGACAGCCACT |
| A_24_P346807 | 3.3168E-02 | AGGTGACAGAGGTACTATTATAATTCTTACTTGCA GAATGTTCAATCTACGAGTGTTCAT |
| A_23_P213045 | 3.3201E-02 | AGCAGGAGCCAAAAAGACCTCACATTAAGAAGCCT CTGAATGCTTTTATGTTATACATGA |
| A_32_P23154 | 3.3257E-02 | AGAGACCCCAACCTGACTCAGCACTATCTGTATCT GAACTGAATTACAGAATTACTGAAT |
| A_23_P384085 | 3.3266E-02 | TCTCTTAAGCCTTCAGTTTATACTCTTAATTTAATTT TCTTTCTGAGCTGGAGAACTGGC |
| A_23_P165346 | 3.3307E-02 | TCCCCTAGTGTCCTTAAGTCCTCCTCCACAGGGAA CATCTATTTGGGCTTTGATGTTTAA |

TABLE 3-continued

| | 888 Significant Genes Identifed from Cathgen Registry and PREDICT Samples | |
|---|---|---|
| A_32_P42197 | 3.3359E-02 | CCTGCTTGGGTGGAGAAGCCATTGTCTTTGGAAA CCTTGGTGTAGTTGAACTGATAGTTA |
| A_24_P98371 | 3.3453E-02 | GAGAGAACCTGCATATATACCAGTCATTATCTGTT TGGTCCTTATACAGTTTTAACTTAC |
| A_24_P881608 | 3.3491E-02 | GGCAGGCCTCGGCCTAAAGGTCTGGAGGTTGCAG CTGACAGTCTTAACATTCCGAAGACT |
| A_23_P55666 | 3.3496E-02 | CCTTTTATATATCCTCTTGAATACAGTTTTCTAGTA CAAGTGGTCTTCAAGAAGCTCATG |
| A_24_P645765 | 3.3500E-02 | TTTTTATTTTCTCTGTTGACTTAGGAACACATCATA AATTCACACCAACTGACACGTTGC |
| A_23_P65068 | 3.3541E-02 | AATGATTCCAGTTGCCATGGCAGGAAACAGGGAG TTATATCTTTGACTTTACAGGAGTGG |
| A_23_P143143 | 3.3598E-02 | AGGCTTCTGAATTCCCTTCTGAGTTAATGTCAAAT GACAGCAAAGCACTGTGTGGCTGAA |
| A_23_P121702 | 3.3762E-02 | AGACTCTCAGCCTTCAGCTTCCTAAATTCTGTGTC TGTGACTTTCGAAGTTTTTTAAACC |
| A_23_P415443 | 3.3777E-02 | GGAGGGCAGAGGGGGTGAGGGTACTATTCTGGAT TGAGAAAACCTATATCCATTCTTTAT |
| A_23_P219197 | 3.3852E-02 | CCCTTGCCTCATCAGTTTTCCTGATTTACAAGTGC AATATTTTAGCCAATGCCTTGGGAG |
| A_23_P146050 | 3.3937E-02 | CAAGCCTAGCATCATGGAGCCAGAAAGTATAGCCT TGCTGTCTGTCTACATCATGATGTA |
| A_23_P102320 | 3.3939E-02 | ATGTCCTGTCACAGAGTGTCCTCTTGGTGTATTCT AAAACGAGCATTCTTTTAAAAAACC |
| A_24_P186944 | 3.3965E-02 | AGGAACCCTGCGGAGGGACTTCAATCACATCGTA GAACTCAGTCTTCTTGGAAAGAAAAA |
| A_23_P62959 | 3.3997E-02 | AGGCCCACTCCAGAATGGCCTCTGGACTCACCTT GAGAAGGGGGAGCTGCTGGGCCTAAA |
| A_23_P56703 | 3.4056E-02 | GACCCCTCGGACTTGAAGAATGGCCATTCCTGTAC TCCACATTCTGGTCTAGCCTTGTTG |
| A_24_P650611 | 3.4079E-02 | CTCAACAGAAGGAGAGGCAGGGCAAGGGAAATGC ATGCTCCAGTAGTTTTTAAAAATCTA |
| A_23_P11214 | 3.4080E-02 | GAAGCTTGAACTGTTTGTTCTTGGTGCCTTGCAGA GAGACTCACAGCAACTCTCCATTAT |
| A_24_P332326 | 3.4117E-02 | ATTTACATTTTATATTTTTGTACATATTGTTAGAGTC AGCCATTTTTAATGATCTCCGAT |
| A_23_P350295 | 3.4126E-02 | TTCCCTTTGTGACTTGAAGAACCCTGACTTTCTGC AAAGGCACCTGAATGTGTCTGTGTT |
| A_23_P154115 | 3.4144E-02 | GGGTTTCCCAGGATGGATTGGTCAGGGGGAGAAA GGAAAAGGCAAAACACTCCAGGACCT |
| A_23_P28953 | 3.4208E-02 | AACTGTGCCTTGTTTCAACAGTTTTTGCTAATTTTT AGGCTGAAAGATGACGGATGCCTA |
| A_32_P193939 | 3.4322E-02 | TTGGGAAACTGTTAATTTGTACTTGGATGCCAAAT ACACCAAAATGAACCCAGCACTTTG |
| A_32_P233250 | 3.4494E-02 | CCTATATACCAGCGTACACCTCTATCAATACATTTT ATGCTGAGACTTTCGGTAAGGAAA |
| A_24_P90349 | 3.4667E-02 | GCTCCTGATGATCACGTATAAAAGTCAGGTGTTCA GCTATCCTCACCGCTACCTGGTCCT |
| A_24_P37020 | 3.4682E-02 | TGCTTCTACGTCCAACTAAAGGGAAAAGAGGGTTG AAGGTCAGCCATGTTAGCTATGAGA |
| A_32_P152046 | 3.4831E-02 | GGCTAATGGCTTCTAAGTAGACATCTTACATTTTT GAGCATCAGAATGCATGCATGTTTC |

TABLE 3-continued

| 888 Significant Genes Identifed from Cathgen Registry and PREDICT Samples | | |
|---|---|---|
| A_24_P916266 | 3.4867E-02 | AGTAAACAGTGTACCATTGTTCTGTGATGGGTTTATAACCAAATTTACAGAGATGTTCTG |
| A_32_P175042 | 3.4873E-02 | TTTAATGTTATAATTCATTCTGATTTCTTGTTTTAAACCATTTCTGAAATATAATATGCT |
| A_24_P876408 | 3.4941E-02 | ACAGCAGCCTTAGTTTAGGAGAAGAGCTAATCACAGGTGACCACTCAAGTTCTTTCAATG |
| A_24_P99984 | 3.5013E-02 | TGAGCTTGGGAGATAAAAGGCAGAACCTGGAATTGTAGCATCCAAGGACAAAAAGAATGT |
| A_23_P131308 | 3.5017E-02 | AGCTATTTGCTACATCCTGTTCGAGAAACGCATTGGCTGCCTGCAGCGATCCATCCCCGA |
| A_23_P23356 | 3.5047E-02 | ACCATTTGTAAGAAAGCCAAAAGACTTTTGCCAGATTTCATATTTCCCCTTTTCATGTAC |
| A_32_P32835 | 3.5123E-02 | TCTTGGTTTTCTCTTCATCTTCAACAAGTCAGTCTCTCTCAAGGGTCTCACGTTGCAGCA |
| A_24_P916586 | 3.5234E-02 | CGTGCTTTGATTTCCTATCAGTCACTCTTAAGAACATACATATTGTTTAAGTAACTCGGT |
| A_23_P139476 | 3.5256E-02 | TCAGCCTCCTCATCTGGGGGAGTGGAATAGTATCCTCCAGGTTTTTCAATTAAACGGATT |
| A_24_P902091 | 3.5334E-02 | GCTCTAAGATTGATTAGGATGATTGTAGCTAGAGTCTTGAATTCTATCTGTATACGGCAG |
| A_32_P101799 | 3.5360E-02 | TGGGAAATGACAAAATCTCCCCCAGATTGATTTTTTACGTGTTGTTGGAAATAACCACAT |
| A_32_P221452 | 3.5419E-02 | ATATATATGACTACTCCTCTGTCCCTTAGGTGTATAAGACTTAGCTGGAATCCAACTAAA |
| A_32_P38404 | 3.5448E-02 | TAAACACATCCTAACAGGGAAGGTAAACTGTACGTCCATCAGTACCACTAGAGGGCATCA |
| A_24_P180680 | 3.5470E-02 | TTTTCCCTGCAAGCTACATCCTACTGCTTTGAACTTCCAAGTATGTCTAGTCACCTTTTA |
| A_24_P526623 | 3.5474E-02 | AAATTGTGACATTTTCCTTCCCCAGAATTACTTCGTTTTATACATTTCACTTCTCTTCTG |
| A_24_P307368 | 3.5714E-02 | TAAGGAGGTCATGGTGGCCAAGAAGGATGTCCACATGCCTAAGCACCCAGAGCTGGCAGA |
| A_23_P35645 | 3.5789E-02 | CAGCTGAAAGACTCGAGCCCGTGCTGTCTCCTTTGGTTATTATGACATGAAAGTGTATCA |
| A_23_P406521 | 3.5968E-02 | CTGTCAAAATAATCCAAACAGGGAAGGAACGTACAAGTAAATAACAAAAGCCCCCATACT |
| A_24_P248240 | 3.5999E-02 | GCTGACTTTGGCTTTCACATTTGTTCTTTCCAGAGCTAACTGATAAGAGTGGAGGAGGAA |
| A_23_P402604 | 3.6082E-02 | AGGCATTTGGTATGTATCTGAATTAATTCTCACTAAAATTCAGCAAAGGACTTGATAGCC |
| A_24_P898945 | 3.6108E-02 | GCTAAGCAAATTGATATTTGAAATGAAAGATGGATTAGGTGAGAGACTTAGTTTATTCAG |
| A_32_P57453 | 3.6113E-02 | AACCAACAGTAACAAAAACCTCAGTAACCAAAATAAAGTTCTATATTTTAAAAAAGGCAC |
| A_24_P298320 | 3.6160E-02 | TTTAAGGAGGGAGTCATGGTGGCCAAGAAGGATGTCATGCCTAAGCACCAGGAGCTGGCA |
| A_32_P82863 | 3.6222E-02 | GTGGGAGTACTGGATATTGTAGAGACAGATATCATCAGGGCAAGGAGATTAAAGATTTTT |
| A_32_P215856 | 3.6276E-02 | GGGGCTTTTTACTCTTAAGCGACATATGTATTAGAAGTTGAATCACGAACTGATAAAATG |
| A_32_P192430 | 3.6318E-02 | GGTGTTGTATGTATGGTGACTTGTGGATTTATGTTTCAGTGTACTGGAAACTTTCCATTT |

TABLE 3-continued

| 888 Significant Genes Identifed from Cathgen Registry and PREDICT Samples | | |
|---|---|---|
| A_23_P22682 | 3.6327E-02 | ACAGTGACTGATGTTGGTTGTAATGGTTGGGTTTAGGATGAACCATTTTAAGGATGCCAA |
| A_24_P186216 | 3.6425E-02 | CTTGCAAACAAGCAGATATTTGTGTGGTTAGTAAATCATACTTCACACTTTTTCTCTAGC |
| A_32_P87872 | 3.6522E-02 | ACAGTATTAAATGGCACCTGATTTTGTGTTAAATTTTAGTTCCCTGTTGTTTAATGCCCC |
| A_24_P213110 | 3.6603E-02 | TGAATGCTAAAATGTACAAGTGGGATTGTGAAGATTTACTGACATCAAAAGTTCTTCTGG |
| A_23_P157022 | 3.6709E-02 | GTAGACGGGTTTTAGGAGCAGGTATCCTTCTTTGAGCAAGAGTGTCATGCAAGTTAGGAA |
| A_32_P139196 | 3.6813E-02 | GAATTGAAGGAGACCTAATAATTGTGTCTTTTTGGTTATTTAGTGACAAACGTGGCTTTC |
| A_23_P80891 | 3.6890E-02 | GACAGTGAAACTCGGAGACTTTACTATGATGAGCAAGAATCTGAGGCCTACGAGAAGCAT |
| A_23_P208812 | 3.7010E-02 | GAAGAAGTCGTTGATGTGATTTTTGAGGAAATGACAGATGTGACTTTGGAACCAAACTTG |
| A_32_P131367 | 3.7026E-02 | CTGTCTCATCTTGATAGTCATTTTCATGATCACAAAATTTTTCCAGGATAGACATAGAGC |
| A_24_P312417 | 3.7046E-02 | AGAGGAGGAAGATTTTTAAAACCTTTATCATTCAGCATTTGTATTTTATGGATCCCCAGG |
| A_23_P140614 | 3.7154E-02 | AGGCAGACCTGAGTGAGCTGGTGAAAAAACAAGAACTTCGCTTCATTCAATACTGGCAAG |
| A_23_P37685 | 3.7206E-02 | GTTAGTGATGGTTTCAGACAGAATCGTGTTCGTGTCTGTTTTGCTCGATTCTTTTCCTAA |
| A_23_P78152 | 3.7225E-02 | TACTGACTGTTAGGTATCTATGCCAATTTGTTTTCATACTTCAGTTGGTTTTGGAATCTG |
| A_23_P141315 | 3.7286E-02 | AGCCAGAAATCGAAGGTCACAGGAAGTTGTCACTGAACTTGGCCCGTGTCTGCTACTCTG |
| A_32_P166272 | 3.7461E-02 | ATACATTTTAATTCCTCACGTTTTATATTGGAGAGTTCGGTACAGACTGTCCATTACTGC |
| A_23_P41025 | 3.7517E-02 | TTAACATTTTAAGCAGACTGCTAAACTGTTCTCTGTATAAGTTATGGTATGCATGAGCTG |
| A_24_P67806 | 3.7555E-02 | TGCTATTTTGACTAGTCTGAGTGAAAAGTGAGGATTTAAATGAAGTAACCCCTAAACTCA |
| A_32_P89837 | 3.7585E-02 | TGGGTCCTGTTTTCCGCTCTTCTAAGAAAAAACAAAAAGACCGTGAGTTATTGCCCAGCA |
| A_32_P17635 | 3.7661E-02 | ACTTTCCTTGATAGTGGGTCAGTCATCATTTATAAGTGCATTTCTAAAAATATTGCTTAA |
| A_23_P88439 | 3.7746E-02 | TGATGATATGTATGCATCATTATAATATAGTATAGTTTCGCTGCCCTAAACATCCTCTGC |
| A_23_P216693 | 3.7918E-02 | CATATCACAAACACAACATTTGATTTTGATCTTTGCTCGCTGGACAAAACCACAGTCCGT |
| A_23_P353905 | 3.8094E-02 | GACTGTAAATGTTTAATATGAATATAGTGTTCTTTTGAAGTAAGGCCAGCTGTTGAACGG |
| A_24_P306094 | 3.8124E-02 | GAACCCGTGTGTGATATAGAGGACTCTTGATAAAAACTGTGTTTATATAAAGATGGTGTC |
| A_23_P434040 | 3.8345E-02 | CAGGCGATGACTTTCAGTGAAGGAAATGACCTGTCTAGGGCCACATAATACCTGTTTGAA |
| A_24_P349869 | 3.8381E-02 | CTTGTGCACAGGTCTTCGGGGCTTCTTGTTTCACAGCTTTGGCAGGGGAACTGGTTCTGG |
| A_24_P218688 | 3.8396E-02 | AACCACCCATATTCAGGAGAAGAGGACAGACACGGCACCTCTGAGTCACCCCTCTCCTGT |

TABLE 3-continued

| 888 Significant Genes Identifed from Cathgen Registry and PREDICT Samples | | |
|---|---|---|
| A_24_P548354 | 3.8493E-02 | TAAGTTGGACTAAATGCTCTTCCTTCAGAGGATTA TCCGGGGCATCTACTCAATGAAAAA |
| A_32_P783 | 3.8628E-02 | ATCAGCCAGTACGCCAAGTACATTTGCTCTTTTCT GTGGCAAAACCAAGATGAAGAGACG |
| A_23_P104493 | 3.8660E-02 | AAAGCCATGGACTTCTATGATCCAGCAAGGCACAA TGAGTTTGACTTCATCTCAGGAACT |
| A_32_P2050 | 3.8669E-02 | AGGGACTGAAGGATTAGAATGAGGGAAGTAACCC ATGCACTGCTTATTTGAGATGGGGAA |
| A_32_P115947 | 3.8778E-02 | GTCTGATTTTGCCTTGTGGTGATAGATTGTCATGA ACACAATGTCCTCTGGAGAAATCTA |
| A_23_P430411 | 3.8830E-02 | TGTCCCCACAAAAAGTGACGCTTTACCTGCGACCA GGCTTCGGGTCCTTCGTGGACAAGA |
| A_23_P141856 | 3.8837E-02 | AGACCTTGTTTACTAGAAATCAGGTGGCCAAAACA TGACTCTCAGAGTGGGGCTTCATGA |
| A_32_P223551 | 3.8937E-02 | TGTTTTTTAAATCGCCTTGACAATCATCAGCTTTTG AAATGTGAATTCCTATTGCCAGAG |
| A_32_P105110 | 3.9322E-02 | ATTTGAGCTGTGAGTTGACAGTGTAACACTTCTCA TAAACTGCATGCATTTGAAATATGA |
| A_24_P563736 | 3.9508E-02 | TTTGAATTAAAATAACACTGATGGGACTCTTAGCAA TGTTTTACCTCTTGGGAATCACTG |
| A_23_P56922 | 3.9626E-02 | AAGTTCTTCTCCCAGAATATGGAGGCACCAAAGTA GTTCTAGATGACAAGGATTATTTCC |
| A_23_P212568 | 3.9655E-02 | ATTTGGCTCCTATTGAAGATGGCTTCTAAGAAAAC AAGATGCACAGAGGACACAGAAGGA |
| A_24_P503710 | 3.9748E-02 | AGGACAAGTCAGAATCAGGGGTGTCAACTGAGAT GCAAATATAGGCAAAGGAGCTGACAA |
| A_24_P738859 | 3.9928E-02 | ACATTCAAATCTACCTAATCAACTGTATCTTTACTA CCTATATAAGTTTTGTATGTGAGA |
| A_24_P171041 | 3.9931E-02 | AGGACCAGAAATGCACTTTGTATTACAGAGTGTTA AGGCTGGTTGCTATAGTATGGAACA |
| A_32_P167705 | 3.9955E-02 | ACGGTCAGTCCTACTGCTGTATGTCAGGTTTGCTC ACAATGAGGTATTCCCACATAGAAA |
| A_32_P195924 | 4.0012E-02 | GGGGTTCTGTTAATTGATCTTAGCCTTAGGGTAAG TAAAATGGGTCTTTTTATATAATAG |
| A_24_P912985 | 4.0081E-02 | GTTCAGACCAACTCCTGGATATGAGCTCAGCCTTC AGCAAGACAACAAAGACCCTGGCCC |
| A_23_P211522 | 4.0547E-02 | AGGACCGCAAGAAAGCCGTCCTGTCCGACATCGG TGTCTCGGCCTTCTGGGCTTTCCTCT |
| A_32_P19135 | 4.0605E-02 | ACTGGCAAATCATGTCTCCTTCATCAGTTCATTGA GAATAAGTTCAAACAGGACTCCAAC |
| A_24_P141736 | 4.0641E-02 | AACAATCTAGGTTTTAGCTGTATGAGCTATGTTTAT TATGGTGCTAATGTTCAGTAGCCA |
| A_23_P109733 | 4.0642E-02 | CTGTGTGATTAGAGTCTGGCTTTCAGGAATATGTA ACACCCACTTTTCTTTCTTTTTTCT |
| A_24_P116378 | 4.0647E-02 | ACACTGTCAATAATTATCGCTTTAATTGGTGTTAAT ATTTGGTAGTACACAGGTTCTCCC |
| A_23_P12680 | 4.0696E-02 | CCCTAGCCCCTGGCAGACATAGCTGCTTCAGTGC CCCTTTTCTCTCTGCTAGATGGATGT |
| A_23_P142447 | 4.0735E-02 | ATTTCTGTGTGTGTCAAAGGGGACTAACAGCAGAA TCTACCTCCCAACTGCCATGTGATT |
| A_23_P24763 | 4.0815E-02 | CTCCCTCCCAATTGGAAATATGAATCATCTACAGC CTCTGCCCTGGTCGCATAAATTTGT |

TABLE 3-continued

| 888 Significant Genes Identifed from Cathgen Registry and PREDICT Samples | | |
|---|---|---|
| A_32_P132276 | 4.0819E-02 | TCCATGGAACGGGCCCGTTTGTCACTAAAACCTGT GCTGGTTAGGATTTGCTGTATTTTA |
| A_23_P42695 | 4.0878E-02 | GCTCTGGTAAAAGATAGATTTGTAGCTCACTTGAT GATGGTGCTGGTGAATTGCTCTGCT |
| A_23_P207387 | 4.1046E-02 | ATTCTGAAGTGTATTCTACATAAACTCTCAGAGGAT GCCCAGCAGGATGGAGTCCCAGTT |
| A_23_P566 | 4.1082E-02 | TTGTAAATACGTGTCGCTCAGATGTCCTTTGAAGT GGGAGGGAATCAATCCGGGGATAAT |
| A_23_P123330 | 4.1405E-02 | TCTGAAATAGAGTACTATGCTATGTTGGCTAAAAC TGGTGTCCATCACTACAGTGGCAAT |
| A_23_P146284 | 4.1493E-02 | ATGCTGAGGAGAACTACAGTTTTTCTTTTGAATTTA GTATTTGAGATGAGTTGTTGGGAC |
| A_24_P842962 | 4.1620E-02 | AGAAGTGTGACTGTAAACATATTAGTGTTTCTGTTA GTGTTGGCATAAGCTTGCCTTTTT |
| A_23_P202737 | 4.1636E-02 | TTTTATAGTACAGGTTTTGTAATGTTACATGTGATG ATATGAGCTCCCACCTTATATGGG |
| A_24_P307486 | 4.1816E-02 | AAGGATTTGATTATAAATGTTCCTCCTTTCACAGAA TTATTCCAGGGTTTATGTGTCAGG |
| A_23_P364792 | 4.2036E-02 | ACATCAAGACTCAAATTGCAGTGCCACAAGTAATA AACATTTATTGGAAGATGAAGAAGG |
| A_23_P213441 | 4.2107E-02 | GGAACCAGCAGTGTTTTTCCCTGAGTAATTATGAA CTTAGTCAAGATCAGAAGCTGGGTT |
| A_32_P14744 | 4.2329E-02 | GTCATCGTCCGGTTTCTCATTGTGATGATGAAGCA TGGTTACACTGGCGAATTTGAAATC |
| A_23_P435051 | 4.2377E-02 | AGTTGCCCAAGATCTGATACAAGGTCGGGGTGTC TATGCAAAGGAAGCTCAGTTTTCTTT |
| A_23_P431638 | 4.2416E-02 | TTGTATTTAGAGAATGGCTCTTGCCACTGTTATGT ACACACAGATCGTGTGTGTAAACAA |
| A_23_P156355 | 4.2417E-02 | AGGTTTGGACCTGCCATATTTTGTTTTATTCTGTGA TCCTAACTAGTTCCTTTTAATAGG |
| A_23_P93780 | 4.2721E-02 | TCGCTGTCTTTGTACCCAGCCTGCATTCTGTTTCG ATCTGTCTTTTAGCAGTCCATACAA |
| A_32_P3342 | 4.2728E-02 | TATAGCATTTTCTGAAGATCATGTTGTACTCTTCTT TCGTCTAGATGATTTGGTCAACAG |
| A_32_P27763 | 4.2738E-02 | CCAGATACAACAAGAATTTAACATGGCAGCCAAAC CAACCCACTAACACACATTTAAATA |
| A_23_P132874 | 4.2771E-02 | TGTGTCAACAGATGGATCACTGGAATGTGGGGATT CTGAAACAGAAATGAAACTGTCCTT |
| A_23_P78628 | 4.2804E-02 | TAATAAGCTACTTGAACACAGCTTCATCAAGCGCT ACGAGACGCTGGAGGTGGACGTGGC |
| A_24_P336137 | 4.2854E-02 | GGAAGACATTGACCACAGAAGGAGTGAGGAACTT AGGAAGGGTCTTGCCACCACTTAATC |
| A_23_P83159 | 4.2889E-02 | TGAATATTTGTGTGCTATCGGTAGCTGTGTTTCTTT GATCAAATGTTCCTGTCCTTTTGC |
| A_23_P88470 | 4.2928E-02 | TGTATAGCAGAGGATCTCATTTGACTTTGTTTTGAT GAGGGTGATGCTCTCTCTTATGTG |
| A_24_P136441 | 4.2940E-02 | AACGCATCCCAAGATTGAAGATCTTTTTCTCTTTTT TAGACCTAGTCAGTTGTTTTCAGG |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |

TABLE 3-continued

| 888 Significant Genes Identifed from Cathgen Registry and PREDICT Samples | | |
|---|---|---|
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P202496 | 4.3346E-02 | ACAGCTATTCCCATATTCTAGGAGTGGCCTAAGAA ATGCGTGTTTCAGTGACTAGATTAT |
| A_23_P97770 | 4.3385E-02 | ACCAGGAAGATTTCTGGAAAGTGAAGGAGTTCCT GCATAACCAGGGGAAGCAGAAGTATA |
| A_23_P23443 | 4.3673E-02 | GACCCGGATTGCGTTTGCCTTAGCGGATATGTTTA TACAGATGAATATAAAATGTTTTTT |
| A_24_P287503 | 4.3704E-02 | TGGCTGGGACCATCCCGTCCGAGTCTGCTTCAAC TGCAATAAAAAGCCCGGTGACCTTTA |
| A_23_P81973 | 4.3716E-02 | AGCTTGGACGACATGGGATCCGCTGTAACTCTGT CCTCCCAGGGTTCATTGCAACACCCA |
| A_23_P40611 | 4.3807E-02 | ATCTGATCTTCCCAGACTGTCTGGCACCACGAGTC ATGTTGGAACCAGCTGCTGAGACCA |
| A_32_P225604 | 4.3854E-02 | AAGCACTTCATGGGCCAGAATGTTGCAGATTACAT GCGCTACTTAATGGAAGAAGATGAC |
| A_23_P85371 | 4.3873E-02 | GCTGGATTGTCACTTTTGGGAGAAGAACAGATTAA ACCTGTTAATCCTGTCTTTTGCATG |
| A_23_P93750 | 4.3878E-02 | ACCTGAAGTGTGAATGAGTTTCCTTGACTTACACT AGATTTTGTTTTGGCTTATAATGAC |
| A_24_P391868 | 4.3917E-02 | CACACAACACACAAGGGAGAGAACCCCCAGATGA GAAAATAGGAAGGAGCAATCATTTGT |
| A_23_P200015 | 4.3997E-02 | AATGCAGAGGGAACACCAGAGGACGTTTTTCTTCA ACTCTGCACAGCTATTGACTCTATT |
| A_23_P34018 | 4.4089E-02 | TGGCACACATATTTATGCTGTCTGAAGGTCACGAT CATGTTACCATATCAAGCTGAAAAT |
| A_24_P583040 | 4.4119E-02 | TACTTGATAATATCTTCCAAACGATTAGAGAAGACA TAACATTCATTAAGAATACACATA |
| A_23_P214666 | 4.4186E-02 | TCTTGAACAGACAGAAGGATGTAAAGGATGGAAAA TACAGCCAGGTCCTAGCCAATGGTC |
| A_23_P14432 | 4.4187E-02 | ATGGTGGTATTGTGACCACTGAATTCACTCCAGTC AACAGTTTCAGAATGAGAATGGGAC |
| A_32_P95739 | 4.4196E-02 | CTATAATGGTTGGAACTAAATGTCACCAAGGTGGC TTCTCCTTGGCTGAGAGATGGAAGG |
| A_23_P150903 | 4.4336E-02 | ATGGCTGGGATCCCAAAAGCAAAGCAACGCTTAAA AAGGCTCCGAAATATTCACTACCTC |
| A_23_P335039 | 4.4358E-02 | TGATGCCTGAAGTAGGTGTTCAGAGTAATACTTTG CGTTATACTGAGAGAGAATCTGAAT |
| A_23_P53646 | 4.4493E-02 | AAATTGAAGTTTTAAGGGACGTCAGTGTTTATGCC ATTTTTCCAGTTCCAAAATGATTCC |

TABLE 3-continued

| 888 Significant Genes Identifed from Cathgen Registry and PREDICT Samples | | |
|---|---|---|
| A_23_P146417 | 4.4503E-02 | TTGCAGAGACCCAGCAGATGTAACTCTCATTGTAG CCATCCCAAAGAAAACCCTTCTTTG |
| A_24_P929867 | 4.4531E-02 | ACACAAAAGGGACATGGAGGTAACAAAGAGCAAG AGAAGTACCAGCAAGTCCATTAGCCA |
| A_32_P61684 | 4.4628E-02 | GTAATGGTACCTGAGGAACTGAAATGGGTATTTGT TTTCGTATGTTTCTGCCAGTAGTAT |
| A_23_P20752 | 4.4709E-02 | AGGATGAGCGTGAGCCAGAAGCAGCTGTGTATTT AAGGAAACAAGCGTTCCTGGAATTAA |
| A_23_P157926 | 4.4722E-02 | ATGTGTCAGAGCCCTTCACACAGTGGGATACTAAG TGTTTGCGTTGCAAATATTGGCGTT |
| A_23_P76969 | 4.4780E-02 | AGTGAGTGTCCTGCAGCCCTTATTCCCTCCATAGA AAGCATCCTCAGAGCACCTTCCCTG |
| A_32_P134846 | 4.4817E-02 | ATTGCCACCTGGGGTATCGTTGTCATGGCAGACC CCAAAGGGAAGGCCTACCGCGTTGTT |
| A_23_P78499 | 4.4849E-02 | ATGCAGAAACAGGAGGTGTGAGCCAGCAATCAGA TGGAGATTCTAGTGCTCATGAAAGTT |
| A_23_P129466 | 4.4874E-02 | TACAAGCAGCCCAAGAAACTCTGAACGGGACCCA ATGGAGGCAAACTTGAGCAAATAATT |
| A_23_P99226 | 4.4887E-02 | ACTTGAATCTTGCTGCTAAATGTAAATGCCTTCTCA AATGACAGATTCCAGTTCCCATTC |
| A_24_P76911 | 4.4991E-02 | TGAGGGATAGGGGACATTCCATCCCAAGCTTCTC CCTTACCCACACCTATCCTTTTGAGG |
| A_23_P34093 | 4.5021E-02 | CCACGGAGGCAGACGAGCTGATGAAGAGAGTGG GTTTCCAGTATGAGGGCACCTACAAGT |
| A_32_P168756 | 4.5077E-02 | GCCAGAAAATGTACTCAGACTTCAGTCAACCTAAT GGGACAGTGTACTCACACTGTGGTT |
| A_23_P54556 | 4.5102E-02 | TGGCAGTATTGTAGCTGATCGGGAAATGTTTGATA TCTCAGCAATTTTGCATTTTTGTGT |
| A_23_P3651 | 4.5138E-02 | AAGTTCCTATCGGTCGTATCCTCTGTCCTGACCGA GAAGTACCGCTGAGCGCCGCCTCCG |
| A_24_P145787 | 4.5203E-02 | TCTGAAGGTCACGATCATGTTACCATATCAAGCTG AAAATGTCACCACTATCTGGACAGT |
| A_23_P302654 | 4.5220E-02 | TGCACCTTTGTACTTCTTTATTGAGTGTACTGGCT GGCAAGAGTTCTCTCTTCTGTTGGT |
| A_23_P502470 | 4.5235E-02 | ACAAAAATGAACTGAAGTTTCACATGAGCTATTTC CATTCCAGAATATCTGGGATTCTAC |
| A_24_P134195 | 4.5328E-02 | AATTCCTTGCACTCTAACCAGTTCTTGGATGCATC TTCTTCCTTCCCTTTCCTCTTGCTG |
| A_24_P780052 | 4.5429E-02 | AGGCATCTTATGTTAATCTACCTACCATCGCTCTG TGTAACACAGATTCTCCTCTGCGCT |
| A_23_P141405 | 4.5476E-02 | AACTGGTTGACTACAAGTCTTGTGCTCATGACTGG GTCTATGAATAAGAGGTGGACACAA |
| A_23_P56553 | 4.5498E-02 | CCTGCCGTTTTGTCATAGGTGAGCTCCTTTGTGCA TTTTAAGCACATGTAAGTGGTTCAG |
| A_24_P565908 | 4.5644E-02 | TGCATAGTCCTCCGCTACACAAAGCTGACCGATGC CCGGACCAGTGTGAGGCCAATGAAT |
| A_24_P919840 | 4.5713E-02 | CCAAATTGAGGATTGTGTCTAGGAAATCTGTAAAG CCATACTACTGTGTTCATTAGCATG |
| A_23_P325661 | 4.5735E-02 | TGCTGGTGGCTTATACAAAAAGTTTACTTTCTTCAT GGATATTCTTGGTCTCACATACTT |
| A_32_P49832 | 4.5739E-02 | GACACAGTTAATATGCCAGAAAAAGAAAGAAAAGG AGTTAGTAACTACCGTTCAGAGTTT |

TABLE 3-continued

| 888 Significant Genes Identifed from Cathgen Registry and PREDICT Samples | | |
|---|---|---|
| A_24_P198820 | 4.5765E-02 | GCAGTTAGCACAAATTTGCAAGTAGAACTTCTATT AGCTTATGCCATAGACATCACCCAA |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_24_P161933 | 4.5792E-02 | AGGGCACGTGCGTGGAGTGGCTCCGCAGATACCT GGAGAACGGGAAGGACACGCTGGAGC |
| A_23_P121875 | 4.5799E-02 | TTAAAACATGTTGGCTACAGTAGCACTTTACTGAA GTAGTATTTTTTGGTATCTCTAGCC |
| A_24_P97785 | 4.5810E-02 | AGACATATACTTCATTTGGGAGCAAATACTTATTGC CTTGAAAAGTAGCACTGTAATAGC |
| A_24_P285880 | 4.5895E-02 | AAGGTATTTTTCCTTTTCCCTCTTACTGGATTTTTC AATTTTCAAACCATATGGCCTAGG |
| A_24_P607880 | 4.5977E-02 | AATGGCCTTTTTCTTTTTCAGTAGTACATACACATC TGTGTCATTTGTTGAATGACGACA |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P209962 | 4.6184E-02 | TCCTTTCAGATGCCTGGATGAATTTGATGTCTACA TGGATATGGTTAATAGGAGAATTGC |
| A_23_P313632 | 4.6221E-02 | CGGAACAGCTCCTTACTCTGAGGAAGTTGATTCTT ATTTGATGGTGGTATTGTGACCACT |
| A_24_P221366 | 4.6257E-02 | TATTAGGCCGTGCTCCAAAGTCATCGTCCGGTTTC TCACTGTGATGATGAAGCATGGTTA |
| A_23_P398005 | 4.6281E-02 | CTACGGTTTAAGCCTGAAGAACTGGTTGACTACAA GTCTTGTGCTCATGACTGGGTCTAT |

TABLE 3-continued

| 888 Significant Genes Identifed from Cathgen Registry and PREDICT Samples | | |
|---|---|---|
| A_32_P142128 | 4.6510E-02 | TGCTTGCAAAGGGTTGTAAAACTTTATTGTGATTAT TCTTGCTTTAAGCTGAAACATCCC |
| A_32_P50123 | 4.6670E-02 | TCAAAAAGGATAAGGAGATCATAGCAGAGTACGAT ACTCAGGTCAAAGAGATCCGTGCTC |
| A_32_P220798 | 4.6798E-02 | TTGGGTAGATATTTTTTCTGAATACAAAGTGATGTG TTTAAATACTGCAATTAAAGTGAT |
| A_23_P159920 | 4.6801E-02 | TTTTGGGGTAGATGCGGCCCCGATCAGGCCTGAC TCGCTGCTCTTTTTGTTCCCTTCTGT |
| A_23_P336854 | 4.6918E-02 | ACAGTGGGAATATCACTTTTGATGAGATCGTCAAC ATTGCTCGACAGATGCGGCACCAAT |
| A_23_P107214 | 4.6963E-02 | TCCATATAATTTTGATCATAGGCCGGAGTGAGTCA TTCCACCTGCACCTTTCTGTACAAA |
| A_24_P154573 | 4.6993E-02 | ATTATTTACACAGAATTTATTTGTATATGAAACTCA TACCATAATTTAATTCGAATAAAT |
| A_23_P203115 | 4.7335E-02 | TAATGTTTTTCATGTTACTGCCTAGGGCGGTGCTG AGCACACAGCAAGTTTAATAAACTT |
| A_23_P123315 | 4.7387E-02 | CTTCCAAATCACTGGTTTGGGAGGGGGTGGATAC ATCCTCATTTTCTGTACATGATGCAT |
| A_23_P123315 | 4.7387E-02 | CTTCCAAATCACTGGTTTGGGAGGGGGTGGATAC ATCCTCATTTTCTGTACATGATGCAT |
| A_23_P123315 | 4.7387E-02 | CTTCCAAATCACTGGTTTGGGAGGGGGTGGATAC ATCCTCATTTTCTGTACATGATGCAT |
| A_23_P123315 | 4.7387E-02 | CTTCCAAATCACTGGTTTGGGAGGGGGTGGATAC ATCCTCATTTTCTGTACATGATGCAT |
| A_23_P123315 | 4.7387E-02 | CTTCCAAATCACTGGTTTGGGAGGGGGTGGATAC ATCCTCATTTTCTGTACATGATGCAT |
| A_23_P123315 | 4.7387E-02 | CTTCCAAATCACTGGTTTGGGAGGGGGTGGATAC ATCCTCATTTTCTGTACATGATGCAT |
| A_24_P178224 | 4.7669E-02 | GGAAGGTTTTTGTCTCCTGTCCAACACTTGTTCAA CATCAGAGAACACATACTAATGAAA |
| A_32_P218989 | 4.7683E-02 | TAAATAGAACTATCTGCATTATCTATGCAGCATGG GATTTTTATTATTTTTACCTAAAGA |
| A_23_P85969 | 4.7694E-02 | AGTAATTTGCGTTAAGATACGCTTAAAGGCTCTTT GTGACCATGTTTCCCTTTGTAGCAA |
| A_24_P329487 | 4.7718E-02 | GTATAAACTTTATTTTTGTTGAAGGTTGTATGTTAA ATCAATGTTACATTCTTATATCAC |
| A_32_P67036 | 4.7805E-02 | TTTCACTGTAGCTTGTGTTTCCTGTAAGTATAGTC GAACGTCGTGATGTTCCTGTTACAT |
| A_23_P385126 | 4.7881E-02 | GAGAATTGATCAACGTGACTATTCCAACAATACAG AGAAGACAACCAAAGATGAGCTGTT |
| A_32_P17343 | 4.7944E-02 | GGAAATGATGTTTGTCTAAAATGGCCAGAGACAAC TTTTATAAGCTTCCAGGAAGTGGAG |
| A_23_P109442 | 4.8052E-02 | TGTCAGTGAACTGATATCTGATGTTTATGATATGG TGTCTTTTTCTTGAAACAAGCTTCC |
| A_24_P309317 | 4.8108E-02 | AAAGGCTGCAGCTTCCTGCCAGACCCTTACCAGA AGCAGTGTGATCAGTTTGTGGCAGAG |
| A_23_P342910 | 4.8131E-02 | GGGCATACTTTGTCTATAGAAAAATATTTTGACCTT TAGGTACATTTTGGGCCAGTAGTC |
| A_24_P921801 | 4.8179E-02 | CTGCAGAACATTATTCCTGCATCTACTGGAACTTC CATGGCTGTGGGCAAGGTCATCCCT |
| A_23_P145718 | 4.8279E-02 | TTTACAAACTTCAATCTTTTCTACATGGATTTTGCC TTCCATGAAATCATACAGGAGTGG |

TABLE 3-continued

| 888 Significant Genes Identifed from Cathgen Registry and PREDICT Samples | | |
|---|---|---|
| A_24_P102283 | 4.8298E-02 | CCTGTTTATTGATTTTTATGAGTTTGTTAGAACATG CGCTTAATGCTTTTATACTCCGGG |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_23_P107206 | 4.8346E-02 | TCATCATGGGCTATAAGATCATGGATGCTACCAAT ATCCTGGTGTCTCCACTGGTCTATC |
| A_32_P135336 | 4.8431E-02 | CGGGCATTCACTCTTTCAGCTCAGAGTTTCTCTTC CTTTCCAATACAGGCTCTACATGAA |
| A_24_P812018 | 4.8509E-02 | GAATGTGGAGGAAGACTTAAAGGCAGATGAACCA TCCAGTAAGGAAAGTTATCTAGAAAT |
| A_23_P328022 | 4.8585E-02 | CCAGCAAAGCGGGAGCCCTGAAAAATTAGGGGGG AAATGGGAGAAAATAATGTGACATTT |
| A_23_P58877 | 4.8615E-02 | AAGGTTTCATGTGATTCATGTGTAAGATGCACAGT ATTTGACATCCTGATTATGTAATCC |
| A_23_P212655 | 4.8645E-02 | TTCTGGTCTCAATGGCTTCGGGAAACACACATATA CACATACACCATGCCCTTGAACTCA |
| A_23_P16694 | 4.8660E-02 | TCCTTGAGAAGACAGGCAGTGGGGCTCTCACTTG GGAAAAGAGAAGTAAATTAAGAGAAA |
| A_24_P930926 | 4.8692E-02 | ATTCCAAATACCAATATCAAAGAAAACTAAGTTGGT AATCTATCTCAGAAAATATATGAA |
| A_23_P58647 | 4.8693E-02 | TGCTTTTTTAGGCTACAGTGTCTCGATGCCATAAT CAGAACACACTTTTTTCCCTCTTTC |
| A_24_P315986 | 4.8775E-02 | TCGATCGCCACACGTATCACAGCCTGTACCTGAAG GTGAAGGGGAATGTGTTCAAAGACA |
| A_23_P57293 | 4.8780E-02 | TTTTTATGAAAACGAAGAGAGATGTTTAAAGTTTAT TTTTCAGCAGGTGAGGTGGCTCAC |
| A_23_P68601 | 4.8851E-02 | CATCACAAGGGCCCTAGTTCAGATAGTGAAAGGC CTGAAATATATGCTGGAGGTGGAAAT |
| A_32_P189093 | 4.8857E-02 | GAATGAGCTCTGACAAGCCATATGCATTTCATAAA CAAACCAAAACATCATCTTCATATC |
| A_24_P9285 | 4.9020E-02 | GCCGTCTGACGGTGATGACCGACCTGGAGGACAA GAACGAGTGGAAGAACTGCATTGACA |
| A_24_P134488 | 4.9043E-02 | TTTGCACAGGTAAGAGAGTAGTTAGCTAACCTATG GGAATTATACTGTGGGGCCTTGTGA |
| A_23_P95612 | 4.9071E-02 | ATAATATGATGCATCTTATCATGGACAAGGACAGT GTTTTCTACCTTTATCAGTTCTCTG |

TABLE 3-continued

| 888 Significant Genes Identifed from Cathgen Registry and PREDICT Samples | | |
|---|---|---|
| A_23_P157875 | 4.9157E-02 | CGAATTGTGCTGAGAAGTTCCAAGGAGCCTGGTG GTACGCCGACTGTCATGCTTCAAACC |
| A_23_P121250 | 4.9171E-02 | GAGATGCCCATGAATGTGGCTGACCTTATTTAATT CCTGGGATGAGAGTTTTGGATGCAG |
| A_23_P46182 | 4.9289E-02 | TGCTAGAGGGCAAAGAGTTGGAGTTCTATCTTAGG AAAATCAAGGCCCGCAAAGGCAAAT |
| A_23_P106602 | 4.9542E-02 | CAAAGCATCCCACTCAAGGGAGACTTGAAACTTCC AGTGTGAGTTGACCCCATCATTTAA |
| A_24_P169645 | 4.9620E-02 | AAGTTGTGGTGAAGAGGTTATTTATGAGTTGCACC AAATGGCCATCTCTGTCTCTTTCCT |
| A_23_P102183 | 4.9621E-02 | TCTTGCCTTTGGACTCTGGTGAAAAATACTTTACA GTGGTCGGTCACAAGAAACCATCTG |
| A_23_P143484 | 4.9628E-02 | TCTTTCTTGCAGCCAAAGAACTTTACACCAAAAACT GAACTGTGTGTAACCATAGTAACA |
| A_23_P500271 | 4.9705E-02 | GAGCACTTAGGTATCATATCAGATGCTCAAGGCTG GCAGCTACCCCCTTCTTGAGAGTCC |
| A_24_P134683 | 4.9852E-02 | CAGCACTAAGCAAAAACTAGAGAAAGCTGAAAACC AGGTTCTGGCCATGCGGAAGCAGTC |
| A_24_P232856 | 4.9988E-02 | GAACCCTGCGGAGGGACTTCAATCACATCAATGTA GAACTCAGCCTTCTTGGAAAGAAAA |

TABLE 5

RT-PCR Validation Data of Genes Identified in Example 1

| | AGE | CDXR0771.CD248 | CDXR0725.LRRN3 | CDXR0603.CCR7 | CDXR0685.B3GAT1 | CDXR0119.VSIG4 |
|---|---|---|---|---|---|---|
| C002\|PREDICT\|00400042 | 23.90144 | 31.556664 | 30.064573 | 26.844992 | 30.77295 | 33.860397 |
| C002\|PREDICT\|00400007 | 27.73443 | 27.314398 | 29.68194 | 28.538946 | 31.030182 | 34.04145 |
| C003\|PREDICT\|00400033 | 29.89733 | 31.262543 | 30.670725 | 27.551256 | 29.768509 | 34.910027 |
| C050\|PREDICT\|00400007 | 32.78303 | 32.032387 | 30.963526 | 26.70526 | 33.042576 | 34.097534 |
| C006\|PREDICT\|00400009 | 33.04586 | 33.466858 | 31.614687 | 27.14089 | 31.789831 | 32.752117 |
| C002\|PREDICT\|00400058 | 33.15811 | 31.022758 | 29.843748 | 26.71145 | 30.762117 | 33.04189 |
| C009\|PREDICT\|00400012 | 34.34086 | 30.803669 | 29.32668 | 26.147238 | 29.26082 | 32.8374 |
| C003\|PREDICT\|00400024 | 35.09103 | 30.575836 | 30.522034 | 26.585863 | 30.607264 | 33.877987 |
| C001\|PREDICT\|00400031 | 37.36071 | 30.77651 | 29.933504 | 26.32894 | 29.542906 | 34.900288 |
| C006\|PREDICT\|00400003 | 38.46407 | 30.984665 | 29.998234 | 26.838911 | 30.313505 | 33.188236 |
| C005\|PREDICT\|00400044 | 39.26626 | 31.393375 | 31.247068 | 27.571873 | 31.912386 | 35.227947 |
| C003\|PREDICT\|00400038 | 39.63313 | 32.429546 | 30.818592 | 28.018356 | 33.13011 | 34.895576 |
| C002\|PREDICT\|00400062 | 39.82204 | 32.387447 | 31.727806 | 27.298477 | 31.103344 | 35.18359 |
| C005\|PREDICT\|00400054 | 41.34155 | 31.043941 | 30.035154 | 26.632122 | 31.440653 | 33.411076 |
| C006\|PREDICT\|00400005 | 42.37645 | 31.642363 | 30.181688 | 26.192575 | 31.053448 | 33.275887 |
| C005\|PREDICT\|00400052 | 42.81999 | 32.813824 | 30.975437 | 27.488724 | 30.037079 | 33.380486 |
| C001\|PREDICT\|00400021 | 43.17317 | 31.730116 | 30.466352 | 26.98397 | 30.561302 | 33.575874 |
| C001\|PREDICT\|00400046 | 43.60027 | 34.11449 | 31.445175 | 27.81912 | 30.9859 | 32.64945 |
| C005\|PREDICT\|00400047 | 43.72895 | 30.526917 | 30.353794 | 27.128366 | 30.111534 | 35.54739 |
| C003\|PREDICT\|00400067 | 45.18549 | 31.855253 | 30.430977 | 26.824644 | 31.09729 | 33.228745 |
| C005\|PREDICT\|00400057 | 48.04928 | 32.5131 | 31.537483 | 27.6469 | 31.478868 | 34.90453 |
| C006\|PREDICT\|00400013 | 48.46543 | 30.491192 | 28.355343 | 25.89573 | 29.883053 | 33.422386 |
| C005\|PREDICT\|00400005 | 48.76112 | 31.304546 | 30.930681 | 27.381277 | 30.85769 | 32.62683 |
| C003\|PREDICT\|00400040 | 49.03765 | 31.934895 | 30.573812 | 26.408766 | 30.732594 | 32.852753 |
| C005\|PREDICT\|00400019 | 49.08966 | 33.19267 | 30.25908 | 27.337442 | 30.599833 | 35.173996 |
| C006\|PREDICT\|00400001 | 49.29227 | 30.150694 | 29.955769 | 27.258993 | 31.551785 | 35.339752 |
| C003\|PREDICT\|00400007 | 49.58522 | 32.8369 | 31.483753 | 27.339058 | 30.967003 | 35.262333 |
| C005\|PREDICT\|00400040 | 49.68104 | 32.189045 | 30.495098 | 26.672123 | 29.379402 | 34.287197 |
| C002\|PREDICT\|00400064 | 49.70294 | 30.34678 | 29.202003 | 25.71258 | 29.528236 | 34.366817 |
| C001\|PREDICT\|00400006 | 49.72758 | 33.188625 | 29.832067 | 26.980844 | 30.55016 | 33.503567 |
| C002\|PREDICT\|00400012 | 50.03696 | 32.770824 | 30.969479 | 27.832727 | 29.516682 | 33.66536 |
| C003\|PREDICT\|00400011 | 50.26146 | 32.851597 | 32.154972 | 28.433493 | 32.20565 | 36.413937 |
| C002\|PREDICT\|00400073 | 50.31896 | 32.018024 | 30.394283 | 26.079958 | 31.219193 | 33.415188 |
| C005\|PREDICT\|00400039 | 50.38193 | 29.761175 | 28.523493 | 25.270235 | 30.014498 | 33.433098 |
| C003\|PREDICT\|00400090 | 50.93224 | 30.371422 | 29.960129 | 26.504063 | 28.856094 | 33.615963 |
| C009\|PREDICT\|00400009 | 50.94319 | 30.50058 | 30.936817 | 27.10471 | 29.143436 | 33.690464 |
| C003\|PREDICT\|00400066 | 51.20876 | 32.973312 | 31.266972 | 27.021362 | 30.43827 | 33.768883 |
| C009\|PREDICT\|00400014 | 51.26352 | 31.87397 | 30.544264 | 26.786346 | 29.928051 | 34.084484 |

TABLE 5-continued

RT-PCR Validation Data of Genes Identified in Example 1

| | AGE | CDXR0771.CD248 | CDXR0725.LRRN3 | CDXR0603.CCR7 | CDXR0685.B3GAT1 | CDXR0119.VSIG4 |
|---|---|---|---|---|---|---|
| C001\|PREDICT\|00400035 | 51.34839 | 34.694942 | 32.834206 | 29.768927 | 31.096935 | 35.321266 |
| C005\|PREDICT\|00400053 | 51.55099 | 32.19286 | 32.12989 | 28.354462 | 31.825367 | 35.16671 |
| C005\|PREDICT\|00400032 | 51.60027 | 31.930347 | 30.228382 | 27.325514 | 30.654083 | 34.103954 |
| C003\|PREDICT\|00400061 | 51.75907 | 31.864277 | 30.563795 | 26.804926 | 31.099852 | 34.626484 |
| C001\|PREDICT\|00400022 | 52.63792 | 31.695314 | 29.969927 | 26.497082 | 29.436895 | 32.768047 |
| C002\|PREDICT\|00400063 | 52.75565 | 32.46284 | 30.105995 | 26.309458 | 28.345276 | 32.78204 |
| C003\|PREDICT\|00400079 | 53.19097 | 31.3935 | 30.93317 | 27.703445 | 30.608965 | 33.467766 |
| C005\|PREDICT\|00400026 | 53.3963 | 30.961302 | 29.769306 | 26.901413 | 30.71094 | 33.529373 |
| C005\|PREDICT\|00400004 | 53.7577 | 31.910904 | 30.925047 | 27.599413 | 29.549301 | 32.707836 |
| C005\|PREDICT\|00400006 | 54.19576 | 32.928684 | 31.95685 | 28.34114 | 29.001562 | 33.63928 |
| C003\|PREDICT\|00400043 | 54.21218 | 30.993982 | 29.856981 | 26.479664 | 30.946032 | 33.738575 |
| C009\|PREDICT\|00400017 | 54.49692 | 32.9345 | 31.741732 | 28.22207 | 32.613693 | 34.801075 |
| C003\|PREDICT\|00400048 | 55.10746 | 30.96503 | 29.646988 | 25.783304 | 31.452843 | 32.532204 |
| C003\|PREDICT\|00400052 | 55.16222 | 30.54691 | 29.596678 | 25.911396 | 29.954422 | 32.666447 |
| C001\|PREDICT\|00400014 | 55.39493 | 32.275867 | 29.820194 | 26.246634 | 30.905886 | 33.10041 |
| C009\|PREDICT\|00400005 | 55.6386 | 32.47342 | 31.76815 | 28.152346 | 31.980215 | 34.0051 |
| C009\|PREDICT\|00400003 | 55.7399 | 34.262543 | 33.073975 | 29.543413 | 30.994389 | 34.036526 |
| C005\|PREDICT\|00400028 | 55.7974 | 32.99754 | 29.489105 | 26.64239 | 30.64671 | 32.487705 |
| C001\|PREDICT\|00400017 | 55.86311 | 30.445406 | 30.610737 | 28.17447 | 31.86047 | 34.799717 |
| C001\|PREDICT\|00400009 | 56.07392 | 34.088543 | 32.236286 | 28.258606 | 29.492018 | 32.835766 |
| C050\|PREDICT\|00400005 | 56.09582 | 32.74326 | 31.64339 | 26.918247 | 30.393908 | 33.22924 |
| C002\|PREDICT\|00400087 | 56.15058 | 32.490337 | 30.942202 | 27.60978 | 28.635477 | 34.086937 |
| C001\|PREDICT\|00400029 | 56.79671 | 33.212605 | 29.993128 | 27.08085 | 29.695372 | 33.585556 |
| C009\|PREDICT\|00400002 | 57.28405 | 32.98339 | 30.817528 | 27.181269 | 31.09348 | 33.91429 |
| C005\|PREDICT\|00400021 | 57.3744 | 33.404793 | 30.642393 | 26.560955 | 31.214054 | 32.88827 |
| C009\|PREDICT\|00400015 | 57.40452 | 30.720182 | 30.466825 | 27.491371 | 31.427748 | 33.424507 |
| C005\|PREDICT\|00400037 | 57.72485 | 33.104874 | 31.129608 | 27.679342 | 28.793905 | 33.326004 |
| C003\|PREDICT\|00400023 | 57.79603 | 31.93142 | 30.693813 | 27.048355 | 29.64088 | 33.916595 |
| C001\|PREDICT\|00400030 | 58.11636 | 32.496456 | 29.798164 | 27.077785 | 29.367426 | 34.069935 |
| C002\|PREDICT\|00400072 | 58.16016 | 32.117584 | 28.991713 | 26.22649 | 29.975126 | 33.962444 |
| C002\|PREDICT\|00400086 | 58.45585 | 30.57812 | 28.465744 | 25.646858 | 30.440062 | 31.013115 |
| C005\|PREDICT\|00400042 | 58.85558 | 33.642117 | 30.628765 | 27.888245 | 29.50378 | 32.30435 |
| C005\|PREDICT\|00400043 | 58.96235 | 31.104029 | 30.611357 | 26.885727 | 29.837095 | 34.012657 |
| C002\|PREDICT\|00400089 | 59.0527 | 33.070858 | 30.970745 | 26.252518 | 30.17873 | 32.4872 |
| C009\|PREDICT\|00400007 | 59.07734 | 32.028816 | 31.532957 | 27.387144 | 30.961983 | 33.373943 |
| C005\|PREDICT\|00400041 | 59.28268 | 32.04792 | 31.071867 | 27.751293 | 27.957197 | 32.179058 |
| C005\|PREDICT\|00400063 | 60.2245 | 32.908283 | 30.392408 | 26.840874 | 29.901918 | 34.214172 |
| C001\|PREDICT\|00400005 | 60.31759 | 31.250462 | 30.192364 | 27.140314 | 31.355988 | 34.108185 |
| C005\|PREDICT\|00400030 | 60.38604 | 33.64841 | 31.306635 | 26.107044 | 29.963058 | 33.05274 |
| C006\|PREDICT\|00400006 | 60.45448 | 32.99032 | 30.295792 | 27.199663 | 30.087133 | 35.2025 |
| C002\|PREDICT\|00400088 | 60.49281 | 34.457623 | 33.07051 | 28.926199 | 30.575459 | 35.69596 |
| C003\|PREDICT\|00400085 | 60.65982 | 32.647964 | 31.16586 | 27.079832 | 29.949297 | 33.396053 |
| C005\|PREDICT\|00400056 | 60.74196 | 32.897434 | 31.495476 | 27.540783 | 30.540134 | 33.22536 |
| C001\|PREDICT\|00400033 | 61.34976 | 31.347414 | 31.464203 | 27.332926 | 29.064856 | 33.882538 |
| C003\|PREDICT\|00400073 | 61.35524 | 33.53371 | 31.388271 | 27.448072 | 31.1762 | 34.012486 |
| C003\|PREDICT\|00400019 | 61.56605 | 32.541313 | 30.975803 | 26.987335 | 31.092806 | 33.100807 |
| C003\|PREDICT\|00400041 | 61.60438 | 32.545685 | 30.921286 | 26.978142 | 30.777018 | 32.641335 |
| C003\|PREDICT\|00400058 | 62.16564 | 32.1681 | 30.637892 | 27.126375 | 29.145485 | 33.797375 |
| C005\|PREDICT\|00400027 | 62.17112 | 32.803238 | 31.239986 | 27.360523 | 29.670156 | 34.500134 |
| C003\|PREDICT\|00400091 | 62.21492 | 32.986107 | 31.785229 | 28.265444 | 29.034729 | 33.754063 |
| C002\|PREDICT\|00400077 | 62.31896 | 35.160587 | 32.647465 | 29.191298 | 33.55413 | 34.813553 |
| C003\|PREDICT\|00400032 | 62.33265 | 31.622807 | 30.417845 | 26.85945 | 31.044086 | 33.15245 |
| C002\|PREDICT\|00400078 | 62.46407 | 31.985334 | 31.285955 | 27.498905 | 30.396612 | 32.90187 |
| C005\|PREDICT\|00400046 | 63.03901 | 34.13626 | 32.493202 | 28.537834 | 31.206366 | 34.101334 |
| C005\|PREDICT\|00400018 | 63.16222 | 33.093517 | 31.221079 | 26.822641 | 28.622694 | 32.937637 |
| C002\|PREDICT\|00400065 | 64.00548 | 29.463318 | 31.10117 | 28.320213 | 29.686617 | 34.091965 |
| C005\|PREDICT\|00400023 | 64.77207 | 33.28558 | 30.998365 | 27.153236 | 30.71424 | 33.523903 |
| C002\|PREDICT\|00400066 | 64.80219 | 31.684977 | 30.386908 | 26.376379 | 29.540575 | 32.51388 |
| C002IPREDICT\|00400068 | 64.82683 | 32.153362 | 31.153578 | 26.542067 | 33.45499 | 34.233837 |
| C003\|PREDICT\|00400060 | 65.30322 | 32.10008 | 28.678185 | 26.240814 | 29.581566 | 31.767967 |
| C003\|PREDICT\|00400080 | 65.3963 | 32.39084 | 30.950315 | 26.685202 | 30.149946 | 32.27304 |
| C005\|PREDICT\|00400045 | 65.4319 | 31.220385 | 30.160843 | 27.253082 | 31.198732 | 31.751291 |
| C001\|PREDICT\|00400025 | 65.94114 | 32.157433 | 30.895208 | 26.977692 | 29.967432 | 33.710323 |
| C003\|PREDICT\|00400030 | 66.06982 | 31.779463 | 30.624678 | 27.294584 | 29.766651 | 32.752487 |
| C002\|PREDICT\|00400080 | 66.26694 | 32.413548 | 30.079193 | 27.03647 | 29.18002 | 33.732056 |
| C003\|PREDICT\|00400037 | 66.27789 | 29.93052 | 30.121061 | 27.710638 | 32.035545 | 32.0223 |
| C002\|PREDICT\|00400076 | 66.40383 | 33.04322 | 31.512157 | 26.819124 | 29.130444 | 32.004425 |
| C001\|PREDICT\|00400053 | 66.66393 | 34.398792 | 31.743744 | 28.260529 | 29.962387 | 31.924767 |
| C005\|PREDICT\|00400034 | 67.31828 | 33.415424 | 31.021103 | 27.079458 | 31.548864 | 34.62193 |
| C006\|PREDICT\|00400011 | 67.436 | 33.012848 | 31.380703 | 27.890787 | 29.972704 | NA |
| C002\|PREDICT\|00400069 | 67.68789 | 33.22445 | 30.511965 | 26.22374 | 29.055523 | 33.890617 |
| C003\|PREDICT\|00400082 | 68.00548 | 33.448643 | 31.87448 | 28.047644 | 30.616394 | 33.841125 |
| C002\|PREDICT\|00400071 | 68.45175 | 34.037506 | 32.08694 | 28.271132 | 29.586443 | 33.45311 |
| C006\|PREDICT\|00400007 | 68.95277 | 30.75065 | 30.800241 | 27.68488 | 30.558825 | 32.02818 |
| C003\|PREDICT\|00400013 | 71.21971 | 36.178303 | 34.07151 | 29.736794 | 29.916168 | 34.683403 |
| C005\|PREDICT\|00400029 | 71.70157 | 33.94084 | 31.627996 | 28.061932 | 29.615993 | 33.52913 |

TABLE 5-continued

| RT-PCR Validation Data of Genes Identified in Example 1 | | | | | | |
|---|---|---|---|---|---|---|
| | AGE | CDXR0771.CD248 | CDXR0725.LRRN3 | CDXR0603.CCR7 | CDXR0685.B3GAT1 | CDXR0119.VSIG4 |
| C001\|PREDICT\|00400039 | 72.34497 | 33.11481 | 30.546974 | 26.911135 | 29.749992 | 33.6878 |
| C006\|PREDICT\|00400004 | 73.52225 | 32.64978 | 30.985353 | 26.650253 | 29.494461 | 32.384834 |
| C003\|PREDICT\|00400036 | 74.11636 | 36.550156 | 33.140453 | 29.189968 | 29.629725 | 31.321623 |
| C002\|PREDICT\|00400082 | 74.17933 | 31.529308 | 31.558626 | 28.053543 | 31.843094 | 33.80352 |
| C009\|PREDICT\|00400004 | 78.88296 | 33.955246 | 32.212135 | 28.050869 | 28.725218 | 33.83596 |
| C001\|PREDICT\|00400007 | 80.13415 | 36.453712 | 32.10783 | 28.341278 | 28.98254 | 32.68926 |
| C001\|PREDICT\|00400018 | 80.33402 | 31.277067 | 30.922739 | 27.717735 | 29.857052 | 32.820457 |
| C009\|PREDICT\|00400018 | 83.23066 | 31.615898 | 30.675495 | 26.860125 | 29.809261 | 32.549946 |
| mean low | 47.41289 | 31.86012826 | 30.61497223 | 27.14176279 | 30.60778385 | 33.86440818 |
| sd low | 8.129722 | 1.259354021 | 0.952778432 | 0.88152605 | 1.031485327 | 0.920347332 |
| mean high | 64.69259 | 32.70707026 | 31.05161784 | 27.37315261 | 30.17837693 | 33.31343427 |
| sd high | 6.148016 | 1.392410096 | 0.95599422 | 0.809956564 | 1.055050698 | 0.960481771 |
| ttest | 3.2E−25 | 0.000603835 | 0.012815205 | 0.133768513 | 0.02480641 | 0.001641762 |

What is claimed is:

1. A method for assessing a physiological age of a mammalian subject comprising:

obtaining a dataset associated with a sample obtained from said mammalian subject, wherein said dataset comprises the expression value of CD248 and the expression value of SLC1A7;

inputting said dataset into an interpretation function that uses said dataset to determine a score wherein said score indicates a physiological age wherein said interpretation function is a function produced by a predictive model selected from the group consisting of a partial least squares model, a logistic regression model, a linear regression model, a linear discriminant analysis model, and a tree-based recursive partitioning model; and outputting said score.

2. The method of claim 1 wherein the dataset further comprises the expression value of a gene selected from the group consisting of CCR7, B3GAT1, VSIG4 and LRRN3.

3. The method of claim 1 wherein the dataset further comprises the expression values of two genes selected from the group consisting of CCR7, B3GAT1, VSIG4 and LRRN3.

4. The method of claim 1 wherein the dataset further comprises the expression values of three genes selected from the group consisting of CCR7, B3GAT1, VSIG4 and LRRN3.

5. The method of claim 1 wherein the dataset further comprises the expression values of CCR7, B3GAT1, VSIG4 and LRRN3.

6. The method of claim 1, further comprising classifying said sample according to said score.

7. The method of claim 6 wherein said classifying is according to the physiological age of said mammalian subject.

8. The method of claim 1, wherein said sample comprises peripheral blood cells.

9. The method of claim 1, wherein said sample comprises RNA extracted from peripheral blood cells.

10. The method of claim 1, wherein said gene expression values are derived from microarray hybridization data.

11. The method of claim 1, wherein said gene expression values are derived from polymerase chain reaction data.

12. The method of claim 1, wherein said gene expression values are obtained using a method selected from the group consisting of nucleic acid hybridization and nucleic acid amplification.

13. A computer-implemented method for assessing a physiological age of a mammalian subject by a computer comprising:

receiving a dataset associated with a sample obtained from said mammalian subject, wherein said dataset comprises the expression value of CD248 and the expression value of SLC1A7;

determining, by a computer processor, a score by inputting said dataset into an interpretive function wherein said score indicates a physiological age wherein said interpretation function is a function produced by a predictive model selected from the group consisting of a partial least squares model, a logistic regression model, a linear regression model, a linear discriminant analysis model, and a tree-based recursive partitioning model; and outputting said score.

14. The method of claim 13 wherein the dataset further comprises the expression value of a gene selected from the group consisting of CCR7, B3GAT1, VSIG4 and LRRN3.

15. The method of claim 13 wherein the dataset further comprises the expression values of two genes selected from the group consisting of CCR7, B3GAT1, VSIG4 and LRRN3.

16. The method of claim 13 wherein the dataset further comprises the expression values of three genes selected from the group consisting of CCR7, B3GAT1, VSIG4 and LRRN3.

17. The method of claim 13 wherein the dataset further comprises the expression values of CCR7, B3GAT1, VSIG4 and LRRN3.

18. The method of claim 13 further comprising classifying said sample according to said score.

19. The method of claim 18 wherein said classifying is according to the physiological age of said mammalian subject.

20. The method of claim 13 wherein said sample comprises peripheral blood cells.

21. The method of claim 13 wherein said sample comprises RNA extracted from peripheral blood cells.

22. The method of claim 13 wherein said gene expression values are derived from microarray hybridization data.

23. The method of claim 13 wherein said gene expression values are derived from polymerase chain reaction data.

24. The method of claim 13 wherein said gene expression values are obtained using a method selected from the group consisting of nucleic acid hybridization and nucleic acid amplification.

* * * * *

SEQUENCE LISTING

<160> NUMBER OF SEQ ID NOS: 1108

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1
aaccgtctga gtcttgtgct cttcaagaca aaacagattg cgtcgctgac aagttctcaa     60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 2
acttctttgg gcagatgcta ggtcagttgt tttcacctaa tatcctcttt tagctgcatg     60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 3
aagagagcaa cattttaccc acacacagat aaagttttcc cttgaggaaa caacagcttt     60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
ctctctcaac cactagactt ggctctcagg aactctgctt cctggcccag cgctcgtgac     60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 5
atgggaaaaa taaggataac tcagaatttc aaaaggaaat cacaaattca gctagtaata 60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 6
tcgtaaacta agtgaataca caaaatgttg atttttctga ccataagaca tattttatgt 60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 7
tctggtgaca ctggcctaga gcctgacact ctcctaagag gttctctcca agcccccaaa 60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 8
gcgttcaatc ttgaccttga agatgggaag gatgttcttt ttacgtacca attcttttgt 60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 9
catcctgctt ctaccatgtg gatttggtca caaggtttaa ggtgacccaa tgattcagct 60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 10
gcctctctcc agaaatgaac tgtgatggtg gacacagcta tgtgaggaat tacttacaga 60

<210> SEQ ID NO 11

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 11
aaatccaatt atcagaatca aagacatgaa ctttaagcct cttatcaatc ttcgcagcct 60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 12
gccctctggg gctgtggtca ccctcgaatg cgtggagaag ctgattcgga aggacatggt 60

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 13
atgatgtcca acctgggccc agtgtgggtc ctccaagtaa ggacaaggac aaagtgctgc 60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 14
ttgaaactct ggaagagtgg attcagcctg gataatggag aactcagaag ctaccaagac 60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 15
caaagtgtgc tccttaaaca ctcatgcctt atgattttct accaaaagta aaaagggttg 60

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 16
gaatcactcc tctcaaatat gcccagattt gctattggat taaaggaaac tacctggatt 60

<210> SEQ ID NO 17
<211> LENGTH: 60

<212> TYPE: DNA
<213> ORGANISM: Artificial Sequence
<220> FEATURE:
<223> OTHER INFORMATION: Description of Artificial Sequence: Synthetic probe

<400> SEQUENCE: 17
cccagaaaac ctccagtagt ggacaacagg ttttcaccat agcctacgtt aacccatttt 60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 18
cccagaaaac ctccagtagt ggacaacagg ttttcaccat agcctacgtt aacccatttt 60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 19
cccagaaaac ctccagtagt ggacaacagg ttttcaccat agcctacgtt aacccatttt 60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 20
cccagaaaac ctccagtagt ggacaacagg ttttcaccat agcctacgtt aacccatttt 60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 21
cccagaaaac ctccagtagt ggacaacagg ttttcaccat agcctacgtt aacccatttt 60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 22
cccagaaaac ctccagtagt ggacaacagg ttttcaccat agcctacgtt aacccatttt 60

<210> SEQ ID NO 23
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 23
aagcatcagg actccaaaaa ggaagaagaa aagaagaagc cccacataaa gaaacctctt 60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 24
ctcagaggac cagctatatc caggatcatt tctctttctt cagggccaga cagcttttaa 60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 25
tagctgtagc tgaggcttaa ctgggaggga tgccgagctt gctggaacta ctgggaccaa 60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 26
ctcccttgac gtttggcaga tgaaaaacaa ctaagccttt ttgaggtgta gagattctca 60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 27
gcagggggcc actgtagtga gcgtggagaa atttggaaac acctatttct taactcaaat 60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 28
tacagggatt agatccgagc cacattaccc atatatgctc agaatggtct gtcaggaaca 60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 29
agattaatgc agaacaaggt cgttagtctc attgtttatc cagttactag ctgcatagat 60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 30
cacgtgttct gaaaccactg gtgtctgctc agatgtgttg ggacaaaatg aaagtgactt 60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 31
agcgaaattt gaagatgaca tcacctattg gcttaacaga gatcgaaatg gacatgaata 60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 32
cactgcgtgg gagggactgg gtcactattg tggtttttac tataactttg taaattaact 60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 33
acacacttgc tcgagaacca aagtgcattt gggtgacatt tgaagattgg ggagacaaga 60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 34
gtggcctgtg ttgccactct cagcacccca catttgcatc tgctggtgga cctgccacca 60

<210> SEQ ID NO 35
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 35
gaagattgat gtgattcgta gaaaggtttc aaaaatccaa cgtttccatg cgagatccct 60

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 36
taaagggcag ggcccacgtg tatagtatct gtatataagt tgctgtgtgt ctgtcctgat 60

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 37
ggccctggtg tcagaactcc ccaaaggcct gtgcgtccaa gtggagtcag gttttctatt 60

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 38
ttaaccggga catttcctga ctaccctgac gttgaagaag gagggtcagc tattattttt 60

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 39
agtaactggt tgttctactt ggtaatttga caccctgtta ataacgcaat tatttctgtg 60

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 40
tcatacctcc ccagagggaa gcaggaatga ggccaaaaag tgtgcattgg ataggggaac 60

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
gggttactgg cttctcttga gtcacactgc tagcaaatgg cagaaccaaa gctcaaataa 60

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 42
gggttactgg cttctcttga gtcacactgc tagcaaatgg cagaaccaaa gctcaaataa 60

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 43
gggttactgg cttctcttga gtcacactgc tagcaaatgg cagaaccaaa gctcaaataa 60

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 44
gggttactgg cttctcttga gtcacactgc tagcaaatgg cagaaccaaa gctcaaataa 60

<210> SEQ ID NO 45
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 45
gggttactgg cttctcttga gtcacactgc tagcaaatgg cagaaccaaa gctcaaataa 60

<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 46
gggttactgg cttctcttga gtcacactgc tagcaaatgg cagaaccaaa gctcaaataa 60

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 47
gggttactgg cttctcttga gtcacactgc tagcaaatgg cagaaccaaa gctcaaataa 60

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 48
gcagatctta gggatgatta aaggcagcat ttgatgatag cagacattgt tacaaggaca 60

<210> SEQ ID NO 49
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 49
tctgaccgct ttttcttggt tatgaatctt aatttcgaat ataagatgat aggtaagcgc 60

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 50
acatcaccat gtagaagaat gggcgtacag tatataccgt gacatcctga accctggata 60

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 51
accaggttaa tggctaagaa tgggtaacat gactcttgtt ggattgttat tttttgtttg 60

<210> SEQ ID NO 52
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 52
tatgatccta tttggtgcat tttctaccat ggtccaagat cattacatgg atacagccaa 60

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 53
atgacggtag aagacttctc attggggagc aactttttga cgcacaactt ttggtgcgtt 60

<210> SEQ ID NO 54
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 54
tctgtgatta tgatttcctc tcctataatt atttctgtag cactccacac tgatctttgg 60

<210> SEQ ID NO 55
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 55
ctaagccaaa ccccagtttc catttttac tgaatcataa tcaaaatcaa agccaaagac 60

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 56
actgaattat gccagggcgc actttccact ggagttcact ttcaattgct tctgtgcaat 60

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 57
tccattagga aacggattgc atcatacctg aacataagct ggactgctga aattgtattt 60

<210> SEQ ID NO 58
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 58
atagaagctt ctaagcagaa gagggacttg ccctaattca ggtgatcaca ggtgtcttgt 60

<210> SEQ ID NO 59
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 59
ttcaaatgca tgatcaaatg caacctcaca accttggctg agtcttgaga ctgaaagatt 60

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 60
ttcaaatgca tgatcaaatg caacctcaca accttggctg agtcttgaga ctgaaagatt 60

<210> SEQ ID NO 61
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 61
ttcaaatgca tgatcaaatg caacctcaca accttggctg agtcttgaga ctgaaagatt 60

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 62
ttcaaatgca tgatcaaatg caacctcaca accttggctg agtcttgaga ctgaaagatt 60

<210> SEQ ID NO 63
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 63
ttcaaatgca tgatcaaatg caacctcaca accttggctg agtcttgaga ctgaaagatt 60

<210> SEQ ID NO 64
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 64
ttcaaatgca tgatcaaatg caacctcaca accttggctg agtcttgaga ctgaaagatt 60

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 65

-continued ttcaaatgca tgatcaaatg caacctcaca accttggctg agtcttgaga ctgaaagatt 60

<210> SEQ ID NO 66
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 66
ttcaaatgca tgatcaaatg caacctcaca accttggctg agtcttgaga ctgaaagatt 60

<210> SEQ ID NO 67
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 67
ttcaaatgca tgatcaaatg caacctcaca accttggctg agtcttgaga ctgaaagatt 60

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 68
ttcaaatgca tgatcaaatg caacctcaca accttggctg agtcttgaga ctgaaagatt 60

<210> SEQ ID NO 69
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 69
tgtagaggca atggatatgg aaaacatttt tcgtaaaata tgggagaatt tatagaaaag 60

<210> SEQ ID NO 70
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 70
ctcagacata gagttaaaac tcaaacctct tatgtgcact ttaaagatag actttagggg 60

<210> SEQ ID NO 71
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 71
cagagttctt ggaggattct gaggtagaga gtagcataat ctcatttgtg tttttattct 60

<210> SEQ ID NO 72
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 72
atcgtagctt gatgttagct ctctgtaacc tttcaggtat attaatcaaa aaagccaaac 60

<210> SEQ ID NO 73
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 73
agccatgatt tcagtttcac ataagaatgt ttactcaatg tttaagtgtg ttgccccaaa 60

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 74
ttgcactatt ccttctccaa gccagaaacc acatttaatt tcataaataa atttatgaaa 60

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 75
tttggggata aaatctggca ggattgctga cctggactct gtcatctaaa gttctcacac 60

<210> SEQ ID NO 76
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 76
tacatcagac tcaaaggtaa taggggcatg cattccattg aggaaattct agggaatttt 60

<210> SEQ ID NO 77
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 77
caatatgata gggaacaggt gctgatgggc ccaagagtga caagcataca caactactta 60

-continued

```
<210> SEQ ID NO 78
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78

caagctactg gcacatagtg aaagattact tctgacattc cattgctctt cttttgaaaa     60


<210> SEQ ID NO 79
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79

caagctactg gcacatagtg aaagattact tctgacattc cattgctctt cttttgaaaa     60


<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80

caagctactg gcacatagtg aaagattact tctgacattc cattgctctt cttttgaaaa     60


<210> SEQ ID NO 81
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81

caagctactg gcacatagtg aaagattact tctgacattc cattgctctt cttttgaaaa     60


<210> SEQ ID NO 82
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82

caagctactg gcacatagtg aaagattact tctgacattc cattgctctt cttttgaaaa     60


<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83

caagctactg gcacatagtg aaagattact tctgacattc cattgctctt cttttgaaaa     60
```

-continued

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 84
caagctactg gcacatagtg aaagattact tctgacattc cattgctctt cttttgaaaa 60

<210> SEQ ID NO 85
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 85
caagctactg gcacatagtg aaagattact tctgacattc cattgctctt cttttgaaaa 60

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 86
caagctactg gcacatagtg aaagattact tctgacattc cattgctctt cttttgaaaa 60

<210> SEQ ID NO 87
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 87
caagctactg gcacatagtg aaagattact tctgacattc cattgctctt cttttgaaaa 60

<210> SEQ ID NO 88
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 88
tagcttagaa ttgggaggat acttaacatc tggaagacaa gttcatttca tcttgagatc 60

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 89
agggcacagt acaactccca ttggaagggc actatagaga tgatccatct gtgatcaata 60

<210> SEQ ID NO 90

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 90
tgtcctgagt tctacagtat gtgaacaata tcgtgtgaag tgtgtttttg catttgtgca 60

<210> SEQ ID NO 91
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 91
gctgtgggct aaaacaaggt agccagtttg agactgggga taaagggtgg attttagtaa 60

<210> SEQ ID NO 92
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 92
tctgcctcca aatctgaaca gtcactgtaa atcattctta agcccagata tgagaacttc 60

<210> SEQ ID NO 93
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 93
aatctgtgtg attgtttgca gtatgaagac acatttctac ttatgcagta ttctcatgac 60

<210> SEQ ID NO 94
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 94
aatctgtgtg attgtttgca gtatgaagac acatttctac ttatgcagta ttctcatgac 60

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 95
aatctgtgtg attgtttgca gtatgaagac acatttctac ttatgcagta ttctcatgac 60

<210> SEQ ID NO 96
<211> LENGTH: 60

<212> TYPE: DNA
<213> ORGANISM: Artificial Sequence
<220> FEATURE:
<223> OTHER INFORMATION: Description of Artificial Sequence: Synthetic probe

<400> SEQUENCE: 96
aatctgtgtg attgtttgca gtatgaagac acatttctac ttatgcagta ttctcatgac 60

<210> SEQ ID NO 97
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 97
aatctgtgtg attgtttgca gtatgaagac acatttctac ttatgcagta ttctcatgac 60

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 98
aatctgtgtg attgtttgca gtatgaagac acatttctac ttatgcagta ttctcatgac 60

<210> SEQ ID NO 99
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 99
aatctgtgtg attgtttgca gtatgaagac acatttctac ttatgcagta ttctcatgac 60

<210> SEQ ID NO 100
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 100
aatctgtgtg attgtttgca gtatgaagac acatttctac ttatgcagta ttctcatgac 60

<210> SEQ ID NO 101
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 101
ctccagagcc taatttttcc cagatgcata tttagctcta gggagaggac taggaggaaa 60

<210> SEQ ID NO 102
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 102
tttacatgag atttgttaac acacattttc tgagagcagg tatggaagac agccatgtgt 60

<210> SEQ ID NO 103
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 103
gtgctgagca gtcagggacc tgtaaggtca catttctttc aggtattctt tctaggtgta 60

<210> SEQ ID NO 104
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 104
aggtctgatg cagtagcttt tactattggt ggaaatcgat gttttttcct tgaaagtcta 60

<210> SEQ ID NO 105
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 105
ctggggccat ttttggcaca atagttgttc aaatgtagat cactatgctg aatgctcatg 60

<210> SEQ ID NO 106
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 106
tggccaatgt cgaaacctac aagatttcct taaaatctct aatagaggca ttacttgctt 60

<210> SEQ ID NO 107
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 107
actgaagact ttgaacactt gctttttgtg attgcttatg tcattagtgc ctcatgactg 60

<210> SEQ ID NO 108
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 108
gaggctcaag ttcgccactt tactcagacc gatgcacagt cttcccattt tacacttttt 60

<210> SEQ ID NO 109
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 109
catgtattta aacctatgaa ttataaaata gtatttagat tctagcgtga gttaaataga 60

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 110
ttggtccaag gcactacacc tgtactgcag gggctcaatg gagctgtctt caggccagaa 60

<210> SEQ ID NO 111
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 111
tgatatcaat cactattact ggaatcatta tcaacatatc aataaatatt tttagaacat 60

<210> SEQ ID NO 112
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 112
aaattgtatg tgatattcca acagcaagtt ggatgcaatg tgtcataaaa atgacctcag 60

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 113
aaacagacaa aacaatcccc atcaggtagc tgtctaaccc ccagctgggt ctaatccttc 60

<210> SEQ ID NO 114
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 114
tctgggacag aggcaagaat ccccaagggg tgggcagtca gggttgcagg actgtaataa     60

<210> SEQ ID NO 115
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
taactgtgtg gcagaggctt catttaggtc tcacaactca ctagacatca aaatgtgtaa     60

<210> SEQ ID NO 116
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
ggggtggtat ctaggaccag agaggaatct actatttcta ctgtgaaata attcagcagg     60

<210> SEQ ID NO 117
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ctgggaatgc tataggacct cctactattc tcttaaggtc ctaggaaagt ttcaggaact     60

<210> SEQ ID NO 118
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
ctgaattgac agtaaacctg tccattatga atggcctact gttctattat ttgttttgac     60

<210> SEQ ID NO 119
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
tataaaaata ttaggtaatt ctatacaatg catagtcata aaccttaaca tttttgttca     60

<210> SEQ ID NO 120
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 120
agcttttgat cttggggcca gaggccgcct tacacacacc ccaggtgtcc atggggagca 60

<210> SEQ ID NO 121
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 121
gaaaactctc tgagttctgg agcactgttc gcggccggac tgagtggcat gtccgcattt 60

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 122
ctgagttgaa tgcttccagg caatctaggt atctactttt aaaccaacct atcgggagtc 60

<210> SEQ ID NO 123
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 123
gttttgagcg ttgtattcca aaggcctcat ctggagcctc gggaaagtct ggtcccacat 60

<210> SEQ ID NO 124
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 124
gttcctgttt ggattagacc atagttgacc catctggcat tgccaacgaa gccttcatta 60

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 125
aaccatgaaa cgctactaac tacaggaagc aaactaagcc cccgctgtaa tgaaacacct 60

<210> SEQ ID NO 126
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 126
cctgtaactg gaggtgttgc acacttgcca ggcattttgt gagttacaag catagctaat 60

<210> SEQ ID NO 127
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 127
tgtgatcagg ctcccaagtc tggttcccat gaggtgagat gcaacctgaa tcatggccac 60

<210> SEQ ID NO 128
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 128
agggcatgtc ttcttattcc atgtgacagt ggctggctga gttgctagta cgtttttgaa 60

<210> SEQ ID NO 129
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 129
gcctgctgtc ttgagtacaa atgtgaatga tcgactgact gcttgttgcc aaactggaaa 60

<210> SEQ ID NO 130
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 130
tctgaactag ttgaactgtg actgacaggt aatcctaata tatccaaatc caactgaata 60

<210> SEQ ID NO 131
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 131
cgtatttatt gtcagctctt taaacaaaaa gcactctatg aagtgctgta ctttacagtc 60

<210> SEQ ID NO 132
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 132
taagctttgg aagagattac acatgatgtc tttttcttag agattcacag tgcatgttag 60

<210> SEQ ID NO 133
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 133
ggttcttcag tctgccaagg aacaaattaa atggtcgtta ttgaaatgaa ggctgtggat 60

<210> SEQ ID NO 134
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 134
aaagccaaca agaattcttc agaatgctgg atgaaaaaat tgaaaagggt cgggattact 60

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 135
tggggaagct ctgtgaaatc gtctgatggt ctgtgtggaa gaaaagaaaa atctgtctgc 60

<210> SEQ ID NO 136
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 136
tttctccgaa cgtgtttgtg atcttctgtt atattttggg gcatgttacc tttatggtat 60

<210> SEQ ID NO 137
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 137
ttaactactt atctctaaac catctatgtg aatatttgta aaaataatga atggactcat 60

<210> SEQ ID NO 138
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 138
aggtgcaagc cttagagaaa gttaaaggtg cagatataaa tgctgaagag gcccccaaaa 60

<210> SEQ ID NO 139
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 139
atcaatagag atcccatcac catcttccag gagctagatt ccaccagaat caaatggggt 60

<210> SEQ ID NO 140
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 140
gggcgggggg tcaaatagaa ggctatatga atcaacttca gtgagctggt gaaagaaaat 60

<210> SEQ ID NO 141
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 141
tttgactgca attgcagcat ttgcaagaag aagcagaata gacacttcat tgttccagct 60

<210> SEQ ID NO 142
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 142
atgtacccaa agaacacatt tgctttgaga agtggtggta ggaggcagac aaaggcagaa 60

<210> SEQ ID NO 143
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 143
ccaaggtcat ccatgacaac tgtattgtgg agggactcat gaccacattt catgtagtca 60

<210> SEQ ID NO 144
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 144
gactgagatg gtcaaaggac tttggaccat aggggatctt tggaaggctg tggggtcttg 60

<210> SEQ ID NO 145
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 145
cttgttcttt ttacataaag gaatttgtag gaaatgcagc caaaggtgca gtcggaaaag 60

<210> SEQ ID NO 146
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 146
ctgtatactt ttataccaac ttattgtagg ctctttgagg tcaggtatgt atttctttcc 60

<210> SEQ ID NO 147
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 147
actctaacct gaacagctca caatgtagct gtaaatataa aaaatgagag tgttctaccc 60

<210> SEQ ID NO 148
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 148
ttagattgag gatgggggca tgacactcca gtgtcaaaat aagtcttagt agatttcctt 60

<210> SEQ ID NO 149
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 149
gcccaaaact gtcatcctaa cgtttgtcat tccagtttga gttaatgtgc tgagcatttt 60

<210> SEQ ID NO 150
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 150
gcatacttta tagttcaaga ttttcggtat ataaaatctg tcctttccta cctggacatg 60

<210> SEQ ID NO 151
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 151
agcttatctt aaatgtattg tattgggggg tgggcagggc ccactctatg ttatgttaag 60

<210> SEQ ID NO 152
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 152
cggactacat aagcgttaaa aattgtgttt ttcagaatct ttaaaatata agacagtgct 60

<210> SEQ ID NO 153
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 153
atctcaatgc ctgcaagcag ctcgctatgg cattaacacc acagacatcc tccaaactgt 60

<210> SEQ ID NO 154
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 154
actcgtctgc agtgcttagc ctaacttttg tttatgtcgt tatgaagcat tcaactgtgc 60

<210> SEQ ID NO 155
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 155
cccattttcg ttggctggca ggttgagatg tttttcttaa acactgcctg tcagtgtgaa 60

<210> SEQ ID NO 156
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 156
acacagatga cattgaaatt cgtttctctc ctcatctatc acactggagc aaaactggct 60

<210> SEQ ID NO 157
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 157
catggtataa tgtattcaga ctttgattac tacttattta aaatggaatg ttttatggtt 60

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 158
ccagttatct ctccaaaaca cgacccacac gaggacctcg cattaaagta ttttcggaaa 60

<210> SEQ ID NO 159
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 159
cgagaggggg tgaagacatt tctcaacttc tcggccggag tttggctgag atcgcggtat 60

<210> SEQ ID NO 160
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 160
tcaaattttt gaagggattt ttgacagaag tgaaaaatgg ggagaaggat atccagacag 60

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 161
ttaatcagta attcacttca gataacaact ctagagataa aatatgcctt aggggttggc 60

<210> SEQ ID NO 162
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 162
ttctactgag gaggagtttt tcaaacagtg gggtgctgtc tgcaatgtgt acagccttaa 60

<210> SEQ ID NO 163
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 163
cctgccgcag atgtctccca aaaagttgag cctttctaga tggcttaggt ggcaccatgg 60

<210> SEQ ID NO 164
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 164
ccactgctag gcctcaatgt aaattcagtt gaaatttgca attctatcag caatttaatg 60

<210> SEQ ID NO 165
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 165
gttgtcaaag caccaacagg acattttggg atgtgaaatg taatttcttg gaatctgtaa 60

<210> SEQ ID NO 166
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 166
tggtggttta tatcaataac gatgctgtac tatagtccat gtaacaaaag atctggaagt 60

<210> SEQ ID NO 167
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 167
gaagggaaat ttggggatta tttatcctcc tggggacagt ttggggagga ttatttattg 60

<210> SEQ ID NO 168
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 168
tggctgttag ggactgtata tcttgtaaaa gaacacttgt cacatgcttg atcagttaca 60

<210> SEQ ID NO 169

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 169
ttcagtttaa ttgcattgtg aacagaacac atggtcttca atatgtagat tctgtgtgac 60

<210> SEQ ID NO 170
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 170
gaaacttggg ggtcaagaga gcttatcaag agccttttat aggtaagctc ttccgtgtga 60

<210> SEQ ID NO 171
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 171
acgggattgt tagaatcaaa tcactctcgt gggaagaatt tttatatggg aaagcggata 60

<210> SEQ ID NO 172
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 172
tccgtagctg ttcaagtttg tgtttcaact gttctcgtcg tttccgcaac aagtcctctt 60

<210> SEQ ID NO 173
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 173
cattgtttgc atctctctat gaagatacgt ctgtccaaac ttttaaaagg cataactgta 60

<210> SEQ ID NO 174
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 174
atgctgtaca atgaatggat tgttcttgtt tctcagatgg gtagagtaaa agtgtctgta 60

<210> SEQ ID NO 175
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 175
ctgctggagg gacactgctg gcaaacggag acctattttt gtacaaagaa cccttgacct 60

<210> SEQ ID NO 176
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 176
aatgatttgc gtgttttaag aactggtgta tataggtaca tcttgaatgt tctgctttcc 60

<210> SEQ ID NO 177
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 177
tattctgttt gtttaaacta gctagtgtag atcctgttgt ttgtaaccaa gagtgttgac 60

<210> SEQ ID NO 178
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 178
atttttgatt gtgagctcac ctatttgggt taagcatgcc aatttaaaga gaccaagtgt 60

<210> SEQ ID NO 179
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 179
gcactggtca ctcctatgtg ctaagacaag gcagacatct gtgtgttctc ttaagtcttt 60

<210> SEQ ID NO 180
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 180
gccagcgctg cggctggatt cccatccagt accccatcat ttccgagtgc aagtgctcgt 60

<210> SEQ ID NO 181
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 181
tcactgcact cctttgtcat atactctgca tcactgtcat actcacaact tcgtgaataa 60

<210> SEQ ID NO 182
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 182
actcctgaag ggctcaagat ggttaaaaac ttagagtggg ttgcagagag agaagagttg 60

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 183
gggaattaca acaagataaa tgtgagtaat agttcatttt cctgcatttt tgatgagggc 60

<210> SEQ ID NO 184
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 184
gccctactgg agggtgtttt cacgaatgtt gttactggca caaggcctaa gggatgggca 60

<210> SEQ ID NO 185
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 185
aacacagctt tttgccttcg agctatcggg gtaaagacct acaggaaaac tactgtcgaa 60

<210> SEQ ID NO 186
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 186
aacacagctt tttgccttcg agctatcggg gtaaagacct acaggaaaac tactgtcgaa 60

<210> SEQ ID NO 187
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 187
tcaaaacaat ttcaggctcg agtcattagt gtcatgctat accgtaatta ccttcgaagc 60

<210> SEQ ID NO 188
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 188
tgaaaggatc tctggatcac cacaaagtct ggctcagtga ctatggcttt gcaaacacta 60

<210> SEQ ID NO 189
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 189
aacaagatga gattatgcct gaggttgcgg aaaaggaaga ttattcagat attataggga 60

<210> SEQ ID NO 190
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 190
ggataaaggt taggtaacac acatagggct gttacggact gagaagtgtc cctgcaaaat 60

<210> SEQ ID NO 191
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 191
cagaaaggat agtatgggaa cattacaagg gggatacatt actgtggaaa gttctgctag 60

<210> SEQ ID NO 192
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 192
agtatatcag agatattttt ggaaaggagt tggtctatgc aatgtcagtt tggaatcttc 60

<210> SEQ ID NO 193
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 193
ctcattaaaa caaacaaaac cacacctgga ttgcctggta cttaaataaa atgcactatg     60

<210> SEQ ID NO 194
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
tggttaagag aatgtaaaaa taccatttat tattatcata tctactaata cattggtgga     60

<210> SEQ ID NO 195
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
tatatagttc tagtatgaag tttaatagtt aaggagttag ctatttgtta tctttaagag     60

<210> SEQ ID NO 196
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
atgagacaat aaatgctata ggaattatgg aggaataatt agctatttat tttcttggtt     60

<210> SEQ ID NO 197
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
accccgtaga agatggaatc acagatgctg cctttgagca gtttttgcaa gaaaggatca     60

<210> SEQ ID NO 198
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
aatgaagggg aaggggaaga tttcccacca actgaatcat ttgtgcacgt gtatagctca     60

<210> SEQ ID NO 199
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 199
agtgtgttgt cgttattaat ttgctattcc ttgtcctatt cagaaaggat ttcaagaggc 60

<210> SEQ ID NO 200
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 200
ggagaagctg taaaaatcac agtataaaat tatgaagttt ggtaactgta aaatgtactg 60

<210> SEQ ID NO 201
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 201
attcactgta aatgattcca tggctccctg tagtacttct acaaagcatc tatcacaatt 60

<210> SEQ ID NO 202
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 202
gggaaaagtt caatctctat tttggtccac aaggatcaag tgcttatgaa ccagaccaaa 60

<210> SEQ ID NO 203
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 203
cgcgagaggg aagaccttct ttggggccgt gatggtgggg tgagggaata tgagtgcgtg 60

<210> SEQ ID NO 204
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 204
gggatgggtc tctctgtctc cccacttcct gagttcatgt tccgcgtgcc tgaactgaat 60

<210> SEQ ID NO 205
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 205
ctgggaaagc aaagctgttt tcatcctata attgaagtag tgtggagcat taacttgtgg 60

<210> SEQ ID NO 206
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 206
tcgacctgag gagcaaaaca aaggcatcag ctcttacacc aaaagagtta acgctgtaac 60

<210> SEQ ID NO 207
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 207
ttcaaatcat gaagtgcata gtatcacatg tgatagaata tttataactt tttattagat 60

<210> SEQ ID NO 208
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 208
tggccttaca cacatcttgc atggatggca gcattgttct gaaggggttt gcagaaaaaa 60

<210> SEQ ID NO 209
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 209
aaccttatga ttgtaaggaa tgtgggaagg cctttagact tcgtttacga cttactcaac 60

<210> SEQ ID NO 210
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 210
ttctgctgaa ggcacctact cagtatcttt tcctctttat cactctgcat tggtgaattt 60

<210> SEQ ID NO 211
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 211
cagaactcta cttcagcaga cactcaactc aaaaagactg gcaaatggac atgtatttac 60

<210> SEQ ID NO 212
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 212
ttgtaacaca catgtattga tgattttcat taagagtttc agtttaactt tgaaaaatat 60

<210> SEQ ID NO 213
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 213
atgtatagtc tgtatacgtt ttgaggagaa atttgataat gacactgttt cctgataata 60

<210> SEQ ID NO 214
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 214
catcctgagt ggtagaagtc cagtgccctt tctctaccca cagccactca caccacccag 60

<210> SEQ ID NO 215
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 215
ccacgtgtca agtaatcctt aaaagaatat cttggaaaag gaaacagatt ttttcctgtg 60

<210> SEQ ID NO 216
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 216
tgacaccatc gagaatgtca aggcaaagat ccaagataag gaaggcatcc ctcctgatca 60

<210> SEQ ID NO 217
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 217
tgacaccatc gagaatgtca aggcaaagat ccaagataag gaaggcatcc ctcctgatca 60

<210> SEQ ID NO 218
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 218
tgacaccatc gagaatgtca aggcaaagat ccaagataag gaaggcatcc ctcctgatca 60

<210> SEQ ID NO 219
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 219
tgacaccatc gagaatgtca aggcaaagat ccaagataag gaaggcatcc ctcctgatca 60

<210> SEQ ID NO 220
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 220
tgacaccatc gagaatgtca aggcaaagat ccaagataag gaaggcatcc ctcctgatca 60

<210> SEQ ID NO 221
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 221
gtacactcag ctttttgtat ctgtaggttt aatatctgtg tatgtaagca aacttggatg 60

<210> SEQ ID NO 222
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 222
gcttggagga aaccagtttg cactatttga tgaggaattt ggccaccaaa ccactgatac 60

<210> SEQ ID NO 223
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 223
gggagggaat ctggttttgt tacttggcag tggttttttc tcacccttcc tttttaacaa        60

<210> SEQ ID NO 224
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
agagctgttc taatctgcgt tttgcatgtt aagtgttaat atcaaacatt ctttacgtgc        60

<210> SEQ ID NO 225
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
tcaactgctg tatgctacaa tggcaaagag gttacttttg acaaatgggt ggtttgtggt        60

<210> SEQ ID NO 226
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 226
ccccagggct gtgcaaacac atgcccctgc cataagcacc aacaagaact tcttgcaggt        60

<210> SEQ ID NO 227
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
atttgctgac acaatatctt ccgcctggtg ctgggcatat cctaagaact tacaactttc        60

<210> SEQ ID NO 228
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
aagctttaac tatatctctc tttaaaatgc aaaataatgt cttaagattc aaagtctgta        60

<210> SEQ ID NO 229
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
gtgtgtagga cggggaggtc acgatggcgc gacgtctgca gaaatttcat gaggaggtat        60

<210> SEQ ID NO 230
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
caaaagtgaa gaaaaagtta gttcataagt aaaggcacta aatcctttcc tgacaatggc     60

<210> SEQ ID NO 231
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
cggcaacaat gcaccagcat tccagcgtcc aacagagcat ccgtgtacca ttccggcatt     60

<210> SEQ ID NO 232
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
ttgcatgggg gttattttat ctttcatgat tgtggtgcac ctgatgctgg cggggtattt     60

<210> SEQ ID NO 233
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
aagaggtgtg aaattttgac gtgatgctct ttttccttag cattgtaatg tatgtgttac     60

<210> SEQ ID NO 234
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
agttgaaata gacatctttt catgaactct gtaatatttg aaattattga taactcttac     60

<210> SEQ ID NO 235
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
tcctggactt ttcctctcat gtctttgctg cagaactgaa gagactaggc gctggggctc     60

<210> SEQ ID NO 236
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 236
ttgatagtag cttcctcctc tggtggtgtt aatcatttca tttttaccct tactgtttga 60

<210> SEQ ID NO 237
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 237
agttcatgtt actgagttat gacaaattta ttatcatgag ggaaaacaag agtagccagc 60

<210> SEQ ID NO 238
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 238
cagtcagtct atggtgtatt ttttctagta gcctgaactg actgaaagaa aatcatgaac 60

<210> SEQ ID NO 239
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 239
ctcatgtgtg taagctcatg aagatctgca tgaatgaaga ccctgcaaag cgacccaaat 60

<210> SEQ ID NO 240
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 240
gacgatgaca ggcttcgact ctgtggtttc taaagcatat aatattctca cgtacttctt 60

<210> SEQ ID NO 241
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 241
gctgacttaa ttttctgttt tgtaaatata tacaaacaag ttgatacaaa ttttgtttat 60

```
<210> SEQ ID NO 242
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242

actgcctgct caacaagaag gttcgggaag aataccggaa gtgggcctgc ctagttgctg     60


<210> SEQ ID NO 243
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243

cgaaggaaga atcggaaaaa caaagagacc gtccggcaca tcacacagca ggtggaagat     60


<210> SEQ ID NO 244
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244

ccagattaaa aactaaccaa ttcatctttg atggagcttg aatcaaacta agggtattgg     60


<210> SEQ ID NO 245
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245

ccccactggt gtctattaca ggccactttg gtagttgtgt atctgctcat gtatgtgatt     60


<210> SEQ ID NO 246
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246

cagtggaggg cttagatcat acaaaaatct ttattgggtc cgtgtgttct catttccttc     60


<210> SEQ ID NO 247
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247

ttgctttttg tgacaaagtg aatacccact gggctaagtt tcatatctaa agcttgtcac     60


<210> SEQ ID NO 248
```

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 248
aaaggactgt tctttgtgga ggagaagatc aagctgtgtg aaggtgaaaa tcgcattgag 60

<210> SEQ ID NO 249
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 249
tctatggtaa tattttgacc ctttatattt gttctaaaat aagtcaaaat gtgaaaataa 60

<210> SEQ ID NO 250
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 250
atacgaagac agcgttcctc agagtaatgg agagctcaca gtccgggcta agctggttct 60

<210> SEQ ID NO 251
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 251
aaagcatgct tctctctcaa aaagaaaaat taaaggattt tattgccagt cgtgtcagtc 60

<210> SEQ ID NO 252
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 252
atattaacag tcaaggtgtt atttgcttgg acatattgaa agataattgg agtccagcac 60

<210> SEQ ID NO 253
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 253
gaatacttgg gccgttacat cgcccggaaa ctcaacatca actacttcga ctacctggcc 60

<210> SEQ ID NO 254
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 254
ttgcatgtct catgataacc aaatgtaaga tgaaaataaa agatgattta cttcaaaaaa 60

<210> SEQ ID NO 255
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 255
cattcagaca agtgtttgta gactctgaag cctaatgtta ctcatgacgt ttgcctcatt 60

<210> SEQ ID NO 256
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 256
tggcctccca ctaactagca ttcctttaaa gagactggga aatgttttaa gcaaatctag 60

<210> SEQ ID NO 257
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 257
cgtttggggt ttcctagccg ctacatctgt tacttttgtt ggtgttatgg gaatgagatc 60

<210> SEQ ID NO 258
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 258
gctgcggcca gaagatcctc cacaagaaag ggaaagtgta ctggtacaag gaccaggagc 60

<210> SEQ ID NO 259
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 259
tgggacatcc agaaggacct aaaagacctg tgactagtga gctctaggct gtagaaattt 60

<210> SEQ ID NO 260
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 260
tgagacacta tggctccaga gttctgctaa caaccacctg aaacaaactt agtaggagaa 60

<210> SEQ ID NO 261
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 261
aatgtcaaaa atgtgccaaa gtctttagat gtcccacgtc ccttcaagca catgaaagag 60

<210> SEQ ID NO 262
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 262
atgggtgtga accatgagaa atatgacaac agctcaatta tcagcaatgc ctcctgcacc 60

<210> SEQ ID NO 263
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 263
cagtaagtac gggaaaaaat gtttactaac ttcctcagag attcgtgata cgcgtttctc 60

<210> SEQ ID NO 264
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 264
gtcttggctg ttcaaccgta ctttctccag aaggatcagc tcaatttgct gctcagatat 60

<210> SEQ ID NO 265
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 265
gccaagggct gtggaactgt ttctgtgatt caggatcctc ttgggagagt atattcaata 60

<210> SEQ ID NO 266
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 266
aaattctcat taatactgtg tttgatggcc tctgctgtgt tttaacatcg tgcttcttat 60

<210> SEQ ID NO 267
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 267
tgctgcattt cttaacgttt ggtctctata cattatacca tctgctgaag tttagctttg 60

<210> SEQ ID NO 268
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 268
tgctcaagaa tgccatgaga gccacaatgg agagtcacct agacactccc tacaatgtcc 60

<210> SEQ ID NO 269
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 269
ggtgttcttg ggtattgggg acaggacaga gagctcattc tataaccaca gttgtctttt 60

<210> SEQ ID NO 270
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 270
taatatacaa cctgtccagt agccgaacag tttgttttta ttgtgttttc taaccgtaag 60

<210> SEQ ID NO 271
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 271
aagagcagag atacacatgc catgtacagc acgaggggct gccgaagccc ctcaccctga 60

<210> SEQ ID NO 272
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 272
aactactggt aatagccaag aaaatttgga ggtgcagaga acatgctgaa acagaatttt     60

<210> SEQ ID NO 273
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
ttacactcag cagggttttg gaaatttgcc catctgcatg gcaaagaccg atctttctct     60

<210> SEQ ID NO 274
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
tgtaatcctg agagattcac atggtgttgc acaagtacgt tttgtgacag gcaataaaat     60

<210> SEQ ID NO 275
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
acggtaatgg atatttgtga atgtctcttt ggccaaatga gtctggaaaa tgatgtgcta     60

<210> SEQ ID NO 276
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
ctgctggagt caggacattt tatagagcct tttccagttt tactaaaaaa tttttccatt     60

<210> SEQ ID NO 277
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
ttgtatacac ctggaggcat ctgttattca gcttatcctt tgagtgggta tttggcacaa     60

<210> SEQ ID NO 278
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 278
gaaagacagt ccaagccctg gataatgctt tactttctgt gttgaagcac tgttggttgt 60

<210> SEQ ID NO 279
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 279
ttgcttctcc gtggatgaaa tagaaactcc tcattgtgtg accaggaatg gttaaatcat 60

<210> SEQ ID NO 280
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 280
tggagacaga atcacagtta tatcaaaaac agattcacat tttgattggt gggaaggaaa 60

<210> SEQ ID NO 281
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 281
gaaaaattaa tactatcatg ttaatactat tattgtcatc ccaagaaaaa agatatttta 60

<210> SEQ ID NO 282
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 282
acagtagaga cctacacagt gaactttggg gacttctgag atcagcgtcc taccaagacc 60

<210> SEQ ID NO 283
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 283
ctcttgttac cttggctctc taagctgtat ctacttctat acaaggcgaa caattttgtc 60

<210> SEQ ID NO 284
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 284
ggttttacag atggctttga aatgtgctga tatttgtaac ccatgtcgga cgtgggaatt 60

<210> SEQ ID NO 285
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 285
agactgaccg agtggacctg gggaccctgc gcggctacta caaccagagc gaggccggtt 60

<210> SEQ ID NO 286
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 286
catggcagag atttataagt acgccaagag gtatcggccg cagatcatgg ccgcgctgga 60

<210> SEQ ID NO 287
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 287
tgtgatcatc agcaataaag atataataac tctgttttct tagcctgtat agaggagagg 60

<210> SEQ ID NO 288
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 288
tgtcagttgt atctgttgct tttctcaatg attcagggat acaagtgggc ttctctcatt 60

<210> SEQ ID NO 289
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 289
gagctgaaaa cacatttgtt gatatttgtc ttgtccacat tgtgatgttc agtatttgag 60

<210> SEQ ID NO 290
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 290
gctaaacttt ctgtatttat acagttaaac ttataaacca aaaattttaa tgaggttaat 60

<210> SEQ ID NO 291
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 291
gtggttccca tttccttatc catggaggag acctctgaac agatcacaaa tgttacgtga 60

<210> SEQ ID NO 292
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 292
aggtccgtcc aatggaagtc gcagagcctt gggtggactg tttattagag gaatatttta 60

<210> SEQ ID NO 293
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 293
aactgcgcgg ctactacaac cagagcgagg acgggtctca caccctccag tggatgtatg 60

<210> SEQ ID NO 294
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 294
gcagtctttg atcatgccag ggctgatctc cccagtaaaa gccccattag tcactttgta 60

<210> SEQ ID NO 295
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 295
acaatgcttt ttgtttcaga tattttctgt acttgaattt caaatattta tacagaacag 60

<210> SEQ ID NO 296
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 296
gggagggctg agatgatcac ttcgttttct gttacggcta cttttatatt tttcaacatt 60

<210> SEQ ID NO 297
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 297
atcacgtaat tgtttccatg aaaagcaata aatgtaacaa agggtttttc tatgggagcc 60

<210> SEQ ID NO 298
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 298
tcctgcgcac cttataccag aattcagtat aatacactac tttctgtttt caaacagata 60

<210> SEQ ID NO 299
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 299
ctgggagtca ctgatgctgc ctctgccttc tgatgctgga ctggccttgc ttctacaagt 60

<210> SEQ ID NO 300
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 300
tggctgcggg gctccaagta agttattggg atgtttttta tattccaggt gtgctgtaca 60

<210> SEQ ID NO 301
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 301
ttgcctcttc ttccgcaact ggtgcaatga gtttttcctt aagagttgcc attttgcaca 60

<210> SEQ ID NO 302
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 302

-continued cctgtcatag ttttatacaa ctataaaata tatacgtgcc aaaataaatt tgataggaac 60

<210> SEQ ID NO 303
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 303
aggcacttcc gaaagcacac cggggccaag ccttttaaat gctcccactg tgacaggtgt 60

<210> SEQ ID NO 304
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 304
aggaggtcag gatggtcagc tccagtatct cccctaagtt tagggggata cagctttacc 60

<210> SEQ ID NO 305
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 305
tataaaaaga taaaataaaa agccggtcag tgtctgttgc acaaaattac aaccgctctc 60

<210> SEQ ID NO 306
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 306
tgctcacttg attgacttgg tcagatattt gaatgatggt attacctaga ttctaatcct 60

<210> SEQ ID NO 307
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 307
tccctataac tcaaaataac ttgtttgtaa aagaaaattt gtttacttac ccattagtaa 60

<210> SEQ ID NO 308
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 308
acggcttttc tattgctgta tgatacagaa ctcttttggc ataaatattt gtgttcccag 60

<210> SEQ ID NO 309
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 309
aaagttctgg ctgtccatta acctccaact atggtcttta tttcttgtgg taatatgatg 60

<210> SEQ ID NO 310
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 310
tattacgctt cactgggccc tggaggatat tgtcttatac agtccactgg gttttggata 60

<210> SEQ ID NO 311
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 311
gaatacagtg ttccttttca tcccatattt gactgaacct aagacacatc aattataagg 60

<210> SEQ ID NO 312
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 312
ataaataata cttccgaatt aaattattta atatttgact gatttcaata actgtgaaaa 60

<210> SEQ ID NO 313
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 313
aactttttat taaagtgtaa ctatagaaac acatcaatga tttttcacaa gtggagcacg 60

<210> SEQ ID NO 314
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 314
tctcgggtcc atatatgaat tgtgagcagg gttcatctat tttaaacaca gatgtttaca 60

<210> SEQ ID NO 315
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 315
aatttgggtc aatacatcct tttgtctccc aagggaagag aatgggcagc aggtatgtgt 60

<210> SEQ ID NO 316
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 316
gacagttaca atgatctttg tatctgaact ttgcacgtct gccgaaaaat ccgaacctgt 60

<210> SEQ ID NO 317
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 317
tgcagaatga tgaagttgca tttagaaaat tcctgattac tgaagatgtt cagggcaaaa 60

<210> SEQ ID NO 318
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 318
ttcagaaaga tgaagtttcc agaaactaag aaggtagcac aatatgtggc atcatactca 60

<210> SEQ ID NO 319
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 319
catgtctgaa agtcacatat tgtgaaaatt tgaagctatc tcagtaaaaa gcagctttgg 60

<210> SEQ ID NO 320
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 320
aactttggca tcatagaaga acttataacc acagtccatg ccatcactgc ccagaagacc 60

<210> SEQ ID NO 321
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 321
aggctttaca caaagttcta accttatcca acatcagaga attcacactg gagagaaacc 60

<210> SEQ ID NO 322
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 322
acattgaaat atgttttgta taaatttgtc atgttgaaca acattttagc atggtaagtt 60

<210> SEQ ID NO 323
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 323
gctcaacaga ggtttagttt acagtctctg aactaaagta gtaacctccc aaattgtttt 60

<210> SEQ ID NO 324
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 324
ttcagcattt ttgtttattt gtttgttctt taacaaaagt tgttttggtt tgagattcag 60

<210> SEQ ID NO 325
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 325
atacaaagaa ctgcatagcg tataatccaa atggaaatgc tttagatgaa tcctgtgaag 60

<210> SEQ ID NO 326
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 326
tcagtaggta ttcttttatg tgctttagta agtctttata tttttagcat aaaagtgtac 60

<210> SEQ ID NO 327

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 327
tactgagagt tttctgtgaa gctacagcat atctaatcag agaatttctg atttgtttcc 60

<210> SEQ ID NO 328
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 328
ttatcattct aacttcaagg acattatatc acttactgta taataaaata atcttacagt 60

<210> SEQ ID NO 329
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 329
gaagacactg aagaacatca cctaagagat tattttgagc agtgtagaaa aattgaagtg 60

<210> SEQ ID NO 330
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 330
tttaacgctc tctgttctga aaaagaggtg tttggttacg tgtgagccaa catcacgttt 60

<210> SEQ ID NO 331
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 331
ccttctaaca ccttttaaat ctatgtactt taatagttaa gagaaaataa gtttgcagat 60

<210> SEQ ID NO 332
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 332
ggacacccaa ggatatgtct tctgaagatc aaggcaagaa cctctttagc atccaccaat 60

<210> SEQ ID NO 333
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 333
gtaaaaggat gtagtctgca atcattttct gactcttggt gtaataaaaa ttaagtggcc 60

<210> SEQ ID NO 334
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 334
aaataggatg gaggatgggt cactgtgtcc gtattaccaa tgacagtcac cccaagaaac 60

<210> SEQ ID NO 335
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 335
aattcagcaa gatatgtgat ggttctgaga atgaatttaa ttgaaataga ccagcagacc 60

<210> SEQ ID NO 336
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 336
ttgaggcctt atgattcagc agcttggtca cttgattaga aaaataaacc attgtttctt 60

<210> SEQ ID NO 337
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 337
ccagatgcgt gaaatggaag agaactttgc cgttgaagct gctaactacc aagacactat 60

<210> SEQ ID NO 338
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 338
tgcttcacag agctcacgac aaatatcatc ccagggagta acaaggtgat caaacctaac 60

<210> SEQ ID NO 339
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 339
ccttggacta gcaatttatg cttcttggga ggccagcctt gactgactca aagcaaaaaa 60

<210> SEQ ID NO 340
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 340
ggtcctacta gactagacag aaatttgact caaaatggtt gaggccatgc caacctgaat 60

<210> SEQ ID NO 341
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 341
actatgtgcc agcatttccg tatgtgcaga agttcatcaa tagatataga ctcaaagagc 60

<210> SEQ ID NO 342
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 342
cagtcatttt tctctattct gaagctctcc cactgttttc aatgtttaac caactgggga 60

<210> SEQ ID NO 343
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 343
ttactgaaga tgttcagggc aaaaactgcc taacttccgg catggatctt attcgtgaca 60

<210> SEQ ID NO 344
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 344
agcatgctca agagtgctaa tttaggtctt tctgtggaat ttggaacaat tctagtttac 60

<210> SEQ ID NO 345
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 345
tcatgtcaca tgaaacgatt ctctgctttt tggttctgaa cttgaagtcc ctaaactgca 60

<210> SEQ ID NO 346
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 346
aggggaacat ctggctgtta atcacttgca cagttgagaa catttcctat acatcggctt 60

<210> SEQ ID NO 347
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 347
caaacatgcg gattcaattc tttaaaactc gttgaacgtt tataccaaag gtcccgcccc 60

<210> SEQ ID NO 348
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 348
tagtactctg acacatacat gtggttatct tttgccctgt tgtgatggat aatttgaaaa 60

<210> SEQ ID NO 349
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 349
tctgcaattt cttgatcaaa atgggaatga ccagaactct tgattgcttt cagtctgaat 60

<210> SEQ ID NO 350
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 350
acatgtgcag tcactggtgt caccctggat aggcaaggga taactcttct aacacaaaat 60

<210> SEQ ID NO 351
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 351
gttgtccttt gaaatgattg accaggaaaa agatcatcct taaattttga agcaagtgag     60

<210> SEQ ID NO 352
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 352
tccgcatttc agccaattta gcagatgact aaccacctta aaacggtcca cacaattatc     60

<210> SEQ ID NO 353
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 353
ccgccaaagc acccctgccc actcgggctt catcctgcac aataaactcc ggaagcaagt     60

<210> SEQ ID NO 354
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 354
gacttgatgc cttttgaata actttcaata gaattgtcta aaattatctt actggttgtt     60

<210> SEQ ID NO 355
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 355
gctaagcgtt aagggaacat tgaattatat aaacagtcca gataatactc cttctttgtc     60

<210> SEQ ID NO 356
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 356
tgctgtctct gatttctagg ctagttactt gagatatgaa ttttccatag aatatgcact     60

<210> SEQ ID NO 357
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 357
cgatgctatg ttgaatgtat tctgatcgga tcgtttatgg ttatttacaa tgcagttact 60

<210> SEQ ID NO 358
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 358
gatcatcttg tatatacttc tgcaattata agatgttttt tgatgatgag agctttccta 60

<210> SEQ ID NO 359
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 359
catacattgg cgtgtacata aacgtttgtg gaaaacttag ttgtgtgatt attctctttg 60

<210> SEQ ID NO 360
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 360
ctagtaaaat gtcaagaaca gacgggagat attagtgtct ttccctctat cattaaaggt 60

<210> SEQ ID NO 361
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 361
gaaccatcca tgattctgat attgtatttc tttccagtat taacatgtgt attgtgtggc 60

<210> SEQ ID NO 362
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 362
catgcagaaa gatcagtttg cagcagcaag tacaaaagga gaataggaat atctgtcgaa 60

<210> SEQ ID NO 363
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 363
tggttgggga gaggggaccg atgtgcctca ttgtttagtg gtgattacaa atatgctttt 60

<210> SEQ ID NO 364
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 364
aaaggaataa gaagaggtcg gttaagctct ctattaagtt gagaaaatgg gaacttcagg 60

<210> SEQ ID NO 365
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 365
ttatgaatgt accaaataaa ccacagctgg actgttaacc tcaccttaga agcttcattc 60

<210> SEQ ID NO 366
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 366
caccatgccc acatacaaca tacctatcag aaatggtttt cattaaggga gtagaatagt 60

<210> SEQ ID NO 367
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 367
gccccatctt gtgccatgtt ttaagtcttc atggatgttc tgcatgtcat ggggactaaa 60

<210> SEQ ID NO 368
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 368
ctgttagaag gtatgggatc atattaagat aatctgtcag ctactactag gcatttattg 60

<210> SEQ ID NO 369
<211> LENGTH: 60
<212> TYPE: DNA
<213> ORGANISM: Artificial Sequence
<220> FEATURE:
<223> OTHER INFORMATION: Description of Artificial Sequence: Synthetic
probe -continued

<400> SEQUENCE: 369
aacgacaaca gaaaaacaat cttattccaa gtcattccag taacttttt gggtacgtac 60

<210> SEQ ID NO 370
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 370
atttctgtaa aacaggttat aacagtgttt aaagtctcag tttcttgctt ggggaacttg 60

<210> SEQ ID NO 371
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 371
aatccatcct attatgagta attaatgggc tatataatag tgagattaac ggagtccctc 60

<210> SEQ ID NO 372
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 372
agaagcttcg gcagctggcc aagccacaga gcgtcttcga ggagctgaac aatgagaaca 60

<210> SEQ ID NO 373
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 373
ggggggtgca ctttcatttt caattgactt tattaaatga aaatccaaat cttccactcc 60

<210> SEQ ID NO 374
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 374
tatcagcact taagtcagcc ttatctggcc acctagatgt ggctttgggc ctattaaaga 60

<210> SEQ ID NO 375
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 375
actccagata aaatgaaaaa cctctccaag tcctggtgga agaagtactg ctgtttcgta 60

<210> SEQ ID NO 376
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 376
agaagtatgg aaacagcctc aagattatca gcaatgcctc ctgcaccacc agttgcttaa 60

<210> SEQ ID NO 377
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 377
caaatatttt ttattcagga tggtataacc taactgataa taggtaataa ggttaaattt 60

<210> SEQ ID NO 378
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 378
gtgggtaatt tcttcccttt tttgattaag ttggttcagc tatggtgcta ttcagtaggt 60

<210> SEQ ID NO 379
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 379
caaattggca tttgaataaa gccctgggac cacctcaaca tgcgtagcct cttgtcttaa 60

<210> SEQ ID NO 380
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 380
gaattgtgta ctaatagcaa ggtataagtt tggtgtagag cctatccagt agcgtccact 60

<210> SEQ ID NO 381
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 381
attatggaag caggagtttc cttttcaaaa ttgttacaaa ttgtagaagc cacagtgttc 60

<210> SEQ ID NO 382
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 382
cttttataga ggactgtttg cccagcttat ccggcagatc ccaaatactg ccattgtgtt 60

<210> SEQ ID NO 383
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 383
tctggagcaa aaatgattat gttgtaagaa cttttggagg ttttcctcct cgtaaaattc 60

<210> SEQ ID NO 384
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 384
gaattaggga aataatttgg tggaaaccgg gaatgagttc tattcttaaa cagccttttt 60

<210> SEQ ID NO 385
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 385
tggtttgctt aggagttcag agttccttca tcatcgaaat agtgattaag tgatcccaga 60

<210> SEQ ID NO 386
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 386
agctggcaga caagaatgtg cccaacgttc acatgaaggc catgcagtct ctgaagtccc 60

<210> SEQ ID NO 387
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 387
atgcttacac gccattatga tccaagcaaa ataaaactgc agttgtcaac attagaacat 60

<210> SEQ ID NO 388
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 388
cttaagagga gatattacag acagcactgc actttgcagt cagctacatc aaggacctct 60

<210> SEQ ID NO 389
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 389
aaggacacca acggcagcat cagcaagtcc gtgttgtctc ccaaataagt ggtgttctcc 60

<210> SEQ ID NO 390
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 390
tgagctgcga aaaagtcggc tcgaacaggt ggctttcaag gagcacgctc tggctgttca 60

<210> SEQ ID NO 391
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 391
cgaccttctg cgactatttg agtatggcgg tttccctccc gagagcaact acctctttct 60

<210> SEQ ID NO 392
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 392
ctgctccaca cactgctgca tcttgggtct cagggaccca gacagatgga cttacatgga 60

<210> SEQ ID NO 393
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 393
ttcagttttc atcatgatgt agagatatca gttttataga ttgtatgttt atttgccata 60

```
<210> SEQ ID NO 394
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 394

cctcacgtga aataaatatt ttatatggtt ttactaaaaa taagactcat gtatctggtc     60


<210> SEQ ID NO 395
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 395

agtgtgaatt ttctaatgct gagtaagttg tgatccagaa gtaaatgtat ctgcaagctg     60


<210> SEQ ID NO 396
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 396

attaaatcta caaatgactg gctgtaccca tgaagtgagt tattctaaag acaatggaac     60


<210> SEQ ID NO 397
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 397

cccagacttc tgatcaacaa atattgctgc tacattaact gattcgcaac aaagaaagaa     60


<210> SEQ ID NO 398
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 398

ttgagatagt cactcagagg ttttcacata caggattaac cttgctgcag tgcgtgtgca     60


<210> SEQ ID NO 399
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 399

ccccgaatct ggcttggcag aatatatctt taacaagaac accctgggag acagtgataa     60
```

-continued

<210> SEQ ID NO 400
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 400
tgggttattt cttgctttcc aaattccctt gtctgtagct atctttcatc acttgcaaaa 60

<210> SEQ ID NO 401
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 401
atgctgtgta tttgtacagg aatttgagca aaaaatgtat agagtgtgat gtccaattgg 60

<210> SEQ ID NO 402
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 402
gtggaacaaa ctgccaaaag tttagaccta acccaatatt gctttcctga gaaatctctg 60

<210> SEQ ID NO 403
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 403
aagtcttttg tgaattattt cctgaagtcg tggaggagat taaacaaaaa cagaaagcac 60

<210> SEQ ID NO 404
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 404
taggcttacc atctgatttg taattacaat tttggaattc tctgttttag ttgctgaggc 60

<210> SEQ ID NO 405
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 405
atttcttcat atctgacgtt tctgaaaccc tttgtgtctg ctgttgtgtg aagattgaca 60

<210> SEQ ID NO 406

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 406
gacaagttgg tttgagggag aaaactttaa gtgttaaagc cacctctata attgattgga 60

<210> SEQ ID NO 407
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 407
gacaagttgg tttgagggag aaaactttaa gtgttaaagc cacctctata attgattgga 60

<210> SEQ ID NO 408
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 408
gacaagttgg tttgagggag aaaactttaa gtgttaaagc cacctctata attgattgga 60

<210> SEQ ID NO 409
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 409
gacaagttgg tttgagggag aaaactttaa gtgttaaagc cacctctata attgattgga 60

<210> SEQ ID NO 410
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 410
gacaagttgg tttgagggag aaaactttaa gtgttaaagc cacctctata attgattgga 60

<210> SEQ ID NO 411
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 411
gacaagttgg tttgagggag aaaactttaa gtgttaaagc cacctctata attgattgga 60

<210> SEQ ID NO 412
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 412
gacaagttgg tttgagggag aaaactttaa gtgttaaagc cacctctata attgattgga 60

<210> SEQ ID NO 413
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 413
gacaagttgg tttgagggag aaaactttaa gtgttaaagc cacctctata attgattgga 60

<210> SEQ ID NO 414
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 414
gacaagttgg tttgagggag aaaactttaa gtgttaaagc cacctctata attgattgga 60

<210> SEQ ID NO 415
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 415
gacaagttgg tttgagggag aaaactttaa gtgttaaagc cacctctata attgattgga 60

<210> SEQ ID NO 416
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 416
gctctacaaa gtaccttatg tagcccaaga aattcaagag gaaattgatg agctccttca 60

<210> SEQ ID NO 417
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 417
acttctcttt ctgcaaaggc atctgaatgt gtctgtgtcc ctataggcat aatgtgaggt 60

<210> SEQ ID NO 418
<211> LENGTH: 60
<212> TYPE: DNA

<213> ORGANISM: Artificial Sequence
<220> FEATURE:
<223> OTHER INFORMATION: Description of Artificial Sequence: Synthetic probe

<400> SEQUENCE: 418
acttctcttt ctgcaaaggc atctgaatgt gtctgtgtcc ctataggcat aatgtgaggt 60

<210> SEQ ID NO 419
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 419
acttctcttt ctgcaaaggc atctgaatgt gtctgtgtcc ctataggcat aatgtgaggt 60

<210> SEQ ID NO 420
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 420
acttctcttt ctgcaaaggc atctgaatgt gtctgtgtcc ctataggcat aatgtgaggt 60

<210> SEQ ID NO 421
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 421
acttctcttt ctgcaaaggc atctgaatgt gtctgtgtcc ctataggcat aatgtgaggt 60

<210> SEQ ID NO 422
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 422
acttctcttt ctgcaaaggc atctgaatgt gtctgtgtcc ctataggcat aatgtgaggt 60

<210> SEQ ID NO 423
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 423
acttctcttt ctgcaaaggc atctgaatgt gtctgtgtcc ctataggcat aatgtgaggt 60

<210> SEQ ID NO 424
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 424
acttctcttt ctgcaaaggc atctgaatgt gtctgtgtcc ctataggcat aatgtgaggt     60

<210> SEQ ID NO 425
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 425
acttctcttt ctgcaaaggc atctgaatgt gtctgtgtcc ctataggcat aatgtgaggt     60

<210> SEQ ID NO 426
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 426
acttctcttt ctgcaaaggc atctgaatgt gtctgtgtcc ctataggcat aatgtgaggt     60

<210> SEQ ID NO 427
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 427
aagcactttc atacgcaggc atctcttgtt acctacatct aagctgttcc cgaaagagtg     60

<210> SEQ ID NO 428
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 428
agagatgtaa tctgtataat gattcatatt ttcccatgtg aatacagtct gataaagatg     60

<210> SEQ ID NO 429
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 429
actaaagcta attgaaagag tcatgcaact cagttgggaa ttaaccactc aattcaatag     60

<210> SEQ ID NO 430
<211> LENGTH: 60
<212> TYPE: DNA
<213> ORGANISM: Artificial Sequence
<220> FEATURE:

<223> OTHER INFORMATION: Description of Artificial Sequence: Synthetic probe

<400> SEQUENCE: 430
tcactggaat aactttaaaa aagaattaca atacatggct ttttagaatt tcgttatgta 60

<210> SEQ ID NO 431
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 431
aattagggat gactgcatta tcaaaatact ctcagggttc ctataaatgg cagctctcct 60

<210> SEQ ID NO 432
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 432
gaaatcttac tgaaccaaga aagttttgca gaatttctga aggccgaata ttcagactta 60

<210> SEQ ID NO 433
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 433
tgtgcatgga cttggtgaga ctgttgcctt aatgacatcc tgcaccgtgt ataacttagt 60

<210> SEQ ID NO 434
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 434
ctcaagaaac aaatgctagc ttcatatgta tggctgttgc tttgcttcat gtgtatggct 60

<210> SEQ ID NO 435
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 435
actgagaaca tttgcagcca cacatgtaca tatgtgtaca caggtagaca gatggacaca 60

<210> SEQ ID NO 436
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 436
gccatgttgc cacatgagca agcttgggtg ctcccaaggt tcaaatactt tttattagac 60

<210> SEQ ID NO 437
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 437
gtccaagtga gttagccttt ttagggttga ttaattaaaa gagcagcaag aatggcattt 60

<210> SEQ ID NO 438
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 438
cctaatcgtc ccactaaatg gaatgcctat gattagcttc attaagagtt ttatactgtg 60

<210> SEQ ID NO 439
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 439
ggcgttatgc tccatgtatt ctgcaacttt tcatcataca ttaggttttg gcgatttagc 60

<210> SEQ ID NO 440
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 440
cgaggccatc ctgaaggtgc tggagaacct gacaccggag gagctcaaga agttcaagat 60

<210> SEQ ID NO 441
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 441
acctgctaca agcacttcta ctacttcatc cgcgagttca gtctggtgga ccagcgggag 60

<210> SEQ ID NO 442
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 442
tcctatacat cgaaggtgtg catatatgtt gaatgacatt ttagggacat ggtgttttta 60

<210> SEQ ID NO 443
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 443
tttacacttg cttgatgtga taactctaaa gactttttaa ctgataaaag cgcacatggc 60

<210> SEQ ID NO 444
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 444
aacagctggg gacaactgcg gtgatgatgt aaaaaccttc ccataaaatg taagaaaagc 60

<210> SEQ ID NO 445
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 445
aagcctgacg agccctctca cagtggaatg gagagcacgg tctgaatctg cacagagcaa 60

<210> SEQ ID NO 446
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 446
aatatctgat agatacactg catctttggt catctaagat ttgtttacaa atgtgcaaat 60

<210> SEQ ID NO 447
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 447
aagctgtgcc tcgacacatc ctcatcccaa gcatgggaca cctcaagatg aataataatt 60

<210> SEQ ID NO 448
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 448
aaatgctatc aagaaacccc gatcacaaag atacaaatct cttaagtgga tggaccccag 60

<210> SEQ ID NO 449
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 449
ggaatttatg ctggtaggaa actttcaaat gtgaagaata ttggcaggtc tattctcatc 60

<210> SEQ ID NO 450
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 450
gagcagacaa taaattgtat tcctacagat attcacctac cacttcccat gttggggcat 60

<210> SEQ ID NO 451
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 451
gccattgaag catgaatata ttgaagatgt tggagaatgt cacaaccaca tgattgggat 60

<210> SEQ ID NO 452
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 452
ctttgtcacc agtggctttg gtatttccat gtctggcatt gcataaactt ctctggtgtg 60

<210> SEQ ID NO 453
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 453
ccataccctc aacctcagtg ggctggaaat gacagtgggc cctgtagcag tggcagaata 60

<210> SEQ ID NO 454
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 454

-continued taggaatgtg atgttagaga actacagtaa cctggtcttc cttggtatta ctgtttctaa 60

<210> SEQ ID NO 455
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 455
gatatttgtg gaaaactgtt tactcgaaga gaacatgtaa aaagacattc cctggtgcat 60

<210> SEQ ID NO 456
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 456
ttataaatgt ttattttgta cttaatacct gtaaagtctt agttttcaga cattaagtga 60

<210> SEQ ID NO 457
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 457
ggatttcgca gtcatctttt tggggaaact gaaagtacca tctcatttgc atgaagtgac 60

<210> SEQ ID NO 458
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 458
gctttggcaa aatttttaag atttctttga tgtccgatgt gctcatttct tggtttgttc 60

<210> SEQ ID NO 459
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 459
taactagcct ttactttgaa gaatcgtgac agagtagact caatattgta gctgactaga 60

<210> SEQ ID NO 460
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 460
ttaaccaatt tcacctgtaa atctgtctgt gctttgtaat tttggtgata ctgttgactc 60

<210> SEQ ID NO 461
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 461
agacaacgtt tgttattatt actgctacta ttactatttg ctcctcatga gatcaaggtg 60

<210> SEQ ID NO 462
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 462
gactgctaaa ctgttctctg tataagttat ggtatgcatg agctgtgtaa attttgtgaa 60

<210> SEQ ID NO 463
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 463
gcagcaccac ttgagatttc cagaggaccc agacctttgt tcattctaaa gagactgata 60

<210> SEQ ID NO 464
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 464
tcattgttct aataatcacc aattcagact cagatcctcg tggtctatgg agcatgctgc 60

<210> SEQ ID NO 465
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 465
cggcaatgga cttatcgtag ttggggaaac gggtgttccg aataatatcc tggaagttat 60

<210> SEQ ID NO 466
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 466
cttccaacac acatatgcag gcgtctctaa aattccggag atatggtcac caattatttt 60

<210> SEQ ID NO 467
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 467
acatttagta caggtaccat aaccaagaga tttcttagtt ttgatggatt aagagagagc 60

<210> SEQ ID NO 468
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 468
tcactctctc tttgtcatga aagccagctc cttgtggcga ggtaaagtgg aattccaata 60

<210> SEQ ID NO 469
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 469
aggttgcagg tgaacatggc cttgaggtaa atctgtccct tgctgaatac agtttcagta 60

<210> SEQ ID NO 470
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 470
agggaggctt gagtacatat accaatgaag agatattcag catttgtcta tttgataagg 60

<210> SEQ ID NO 471
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 471
aagcactggc tacagttatt ctgaaaaatc ccaaacgcaa aagggaggca aagctgtctc 60

<210> SEQ ID NO 472
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 472
gaagactatt tgaacagcct tttagaagga tgtttaaaag atactgaaga ttccctttcc 60

<210> SEQ ID NO 473
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 473
aatgctattc tcatccagcc atattagtct tctggctttt ctttagcttc atcaaataag 60

<210> SEQ ID NO 474
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 474
cttggaaacg cttggtgata gataaaaata aatacaacac actcaaatac aggatgacag 60

<210> SEQ ID NO 475
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 475
gcccacggga gcttactaat gatgaaccac ccgaccaaca cgcactggta ccacagtctt 60

<210> SEQ ID NO 476
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 476
gaacacagaa gagaggaggt tgtgtctctt gctcatagca agcctgtggg tagaggaaag 60

<210> SEQ ID NO 477
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 477
ttttttaaag cagtaagttt atagcatgca ttcccagtgg ccttctcatc tgggcctgga 60

<210> SEQ ID NO 478
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 478
agtgtcttgg gcgtggatca gtcttctcca aaatacgagc agtgtatgaa gatattgagg 60

<210> SEQ ID NO 479
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 479
atgaattcag gtcttttaag ttttattcca ttgtaagaat aaacaagttt gttcattcat 60

<210> SEQ ID NO 480
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 480
gtctgtctgt aaggagatgc catctactaa ccaatttgta ttgtgtttcc aataaattcc 60

<210> SEQ ID NO 481
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 481
acagtccctc gctttttgtt gttgttggtt ttcttaaccc ctttaatgga actgcctgga 60

<210> SEQ ID NO 482
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 482
cgaggctgta gctgggctac ttgatcttgc tgaaagtgtt tctaaagata gcaccacttt 60

<210> SEQ ID NO 483
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 483
ccagaatcga aaccgagaga ttgttgagca tgtcattcat ctgttcaagg aggaagtaat 60

<210> SEQ ID NO 484
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 484
ccgctactac aaccagagcg aggcggggta tcacatcctc cagggaatgt ttggctgcga 60

<210> SEQ ID NO 485

<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 485
tggccactgg cgtcatctct acgctgcaga ttcaccaaga gaacatggga caggctctca 60

<210> SEQ ID NO 486
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 486
tctaagggac ttgctcctga tcttcctgaa gatctctacc atttaattaa gaaagcagtt 60

<210> SEQ ID NO 487
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 487
agggagacga gaacaccaca caagacattt ttctacagta tttcaggtgc ctaccacaca 60

<210> SEQ ID NO 488
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 488
tggggctttc tgacagttcc atgctgatgt atcaggccat ctgtgtcatg cttatgtatt 60

<210> SEQ ID NO 489
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 489
ggtgacagtt aaactccttt ttgcatgaaa aaatacagat tcttattaaa acaataatcg 60

<210> SEQ ID NO 490
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 490
ttcttctcct aagagaatag acagtttttc cagattcatc atcattgact gtcaagaaag 60

<210> SEQ ID NO 491
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 491
attagaggaa ggttgtaaat attttctagg agttctattg taaagaaaag tatttttgaa 60

<210> SEQ ID NO 492
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 492
accatcgtgg aatcaaacgc tacatctaca tccaccactg ggacaagcca tcttgtaaaa 60

<210> SEQ ID NO 493
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 493
ggaccccatg gaaaagatgg ggaagagcaa aatacatgga gacgacgcac cctccaggat 60

<210> SEQ ID NO 494
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 494
acgtgtaagt aatgtttcta caggtctttg caacaaactg tcactttcgt ctccagcaga 60

<210> SEQ ID NO 495
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 495
agcttccagc caaggatgcc ctggccgatt ggaaatgctg taaaatgcaa actaagttat 60

<210> SEQ ID NO 496
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 496
tttaaaccca cgaaaaaacc gggaacgagc tgccgaagtt ttcttcgaga ccttcaatgt 60

<210> SEQ ID NO 497
<211> LENGTH: 60
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 497
ggatgagacc aattgactct cccattggtt gttagatagt tgaaatggtg cgttggtggt     60

<210> SEQ ID NO 498
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 498
cttgtcagtg taatgaatgt ggaaaaatct tttaccgtaa atcagacctt gctaaacatc     60

<210> SEQ ID NO 499
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 499
attctcagag accaagtgcc cacttagccg tgaaaaagat atttgttggc ggcattaaag     60

<210> SEQ ID NO 500
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 500
gagaagtctc agctaagctc acgtcctgag aaagctcaaa ggtttggaag gagcagaaaa     60

<210> SEQ ID NO 501
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 501
accaacaccc acaggatagt ggacggcaaa gtggtgtttg agaccaacat cacagacgtc     60

<210> SEQ ID NO 502
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 502
cttcatttaa tatatcaata ttgggcctaa aacagtattc tgtaaagctt aaattggtat     60

<210> SEQ ID NO 503
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 503
ttctctgaag tggctgagaa acacaacaac aggaacagac aaactcaacc agaactccca 60

<210> SEQ ID NO 504
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 504
aattaggaat actaattaat tgaattttca ctcatgagta tgttctgaat atttaatatt 60

<210> SEQ ID NO 505
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 505
gtgtgaaaca tggttgtaat atgcgactgc gaacactgaa ctctacgcca ctccacaaat 60

<210> SEQ ID NO 506
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 506
tgccccacgc aatatttgga acacttatgt gaaaaatgat ttgtttttct gaaattcacg 60

<210> SEQ ID NO 507
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 507
gcttttctaa gaatggagta ctcgttttca agagatttgt cctaattata ttttccagcg 60

<210> SEQ ID NO 508
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 508
ggcccacgtt tttatcatta agacctattt gttagctagt agagctttat gttcgctgtc 60

<210> SEQ ID NO 509
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 509
tggcagatga tttgtcattt atttatatta ggttttactg cctattgaga caaccaggtg 60

<210> SEQ ID NO 510
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 510
attggaggcc attataagaa tgtttggaaa tagcttgacc cctgaaagat atctataaac 60

<210> SEQ ID NO 511
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 511
tgacactgta tttatcttca gtctcttgtt ggtatctaac tttggttctg aagtttatgg 60

<210> SEQ ID NO 512
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 512
aattagttga tatactaatg agaaaatata ctagcctggc catgccaata agtttcctgc 60

<210> SEQ ID NO 513
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 513
accctattgt ggcctcatcc aaactgtatc ttcctttact atgtatacct tcaccgtgta 60

<210> SEQ ID NO 514
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 514
aggcgcagga ggcaggagaa gcggagggcg cagagacaag cggccctacc cagaggccgc 60

<210> SEQ ID NO 515
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 515
attctgtggt acaacccagg ggtaaactat tattccagta gtcagtacac ttttctagat 60

<210> SEQ ID NO 516
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 516
tgtcattctg aaaacatcct atgcgatgga atggagaagg aagtgatgac tcagagtgtg 60

<210> SEQ ID NO 517
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 517
acctttgaat ttgcggatgc tgaggaggat gatgaggtca aggtgtgagg ggctggggca 60

<210> SEQ ID NO 518
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 518
tcatggcagg ctttggccag tgaacaaatc ctactctgaa gctagacatg tgctttgaaa 60

<210> SEQ ID NO 519
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 519
gagtacaata ttaatgtaga caaaccatga agtttattat ttcatataag aacattacag 60

<210> SEQ ID NO 520
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 520
actcacaatt ccaaacatac aagaggctcc ctcttaacgc agcacttaga cacgtgttgt 60

<210> SEQ ID NO 521
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 521
tattagtggt aacgtgatag aatttattcc cgatatctga tgttacaaac tttagggtcc 60

<210> SEQ ID NO 522
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 522
tattagtggt aacgtgatag aatttattcc cgatatctga tgttacaaac tttagggtcc 60

<210> SEQ ID NO 523
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 523
tattagtggt aacgtgatag aatttattcc cgatatctga tgttacaaac tttagggtcc 60

<210> SEQ ID NO 524
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 524
tattagtggt aacgtgatag aatttattcc cgatatctga tgttacaaac tttagggtcc 60

<210> SEQ ID NO 525
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 525
tattagtggt aacgtgatag aatttattcc cgatatctga tgttacaaac tttagggtcc 60

<210> SEQ ID NO 526
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 526
tattagtggt aacgtgatag aatttattcc cgatatctga tgttacaaac tttagggtcc 60

<210> SEQ ID NO 527
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 527
tattagtggt aacgtgatag aatttattcc cgatatctga tgttacaaac tttagggtcc 60

<210> SEQ ID NO 528
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 528
tattagtggt aacgtgatag aatttattcc cgatatctga tgttacaaac tttagggtcc 60

<210> SEQ ID NO 529
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 529
tattagtggt aacgtgatag aatttattcc cgatatctga tgttacaaac tttagggtcc 60

<210> SEQ ID NO 530
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 530
aagttgttaa gagtaaggcc tactttaaga gatatgtgaa atttagaaga cgacgagagg 60

<210> SEQ ID NO 531
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 531
ggggtttccc tttgggcctc agtgttacaa attactagtg ctattttcat tattattgta 60

<210> SEQ ID NO 532
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 532
ctgcaaagcg acccaaattt gacatgattg tgcctatcct tgagaagatg caggacaagt 60

<210> SEQ ID NO 533
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 533
gcaagtggtc accagcatta cacagcaatg aagcagaata aagtaggcca gaatgcatca 60

<210> SEQ ID NO 534
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 534
ctgcagtagt ttgcttttag tattgttgtt gcacttgagc agagacaaac ctttattcat 60

<210> SEQ ID NO 535
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 535
aggcttagta gctcagtctt taacaagggc tagaaaagaa tgtaatctga tatggaagga 60

<210> SEQ ID NO 536
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 536
aggagtggtt tgcccggtac ttcacattct gaaagaattg tgttggcaca gctctgtata 60

<210> SEQ ID NO 537
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 537
gaaattacca aaatccggag gaagctgact taccagttca gtgaggccat tctccaaaga 60

<210> SEQ ID NO 538
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 538 ggacctttc attcttttct ttatattcta gacagtctct gttgtctcat tgtgttgctg 60

<210> SEQ ID NO 539
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 539

-continued gctgagcttc ctcacacacc agcgcttcca gttcagtagc ctacagcagg ggaagatgtt 60

<210> SEQ ID NO 540
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 540
ctgtgtatat ttacgttaaa cacaattatg ttacctaagc ctctggtggg ttatctcctc 60

<210> SEQ ID NO 541
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 541
atttaggtct ttcatagctt ttttatttaa aggtatatga ttaagataaa ggaaaagtaa 60

<210> SEQ ID NO 542
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 542
aagtatccca agggttactt tgtccagaac acagactttg acttcttcaa ctacgcggga 60

<210> SEQ ID NO 543
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 543
cacccaggtg ctaagctaca cagactggat tcagagaacc ctggctgaat ctcactcagg 60

<210> SEQ ID NO 544
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 544
aattcagaaa ttgggttttg gttcagtgat tctcaagaaa aagatctctt gcccattaag 60

<210> SEQ ID NO 545
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 545
tgatgcatga ggtaggtgtt ccgagtaata ttctgcatta tattgagaga caaattttgt 60

-continued

<210> SEQ ID NO 546
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 546
agttgcctgg atcatttgaa atttctggga gtctgaggag tactgacata attacctgct 60

<210> SEQ ID NO 547
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 547
tatgcgtgtg tttatgtaca gaaattttag tgtttttgtt tgtctgttat tgcccaaggc 60

<210> SEQ ID NO 548
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 548
tcgagtctcc agctaactct gaaacctcag acctcactct gtacctggtg gtagcggtgg 60

<210> SEQ ID NO 549
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 549
ccctcaacta cctccaaaac cgttgaatat attctttgct gtctgcatct ctttgagtag 60

<210> SEQ ID NO 550
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 550
gaactgaatg cagcctggac actggcctca ataccttgtt taggatttct tcaccctttt 60

<210> SEQ ID NO 551
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 551
ttgttaggct tttgtgaagc atttttgaac ctaataaata atgtcaaaag tccctagcgc 60

<210> SEQ ID NO 552
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 552
actgaggaaa attaattgcc atttgtatat tccttagtac cagattatcg ttgattatgt 60

<210> SEQ ID NO 553
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 553
gggtcttccc agttgagact gctggagctg agacacagta ctctcttaaa gaaggtgggg 60

<210> SEQ ID NO 554
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 554
agaccttgga aatgtggaca taagctcttt ctttcctttt gttactgtat ttagtttgtg 60

<210> SEQ ID NO 555
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 555
tcaccaactg gtacaagccc ggtgagaccc ggaagatgat cagcacgtgg accgccgtgt 60

<210> SEQ ID NO 556
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 556
ccagcagttc ctgttcaacg tgtaaagaga cctgatgttt tccctaataa agctgataac 60

<210> SEQ ID NO 557
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 557
tgttcatgtt ccagctctac accatgcgac gaggaggtct cttctatgcc accggcctct 60

<210> SEQ ID NO 558
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 558
aaggtggcat cgtctcaaag aacttttgac tggagagaat cacagatgtg gaatatttgt 60

<210> SEQ ID NO 559
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 559
gccatacgaa atttgaacgt agctttggaa aaagggacta tttgtggagt aatggcatta 60

<210> SEQ ID NO 560
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 560
atgtcatgag cctttctctt gctcctgaca ccagactgtt cgtctctggt gcttgtgatg 60

<210> SEQ ID NO 561
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 561
aggtatttca tctgtttgtt ctgaaaatgc agctgctgtc tagatttatg tgtgctctga 60

<210> SEQ ID NO 562
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 562
tgtatgagca ggacggctgc attggattgt acaactgttt tgtgatgccc ccagacactg 60

<210> SEQ ID NO 563
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 563
gtttcctctg cattgggttt gaagtagttt agttatgtct ttttctctgt atgtaagtag 60

<210> SEQ ID NO 564

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 564
ccagagtttt ggggcttttt taggctcaac tatcatgcat tattattctt tcataaaaaa 60

<210> SEQ ID NO 565
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 565
ggcagctttt accacattag cttgttatta tcaaaaacta ccacctactt taaacctgga 60

<210> SEQ ID NO 566
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 566
gtgcctatat gacaaaatcc tgcctaacca cactgcttta ttttacactt aagaagttct 60

<210> SEQ ID NO 567
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 567
ctgctgtagc aatggctaaa gggtcaagat cttagctgta tggagtaact atttcagaaa 60

<210> SEQ ID NO 568
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 568
caaaaagtct tccttccaag cgtgtatgat gaaatgagta aattgattaa ttggcgtaac 60

<210> SEQ ID NO 569
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 569
tatgatgaaa ccctggaaga taggtagcaa ctagactgtc gtttttggtg gagcggttca 60

<210> SEQ ID NO 570
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 570
agaaaggtgt tttcaaaagt atttggccgt agattttcac atccatcata aggttggcat 60

<210> SEQ ID NO 571
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 571
ccataagttt gctgtcagtt attgtatggt cagtacccca gtcctagtac acatatttta 60

<210> SEQ ID NO 572
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 572
cacactggac aggtgactgt atggtagaga ctgtgatctg ggaacttttt gctgtacaaa 60

<210> SEQ ID NO 573
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 573
cttcctgact acttgttcca aactctgagt cagatctaaa gtcactttaa gtcacagaac 60

<210> SEQ ID NO 574
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 574
atgggtgaac tgaattacgc ctaagaagca tgcactgcct gagtgtatat tttggattct 60

<210> SEQ ID NO 575
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 575
ctttacagag agaggcctac taatcaatgt gcttagagaa acaaactacc tttacattca 60

<210> SEQ ID NO 576
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 576
ttcgtgctgg gcctgctctt ccttggggcc gggctgttca tctacttcag gaatcagaaa 60

<210> SEQ ID NO 577
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 577
ttcgtgctgg gcctgctctt ccttggggcc gggctgttca tctacttcag gaatcagaaa 60

<210> SEQ ID NO 578
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 578
ttcgtgctgg gcctgctctt ccttggggcc gggctgttca tctacttcag gaatcagaaa 60

<210> SEQ ID NO 579
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 579
ttcgtgctgg gcctgctctt ccttggggcc gggctgttca tctacttcag gaatcagaaa 60

<210> SEQ ID NO 580
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 580
ttcgtgctgg gcctgctctt ccttggggcc gggctgttca tctacttcag gaatcagaaa 60

<210> SEQ ID NO 581
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 581
ttcgtgctgg gcctgctctt ccttggggcc gggctgttca tctacttcag gaatcagaaa 60

<210> SEQ ID NO 582
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 582
ttcgtgctgg gcctgctctt ccttggggcc gggctgttca tctacttcag gaatcagaaa 60

<210> SEQ ID NO 583
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 583
ttcgtgctgg gcctgctctt ccttggggcc gggctgttca tctacttcag gaatcagaaa 60

<210> SEQ ID NO 584
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 584
attttagtgc ttgccaccac cagatgagaa gttaagcagc ctttctgtgg agagtgagaa 60

<210> SEQ ID NO 585
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 585
agcatccaca gtgttagtcc aaagggtcgg accgtgtcgt cagcctagcg tttggtcagt 60

<210> SEQ ID NO 586
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 586
taaacagctg tcttgtctgt gtgtatattg tttgatcagg gtacatggca gccagtcaca 60

<210> SEQ ID NO 587
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 587
accagcactt tatacacttc tggctcacag gaaagtgtct gcagtagggg acccagagtc 60

<210> SEQ ID NO 588
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 588
tggcccagtt caacgcagcc aatgacattg acatgatctg ccgtgcccac caactggtga 60

<210> SEQ ID NO 589
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 589
aatacagtca acttacggtg cacagtaata tgaaagccac actttgaagg taataaatac 60

<210> SEQ ID NO 590
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 590
agtctgtgcc tgaatgtatt tacatctgtt tgtagcccaa aagccaaaag catacatacg 60

<210> SEQ ID NO 591
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 591
aagcctcgtt ttgttttgct ttgttgcaaa cctataaagc gttatcacca gagctatctg 60

<210> SEQ ID NO 592
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 592
ctacagtata cttatgccac aatgtacgtt tccatgcaaa atcttctatt tgtaagtgtg 60

<210> SEQ ID NO 593
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 593
ctgttccggc attactatgt catggtcatc tgctacgtct acttcacccg catcatcgcc 60

<210> SEQ ID NO 594
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 594
ccaacatatc ctgttcccca ctactcattc ttttagcaaa tgacagaagc taattcctat 60

<210> SEQ ID NO 595
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 595
ggccttagta gaattagctg tatttagaca aagttagact ttagtgtgaa atgtaatcgg 60

<210> SEQ ID NO 596
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 596
ggaatatata tgacaattat tttctgtaca ttaatgtcta aacattatac ttactttttc 60

<210> SEQ ID NO 597
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 597
agccacctca gtaaaattgg agaggattct tttgcattga ataaacttac agccaaaaaa 60

<210> SEQ ID NO 598
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 598
taatccatct cagaagttga agatgtgatg ttgctcggcc tttggaataa tttttaaatc 60

<210> SEQ ID NO 599
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 599
atgcaagctc cttctctctt gtggcttgcc gagcctggtt agctctgaga ccggaagttc 60

<210> SEQ ID NO 600
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 600
tgatatttgc ttggaaatta agttagttga actctttgaa ccacagtaga aaccgctttg 60

<210> SEQ ID NO 601
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 601
gggctagctg aagcccattg gtttccacga tttcaattgg ctgagaaggc agagagctag 60

<210> SEQ ID NO 602
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 602
aagccaaaaa tgtgatagct gtccttgaag aattcatgaa agaagctctt gaccaaagtt 60

<210> SEQ ID NO 603
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 603
gccccagcca acttcatggg tcactttttc tggaaaataa tgatctgtac agacaggaca 60

<210> SEQ ID NO 604
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 604
cgtgtatctt ttggaatctg aggaggagac tgccattgag atgtcccaac acctttttca 60

<210> SEQ ID NO 605
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 605
gctattccaa agatttcaag ctgttctgag acatcttctg atggctttac ttcctgagag 60

<210> SEQ ID NO 606
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 606
aacaggtcca acctacatgc ccaaaggagc ttctaggaca caagaattgc atcgatgaaa 60

<210> SEQ ID NO 607
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 607
gtgaagcaag gctttgagcc tccctccttt gtgggctggt tccttggctg ggatgatgat 60

<210> SEQ ID NO 608
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 608
cttcacgtca tgaaggccat gcagtctctc aagtcccggg gctgcgtgaa ggaacagttt 60

<210> SEQ ID NO 609
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 609
acatcaaacc tgcccaatca aggtctgcca aaggaaggag tctgcaaatg acatttctca 60

<210> SEQ ID NO 610
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 610
cttacctatt gtagcacggc cggaaagtga gccgccttag ctgctgattg tactagagca 60

<210> SEQ ID NO 611
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 611
ctatgaagtt aggaaagccc tgaaacaaga gatggctagt gtttcatcca gacaaagagg 60

<210> SEQ ID NO 612
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 612
caagaatgtg cccaaccttc atgtcatgaa agccatgcag tctctctagt cccgaggcta 60

<210> SEQ ID NO 613
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 613
atttatttat tactttagtt acgaattcca atatacttta aaatggtatt tgttttacag 60

<210> SEQ ID NO 614
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 614
aatgggtgtt gtatggggag gcaagtgtgg ggggtccttc tccacaccca ctttgtccat 60

<210> SEQ ID NO 615
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 615
aatgggtgtt gtatggggag gcaagtgtgg ggggtccttc tccacaccca ctttgtccat 60

<210> SEQ ID NO 616
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 616
aatgggtgtt gtatggggag gcaagtgtgg ggggtccttc tccacaccca ctttgtccat 60

<210> SEQ ID NO 617
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 617
aatgggtgtt gtatggggag gcaagtgtgg ggggtccttc tccacaccca ctttgtccat 60

<210> SEQ ID NO 618
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 618

-continued aatgggtgtt gtatggggag gcaagtgtgg ggggtccttc tccacaccca ctttgtccat 60

<210> SEQ ID NO 619
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 619
aatgggtgtt gtatggggag gcaagtgtgg ggggtccttc tccacaccca ctttgtccat 60

<210> SEQ ID NO 620
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 620
aatgggtgtt gtatggggag gcaagtgtgg ggggtccttc tccacaccca ctttgtccat 60

<210> SEQ ID NO 621
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 621
aatgggtgtt gtatggggag gcaagtgtgg ggggtccttc tccacaccca ctttgtccat 60

<210> SEQ ID NO 622
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 622
aatgggtgtt gtatggggag gcaagtgtgg ggggtccttc tccacaccca ctttgtccat 60

<210> SEQ ID NO 623
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 623
aatgggtgtt gtatggggag gcaagtgtgg ggggtccttc tccacaccca ctttgtccat 60

<210> SEQ ID NO 624
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 624
atgacattca cgcatgctgg gtataggcaa ggaaagtaat tttcaaagta catttgcagt 60

<210> SEQ ID NO 625
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 625
tttttgaagc tgatctcttt accacgaggc acatttctca ctgggtgctg caaggagtat 60

<210> SEQ ID NO 626
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 626
ttaggcatga aatcaatcag aagagaaaga aaaatgctgg aacatgcttg atgtattatg 60

<210> SEQ ID NO 627
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 627
actggagaaa ggccttatga ctgcagtgaa tgtggcaaat cctttcgcca ggtattattg 60

<210> SEQ ID NO 628
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 628
atggactctt ctcggctcag gctctgctgg tggaaagcga ttcactgtat aaactttttt 60

<210> SEQ ID NO 629
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 629
agccttgggt gttagaatgg tctgtttcaa attttcaggc atgctatttc gacttactta 60

<210> SEQ ID NO 630
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 630
cagtccgctt gaaacaccgc tgtaaaagtg gtaaaaaatg atttcattgt gattatgtta 60

<210> SEQ ID NO 631
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 631
ttctccatca ggggcaaatg tttacttgta attttcttcc tacagttcgt gttaaattac 60

<210> SEQ ID NO 632
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 632
tggacacgaa gtgatttttg taacctgagc agttaatgaa tgtgccaaca ttttctagga 60

<210> SEQ ID NO 633
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 633
agatgataag tcagttgtag catccatcac cgagagtctg cagaagaaat caaagcacct 60

<210> SEQ ID NO 634
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 634
tgtaagaagg agaaagccca agtcatcacc gaggagaaga atttcaaagc cttcgctagt 60

<210> SEQ ID NO 635
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 635
ttctgatcag ttctttctgg attttccggg catttttgtt accaggtgtc tgaaagatcc 60

<210> SEQ ID NO 636
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 636
gcaatgagtg aactgactgt ggctacattc ttgaagatat acgggagaga cgtattatta 60

<210> SEQ ID NO 637
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 637
gttaggatgc attataaact gaagaggctt ttaaagatta catgtattaa tatatgtatt 60

<210> SEQ ID NO 638
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 638
atgcagtctc tcaagtcccg aggctacgtg aaggaacact ttgcctggag acatttctac 60

<210> SEQ ID NO 639
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 639
cagctcatac gcattctttt gtgttaggcc actgagattt cagagcgtgc cctaataaag 60

<210> SEQ ID NO 640
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 640
ccctctgtac ctctcataac tggtcaacga ctgtaacagg ttacatcagg tgtttttcta 60

<210> SEQ ID NO 641
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 641
ccaggctgcg cagtgaagaa aatgagtagg cagctcatgt gcacgttttc tgtttaaata 60

<210> SEQ ID NO 642
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 642
aaagttgaag gcgtcagaaa tggttgtcgc tacggtcttt tgtatgttct tgtgttgcga 60

<210> SEQ ID NO 643

-continued

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 643
ggttgcaccc accctgtaga agatggaatc atggatgctg ccaattttga gcaagttttt 60

<210> SEQ ID NO 644
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 644
ttggtacatc tgtgtctgct aatacagtta gctttctcac ttttctgctt gtttgttcag 60

<210> SEQ ID NO 645
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 645
atctatattt gttattactc agtgactctc taatttcaca tcagcatgtt cagcttgtgc 60

<210> SEQ ID NO 646
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 646
agttcctgca gtaattatta gtaccccatt taatggctaa gtaattatag ctaacagtgc 60

<210> SEQ ID NO 647
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 647
gcagtccagt ttctctcccc tctgacccct agaaggggag ttgtagcccc atgaactagt 60

<210> SEQ ID NO 648
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 648
gacgccagca aggtggtcac agtgttcagc gttgctgacg gctactcgga gaacaatgtt 60

<210> SEQ ID NO 649
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 649
aattaaaatt ctgaagctcc ctagttagtt agatccaatt gctggttaca ttttgggaag 60

<210> SEQ ID NO 650
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 650
ttgacattct gcgaaagcaa caagcaaact gaagaccaac tcctatgaga aatattatga 60

<210> SEQ ID NO 651
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 651
attaaggaag aaccactttc tgaggaagaa ccatgtacca gcacagcaat tgctagtcca 60

<210> SEQ ID NO 652
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 652
aggcaagtgt agaagttaca tctctatttc ccacagagag gaatattcac atatgtgcag 60

<210> SEQ ID NO 653
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 653
ggaacccagt ccagcctcct ggctgttgac ttcccattgc tcttggagcc accaatcaaa 60

<210> SEQ ID NO 654
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 654
ggtaattgta gggcgaggat tataaatgaa atttgcaaaa tcacttagca gcaactgaag 60

<210> SEQ ID NO 655
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 655
atgaatccaa gtgtttcatg tgaagatgtt gagccattgc tatcatgcat tcctgtctca 60

<210> SEQ ID NO 656
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 656
gtaaggtggg cgctgtgtct attgaggtgc ttagcaataa agaaaggtag tgagttgaaa 60

<210> SEQ ID NO 657
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 657
ttgaagaagt cttgaatagc tctttactgt cttacttggg gttgataaga tttgagtgtt 60

<210> SEQ ID NO 658
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 658
ttaacttgta gattcagtgg ttcaatacct gtttagttgc ttgctaatat ttccagaagg 60

<210> SEQ ID NO 659
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 659
cctgtgggct gattccagac tgagagttga agttttgtgt gcatcatcat gtgccattaa 60

<210> SEQ ID NO 660
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 660
gaaccagtta tatgcaagga tcatagcttg ttagcagatc agggattata attcagatgt 60

<210> SEQ ID NO 661
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 661
ctgtcctgaa atattataag gtggatgaga atggcaaaat tagtcgcctt cgtcgagagt 60

<210> SEQ ID NO 662
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 662
tcaacccttg gaataacagt ctagctgatt gttccaccaa agaatccagc ctgctgctta 60

<210> SEQ ID NO 663
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 663
aacaaaggtg tggtagacac tcttgagctg gacttagatt ttattcttcc ttgcagagta 60

<210> SEQ ID NO 664
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 664
tcggtattgt tacgctgtac ttatgtattc cctgtacctg aacacttgtt gctgcctcac 60

<210> SEQ ID NO 665
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 665
tttacaataa atttctttta aaatatactt tctatttttc tgtactgaca tatgcaataa 60

<210> SEQ ID NO 666
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 666
tggcgaattt tccttcagga tatcaagaaa ccagactgat gactgggata gtgggctgaa 60

<210> SEQ ID NO 667
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 667
ggttttcttt ctgtgtgtgt gtaagccact gcttataata aaaccaacaa taccctcaga 60

<210> SEQ ID NO 668
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 668
tcctaatgac tttgacccca agacgttggt tcagattaca tgatgtcagt agtggtgggt 60

<210> SEQ ID NO 669
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 669
ctttgacctc ataatattat gttggaaatt acacgatagt aaacataatg ataaatgggg 60

<210> SEQ ID NO 670
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 670
tacaagttgg attactatga tgtgtctcaa gaagttttgg ctgtttacct tcagcaaatt 60

<210> SEQ ID NO 671
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 671
gaaaactttc gtgctctgag cactggacaa aaaggatttg gttgtaagag ttcctgcttt 60

<210> SEQ ID NO 672
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 672
gatgagcttc agaaacaaaa agaagagcta caacgtcagc atgatcaact ggaggctcag 60

<210> SEQ ID NO 673
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 673
gaagaggacc tctctgtgaa gcaactgcta gaagaagagc tgtcaagtct gctggacccc 60

<210> SEQ ID NO 674
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 674
tcccttgctc atttaaaaaa tgttggtgtg aatgatttgg ggacccttgg tctatcaaag 60

<210> SEQ ID NO 675
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 675
cgaccagatg cagacctggg tgagcgaagg ctactttcct gatggtgttt actgccggaa 60

<210> SEQ ID NO 676
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 676
tgtttttctt agagaacatc atttgtcata tttatttgat caagaagttg aagatttata 60

<210> SEQ ID NO 677
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 677
tctctggaca aggaaactag ctggtttctt ttgagtgttg taacatttta taccattgta 60

<210> SEQ ID NO 678
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 678
tcctgttaat cctcaaatat ctgaacttct gtgttaccca agtgtcttat acaagcttct 60

<210> SEQ ID NO 679
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 679
ctctaaataa tgatggggct aagttatacc caaagctcac tttacaaaat atttcgtcag     60

<210> SEQ ID NO 680
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 680
ggttgggttg attgtatgtt gaggatctat tactgaccgt atgatgaggc caactttttt     60

<210> SEQ ID NO 681
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 681
acacgtctgt ttagcccgca attggaaagg atatatgtgg caatattaac ctggtacatg     60

<210> SEQ ID NO 682
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 682
tctttacctc tcctttgagt taggtccacc tcagttttct aaaggtcaaa ttaaggcccc     60

<210> SEQ ID NO 683
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 683
aggagctaaa gctgaaaatt aaattttaga tctttcaata ctcttaaatt ttatatgtaa     60

<210> SEQ ID NO 684
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 684
ctgttgcagg cttagtgaaa aaggactgct gtctttcctt ggttcaagtg ttagaatgga     60

<210> SEQ ID NO 685
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 685
aaatcctacg gcaagctttg acaatgtaac atctttatct tgtggttagg aaaatggacc 60

<210> SEQ ID NO 686
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 686
tcattgactg tggcaatgct ggctcttgtg aagggggcaa tgaccttccg gtgtgggagt 60

<210> SEQ ID NO 687
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 687
ctcatggcgg aattagaaga actagaacag gaggaaccag acaagaattt gctggaagtc 60

<210> SEQ ID NO 688
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 688
aatccctctg acatctccac tgcccccaaa gacctccgtt gaacattctg tatggaaaag 60

<210> SEQ ID NO 689
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 689
agagcctttc tgaagagaat tatatcaaac taattacaac caagaaataa tagtatgaag 60

<210> SEQ ID NO 690
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 690
tcattttaga aacatgctgt ttttgaaaca gatgtgtgat ggatgttgta catcctttgc 60

<210> SEQ ID NO 691
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 691
tgtttttggt ttcttattca aagatgataa tttagtggat taaccagtcc agacgcactg 60

<210> SEQ ID NO 692
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 692
ctaactgcag cctgtagaca atttgctatt aaagattcag tgcacaaaat atagctaaca 60

<210> SEQ ID NO 693
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 693
tctgaggttc ctacctgaaa cttctaactc tagtcctctg aaaatgttaa ccaagaattc 60

<210> SEQ ID NO 694
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 694
ttactttctt ggctaaccag tttcttagaa gaaaatgtgt cagggacttg gggatctaca 60

<210> SEQ ID NO 695
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 695
tcctaattta ttgcatcaaa ctacttgtcc ttaagcactt agtctaatgc taactgcaag 60

<210> SEQ ID NO 696
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 696
caagttcgcc accggggtag agcggcagga ctggatggag ctgttcattg acacctttaa 60

<210> SEQ ID NO 697
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 697
taatactgga tgtatgtaag tgttttactg cactgtattg aattggtgtc ttttgcacag 60

<210> SEQ ID NO 698
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 698
tcagaaaaat gtatactggg gaaaagttgt atgaaggtgg tgaacatggg agacttttag 60

<210> SEQ ID NO 699
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 699
ttttttctca ccaaatgacc ttacctgtaa tacagtcttg tttgtctgtt tacaaccatg 60

<210> SEQ ID NO 700
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 700
cccacgcttt ggaccttatg cagctctaca cccacgtgtc tgagaacttg ccaccttatg 60

<210> SEQ ID NO 701
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 701
aatgttatga taggacatag tagtagcggt ggtcagacat ggaaatggtg gggagacaaa 60

<210> SEQ ID NO 702
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 702
tcggtgttga cagtgtggca tttctgttat ctaatttctg gttttgactg aaagcgaagt 60

<210> SEQ ID NO 703
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 703
gaaaagaacc cagtgctgta acggaagtct aatagctgct cagtacatag taaatgctat 60

<210> SEQ ID NO 704
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 704
gccgaattca gttgacacga ggcacagaaa acaaatatca aagatctaat aatacaaaac 60

<210> SEQ ID NO 705
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 705
aagacaagaa ctttcttctt tacaaccagc gctccagata acctcaggga accagcactt 60

<210> SEQ ID NO 706
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 706
taagctaaat tttggtgcac agcaggttgt acatgatttc atgtttatgt agcaaaatgc 60

<210> SEQ ID NO 707
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 707
tggacatctt attagacatg ctttcagagt ccactgctga atcccactta atggagaagg 60

<210> SEQ ID NO 708
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 708
actcacgtta actcacattt atacagcaga aatgctattt tgtatgctgt taagtttttc 60

<210> SEQ ID NO 709
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 709
cattttctgt ctgttctagt ctaagaatat tgttatagat ggaagttagg accattagcc 60

-continued

<210> SEQ ID NO 710
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 710
tatgctatct gcggggccat tcgtaggatg ggtgagtcag atgattccat tctccgattg 60

<210> SEQ ID NO 711
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 711
gcacattgtt tttcctgcct ttttatggct gtctaaagtc tagggaaaag ggaagactgg 60

<210> SEQ ID NO 712
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 712
aaagttgagg actagagcat cgtagtgtct aagtgcacct aataacttaa tgcatgtgca 60

<210> SEQ ID NO 713
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 713
ttatcatctg cgaataccgt ttttccttta aatgcaatgt gtctttcaaa gctgacttga 60

<210> SEQ ID NO 714
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 714
ataagctgag ccgcgattct cccagcaaca agctgctgta cgcaggagga tctcggtgat 60

<210> SEQ ID NO 715
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 715
gaacatcttg ttcttcaata tcacgggttt ttgttaatgt ttcataagta attctcccca 60

<210> SEQ ID NO 716
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 716
ctttggacgt agtggaagct acaatgattt tggcaattac aacaatcagt cttcaaattt 60

<210> SEQ ID NO 717
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 717
atgatgctca gttttaaaca ttaaaagtgt acaagttgcg ttgttacaat aaaactaaat 60

<210> SEQ ID NO 718
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 718
gggactcccc tggtgatggg gcaggaccag aacaattaaa aatgtttctt ctgtcaaaaa 60

<210> SEQ ID NO 719
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 719
tgccgtgact tatccaacct gtgaactgat tgtgatctgc ttggtaactt ggtttggtgt 60

<210> SEQ ID NO 720
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 720
ttatatgtat gggcattact cttagtgata tttgtttcct gtcctttgtt gctcatgctg 60

<210> SEQ ID NO 721
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 721
atctgtgaca tctgttgtag aaacctcaat atcgagcgcc caacctacac taaccttaac 60

<210> SEQ ID NO 722

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 722
ttgtaaggat atgtcatgta tttactggtt tttcttgtat ctggtgcata gccagagttc 60

<210> SEQ ID NO 723
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 723
ctggttttcc aaaaggagag gtagatgcat atttttgtgt ggaaccattt atcttaaaac 60

<210> SEQ ID NO 724
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 724
ccaggggtgc atactagggt aaagaaaaat tttgtaatag caacagtggt ttgggatttt 60

<210> SEQ ID NO 725
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 725
cataacctgt agccacaaca acattgctac aaatgattat atcacgtggt accaacagtt 60

<210> SEQ ID NO 726
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 726
tggacatcaa tgtccttgtc tttttggccc aattgtttta gtcaccagaa actttttcag 60

<210> SEQ ID NO 727
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 727
aacttggaca actgtccctt caatgaccag ccaaaactga aagaggaaga gttctgctct 60

<210> SEQ ID NO 728
<211> LENGTH: 60

<212> TYPE: DNA
<213> ORGANISM: Artificial Sequence
<220> FEATURE:
<223> OTHER INFORMATION: Description of Artificial Sequence: Synthetic probe

<400> SEQUENCE: 728
ctgtggtctg cctcagtttc ccctcctaat acatatggct gttttccacc tcgataatat 60

<210> SEQ ID NO 729
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 729
gtggagattg gaaaccccac ctacaagatg tacgaaggcg gagagcctga tgatgtggga 60

<210> SEQ ID NO 730
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 730
gtggagattg gaaaccccac ctacaagatg tacgaaggcg gagagcctga tgatgtggga 60

<210> SEQ ID NO 731
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 731
gtggagattg gaaaccccac ctacaagatg tacgaaggcg gagagcctga tgatgtggga 60

<210> SEQ ID NO 732
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 732
gtggagattg gaaaccccac ctacaagatg tacgaaggcg gagagcctga tgatgtggga 60

<210> SEQ ID NO 733
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 733
gtggagattg gaaaccccac ctacaagatg tacgaaggcg gagagcctga tgatgtggga 60

<210> SEQ ID NO 734
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 734
gtggagattg gaaaccccac ctacaagatg tacgaaggcg gagagcctga tgatgtggga 60

<210> SEQ ID NO 735
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 735
gtggagattg gaaaccccac ctacaagatg tacgaaggcg gagagcctga tgatgtggga 60

<210> SEQ ID NO 736
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 736
gtggagattg gaaaccccac ctacaagatg tacgaaggcg gagagcctga tgatgtggga 60

<210> SEQ ID NO 737
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 737
gtggagattg gaaaccccac ctacaagatg tacgaaggcg gagagcctga tgatgtggga 60

<210> SEQ ID NO 738
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 738
gtggagattg gaaaccccac ctacaagatg tacgaaggcg gagagcctga tgatgtggga 60

<210> SEQ ID NO 739
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 739
gaggctacgt gaaagaacac tttgcctgga gacatttcta ctggtacctt accaatgagt 60

<210> SEQ ID NO 740
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 740
cctttcctta tctgaggtgt agtggtctaa catttaggaa gccttgcttt gactttatcg 60

<210> SEQ ID NO 741
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 741
ctggtactaa aaattgtggt tgttttttct gtttacgtaa cctgcttagt attgacactc 60

<210> SEQ ID NO 742
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 742 catcctttc aatgcggatg gtgtcaccct cccggcatct gtcaccagtg atccgtagac 60

<210> SEQ ID NO 743
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 743
tatgaaagga gtcagagtgg ggtgaaagtc tataaatgta agacatttgg gaaagccttc 60

<210> SEQ ID NO 744
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 744
ctgaaagtga ttggacattt tataggaatt gatagagatg ttggtcctca aaagctacaa 60

<210> SEQ ID NO 745
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 745
gagtccatag cactttgtaa actaatgtga agtttcttgt tgaatcataa aagctacctg 60

<210> SEQ ID NO 746
<211> LENGTH: 60
<212> TYPE: DNA
<213> ORGANISM: Artificial Sequence
<220> FEATURE:

<223> OTHER INFORMATION: Description of Artificial Sequence: Synthetic probe

<400> SEQUENCE: 746
gcaattcatg tagtttctgg gtcttctggg agcctacgtg agtacatcac ctaacagaat 60

<210> SEQ ID NO 747
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 747
gcaattcatg tagtttctgg gtcttctggg agcctacgtg agtacatcac ctaacagaat 60

<210> SEQ ID NO 748
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 748
gcaattcatg tagtttctgg gtcttctggg agcctacgtg agtacatcac ctaacagaat 60

<210> SEQ ID NO 749
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 749
gcaattcatg tagtttctgg gtcttctggg agcctacgtg agtacatcac ctaacagaat 60

<210> SEQ ID NO 750
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 750
gcaattcatg tagtttctgg gtcttctggg agcctacgtg agtacatcac ctaacagaat 60

<210> SEQ ID NO 751
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 751
gcaattcatg tagtttctgg gtcttctggg agcctacgtg agtacatcac ctaacagaat 60

<210> SEQ ID NO 752
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 752
gcaattcatg tagtttctgg gtcttctggg agcctacgtg agtacatcac ctaacagaat 60

<210> SEQ ID NO 753
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 753
gcaattcatg tagtttctgg gtcttctggg agcctacgtg agtacatcac ctaacagaat 60

<210> SEQ ID NO 754
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 754
gcaattcatg tagtttctgg gtcttctggg agcctacgtg agtacatcac ctaacagaat 60

<210> SEQ ID NO 755
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 755
gcaattcatg tagtttctgg gtcttctggg agcctacgtg agtacatcac ctaacagaat 60

<210> SEQ ID NO 756
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 756
ttttgtctta aaggtcttga gggttgacca tgttgcgtca tcatcaacat tttgggggtt 60

<210> SEQ ID NO 757
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 757
tggccagaga gatgttcttg tttctggtgt tgtcacgtct tcttgttttc tctaagttta 60

<210> SEQ ID NO 758
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 758
gggaagatga tgagtgaaca ataagccttg taatatacat gggtatgtat cttaatgtac 60

<210> SEQ ID NO 759
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 759
caggcagaat atgatctgtg tccaaaagtg aacttgagtc aggattgaat caatttcagc 60

<210> SEQ ID NO 760
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 760
ctcaccctga gacgggatag aaaaggaggg agttgctctc aggctgcaag cagtgacagt 60

<210> SEQ ID NO 761
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 761
ttgacaagtt cttcccacca gtgctgaaca tcacgtggct gcgcaatggg gagccagtca 60

<210> SEQ ID NO 762
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 762
ggaagattaa gttccagcat ttctgacttg ttattttgag ttactctgct actcttaggc 60

<210> SEQ ID NO 763
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 763
gccactttga caggcattat tgtggcaaat gttgtcttat tgcttcaaca aaccagacaa 60

<210> SEQ ID NO 764
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 764
cagggcaggg ctggcacctc tcaacgtctg tggactgaat gaataaaccc tcctcatcca 60

<210> SEQ ID NO 765
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 765
gccttccgtg tcccaactgc caacgtgtca gtgttggacc tgacctgccg tctagaaaaa 60

<210> SEQ ID NO 766
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 766
gccttccgtg tcccaactgc caacgtgtca gtgttggacc tgacctgccg tctagaaaaa 60

<210> SEQ ID NO 767
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 767
gccttccgtg tcccaactgc caacgtgtca gtgttggacc tgacctgccg tctagaaaaa 60

<210> SEQ ID NO 768
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 768
gccttccgtg tcccaactgc caacgtgtca gtgttggacc tgacctgccg tctagaaaaa 60

<210> SEQ ID NO 769
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 769
gccttccgtg tcccaactgc caacgtgtca gtgttggacc tgacctgccg tctagaaaaa 60

<210> SEQ ID NO 770
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 770
gccttccgtg tcccaactgc caacgtgtca gtgttggacc tgacctgccg tctagaaaaa 60

<210> SEQ ID NO 771
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 771
gccttccgtg tcccaactgc caacgtgtca gtgttggacc tgacctgccg tctagaaaaa 60

<210> SEQ ID NO 772
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 772
gccttccgtg tcccaactgc caacgtgtca gtgttggacc tgacctgccg tctagaaaaa 60

<210> SEQ ID NO 773
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 773
gccttccgtg tcccaactgc caacgtgtca gtgttggacc tgacctgccg tctagaaaaa 60

<210> SEQ ID NO 774
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 774
gccttccgtg tcccaactgc caacgtgtca gtgttggacc tgacctgccg tctagaaaaa 60

<210> SEQ ID NO 775
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 775
tattcagtta taattgaaga cctctacgct gcacatatat aaagccgtaa gtttggtttg 60

<210> SEQ ID NO 776
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 776
gatggggaga ggagacgctg ccagatggaa ggacgctcaa atactggact gcggccaact 60

<210> SEQ ID NO 777
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 777
tacagagcta agaatcctgc tgacaaacca ctaattggaa tttctacata caatgttgtt 60

<210> SEQ ID NO 778
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 778
ataaaccaag ttaaagtatg gcccgaccat ttaagaaaac aaccatctga gacacgcagg 60

<210> SEQ ID NO 779
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 779
cattattgtc cagtgaattc aagaccgaat acaatatcgg gagaaaatac aaactccctg 60

<210> SEQ ID NO 780
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 780
caaatccagg gacaaattta gtgtttgaag atgaaatcac tgcattacaa cctgaagtag 60

<210> SEQ ID NO 781
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 781
gctcttctgc tacttcaaca ttttctagct tttccgtgta tctaaacaca atttgctaca 60

<210> SEQ ID NO 782
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 782
tgcaggctta gtgaaaaagg actgctgtct ttccttggtt caagtgttag aatggagagc 60

<210> SEQ ID NO 783
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 783
aaagtttggt tctgtgtctg tgttttaata agacgagagg acgagcgatt gaggtgtatg 60

<210> SEQ ID NO 784
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 784
tctaaacata aagaaagctc ttctgtccgg ttactttatg cagattgctc gggatgttga 60

<210> SEQ ID NO 785
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 785
gaatattaag tgctacttga ggtacatgtt cagactaaca ttcttttgca gtatagtgag 60

<210> SEQ ID NO 786
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 786
aggtgtcccc ataagcgcca tgttcatcac acctggagtc accccatgga aaaccacatt 60

<210> SEQ ID NO 787
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 787
ccttatttct atgctgaagc agattctgaa cgtcttaaaa tctgttcatt atcagatgct 60

<210> SEQ ID NO 788
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 788
acatcgtaaa cttatagtct cagaagatag aaaaactgtg cgctatggaa atacaacaca 60

<210> SEQ ID NO 789
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 789
agtaaaggca agcaggtgtg aagagcaggg ctcagcagca agtcacattt ttctactatt 60

<210> SEQ ID NO 790
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 790
gagggcagtc agaggaagca cagcaagaga catatccaca aagaccatgt ggtggtgccc 60

<210> SEQ ID NO 791
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 791
cacagatgtt tttcaagttc ctcagtttgt actgaaatta gggattcatc agggcaggaa 60

<210> SEQ ID NO 792
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 792
tccctagaga ctacctagtt gtagtgtgac ctacatttat aattattgtc atgtccgaat 60

<210> SEQ ID NO 793
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 793
tttctgggtg gcttgctggc cacaatcttc ctggacatcg tgcacatcag catcttctac 60

<210> SEQ ID NO 794
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 794
ggaggaagag accaagaaat aaaacctccc actttgtctg tacatactgg cctctgtgat 60

<210> SEQ ID NO 795
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 795
gtaatttatt tgttttgcta catactgttc cagactttta aaggggacaa tgaaggtgac 60

<210> SEQ ID NO 796
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 796
aacagcacgc ctacgacggc aaggattaca tcgccctgaa cgaggacctg cgctcctgga 60

<210> SEQ ID NO 797
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 797
tgtcctgaag atcagtgact ttgggatgtc ccgagaggaa gccgatgggg tctatgcagc 60

<210> SEQ ID NO 798
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 798
gagtcaaatc agcattgacc tgagtttgag ttgacttaac attgatttca agcattaatc 60

<210> SEQ ID NO 799
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 799
tctttcccaa ctgactgtag ggttgtgtct tttcccaatt aaatatctgc agaactttgg 60

<210> SEQ ID NO 800
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 800
tctttcccaa ctgactgtag ggttgtgtct tttcccaatt aaatatctgc agaactttgg 60

<210> SEQ ID NO 801

-continued

<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 801
tctttcccaa ctgactgtag ggttgtgtct tttcccaatt aaatatctgc agaactttgg     60

<210> SEQ ID NO 802
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 802
tctttcccaa ctgactgtag ggttgtgtct tttcccaatt aaatatctgc agaactttgg     60

<210> SEQ ID NO 803
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 803
tctttcccaa ctgactgtag ggttgtgtct tttcccaatt aaatatctgc agaactttgg     60

<210> SEQ ID NO 804
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 804
tctttcccaa ctgactgtag ggttgtgtct tttcccaatt aaatatctgc agaactttgg     60

<210> SEQ ID NO 805
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 805
tctttcccaa ctgactgtag ggttgtgtct tttcccaatt aaatatctgc agaactttgg     60

<210> SEQ ID NO 806
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 806
tctttcccaa ctgactgtag ggttgtgtct tttcccaatt aaatatctgc agaactttgg     60

<210> SEQ ID NO 807
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 807
tctttcccaa ctgactgtag ggttgtgtct tttcccaatt aaatatctgc agaactttgg 60

<210> SEQ ID NO 808
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 808
tctttcccaa ctgactgtag ggttgtgtct tttcccaatt aaatatctgc agaactttgg 60

<210> SEQ ID NO 809
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 809
gttaactttg gtgacctttc gtgtacttta cacgaaatac cttatataat aagtactggg 60

<210> SEQ ID NO 810
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 810
cattactttc ttggctgaga gctgtagtct gtggtagttg ttttgttttg ttttttgttt 60

<210> SEQ ID NO 811
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 811
acaggtgtct cccactttgc aacctacgtg gcagccatga gggccatcaa catcgcagat 60

<210> SEQ ID NO 812
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 812
gctaagtaca gatcattcaa ggtggccgac gaggcggaga agtacaatct ggtcctgggg 60

<210> SEQ ID NO 813
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 813
ctcagaaata cgaacagaaa tacagcagac gaacatattt attggtactg aaaagagatg 60

<210> SEQ ID NO 814
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 814
tgtatcgatt tgcccaggat cactttgacc gcaacataag ccctaccatt gaggtatctt 60

<210> SEQ ID NO 815
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 815
gttgaaatgg taatcatctg catgtttttg tcacttattt caggttagtg attgcctaac 60

<210> SEQ ID NO 816
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 816
agcaccctcg agaccccaac cagatcctga tcggctacag ccgaggcctc gttgtcatct 60

<210> SEQ ID NO 817
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 817
aacctcaatg tcatcttggc caagtatggt ctggacggaa agaaggacgc tcggcaggtg 60

<210> SEQ ID NO 818
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 818
tctaaccaag ggcctaatgt ttgttacaga aatgatccca gagacctaca agatgtggga 60

<210> SEQ ID NO 819
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 819
gttgggtgag aacaaccaaa atcttatcat ggtctcagtc ataatcatta gggggaactc 60

<210> SEQ ID NO 820
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 820
tgcaccaggg ccttgttgaa cagatccaca ctgctctaat aaagttccca tccttaatga 60

<210> SEQ ID NO 821
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 821
cagaaatttt ggaatacatt ctatctagca caatttgaat ttttaattat caagattttt 60

<210> SEQ ID NO 822
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 822
taaatatgta tgatgtgttg tgctttttta accaaggagg ggccagtgga ttcccacagc 60

<210> SEQ ID NO 823
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 823
cttagaacat tgtttagctt tcctaagtat atataaatgc atatatgtat aaaattggga 60

<210> SEQ ID NO 824
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 824
tccttattta tagctctgat agctttaatt ttctaagcag tctgtctatc agatgtgcac 60

<210> SEQ ID NO 825
<211> LENGTH: 60
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 825
gggtatgaac tagtcaaaat atgaaccatt atgattcaag ttagattttc ctctggagag     60

<210> SEQ ID NO 826
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 826
ggagctctgc cctgcaggga gttgccccaa ccctttccgg aactcagtct ttagaaaaga     60

<210> SEQ ID NO 827
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 827
gagcctgggg acaaagcctc caaaaagcca tccagaggga gaaggaaact gacagccact     60

<210> SEQ ID NO 828
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 828
aggtgacaga ggtactatta taattcttac ttgcagaatg ttcaatctac gagtgttcat     60

<210> SEQ ID NO 829
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 829
agcaggagcc aaaaagacct cacattaaga agcctctgaa tgcttttatg ttatacatga     60

<210> SEQ ID NO 830
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 830
agagacccca acctgactca gcactatctg tatctgaact gaattacaga attactgaat     60

<210> SEQ ID NO 831
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 831
tctcttaagc cttcagttta tactcttaat ttaattttct ttctgagctg gagaactggc 60

<210> SEQ ID NO 832
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 832
tcccctagtg tccttaagtc ctcctccaca gggaacatct atttgggctt tgatgtttaa 60

<210> SEQ ID NO 833
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 833
cctgcttggg tggagaagcc attgtctttg gaaaccttgg tgtagttgaa ctgatagtta 60

<210> SEQ ID NO 834
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 834
gagagaacct gcatatatac cagtcattat ctgtttggtc cttatacagt tttaacttac 60

<210> SEQ ID NO 835
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 835
ggcaggcctc ggcctaaagg tctggaggtt gcagctgaca gtcttaacat tccgaagact 60

<210> SEQ ID NO 836
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 836
ccttttatat atcctcttga atacagtttt ctagtacaag tggtcttcaa gaagctcatg 60

<210> SEQ ID NO 837
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 837
tttttatttt ctctgttgac ttaggaacac atcataaatt cacaccaact gacacgttgc 60

<210> SEQ ID NO 838
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 838
aatgattcca gttgccatgg caggaaacag ggagttatat ctttgacttt acaggagtgg 60

<210> SEQ ID NO 839
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 839
aggcttctga attcccttct gagttaatgt caaatgacag caaagcactg tgtggctgaa 60

<210> SEQ ID NO 840
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 840
agactctcag ccttcagctt cctaaattct gtgtctgtga ctttcgaagt tttttaaacc 60

<210> SEQ ID NO 841
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 841
ggagggcaga gggggtgagg gtactattct ggattgagaa aacctatatc cattctttat 60

<210> SEQ ID NO 842
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 842
cccttgcctc atcagttttc ctgatttaca agtgcaatat tttagccaat gccttgggag 60

<210> SEQ ID NO 843
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 843
caagcctagc atcatggagc cagaaagtat agccttgctg tctgtctaca tcatgatgta 60

<210> SEQ ID NO 844
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 844
atgtcctgtc acagagtgtc ctcttggtgt attctaaaac gagcattctt ttaaaaaacc 60

<210> SEQ ID NO 845
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 845
aggaaccctg cggagggact tcaatcacat cgtagaactc agtcttcttg gaaagaaaaa 60

<210> SEQ ID NO 846
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 846
aggcccactc cagaatggcc tctggactca ccttgagaag ggggagctgc tgggcctaaa 60

<210> SEQ ID NO 847
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 847
gacccctcgg acttgaagaa tggccattcc tgtactccac attctggtct agccttgttg 60

<210> SEQ ID NO 848
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 848
ctcaacagaa ggagaggcag ggcaagggaa atgcatgctc cagtagtttt taaaaatcta 60

<210> SEQ ID NO 849
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 849
gaagcttgaa ctgtttgttc ttggtgcctt gcagagagac tcacagcaac tctccattat 60

<210> SEQ ID NO 850
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 850
atttacattt tatattttg tacatattgt tagagtcagc catttttaat gatctccgat 60

<210> SEQ ID NO 851
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 851
ttccctttgt gacttgaaga accctgactt tctgcaaagg cacctgaatg tgtctgtgtt 60

<210> SEQ ID NO 852
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 852
gggtttccca ggatggattg gtcaggggga gaaaggaaaa ggcaaaacac tccaggacct 60

<210> SEQ ID NO 853
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 853
aactgtgcct tgtttcaaca gtttttgcta atttttaggc tgaaagatga cggatgccta 60

<210> SEQ ID NO 854
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 854
ttgggaaact gttaatttgt acttggatgc caaatacacc aaaatgaacc cagcactttg 60

<210> SEQ ID NO 855
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 855
cctatatacc agcgtacacc tctatcaata cattttatgc tgagactttc ggtaaggaaa 60

<210> SEQ ID NO 856
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 856
gctcctgatg atcacgtata aaagtcaggt gttcagctat cctcaccgct acctggtcct 60

<210> SEQ ID NO 857
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 857
tgcttctacg tccaactaaa gggaaaagag ggttgaaggt cagccatgtt agctatgaga 60

<210> SEQ ID NO 858
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 858
ggctaatggc ttctaagtag acatcttaca tttttgagca tcagaatgca tgcatgtttc 60

<210> SEQ ID NO 859
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 859
agtaaacagt gtaccattgt tctgtgatgg gtttataacc aaatttacag agatgttctg 60

<210> SEQ ID NO 860
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 860
tttaatgtta taattcattc tgatttcttg ttttaaacca tttctgaaat ataatatgct 60

<210> SEQ ID NO 861
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 861
acagcagcct tagtttagga gaagagctaa tcacaggtga ccactcaagt tctttcaatg 60

<210> SEQ ID NO 862
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 862
tgagcttggg agataaaagg cagaacctgg aattgtagca tccaaggaca aaaagaatgt 60

<210> SEQ ID NO 863
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 863
agctatttgc tacatcctgt tcgagaaacg cattggctgc ctgcagcgat ccatccccga 60

<210> SEQ ID NO 864
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 864
accatttgta agaaagccaa aagacttttg ccagatttca tatttcccct tttcatgtac 60

<210> SEQ ID NO 865
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 865
tcttggtttt ctcttcatct tcaacaagtc agtctctctc aagggtctca cgttgcagca 60

<210> SEQ ID NO 866
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 866
cgtgctttga tttcctatca gtcactctta agaacataca tattgtttaa gtaactcggt 60

<210> SEQ ID NO 867
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 867
tcagcctcct catctggggg agtggaatag tatcctccag gtttttcaat taaacggatt 60

-continued

<210> SEQ ID NO 868
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 868
gctctaagat tgattaggat gattgtagct agagtcttga attctatctg tatacggcag 60

<210> SEQ ID NO 869
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 869
tgggaaatga caaaatctcc cccagattga ttttttacgt gttgttggaa ataaccacat 60

<210> SEQ ID NO 870
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 870
atatatatga ctactcctct gtcccttagg tgtataagac ttagctggaa tccaactaaa 60

<210> SEQ ID NO 871
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 871
taaacacatc ctaacaggga aggtaaactg tacgtccatc agtaccacta gagggcatca 60

<210> SEQ ID NO 872
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 872
ttttccctgc aagctacatc ctactgcttt gaacttccaa gtatgtctag tcacctttta 60

<210> SEQ ID NO 873
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 873
aaattgtgac attttccttc cccagaatta cttcgtttta tacatttcac ttctcttctg 60

<210> SEQ ID NO 874
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 874
taaggaggtc atggtggcca agaaggatgt ccacatgcct aagcacccag agctggcaga 60

<210> SEQ ID NO 875
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 875
cagctgaaag actcgagccc gtgctgtctc ctttggttat tatgacatga aagtgtatca 60

<210> SEQ ID NO 876
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 876
ctgtcaaaat aatccaaaca gggaaggaac gtacaagtaa ataacaaaag cccccatact 60

<210> SEQ ID NO 877
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 877
gctgactttg gctttcacat ttgttctttc cagagctaac tgataagagt ggaggaggaa 60

<210> SEQ ID NO 878
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 878
aggcatttgg tatgtatctg aattaattct cactaaaatt cagcaaagga cttgatagcc 60

<210> SEQ ID NO 879
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 879
gctaagcaaa ttgatatttg aaatgaaaga tggattaggt gagagactta gtttattcag 60

<210> SEQ ID NO 880

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 880
aaccaacagt aacaaaaacc tcagtaacca aaataaagtt ctatatttta aaaaaggcac 60

<210> SEQ ID NO 881
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 881
tttaaggagg gagtcatggt ggccaagaag gatgtcatgc ctaagcacca ggagctggca 60

<210> SEQ ID NO 882
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 882
gtgggagtac tggatattgt agagacagat atcatcaggg caaggagatt aaagattttt 60

<210> SEQ ID NO 883
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 883
ggggcttttt actcttaagc gacatatgta ttagaagttg aatcacgaac tgataaaatg 60

<210> SEQ ID NO 884
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 884
ggtgttgtat gtatggtgac ttgtggattt atgtttcagt gtactggaaa ctttccattt 60

<210> SEQ ID NO 885
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 885
acagtgactg atgttggttg taatggttgg gtttaggatg aaccatttta aggatgccaa 60

<210> SEQ ID NO 886
<211> LENGTH: 60

<212> TYPE: DNA
<213> ORGANISM: Artificial Sequence
<220> FEATURE:
<223> OTHER INFORMATION: Description of Artificial Sequence: Synthetic probe

<400> SEQUENCE: 886
cttgcaaaca agcagatatt tgtgtggtta gtaaatcata cttcacactt tttctctagc 60

<210> SEQ ID NO 887
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 887
acagtattaa atggcacctg attttgtgtt aaattttagt tccctgttgt ttaatgcccc 60

<210> SEQ ID NO 888
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 888
tgaatgctaa aatgtacaag tgggattgtg aagatttact gacatcaaaa gttcttctgg 60

<210> SEQ ID NO 889
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 889
gtagacgggt tttaggagca ggtatccttc tttgagcaag agtgtcatgc aagttaggaa 60

<210> SEQ ID NO 890
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 890
gaattgaagg agacctaata attgtgtctt tttggttatt tagtgacaaa cgtggctttc 60

<210> SEQ ID NO 891
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 891
gacagtgaaa ctcggagact ttactatgat gagcaagaat ctgaggccta cgagaagcat 60

<210> SEQ ID NO 892
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 892
gaagaagtcg ttgatgtgat ttttgaggaa atgacagatg tgactttgga accaaacttg 60

<210> SEQ ID NO 893
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 893
ctgtctcatc ttgatagtca ttttcatgat cacaaaattt ttccaggata gacatagagc 60

<210> SEQ ID NO 894
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 894
agaggaggaa gatttttaaa acctttatca ttcagcattt gtattttatg gatccccagg 60

<210> SEQ ID NO 895
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 895
aggcagacct gagtgagctg gtgaaaaaac aagaacttcg cttcattcaa tactggcaag 60

<210> SEQ ID NO 896
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 896
gttagtgatg gtttcagaca gaatcgtgtt cgtgtctgtt ttgctcgatt cttttcctaa 60

<210> SEQ ID NO 897
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 897
tactgactgt taggtatcta tgccaatttg ttttcatact tcagttggtt ttggaatctg 60

<210> SEQ ID NO 898
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 898
agccagaaat cgaaggtcac aggaagttgt cactgaactt ggcccgtgtc tgctactctg 60

<210> SEQ ID NO 899
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 899
atacatttta attcctcacg ttttatattg gagagttcgg tacagactgt ccattactgc 60

<210> SEQ ID NO 900
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 900
ttaacatttt aagcagactg ctaaactgtt ctctgtataa gttatggtat gcatgagctg 60

<210> SEQ ID NO 901
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 901
tgctattttg actagtctga gtgaaaagtg aggatttaaa tgaagtaacc cctaaactca 60

<210> SEQ ID NO 902
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 902
tgggtcctgt tttccgctct tctaagaaaa aacaaaaaga ccgtgagtta ttgcccagca 60

<210> SEQ ID NO 903
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 903
actttccttg atagtgggtc agtcatcatt tataagtgca tttctaaaaa tattgcttaa 60

<210> SEQ ID NO 904
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 904
tgatgatatg tatgcatcat tataatatag tatagtttcg ctgccctaaa catcctctgc 60

<210> SEQ ID NO 905
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 905
catatcacaa acacaacatt tgattttgat ctttgctcgc tggacaaaac cacagtccgt 60

<210> SEQ ID NO 906
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 906
gactgtaaat gtttaatatg aatatagtgt tcttttgaag taaggccagc tgttgaacgg 60

<210> SEQ ID NO 907
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 907
gaacccgtgt gtgatataga ggactcttga taaaaactgt gtttatataa agatggtgtc 60

<210> SEQ ID NO 908
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 908
caggcgatga ctttcagtga aggaaatgac ctgtctaggg ccacataata cctgtttgaa 60

<210> SEQ ID NO 909
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 909
cttgtgcaca ggtcttcggg gcttcttgtt tcacagcttt ggcaggggaa ctggttctgg 60

<210> SEQ ID NO 910
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 910
aaccacccat attcaggaga agaggacaga cacggcacct ctgagtcacc cctctcctgt 60

<210> SEQ ID NO 911
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 911
taagttggac taaatgctct tccttcagag gattatccgg ggcatctact caatgaaaaa 60

<210> SEQ ID NO 912
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 912
atcagccagt acgccaagta catttgctct tttctgtggc aaaaccaaga tgaagagacg 60

<210> SEQ ID NO 913
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 913
aaagccatgg acttctatga tccagcaagg cacaatgagt ttgacttcat ctcaggaact 60

<210> SEQ ID NO 914
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 914
agggactgaa ggattagaat gagggaagta acccatgcac tgcttatttg agatggggaa 60

<210> SEQ ID NO 915
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 915
gtctgatttt gccttgtggt gatagattgt catgaacaca atgtcctctg gagaaatcta 60

<210> SEQ ID NO 916
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 916
tgtccccaca aaaagtgacg ctttacctgc gaccaggctt cgggtccttc gtggacaaga 60

<210> SEQ ID NO 917
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 917
agaccttgtt tactagaaat caggtggcca aaacatgact ctcagagtgg ggcttcatga 60

<210> SEQ ID NO 918
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 918 tgtttttaa atcgccttga caatcatcag cttttgaaat gtgaattcct attgccagag 60

<210> SEQ ID NO 919
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 919
atttgagctg tgagttgaca gtgtaacact tctcataaac tgcatgcatt tgaaatatga 60

<210> SEQ ID NO 920
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 920
tttgaattaa aataacactg atgggactct tagcaatgtt ttacctcttg ggaatcactg 60

<210> SEQ ID NO 921
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 921
aagttcttct cccagaatat ggaggcacca aagtagttct agatgacaag gattatttcc 60

<210> SEQ ID NO 922
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 922
atttggctcc tattgaagat ggcttctaag aaaacaagat gcacagagga cacagaagga 60

<210> SEQ ID NO 923
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 923
aggacaagtc agaatcaggg gtgtcaactg agatgcaaat ataggcaaag gagctgacaa 60

<210> SEQ ID NO 924
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 924
acattcaaat ctacctaatc aactgtatct ttactaccta tataagtttt gtatgtgaga 60

<210> SEQ ID NO 925
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 925
aggaccagaa atgcactttg tattacagag tgttaaggct ggttgctata gtatggaaca 60

<210> SEQ ID NO 926
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 926
acggtcagtc ctactgctgt atgtcaggtt tgctcacaat gaggtattcc cacatagaaa 60

<210> SEQ ID NO 927
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 927
ggggttctgt taattgatct tagccttagg gtaagtaaaa tgggtctttt tatataatag 60

<210> SEQ ID NO 928
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 928
gttcagacca actcctggat atgagctcag ccttcagcaa gacaacaaag accctggccc 60

<210> SEQ ID NO 929
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 929
aggaccgcaa gaaagccgtc ctgtccgaca tcggtgtctc ggccttctgg gctttcctct 60

<210> SEQ ID NO 930
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 930
actggcaaat catgtctcct tcatcagttc attgagaata agttcaaaca ggactccaac 60

<210> SEQ ID NO 931
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 931
aacaatctag gttttagctg tatgagctat gtttattatg gtgctaatgt tcagtagcca 60

<210> SEQ ID NO 932
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 932
ctgtgtgatt agagtctggc tttcaggaat atgtaacacc cacttttctt tcttttttct 60

<210> SEQ ID NO 933
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 933
acactgtcaa taattatcgc tttaattggt gttaatattt ggtagtacac aggttctccc 60

<210> SEQ ID NO 934
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 934

-continued ccctagcccc tggcagacat agctgcttca gtgccccttt tctctctgct agatggatgt 60

<210> SEQ ID NO 935
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 935
atttctgtgt gtgtcaaagg ggactaacag cagaatctac ctcccaactg ccatgtgatt 60

<210> SEQ ID NO 936
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 936
ctccctccca attggaaata tgaatcatct acagcctctg ccctggtcgc ataaatttgt 60

<210> SEQ ID NO 937
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 937
tccatggaac gggcccgttt gtcactaaaa cctgtgctgg ttaggatttg ctgtatttta 60

<210> SEQ ID NO 938
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 938
gctctggtaa aagatagatt tgtagctcac ttgatgatgg tgctggtgaa ttgctctgct 60

<210> SEQ ID NO 939
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 939
attctgaagt gtattctaca taaactctca gaggatgccc agcaggatgg agtcccagtt 60

<210> SEQ ID NO 940
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 940
ttgtaaatac gtgtcgctca gatgtccttt gaagtgggag ggaatcaatc cggggataat 60

<210> SEQ ID NO 941
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 941
tctgaaatag agtactatgc tatgttggct aaaactggtg tccatcacta cagtggcaat 60

<210> SEQ ID NO 942
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 942
atgctgagga gaactacagt ttttcttttg aatttagtat ttgagatgag ttgttgggac 60

<210> SEQ ID NO 943
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 943
agaagtgtga ctgtaaacat attagtgttt ctgttagtgt tggcataagc ttgccttttt 60

<210> SEQ ID NO 944
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 944
ttttatagta caggttttgt aatgttacat gtgatgatat gagctcccac cttatatggg 60

<210> SEQ ID NO 945
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 945
aaggatttga ttataaatgt tcctcctttc acagaattat tccagggttt atgtgtcagg 60

<210> SEQ ID NO 946
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 946
acatcaagac tcaaattgca gtgccacaag taataaacat ttattggaag atgaagaagg 60

<210> SEQ ID NO 947
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 947
ggaaccagca gtgtttttcc ctgagtaatt atgaacttag tcaagatcag aagctgggtt 60

<210> SEQ ID NO 948
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 948
gtcatcgtcc ggtttctcat tgtgatgatg aagcatggtt acactggcga atttgaaatc 60

<210> SEQ ID NO 949
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 949
agttgcccaa gatctgatac aaggtcgggg tgtctatgca aaggaagctc agttttcttt 60

<210> SEQ ID NO 950
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 950
ttgtatttag agaatggctc ttgccactgt tatgtacaca cagatcgtgt gtgtaaacaa 60

<210> SEQ ID NO 951
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 951
aggtttggac ctgccatatt ttgttttatt ctgtgatcct aactagttcc ttttaatagg 60

<210> SEQ ID NO 952
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 952
tcgctgtctt tgtacccagc ctgcattctg tttcgatctg tcttttagca gtccatacaa 60

<210> SEQ ID NO 953
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 953
tatagcattt tctgaagatc atgttgtact cttctttcgt ctagatgatt tggtcaacag 60

<210> SEQ ID NO 954
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 954
ccagatacaa caagaattta acatggcagc caaaccaacc cactaacaca catttaaata 60

<210> SEQ ID NO 955
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 955
tgtgtcaaca gatggatcac tggaatgtgg ggattctgaa acagaaatga aactgtcctt 60

<210> SEQ ID NO 956
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 956
taataagcta cttgaacaca gcttcatcaa gcgctacgag acgctggagg tggacgtggc 60

<210> SEQ ID NO 957
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 957
ggaagacatt gaccacagaa ggagtgagga acttaggaag ggtcttgcca ccacttaatc 60

<210> SEQ ID NO 958
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 958
tgaatatttg tgtgctatcg gtagctgtgt ttctttgatc aaatgttcct gtccttttgc 60

<210> SEQ ID NO 959

-continued

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 959
tgtatagcag aggatctcat ttgactttgt tttgatgagg gtgatgctct ctcttatgtg 60

<210> SEQ ID NO 960
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 960
aacgcatccc aagattgaag atctttttct ctttttaga cctagtcagt tgttttcagg 60

<210> SEQ ID NO 961
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 961
acagctattc ccatattcta ggagtggcct aagaaatgcg tgtttcagtg actagattat 60

<210> SEQ ID NO 962
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 962
acagctattc ccatattcta ggagtggcct aagaaatgcg tgtttcagtg actagattat 60

<210> SEQ ID NO 963
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 963
acagctattc ccatattcta ggagtggcct aagaaatgcg tgtttcagtg actagattat 60

<210> SEQ ID NO 964
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 964
acagctattc ccatattcta ggagtggcct aagaaatgcg tgtttcagtg actagattat 60

<210> SEQ ID NO 965
<211> LENGTH: 60

<212> TYPE: DNA
<213> ORGANISM: Artificial Sequence
<220> FEATURE:
<223> OTHER INFORMATION: Description of Artificial Sequence: Synthetic
probe

<400> SEQUENCE: 965
acagctattc ccatattcta ggagtggcct aagaaatgcg tgtttcagtg actagattat 60

<210> SEQ ID NO 966
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 966
acagctattc ccatattcta ggagtggcct aagaaatgcg tgtttcagtg actagattat 60

<210> SEQ ID NO 967
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 967
acagctattc ccatattcta ggagtggcct aagaaatgcg tgtttcagtg actagattat 60

<210> SEQ ID NO 968
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 968
acagctattc ccatattcta ggagtggcct aagaaatgcg tgtttcagtg actagattat 60

<210> SEQ ID NO 969
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 969
acagctattc ccatattcta ggagtggcct aagaaatgcg tgtttcagtg actagattat 60

<210> SEQ ID NO 970
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 970
acagctattc ccatattcta ggagtggcct aagaaatgcg tgtttcagtg actagattat 60

<210> SEQ ID NO 971
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 971
accaggaaga tttctggaaa gtgaaggagt tcctgcataa ccaggggaag cagaagtata 60

<210> SEQ ID NO 972
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 972
gacccggatt gcgtttgcct tagcggatat gtttatacag atgaatataa aatgtttttt 60

<210> SEQ ID NO 973
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 973
tggctgggac catcccgtcc gagtctgctt caactgcaat aaaaagcccg gtgaccttta 60

<210> SEQ ID NO 974
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 974
agcttggacg acatgggatc cgctgtaact ctgtcctccc agggttcatt gcaacaccca 60

<210> SEQ ID NO 975
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 975
atctgatctt cccagactgt ctggcaccac gagtcatgtt ggaaccagct gctgagacca 60

<210> SEQ ID NO 976
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 976
aagcacttca tgggccagaa tgttgcagat tacatgcgct acttaatgga agaagatgac 60

<210> SEQ ID NO 977
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 977
gctggattgt cacttttggg agaagaacag attaaacctg ttaatcctgt cttttgcatg 60

<210> SEQ ID NO 978
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 978
acctgaagtg tgaatgagtt tccttgactt acactagatt ttgttttggc ttataatgac 60

<210> SEQ ID NO 979
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 979
cacacaacac acaagggaga gaacccccag atgagaaaat aggaaggagc aatcatttgt 60

<210> SEQ ID NO 980
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 980
aatgcagagg gaacaccaga ggacgttttt cttcaactct gcacagctat tgactctatt 60

<210> SEQ ID NO 981
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 981
tggcacacat atttatgctg tctgaaggtc acgatcatgt taccatatca agctgaaaat 60

<210> SEQ ID NO 982
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 982
tacttgataa tatcttccaa acgattagag aagacataac attcattaag aatacacata 60

<210> SEQ ID NO 983
<211> LENGTH: 60
<212> TYPE: DNA
<213> ORGANISM: Artificial Sequence
<220> FEATURE:

<223> OTHER INFORMATION: Description of Artificial Sequence: Synthetic
probe

<400> SEQUENCE: 983
tcttgaacag acagaaggat gtaaaggatg gaaaatacag ccaggtccta gccaatggtc 60

<210> SEQ ID NO 984
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 984
atggtggtat tgtgaccact gaattcactc cagtcaacag tttcagaatg agaatgggac 60

<210> SEQ ID NO 985
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 985
ctataatggt tggaactaaa tgtcaccaag gtggcttctc cttggctgag agatggaagg 60

<210> SEQ ID NO 986
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 986
atggctggga tcccaaaagc aaagcaacgc ttaaaaaggc tccgaaatat tcactacctc 60

<210> SEQ ID NO 987
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 987
tgatgcctga agtaggtgtt cagagtaata ctttgcgtta tactgagaga gaatctgaat 60

<210> SEQ ID NO 988
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 988
aaattgaagt tttaagggac gtcagtgttt atgccatttt tccagttcca aaatgattcc 60

<210> SEQ ID NO 989
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 989
ttgcagagac ccagcagatg taactctcat tgtagccatc ccaaagaaaa cccttctttg 60

<210> SEQ ID NO 990
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 990
acacaaaagg gacatggagg taacaaagag caagagaagt accagcaagt ccattagcca 60

<210> SEQ ID NO 991
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 991
gtaatggtac ctgaggaact gaaatgggta tttgttttcg tatgtttctg ccagtagtat 60

<210> SEQ ID NO 992
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 992
aggatgagcg tgagccagaa gcagctgtgt atttaaggaa acaagcgttc ctggaattaa 60

<210> SEQ ID NO 993
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 993
atgtgtcaga gcccttcaca cagtgggata ctaagtgttt gcgttgcaaa tattggcgtt 60

<210> SEQ ID NO 994
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 994
agtgagtgtc ctgcagccct tattccctcc atagaaagca tcctcagagc accttccctg 60

<210> SEQ ID NO 995
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 995
attgccacct ggggtatcgt tgtcatggca gaccccaaag ggaaggccta ccgcgttgtt 60

<210> SEQ ID NO 996
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 996
atgcagaaac aggaggtgtg agccagcaat cagatggaga ttctagtgct catgaaagtt 60

<210> SEQ ID NO 997
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 997
tacaagcagc ccaagaaact ctgaacggga cccaatggag gcaaacttga gcaaataatt 60

<210> SEQ ID NO 998
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 998
acttgaatct tgctgctaaa tgtaaatgcc ttctcaaatg acagattcca gttcccattc 60

<210> SEQ ID NO 999
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 999
tgagggatag gggacattcc atcccaagct tctcccttac ccacacctat ccttttgagg 60

<210> SEQ ID NO 1000
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1000
ccacggaggc agacgagctg atgaagagag tgggtttcca gtatgagggc acctacaagt 60

<210> SEQ ID NO 1001
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1001
gccagaaaat gtactcagac ttcagtcaac ctaatgggac agtgtactca cactgtggtt 60

<210> SEQ ID NO 1002
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1002
tggcagtatt gtagctgatc gggaaatgtt tgatatctca gcaattttgc atttttgtgt 60

<210> SEQ ID NO 1003
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1003
aagttcctat cggtcgtatc ctctgtcctg accgagaagt accgctgagc gccgcctccg 60

<210> SEQ ID NO 1004
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1004
tctgaaggtc acgatcatgt taccatatca agctgaaaat gtcaccacta tctggacagt 60

<210> SEQ ID NO 1005
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1005
tgcacctttg tacttcttta ttgagtgtac tggctggcaa gagttctctc ttctgttggt 60

<210> SEQ ID NO 1006
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1006
acaaaaatga actgaagttt cacatgagct atttccattc cagaatatct gggattctac 60

<210> SEQ ID NO 1007
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1007
aattccttgc actctaacca gttcttggat gcatcttctt ccttcccttt cctcttgctg 60

<210> SEQ ID NO 1008
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1008
aggcatctta tgttaatcta cctaccatcg ctctgtgtaa cacagattct cctctgcgct 60

<210> SEQ ID NO 1009
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1009
aactggttga ctacaagtct tgtgctcatg actgggtcta tgaataagag gtggacacaa 60

<210> SEQ ID NO 1010
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1010
cctgccgttt tgtcataggt gagctccttt gtgcatttta agcacatgta agtggttcag 60

<210> SEQ ID NO 1011
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1011
tgcatagtcc tccgctacac aaagctgacc gatgcccgga ccagtgtgag gccaatgaat 60

<210> SEQ ID NO 1012
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1012
ccaaattgag gattgtgtct aggaaatctg taaagccata ctactgtgtt cattagcatg 60

<210> SEQ ID NO 1013
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1013

-continued tgctggtggc ttatacaaaa agtttacttt cttcatggat attcttggtc tcacatactt 60

<210> SEQ ID NO 1014
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1014
gacacagtta atatgccaga aaaagaaaga aaaggagtta gtaactaccg ttcagagttt 60

<210> SEQ ID NO 1015
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1015
gcagttagca caaatttgca agtagaactt ctattagctt atgccataga catcacccaa 60

<210> SEQ ID NO 1016
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1016
agggcacgtg cgtggagtgg ctccgcagat acctggagaa cgggaaggac acgctggagc 60

<210> SEQ ID NO 1017
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1017
agggcacgtg cgtggagtgg ctccgcagat acctggagaa cgggaaggac acgctggagc 60

<210> SEQ ID NO 1018
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1018
agggcacgtg cgtggagtgg ctccgcagat acctggagaa cgggaaggac acgctggagc 60

<210> SEQ ID NO 1019
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1019
agggcacgtg cgtggagtgg ctccgcagat acctggagaa cgggaaggac acgctggagc 60

<210> SEQ ID NO 1020
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1020
agggcacgtg cgtggagtgg ctccgcagat acctggagaa cgggaaggac acgctggagc 60

<210> SEQ ID NO 1021
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1021
agggcacgtg cgtggagtgg ctccgcagat acctggagaa cgggaaggac acgctggagc 60

<210> SEQ ID NO 1022
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1022
agggcacgtg cgtggagtgg ctccgcagat acctggagaa cgggaaggac acgctggagc 60

<210> SEQ ID NO 1023
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1023
agggcacgtg cgtggagtgg ctccgcagat acctggagaa cgggaaggac acgctggagc 60

<210> SEQ ID NO 1024
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1024
agggcacgtg cgtggagtgg ctccgcagat acctggagaa cgggaaggac acgctggagc 60

<210> SEQ ID NO 1025
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1025
agggcacgtg cgtggagtgg ctccgcagat acctggagaa cgggaaggac acgctggagc 60

<210> SEQ ID NO 1026
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1026
ttaaaacatg ttggctacag tagcacttta ctgaagtagt attttttggt atctctagcc 60

<210> SEQ ID NO 1027
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1027
agacatatac ttcatttggg agcaaatact tattgccttg aaaagtagca ctgtaatagc 60

<210> SEQ ID NO 1028
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1028
aaggtatttt tccttttccc tcttactgga tttttcaatt ttcaaaccat atggcctagg 60

<210> SEQ ID NO 1029
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1029
aatggccttt ttctttttca gtagtacata cacatctgtg tcatttgttg aatgacgaca 60

<210> SEQ ID NO 1030
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1030
tcctttcaga tgcctggatg aatttgatgt ctacatggat atggttaata ggagaattgc 60

<210> SEQ ID NO 1031
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1031
tcctttcaga tgcctggatg aatttgatgt ctacatggat atggttaata ggagaattgc 60

<210> SEQ ID NO 1032
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1032
tcctttcaga tgcctggatg aatttgatgt ctacatggat atggttaata ggagaattgc 60

<210> SEQ ID NO 1033
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1033
tcctttcaga tgcctggatg aatttgatgt ctacatggat atggttaata ggagaattgc 60

<210> SEQ ID NO 1034
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1034
tcctttcaga tgcctggatg aatttgatgt ctacatggat atggttaata ggagaattgc 60

<210> SEQ ID NO 1035
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1035
tcctttcaga tgcctggatg aatttgatgt ctacatggat atggttaata ggagaattgc 60

<210> SEQ ID NO 1036
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1036
tcctttcaga tgcctggatg aatttgatgt ctacatggat atggttaata ggagaattgc 60

<210> SEQ ID NO 1037
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1037
tcctttcaga tgcctggatg aatttgatgt ctacatggat atggttaata ggagaattgc 60

<210> SEQ ID NO 1038

<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1038
cggaacagct ccttactctg aggaagttga ttcttatttg atggtggtat tgtgaccact 60

<210> SEQ ID NO 1039
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1039
tattaggccg tgctccaaag tcatcgtccg gtttctcact gtgatgatga agcatggtta 60

<210> SEQ ID NO 1040
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1040
ctacggttta agcctgaaga actggttgac tacaagtctt gtgctcatga ctgggtctat 60

<210> SEQ ID NO 1041
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1041
tgcttgcaaa gggttgtaaa actttattgt gattattctt gctttaagct gaaacatccc 60

<210> SEQ ID NO 1042
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1042
tcaaaaagga taaggagatc atagcagagt acgatactca ggtcaaagag atccgtgctc 60

<210> SEQ ID NO 1043
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1043
ttgggtagat attttttctg aatacaaagt gatgtgttta aatactgcaa ttaaagtgat 60

<210> SEQ ID NO 1044
<211> LENGTH: 60

<212> TYPE: DNA
<213> ORGANISM: Artificial Sequence
<220> FEATURE:
<223> OTHER INFORMATION: Description of Artificial Sequence: Synthetic probe

<400> SEQUENCE: 1044
ttttggggta gatgcggccc cgatcaggcc tgactcgctg ctctttttgt tcccttctgt 60

<210> SEQ ID NO 1045
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1045
acagtgggaa tatcactttt gatgagatcg tcaacattgc tcgacagatg cggcaccaat 60

<210> SEQ ID NO 1046
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1046
tccatataat tttgatcata ggccggagtg agtcattcca cctgcacctt tctgtacaaa 60

<210> SEQ ID NO 1047
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1047
attatttaca cagaatttat ttgtatatga aactcatacc ataatttaat tcgaataaat 60

<210> SEQ ID NO 1048
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1048
taatgttttt catgttactg cctagggcgg tgctgagcac acagcaagtt taataaactt 60

<210> SEQ ID NO 1049
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1049
cttccaaatc actggtttgg gagggggtgg atacatcctc attttctgta catgatgcat 60

<210> SEQ ID NO 1050
<211> LENGTH: 60
<212> TYPE: DNA

<213> ORGANISM: Artificial Sequence
<220> FEATURE:
<223> OTHER INFORMATION: Description of Artificial Sequence: Synthetic
probe

<400> SEQUENCE: 1050
cttccaaatc actggtttgg gagggggtgg atacatcctc attttctgta catgatgcat 60

<210> SEQ ID NO 1051
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1051
cttccaaatc actggtttgg gagggggtgg atacatcctc attttctgta catgatgcat 60

<210> SEQ ID NO 1052
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1052
cttccaaatc actggtttgg gagggggtgg atacatcctc attttctgta catgatgcat 60

<210> SEQ ID NO 1053
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1053
cttccaaatc actggtttgg gagggggtgg atacatcctc attttctgta catgatgcat 60

<210> SEQ ID NO 1054
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1054
cttccaaatc actggtttgg gagggggtgg atacatcctc attttctgta catgatgcat 60

<210> SEQ ID NO 1055
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1055
ggaaggtttt tgtctcctgt ccaacacttg ttcaacatca gagaacacat actaatgaaa 60

<210> SEQ ID NO 1056
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1056
taaatagaac tatctgcatt atctatgcag catgggattt ttattatttt tacctaaaga 60

<210> SEQ ID NO 1057
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1057
agtaatttgc gttaagatac gcttaaaggc tctttgtgac catgtttccc tttgtagcaa 60

<210> SEQ ID NO 1058
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1058
gtataaactt tatttttgtt gaaggttgta tgttaaatca atgttacatt cttatatcac 60

<210> SEQ ID NO 1059
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1059
tttcactgta gcttgtgttt cctgtaagta tagtcgaacg tcgtgatgtt cctgttacat 60

<210> SEQ ID NO 1060
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1060
gagaattgat caacgtgact attccaacaa tacagagaag acaaccaaag atgagctgtt 60

<210> SEQ ID NO 1061
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1061
ggaaatgatg tttgtctaaa atggccagag acaactttta taagcttcca ggaagtggag 60

<210> SEQ ID NO 1062
<211> LENGTH: 60
<212> TYPE: DNA
<213> ORGANISM: Artificial Sequence
<220> FEATURE:

<223> OTHER INFORMATION: Description of Artificial Sequence: Synthetic probe

<400> SEQUENCE: 1062
tgtcagtgaa ctgatatctg atgtttatga tatggtgtct ttttcttgaa acaagcttcc 60

<210> SEQ ID NO 1063
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1063
aaaggctgca gcttcctgcc agacccttac cagaagcagt gtgatcagtt tgtggcagag 60

<210> SEQ ID NO 1064
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1064
gggcatactt tgtctataga aaaatatttt gacctttagg tacattttgg gccagtagtc 60

<210> SEQ ID NO 1065
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1065
ctgcagaaca ttattcctgc atctactgga acttccatgg ctgtgggcaa ggtcatccct 60

<210> SEQ ID NO 1066
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1066
tttacaaact tcaatctttt ctacatggat tttgccttcc atgaaatcat acaggagtgg 60

<210> SEQ ID NO 1067
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1067
cctgtttatt gatttttatg agtttgttag aacatgcgct taatgctttt atactccggg 60

<210> SEQ ID NO 1068
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1068
tcatcatggg ctataagatc atggatgcta ccaatatcct ggtgtctcca ctggtctatc 60

<210> SEQ ID NO 1069
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1069
tcatcatggg ctataagatc atggatgcta ccaatatcct ggtgtctcca ctggtctatc 60

<210> SEQ ID NO 1070
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1070
tcatcatggg ctataagatc atggatgcta ccaatatcct ggtgtctcca ctggtctatc 60

<210> SEQ ID NO 1071
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1071
tcatcatggg ctataagatc atggatgcta ccaatatcct ggtgtctcca ctggtctatc 60

<210> SEQ ID NO 1072
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1072
tcatcatggg ctataagatc atggatgcta ccaatatcct ggtgtctcca ctggtctatc 60

<210> SEQ ID NO 1073
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1073
tcatcatggg ctataagatc atggatgcta ccaatatcct ggtgtctcca ctggtctatc 60

<210> SEQ ID NO 1074
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1074
tcatcatggg ctataagatc atggatgcta ccaatatcct ggtgtctcca ctggtctatc 60

<210> SEQ ID NO 1075
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1075
tcatcatggg ctataagatc atggatgcta ccaatatcct ggtgtctcca ctggtctatc 60

<210> SEQ ID NO 1076
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1076
tcatcatggg ctataagatc atggatgcta ccaatatcct ggtgtctcca ctggtctatc 60

<210> SEQ ID NO 1077
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1077
tcatcatggg ctataagatc atggatgcta ccaatatcct ggtgtctcca ctggtctatc 60

<210> SEQ ID NO 1078
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1078
cgggcattca ctctttcagc tcagagtttc tcttcctttc caatacaggc tctacatgaa 60

<210> SEQ ID NO 1079
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1079
gaatgtggag gaagacttaa aggcagatga accatccagt aaggaaagtt atctagaaat 60

<210> SEQ ID NO 1080
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1080
ccagcaaagc gggagccctg aaaaattagg ggggaaatgg gagaaaataa tgtgacattt 60

<210> SEQ ID NO 1081
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1081
aaggtttcat gtgattcatg tgtaagatgc acagtatttg acatcctgat tatgtaatcc 60

<210> SEQ ID NO 1082
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1082
ttctggtctc aatggcttcg ggaaacacac atatacacat acaccatgcc cttgaactca 60

<210> SEQ ID NO 1083
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1083
tccttgagaa gacaggcagt ggggctctca cttgggaaaa gagaagtaaa ttaagagaaa 60

<210> SEQ ID NO 1084
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1084
attccaaata ccaatatcaa agaaaactaa gttggtaatc tatctcagaa aatatatgaa 60

<210> SEQ ID NO 1085
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1085
tgctttttta ggctacagtg tctcgatgcc ataatcagaa cacacttttt tccctctttc 60

<210> SEQ ID NO 1086
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1086
tcgatcgcca cacgtatcac agcctgtacc tgaaggtgaa ggggaatgtg ttcaaagaca 60

<210> SEQ ID NO 1087
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1087
tttttatgaa aacgaagaga gatgtttaaa gtttattttt cagcaggtga ggtggctcac 60

<210> SEQ ID NO 1088
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1088
catcacaagg gccctagttc agatagtgaa aggcctgaaa tatatgctgg aggtggaaat 60

<210> SEQ ID NO 1089
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1089
gaatgagctc tgacaagcca tatgcatttc ataaacaaac caaaacatca tcttcatatc 60

<210> SEQ ID NO 1090
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1090
gccgtctgac ggtgatgacc gacctggagg acaagaacga gtggaagaac tgcattgaca 60

<210> SEQ ID NO 1091
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1091
tttgcacagg taagagagta gttagctaac ctatgggaat tatactgtgg ggccttgtga 60

<210> SEQ ID NO 1092
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1092

-continued ataatatgat gcatcttatc atggacaagg acagtgtttt ctacctttat cagttctctg 60

<210> SEQ ID NO 1093
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1093
cgaattgtgc tgagaagttc caaggagcct ggtggtacgc cgactgtcat gcttcaaacc 60

<210> SEQ ID NO 1094
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1094
gagatgccca tgaatgtggc tgaccttatt taattcctgg gatgagagtt ttggatgcag 60

<210> SEQ ID NO 1095
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1095
tgctagaggg caaagagttg gagttctatc ttaggaaaat caaggcccgc aaaggcaaat 60

<210> SEQ ID NO 1096
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1096
caaagcatcc cactcaaggg agacttgaaa cttccagtgt gagttgaccc catcatttaa 60

<210> SEQ ID NO 1097
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1097
aagttgtggt gaagaggtta tttatgagtt gcaccaaatg gccatctctg tctctttcct 60

<210> SEQ ID NO 1098
<211> LENGTH: 60
<212> TYPE: DNA
<213> ORGANISM: Artificial Sequence
<220> FEATURE:
<223> OTHER INFORMATION: Description of Artificial Sequence: Synthetic probe

<400> SEQUENCE: 1098
tcttgccttt ggactctggt gaaaaatact ttacagtggt cggtcacaag aaaccatctg 60

<210> SEQ ID NO 1099
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1099
tctttcttgc agccaaagaa ctttacacca aaaactgaac tgtgtgtaac catagtaaca 60

<210> SEQ ID NO 1100
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1100
gagcacttag gtatcatatc agatgctcaa ggctggcagc taccccccttc ttgagagtcc 60

<210> SEQ ID NO 1101
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1101
cagcactaag caaaaactag agaaagctga aaaccaggtt ctggccatgc ggaagcagtc 60

<210> SEQ ID NO 1102
<211> LENGTH: 60
<212> TYPE: DNA
<213> ORGANISM: Artificial Sequence
<220> FEATURE:
<223> OTHER INFORMATION: Description of Artificial Sequence: Synthetic
probe

<400> SEQUENCE: 1102
gaaccctgcg gagggacttc aatcacatca atgtagaact cagccttctt ggaaagaaaa 60

<210> SEQ ID NO 1103
<211> LENGTH: 2558
<212> TYPE: DNA
<213> ORGANISM: Homo sapiens

<400> SEQUENCE: 1103
agtccggggg catcgcgatg ctgctgcgcc tgttgctggc ctgggcggcc gcagggccca 60
cactgggcca ggacccctgg gctgctgagc cccgtgccgc ctgcggcccc agcagctgct 120
acgctctctt cccacggcgc cgcaccttcc tggaggcctg gcgggcctgc cgcgagctgg 180
ggggcgacct ggccactcct cggacccccg aggaggccca gcgtgtggac agcctggtgg 240
gtgcgggccc agccagccgg ctgctgtgga tcgggctgca gcggcaggcc cggcaatgcc 300
agctgcagcg cccactgcgc ggcttcacgt ggaccacagg ggaccaggac acggctttca 360
ccaactgggc ccagccagcc tctggaggcc cctgcccggc ccagcgctgt gtggccctgg 420
aggcaagtgg cgagcaccgc tggctggagg gctcgtgcac gctggctgtc gacggctacc 480
tgtgccagtt tggcttcgag ggcgcctgcc cggcgctgca agatgaggcg ggccaggccg 540

```
gcccagccgt gtataccacg cccttccacc tggtctccac agagtttgag tggctgccct    600
tcggctctgt ggccgctgtg cagtgccagg ctggcagggg agcctctctg ctctgcgtga    660
agcagcctga gggaggtgtg ggctggtcac gggctgggcc cctgtgcctg gggactggct    720
gcagccctga caacgggggc tgcgaacacg aatgtgtgga ggaggtggat ggtcacgtgt    780
cctgccgctg cactgagggc ttccggctgg cagcagacgg gcgcagttgc gaggacccct    840
gtgcccaggc tccgtgcgag cagcagtgtg agcccggtgg gccacaaggc tacagctgcc    900
actgtcgcct gggtttccgg ccagcggagg atgatccgca ccgctgtgtg gacacagatg    960
agtgccagat tgccggtgtg tgccagcaga tgtgtgtcaa ctacgttggt ggcttcgagt   1020
gttattgtag cgagggacat gagctggagg ctgatggcat cagctgcagc cctgcagggg   1080
ccatgggtgc ccaggcttcc caggacctcg gagatgagtt gctggatgac ggggaggatg   1140
aggaagatga agacgaggcc tggaaggcct tcaacggtgg ctggacggag atgcctggga   1200
tcctgtggat ggagcctacg cagccgcctg actttgccct ggcctataga ccgagcttcc   1260
cagaggacag agagccacag ataccctacc cggagcccac ctggccaccc ccgctcagtg   1320
cccccagggt cccctaccac tcctcagtgc tctccgtcac ccggcctgtg gtggtctctg   1380
ccacgcatcc cacactgcct tctgcccacc agcctcctgt gatccctgcc acacacccag   1440
ctttgtcccg tgaccaccag atccccgtga tcgcagccaa ctatccagat ctgccttctg   1500
cctaccaacc cggtattctc tctgtctctc attcagcaca gcctcctgcc caccagcccc   1560
ctatgatctc aaccaaatat ccggagctct tccctgccca ccagtccccc atgtttccag   1620
acacccgggt cgctggcacc cagaccacca ctcatttgcc tggaatccca cctaaccatg   1680
cccctctggt caccaccctc ggtgcccagc taccccctca agccccagat gcccttgtcc   1740
tcagaaccca ggccacccag cttcccatta tcccaactgc ccagccctct ctgaccacca   1800
cctccaggtc ccctgtgtct cctgcccatc aaatctctgt gcctgctgcc acccagcccg   1860
cagccctccc caccctcctg ccctctcaga gccccactaa ccagacctca cccatcagcc   1920
ctacacatcc ccattccaaa gccccccaaa tcccaaggga agatggcccc agtcccaagt   1980
tggccctgtg gctgccctca ccagctccca cagcagcccc aacagccctg ggggaggctg   2040
gtcttgccga gcacagccag agggatgacc ggtggctgct ggtggcactc ctggtgccaa   2100
cgtgtgtctt tttggtggtc ctgcttgcac tgggcatcgt gtactgcacc cgctgtggcc   2160
cccatgcacc caacaagcgc atcactgact gctatcgctg ggtcatccat gctgggagca   2220
agagcccaac agaacccatg ccccccaggg gcagcctcac aggggtgcag acctgcagaa   2280
ccagcgtgtg atggggtgca gacccccctc atggagtatg gggcgctgga cacatggccg   2340
gggctgcacc agggacccat gggggctgcc cagctggaca gatggcttcc tgctccccag   2400
gcccagccag ggtcctctct caaccactag acttggctct caggaactct gcttcctggc   2460
ccagcgctcg tgaccaagga tacaccaaag ccccttaagac ctcagggggc gggtgctggg   2520
gtcttctcca ataaatgggg tgtcaacctt acccaagg                             2558
```

<210> SEQ ID NO 1104
<211> LENGTH: 55435
<212> TYPE: DNA
<213> ORGANISM: Homo sapiens

<400> SEQUENCE: 1104

```
ctctaaggcg gccacacggg catggccgtg gggctggcga ctggtgttta gcaactccga     60
ccacctgcct gctgaggggc tagagccctc agcccagacc ctgtgccccc ggccgggctc    120
```

tcatgcgtgg aatggtgctg tgccccttgc cagcaggcca ggctcaccat ggtgccgcat 180
gccatcttgg cacgggggag ggacgtgtgc aggcggaatg gactcctcat cctgtctgtg 240
ctgtctgtca tcgtgggctg cctcctcggc ttcttcttga ggacccggcg cctctcacca 300
caggtcagcc acccagagca tctcgggacc cctgtccagg aggggcgtgt gggcctgagg 360
gatctggggt cccgttctag catcacagct ccctggtgcc atgacagtgt gtgaatccct 420
ctgcctctct gggtcctggt tttctcatct gtaacatggg tgtgataaac actttgcagg 480
actagaggga agaaccagtg atgtggctgg ggagtgatta caaacccagc accatcaggt 540
gaggagaggc gagggtgcct catgatgaca aacacagggc caagagctgt ggcggggaaa 600
gaggggggtc ttgtgtgagt tcaaacaggc accagagaac acctcctaaa ggctgctcaa 660
atgacaagag atccaggaag cgtgctctag gcagaggtga cagcagatgc caggtgcagc 720
ggccggagcg cagaggccag caggcccata ggtcccatcg ccacacgtgg gcttgcggca 780
accatgagat gcttttgggc agaagagcga caggccagtt tggagcttgg gagacccctc 840
aggtgctgag tggagagggg gtgattctgg ggcaggcagg gggccgagaa ggggcagcct 900
gggggagatg cggcagtgca gacaaaaggg acagacgtga gaactgtttt caaaaggggg 960
agcttcagga tgtgggggcc gattggatgt gggctggggg acaggaaggg gagccaggcc 1020
ccgggtttcc agcctgtgta actgccatga agaagctgcg tttcctggga aagagcccct 1080
ttccctgtca gcccccatct cctacaggag agggagggac attcccatgg tgttaaggac 1140
aaaatcattc tgccactagt taaactggta aggaaggctc tattcaggac tattgtggta 1200
ggggggtagt tatcaagacc tcctggggag agagatggga cccaaccaca aatacaacaa 1260
agatggctgg agatttatag ccagcgagca gagggagggg gtcggggaca gaaaatgact 1320
acaggagaca tcagggtagg gggattcttg ttgaaggcag gccagggtga tcagacattg 1380
atctgggatg aggaatttga tccagtatca ggatgctgga gggtgaggga tcctcactaa 1440
actgacttgg caggactttt gctacagctg gactatgcag gctgaagaca aggcccaagg 1500
acaaagccca gtggaaaaga gggctcagag gagcctgtct aaagtgtggt caaggagaga 1560
ggctttgtca atgggctcct ggaagagtcc ctattcccag aaagtcctct tcccgcagct 1620
cactaatgtc taatgccatc tctacaactg gggtcaggca ttagactttg tcttccatta 1680
aaaggaaaac acccactcct ggagaactga gccacgacta tagtgaccct gttaagcctc 1740
gagcagttat ttaggaagaa gcatggactc tggaggcaga gaaaccctga actttgactc 1800
tgctagcaaa tggctaggca atatcctctc tcctccctgg gcctcagttt ccttgtctgt 1860
aaaatgggat gtggggcagt atatgtctac tagaattatt atgaggaata aaccaaggat 1920
tcatcaatgc ccagcataca gtaggtgctt actacgtgtt acttcccccct ccctccctta 1980
tgtacctgtt aaagtcctat ctacatcagg aaccatctca tcatccatag ctgatgaaag 2040
taactgtaac cccgctgctg gctgcctggc ttcagagctg gttatatggg tgtctctttc 2100
tcccaccaag ctgcatattg ctgaacaaca tatgggtttg ttttttttttt taaccaaaac 2160
gtgagcctag ccctgtgtca ggcacagaga gaacgctcaa ctatctgctg cattaaactg 2220
gcaatggaac aaaaaaatct gcaatctgtt ctctttaatt ttcctcagca acaaaaaatat 2280
atctcctgca ggaagattat tttgtgaaaa caaattggaa tgcctattat taaaagccaa 2340
actcatctgg ggcctacttt gccaaagctg cctttcccat ctgtttggaa atgcaaatgt 2400
attccagtct ggattaacct gccagataaa ttgaaggaag gatgtagagg cttagaacaa 2460

-continued

```
ttatttggca gaaactggct ttctcagcat cttactttga aatctgggat ttctctgttt   2520
gatctctttg cctgtgactc agaaactaaa cacttcttgt tttgtaagct tatgcaacag   2580
gcaaaaatca taaacaatat ggaaaatggt agaatgttct atttgtgaaa aagaactttt   2640
atccttgata aaatcacagg attttatctt ggtgtatgag tgtctcattt aaaaatactg   2700
agcattttga gacttccagt taaaccatgg tgaatcacag gtgtatccat ttttttccct   2760
ccttcctaga attccactaa cattttagta atgggatttt taaaaggtaa aaccaccaag   2820
aataaagaga atataaaagg agacagttga gaaaaagaaa tagagaggct acaacaaatt   2880
agataatatg gaggtgggtg gagctgatga cctcattcac agaaagctgg aatcttagtc   2940
tgtggaagtt gataccaagt cagtttgtct tgcagactcc agaacgtaac agagcaagat   3000
gctgcactag gcagggtgag gctggggttg aaagcctggg catggtttgg agttttgtaa   3060
ccagagcagt tagaccccta gggaccttcc aattcagttg ggggactcat ccacccatct   3120
ccacccactg cctgccccaa ggaaccagag aagctggact tgagggtatt gggccacccc   3180
tgtgtgtgtt ggggagaggg ccatgctgag gcacctactt caaactaatt aacagacatc   3240
cttgtctgag tggggtcccc agcacggttt cagatcgctg tcagctgagc ttaggcacca   3300
tgtcattcct cagccaaagg caggaagaga cttctctcac tgaggcctca gagaaaagat   3360
ctctaaattc tgctataaag gagactcctc taccatccca cccagcccca gtgaaaaagc   3420
cagatcagca cctgtcaccc tgccctgagg gccgtcagtt gacaaaccct actcatacat   3480
gcagaagttt agcgcttcaa acttacatac gagcagaaag ccacgccacc agaaatgtga   3540
ggaggctcct aatgtgaaac agagtaaacg aagagaaaag gggtctcta atgagagaaa    3600
caaagagaaa agtgggtctc tagtgaagca gagacaaggc ggggaggaga aggaagcttt   3660
gtaaatctcc tcttaagctt tctggagctg cgagtgaaga tatagttacc gtacaacaga   3720
ggggatgtga aaagaaggaa caatcagaga acaagaaaga atctggggaa attaaaaata   3780
gaagaactaa gataaaaatg tgagtagctg cccaacacat agaaaggata aatactcgaa   3840
gtgttggaga ccctgaatac cctgatttga acattacaca gtgtatttaa caatatacca   3900
actgtatccc ataaatatgt acaaatatta tatattaata taaaaacttt ggctaggcct   3960
ggtggctcat gcctgtaatc ctagcacttt gggaggccaa ggcgggtgga ttgcctgacc   4020
ccaggcattc agggccagcc tggcaacat ggtgtgagac cccatctcca aaaaaaaaaa    4080
aaaaattaat gtcaataact gggataaagt tgtagaaatc tcccagaaac tagaacaaaa   4140
ataaatgaaa atagaaaaag aaaatataag aaaattagaa tgttcaatgt ccagctacct   4200
aatgacactt ttagagacag ctaacagaag aaaaatagag gagaaacagt ttgcagagaa   4260
tctaagcagt ttctcagaag tgaaaggcaa gcatagcact gtcaattttg tttacaaaag   4320
aaagaaaacc ccatactatg gcccatcacc atgaaattac caaaaagtgg agataaactg   4380
atgatctttg gatggttctg gtggaataaa accaacctca tctaaggaac aggaaatcag   4440
aatggctttg aacatcttaa gcaaactgga agctagaaga caagggagaa acaccttcta   4500
aacctgaggg gaaattattt ccaacgaagt atctcacaca tggccaggct aatatcagag   4560
gtaaaggtag aataaaggca tttttactca tgtaaggact cagaaaagtt tatctcccat   4620
ccactctttc tcagaaagct accaaaggag atgtttcagc aaaacaagga agtaaaccaa   4680
gaggacaaag gatcccagaa acagggggcc ctctaaagga caagtcccag aatgacaacc   4740
aagaaggaaa ccatgacaag cactgggcct agagagcagt cagtccaaac tggagcagga   4800
aggtggaaag ctcacagacc aaggccccag gcaggataaa agagaactga tgtgcttgag   4860
```

-continued

```
agagcagaaa atactattgt taggtagttt agtagacatg ttaaaatgtt tggaagaaat   4920
tagtgggtga ttcccagaaa acaagacaaa taaaaatcag tcaattaact ttaggctaca   4980
agcaaggaga catggttgta gtacattact tggctcaatg gtaaacactg tttggcgatc   5040
aaaacattgt aaatcttgat ttactaaaaa attgatataa atataatgct gaaataggtg   5100
gagagaaagg gagtaagaac taactcctca tcaatcatgg cagggaaatt gatagatgtc   5160
aaaatgatga atcaagaaat agcattatga ccatattatc tagaaatagt gatactatgg   5220
gaaacagcta gaagaactga gcatgttcac tactgggaag ttgcaagata gggatagaga   5280
gaggtgaggc aagagctgcc tttttatcag tagagcactt tttttttttt ggagatagcg   5340
tctccctctg ttgcccaggc tggagtgcag tggtgcgatc ttagctcact gcaatccccg   5400
cctcctgggt tcaagcgaat cttgtgcttc agcctcctga gtagctggga ctacaggcat   5460
gcaccaccat gcccagctaa tttttgtatt tttagtagag atggggtttt gccatgttgg   5520
ctgggctggt ctcgaactct taacctcaag tgatccacct accttggcct cccaaagtgc   5580
tgggattaca ggcataagcc actgagcctg gctattagag cacttttaac ttaaagaata   5640
tatacatgtg ggtgccagtg cagtggctca cacctataat cccagcactt tgggaggcct   5700
agctgggagg actgtttgag tccaggagtt tgagactagt ctgggcaaca tagtgagaca   5760
ctgtctctac aaaaaataca aaaattagct gggcttggtg gcatacatct gtggtctcag   5820
ctactcggga gcctgaggtg tgaagattac ttgagcccag gaggtggagg ttgcagtgag   5880
ctgaaatcat gccactgccc tcctgcctgg gtaacagaat gagaccttgt ctcaaaaaaa   5940
aaaaaaaaaa atatatatat atataatata tatatgtttt tatatattat atatgtttat   6000
atatattata tatgtttata tattatatat gtttatatat tatatatgtt tatatatatg   6060
tttatatata ttatatatat gtttatataa atatatggac taaagttaat taaaaatata   6120
ttgttggcag ggcatggtgg ctcacgcctg taatccaagc actttgggag gccgaggcgg   6180
gcggatcaac aaggtcagga gattaagacc atcctggcaa acatggtgaa accccatctc   6240
tactaaaata cacaaattta gccgggcata gtggcgcgca cctgtagtcc cagctacttg   6300
ggagggtgag gcagggggat tggttgaacc tgggaggcgg aggttgcagt gagccgagat   6360
ggcaccactg cactgcactc cagcctggtg acagagcaag actctgtcta aaaaatatat   6420
atatataata tataattata tatattattt tatatatata tatatagaga gagagagagt   6480
catgatgggc atatttcttt aaaaagcaga ttttctggtg cattggaaat gttagcagtc   6540
ctggtcctgt gctgcggtta acattgggtg ggtctgtcac ctccctttttg cggttcagct   6600
tcctcatcta tcacatgagt gggctgggct agaagatctc aagagtcccc tcatagcacc   6660
aacatttgat gatttggaga tttttaaagc atcagatcat caaccgagta tgtttggctt   6720
tggttaaaaa aaaatagttg caagtacaac aattcaactt ggatgatgtt tgaaagtcca   6780
tttgcctgcc tcgcccacaa cctcaccctc tgaagaaagt ggccccatgc cagggttgcc   6840
agaagtagca gaactgaatt aagttaaaaa attttataaa cagcacaccc agttaaactg   6900
gagtttcaga taaacagcat tttttttttt tagtataaga atgaactata tgttgttatc   6960
tgaaagtctg atttaactgg gcttagcagc ccttctgctt cagttgtcag gtcctggtca   7020
cgtgactgtt acttgcgaga cagcttattg ggcaaggagt tggcgcctta gtcagagatc   7080
cgtggacagg ctggagccag cggcctagga aggggtcagg cgtaagaact ctgccaaagg   7140
gggctgtttc taccgcgtgg tgttgcaccc attcaatctg atcctctctc tctcagcatt   7200
```

-continued

```
ttcgaggaga agcactagag aatggaccca aaacagatgg agaaactgac tcgcaaggcg   7260
gccatggtct gcttaggagt gggtctcctc accagctagg ctgggaactt ctcaggacag   7320
gaaccctgcc tagttcatgt tggggtaccc actgtgatgc gtggcacgat gcgggttgaa   7380
tgaatgcatg aacagtactc ggctctgtcc tctggtcacc tgccatctgc tacacgagag   7440
agattttatt ccatggctag gcagatgcgt ggtgcagatg gaggagagct gttattttca   7500
ggattaccaa acattggctg tcatccaggc gctgtgctaa gtgcttgcgt gcattctccc   7560
gtttaagccc cccaatgacc ctgtgaggca gagcagtccc cccttatccg ccatttcgct   7620
ttctgtgatt tcagttaccg atggtctgaa aaatgggtga gaacagtact ggaagatatt   7680
ttaagagaga ccacattcac ataactttta ttacagtata ttctaatcgc tccatttgat   7740
tattagttac tgttaatctc ttactgtgtc taatttatga attacatttt atcgtaggta   7800
tgtacatata ggaaaaaaac aacgtccaca gggttcagtc tctgtggttt caggcatcca   7860
ctggcggtct cggaacctgt ccgctgagaa taagtaggga ctactgtagt tattaccctc   7920
atgttacaga tgagaaaaat acaaaactca gagtggtcac agaagatgct taaggccaca   7980
cagcttgtgg gggattggtg gaggcggggt gtttaccagg attggaaccc agttctgtgg   8040
ctccaaagcc agttctttct ccatggtctc tgctgccatg tgctagacag gggagtcaga   8100
tgggatagtg cttcaaagac tgtgaagaac ggaaccactg tgcagtctgc atctcttgct   8160
ataaccccag ttcttactgt gttttcagga aattagttac ttccagttcc ctggagagct   8220
cctgatgagg atgctgaaga tgatgatcct gccactggtg gtctccaggt gagagcgggg   8280
gtttgaccag gtggtccgga accaggaggg tagaggatgg cttctgttgc tgccctgctc   8340
ctgctgtggg tggctggaga gcaaccacag gccctgggat gagtgtgacc gtggggcctt   8400
tatgggcagt gccgtgggct gccggcttct gagtcattca gtggccccag ttgttggttc   8460
catccagtag aatttttagt ggatagaaca ggtgatttgg aatcaacgga tatgacccga   8520
ctccaagata gctcaaggcc agggagttga gggttggctt cccagaggag gggctgttca   8580
tggtaatgca gcaaggcctg gggaaaagag aactaactct gaggatactc cagtgatcac   8640
agcctggctt ggctgtgtaa ccttggacat attacctcac ctctctacgc ctcagtttcc   8700
tcatctgtaa aatgggaata acaacaccta cttcgaaggg ttgtcatgaa gactatatgt   8760
tgtgtatgct gagcactcag gaggttggga cttggggaca agggcgggat ggtgcgagat   8820
gaatttggac ggtgagctct tgcccaatca tgaacgacct tgaacaccag gctgaagaat   8880
tcagacctta cccagtaggg tgcgggccat ggaaatcatg ggagatcact tggtcccttt   8940
cactgatgtg ctaggtgaac ttgagcaacc ctatccctgt ccaggtcttg agtattccag   9000
atgtataatg agtggctgct ccaggtggtg tctaagagcc ttttgctctg aggccatgag   9060
aaatcttcat cttccaggac tcctctgcag agaggaaaga ggatgagcct ctgcatgcgt   9120
tctgcctccc agcctccctg ctgctgagca gtgagccagc tccttggacc tccccccttt   9180
gtgaagtgga gataatcccc aggccaaggg cgctttgtat tttctgcaca gaggcctttg   9240
caagcagcat ttaaatttct caggactcag ccttcaaggc tctgctgaaa tgctacctcc   9300
ctcaggaagc cttccctgac tcctcaactc actctagtga ctgtctcctc tttctgcatc   9360
tttggagtca ttcactgagc ctgtgaatct gtcagggtca gcagtcctct gtgttgctga   9420
atctgtacga cacgtccagt tcttccacac ggcctctcca cagccatggg tgcagctgat   9480
tactcttgcc ctcatgaaat gcccttccct atggactcac actcttctaa ctttttgcct   9540
gctttctgcc cctccatctt ggtctctctc cttctactca acctccaaat gttcagcttc   9600
```

tccagccttt tctcatctaa tttcatagct ttaacatacc acctacaagc ccaatgcccc 9660
cagatggaga tctccccaga cctctcctgt gagctccata cttcattaac caactgccta 9720
tttgacatct ccacttggat gtttcacaaa cgtttcaagt tttgttttgt ttgagatagg 9780
atcttgccct gtcgcccagg ctagagtgca gtggcacaat ctcagctcac tgcagcctcg 9840
gcttcctggg ttcaagtgat cctcctacct cagcccccca agtagctggg accacaggca 9900
cacaccacca cacctaatta ttttttgtat tttttgtaga ggcggggtct caccatgttg 9960
cccaggctgg tctcaaactc ctgagctcca gcaatccacc tgcctcagcc tcccaaagtg 10020
cgggaattat aggcatgagc caccgtgccc agccacactt caagtttaat gtcaccaact 10080
tgaagttcca cccagaaaac tgcctccttt tcctgttttc ttcttgtctg caaatggcag 10140
ctccatcacc caggtcttcc atcgggcctg tcattggcta tcctctttct ctcaacccca 10200
cagccccatc cacagttcca gtggattctg cctactcagt cgaagaatgg agcttcctcc 10260
caaccctaca ggcccgggca ctctcttctc acgtccagac tccaccgcca cctcactggt 10320
ctcctcgcct cacttcttgt ccccgtccca tctattccac ccagtggcca gaaggatctt 10380
gagaaaagca gattgggccc tgcccctcat ttaccttcaa cagcttccat gacatgtaga 10440
atcaacctgc agaccattaa cctggtctag gaggccctgc atgatctgcc tcgcccaccc 10500
cacctcatcc catgtcacat actccagtcc caccagcctc aagttcccta agcagaccaa 10560
gcccttacca tctcagggcc tccacacgtg ctgttccttc ctctggaaca tgcttcccca 10620
acatcttaca tctcttcttc ttcctctttt tttccatctc aacttgcaca tcatcttctt 10680
aggaaggccc tccccaccaa ccccttcatg ccaccctggc tctcccttac tgtaccctgt 10740
tccctcccgg ccacagcaca tatcatatgt tgtcattcta tatgcattca cttgttaact 10800
ggtttcttta tccactgggc tgtaagcttt gcaaagttaa cgaggctact ctgcctagat 10860
tcaactctgt gttgtcagca cctagccaag tgccaggcac atagtaggtg ctcattaata 10920
ctggtcaagt gaattaatta atggatcctg caatcatgca ttgtgctttc tggacacttg 10980
gccctgtgct gggtgctgca gacacagaga tgatggagag actgtcctgt ggtgttcaca 11040
gactgctggg gagactgaca ggaaaataga caatcacaga acagctaaat aagtgcactg 11100
gtggaggaag ccaggaccct tggcaggcag ttctgtctgc cctttcctgc tgactgtcct 11160
aactgcctgg gcattgcccc tctctcagaa cagaggcacc ttagaggcca ttgtatggac 11220
cctggtgtca cacagcctgg ccttgctatg tattagctgt gtggccttgg acaagtcact 11280
caaaacaaaa aaatcctgtt cagaagtcag aggccagggt cctcgacctg cctccaccac 11340
aagcgatcat gtgatctgag gtgaggcccc caaccctggg cttctttacc cagcaacgaa 11400
ggcccgtcca gctctccacc ttctggctct caaatgcctg gtctccctcc accagactca 11460
gtgttctctt ggctggaaat gcatgtgata ttaagttgag aaaagccagg acgtgttcat 11520
acatttcatt tgtttattat agagtttgga ctggtgcaga gcaaccgtgt cactaagaaa 11580
tggaaccgct ttaacatttt cctatgaagg gaaaattaaa ccttcagggg ggagatatga 11640
cgcatttctg agtcctaaaa cccctcgttc ctgaactctc cctcctttgg cctcaaactg 11700
gcctattatc catcctggcc aggagtccat ccacactgtc ccctgagctc ttgctcctgg 11760
ccagcccagg gctgggtgtc cctgcctttg aggaacagcc actctggtgt gaggttgtta 11820
ctcagggcag agcaaaatca ccagagctgc tttgaaaaat tcagatgtca ggcctgaccc 11880
tgagctgact gagctagaac cccaaagggt ccaagcagag gtttgctttc agagctccga 11940

-continued

```
aagtattctg aggattttaa atctcttgat tgtcctgggg tcagaccttc tggctccaca  12000
gcttaggagc ccagcaggag gctgtggtgc tcccatcccc aggggctcca agctgtgacc  12060
caggaaggca agggttttct gcagtgtgtc ctggctacag ggcagtagcg ggggagtggg  12120
gggatggggg cagggggtta catttgggct caccagcttc cagttccaac catctgcagg  12180
tctgggcctc gaagcctggc tcccatgaca tctgttccca cctcctctcc aggacaaaca  12240
gccacccttt ccccatgcca agccctggaa ccaggctggt cacccactag tcccacagca  12300
tgccacaagg gtctatctcc acactcctgc tcctgcccag cccctgccat gcacgccctc  12360
ttttaattct tttaatttaa agtctcactc tgtattcaag acctagctca aggttctgtg  12420
tgggaagtcc ttccacctcc ccatttgttg gtaaaatgga tgatgatctg tctccaatgc  12480
tgacgctgtg tgtgacctgc atgagctgag tgtcgttagc tcagtgacct cacggtcgca  12540
gctggcatgc cacacaatgg gggacaggca tcttttagtc cagtagtgac atctatgtga  12600
gcaaaccaac tagtatccct attcggaaga gccactcatc tcactgaaca agaaagccac  12660
tgtcaagggg tcgggccagc ggcatggccc cctccgtggg cagggtcgtg tgcatctttg  12720
ttttttttctg agatcccagg aggggatcag gtcattgacc cccttgtctt tcacactgac  12780
ctctgcctgg tactcagcgt gacagattcg ttcagaagtt ggagatctaa acaacaagca  12840
aagggaggtg gtgaggtgta aagaagtgtg ggtgactgca agggtggacg tgagggctga  12900
aaggcccctg ggctgccatg gaggggtcac aggcacacct tgctctggag aaaggaggcc  12960
cagtgggagg gcagtggggc cagcggggtt ggagctgagt tcagtcactc ttcccataat  13020
ctggcatctt ccagctgtgg gctctttttt ttctagaatt tctccaaccc agcccctggc  13080
ccaagtccct cctcagacat gtgtgcttca gtccaactga gtgcagccca cgcttgacca  13140
gtggtggctt catctgtcac aatgtggcgg gggagcagga agcatgggcg ggggtggttg  13200
aaatctgcaa aggctacagg gcaggaacag ggctttggag tcaccctcta gatgtgcaaa  13260
tgtaaacaag ccttttagca tctgagcctc agtgtcctta tctataaagt gggaagaata  13320
cctccttcac gaggttatta cgaaaagtaa gtaagagaat gtacgtgaag acccagcatg  13380
gctcctggta cgttatggat gtcccatgtt tttctttttt cttttttttt ttcttttttg  13440
agacatagtc tcactctgtc acccaggctg gagtgcagtg gcatgatctc agctcactgc  13500
aatctccacc tcccgggttc aagcaattct cctgcctcag cctcccaagt agctgggatt  13560
acaggcaccc gccaccatga ccagcaaatt tttgaattct tagtagagac ggggtttcac  13620
catgttggcc aggctggtct cgaactcctg acctcaggtg atccgcccac cttggcctcc  13680
caaagtgcta ggattacatg cgtgagccac catgcctggc agatgtccca tgtttttcta  13740
acttattaaa gcatcaccag gctcctcaga tgtgtcatga atgctccccc agcccgtggc  13800
cacctctgtc actgctctca gcaggaagcc ccttggatgg cttcttccat cttcatggtt  13860
ctaattagca cctgcagctc acctgtcccc tgccctggaa agccaccctt gactgaggca  13920
cacccgggtg ctccctcaac actggtacag accatgcagc atgccctgct tcacctgagt  13980
cgtgcacacc tgcacatcca cagggcctcc gcaggggccc tggccaggtc ctgcccactt  14040
ctccatgatg cactcacctg gcacccagag ccattccttg cgccatgaca gtcagagcct  14100
ccttatctgt catgaattcc tattcttttt tgtttttaat tgagacaggg tcttactctg  14160
tccctcaggc tggagtgcag tggcatgacc acagctcact gtaactttca actccagggc  14220
tcaatcgatc ctcccgactt agcctcccaa ttagctggga ctacaggcac acgccaccat  14280
gcccagctaa ttttttaaat tttgggtaga catggggctc tcactatgtt gccaaggctg  14340
```

gccttgaatt cctgggctcg aggcatcctc ctgccttggc ctctcaaagt gctgggatta 14400
caggtgtgag tcaccgcacc ctgcccaatt cctattctta ctgcctcttg cttttctatg 14460
cccttcactc ctacaaccaa gcagccttca tcagcttccc attcacacca gcattccttg 14520
cttcaagtag tgccttcagt tatctcctgg ttctctgtgt gtgtgtctgt gtgtattcgt 14580
tatcattgcc gtgtaacaaa ttatcacaaa cttagtgaca taaacacact tcatggttgc 14640
ctcagtccct gggccagcag tctgggcggg cttggctgag tcctctgctc agagtcttag 14700
gctgcaatcc aggtgtccgc tggctctgt tctcatccgg aggcccaacc agggagaatc 14760
cgcctccatg ctccctcagg catggacaga agtgattccc catggctgct gcctgagggc 14820
ccagcattga cagctgtgca gtggagccac tcaggttcta gaggctgcct gcagctcccc 14880
acccagctgt ctccacaggc agctcacagc atagcactgt aggtcatcaa ggccagcagg 14940
aagcccggtc ctcaccagtc ttctgagtca aagtcttcta ccacataacc acagggagac 15000
atcccaccac cttgttgtgt tctcatagaa gtcacaggca ctgccacact gcgggaggag 15060
gatataccag ggcttgggtc atcggggtgg cctgagggcc tgtccacctc cttctctctc 15120
ctggaacctt ccttctctct tcctctgtcc ccagagcagc tggatgtctt tcagaagtca 15180
cttctgctca cctctctccc tggagccggc ttgggttgag tggagccact gctcagcttc 15240
tgtccaagta gttcatcaag aactttcttc tgaataagga ctgctccctt actgtaaaaa 15300
taattctgaa gaatataact ctcccccttt catctgattt ctcactgccc catacagggc 15360
ctgctactgc ctgtgcctga tcaatacatt ttcaatgaat aagaagcagc agagggcagc 15420
ggcagcagag ttcagggaaa gtctcaccat cagcatttgt atgggccctg gaggacagtt 15480
aggagctgaa ctttaaagat gttttcatat tttaaaaaat tagataaagc cctggcaaca 15540
tagtgagacc ccatctctac aaaaaaaaaa aaaaaaaaac ttttaaaatt agccaggcat 15600
gatggtgggc acctgtagtc ctggctactt gggaggctga ggtgggagga tcgcttgagc 15660
ccagaaggtt gagcctgcag tgagccatgt tcatgccatt gcactccagc ctgggcaaca 15720
aagcaagacc ttatctcata aaaaaaaaaa attagataag caaattacaa acattttgga 15780
taacagagaa gaaaccatcc tctcactcca cattgctaat tctgccactg tgatttcttc 15840
tctacaaggt ttgttcttat tcttactggt gaattcacca gatgtgaggt gaggtccttg 15900
gctgatggga tcagaagccc aactgtctgg gccccagagc tggttgggcc tgtcccccga 15960
tgctagcaag gggcaatcaa atatgccaca tactgattta ttcattccca gagatcaaga 16020
cacttgccag caaggacagt catatgcagg ctctggccag agcctctctg tgggcttacc 16080
atgcagggaa cccactggtg aaatctgctt gctggtgggt acatttagtt atttaactgt 16140
ataacccggc gtaactccag gtttgcggtt ttcagtttat ttcagccctc ccaccacccc 16200
cgccttatag tggagtccca tcatatgtgc atttaactta agtgaattca attacatgtg 16260
ctctgaaaaa gggagaaaat catttaaatg agacaggaga ctcctccttc caagggctct 16320
tccccaggtg agggccacga gagaggaggg cctgaattgc ctccaccagc cgctgtgccc 16380
aggcacctcc tgaacagtga gcacctccct gaagccagag agtttctagg gcctgcagag 16440
gggtgggtgt tttagatcac ggcctctgag tgtatgctga tgctctcatc tggtgtttgc 16500
ttaaagaaac agcaacccac tccaaggctg gaagggaaac tgtcttgaat gaacttacac 16560
aaaactatac ctcctggact ctatgggcaa cttaagagat tttcaaaggc aaaattaatt 16620
acactttgtt tttgctttac tgacttgaaa ctgaatacac tgaatatggt cctactcccc 16680

-continued

```
tgtactagca ggaagcccag tgtgtccctc tggaggcctc caccccgtgg ccacagtcag  16740
cttatttcat tcagtggaag cttctggtgt aaacagagct ggaacatggg gtcctgccac  16800
cagccctgct gctctggttc cctccacggg gtggccctgt ggaacgcagg tcccgcacgc  16860
tctggtggaa gtctgcacac tgccccttgc aggtgcacaa cgctgctcag gccacaggga  16920
tgcctccaga cccctaggtc cccccgaagt gctcaataat tgttcctaaa gcagcctcag  16980
tcatgtcctg agatcagctc cccgggagtt gagccccaat tccctttcc ctcctactgg  17040
gttcattttg gaggccttga atgccaggcc atctcggctg ggggactcta gcgtaccctg  17100
gtgctaactt caaatcacag ggaactgggg ctcaggtctt agtctttttc ctctcagaag  17160
gccctgatcc tctggtgcaa atgggcacag ttttccataa ctctgcagat ctcaagttct  17220
caaggaggag gcattcatca agccacaaca gctcctccct tcccctgaca gtgctgcctt  17280
ctcatccgac atttgctgct caaaagattc tttgcaaaat aaaattgcct gcaggggaac  17340
ttgctctgtc cacccaggaa cagagacgcc ttggacaaaa attagaaaat tctgcctcac  17400
attacattag tataggaacg aatcatctgg acgggacctg cattggggcc cccctcccat  17460
ggttttgccc tcctcagccg tcttccgtgt gctgccacag ttcactaacg ccatgccaat  17520
tatatcttta tttagaaaag tcaagccttc agggcctggg agccttactt tcccattctt  17580
ccccgagcag gccacttgtc actaccccaa tcctttttgc tttcaactta cagtataacc  17640
caaaaagtat cttccacaaa aataaatctg tagcctgctt gctttggttt tcccccaatg  17700
tgatgtcata agaatttcca cgctgcacct tcaccttggt gatcctgttt tactcaccca  17760
ctcgggaggc acagagtttg caaagtcttt tgcctgtcac aaggcacttg ggaggctgct  17820
agactcttga gggagctgcc ctgcctcggg actgtggtct cacctcgagt tcaccctctt  17880
agcctcagcc ataaaatagg cacaatgctg tctgctaatt tacaaagcag gtcccggcag  17940
gtgctctgtg tgtgtgtttg tgtgcccatg tgtgtttgtg tgtgtggccc attatggccc  18000
cattccactg aggctagact ttgcacctca ccttgggagg tcaactgagc cttgttttca  18060
cacatcccca gacaagcttg acacaaggaa ttaggggtaa gtcagaccag catctggatc  18120
cagctagagc ctccaattct ccacttgctt tttgccaaac ccttctctcc cctcattctt  18180
cagtttctta aaccaggcgt ccttcagggg aaactgaatc catgtgtttg tgattcacta  18240
gggctgtgca tgatagagtg ttctgtgagc tccacaacat agcaaagaca gccaagcgtg  18300
ggtgtgggtt tgtctgtgaa gctgtgttgt gtgtgtgtgt gtgtgtgtgt gtgtgtgtgt  18360
gtgtgtgttg tgtatgtatt gttttccttc ctatttcttg taaggacttt aaactgattt  18420
ttcttagaat caggaaatca tgtttggcca gagaaactca acactccctt ctccccttcc  18480
tgaggaactc tagtgtggca gaaaattccc aaacacccac attctaactt attggaaatg  18540
ggcctgggcc aagcagccgt caaagtctgg tttgggagcc agtgtgcagg gggctgccca  18600
gactccccag gacaggccgt gagcaggagg aggcagagga gcgggtggcc agagggccaa  18660
accggtacag cctgtgcttc ggatgctgcc ctccgagtca gggggtagcc acagtttggc  18720
gagctccact gaaccttctg gtgtgagccc tgggacctgc ctttggccct tctgcccagt  18780
cagatgattt gccttactca tcaagagggg aaacgtggcc cgctgtgggc tgcgggtggg  18840
gtcagacctc cagcctggtg actccgaaaa gctcccaggc tttatcctgc accacagact  18900
tccatgctct cgctcccttc cagttagaga attcctactt ggccttcgag gctccatcca  18960
gctgtgccct cctctgggag gcccagcccg atgcccggag ggctggccct gctctggcgc  19020
tcagtcacag ctaccccac ccccgggttg gtgttgctct gctgctggtc tccccacccg  19080
```

ctggccagag caccaggaag aacacagacc cacctcattc ccttctgagc cccacagcac 19140
ccagtgcaaa tgttcaacac cgggcagggt gggcacatat ctcagagcct gggaaggtgg 19200
gtgaggtttt gaaaactgtg ctgccgccct tctctgtgga gaaccgctgc actggagaga 19260
ggcccacagg atggccccgc ctgagccctg tgcggggcag actccagggg ccctgctggt 19320
gcagggaggg gaggcaggag acctgagttc ccctgactcc tcatgatctt tgccacatgg 19380
gcaaggaagg ggtgggggat tcagttcacg tggagttgga aactggacct ggccctgact 19440
gccttaggga atgcagcctt cttggtggag aatggttgag aatggccggc agtctgacag 19500
tgagctctga gggctgcagc tgtggctcct ccagcttctg cttttgatcc agttcaagct 19560
tatcattctc acaggtccca gtggagcgcc ctcttggcac ccaggcctgg gaaggaggga 19620
ccttcagagg gcagcagggc atgccagggt agcagcaccc accgcccaca ctctgagccc 19680
cacactctct cccaccttcc ctccatggaa atcaaggtgg aggccaagag gtttggtcca 19740
tgtggctcca gagggctggc tgggcccagt gtggcccaat gctcttcccc ggaggcggat 19800
ttcattgtga caccaggaag gacttcctaa taagcatcac gagctcttag tggaggggct 19860
gactcagaag gtagtgagtg ctctgtcctc tgagatatgc aagcagaggt ggtggaggaa 19920
tttctgccct tgggagggtg tgctgagacg agatggccca gactttagct gagtgggagt 19980
ctgggcatgc tgccttaggc ctcaggagga gtcggcttga gtgtggggct ttggcagagc 20040
cgtctgggaa gcatgacttg gagctggcgc taatgggcat ggcactggct gtcagctgtt 20100
gggcctgcct tctgctcagg ggaaaagaag agtaagccat gatgctcaga tggactgaag 20160
ggacccctct tgcccgcaga cccccgaagc ctccttcctg cggcctgtct ggtagacttc 20220
ctgcagctgc atcccagggc cagctgggga gagcctctgt ggctaggtca gccaaggcca 20280
gagcccaagg acttggctgc agggcttggg gctcctcact gtccctcagg tcctcccact 20340
gccaggaggt tgtgactgga tgctgtcatg ccagcagact agggcttgaa cccacttatt 20400
gtgtgacttt agcaagttgc ttgcacacct ccagtgactg ggaggtcacc acttctcaag 20460
gtagttcctg ccagagcagg acagctctgc cagaaagtta ttcctggtgc tgagctgaga 20520
gccctagggc ttttcccatc atccccagca ttcccaggtc tgctccgctc cggaccacac 20580
agcacctgcc ccccagcccc ccagctgctc cccgcaacca ggcacgtgcc tctatcacct 20640
gctgcctacc cagctgccct ctacaggaca cacacacccc gccccgtccc tttctcaatg 20700
agtcaaagca ggtctgcagc agcctccacc agcccccggg cttctgaagc cacaggcagg 20760
gggcccacca gccctttggc agccccgcgt cccaggtgac tcaccagctg gcagcaaaca 20820
aagcccaaag tcccctcccc acgtgtgcag ccacggctca gcctccccct cccaccccgg 20880
tgtttgtgca ctccaagctg tggaagccaa gtgcggccca acacatgtct gtgttcaggc 20940
tcattgtgtc agaattgact gctggggtct gcttggattc ccaactccct catccagcac 21000
attagctatt cctcccagct tcctgtcctc tacaaatctg ctccacatgc tgtcgggggc 21060
cttggccaag ccattgatta aaatgaccag aaaggagagg gccgaaagca gagtcctgaa 21120
gctgatctct agacaccctc tctactgccc aggacattca gctccttgtc ccttcaccaa 21180
gcccccatct cttcccagat ttctggtgcc aactgtctcg atgtcacaca gacacacaac 21240
accgtgggca ttcccctaag cccatccggg gaccaaggct ggtactggtg atctgttctc 21300
aggaaacctt caatggctgc tcagtcacct gggcacacaa gtcgtccttt tcacgtctga 21360
tctagaatgt caccctggtt cagcatcaca cacatcagca accctgcacc caggcctgtg 21420

```
ccagaccttg ggttttaagg acctagagcc aaactagact tagccttgcc ttggaggagt  21480
tccagtctgc tgggacaggt ggtcacagac agacagtgaa gacagaggaa attataacaa  21540
ttgaaatgca gtgcgtactt atcacatgcc atgtaccact ccaacccaag atttggcctc  21600
acagcaaacc ggcatcatcc gcactcatcc tcagtggaaa ctgaggcaca cccaggccca  21660
gtcacatgcc caagggctcg cagtgagtga gggatgctta cgggagcttc ctcgccttgc  21720
ctagggccag ggcagccttc agagggcggt ggtgcctgag tggagacttc agagctgagc  21780
agcatccaca ggacaggaaa ggagaagaag gcggggactg ggctcccggc actccgtgcc  21840
agcccgtcct gtgccaggtg ctgggtcagg ccctggggat tcgggttgag cccactagca  21900
gggtgctccg taacaaactg ggaagcacag ggtgccctgg ggaagtgggt gagatggctg  21960
cagtcaggga aggcttccca gaggcagtga tgtctaagct gacccagggt tggggacatt  22020
gggccagggt tggggaaggg atggtggatg gagagttcca ggcgggagga acatccagtg  22080
caaaggtact tccaggagca gagtggacga ggaggagagc ggcccagccc caggggacgc  22140
agggcaggga aggagctggg atggttgcgg agggcaatgg ggagtcaccc caaactgggg  22200
gaggggcatc cggcagctgg gcagcctgca ggctctcttg gctctctctg tagggaggtg  22260
cgactacaac ttcgacttcg tgggggcgtg gtttctaatc cctcaccttt gtaaccagcg  22320
cttggcaaat ggcagagctg ccctgcacct cccagtgtga gatggggtca ggagtcccac  22380
ctcaggggtt ggtgcgagaa ccaggggagg gtcagtcagc agccttttc tccttccacc  22440
gggagcctgg cagtctttgc ctcccttccc ccacccctgc aagtggagca attaccagat  22500
tgagacaggc tgggccttcc cactgcctct gcgggttaat gtctctaatc actgcaatct  22560
cttgatccac aatccctggg ctctgagtgg tggccagatg gcttaggagg gagttccagc  22620
ctccagactc ccagaggctc ttccctgggg ccctcaaaca ccgcaggtgc tcccaggagc  22680
acccagccaa gcgtggtgtg ggagagaggt ggttgcctat tctcccctca ccataaatca  22740
cagagccaga aggaatgttt gaagtcatcc tcatggaacc tcccactcta tctggaagcc  22800
tccatctagc atctcaacag gtggccatcc aggatccacc tggatgcctc caacaatggg  22860
aagctcacca ccacaaatct gaggctcatt accaagggca ggctgtgaac tccgagattg  22920
aactaaaatg gctttacatg ggctggatca cattaaaatc atagtcagct gggctgggtg  22980
gctcacacct gtaatcccag cactttggga ggtgaagaca ggaggatcat ttgggctcag  23040
gagttccaga ccagattggg catcatcaag atacccccat ctctactaaa aatttttaaa  23100
aattagccag gcatggtgtc gagtgcctgt agtcccagct acttgggagg ctgatgtgag  23160
agaatcattt gagcctagga ggtcaaggct gcagtgagcc atgatcgtgc cactgagccc  23220
cagcctgggc aacagagtga aaccctgttt caaagaatta ataaaaaata aaatcatagc  23280
ccaaaccaga tcttttcccc caccaccaga gttaaaccag gtttgtgcca cagacaggca  23340
ctgtgggagt gggaacccca caaggttctg aatcagaaat ccctgttcca atcttgacat  23400
tatggttcac caactggagg gcctggccag ttgcctccat ctccctgtgc tccattttcc  23460
ccatctgtaa ctcagaacta ttgtattggg ctgtccaata caacagccac gagtcagagg  23520
aggcctctga gacccaaaag caggcagtgc aactgaggaa ctgaactttt atttaattta  23580
atttaaaatt taaaacctga agcaatataa attttttttt gaaacggagt ttcactcttg  23640
ttgctcagga tggagtgcaa tggcgtggcc tcagctcact gcaacctctg cctcccaggt  23700
tcaagcgatt ctcctgcctc agcctcccaa gaagctagga ttacaggcat gcgccaccac  23760
acctggctaa ttttgtattt ttagtagaga tggggcttca ccgtgttggt caggctggtc  23820
```

tcgaactcct gacctcaggt gatccacctg tctcagcctc ccaaagtgct gggattatag 23880
gcatgagcca ccgtgcctgg cctaaaaatt tttatattga tgacatattg aaatgataat 23940
atttgggata aactaggtta aataaagtat taaacttaat ttcaccaaaa aactaatttc 24000
acctgtttct ttttactttt taatgtgacc actagaaaat tctaaattac aaatgtggct 24060
cgcagtggaa ctccacagtg cttcactcag aaggttaagg atccactggg ctgggtgttc 24120
aggtgtctgg ggaacagtaa agtcccagag agatgatggc ttctgaggct gctgggtcct 24180
ccaggaggtg tcatctccat cacacaagaa gacgggctca atctagaaag aatagagaat 24240
gtgaaggact attcgaaaca aaacaaaaat tacttataac acccaaagat aataattaca 24300
tttcctatag agtttgcttg tttccgtgcc cgtccacgcg acctggtctc ccaccaccac 24360
tgggcaccag ctgcaagttc tcagaaaagt cacctttaac agcttgacct tgaagcctgg 24420
gaccttgagg agcctcagca gggaggaatc cctcaaaaag ccaaagggca gggccttaca 24480
cctcctttct gtgcctgtga gctctgagtg gaagccacga cctctgcatg cccagctccc 24540
attcttcttg gcctccgccc tcacctgcgg tggccctggc actccggggg aggctggcct 24600
gtgctgccag ctgtcaccag cagttcccgc ggctgctcac ctctcccttc cgccatttgt 24660
gggaagggag ggaggctcca gcacagaacg acttgggtcc caggattctc tccatttcgt 24720
ccatgggtgc tctcctgtcc agagctgatg gggccccag ggtggggtca gggatccctc 24780
ttgctctgtc taaaacctac actccctccc acatctcaat ctgtccctga gttggcgcca 24840
cccccgtgtt aggcctcttc gtccccggtg gggggccttc tgaggggcct ttatcctttc 24900
ctgaaatcca gtcctcacct gcaccccact ccacacaatc cctcagacac atctatgtgc 24960
ctagactgca aatctggagg gagtccacca tcccaggagg ttccagggct cactgcagag 25020
atgcaaacaa tctggtaact tgcttttcca cttagcattg atttaggaac acccttccag 25080
ggacacgatc actccggatg gctgctatac cgtcccttcc tatctaatct gcattggtga 25140
gttcttaggt caggtttttg atcttacaag tactacttca gtgaccctcc cagtacacca 25200
tgtgtacttt gatcttctca aatggaagga atttttcgtt ctcccttcta gacatccagc 25260
aaattctgct gcctgagttg tgctgaagtg ccacaaggcc accctactcc tgagctcagc 25320
ctatcttctc tatcccttct atcaccaatc tgtcactaac cctcagatat tacctgagct 25380
cgggccacat cgaacagcac ggtgtctcac actttccagc ctcccttctg ccttccactg 25440
tctcactgct gcgcatgtct gccccatctc caaatcctct cccatttcca agagccaggt 25500
caaatgccac ctcctccagg gagcccttcc tgactttcct agctcgaagt gattccccct 25560
tctctgaaca aagacagcat ttccttgtcc ccgcttccct tgcggttctg atgctcccac 25620
atagtccagg ggccatttga gtgcacttgt ggcccagtgt cctttccttc tccctcccca 25680
ttccctggca gattaggaac tccttgaggt cagggacagg ttctgatttc ttcctgtggg 25740
cacagggcat ggcacggagt gggcatgtgc gaaaggtttg aatgcacgtg aatgaaggag 25800
gacaggcctg ggtctggccc tgagttctgg cccagccggg cactgctgtc ctgtgtgacc 25860
tcaggcaggg cctgctctcg ggtacatggc ttccctgtgg cctgaggcgg ctggacccca 25920
ctgcgggggg ttctgtcatg gtgggaggac tgtttggccc tgggttgacg caccggccct 25980
gcgtgggata atctctcttt gatgatgatt gcagggcagc cccccatttc ctctggctgc 26040
acaatcccat tatgagccct tcaggattta tgtctaagac ccaccctaag cccatcacta 26100
acatatggca tcctggcaga tgaggatgag cagagattgt aaacactcat tcattcattc 26160

```
actcactcct tcactcagca gtctgctacc aaactgcgga cccagcattc aatcagaacc  26220
tggcccaacc ctggaggtgc ttccagtaaa gagtccgcag tccagtgagg tgggggcagg  26280
gacagtggga ggcacaggga ctgtggagcc agagaaggag gcttcactca gcctggtggt  26340
cagagacggc ttcctgcaag aggggatgct caaagtgtgt cttaccagaa gagtaagcca  26400
ttgcgccagc gagcaggcag ggcagggccc tcacaggcgg tggctcccgc tgggggaggg  26460
ggccggtgtt cacgctcagc ctggggctgg atgctgctgc atggaatcta atgataagag  26520
gagcgtggct ggggattatc tgctcttgtt tacatgatta aaaccagaca aatacttctt  26580
tatctgaaag aatgaaaggg ctttggggaa aaatcctttt gtcaacaaag caaagcacaa  26640
gcatttcctt aattaatctc acttcacccc acacccccca ccgtcccaca ccccccacaa  26700
tggctgcaag aagcgttgct ctagggctcc agggctccag ggctccagga cgccagtact  26760
ctggggctga cctgcactgg taggcagaaa gcccaggcca gggtggctag gggtggggag  26820
gagccgagag gagagagacc cacagccctc tcaacacagc cccctgtgac aaggagcctg  26880
ggcccaggca caaacccaag atgtccccat tttacagatg gagatcctga ggcccaaaga  26940
tggggaagtg acttgcttgc ctgaggccac acagccagtt ggcagagctg ggactaggac  27000
ctgggtcacc agcccccagc ccagcgctct cactcactcc tcattagctc gtccaggagc  27060
ccgcaggaac cgcctgcggt gccgtcctct cgggacccac agggaagtca gactcatccc  27120
tcctctcaca aacagacagg cagcgtcctg atggagcagc caggggctgt gggggtccta  27180
gaatgggctc ctcactctgg gggagaggca ggtagatctc agaggtagac caagcttggt  27240
cctgcctggc tgggcagggg tcaggagagt gaaggaagct tctgagagga caccaagcat  27300
gggaaacttg aggcaacaaa gtaaagcaca cgcatttcct taattaatct ctcactcccc  27360
caacagtgtc cccaccatcc cacagccacc ctggcctggg ctctctgcct agcagtgcag  27420
aggtctcaag gcacagatgt gtgtggcctg cgcccccggg cgtgggggag agggcagagc  27480
agaaagagag gctggaagga gcacaggact ggattgttgg aagaatgggg ttccctggag  27540
cactgtgagg cagctggaca tggccaggag gggctgagtg agcgctgagt gccagccagg  27600
ccctggcctc cccaccacag cccctgaccc cctcgccctc ccagcttgat gtccggactt  27660
gcctccctgg atgccaagac ctctagccgc ctgggcgtcc tcaccgtggc gtactacctg  27720
tggaccacct tcatggctgt catcgtgggc atcttcatgg tctccatcat ccacccaggc  27780
agcgcggccc agaaggagac cacggagcag agtgggaagc ccatcatgag ctcagccgat  27840
gccctgttgg acctcatccg gtaactattg ccacccacac cccgcttggg aacgccaggc  27900
ccgagcctgc cctgccaggt cccccagagg ccaggacggg gtgtggagat gggggtgatc  27960
acggagtcca tgatcaccct ggtgggttga gctctgggct gcccgctggg ctcatgctgc  28020
atcgtctgcc ccaccaggct agaagcacct tgcagcctgg acggggtctg cccctctctg  28080
cctgtggatg ggcgcagagc agacatctgt gagcatttgc tgatgcccag cctgtagggt  28140
gggaggctgg ctgttattgg cccctccctt tgtttattgg tcctcttttt acagatgagg  28200
aaatggggct caaaaaggtg ccgtgacttt tccagagtca ccggtaggta ggtagtggag  28260
acaggattca acctagtcct gtctgactcc aaggacaatg ccctttgccc tgtggtgcca  28320
ccccctagca atggcagtgc cacatcctag ccacagcagt gcagctaacc ttgcttctca  28380
gacctaggct ccctctccag ggaagcactg cagacccagc ggcacagcca ccttccactc  28440
cctttccccg ggtcccctgc aggtcacccc tgctcctgtc cttcgtgcat tcgctccctc  28500
accagtgcca gttctgtgcc aggccctgga ccaggggact cagagccagc ccttgccctg  28560
```

-continued

```
gaggagtggt cagacccacg agcagacagg gacaacatgg gggcctgggg ctgcaatggg  28620
gaagctgggg ctgccggtga gagcaggaag ccactgccct tctaagggag gggaagatgg  28680
ggaggcaggg agggcaggcc tgggggcgat agctgtgcga aggtcctgag ctgcagggaa  28740
ccgtctgcgg ggagaaggca tagcaccatc agtgtgacac agcagaaggg gtgagaggca  28800
ggcagaaacc cctgctggag aattcaggtg gggaccggcc tcaaagtgca ccgtgaacca  28860
ggccaaaagc taagttgcat cctaaaggcc acagaaaatg agttttatac agagaagcgg  28920
catgatccaa ttcagaaggt tcaatctgac cagggatcag agttgcaggg gaggtaggag  28980
gggaaggcag agccagggac agggccaagt ggtggccctg gggatgggga agggggcaga  29040
tggcagggct gctcaggagg gatccttagc aggaggtggg tgagtaggag gtgaggtgtg  29100
ctgatcaccc agcatgaaga tttctggccc acgcatccaa gtggatggtg gtgtggtcac  29160
caagcgatgg atggtctgga gcaggtgcag gcatcctggg gtaggtgtca actgatggtt  29220
ggccagtgga tgagaatctc atgggggagt ctaagctgga gacggaggtt tggaaatcgc  29280
cagggagagg tgttaggtgc taccctagtg gcagaggggc tcttgcagga caggtggtga  29340
gagagcaggg attgggatgg agcctgggaa gccccaccca ggaatggtgt gctgggctcc  29400
acaggctacc ccactaagcc cgctcaggga acaccttcta gtacctctca cttcctggtc  29460
aatttcagat ctaagaagtc taggcctaac attaaaactc caaactcctg cagtttaaac  29520
taagcctgtc ttagcctttt ggatctgact cagactggga aagctgcagt gggaagaggg  29580
tcgtggtgag tttgtttctc tttcctgctc tgcctgctcc ctggtgagag gtgagggagt  29640
gggctaggaa gggctgccca gactgggaga ggggtgagct ggagcaggtg ctccctcgtt  29700
gtgtctctcc aggactactt ctatgggttc tctggagccc ctcttctctc tcgcatctct  29760
cacctgctgt cccctggact caggcaattt attccatctg gctacttaca acatccccta  29820
gaccagggct ctggttgact cctctgctgg ggtcacctca cccctctggg tgaccctgtt  29880
gggtcatgtc tggcccatgg gaagcataca tatccctatt ggaagtgctg gcctttccca  29940
gggcctttgg acatgagtca ggcaccagcc cctacattcc tcaaattcta agagactcaa  30000
gccaaggtct ctgaatagtt ctcttggctt aaggttgtgg agaagcattc ctttcctccc  30060
ccgtggggat agatgcccat acacaggctc ccacccactg tctaaagaaa ctctcgttcc  30120
ctgtatcagc tagttactgc tgcataacaa accaacccaa catttatcag cttaaaacaa  30180
cagccacaag tctataggtc agctggaaag ttctgctggt ttggactgag ctcactcaca  30240
tgtctgcagg cagctggtgg ctcaactggg gaacagttgg tctaggggag tctggctgag  30300
atgattcagc tatactctgt gatctttgta ctccagcagg ccagcctaga tttgtttcat  30360
ggtggcgaca ggattccagg agagagctag cccaggcatt ttttttaata acaaaggtag  30420
aggagcaaga gaggaaatca aaacatgcaa atgtttctca agcctctgct ttcagcaagt  30480
ccactaatac cctcttggcc aaagcaagtc aggtggccaa gcccagactc agggtgggaa  30540
gggaccacaa tgttacaagg gaaatggagt ctacaaaccg aggccatcga tgcaatcagt  30600
ctaccactcc cttcatttct ccaggaagat cttcagcttc tcttttaccc tttagagtgt  30660
gtgatgaact aaggatcatc aaatatttgc catgctgttc ctatcgcgtg gctgtcacct  30720
atagggtctg gagccagaaa gagatccagg cagggtctgt tctgtgtttg cttacttggc  30780
tggcaagact tcatccaata ccagggcttt gaacaccttc tggactctgg cacttccgaa  30840
tttagtctcc agcctggaaa actctcacct gagttccaga ttctcacata aagtgtctag  30900
```

-continued

```
aggtatctca aaattaacag gcccaagctc aactcttgat ttctccataa atctgccctt  30960
ttctcgccct gcccatcttg gtctgacatc tctcattctc tcataccctg cagccagttc  31020
ctcagcaaat tctgtgagct ctaccttgaa aaccaaatcc caagccatgg cccttccacc  31080
tcccctgcca ctcccgccat tgccgcccac tccagtgtct ggcctggcct ccgcttcctc  31140
tctgcttcct gtcctctgtt ctcagcactg cagccagagg catccttttc aaaacctgct  31200
ctcaacccag cacatggcaa caaagtcgta gcctgcaccg cagcttacag gcacttgctg  31260
acacacatca gactctgacc tccgccccaa ctctcccttt ccctgccctg gctccagccc  31320
cacccgcctc gttgtccttc ctgtctgggt gtcattgcct cctctctggg tggccctccc  31380
tgcagaaagc atgcagctcc ttccctcact ccatttacat ctctcctggg tgtcgcctct  31440
cctgagacct cccaggctct gcctctctgt tgtcttctct tgagtcactt ctcctcatag  31500
cctttcttac tacccaacat gatcatatct acgtgtttct tttcctccca catccactgg  31560
aatgtaatat gccctgtgaa gcctggctct ttaacctccg ttccctgctg tatcctggag  31620
cctaggacag cacctggcac cgagtgggtg cgcagagttt gctgaatgca cacgtggggt  31680
ttaaggtcat cagtggcatt ggggtctgat ccccaggagg aactggaatg gtccagggag  31740
aatgtgccca gcaagcaggt gcagaggcct aggacgggcc ttggctcacg gccgcactgt  31800
gggctttgca cagcaaacag agcaggggca agcagagagg caggaggaga actaggagag  31860
tgaacatcct aaagacgagg aaagaggaac ttcaagaaac ctcatttgta agatctgtta  31920
tttctaggat ctggtaactg tgattcatgg tttcttgggt cttatgattc agaacggctt  31980
ctccacatgg tggaaggagg tatcggtgct gcctccttca ccactgcctg cccttactca  32040
ggggctgcgg ggctccagat cagaaacacg tgccacagtc aaatgttcca gagtgtttcc  32100
tgctcttggg ttgcttttca cgtggtgaaa actgatcctg ctgcttagag ccgcaccccc  32160
cacgccccag ccctacccca cccgctctca acccagaggc aagttgttct gcaaagctgg  32220
gtgttgggcc tcgctctcac cgtttcttgg tcagagagcg gggctacagg gagagaacac  32280
aggcgtcctg ggacaggaaa ccagaaccta ggagacctgt ggcctcatct ccactctgat  32340
aataataagt tactgtgtgg ccctgggcag gccagttccc ctctccaggc ctcagtttcc  32400
ccagtgattt tcaagatccc gtctagctct gtggttctga aacacaaagg cctatgagcc  32460
agtgaggagg ctgcagggca tgaaccaaag cttctggagg tgggttctgg gagatgaggt  32520
tgggagggct gggcagagcc caaccttgaa gacaggaggc ccaggttgag gggctggctg  32580
ttaggctttg ggaatgggaa gctggtgggt ttgggaagga tggattagag cagggtggag  32640
tggacagaag gtgagcagag gcatggatgg ggtgccctgg gaggagcaca gtcacttcct  32700
ttccattcag ctccgctgta ttcagctgct gctctgggtg aagacattgt gctgggagct  32760
gggaagcaag tacaaatgcc cctcacgccc ccaccccagg gctgcccacc atcttaggac  32820
agacggacaa gtgggtgcac tgacagccac tcctgatgct ctgagaggct gtgaaggaga  32880
tggggacact ggcagtgagg gaccaggggc ctcctgaccc ttgccctggc ccagaacagg  32940
tgcctaccag gtgctgaaga ctgaacaaaa acactgatga ccaggaagag aactgagaac  33000
cagggcaagt gggacaaatg gaaagtggga gcccactgcg tggggacata aggcacacca  33060
caggggcaaa gatctgcatc cttgtctcaa agatgactcc agaggaacac aacaggccat  33120
gtccctggat gaccctccaa gacaggaatt cattttccag ggctccgggg ggccgctcca  33180
gaaggctggc gcctgctcac agtgcagcac gcaaaacaga aacccaagca gagcactaat  33240
caggtctggc cccttctctt ttttttcgaa tcttattaaa acaccacaga gattaagtaa  33300
```

```
tgactgggct ctatttatag ctcccaacta ccctctcagg gattggagga agcttccagg  33360
agctgtgctt gggaaggaac aattcccacc tttagggctt ggtttgggga catgttatta  33420
ggggtgggtt tggaagcatc tcggtgagaa tttgcaagta gcaggtgaag aggggagctg  33480
agaggtggac tctggctctg cctagaaaac gtgcagggag gcacagggca gagtgtgtgg  33540
gtatttgata ggcatggcta ttaacgtccc caggcacgtt ctgtgtttta tgtagctgcc  33600
accaggagca cggacctcat gggacaagca gaaaagtctt cccgtgaagg ctcaaagcca  33660
aaagaaaatg tacatttccc catttaataa tcaaaggtat aattcttgat taaaatctgc  33720
aggataaatt cattggttat tagtatgagc acacacgagt caggacttgc ttttggctgc  33780
cagatcagca gaggcttaag taaggtaagg tttgcatttg ttcctgaaga acagtccaga  33840
agtgggaggt gggcagctgg cagtcaccag ggtcccaggc cctgccctcc tgtgtgccgt  33900
gccatgctta gcacctggct ttcatctgag tctcatggtc catgaaggtt gctcaagctc  33960
tagctattat ccccatgttc caggcagaaa gaagaaagtt ggaggaacgg accaaagggt  34020
cctggctgaa tgggcacctc cttaagagtt ttccaggaat caccacccaa cgacttccac  34080
tcacctctcg atggccaccc cattagcaag agaatcagag cttgatggca ggtcccattt  34140
ggtccccaca acataatagg acttctgtta aggaaggacg ggagaatgga gactgcatag  34200
gcaactagct gtccctgcca aggcccacat ttaaaatgat tgtaattgta aaggaagttg  34260
taaagaaatg tctatatagg tataagttcc atttggcttc ttacgagctt ccaaatgttc  34320
tccgtgtgtg taaactgagt cttgaaagag gggaagaggg ttaccgagga caagagtgag  34380
tgggaggcga cccaggtgga ggcagtgtga gtgtggggcg gcaggttgga ggaagagcag  34440
gcatgcaacg gaagcctctt accagatgct cacctcagag ttggcatttc tcacaagaca  34500
cactcctaga aggggactgt gaagacaaag atacaaatgc ttttagagaa aggttgctgc  34560
caggaccatg tgagggtgcc catctcacca aacctcccac attgtgcact gtcatttgaa  34620
aaatactttg tcagtttgac aggtggaaat atcttgaatt tgttgatgaa actaaacatt  34680
ttaaaaagca tttttggcca ctgacttttc ttcttttgta acacgaattg cctggtagta  34740
tctttccatc gttttcctgt cgggtttttg tggtctattg gtttacgcag caaatattta  34800
ctgagtgctt ggtatgtgcc gggaactctt cccggggctg gagacacaac agtgaacaaa  34860
cacagagctt ccgccctcca gggagctgat attctgatga gaggagatag tgaaggtaga  34920
aaccaggcca agatttgtaa aagctcttag tagatttagg atggtagtgc ttggtcacgc  34980
agtctctcca gctcgtcact tgctttgtgg ttttatttgt attgcaatct gtcttagctt  35040
ctcaagcatt cagctttcca ttttagcata gttttaggtt tacggaaaag ttgtagacag  35100
tacagagaga tcccacacac ccttcacctg gcctcccctg atgttagcgg tttacataac  35160
tagggtacgt tagtcaaaac tgagaaatta aattggtaca acactattaa ctaagttacg  35220
gatctcgttt ggattccatc agtttttcca cgaatgtcct ttttctctgt tgcaggatcc  35280
aatccaggat gctatgttgc gcttagggat ttctttattt tcatgtagta aaatctattg  35340
atttattgct cattttgttc ttagagagtc atttcctata ctgagacatg ataagatctc  35400
aacctatatt tcttctagct ttttatggtt tctttgcctt tttttttttt tttttttttt  35460
ttttagtcag agtctcactc tgtccccagg ctggagtgca gtggtgcgat ctcagctccc  35520
tgcaacctcc gcctcccggg ttcaagcaat tctgcagcct cagcctcctg agtagctggg  35580
actacaggcg agcaccacca cactcagcta atttttgtat tttttagtag agacggggtt  35640
```

-continued

```
tcgccatgtt ggccaggctg gtctcaaact cctgacctca ggtgatgtgc ccaccttggc  35700
ctcccaaagt gctgggatta caggcatgaa ctactgtgcc cagctggttt catttttcaa  35760
agacttattt atttctttaa accttttgga atttattttg gtgtaagcat ctaacatcta  35820
ttttttccaa accgttggtc agctgcacag cattctataa tgaatccttc gtttcctcac  35880
tgatttgtga aacaactttt atcaagtacg aaacacttag aggtgctagt ttctgtttct  35940
aggctacagc ttacatggac ttttccatcg actgctgtgt cagtatcaca gtttgacagt  36000
tacttttttt tttttttga gacggtgtct tgctctgccg cccaggctgg ggtgcagtgg  36060
cgcgatctcg gctcactgca agctccgccg ggttcacgcc attctcctgc ctcagcctcc  36120
tgagtagctg ggactacagg cacccgccac cgtgcccagc taattttttg tatttttagt  36180
agagacgggg tttcaccgtg gactcgatct ccgacctcgt gatccgcccg ccttggcctc  36240
ccaaagtgct gggattacag gcgtgagcca ccgtttttta tctagtagga aagactcctc  36300
cacctttagc tttataataa aatatgttac taagaataat gagcccacct atgtgcgagg  36360
tcccgtgtta ggccccacag ataggacatg aacaaccaag tcccacctgc aaggcggcca  36420
ctatatgggg gaggcagaca ggtgagccag tgaccgcacg gtggtgtggc ggagcagcag  36480
cgacctacac acagaagggc cgcagggtct cgtggggcag tcagggaggg ctggacagag  36540
gaagaggtgc ttgatctgtg gtagatttga gtagttcacc agaccaagag gcaggcaggg  36600
cattccgggc agagggaaca gtgtagacaa atgcctggct ctggaaagta tgtggcacag  36660
tctgggggcg gcaggtgctg gcgctgtgga gtgtccatga tgtagtgggt gagactgcag  36720
aggaggctgg cctgaggaag gcccgaccac caaaggagat gtccagatga ccccaaggcc  36780
acaaccccca gggccctcct gtcctgggct ctggaatttt tcaattgctg attctcttcc  36840
taggaacatg ttcccagcca acctagtaga agccacattc aaacaggtga gtgagtctct  36900
gggcagtgga ggggagggaa ggggcagcag gcaggagggc aggcagcagg gctagtggca  36960
tggctgggaa gtgacaggtg tgctggccag tcacgctgtc tgctggaggt gggatgctag  37020
aggggagggt acgctgggga acctagatcc ttagagaccc ccatggccac atccctgtcc  37080
tgggttccag ttttcatgat gaaaaagtgt gggggtggag agaagccttc actgagtgcc  37140
tgctctgctt ccacatacac catctcgccc atccacacag taactcggca ctgaggtagg  37200
atgagcccca cttcctgaag aggaaactga ggctccgagg agtcaatgat ttgcccaagg  37260
ttataccact agtaaatgac aaagccagta ggtaaaccca ggcctatctt cttagcctgt  37320
tttctctttc tttttaaagt aatcattttt cccctaacaa gaataataat gatgttcact  37380
gtagaaaatt aggaaaatac caaacaatat aaagtagaaa acaaaaaatca tctctagttc  37440
tagtacatag tccctggtag cagaggatat atttctggtc tttttcttc tgcttatttt  37500
taaataatat tataatcata gtgcatatac agttttcatc ttgctttttt tcacttccat  37560
tatatcctga gcattttccc cggttatgaa atatttctta aaagtacaat gtttagtggt  37620
actacaatgg cctgtgataa ggctgcgctg taatttattt ccccactcccc ctttcagtgt  37680
tcccttaggt tgttttcaaa gtttttcctt cgtcgaaatt gtggtgaatg tccttgtgct  37740
cagtctttgc ctgccctttg aataatttcc aattcttttt ccctttctaa actgtcagct  37800
ggttggttga cttaatccag caagggtttc ctgaacccct ttcctgggct gggccctgtg  37860
ttgagcctgg ggacacaaag gaagtggctg aggtatagag aggaggcttc tgaataggga  37920
gctgtgaaag ctttggcata tcgccgcgtc tctcctgaca tccatgaaat aagccagatt  37980
gtgaagggga ctgaatgcta ggctagggag tttctattgt aattgggaat cattgagggt  38040
```

-continued

```
gtgagagata aagagaaaga atgttgctct actctgtaac tctctggaat gccctttctc  38100
ttttggcaaa ctcctaccca tccttcagga ctcaagtcaa atgtcccctt ctttgtgaag  38160
ctaactcttt cagccaatta gtcactccct ccgcaaggca gaaatcatgt caggttcatt  38220
tgtgtatctc cagcaaccag cacagagtgt tcaacgtgat gatgacgatg atggtagcag  38280
taatgcttcc atggggctta acatgtacca ggaactgttg taagcacttt atatacatcg  38340
tctcatttca tttcatgcag tagatgctat cacggtccca ttttacagag gaggaaaagg  38400
aagcagagac ttcaggtctc atatgtttcc tgagtggttg gccttatcga tgcagtgatg  38460
tttgagggga gaggaggctc cctttttggg ctcccagtac ctgagggatg atggggtgag  38520
acccatgaat gctctggggg cagagaggga aaggtacgtg gctcaggaag gtcattttct  38580
tgtgcatggg cttcatctca ttaacaaggc ttggggcagg ctatgcttct tcaaaaagaa  38640
ggtccaagtt tccacctggt gggcagcagg gccagcaggc caccaggtgg atggatactg  38700
gatgattggg aggggacaga tgggtggata aagggttact tgggtggata aggggctggg  38760
caggcagtta agagggaccc agatggggtg atgaggtata gaagtaagaa gaggaatgaa  38820
ggcaggaggc agcgtggctg ggtggtgtgg tggtagagga aggagttgca gctttctttg  38880
ggtaaaatat tgatagcaat ccctgctctg cctgcctcac agggttactg tcaatcaaat  38940
aggataggaa tggatacaaa tgtgccttca agatgctatt attgttgtcg ttaatattag  39000
taacaaccct tggccctgac ttctctctgg gtggggtgtc acccaccagt accgcaccaa  39060
gaccacccca gttgtcaagt cccccaaggt ggcaccagag gaggcccctc ctcggcggat  39120
cctcatctac ggggtccagg aggagaatgg ctcccatgtg cagaacttcg ccctggacct  39180
gaccccgccg cccgaggtcg tttacaagtc agagccgggc accagcgatg gcatgaatgt  39240
gctgggcatc gtcttcttct ctgccaccat gggtatgtgc tgcccacctg cccagcagtg  39300
ccgtggagcc gggcccccag cccctcccag cagcctgctc ctccacctct tactgaggtc  39360
tggggagaat gctggagagg tttactgtga aaaactggaa atattcacca cacctgttta  39420
tttaaatcct tcgcctcccc accccacccc aggggcttcc ccctggcacc tccccctcag  39480
gcccgtctgg gccatttctt aggcccgcag ctggcatccc tgccacaccc ttccctttgc  39540
tgccctcctc tgggatgcca ggcccctcac ctatgcaagc cccttggagg cccgcacctt  39600
ggtttttaaa ttttgtgtta tttttcttaa agatgggtcc caaattatac aagcttcaga  39660
ccccacaaag cctgtggaaa tgtcctgcct gccatccccg actcctccac tgggttttct  39720
tgtcaaggaa aagacctcac caacctcgtt catgcaaaaa ctctaggggt gactttctac  39780
ctcgtcctct gccttggccc ccacctttgc atccggtcgg gtctgccccc aaagtcccct  39840
ccaagccgtg cgtttccttc taccccgcgt cactgcccgg gtcaaggccg tgtggtctct  39900
cgcctggttc ctgtgaaagc tgcctagaaa acttccacgg ctgtccctgc tggtgtgtcc  39960
agctcaggag gtcacaagtc tgaccgtgct ctgcccattg cccctggaaa ggggccgaac  40020
ccctagtgcc ggctgaaaag ccccgtgaga ctggcccgtg tgctcctctc cgcacaaccc  40080
tcagcccggc tgctcttgcc actccccctc cacgtttgtc atcttcaggg tgctccccac  40140
aagtgccatg ccctcaggag agtcctccgc agactaggcc gagtgccccg agctacactg  40200
cctggttact ctgtgagcac tagactcgat tgcaaggata tcattgcttg ctgtctgcac  40260
agccatgacc agccccatac aggctgacgg gcttgtctcc atccacccca gagcccaccg  40320
ctgccgtggc tacagcaggc actcagcaga cctggtaggg agatgggtgg acggctgggt  40380
```

-continued

```
gacaatgggt aatggagctc ttctcatctg ggccaaaacg ccaggtgtgc agaggggccg  40440
gggcctcggt gacccaagtg tgtgaaacga aaatgtctga aagtgcctct cggcacatct  40500
gacaagcagt ccccaaactc agcctttctc agggctggga acataagaga agggcatcta  40560
ctggcagaac aaaagaaccg gagacccttg gactcaactc gctgagcgtt cgctgcgcat  40620
gtgtaactgt ccgtgcatct gtgaacattt gtgtgagtgt actgaggcag gtcgtatgag  40680
ggtaccgagg cagggcgtgt gagtgtactg aggtgggaca tgtgagtgta ccaagacaaa  40740
gagtgtgagt gtaccgaggc gggcgtgtga gtgtactgag tgtgcgtgtg agtgtaccga  40800
ggcggtgtgt aagtgtacca aggtagggtg tgtgagtgta ccgaggcagg gtgtgtgagt  40860
gtactgaggc agggtgtatg agtgtactga cactgtgtga gtgtaccaag ctggtgtgag  40920
tgtaccgaga catggtttgt gagtgtacca agatgaggag tgtgagtgta ccgaggcaag  40980
gtgtgtgagt gtactgaggt ggggtgtgtg agtgtactga ggcgggttgt gtgagtgtac  41040
cgagtaggca tgggtgtacc gaggcagggt gagtgagtgt gacgagtcag ggtgagtgta  41100
ctgaggcagg gtgtgtgagt gtaccgaggt ggtgtgtgtg ggtgtttcga ggtggtgtga  41160
gtgtaccgtt gtgagatgtg tgagtgtcct gaggcagtgt gagtgtaaca aggcagtgtg  41220
tgtgagtgta atggggcagt gtgtgtgagt gtaccaaagc ggggtgtgcg agtgtaccga  41280
ggaggggtgt gtgagtgtac cgaggtgggg tgtgcgagtg taccgaggtg gggtgtgcga  41340
gtgtaccgag gtggggtgtg tgagtgtacc gaggcagtgc gtgtgggtat gtgagtgtac  41400
caaggcagtg tgagagtacc aagacgattt gtgtgagtgt tccgaggcag ggtgtgtaag  41460
tgtactgagg cggggtgtgt gagtgtactg cggcagtgtg tgtgagtgta acgaggtggt  41520
gtgtgtgagt gtaccaaggt ggtgtgtgtg agtgtaccga ggcgggtttt gtgaatgtac  41580
caaggtgggg tgtgtgagtg gacaaaggca gggtatctga gtggactgag gtggtgtgtg  41640
tgagtggacc aaggtgcggt gtgggagtgt accggtgcag ggtgtgtgag tggactgagg  41700
tggggtgtgt gaatgtattg aggcagtctg agtgtaccaa ggcaaagtgt gtgagtgtac  41760
tgaggcgggg tatggcagtg taccgaggtg atgtgagtgt actgaggcgg gtgtgtgagc  41820
gtactgaagc aaagtgtgtg agtataccaa ggcagtgtgt gagtgtacca aggcaatgtg  41880
tgtgagtgta ccgaggtggt atgtatgagt gtacacaggc aaggcatgtg agtgtaccga  41940
ggcaagtcgt gtgagtgtac cgaggaaagg tgtgtgagtg taccgagacg ggttgtgtga  42000
gtgtaccgag gcaggttgtg tgagtgtact gaggtggtat gtgtatgtgt attgaggcag  42060
tgtgtgtgag tataccaagg ttgggtgtgc gagtgtaccg aggtggtgtg tgtgaatgta  42120
ccgaggcagc gtttgtgagt gcaccaaggc agtgtgtatg agtggaccga ggtgggacgt  42180
gtgagtgtac tgaaacaaga cgtgtgagtg tactgaggcg gggtgtgtga gtgtaccgag  42240
gtggggcgtg tgagtgtact gagttgggtt gtgtgagtgt actgaggcgg ggtgtgtatg  42300
tgtactgagg cggtgtgtgt gagtgtacca aggttgggtg tgcaagtgta ccgaggcggt  42360
gcgtgtgagt gtagcgaggc aggttgtatg agtgtaccaa ggtggggtgt gtgagtatac  42420
caaggtgggg tgtgtgaatg tactgaggtg gtgtgtgtgg gtgtatgtgg atgtgtgagt  42480
gttctgaggc ggggtgtatg agtgtgtcga ggtggtgtat gtgaaggtat caaggtgggg  42540
gtgtgtgagt gtacagagag gcaaggtgtg tgtgtaccaa ggtggtgtga gtgtaccaag  42600
acaaggtgtg tgagtgtact cagatggagt gtgtgagtgt actgagatgg tgtgagtata  42660
acgaggtggt gtggtgtgtg aatgtacaga ggcatggttt ctgagtgtac tgagttgggg  42720
tgtgtgaatg taccaaggca atgcgagtgt accaaggtgg tatgtgtgag tgtactgagg  42780
```

```
cagggtgtgt gagtgtacca aggtggggtg tgtaagtgta ccgagatggt gtgtgtgtgt  42840
actgagacag ggtgtgtgcc aaggtaaggt gtgtgtgtaa caaggagggg tgtgagtgta  42900
ccgaggtggt gtgtgtgagt gtaccgaggc agtgtgagtg tactgaggca aggtgtgtga  42960
gtgtactcag acggggtgtg tgagtgtacc aaggtggtgt gagtatactg aggcaatggg  43020
tatgagtgta ctgaggtggt atgtgtcagt gtaccgaggc aaagtgaggg tattgtggtg  43080
gggtgtgtga gtgtaccaag gtggtgtgag tgagtgtact gaggcggttg agtgtactga  43140
ggcgaggtgt gtgagtgtac cgaggcaggt tgtgtgagta taccgaggcg ggctgtgtga  43200
gcgtactgag gtggtgtgtg tcagtctatc aaggcagggt atgtgtgtgt accgaggcgg  43260
tatgtgaggt actgaggcag tgtgagcgta ccgaggtggt gtgtgtcagt ctatcaaggc  43320
ggggtatgtg tgtgtaccga gacggtatgt gaggtactga ggcagtgtga gtgtaccgag  43380
gcggtgtgtg agtgtactga ggcggtgtgt atgagtgtac caaggcaggt tatgtgagtg  43440
taccaagact ctgtgagtgt accgaggcag cgtgtgtctg taccgagatg gtatgtgtga  43500
gcctaccgag gcggtatgtg tgcatgtacc gaggcggggt gtgtgagtgt acagaggtgg  43560
gttgtgagtg tacagaggca gggtgtgagt gttttgaggc agtataagtg taatgagagg  43620
tggtgtgtga gtgcgaggca ggatgagtgt actgaggcag ggtatgtgag tgtaccaagg  43680
cagtgtgagt gtaatgaggt ggaatgagtg tactacggtg gtgtgggtgt accgaggcag  43740
tgtgagtgta atgaggcaga gtgtgtaagt gtaccaaggc ggtgtgagtg taccaaggca  43800
gggtgtgtga gtgtactgaa gcaggttgtg tgactgtacc gaagaaagtt gtgtgagtgt  43860
actgaggcaa tgtgagtgta tcgaggcggt atgtgtgagt gtaccgaggc cagttatgtg  43920
agtgtactga ggtggtatga gtgtactcag gcagagtgag tgtaccgagg tggtgtgtgt  43980
gaacgtactg aggtggtatg tgtgagtgta ctgaggcggt gtgtatgtgt gtaccgaggc  44040
agggtgtgtg agtatgctga ggtggatggt gtgagtgtac tgaggcaggg catatgagtg  44100
ttctgaggca gtttgagtgt aacaagggtg atgtgtgaat gcattgaggc agggtgagtg  44160
taccaaggca gggtgtgtga gtgtactgag gcggtgtgag tgtaacaagg tggagtgtgt  44220
gagtgtacca aggtggtgtg accgtatgtg tgtaccaagg tggggtgtgt gagtgtagca  44280
aggcgggttt tggtacgagt ggagtgtgtg tgtgtaccga gacagggtgt gtgagcctac  44340
caaggcagtg tgagtgtacc gaggcagggt gagtatactg aggcggggca tgtgagtgta  44400
ccaaggtggg gcatgtttgt gtattgaggc agtgcatgtg agtgtacaga ggcggggtgt  44460
gtgagtttac caagacgtgg tgtgtgtact gaggtgtgag tgtaccgagg caaagtgagt  44520
gtaccaaggt agggtgtgtg agtgtaccaa ggcaaaatgt gtgagtgtac ggaggcaggg  44580
tatgtgagtg taccgaggca gggtttgtga gtgtaccgag gtggtgtgag tgtaccgagt  44640
tgtggtgtgt gagtgtaccg aggcatggtg tgtgagtgta ccgaggtggg gtgagtatac  44700
caaggtgggg gtgtgtgagt gtattgaagc aagggtgtgt gagtgtaccg atgcagtatt  44760
tgtgatagta ccaaggtggg ttgtgtgaat gtactgaggc ggagtgtgtg agtgtactga  44820
ggcggtgtgt gtgagtgtac tgaggtgctg tgtgtgagtg taccaaggca ctgtgtgtga  44880
ctgtaccaag gcaggtggtg tgggtgtact gtggtgggtt gtatgagtgt actgaggcag  44940
agcgagtgta ctgaggtggg atgtgtgagt gcttggaggc agggtttgtg agtgtaccga  45000
ggcgaggtgt ttgagtgtac cgaggcagta tgtgtgagtg tgccaaggtg gtgtgtgtga  45060
ttgtaccaag gcgggttttg tgattgtacc aaggcagggt gtgtgagtgt accgaggtgg  45120
```

ggtgtgtgag tgtactgagg caggttctga gtgtgccaag gcactgtgtg tgagtgtacc 45180
gaggtggtgt gtgtgattgt accaaggtgg gttgtgtgag tgttccgagg cagtgtgtgt 45240
gagtgtaccg agggggtgtg tgtgagtaca cggaggcagg ttgtgtgagt gcaccaaggc 45300
agtgtgtgag ggtaccgagg tgggttgtgt gagtgtacca aggcggggtg tgtgagtgta 45360
ccgagaaaaa atgagtgtac cgaggcaggg tgcgtgagtg tactgaggca gggtgtgtga 45420
atgttctgag gtggtatctg tgagtgtact gaggtggggc atgtgagtct accaaggcgg 45480
ggcgtgtagg tgtactgagg cgggttctgt gagtgtgccg aggcagtgtg tgtgagcgta 45540
ctgaggcagt gcgtgtgatt gtaccgaggc aggttgagtg caccaagaca gtgtgtgtga 45600
gggtaccaag gtgggttgtg tgagtgtact gaggcggggt gtgtgagtgt accgaggcag 45660
gttatgtgag tgtaccgagg tggtgtatgt gagtgtactg agggggtgtg tgtgagtgta 45720
ccgaggcagg tcgtgtgagt gtatcgaggc aaagtgagcg tactgaggca gggtgtgtga 45780
gtgttctgag gtggtatctg tgagtgtatt gaggcagggt gtgtcaatgt tctgaggcag 45840
tatctgtgag tgtaccaagg ctgggtgtgt gaatgtatca aggcggggta tgtgagtgta 45900
ccaaggcact gtgtgtgagt gtattgaggc ggtgtgtgtg tgtactgagg cagtgtgtgt 45960
ggatgtgtga gtgtaccgaa gtggtatgtg tactgaagtg gtgtgtaagt ttaccaaggc 46020
agggtgtgtg agtgtatcga agtggagtgt gtgagtgtac tgaggcatgg ggtgtgagtg 46080
tactgagctg gggtttatgt gcgtgtgagt gtaccgaggt ggagtgtgtg agtgtgctaa 46140
ggtggggtgt gtaattgtaa tgaagcaagg tgtgtgagtg taccgaggca gggtgtgtga 46200
gtgtaccgag gcgaggcgtg tgagtgtacc taggcgggat gtgtgagtgt accaaggtgg 46260
tgtgagtgta ctgagacagg gtgtgtgagt gtaccaagat ggggtgagtt taccgagaca 46320
gtgtgagtgt accgagtcgg tgtgtgtgag tgtacagatg catggtttga gtgtaccaag 46380
gcagggtgtg tgagtgtatc gaggctaggc gcgtgaaagt aacaacgtgg ggcatgtggg 46440
tgtaccgagg tggtgtgtgt gagtgtacca aggcggggtg aatgtactga ggtggggtgt 46500
gtgagtgtaa tgaggtgggg gggtgtgagc ataccaaggc agtgtgagtg tactgaggca 46560
gttgagtgta ccgaggcgag ttgtgtgagt gtactgaggt ggagtgagtg tactgaggcg 46620
gggtgtgtgt gtaccaaggt ggtgtgtgtg aatgcaccga ggtggtgtga ctgtaccaag 46680
gcagtttgtg tgagtgtacc gaggcgggtt gtgtgagtgt accgaggcga tgtgaatgta 46740
ccaaggtggt gtgagtgtac tgaggtggtg tgtgtgagtg taccgaggca gtgtgtgtga 46800
gtgtaccaag tcggggtgaa tgtaccgagg tggggtgtgt gagtgtaaca aggtggagtg 46860
agtgtaccga ggcagttgag tgtaccgagg caagttgtgt gtgtgtaccg aggcagggtg 46920
tgtgagtgta ttgagctggg gtgtgtgagt gtacctaggc aggttgtgtg agtgtactga 46980
ggcgggttta agtgtaccaa ggcagtgtgt gtgtaacgag gcggggtgtg tgagtgtatc 47040
gaggcagggt gagtgtacca aggcgagttg agtgtaccga ggcggtgtga gtgtaacgag 47100
gcagagtgtg tgagtgtacc gaggcggtgt gaatgtactg aggcaaggtg tgtgagtgta 47160
ccaaggcggg gtgtgtgagt gtaccaaggc agggtgtgtg agtgtaccaa ggcagggtgt 47220
ggcttactgt gtatgctcat gcctttatgt gcccacatct gccagtgcct gtgtctgtgt 47280
gcacgtgcat ctctgtgtcc ctgcatcagt gtgtgcctgg cctctccgtg cctgtgtctg 47340
tgtgcacctg tgtccctgtg ttcccccatc agcatgcgcc tggcttacct gtgcctgtgt 47400
ctatgtgcac ctgcgtctgt gtgtgctcat gcctgcgtgt gcccacatct gcctgtgctc 47460
atgtctgggt gcagctgcat tcctgtgtcc ccgcatcagc gtgtgcctgg tctttccgtg 47520

-continued cctgtgtctg tgtgcacctg cttctgtgtg tgcctgtgcc tgtcagtgtc cacatctgcc 47580
ggtgcctgtg cctgttggtg cagataccag tgtctgcccg cgtgtgtgag tgagcacact 47640
agcacagcgg ctccgagcag ggctttcttt ggttccctca acccagcctc ctttccccac 47700
cccatccctg ggatgtggct ggtgctaagg tcctgctggc cctgccgtga gggagccccc 47760
gtgccacact agggttccat gcacactggc tcccagcagc cagtcctcgg atgcccctgg 47820
gaaaatccaa atgggcctga ggaggggcag gaagcccgtg cgtggtggtg gtggagcccg 47880
gggagggcgg agccggcagg ggagtctggg tctgcatcag ccaggcggca ggaagacagg 47940
cgggcggggt aggcccaggg tcacctccaa ctccagcctc tcctacccac cctggcaggg 48000
ccctcacctc actccgtcac cacggggtag ctgctccatg gactgtgtgg ctcaggcttc 48060
tcaggacagg gaaagagccc ttctctggtg tcccacaggc cagggtttga atcccaccct 48120
gcctccctag ctgagcccca gcaccatgac agtgggcctc atgagggcag ctgtagagag 48180
tgctctgctc cccacgtcgg tctcaccagg aggtagggca gccactcagt ccctgtttca 48240
ggactggcct gacagagctc accccacgga gccgttccca caccaccctt tcctggtgtg 48300
tgcgagctgg ggaggaaggc ctagaatgcc gggggaggcg ccaggagcat caggaaaggc 48360
cctagtcctc actcaccatt gaccactgtg cgtctaacat gctccagcta aggagatgca 48420
gttcttgctc tcgctgagct aacctcgcag aggagacggg aaaaaaccca gacagttatg 48480
ttgtaatagg ccctaagagg tgagatattg aagaataaat gggagtttgc aaaggggatc 48540
ggggatggct tccaagctgt ttggagagcg ggcagccagt gcctggggca ctgtgtaaac 48600
ggcttgcgca aaggccctga ggcagtgaag agctggactc cctccttcca gaaacttaaa 48660
gaaggccagt ggtgccaggg cacagtgaga tgggcaggag caggagggag aggcaggcag 48720
ggcccactcg agtggggctg aggcatcgag ctgggtgagg cagcggggag cttgtcatgg 48780
cctaagcgca cagcgaagcc aggggtgcac ttggcaggga gcacttttat cctgaggagg 48840
tgacattggc tgctgcgtgg aggaaggtga gagaggagga cgtgagagca ctgtgggatc 48900
ggtagtagag tggaggagga gagagggaga gagagagtgg ggggagtggg gggagtgctg 48960
gagcatcaag gctgctggga agccagccat gctgagaccc atgtgggcct gtgggtctgt 49020
ccctgcttta ccacagcact gtgtccctga cccgcaggca tcatgctggg ccgcatgggt 49080
gacagcgggg ccccccctggt cagcttctgc cagtgcctca atgagtcggt catgaagatc 49140
gtggcggtgg ctgtgtggta agcctcctca tttacccacc tcaccccggc cagccctggg 49200
tggatggagg gaagacaaga ccccaccctc ttctcccgta aagtgagcag aaagctgtgc 49260
ccaggctcag ccctgggccg gggcctccgg agctacatgt gtttccatgg gtcccccagc 49320
cccagccagg cctggctccg gccctgggcc tgccccttcc agcctggtct aagagctctg 49380
cccggctctg ctgctctcct gggctcagtt tctccatcac atggagcctt atcagctcag 49440
cttttggaga aaggaaagct ggcggtaagg actagcccac agttcagagt cctcggccca 49500
cagttcagag tccaggagct cagtggggaa cgcagaggga gggctgccca ggcgcactgt 49560
gtagactctg gcgttgttgg gcctgaaatg ggggcctcct gaaggcaggg cgggggaagg 49620
agtggcagag gttgtctgga gctggggcgg tggaagtaac ggtatgaagg acgccatgtg 49680
ctgagcctgg gccgggcacc ttggcagtct cgctctgtcc tcgcaggagc cccaggaagc 49740
tcagggggaa ggccgcgcag cgatgcgggg ctggggccgg ggtgtgtctg cctgcctggt 49800
tcctgagcct ggctgccccg ccgcccccag gtatttcccc ttcggcattg tgttcctcat 49860

-continued

```
tgcgggtaag atcctggaga tggacgaccc cagggccgtc ggcaagaagc tgggcttcta  49920
ctcagtcacc gtggtgtgcg ggctggtgct ccacgggctc tttatcctgc ccctgctcta  49980
cttcttcatc accaagaaga atcccatcgt cttcatccgt ggcatcctgc aggctctgct  50040
catcgcgctg gccacctcct ccaggtagcc ccggggacgg gcaggacggt ggggagctgg  50100
gaggggctga gccctgtccg tctgtccagc catcattggt tcatagccac agaaccacca  50160
aaacgccagt gtggcccacc tcacaaatgc ggggacggct ggtgctgggg taacaagact  50220
gacgtggggg acttttggcc tttgtcgagg cctctccttc ccccacggcc ccagtcctca  50280
agctcactga gtccgcatgg gggcggcctc gacgcgccag ggcagacagc acagtagagt  50340
cagtgggaaa tcacattggc aacgcactgc tgctgccttt tgccccacaa ggtgcttctc  50400
ctggagtcgg gccctgtgtt gctctaggag ctcggcctgt ccactgccgc tgggatgtcc  50460
tggctgggtg ccctgtcaca accttggcag tgtccctaga cctcagggac ttgagccatg  50520
gctctgtcac tcactcgctg tgcctgggca ttgctttcct catgcacaga ctgggggaga  50580
ctccagcttc cagctcacag ggttgcagtg gaggtcgagc ccctccttgc caggctgggc  50640
caggtgaacc agcacttggc cttaaggatc ccaaacctca gcccagtgca gagacctcag  50700
gaatttagag ttgtgcaaac catgtcgttg gtggaggggg caggaaggaa gtggtccctt  50760
atggagcatc tagtgctgtg aaggcagttt ggctctcccc atggcaagtg tctgagctcc  50820
acattaaggg agtcgcagga acttaagcca catctttctg gcactgaagg cctcactctt  50880
ccctctagcc ctcacttggg tctcagtttt tccatctgta aaatgccctg caggcctctg  50940
tacccagcag tcatatgaca cccacccctg gcagcagatg cacctcctgc aggattcagg  51000
agcagacccc agtgaagaaa agcccaggag ccattgccag gaacaccctc ccgcagatag  51060
ggggtcagag ggcaggacaa agccccaaac atgccagctc ccatgccagg ggccaagcca  51120
gccagagcca gcagcccccct ggccatctcc tgccagcagg aaccgcagcc tcaagcccag  51180
caggtctgga gctcctgaga ggctctggcg agtagaaccg gccttccagg cagaggcccg  51240
ggggagagga agacacaggg gccacaccgg cctgttttag tcccagcact gccactggga  51300
actctcatga caaacatagt aataataata gtcatggtca ccattgactg agtgggtaca  51360
atgggccagg tgctgtccaa gcccgtagtc gtttaatcct cctagtagct ctgtgaccca  51420
ggtctttttg ggacaaagat gctgaggcac agggttcagg aacttgccag gaccacttga  51480
caggaggctg gaatctaagc ccagacagcc tggcccaggg ccctgctgct cagacctcca  51540
tatccctcgg cacagcagtg tgacatgggt cagccccgcc ctctgggcgt cagcttcctc  51600
atctgtaaaa tgcacccaaa cacctccctc ataggaagaa ccaagtgaga gcactgcagt  51660
gcccgcggtc cttacctcct gccggagcag cgctgcagag gcacaaacac tcctggcggg  51720
gtggctgcct ggggaggggt gagcttcccg acagaggccc cagccatcct ggaggagggt  51780
gctgggcaga caccggcccc tctaaccgta gctcagccac actgcccatc accttcaagt  51840
gcctgctgga gaacaaccac atcgaccggc gcatcgctcg cttcgtgctg cccgtgggtg  51900
ccaccatcaa catggacggc actgcgctct acgaggctgt ggccgccatc ttcatcgccc  51960
aggtcaacaa ctacgagctg gactttggcc agatcatcac catcaggtgc accctgacac  52020
tgcacctggg tggatggggc gggggctggg ggccttgggg attcccaggc tcccagactt  52080
gaggggtatc tgaagcgagc gagcctgggc tcggagcaca gcaggcagag ggccagggct  52140
gggagctccg agcctggagg acagcccggg agggagggca ttgctggtgg ccacagggcg  52200
agcggaggcc agggacagga ctcaggacct tggagaggcc gcccgtgtgg caggagccaa  52260
```

cgaaggggtg ctgggatgcg gctgaggctg acggaggcct cacagcccag ccaagcacac 52320
aggtctgacc ctggaggcca ggccccagag gcaggcaggc agagccatgt ggtggtcagt 52380
cagagtccct gggcagcccc atagcaatat agcttcctgg aacccacaga ggcacagctc 52440
cagacacagg tgtttgcaca gttcccaggg attctcctga ggccaggaat gggggtccat 52500
ggggcttcag gactgtgagg agggacttga ccccgagagc tccctggtgt ggcattccta 52560
cccaccccc gcaccaaatg gctgtcccag aggccctgac actcaacctc ttccttggag 52620
ccagaccctg acaatgcacc ctgcccctcc tgctgctcct cttccccttc ccaccccctg 52680
cagtatcaca gccactgcag ccagcattgg ggcagctggc atcccccagg ccggcctcgt 52740
caccatggtc atcgtgctca cctccgtggg actgcccacc gatgacatca ccctcatcat 52800
tgccgttgac tgggctctgt gagtggactt tgcctctagc tctagccctc tgggaggggc 52860
tgacttcagg gtcagcaggg atcagggtga gcggctgagt cccttcccca gggtagaagg 52920
ctggggactg ccccgcttgg cactgtggga gtgccctact cattagcaca ggcctggctg 52980
cataatttgt ggggtccagt gttcaaaaat gaaaatgtgg aacccagtcc aaaaactgta 53040
aaggccaggc atgatgactc acgcctatat gtcccagaac tttgagaggc catggcagga 53100
gcattccttg agcccaggaa ttccagagcc cagcctgggc aacacagtaa aatccccatc 53160
tctactaaaa attagaaaag aaaaaattag ctgggactgg tgacatgtgc ctgtaatccc 53220
agctattcag gtggctgagg cacgagaatt acctgaacct gggagatgga ggtttcagta 53280
agccgagatg gcgccactgc actccagcct gagtgacaga gcaagactct gtctcaaaaa 53340
acaaacaaac aaacaaacaa aaaacaaacc tataaagaat ttcaagacag aaacagcaga 53400
ggattaaacc aaacctaacc cttctaagca tggggacctg tggaacccac agctgcatgc 53460
caagaagctg cttcaatgat gccaaagggt gggcttggga ggagccagga agccatctgg 53520
ctgcaggctt tgcatgacag ctggtcaccg gccgtgctgt actgtgctgg gttgagcact 53580
gccctcttcc agctcccctt caagtgccca ccactcaccc ccaaccttgg ctcaccaggg 53640
accgtttccg caccatgatt aacgtgctgg gtgatgcgct ggcagcgggg atcatggccc 53700
atatatgtcg gaaggatttt gcccgggaca caggcaccga ggtgagagca gtgagatcca 53760
gaggctgcca ggagggtgga gccacgcagg gtgggcaggg caccagatct tccaccaacc 53820
agctcggcag cctccagcca atccctccct ccatgcctct gggcctcggt ctcctcatcc 53880
gttacagaat gactgattcc tctaacatct atttattgag cacccgctgt ggctggcgct 53940
gatatagaca caggaggaac agtagaacaa gatatgataa aattccccgc cctcgtgtcg 54000
ggatggtctg tccagtttag ccaacatgtg agcatttgta ggtctgtgca ggctgtgtgg 54060
gcttcaggct ccttctacag gcaaatggag aaggctgtcc ccacatcatg gggaagaagc 54120
tgaggtcagg caggggatcc accaattccc cagatggacc ctgtggatta agtcccctcc 54180
tctactaagc cagctccagt gggaggcagg acgcttggga acaggagccc agggaggccg 54240
tgacctgccg aggtcacaca gcgtgtctgc aggaaaatcc atcttgtggt tcctagccct 54300
gagctcattc tgccccactg gccctcagtc ctccctcgta tctaaccttg gtccctcctg 54360
ctgctacaaa gacctgtttc ccttcaccag aaactgctgc cctgcgagac caagccagtg 54420
agcctccagg agatcgtggc agcccagcag aatggctgtg tgaagagtgt agccgaggcc 54480
tccgagctca ccctgggccc cacctgcccc caccacgtcc ccgttcaagt ggagcaggat 54540
gaggagctgc ccgctgcgag tctgaaccac tgcaccatcc agatcagtga gctggagacc 54600

-continued

```
aatgtctgag cctgcggagc tgcaggggca ggcgaggcct ccaggggcag ggtcctgagg  54660
caggaactcg actctccaac cctcctgagc agccggcagg ggccaggatc acacattctt  54720
ctcacccttg agaggctgga attaaccccg cttgacggaa aatgtatctc agagaaggga  54780
aaggctgcat gggggagccc catctaggga gtgatgggcc cggcattgcc tgaggccccg  54840
ctgtgacagt ttccccggtg tgagcccggt gagggcggca ggcaggggtt atccggcccc  54900
actttctgga tgacagactt gaggctctga gagctgaaaa cacttgtcca aggtctcacg  54960
ttaaggtcaa gacactaact caaatctttc aagccccgcc tctcctcttg gaggacaggg  55020
cagcctgcag ctgtgtccag gcccaggccc caccccataa caggtggcct cagccacaca  55080
gttctcccca aggggagcag cccagggcca agccccgctg ccttccccag gccacagtgc  55140
gtccagtctc ctgtcctgcc acgtgtcttt tgcaaagctc cttggatgtg gagacagatg  55200
tctttactag agctgaaagg ccccccttgac acatccaggc caacctccca tggaataggt  55260
aggcaagcca ggactccggg aaggaggtgc agccaggatg ctctggtgga gctgccgatg  55320
gggccctggt gtcagaactc cccaaaggcc tgtgcgtcca agtggagtca ggttttctat  55380
tcctttctgt gtttgcaaat tcagtgttaa ctaaataaag gtattttgtt tttca       55435
```

<210> SEQ ID NO 1105
<211> LENGTH: 11704
<212> TYPE: DNA
<213> ORGANISM: Homo sapiens

<400> SEQUENCE: 1105

```
agacaggggt agtgcgaggc cgggcacagc cttcctgtgt ggttttaccg cccagagagc     60
gtcatggacc tgggtgagtg agcctcttca tgtgagaagg aacagtacca gggtcttgga    120
cacccagact gaccctgtgg aatgggggtg gaggatgcgg gtggagcgca taggggtgct    180
tcctggagaa atcagttctg atttggtggg cattggaagc tacttccaga gaatgccccc    240
tgctgtccca ggaggggtgc acctgccctt tcagacctgg agaaggggtc agcctttggt    300
gccagtgggg acaagggagg ggccgagatc atgtctttct aaaacagcag ggacataaga    360
gagtggcggg gctgggcttg gtggtctggc agaacctgtt ctcatcatga gggtgatagg    420
ttaggccctc tgggacctct ggggacaggt ttcaacagag aaattctccc tagagagctt    480
aggacctttt acccactctc tgattcccac ctttctcccc tgccaaatat tcatatacct    540
gtccacttgg ggtcatgagg agatgcaaat gaaacgtgac tgggttgtga gaatggtgcg    600
gtgcattgca aatgcaagct ctggttgctt tctctctgct gcacatccca cctgctttga    660
tctggctttg ctgttgcctc ttgcaagtta aggaacgggc aggcaacatg gaatgggatg    720
gcaaggggca ctcagcttgg agaaatcata gccaggcctt cagcacagcc cctgcccctg    780
agcaaacctc acgcactctg ccccggcaga taactctact ctttagaaag ccctttctca    840
ggtctaacct agaaggggtc aaggggaagc actgagggtg ttctgagtgg ttcatccagc    900
tccagacgcc ccctttataa atctcagctg tggagtcaga ccaggctgag gctaagaaga    960
ccaggttcct agatggcttg tctcaccagc aaacaatgca ccacggcggc ctcaaagccg   1020
caaagggttg gctttaaaaa gtgaaggttc cctggtgctg tcctcacacc cctcctcgcc   1080
acaccacagc ctccttgatt tcatctctta ctttcccgcc tgccctgaac gctggatctg   1140
gacccagcaa acagctgtga aagggttaaa gtggtcaccc cacccactga ctgtgaactc   1200
ctgaaaggca ggttcaggtg ctttgaggat gtgaggagaa aatgtctgcg gaatgaatga   1260
atacaccgta tcaagaactc cgtagagttt agtttttgaa aatctcttcc aaatgcctca   1320
```

-continued

```
tttcccagcc aatctaccct taaatcccac tcccctgcac cccctccacc accccccatc   1380
acaatcccac agtacagacg tcacccacag aagaccctgc tccagccttt catactggcc   1440
tccaggaagg aaaccaagca gtgcccagtg gtgtgctact gggcatttga aaagcagctc   1500
cccggggtgg agcactggta gctgactcca gggtggaggg aaagtcctga atttgtagtg   1560
cttgccaatt tccatggtgt aaattctccc accctggctg attgatttca agccatctac   1620
atgactgaac agggggttgg gaagatgtgc agagtgtctt accccagact aggtttaggg   1680
gtgctagact cctaggcttt gatgcaggga gagagggtaa tctctggtcc aggaagaagg   1740
gatattcttg ccacttcact caacttgaga gagccccaac ggtcaaaccc gaaatactgg   1800
taggagggga agccgctgac aagctttact caaaacgggc tctctgggcc gttgatgggg   1860
tgggtgggcc ttggaggatc tgttgttctg ctcttcatct gcccagcaag gagcaagagg   1920
tgggtgagga gggagggttt ctgttacaca aaatgaaaac tcccaagcag ggctgagctg   1980
gccttttca cggtttgaat gagcagctct gaggcaccct ccccaccttc gagcaatgag    2040
accgaagatc tttcataatt ctcaaaagca aagcaaggaa aaaatgaacc catgagagat   2100
gtgtgcctca cagctcggac ataaatggtg gcaaaggggg atgctgaagc taattcaggg   2160
ccagtttctt gcctgccaga aacttggctg gggaggagag gaacgctgca gcctggggtc   2220
gctgttggaa aaaatctctc ctctttgctt cggacattca ggcaactctc attgtttgag   2280
ggattcaggg atgaccagtc tggtggggag agtgacacat atgtcacaaa gccactgcaa   2340
cagaataaga tacagcattg accagggcaa gggcaagaca agaagggaat agtgaacctg   2400
ggtcagagag gtatttaagg tgggttttca agggtgtgta ggagttgtca agcccaacaa   2460
ggagctgcaa tgggcccagg atgtggcagg aatggcaaac tccattgcca tcagaggccg   2520
acaaggtaat agagggaatg ggcataaggt gcaggaagtg gaggggagta gagtgaccca   2580
gagggtgcat gccccaccta aaggcattca aatctattat ttcaaaaact ccatgctgac   2640
aagcagagtg tcctggggac taaggctgca gccgtgtaga tggtcagctg agacaacagt   2700
aacagagaca agaaagaagc aagcggaggg gagggtggag tagctggcca tgccaaggag   2760
gaagatgagg aggaaggacg caggcacagg agacccaatc cttaaaacgt ggtacggcat   2820
ccctaaggaa tttgaacttt atcctgaaaa caatggggac ccatcaaaga tttttatttt   2880
tcaagtaggt gaattaaagg atgagatttg tgttttggaa ggagttctgt ggcagcaaag   2940
aggcagcaaa gcccgtgtca gaacagaggt ggggccggct cttttggggg ccgggatgtt   3000
gggggatgga agcaggaagc actggtggcc agtggggcat ggggagcaaa gattcccctc   3060
atgctccgtg gagcgtccta gatgcagcag gctcatcaga aacacagcct gatgcagtag   3120
ccagagccca aaccttgcta tcctgttcaa atctcaggtc cctctcttag cagctgtgtg   3180
gccccaggca tttggcttaa tctctctggg cctctatttt ctggaatcta agatgaggat   3240
caccagggta gctcatgaga tgttatgagg gagagacaca tacagaccca gtggccgcac   3300
agaaggatgg ttaggagtgt ggttgctgga gttggagggt ttcaaagcct gctcccctgc   3360
tggccattgt gtgactctga gaaagttact tgctgtgttt cagtttctca ttggtaaatg   3420
gggataatag tagcgcctac ctcatggggc ttttgagagg atgaaatgag accatacatg   3480
cagacagtgt ggcacgcagt gagagctcag tgaatatgaa ttatctcatt ggatacagca   3540
gttgataaca tagaaaatgc aaggtctacc aggctctcac ccatccctgc ctactgtctg   3600
aaagtggatt ccccagatct ctagacctct caccacctcc ctgcttctcc tctgcctccc   3660
```

-continued

```
ttatccaaaa aaaaagagag agagagaaaa gttgtgttgg caggtgagga agttcaaaga   3720
ggaaaaagct tggggtcgct cttggggcga gctgattggg caactgtgat ttcctgggca   3780
gtctggagga cctggaaaaa tgtggggatg gaagttcatg gtttggagat gggggcagcc   3840
agccaataat tttctttcct ggatgggcag tctctcatgt tgggggctcc ggttggagtt   3900
ctagggaatt ttcatgatga tcattactga aaactcaaga actcagaaaa cacccaacat   3960
ctaggtcaac cactccttag ccccagagat tcccaacttc attggtctca ctgaagctgc   4020
tgcccaagac cagtttcttt atgactttgt aacagacagg gatgatctga ctcaaggcca   4080
ctgaccaggc tccctttgc cacatacaag agttccccta agtttccctg tgatgtttct    4140
tgaaagccac ctgttttgga cctacaagac ccttgctcat ccacctcctc caaaacacct   4200
ggaatgagaa atcacaggca cacacgccag cactccccca actcccctcc cctgacggga   4260
acagcaggag tgggacagcg tccgggagaa ggggttatca acagagttca acagaaacac   4320
agttcttgct cctcagatct cacccgttgt gacttatcaa aactttgagg tttctcattt   4380
ctccctgaca gtcagagcgg gctttctcta gagtaaccga aagacactta cgtgttttaa   4440
agaaacctcg agactcgacc tctagatgag tcagtggagg gcgggtggag cgttgaaccg   4500
tgaagagtgt ggttgggcgt aaacgtggac ttaaactcag gagctaaggg gtaattcagt   4560
gaaaaagggg aatgagcggt ggggagctct gttgcaacag ggtccaatcg cagcaggact   4620
acaaatgccc gagcgcaggc tggaacgag gggacagcgg ctgcctgtcc ccagaataga    4680
aaatgcagct aggaagccct ctttgagtgg acagcggagg actggactgc caggccaagc   4740
atcaggggct tcatcctcag ggccggttag agcccctgag gatttaggag gaaggtgagg   4800
tggggactgc catcagagct aagctttagg cagatgtgtc tagcagtagt gtgcaggact   4860
atttgctcaa ggcgggagaa atacctattt atttatgtag cccgatgcag tctctccttc   4920
ccggaggaac tcccaagccc agaatccctg gctttacaca atttccgggg aacacattaa   4980
ccaactgcaa cctgggtgcc atgcagggag gcttccagca ggtggtgctg tggccaagga   5040
cacggaagcg ctgggctctc actgcttccc cagcctccag gagaaggtgc cttaaacagg   5100
ttcccacgca tttcctggcg ctattgagct tggagctgcc aagggcctgc cttcacttgt   5160
ggcatcgcag ttactgactc tccagtgggc caggccctac ctagctggga cctgagggtc   5220
aggatacggg aagagggcta ctgccgccct gacttgtagg taagctaaaa catctaggca   5280
aattactctg tcaactgtcc tccctgctca gcctcaggaa gaaataagtt cctgctgggc   5340
cccaggctca gccacaaaac cagactgagc acatctgggc cttgtgctac accggggtcc   5400
ccatcagctg ctcagacccc aggaagcctc ctgacttcca gaacacgtcg cttcccaaag   5460
ctgaccctgt tccccctttc acctgccccc caagcctaag ttagaaaaca agttaaagga   5520
gagaaagtgt gtgcaggcac ttcagttaag caaaaaaata aagaagtcgt gacatcagga   5580
aagagcgtcc ttcccccaca ctgcaacagg acagcatccc ttctgtgtcc tctcgggcca   5640
tcttgatgcc ctctcccttg gaaaaaggac aggcattcgt ttacttgtca ttcatgtatt   5700
tattcatcat tcatgtattt atcattcata tattcatcag cacacaattg tggggcacct   5760
cctcaattct gggcctgcac aagataaaag ggaagggatc tctgtcccaa aggcaggcca   5820
agggtgtgcg cccagtggac caacagtcag tgctgaatga atgtcatttc agtgaggggg   5880
tgttgtggag ctggtggagc cctgaggcag tctccatcgc tgtggaccag taaggaacct   5940
catccctcta cccagcctgt gaggtcatcc tccttcctca gcccacctcc ctcaggagac   6000
actcaggctt ggcttcatgc acgtgtggct gcgcactcac ctggatgcca ggaaaatgct   6060
```

-continued

```
cctgggccag tggctaccag caccaaagca gggctggaaa cgtgtgcacc taccccacga   6120
cctcatagct ttgccgcctc atcccacatc aggtggagtg ggagggggca ctcagaccca   6180
ccaaccaagc tcagtcttga ggggtggtct gggctagaga agacttccca gctccaagaa   6240
gcagcccaga tgggccaaga caggggggtgg gaggggctgc cctgcattct gatgctgctt   6300
ctttccagga cctgggagtg gaggaggaca agaaggaggt gaggacagtg atgccgggca   6360
gcaggccagg tgttcaaagg cacaatctgg ttctgatgtt ctctttcagc aaacacagtg   6420
cctggagctt gggaggaaag ttcccaacag cgtctccccc tccactgctt tctttaataa   6480
caaagacttg tccctgccaa gcaataactt tctcgccttg tctcctacag ggaaaccaat   6540
gaaaagcgtg ctggtggtgg ctctccttgt cattttccag gtgaggttct ctgccaagga   6600
aagctctgtt cccttctcca cacggcctcc caagtcaggg gtttagtgga ggagctgggc   6660
atttgctaga agatacaaga cccagacata agcccgcctg ccactcatta agctaatggc   6720
tgccccctca ccatctgctg agtgaccctg gagagccaca gatgttctct ggacttcctt   6780
tactccattt aggttaaaac atgggggaaa ataacttacc accttcccta tcccacctcc   6840
aatctccctg cccaggagac agaaatatgg actctgagtt cttagagaga gaagagctgc   6900
aaaaagcaaa aaatgttact gggttttgtg cacgtgtgct gagaaaatca ccctggatct   6960
ggcgatcttg ttactatcct atcgccccaa agttgtctct ttccaacctt cacccaaagg   7020
cttccctcgc agcccccgtt ttctttggtg aaatagagac ccatccggcc tccctggcag   7080
gggagggaag agaggatggg gccctaggga tggggagagg ggtggatgag cacacacttt   7140
atagcaggcc tgaactcggc aggaacaaag accctcactt tacaaagttc tgtttctcca   7200
tccagaaaca gacagaaagt gtgcctcacc aagtgccaaa gttagaagaa actgtaactc   7260
gcagagtcaa ctttctccca tttgttagag gtgggagctc agagtagggg taggggagtc   7320
caactgaggc cagagctaga gaggcagtgc ttcagaattc ggctcatccc caggtctgga   7380
ggccagaggg gcagctttcc agaagctcag gccagaggca ggccccaagc tgggcactgt   7440
tcccaaaacc ccatcccaga ggccccccgg agcctgggct gcagcccata gcctggcccc   7500
cttccccatc accactccct cctctctctc ccctgtctcc aggactctgg ggggctgtat   7560
tgctggcagt ggaggctgga agggtgggaa ggggaggagg acagctgagg ctcattcttc   7620
cctttcactt ggggaggggg tgctcagata gggcaggatg tggtggggct gtgggctgca   7680
gaggcagtga ggctagggga gggagaatta taaaacagga acaaggttca aggggagaag   7740
ggaaggcagg actggatgat gcagagtgca cttcatagag gccgggagta ctgccctcca   7800
ggaaggctga gacccccctca tgtccaggga ccccgggtct aaggccttgg gccgtaacca   7860
tggctgggcc aaaggcagca gcctccttca gggctcccag gctgcagcca tgcccaggaa   7920
agggaagagg ggttgccact gacttttcgt ctcaggctag caatggccaa agaaaaggct   7980
cctggacatc attttgtcct caccatgttc ccaagcagga cagtgatgaa tccagaacct   8040
gggtgtgaaa aagagataga gacaagatgc ggtgaatccc tccagcataa atggatagaa   8100
acccaccgtc gctgagctgc tgaatctggt tcctggtgat agaaccatga gcctcgtgag   8160
gcaggtcctc cagcccagct ccctgccctg cacaaacccg tccatcgctg tgcgcagagg   8220
caggggcagg catggacccc ctccttcatt gataaaatca cagcaggctg ctgaaccttc   8280
acccgaccct gcagacggct aaaaaaagct ccagcagctg agtcctgctg attgggatct   8340
gccggaagag atgcgaggaa gagagaggca gagaggtggg gggagagggc gggagcacag   8400
```

-continued

```
agggagagtg ggagatgaga gctgcgcttc cttccaggga cacagctgct gaggagtcct   8460
cgcccccacc cccatggccc atcatccatt cacggagttt atggcacttg ggctcacgtt   8520
gcctgagctc ctgctgggtg ctaagagggg acccaggatc tagagtctct ccaggtcacc   8580
caccacccat gatcacagca gtttgcccca aacccaaggc ttcatggcct caaaatggga   8640
gcatttgcct tcctctcttc ttactccagg ccctcctcaa ccttgacccc caggtggatt   8700
ttccccctaa agctgaggtc ttttgtaagc cccctggaaa actccaccaa gttctaaagg   8760
agggtcaaga agaaagacac atgttccctc tctcacggag cttccagggg gcaaaattaa   8820
agctccatgg agaggaaatg gtgctggagc ctgggctagg tacctcacag caaccatggg   8880
aagcaaatag gattcatctc catttcacag aagagaaaac tgaggctctg agagagagag   8940
agagagacag aaagagttta accagctcaa ggctcatctg gccccagagc ccagctgatt   9000
tccagtcccc tgtcagcaca tgtagagtct ctcagacttg gcaaaatcag ccacttgcta   9060
cttactagca gaactgtaga atctcaggcc ccaccttagc ctactgattc aggatagaca   9120
tgttcacagg attaatcagg tgatgcgtat tggagttaaa atttgagaag cactgattta   9180
aaaccaaaga atcacctgga gactttagga aaacacagat tcctagaccc atcacttgag   9240
attctggttc agaattctca ggtggggcct gagaatttgc attcctaaca agttcccagg   9300
tgatgctatg atactgatga tgcggacctc acgatgaaac cactattcct cccgcctggg   9360
caacatggca gaatcccatc tctactaaaa atacaaaaat tcgctgggtg tggtggcata   9420
aggctgtggt cccagctact caggaggctg aagtggaagg atcacctgag cctggagagg   9480
ccgaggctgc agggagccat gattgcacca ctgcactcca gcctgggcaa cagagtgaga   9540
ccatgtctca agaaaaaaaa aaaagaaaga aaccactgct ctaggctaaa tcccagccag   9600
agttggagcc acccagctaa actggcctgt tttccctcat ttccttcccc gaaggtatgc   9660
ctgtgtcaag atgaggtcac ggacgattac atcggagaca acaccacagt ggactacact   9720
ttgttcgagt ctttgtgctc caagaaggac gtgcggaact ttaaagcctg gttcctccct   9780
atcatgtact ccatcatttg tttcgtgggc ctactgggca atgggctggt cgtgttgacc   9840
tatatctatt tcaagaggct caagaccatg accgatacct acctgctcaa cctggcggtg   9900
gcagacatcc tcttcctcct gacccttccc ttctgggcct acagcgcggc caagtcctgg   9960
gtcttcggtg tccacttttg caagctcatc tttgccatct acaagatgag cttcttcagt  10020
ggcatgctcc tacttctttg catcagcatt gaccgctacg tggccatcgt ccaggctgtc  10080
tcagctcacc gccaccgtgc ccgcgtcctt ctcatcagca agctgtcctg tgtgggcatc  10140
tggatactag ccacagtgct ctccatccca gagctcctgt acagtgacct ccagaggagc  10200
agcagtgagc aagcgatgcg atgctctctc atcacagagc atgtggaggc ctttatcacc  10260
atccaggtgg cccagatggt gatcggcttt ctggtccccc tgctggccat gagcttctgt  10320
taccttgtca tcatccgcac cctgctccag gcacgcaact ttgagcgcaa caaggccatc  10380
aaggtgatca tcgctgtggt cgtggtcttc atagtcttcc agctgcccta caatggggtg  10440
gtcctggccc agacggtggc caacttcaac atcaccagta gcacctgtga gctcagtaag  10500
caactcaaca tcgcctacga cgtcacctac agcctggcct gcgtccgctg ctgcgtcaac  10560
cctttcttgt acgccttcat cggcgtcaag ttccgcaacg atctcttcaa gctcttcaag  10620
gacctgggct gcctcagcca ggagcagctc cggcagtggt cttcctgtcg gcacatccgg  10680
cgctcctcca tgagtgtgga ggccgagacc accaccacct tctccccata ggcgactctt  10740
ctgcctggac tagagggacc tctcccaggg tccctggggt ggggataggg agcagatgca  10800
```

```
atgactcagg acatcccccc gccaaaagct gctcagggaa aagcagctct cccctcagag  10860

tgcaagcccc tgctccagaa gatagcttca ccccaatccc agctacctca accaatgcca  10920

aaaaaagaca gggctgataa gctaacacca gacagacaac actgggaaac agaggctatt  10980

gtcccctaaa ccaaaaactg aaagtgaaag tccagaaact gttcccacct gctggagtga  11040

aggggccaag gagggtgagt gcaaggggcg tgggagtggc ctgaagagtc ctctgaatga  11100

accttctggc ctcccacaga ctcaaatgct cagaccagct cttccgaaaa ccaggcctta  11160

tctccaagac cagagatagt ggggagactt cttggcttgg tgaggaaaag cggacatcag  11220

ctggtcaaac aaactctctg aacccctccc tccatcgttt tcttcactgt cctccaagcc  11280

agcgggaatg gcagctgcca cgccgcccta aaagcacact catcccctca cttgccgcgt  11340

cgccctccca ggctctcaac aggggagagt gtggtgtttc ctgcaggcca ggccagctgc  11400

ctccgcgtga tcaaagccac actctgggct ccagagtggg gatgacatgc actcagctct  11460

tggctccact gggatgggag gagaggacaa gggaaatgtc aggggcgggg agggtgacag  11520

tggccgccca aggcccacga gcttgttctt tgttctttgt cacagggact gaaaacctct  11580

cctcatgttc tgctttcgat tcgttaagag agcaacattt tacccacaca cagataaagt  11640

tttcccttga ggaaacaaca gctttaaaag aaaaagaaaa aaaaagtctt tggtaaatgg  11700

caaa                                                               11704
```

<210> SEQ ID NO 1106
<211> LENGTH: 33415
<212> TYPE: DNA
<213> ORGANISM: Homo sapiens

<400> SEQUENCE: 1106

```
ggagggagcc gcacgcggcc cagggcagcg gtctaggggc gccggggccg gggcgtaggg     60

gccgttgccc gcgatggacc gcaccggaga cgctccggac tcgtcgccgc aggtcagtgc    120

tccccgcgcc cccgcgggcg ccccgccgcg cacagagccc ctttctgcgt ccccatcggt    180

gcccacgcca tgtcctcccg ggcgcgcgct ggggtgtgtg tgtgtgtgtg tgtgtgtgtg    240

tgtgtgtgcg ctgcgcgcgc tgggggcagc tggaaagggg gccgagaacc gagctcgggc    300

tgggaggcgc tgctgccgag gggctgcgaa acaaaacccg gcacagcctg ccctcgtcga    360

ccgggattag gggaagagct ggttctcagc agcttctaac aatcggcccg ggctctcagt    420

cgtcagttcc cggccccctc agcaggtggt ttctggtggc cggatgagga gtcaggggtc    480

agtcgtcccc cacctcccca cccctgctgc ccaacagcgc tctctggatc gctctctggc    540

tcctgggcac tgccaagtta actctcttga gggggcccga gctctgcggg gcgcgctgag    600

ggacccaggg gtagcaaggg tggcaaaggg cccttgggac cttcggtgta gcaaggagga    660

aggaggcgcg accagttcac caccctccca tctgcacctg ggctcaggtc tgaggtccca    720

atccctccaa agtcagagca cacaacttcc agaaaaagga ggctgagagt tgaggcagga    780

aatagagaag gaagccacca ggtccgacag tgccagggta aggaggtgac agccccgtac    840

caagcagcta aggtcaagaa ccaccccccac atgcacacac atgggagcct tggccaactt    900

ccctgtcccc ttcctccccc agccaggcct agctgcatgg attcttgtag aagctggagc    960

tgaaggactc tggacataca ggaaggggac ctttactgac agttgctagc ccagtgcatg   1020

ggcacctgca taggtggggt gcccaatggg gcctagagct tgggctgtgt agcacgcact   1080

gttgaaaatg ttggggtacg gatgtcgtag ggcctagcac tgtgcaatgc ctggatgtgt   1140
```

-continued

```
ttgtgtggaa atgggaggca catcactccc taagttacta gggctgtggg gcatgtggct   1200
gcacaggact gttgttctag ggttttctaa gatttgtctt ctgtgcttat gtcgccctac   1260
ctctgctggt agccactgca gagactgaga catttcctcc cagagtctgc tcagttggtg   1320
accattaatg gccttactgg accaaacatc aagccttccc tttcttccca tggggtgaag   1380
acccttttccc agggtcttca gacagacttc tcactctgcc cagtccatgc ccagcactgc   1440
caaaggttcc agagcttaga gacattttcc ctcttcccct tttcatggaa gcagaaatac   1500
ttgctaaggt taatgggact gggagagtta atgcatctgt gccccattca gcactggagc   1560
caggagctcg ctgttcctgt ttctgtgcct gaccccagga tgcttgggga tcactccagg   1620
tccaggtgag ctggaagctt gcaggcgctg tgttgaatat gtgtgtgtag gtttctggtt   1680
gggcagttac tcactgttcc accagaagca gggggcaggt aaatcactga ggagataagc   1740
tccagcaaca ggattggagc ccgtggcgga gaccaaggag cttcacagga ggatgccctg   1800
gggcaagccc agttcctcag cttcggcttc tggggagacc tgaaggttct cttagtggtt   1860
tctcggggat aaggggacca agtcagatat acttttccta ggtgtggagc acagggtgat   1920
gaggccggcc aggagctggg agtgtgagat ggggaagagg atgcaccaac cgaaaggctg   1980
agcggacagg agcatggtgc tccattgttt ctggaagaga gggatgagtg ttcctctctg   2040
atgagaatgg agaggaggag aggaacgggc tcaggaggag gaggaatccg agagagagcc   2100
tgactgaggc agagaaagag gcagtgagac aagagacaaa ggcacggagg cgcactggcg   2160
gacagcagag ggaggcacac aggcagaagt cagggcctcc ctgactgagt ggtgagttgg   2220
ggcaggctgg gggcctcccc ctgttcccct acatcgacct cagcaattgt ccacccctgc   2280
aggaggcccc tcactagagc agttggacat tctactgagg aaggtgcttt cctgtggctc   2340
tcaggaatgt gagggtcttt tagacagaag cccaaaggca gagggaggcc aggctatgag   2400
gtcaagcaca tcaagagctt gcagggactt tcagggacac ccttcacccc tgagcatctc   2460
acaatgctga gggctcctct ccatcttctg gccctgcccc agccctcctg gtcctggaat   2520
gcagggcagt ggggaaggat gtggggtctg ggaaacctg  gcactcagga gaagaagaga   2580
agtcatgcac cccctcccca ggcccccagg caaaaagacc tttggggacc ctactgaaga   2640
ctagccaggg gacatggaag aagtgcagtg gggacaggcc cttggccagg ctgtctgagg   2700
tccagtctca tctccatctg tggctagccg agtagacttt gaaaaaaaca gagctctcta   2760
agccccggct tcctggcagt ctataaattg ggaaactgtc atctcaccag tttttagaag   2820
aaatactaga tgaattttaa tttaatctat ttattttata caccctcacc cccttgcttc   2880
caggatgagg atggctctag aatttggagt agcagcgtca ggccagccct ggagccaatc   2940
ccactggaat cggtgcaggc tgtcccacct ccctcctcac ccccactggaa taggtggagg   3000
ctatcccacc tccctcctca ccccactgga atcggtgcag gctgtcccac ctccctcctc   3060
accccactgg aataggtgca ggctgtccca cctccctcct caccccactg gagtcggtgc   3120
aggctgtccc acctccctcc tcaccccact ggaataggtg caggctgtcc cacctccctc   3180
ctcaccccac tggaatcggt gcaggctgtc ccacctccct cctcacccca ctggaatagg   3240
tgcaggctat cccacctccc tcctcacccc actggaatcg gtgcaggctg tcccacctcc   3300
ctcctcaccc cactggaata ggtgcaggct gtcccacctc cctcctcacc ccactggaat   3360
aggtgcaggc tatcccacct ccctcctcac cccactggaa tcggtgcagg ctgtcccacc   3420
tccctcctca ccccactgga atcggtgcag gctgtcccac ctccctcctc accccactgg   3480
agtcggtgca ggctgtccca cctccctcct caccccactg gaatcggtgg aggctgtccc   3540
```

```
acctccctcc tcaccccact ggaatcggtg caggctgtcc cacctccctc ctcaccccac   3600
tggaatcggt gcaggctgtc ccacctccct cctcacccca ctggaatcgg tgcaggctgt   3660
cccacctccc tcttcacccc actagaatag gtgcaggctg tcccacctcc ctcctcaccc   3720
cactggaatc ggtgcaggct gtcccacctc cctcctcacc cgcttgagtc ctcacacctc   3780
cagactctgg gctggaccca cccttcctta tcccaaccca aagaacccag agcccgcctt   3840
ggctcagagt tcgtccttgc caaacacaaa ataatacttt cgtgtctaat tattgttaaa   3900
tgtaatcctt ccaatttatc agcaaatggt cgtctaaaaa aaaaaatctt gacaccaaaa   3960
ttccagatct gtgagccctt cttatccatg ctgaaaggtg acagggtggt cagagagccc   4020
ccaaaattca gttcacttgc accaacactg accaagcact tacggtgttg gaggctctgc   4080
accaggtgct gggaacgtga aacatcaaat aatccaaaag tccaaatcta gtgttttctg   4140
tttagctttg gaagggttat gtgggttgct ttttttttt ttgcagctac agcaaattta   4200
cttttctaat gaggtttagc tccagccaat attaaaatga gcctgcgctc cctgcgcaca   4260
caccagctga cagcagggca ggaggcagcc tccgcgccaa gtgcctggca gggattaagg   4320
ctttacctct gataagcgca aaagtggaga gtatgagtct ggatcaagag ttgactggat   4380
ttgaggacta accttgccca gggggctgtg gattccacgg ctcagtcttc tgagccatgg   4440
caggagctct ctcttctcat acgtgggaaa tgtgagccag ctctctgctc acaggaagaa   4500
gacctagagg gatgggggag tggagacatg acggcacggc gtggggagtg ccaatggcac   4560
tgtagttgga ggcctggctc tgcccgtcct ctctggctgg ctatgtgggc tggggtcctc   4620
tccttcccct ctgcccatct tgcttcctct gtctgtggca ggtgagcaat ctggcctctg   4680
aggccatgag tctctctttg aaccctgggc tactcatttg tccattgttc agaaactgtt   4740
agagccccac actgggcatg gggggctgca tccgtcccca ccctgagcag ctcctcagtc   4800
acaccagcca catttcaagt gggcaacagc cacatgtggc tagaggctgc catcttgggc   4860
ggtacagata cagaacgttc ccggcagcac ggaaagttct agtgggcaga gtgttgtgga   4920
cctgagcctg cacaggtgtt ttgggcacgg aaagttctag tgggcagagt gttgtggacc   4980
tgagcctgca caggtgtttt gggcacggaa agttctagtg ggcagagtgt tgtggaccgg   5040
agcctgcaca ggtgttttgg cagggtggct aagtgccagg tcctactggc tggattcagg   5100
tcctagttct gccacttagt agctgtgtgg cctcaggacg ttgcttaacc tctctgtgcc   5160
tcagacttct cacttttaaa atgagggtaa taataggatg tttctgagga ggaaatgagt   5220
cattacagtt aatcatgcta atcactcaga gcatgcaaca gcaagagctt ttttattttt   5280
tatttgaaaa tagaaagcca tttttattat tcatttattt aacaattcac ttaaaggctt   5340
attgaaaagc ccactctgcc aggccgcccc cccacccacc caatcaacac aagtcctggc   5400
tacctctgtg acccttcctg agcctccacc tcctccccta ggatgggatt attcctgact   5460
gagtgctcac tgaagcccag ggagctagaa tgagatgagg aaagcaacct tgctttgtgc   5520
agacgcagcc agatagaggg gctgatgctt tttggaggtg agtgccactg aaattctgtt   5580
ttgtcactaa aaagcatctg ctaagccccc acactttcag aataagagca gcaaaggagg   5640
catggttagc tgccaccagc cagcaccatg tcgagcaggg atggaggaag ggatgtgaga   5700
ggcccctgcc tgggctcacc cctccctggt ctggagggcg agagcccaga ggctgctgtg   5760
ggcttagtgg agggagcaga gcctggaggt ctcagaggcc aactgtgctg ccacgagccc   5820
cccgggcgct ggtcccagct gcgtctgcaa ctcactgtgc cacagacact ggtggggcct   5880
```

-continued

```
cagtttcctc gtctaagaca ggagggacag ggctgcatga gcgtttcctc acctggaaaa   5940
atcacttcca cagagcgacc caagccggag gccagaggga gggaccctgc ccaccaagcc   6000
accaggggtg gaaggtgagg gctggcctga ggggcaggag ctggccattg gtagccaggc   6060
tggtgctgga caccccaggc tacctggctg ccagccttct cccagaagtt ggattgtgca   6120
accctgggct actcccttct tttcacagat gaggggacag acacccagag cagccctgct   6180
cctgtctagg ggccacagag caatttcaca caaggcagag gctgcatgcc ccagtgccct   6240
cccgggcaga ttgttggtac tactggcagg cagatgtgtg gggctggggg ctgccacccc   6300
cggggtcggg gcgcaacgct gagactccca gggcccctca cctcctctct tctccctcag   6360
acggctggac ccaggaaaac caacctcaac tatccctgac agagccctgg ggaaggtcag   6420
ctccttcagg ccacaggcgg caaattaaaa atacagacaa actaatgaaa cccgtgaatt   6480
gctagcctgc cagagtgtgt ctacgcaccc tgaccacagg acctcaccag gcgggtgacc   6540
atcagtggac cctccgtggc ttcagacctg ggtttggggc tgcccggtgc ctacctagcc   6600
cggacctgaa gccctctggg tccccgtagc tgatgggggg tccccttggg ggcgtcttcc   6660
gaagcctaag gaggtcacca ctgctctgac acccttgaag ataagtcctg acccccaagg   6720
agtgccggtg ctgggtccct ctgaggcagg gctgtggcaa atgccacccc cgtggagttg   6780
ctggcaggcc gtaggtgcat atcaacaata tcgtcacccc cccagccctg cttgcctgcc   6840
ccagcccttc ttcttccctc ctcttccctc atccacagac cacagagtgg gagagacggc   6900
cgctcgtggc acggggagga cactgagccc agagaggcca agggaccggc cagttgcacc   6960
cacactgcag ctgaccgaca caggcccggc ccagctctgc cagcctgcct gggctgaagt   7020
acagcctccg ggcgagctgc tttcctcacg gtcagagagt ttctgcgtgg tagctgaagt   7080
attactctcc taactcatcg cctgtcgata ttagcttctt ctcccacaca taaatctctc   7140
tctcagaaca agtgctccag cactgtgtct ctgcggctcc ccaggcctga ggacagcgag   7200
gcggttgcag gctgtcagtg gggcgtgcac actcttccga gtggcgtacc tggagccttg   7260
gaggggggcc tcccgcaggc atacctggtg cctgtcaccc cgtgattccc aggaaggtgc   7320
atgcttgaga tcacacacag acacccaacc cagccgtgaa tgctcactga agcccagggt   7380
gcaggctccg aggagtgtgc tgtccttgac tgtgtctaaa cggatgttct ggatgaatga   7440
cagactcgtt ttcattgtta tttaaaaaac acataacata aaacttacca tcttagccat   7500
tttcaagtgc acagttcagc agtgctgagt atatttacat tgttgtgaaa cagatctcca   7560
gatctgtctc atctcggcca ttggaaactc tgtacccatt ctggaaacca tcattctcag   7620
caaactgtcg caaggacaaa aaaccaaaca ccgcatgttc tcactcatag gtgggaattg   7680
aacaatgaga acacttggac acaggaaggg gaacatcaca caccggggcc tgtcgtggga   7740
tagcgggaga ggggagggat agcattagga gatattgcta atgctaaatg atgagttaat   7800
gggtgcagca caccaacatg gcacatgtat acatatgtaa caaacctgca cattgtgcac   7860
atgtacccta gaacttaacg tataataaat atatatatat atatatatat atatatatat   7920
atatatatat atataaagaa agaaactctg tacccgttaa atgactccca ttctccacaa   7980
catcccagcc cccacaagcc accatcctag tttctgtctc tatgaatttt actactctgg   8040
atacctcata gaaattgaat cctgtgatat ttgtcctttt aagactggct tatttcactt   8100
agcatagtgt cctcaagatt cgtccatgtc agggcatgtg ttaaaatgtt ctccctttttt   8160
aaggctgaat aatattccat tgcatgtgta ttccacattt tctttatttt ctttatccag   8220
tcatctggtt gacaggttat ttgatgtcag gctgtggagc aaaagctcaa taaatggcaa   8280
```

-continued

```
ttctccccac ttgcccttcc cactcaggag atgtctgagc agaggggcca cccagcaaat   8340
acttctgccc agagggaagc tatgtcacag tgtcatggga gcatcaagaa ggaggcaccc   8400
cattctacct ggcatctggt ctggcctctg ggctcccctt cctgcatcca gggctgccca   8460
ggcaccctgt ggtgcccagc cctgagtgtg aagcccctgg gctgagtgta cctggcctgg   8520
tcctgggggc caagcaactc agcaagtgga gggactatga gggagggaag catgtcccag   8580
gcaaacgtac cggtgtgaag ggatgccagc ctcctgctct catccctgct gccttcccgg   8640
gaccccgaga aagaaatcgg ccgggtactc ctagagtcta cctggggatg ggagcccagg   8700
agagcctgga gatcccctcc cccaggtatg tggaggcctg tcttgagcct gtgccttggg   8760
ctacatgtcg gtggtggacc gtggatccgt agccgccctg gtgctcactg tgtgataggt   8820
agcctgggaa acccagagat agtatcagca cactccactg tcaggggcac tgagactgag   8880
gaccgcggga tcatcgcacc cacacctcct ctgctgtgta gggcacacac tgcccactct   8940
ggttcacaca tgtgctcagg gggcaagtcc cctacccaag ccccttcgac tttttttttt   9000
ttttttgaaa cagagtctcg ctctgttgcc caggctggag tgcagtgacg caatctcagc   9060
tcactgcaaa ctccacctcc cgggctcaag ttattctcct gcctcagcct ccccagtagc   9120
tgggattata ggcacctgcc acaacacctg gctaattttt gtatttttcag tagagacagg   9180
gtttccccat gttggccagg ctggtctcca actcctgacc tcaagtgatc cacccacctc   9240
agcctcccaa tgtgctgggg ttacaggcat gagtcactgt gcctgaccca gttcaacatt   9300
ttatgttaat tgtttcttct tcaggcaggg gggttagctg acaccccaga ggagggaggg   9360
accttagggg cagggcaggt gtaacagagg gaggtggggg agccctggaa gtaggaggtg   9420
gtgaaaggaa agttctccag gagcctgagc ctgcatcctg gggagacggg gcagggagtg   9480
acagtgccca gggctcgctg gccctagagc cccatggaca agtcagttct ctgacagctc   9540
tggaggcagg agaagagaag agggatgggg aatctctgaa atcaccggtc cttcctgagt   9600
gcctttctgg gaagctgggc agagacacag gaccagactg ggcagggtga cgggagggaa   9660
gcagcaaccg cacactgggg catacccgcg acttgactct agctcagtgt gtcagttcca   9720
aacctcagtc tccccacctg aagaagcagg gtgacaggat gggtgcccac ctcatctcag   9780
gtggctgcac cgaggctaca gcaggaaaag gcatgagaaa gtgccttgtc gcctggtcca   9840
cctgtgcagg ggcacgtcct ccaagcagga acagagggag ccagggccac agcgccaggt   9900
tccaggggcc ccgcctcccg acagtggtca ggctgcccgc cccccccgc cccaggccac   9960
accctttgt cacaactgca tgctggtgtg cccagtttcc attgagctca agccacagca  10020
ccgcctcgtg ctggggagag aagaatgtgc tggaaaggct gcccgaaggc tggtcgccac  10080
tgagccatga ggaaggggcc aaggtgcctc cttcctctgc ccttcctctc ccaggcactt  10140
ggattcagct gagttttact tttttttaaa ttttttataa attcagcatt tattttagat  10200
tcagtggtac atgtgcaggt ttgttacccg ggtatattat gtgatgctga gatttgaggc  10260
ataactgatc ctcttaccca ggtactgagc atggtaacca gtaggtagtt tttcaaccct  10320
tcccccctcc cttcttcctc cctctaggac tccacagtgt ctattgttcc catctctatg  10380
tccaagagta cccaatgttt agctgccatt tataagtgag cagtatttgg ttttctgttc  10440
ctgtgttact tcacttagga taatggcctc cagctgcaac catgttgctg caaaaaaagc  10500
attatttaat tcttctttat ggctacgtag tattccatgg tgtatgtgta ccacgtcttc  10560
gtcatccagt ctactgctga tgggcaccaa gcttgattcc atcagttccc tgttatgaat  10620
```

-continued agtgctgcga taaacatgag tgtatgtgtc ttcacggtaa aacgacttat attcctttgt 10680
gtagacactc aataatggga ttgctgggtc aaatgtttta agttctttga aaacctccaa 10740
accacattcc acagtggctg aactcatcta cattcccacc aacaatgtac gagtgttccc 10800
ttttctccac agcctggcca gcatctgttg ttttttggct ttttagtaat agccattcgg 10860
actggtgtga gatggtgtct cgtgactttg atttgcatct ctctaatgat cactaatctt 10920
gagcattttt tcatatttgt tggccacttg tacgtcttca tttgagaagt gtctgttcat 10980
gtgttttgcc cactttttaa tgtgggtatt tgttctttgc atttaaatgg tctaaattcc 11040
tggtaggttc tggatgttag acctttgttg gatgcagatc tgtaggttgt ccgttcactc 11100
tgttaagagc ttcttttgct gcacagaagc tctttagttt aattaggtcc tacttgttga 11160
tttttgtttg tattttgcag ttgcttttga ggacttagcc ataagaattt tcccaaggct 11220
gatgtccaaa atggtgttcc ttaggttttc ttctaggatt cttagatagt ttgaagtctt 11280
acaacattta aatctttggt ccatcttgag ttcattttca catatggtga gaggcagagg 11340
tccagtttca ttcttctgca catggctagc catccgctga atcttaaaac aaggtggagg 11400
tggtggtgtt tgtattcacc actgtgttct atatgatcta acattcatag tgccaattgt 11460
gtgccaggcc ttatgctagg tgttttccgt tgattccctc atttgatctg aaagtagccc 11520
tgtgagagtt aaaggtgagg aaactgagtc acagggatat tggcatagct cctgctttgg 11580
gttgggctct gggccctggt gtgggaatgc agaggtgagt aagaccaggc gcccccggag 11640
gagcttctgg ctcggggcta gggtgcaaat gtgaaaaccg gcaagcaaaa ggcagggccc 11700
agggcaggaa gtcccacagt gtgtgcacct tgagtgagca gatcggggca ggggcagggc 11760
cagggaaggc ttcagagtgg gagagggaat gccaaaggca cagagcccag gagagtctcc 11820
cctcgccagc acctcaccca gaaccacaga gacaacagcg ccaagggaaa ctgagcagcc 11880
tagggcagca tgacagcagg aaggcagtac tgtggggcag ttggctgctc acatcctccc 11940
tctgggatgt ccccaccttg ctcacagcct gagaggttct gcagggctgt ttcagctaac 12000
ccaagccttg gacactcagt tccagggcca gacccacctg ctcacctggc ttgcttatgt 12060
ccaggctgtg ctgggctcca gcaggtacca agtcagtcac catgacctgt gccaggctcc 12120
atgctgtgga tggacacact catccagccc atcacgagag acccttgctg caaccggcac 12180
tcagcatccc aagcagtgca accttgggct gggcctcctc tgtagagagg gtcagatgag 12240
gcgagggtca cagccctcct agcttccagg gtccaggatt ctagggcatc ccagcctttc 12300
tgggttctgg actgccctct gccactgctg ggcagcctgg caaaagggga ggtcagtgct 12360
attagcagca gcagcttcga cggcttgccc ctggaccctg ccgttcactg ggtagcagaa 12420
tgtgcctcac actctggggc cctacgggcc tggcccccac tgagcaggcg ccctgtggtg 12480
ggtgtgcgcc cactggaggc agcattccac ccatgggtgt cctgagcaaa ccacaggcct 12540
ctcctagggt gcatacattg ctggctgact ggggagtctc tcagaacggg agcaggttgg 12600
ttggtgtgtt aagagcgttt tgctggaacc agggtccaag ggcaggaccc aaatcctggc 12660
gtggtctatt catagagctg gaatgatgtg cacggctgat tctaccccac ctgtctccaa 12720
caggtgaggt gaggctggag gcgggtaggg atgtggggaa acctctgaac aggagcaagt 12780
gagaacccct ttgctcccat catgcaggcg agaggagcca ttctggggtc accagctcat 12840
gaaggctgca gtgagccccc ccggggaggg agcaaagcag agaaaccatc cagcctgcaa 12900
gcaggtagca gtgggctctg gttggagaac ccaccaccca ccgcacccag aacagacctg 12960
cagttgatcc attatcatat cagctcatcg ccttttcaaa agcatcctgg tttggatcag 13020
gaagtgtaag gtcacactag ctctgatgaa caagggcagg gaagtctcag ctgccagccg 13080
ggtgtgcagc tgcagcacag aggcctgccc ggagcacaca gctaggaaga aacccgtatg 13140
tccccagagg ccgggggcca gctggccata ggcaggaggg ggcccgggag ggagccagca 13200
gtggacccag ggccaggaga ggtgggacag aggcacggca aggacccctg cctggccact 13260
gctgcccaga ggagtgcaag gggatggctg ctttctatct ggacctggga cacttgagac 13320
agtcactcaa ccccctcatg cctcagtttc ttcatctgta aaacatgaac aaacctttgg 13380
gattacaagg gtttaaacat taaatgagat aaccaacgtg cagtcctttt ggaagccata 13440
aatcagtact gcgtgtgagc tgttgtgttt agtaggttta ggagcagcag cccccgcaaa 13500
ccccagggct gcagagagag tagaactggc ctcttggcct caccccatct atgttccagg 13560
atccgaagcc actgggtgcc aaggacaggc acgtgagcta ctctcttatt tgaacaggga 13620
cccaattgtg gatttgtcaa cagggcacag agcaacactg atacccagct aagagcgtgc 13680
agacacgtgc ctgtgaatac acgtgtgctg actcacgggg tgccggccat gatcacacat 13740
gcacacacgc atgcacatgg gtgtcaagca gcaggccagc tgccctgtga agtcactcag 13800
gcgggcagtt ctgtggtggc cagcacagcc tcgatgccct gtcagaacag aatactcaac 13860
cccaggggtt ttcttgagtc gaattccaag caacgcattg aggaggacag ggagcaggca 13920
gggagcaggc acctgagtcg ctgtggtcag actggcgtct ccccaaatca tcagcctcaa 13980
gagagtgctg ggcaaggggg aggggacacc gggaccaaac ccatgcttgc tgttcctcac 14040
tgcggggccc cctaactgcc actcaggccc aggtataccc ccacacgcac tgtaccctgg 14100
ccaagtcctg gcagagagga gcaggcaggg catggaggcc caggcaaggg agcagttgac 14160
agctggaagg aaacgagaca ggtgctggtt tgcaatggcc aggcctggtt tgcgcttggg 14220
catcttgact caacttgaga accctctccc tggctctgga ccccccgcgg ctctgggtgg 14280
gaatggggca ctgccctctg gcatgggaat ggggcactgc cctctgggtg ggaatggggc 14340
actgccctct gggtgggaat ggggcactgc cctctggccc cccctgtggc tctgggtggg 14400
aatggggcac tgccctctgg catgggccac gttgcatctc accacaggac gaggaaaagc 14460
atgccatgtt ggaatttcag ggacggaagc tggcggggca gagatggcca gggaacagga 14520
gagaacagga gggacatggt gggagtggtg ggcgggcgca gggcaggcat ccctgagtgc 14580
caggctgggt acgttgcagt caggagtgca caggaggatc tgagcaggtc gcaggctggg 14640
gttggagggt ctgacagtgt gtggactctg aattgaggag gaaaggcagg cgtcagagag 14700
atcaccataa gggccattgt gggtaaaaac ttgacctggc ccaggattag gggatggagc 14760
cctaggccgg ggcagcagtg gaaggagctg aggccccgct gatgcaggga gaaggtggag 14820
tcaagggcag ccctgaggtt ttcatgccgg gaccatgaca gaaagaaggg ggcttggatg 14880
agagctgctt ccagaggaaa gatggtggtt ggatctgagg ttgtgtgtta ggtcacaatg 14940
ggacatgcca gacaacaaga ggtgtagcag ctccgtgtga gagatgggga agctgaggcc 15000
aagggaaatc aaaggacgcc gtcaggggcc tcgtgctggt gttttctcct ctgacgatcc 15060
cagaccctct cctctccacc tgcctcttct ttggaggtga cgtggggctt tcaggtccgt 15120
ggcttccatc tgccctccag caagcagccc ggagtttggt tggaaggagg cagcaggaag 15180
ccaggccgag cagacccgtt tcctggccct tccaggctgc aaggtcagca gtgacagcag 15240
ctgctcttta ttggcccaac tatgtggcag acggtttgcc tgattttttt ttttctagtt 15300
atcctgacag cctagtggta ggagcagtat ttttattccc gttttacaga tgggaaaatg 15360

-continued

```
aaggcccaga gaggttacct caccagaatc ccgtagcaga ggcagaaaga ggctggcagg  15420
tgcacagggt cgtctggctg tggggttcag aacctttctg catcgcaggg cccctccatg  15480
catggctctt ccaggacaga ggagagcaaa gaggtggtgg cagggggggtg gcagaaggct  15540
atgactgtgg ctgggttctg ccgtcaccct cagtagctat gggactaggc agggtctgag  15600
gagctgaggg ccagacatgg cccatctgcc ttggtgtggg ggacagactc tcaggtatcc  15660
ttggaagccc caccccccgg tgctcatgcc ttcgtgcagt cctcaccttt ggtgtggatg  15720
gcattcgtga ccagctccta gccagcagac tgtgcaaaag cattgggcca tcactcccag  15780
gattacactg tgctctgtaa gattccatct gctagcagat tggctctaga tcccttcctt  15840
gctggattga cgaagtaagt ggccatgttg gagaaaccga tgtggcaagg atctgcaagc  15900
agcccccagg agctgagggc agtcccagct aacagccagc aggaagccat ggcccgcatt  15960
cccaccacca cccaagtgag cttggaagca gagtcttcct cagtcagccc tccagatgag  16020
gacacagccc tgccaatact tcgcagcctt ctgagaccct ggactcctga cccttaggaa  16080
ctgaagagag ccaatggggg ctgtcctctg ccaagtgtgt aggaattggt tagatagcaa  16140
taggatagga aatgaatata cttgtcttgg gagtggggac atttccttcc aaaagtgggc  16200
ctggctttta gaatgggcct agggcaagga tggaaaggta gcaaggaagg agggcaaagg  16260
aggttgggga gcgaggacct ttcaatacca gacttctccc ccaatcccag gctgggctcc  16320
agggttctgt acaaggacta cttgccagtc ccacaaatcc caaagatagc atgaccctca  16380
gtaatcccta tcacgcaggc aggggtcaag tggccaagtg gtgctctgtg caccatcgtc  16440
cggtcatggt tagcacattc ctgccgaacg ccttcctcca ctcggccaag cagaagcacc  16500
cccactccca tcacccatca tgacctgctg tgggatggct cctctctggg gtcttccatg  16560
ggcctggctc accattgtcc agcgtcccac aatcctttat caggtttgct tccttcagct  16620
agccttctct ccagctgccg ctccctctcc ggctgtccgt ccccctgcag agcatctgtg  16680
tgcccatccc cgcttcccca cccgcccccg ggcgtgcccc agcagagagc agcagcaagt  16740
gatgtcgtca cacggtgaag ccccaattct tgcttcaggg cctcctgcat ggaggctctg  16800
gggtgagtgg atgaactgct gcctgaagac cactagctac atgattcagg gaacttcagt  16860
gacaccagcc ggggccaaca gtgtattcgg ttgagattcc tgcagttagc cagaatggac  16920
tttgacttgc agagtactat actaagccaa accccagttt ccattttta ctgaatcata  16980
atcaaaatca aagccaaaga ctatttctga aaaaaagaaa aacaaaggaa ctacctaaaa  17040
aaagtcagtg aattacattt ctgatgctgg aagaaaacca aagcgtgaaa atattctctg  17100
caccaaatca gaacaaaact aatacttcct tctgcccaag tccttggctg ggttttccca  17160
gttagaaggg aacaagatgg tttgagctct ggaattcacg ctgcccttcc atcagcagtc  17220
ccaagcgtga gcctgcagtg acccaggctg ggaagcagag tgcagacatc ccagggccca  17280
agcttgccac tcttcctcca tgagcaaggc gagggcaggg tgggggggaga gcagcagtgc  17340
cttcctgggg gcactcggcc cgaccactga ggtaggccat gcaggggatg aaaggtcagg  17400
gggctctggc cctggagcag ggttgcccag tgggtgggca cgagggtggg ccaggggagg  17460
gtctgcaggg ggacgtggtg tgggcacggg tggcactgga cacagaggcc aaggcccgag  17520
tttgagcagc tctgctgaca cctaacgcag tgaccttagg ccgatcactc aggttctctg  17580
agctttggtg tcctcacatg caaaatgggg acgagatctg tgtgtctgcc tcatgctgtg  17640
gctgctctga acatcgaggg actgggcttt atggaaaagg gagtcttact gtttcaatgt  17700
aagattcaga gtggaatctg ctatggggcc cctccccagc cctctgcagt cggtgaccag  17760
```

-continued

```
ggcaaaggag gagcaggggc ctgggaaagt ggctcctata tggtgtgagg tcagtgcctg  17820
tgtcctgccc cccagcaggg ctgtggtggg cccgggaggc ggtggtgctg gggcaggag  17880
ggccggggtt aggttaatga agtatggatt gactgggctg ggagctgatt agctgtggca  17940
tcaggcgttt cctgagcagc gcctgcagaa tcaatactaa tccgctgatc ccattagggg  18000
cacctggaga tctgtgggac aaagcctgtc cctccctctc tttgggggca ctggggttcc  18060
tgggtgacag agatgatatg aacagcagct gtcttaacca gcaggttggt gtcctgcacc  18120
cggtccgcac agcacactga ccggcgccgt gtgatgcctg gggctccctc tgctgtcacc  18180
actgagccca cgccctcaag agtcagtgac gccggttccc agcctgttca cagcactcac  18240
cgtctcgctt gctactgtca tcacagaatg tcatgtaaac tgttgaaata gcgtgttgaa  18300
gtaaatgtgt tgtttctatg aaaatttcat aaggtgagtc cagaaaaaag ttctccaagt  18360
taggtaaagg ctggcaggga aaagtcatat tctaaagggt gctacactca gactgctcac  18420
caagtgctcc tcagcccttg aatcactttg aagaaatcaa aacgagatcg cagcgggatg  18480
ctgcgatgtg gctgatgtca gacggtcagc acagacctcc ctgaccccgt gtcggctgag  18540
cggaagtgct gagagccagc aaggatgggt cgttcggatt tgggaaaaat tagcatgcat  18600
tgtgcagtcc tggggaaaca tcatctatgg gacaactggc tctgcgagtt acttacattg  18660
aaatgtatgg catgtatgta tcatttggaa agattcttcg ccttaatgga ctttttttgat  18720
gaaccactta actactgttc ccatcttact gggtaaaaag gcctttctcg tcctccaggg  18780
atgagtacct cggacagtgt ctgagcttgt ttgtaaccta ccacgcacac gcatgcaggc  18840
ctttgggaac attttgcgtt cacacgtcac ctgcactgga gcgagctgtg tcgtctcttc  18900
cgctctggac tgagcaaagc ttccccaccc tggattgccc acagaatcca acacagtgct  18960
ttgcctgcta cagatgctca attaatattt gttgagtgaa attaaataag ctcctctcct  19020
cagggcctga ggcattgctg aggccttcgt ttgaacacct gcaggctcag aagaaaacct  19080
ttccatgctt ttacaattgg ccagccttga accacccctg cacatgctcc agcctcacat  19140
gttctgcccc agcctgggtc aatcagagcc ttcccatctg agtcccagac accccctagt  19200
ccttattcac agcgcacagc accctaaaac ccatagacaa attcctctct ggaggtgcca  19260
tggctcatac ctgtaatctc agcactttgg gaagccaaag caggaggatc tgttgagccc  19320
agtaggttga gaccagctgg acagcatagt gacaccctgt ctctacaaaa aagaatttta  19380
aattagctgg acatggtggc aggtacctgt ggtcccagct acttgggagg ctaaggcagg  19440
aggatcactt gagttccgga actcaagcct gcagagagct gtgatcatgg cactgtactc  19500
cagcctgggt gacagagtga gaccctgtct ctcaaaacaa aaccaaatgc cacaaattcc  19560
tgcagagagg tgttcccagt atggccgatc tccataggca tactggccct taagtcagga  19620
ctcagttcca cgggccctta agtcaggact cagttccatg ggtgctggcc cttaagtcag  19680
gactcagttc cacgggtgct ggcccttaag tcaggactca gttccacgga ggctgttttg  19740
ttggcgctct tgcctcgcct ctggccctag gtgcccactg agctacactt tcctcacata  19800
ggacatccct tcatcttcgc agagccctat ggtaacctcc agttgctaaa atggcaggat  19860
cgttgaaact tccagctcaa cctccctatt gtaaagacga ggtcaaggag ggcaatcagc  19920
atgacccagg tccccgtgga gcacctgccg gacacgtcca ggccgccacc ctcccactcc  19980
catgtgctgc cccagcttct gctccccatc tgggaaccac cctccactct cccacaggga  20040
agtgcttgct tccctctgag gctctgaggg cacccgggga gggcagggca cagccttttg  20100
```

-continued

```
tgtctctact tgccgagacg cctgagatct gaggttggtc acagatatgg tgcaagtgtc  20160
aggatgggag ttgtgaccac ggcaggcctg ggccctacac tcacacacac tgcccacgcc  20220
gcgtcctgcc tctccacgaa gtccccttg tgcctccacc catctcctcc tccagcaccc  20280
cattcttccc cgtgcttgcc tccatctcct gggctctcct gggtgtggcc aagccactcc  20340
tgcacctttg tgctgattct tctgcctgac ccaaggtcct agaagccatt ctggggtcct  20400
tgttagagac agcctgcgac cacagacaaa caccgccctc ctccaagccc caggcagaag  20460
cagcaggctg cgagagggga ccagtgctgg ccaaccttgc agccccgtct cagactgggg  20520
cccagagctg ggggcaggtg cagcccaccc gctgcctggc cccaagcccc tgcccagccc  20580
aggcatcaca tcccacgacc tgccccctgc cggccagctg gcgttctcca ggctgggggc  20640
tctctgtgtt ctgcttgata actgcctggt aattagctcc acgattttgc tactatgctt  20700
ataatagcct ccattaaagt tatggggttt tcaagccata atggcttcca gagtaattaa  20760
tgcacaactg ggtttattgc tgagtttatt tttagaggtt ttctccctct ctccccctcc  20820
cttttctctc atagatgttt tgaccaaaaa gactggatgg gagcagaagg caccccacgg  20880
cacccttgcc cacaggcccc atcctcccct ctcttccctt cccgcccctc cttcctgctt  20940
cagcctccaa gcaggtgcta gggccctgca gtgggggcag ccattgcaga ggagggtggc  21000
tgtggtccag gccagaggaa gcatttggcc tgtgtgtgcc ccttacccac cctgcgcctg  21060
gcccaggttc gagaggcttg gaggcctggg acctcttatc ctatgccccc gatgacagca  21120
tagagccaga tggcctggac tcaattccag ctccaccatt tcctaatggt tgacctcagg  21180
caagttactc cccttctctg gcctcgatga acccacaggg accacagcca tgcctactgc  21240
acagggctgc tgtgacgttg caggagcagg tgcatgtgaa gagctgagcc tcatcttcgg  21300
acatctctca tgctataggg aagtttgtat aaacaacagt gcaagcgggg gctgagaggc  21360
tgccccaaag gaaaggcagt ggcccacagg gactgagctg gcaggacact catcttctct  21420
ccttggcttt ctccatcctg gtattagaac ctgcaccaac accaggagca cttgagaaag  21480
ctccttcgag agtctctgag aacacagaag aaatcttcct ggacatttct gaagccccag  21540
ccaggcccag cctccccatc cttcatcaga tgtggcctaa gatccaaacg tgtcttggcc  21600
aaagaaccaa aacgtgtctt gacacgcagc cccatgcagc cccagcagtg gcctgggtgt  21660
ggagggacag gctaaatctg ggggatgtgg catgaagtca cttgcatctc agaccacaag  21720
acccagcagg catcccgtgt ggggttctag gctctgtccc tcactgggcc agcaaagagg  21780
agtttacggg cggacacaga cacacacggc ctagaatgtc cactagggga actacgtgcc  21840
tgtgacgttg aaccccagtg ggtcttccac tccccgggga atgggtgggg gagactctct  21900
ggatggagtg ggcctctgat ggcggggtgt gggcagggga tgccggccgt cctgggaaac  21960
cacagtgctc cttaatggag gggatgccgg ccgtcccggg aaaccacagt gctccttaat  22020
ggaagacaaa tcctggtctt ccacaggcgt cagaactatt tggagagagg acccggtgag  22080
gagaggaaaa cacgctattt tggaaactca ggggctaaaa accctcctcg gccatagcac  22140
tcgactctgc ctgaaatggt gagcacacgt gagctggggc aggagcaggc agcatggccc  22200
ccaggtgagg tactgtccgt atccaacact gggcactggg acgggtgggc acagtgaggc  22260
tggctgggct gcccgaggct gcctgccctc cccaccaccc ccacgggtcc ctgctgcatc  22320
atgcatggtg ctcagcacag aagtgaaaag ggaggagaag aggatgtgac agtttccaag  22380
gcggtcagga ggtctcttcg cccagtgtcc ttgccatgtg agagaacggt tcccagagat  22440
gctaccagtg gaccctctgc aggactgagg aatcccagtg gctcattctc ctcacttggg  22500
```

-continued

```
ccccctgctg ttctcatttt ggaggactgt ctcccctcaa tgtggcagcc cctgcgggga 22560
cccctcttct tgctgctgcc cagcccagca cctggtgctc tgtcctgcac agagcggtgc 22620
tccacaagga tgtcctattg acacggaaga ggaaggcact ctcgtacttc cccccaggga 22680
ccatcccaga aacatctctt ctttgtcctc aaaagactgt caccaaaatg caaattgaaa 22740
ccacagtgag atactatctc acaccagtca gaatggctat tactaaaaag ccaaaaaata 22800
ttagatgctg atgaggctgc agagaaaagg caacacgtat actctgttgg tgggaatgta 22860
aattagttca gccactatgg aaagcaattt ggagatctct caagaactta aaacagagct 22920
gccattctag ccagcagtcc cattactggg tatgtatcca aaggaaaata aagtgtttca 22980
caaaaaaaac acctgcacct gtatgttcat cgcagcacta ttcccaatag caaaggcatg 23040
gaatcaatct aggtgcccat cagtggtgaa ctgggtaaag aaaacatggt gcatatacag 23100
caaggaatac tacacagcca taaaaaagga caaaatcatg gcctttgcag cagcctggat 23160
gcagctggag gccattatcc tgagcaaatt gacacaggaa cagaaaacca aacacgatgc 23220
attctcactt atgagtgaga gctaaacact gggtactcat gactgtaaac atgagaagaa 23280
tacacactga ggactctcaa aggaagaacg gctgaaaaac gccctgttgg gtactatgct 23340
catacctggg cagcgggatt catcatactc cagatctcag catcacatgc aatatgaccc 23400
ataacaaacc tgcacatgtg cccccaaatc taaaatgttg aaattatttt taatataata 23460
attcgtggtc catatatggt taaaaaaaag aaaaaagaga gagagaaaat aaaacctctc 23520
accccttat ccaggctttg ataagtagct ggcattttag ggctgcacgg gagttaccct 23580
gtttaattct gagaatgacc ttatgaggta gggatccaca gtgccccatt ttatagatgg 23640
gaaaactgtg gcatggagaa cggaaatgac ttggcaaagg tcttacagcc tgtgggtggc 23700
acagttggga tttaaacctg gtgtctctgc agtctgtgct tctgacccct gcaccctact 23760
gactttcata aatggagcag agccatggcc ctgtgcctgt gggaaggaca gagcccattc 23820
cactctaaca ggcagacaaa agaggtcctc aggtgatgga cagttgaggc tccattgtgg 23880
aacccccgat gctgtgtgtc ccagagcagg gcccagcctt gctggcatcc attcctatac 23940
ctgggtctct ggctatccgc ttctgctctc tcttgcaggt gtccaccccc cagggttcct 24000
gacccctgcc cctggacagc gacccccttct cagactccag ttgggccgga ctctccaaac 24060
ctgcttccgc aatgggtggg ttgtgagtgc tggtaagacc tgctagccaa cattcagctg 24120
ctctgtcctc tccatgcctg gccggcccgg cccatgcctg ttcttttctc ccctgtgctg 24180
ccgccgcccg tggccgcccc tctcctgaac ttaccgccac tcaggtaatg aggagccgtg 24240
ggtgcagcca gccttggaga tgccgaagag acgggacatc ctagcgatcg tcctcatcgt 24300
gctgccctgg actctgctca tcactgtctg gcaccagagc accctcgcac ccctgctcgc 24360
ggtacataag ggtgagcacg cacgcatgcc ctgcctgccc agctgggcct tggtagtgac 24420
agtgaccaca gctgacacgc agggttcttg cttgcactca cttagcagct aggaggaacc 24480
acgggatcat ctaggcccct tcatgagtct tgcacccctt tgggaatggg aagctaatgg 24540
aagctaccca cacagtttta agatgcctgg gatggtaggt tggcagacac caagacagtt 24600
gccttgaaag aagagcttgt tactctcagc acccaagagg agggggcacg ccctgccccc 24660
tggggaagtg ctgaggtcgg aggtgggaag tgaagggagg gggaggtggg aagtggaggg 24720
agtgggagtc tttagtgtgg ttttggtagg aaggaaagtg gttttcatag gaagggaagg 24780
gcgaagcact gtcggcagct gagctggccc agaattgcat agtctgaaga aagtcagtgg 24840
```

-continued gtttaggata tgggtgtggt ttctaattgt ctggtatcgc cctggggtgg tttagggcag 24900
cggaagattg gcttgggtgg gagagctcca taaaggtggt agtgggtatg agctctagat 24960
caggtagttt gcatatgaaa agtgtgtttg caggcaaggt gtgtactgtc actaggaatt 25020
agctagtccc gggaggggca gtccctcccc atatctgcaa gtcccccaag atgtcgacgc 25080
atcttaaaat acagaaaaac ttaaaaaaca aacatcatta atacacacac atacacagaa 25140
agacacgcat gtacaacttc acatgccatt tcatgacatg caaggaaagc gaccattctg 25200
aagtggatgg tgggggagga ataggatttc tggcctgcag tgtgttttaa accctttcac 25260
agagagtata ttgtttgcct ctcttctttt cctgtgtagg aaaccctgat ctagtgctac 25320
ctggtggaaa tagggctgga gagaggaaaa gtcccgtgaa gaactagtgg aagaactagg 25380
ggtagaactc ctttcccctg gctctgggtc ctgggtcgcc tttccctctc actcccaaac 25440
ctgccacgca ccccacagct ggctgcccca gctcttcagc actttgtctc gtgcttttct 25500
gccccctccc ccacttacat gcacaggctc acgtggggtc aggcagctgt tcgtttgcag 25560
cgtgcatgat accacctggc agtgtgataa acaagaaggc agcaccaagc ccatgcagag 25620
agaggtggtg agtgcctgta accccaagat gcaggcagtg tccaaaaatc acagcctgaa 25680
gtcgtgctgc tcctcacagt caaataccaa gtcctgcaaa cccatagctg ttcctgaagc 25740
ttccatgagg aagggccaag ctcaacattg cggcagccca ctgcccgtgg ctggcacttg 25800
gcgcctgtct tcctgacatc atcctctcct cccgacccta gggcctcttc tctgtgcttg 25860
tcagttcaga atcattgtta tcttgcaaat acatcactcc agaggggtta aaactactat 25920
atataaagcg acatgatatc gtgtcgattg cgttcttggc agagctccag cgctggagac 25980
gtcaggctgt ttgctaagca ctgatggtgc tgcctgaggc tggggacttg gcattctgtc 26040
tccccagagc atgccaagag caagcgaatg aaagctgcag ctgagtgaag ttagggtcac 26100
caggaggcct ttaggaccca aaattgcaga cgccctgaag ccaatgggaa gggcgaagcc 26160
caggagcaca cgcagtagcc gtgccctaat gtatggggac tgtccaaggg cacaggtcct 26220
ctgcggcctt gggatgattt gggtggcaga gaggtggaca aagtggctcc aaacttcctc 26280
tcaaggcctc agtttccaaa acttgactgc ccataggatg aattaagtcc tctgtctagg 26340
tcagaaccct agacacccat cccgctttct tccacgttgc tcttctcaca gtttgacccc 26400
agactcctct aagcagcccc ctctgagcga ctgcgtgtgt gctggtttcc tcccccgacc 26460
ctcagcaatt gctgtgtgcc tggtgccatt tgcccatgag aactcctgaa gagccacgag 26520
caggcctcct gggtccgttc agatgagctc cacgctagcg tgccacacac cccacatgct 26580
gccgatgaca gtggccggag ggaggcagca gaagagctga tgcccggggt cctccccttt 26640
ggtgtgactt gctggttctg tccccaccga ttgcctgaag ccagaaggaa gcagagttgg 26700
ccactgccct tccgcaagag aggaaactgt gcctggcggt gctctcagcc cttgtggact 26760
cattaatcca cataataact cgataagttc gatgctatta ttagctccat tttacagttg 26820
ctgaaattga ggcgccagaa gctaagcagc ttgctcaagg gcacagggtt cgtaacggca 26880
gaagtgggca gggtctcagc ccaggcaccg ggatttctta cctttaccac ccgacggtaa 26940
gctaggacag gagggccaca ccgtcattgg tgcatgagcc cttccgatgg aaggacagaa 27000
tttggagaga agggacgcat ggaaaacaag aatcccaatg gccctgattt ctcctcttgc 27060
taggactgct agatctacat ataccttggc aactatgggc aaaacccacg agaataaaat 27120
gcggtgaaat aggaagttct gcaccgagat tcagagaatg ccttacgtaa ggccaggagg 27180
gaagaggccc cgcttgactg gagggcttga gaactccggg agctgcctca ggctcctgcg 27240
ggcccacagt gggccctggt tgctgccgca gtgctgcggc cctggggctt tgtggcgtcc 27300
acaccacagc ggggcagtgc cacgtgctct gctagcccag ccctgcacag ggcagtgtgg 27360
ccagctccct ccagatgagt agggctaggg aggggagggt cgggacgcct tttcatagga 27420
aagtcagcac attcaggaac tgaggatgca atcttggaat atgggcaact gcgctcaaat 27480
agctagaggg ctgcaaaggt gggaaggaag aggttatgtc tgtgtcatca gagctaggac 27540
cctcccagag aggattccag ggctgcagat ttcaacctta gagctaacag gtcaggcaag 27600
gcgggggtct gagcagcccc tgcagcgggg gaggaggagg gtgccctggc agggtgggtg 27660
gcgtcccgct ctgaatccag ggccgtagcc ggcgctctcc tcccacatcg ccggtctccc 27720
gactccgcag atgagggcag tgacccccga cgcgaaacgc cgcccggcgc cgaccccagg 27780
gagtactgca cgtctgaccg cgacatcgtg gaggtggtgc gcaccgagta cgtgtacacg 27840
cggcccccgc catggtccga cacgctgccc accatccacg tggtgacgcc cacctacagc 27900
cgcccggtgc agaaggccga gctgacgcgc atggccaaca cgctgctgca cgtgcccaac 27960
ctccactggc tggtggtgga ggatgcgccg cgccggacgc cgctgaccgc gcgcctgctg 28020
cgcgacaccg gcctcaacta cacgcacctg cacgtggaga cgccccgcaa ctacaagctg 28080
cgcggagacg cccgcgaccc acgcatcccg cggggcacca tgcagcgcaa cctggccctg 28140
cgctggctgc gcgagacctt cccgcgcaac tccagccagc ctggcgtggt ctacttcgcc 28200
gacgacgaca acacctacag cctggagctc ttcgaagagg tgagggaggg cccgacagtg 28260
agcagcggga cctccggctg cggggagtgg aggggcttcc cgagaagggg gtgtgggtgc 28320
ggaggcgcgc gcagggggaa cccgggaagc cgggctggga gcggggcagg cagcagagag 28380
ccagggaaag ggatggaact gcgggctaaa gcatccccca caagttaggg ggaagacagg 28440
tggctctgga gcccctaaac catattcctg gccctagagg tatctcctga atgggtttgt 28500
gagtaggtca ttctgcgtga ctaccagaaa cctcttaggt ggaacagttg gagctcgcct 28560
gagtatatgg gctgtgttag tctcggggac aaggggagtc acttcacact ctagagcggg 28620
gagactgaaa ggttttagac aagggagaaa acagcagcag ggccacgctg agaaggggaa 28680
gaccaggccg tctgagaggt caggtgtccc cggcagccca gggcaggttc ttctcaggtg 28740
cccaacccat gggatgggtc ctgggggcag ggctgtactg gacaccccct aggtggccgc 28800
ggctggccat gggcatagat agaggtggct gaaggatgtc gcctcccttg ggcacgcgcg 28860
gccgtcctca tctgcagtgc cggcgccctg actctggacc ccccccttgt agatgcgcag 28920
caccaggagg gtgtccgtgt ggcccgtcgc cttcgtgggt ggcctgcggt acgaggcccc 28980
acgggtgaac ggggcaggga aggtggtcgg ctggaagacg gtgtttgacc cccaccggcc 29040
atttgcaata gacatggctg gatttgccgt caacctgcgg ctcattctgc agcgaagcca 29100
ggcctacttc aagctgcgag gtgtgaaggg aggctaccag gaaagcagcc tccttcgaga 29160
acttgtcacc ctcaacgacc tggagcccaa ggcagccaac tgcaccaagg tgagaccctc 29220
cgcagaactg acagctgtga tgcaatgtct caagtacatc cagaccctcc ctacagatcg 29280
ggagaaggaa acagaggcct caaaatagcc tgggctttct ggaacccccct cccaggaagg 29340
cagtgtatca cctgtaaggc agcgacactg cggacaggca gggaaaggga gagcaatggc 29400
cactggggag ttataacctc ccacagaaca gccgtgctcc agcacctccc tgctgagcac 29460
tcatgcacac acacatgcct acgcgtgcac acatgtgcgc acacacacat gcagatgcac 29520
acacatgcac acatatatgc aggtgaacat gcacagacat gcacatatac acatatgcac 29580

-continued

```
atgaacatgc atacgtatgc acacacacac acttgggaag tcttggggct tctcttttct  29640
gtagttctag acttcccatt tccagcaggt attccgaagg catcacatgt aaaaacagca  29700
aaaatgaggg ggtagtcgag agccacagaa aataaataaa aaacaattga gaaaatcttg  29760
atggaacaat tgaaaaactc tcgaaggaaa aggaggggca ggagaaatgt ttacacagtg  29820
tgggagggag cagggaggca gcagagtgag gtcaggggcc tgtcccacca tgttttgcat  29880
ctctgggcac acagatcctg gtgtggcaca cacggacaga gaagccagtg ctggtgaatg  29940
agggcaagaa gggcttcact gacccctcgg tggagatctg agcctcagga tgcaggtatg  30000
ggcatgacga gggtgggcca cacactgggc agggcggcac caggttgggc cgaatcaact  30060
gtctcattct tttcctcttg ggctttcact gtggaggaca gggcagatgt gggcaggagt  30120
ggagggcgtc gtcaccacag tccccttccc actgggccac ctgaaagtat ccaggcatta  30180
actttcaccc acgcagctgg gtccttctgc caccagactc ttcagagggt gtcaccttcc  30240
aaacatcttg ctgatttttc tgctggcagt gacgcctgca ccccacaagg cactgccatt  30300
cagactctcg ctggccagcg tctgtccccc caagtctgcc tcttcccctg tggattcctt  30360
caccacgtgg ccatggtgag gactcacgga ctcgctgctc cacagcaatg agcccacggc  30420
tgtcatagtg agaggtagcg cagagtgaca gcacggaccc agagcccacc tcagctccca  30480
ggacccctgc tcttcactgt ttgacctgac ttgacttttc tgggcctcag tttcttcatc  30540
tgtgaagtag gttgctgaga gcacctagaa cagttcatgg cacttaaatc tcatcagtgt  30600
ggctattttt attcaagtct ttaaagccct ctctggaagt aggccacagg atccacctac  30660
acttcagaag caaagaaatg atgttgagag aagctaaatg aatgttccaa ggtgacacac  30720
tggcacgagt gaattgtgct gggtggttgg caaagccagg cattttcagg ggcttttctg  30780
tgatcttatc ctgtctctta aaagcagctg gtactcctga ctccctactc taggttatgc  30840
caaacagagg ttgaggcctg agacagacat ttgtcctctt gccctggagc taagcaatag  30900
cttctgtatt gtgtttgccc gcagaggacc acagggtgtc actcagtcac cttggccagc  30960
gccacttaga atgcatctgt accgagcctc acttctgcct cctgccctca ctgccctcac  31020
tggaagcacc ttccccacct gcccctcaga aaggccccca caggacctgg gggcctgggc  31080
tttgcagagg tcctggtggc cctgcctggc cattccctcc ccggccccac cctcagccga  31140
cacctcactc attcctcctc tcccctcaca ggagcctcct cctcagaccc tgttcttggc  31200
cttccatcct ctccccacgg ctgatggtcc ctccaaggcc gactcctaag gaatcaccat  31260
caccctcctt tctattctgg gggcttctga gagagcccag cctgatgcca gaacaaagga  31320
cagagaattt aagcacagaa atcccagacc tgttgttctc tccatccagc gtgaccaggg  31380
cccgagagac ctgatggcca gggtggggtg tccagcacca gccaagctgg tgctccagcg  31440
cacctcccca gagctccccg cactgacggg gctgcaggag caggtgcagt gggcgcccac  31500
actggccctg cagtgatgca gggcgggagg gagataagaa gaccccgcag tcaagtggag  31560
catggccctc cctggctccc tgtccctggg ctcagcacga ccacacagga cacccagcca  31620
gggaattctg aagaccagag agcagcccac gggcatcacg agcgctctgc tcctctcctg  31680
ggcccctgct cttcccgaga gctgccccca aatcagacat acctctgtgg ctctcctctg  31740
gttcacgttt acagagcata aggctgtctt ggatcccaac aggcacccag ccctgcatgg  31800
ggggagcctg ggcctaatag gcaccccctg tacctcaggc tgtggcggga gcagagtccc  31860
cccctccggc ccctcttcct ttacccccttc tcctccagca gtggcaaagg ggtaggctct  31920
agagccagca caggtcactg cctgacctgg actaagaacc ccacggcccc actgtccaca  31980
```

-continued cactgcctcc ccaccgccca cctcggctgc taggcccctc gcctggactg gactggggag 32040
ggaaagcgcc ttttcctgca gctcttcaga gccacagacc tcagggtgga gtgagcccat 32100
ggtgggcagt gggcaaggcg gtgggtggtg ggcaaggtgg gacctcctgc agcctggaaa 32160
gaggagggag gccaaggcca ttccctaact ccctcctgcc cctggtctga ggaggaggga 32220
ctctggagta gcagaggggc tgggaaagag ggggcagggg ctgctgggac actgagcagg 32280
agggaggcct gagcacactg ctttggaaat tattctaaac acaaaaaagg gaaagaaaat 32340
gttatttctc cctaagtcag gagcatgcag agctagccca cctcatgtcc agctgtccac 32400
tttccatcct ggagaaagaa cagtgtgcct caaactcctg ccctccccag gcctctgggg 32460
cccactggaa agggctctga ccccctggcc cagccgggct ctctagtggt gatccggctc 32520
attctcctgc aagttggaag cacaattttc cccccaagtg gaggaaaagg aaagggcccc 32580
agcctactga agaggtgttt attttttaac taacagcctc ccaccccatt aagactcacc 32640
aggagaggtc tgagggccat tcagaaccca ctcctgagtg ggtgggtggg tgggactcag 32700
tccagagacc taacattcag aatatagcat tggttgccta ttttgagatg gatttaatct 32760
cccacagtat tcatgagacc atctgatgga atcagatccc tgagccacct tgcaggacgt 32820
tttccccaac ctcttacacc ctggatgtca ctttggaaac caagcccttg gaagcaagtg 32880
gggtggcatg ggagagaagg gaggaggtgg gcacaggtgg tgagcttatg tgtgggcact 32940
ctactgcctc acagaagcca gccaagtgcc aaggtcagct tggctggtct gaggccacct 33000
tcttagccaa aaacctaggg ttcattttca ggactttgat aatgaacaac aaaatgggga 33060
cttctttggg cagatgctag gtcagttgtt ttcacctaat atcctctttt agctgcatgt 33120
atatttattt ataattataa ccctggtgga ctgcagcctt catctttatt gggaatgagt 33180
ttgttataaa tcagaaatgg gtccatgatg accactgttt tccaaaccca gtctgttccc 33240
tgctccctcg ctggcaagcc ccaccacaca ggagtgaggc caggggctag gagttctaag 33300
aacagaggct ggggtgaggg tggcacccag gcagctgcat ctggtctgtt ttaatttaac 33360
tgtatttaat ttgctttcaa aattaaaagt caaatacagt ttttaacagt cctaa 33415

<210> SEQ ID NO 1107
<211> LENGTH: 18388
<212> TYPE: DNA
<213> ORGANISM: Homo sapiens

<400> SEQUENCE: 1107
ggagtttgag tgagagatat agggaaggaa gggaagtaag cagtcacaga cgctggcggc 60
caccagaagt ttgagcctct ttggtagcag gaggctggaa gaaaggacag aagtagctct 120
ggctgtgatg gggatcttac tgggcctgct actcctgggg cacctaacag tggacactta 180
tggtaaggca gaaagggggg cctggctgcc attgctggct taggcaaaag gctagagggt 240
tggtgtttaa tgtctactat ggaaagccta ttcctactgg gcaggtgagt cttctcagcc 300
aaactctgca ggctctctca gccttgagca aaacggatgg atgtagttga aggctgctga 360
agaagccaga aggcaagttt gggcagaaat tgaaaaagga tttttctctt ggaaaacatc 420
tgcattattt tctagggctt gtatctcagg ggcatcaaga aggttcccaa tgacatccga 480
atctttcctc catctgctgt ctctcatcta aaattctaca attggactta accactctgc 540
ttccaagctt tggtctctgt taaaatatac agcccccgaa gaaggagtgt tttctaagag 600
ttggatagga ctatagaagt aacctatacc acccttcatt gtcatgaata agtgctcaga 660

-continued

```
aacatccagt agtgattgag atttcactgt tcactacctc cccagaccat ctagtccatc    720
caggagcagc tccaactgtt agaaagttct tatttgtgtt gaactaaatc cagttccctc    780
tgacttccat ccaaaaaccc cagctttgct tcttggggct acacagaaca tagatgcttc    840
cttgccctgt gatagccctt caaagccctg aggacaagta ctatgtctcc ttgactcttc    900
tctcctccaa gctgaacagc cccagctttt tcaactggtc ttcataggac ttggtttctt    960
acccattcct gggataactc acttccctat agacatggct caatttgtct gggctattta   1020
tgggctggat acaaatccca aaggaggatg gactattcca tagtggcatt atttccttgg   1080
agcttgggaa gctctatcct catctacact cctgagaagt gagatggatt ttcaggaaac   1140
tcaacctggg taacagctaa gtgagatcca atatagggta aagggggatt ttgctgcttc   1200
cctatcatcc ctagagaaaa aggctggata ggtgttagct tggtgtcact tgttaggtca   1260
gaaagaatcc agctttccgt agctgactct gattaggtta ccctatcctg gggctctgtg   1320
acccatcaca ctctggaacc tcagagttag aaaagactct gaattaagtc aaccaagaga   1380
aaaaataatt tgcccccaag ccaaagagca ttagtggcag agttaatgct cctgaaaaaa   1440
catttttctt tctataacta ccacatttcc attctctagc aggttttata atgtatctct   1500
ctaccttctc caagtctgtt ggtttgagct agggcttaag cctggggctt gagggagcat   1560
tttagaaatg ttaaatttaa atcctttgtt tgtgtgtgtg tatgtgtgtg tgcattcatg   1620
tgtgtgtgtg tgtgtgtgtg tgtgagagag agagagagca ctcatgtgtc ttgttccttc   1680
cccagcctat gagcttttcc agacctggaa gcaggccttc catttgtaca caggatctta   1740
tactatagac ctcaggctca ggttatgctg agctgcaaat aataccttcc ctctccctgg   1800
acctcattgt tcctagccca tctgtacagt gaggaggttg acttgactgg tcttaaaggg   1860
gtttctcagc tggacaactc tgtgggactg cagcttcact gctaaaaacc ctgtagcggc   1920
cagagtaagc tgctagcctc ttcctgtggg gctaagagat atgtcaagat aatcaaaatt   1980
taaaaaattt ctaatattca cattttatat acattttaaa catttcagaa acattttata   2040
aacatctatt atataagtta atcctccatc caggaggcat tccaggaaag ggagagaagc   2100
cagtcatgtg gggaatggg atagagatat ggaaaatgtc aacctctttg tgatgatggg   2160
aggaagggga ttcagaaaga gacctagaat gggtcttata aaggagcaca cacctagtaa   2220
attcaacctt tcttttcttc agtgccatta cacaggcatc agacatttgc ttttataagg   2280
ctgggtctca ggaccacatt aagctcaata ctgtatatat acttatcagc aataagtata   2340
tatacttatc agcaataagt atatatacgt atcagtaata agtttatata cttagtaata   2400
agtatatata cttatcagta ataagtataa tataatataa tgttatatat tatatataag   2460
taattatcag taataattat ataattatta tatattatat ataagtaatt atcagtaaag   2520
tggaagtaat aataaaggaa gtaatataat ataataagta tataaatata taatataata   2580
taatatatta tgaatatatt atattatatt attattatat aatatatatt atatattgta   2640
ttatataatt attatatata ttatattatt atataattat attatatatt atattattat   2700
atgatatata ttatatatta atattattac ataatatata ttatatatta tattatatta   2760
ttatataata tatattatat attatattat attattatat aatatatatt atatattata   2820
ttattatata atatatatta tatattatat tatattatta tataatatat attatatatt   2880
atattatatt attatataat atatattata tattatatta tattattata tattatatat   2940
tatatattat attatattat tatataatat atattatata ttatattata ttattatata   3000
atattttata ttatattata ttattatata atatatatta tatgatatat tatattatta   3060
```

tataatatat attatatgat atattatatt acattatata ttatattata tgatatatta 3120
tatgatatat tatattatat gatatattat attatatatt atataatata atataatata 3180
tcatataata tatcatataa tataatatat catataatat attatataat aaaatatata 3240
atataatata taatataata tattattata tatataatat attatataac atattatata 3300
tataataata tataatatta tataatatat tatattatat ataatataat ataatatata 3360
ttatattata ttatatatta ttaatatatt ataattatat aatatatata ttatataatt 3420
ataatatatt aataatatat cgtattatat atattatatt atattatata ttatattatt 3480
aaaatattat ctatattata aatatattat attatatttt tattatatta taatattact 3540
tcctttatta ttacttccac tttactgata gtgactcaaa gttcagatag gtttagtaat 3600
ttacccaagg tcacacagag agatatgtgg taaggcagac cttgcgctta gatcagtgtt 3660
attcctacta catcatacag tccttcatta ccctcctgct ctcattaggg gctcctactt 3720
gattctaggg gaactacaag gaaaggtaga aggtacaagt cagtggtatt gtggtttact 3780
tcactttgga gatcagaaaa catgaggaat agtacaatgt catttttctt gtgatgtcct 3840
gtacctataa tccagtctct ttatgcaact aatgaagcag gaggaggaag aggagataag 3900
aataagaaaa agaagaagga agaaaaaagg aacggaagca taatggaaca atgagtggaa 3960
gaaataaagg aggaagaagg gagaggaaaa aaaaagtaaa aggggaaaaa acatgccatt 4020
ttgggaagtc tagttaccaa ctctgtccta ttcattctgg gatggaggag ttaagcctga 4080
cctacttcca gaagtgattt tcaaaactga gaaattgaga ctatctagca attttcttga 4140
taggccagac tgagctttgt gagaatttcc agcaaattcc cagggaggaa aaacacaacc 4200
caggcctttc agctccccta aggtcagaag gaagacctgc atatgcatag acaaaggcat 4260
tttcaactca cagcagaatg ctgctttgtt gcccaagagg ggaatgtgag aatgcttttc 4320
agagaagagg agggacattg ggaaagtcca gaggaagatt aatgggaaat agcctattaa 4380
accaagaggc tcagatagtt ttcatggggt ttaagcatgg tatgtttgtg cttgcatgtg 4440
gccaaaaata tgtatgggca tgtgagtcca tgataatgaa aagctgtatc tgcaatcaca 4500
tggaggtgtg aactatctat ggcacagtga aacccactac ctggtgaaaa ttcaccacca 4560
gctggaacct ataattacat aacttctatt tctattatag cctattaaca cttgaccacc 4620
taagattaga agggacctta aagagcaagg ctaagaccca aacaaagcct agaacttccc 4680
ccagacagtt taatccatcc atagacagct ctgattaatc acaaagttcg ttctaaggca 4740
aaccatctgt tctgcgatgt gaaaagcaga caagaataac ataaaaagaa atagaattag 4800
gaaaatagag caaaccaaaa tctgcccctc ttgtattccc attcgtaggt ctgagttctg 4860
ctctctgcca aattcgaagc attccagaga gtatgtagtg gatctagcaa catggactta 4920
tgttatttat tcttttctac tcaagggctt tttcttgact aaaatatgct attgatgttc 4980
taagggtccc tggtgagggc acaggctaga ggcttgattt tatatctcta ttaacagaag 5040
tcctgatgct ggacagtata ttctgggagt tagaacgcat acactcaacc catccaaaag 5100
atgtcatctt ccatccgctt gactgaatac tgggatttct aggctcaata aaagactttt 5160
attcaggaat acctcatatc tttgaaacca cctctcttag gagagacatg aatatattgc 5220
ctaaatatac ccaccccaca ctcctggccc cagctaaata aaacaaaaaa tcttctaaat 5280
aagagcttat ggatggaaaa ttctgatggg aggcaatggc tgtttcaaca tccccacctc 5340
cttccccacc cccaccccca tccccaaggg tttccttctc aaacacgcca aggagcaatc 5400

-continued tcccattgct tctatcacca cccctactac agccagcttc aggatttcac tcagaacctt 5460
ttcctctcta gaccaaaaat ggatgcaatc ttttccccct caagatgaaa ttttcctatg 5520
tatccttgct aagaactaag agaaaccaaa aggaaaataa acaaaagaaa tcagaaaaaa 5580
agtcaggttt acaaagtgca ggttttgaat ttaacaatag ctaatgattt tgttaaacag 5640
gaatgtgtat ccagacttct tcctcacact tggttccacc ctcagtattt ccttttgcct 5700
gtcttccaga gaacatctta gggttgggac cccactcact gaggatttct aagggaacaa 5760
gagaagataa cagggcagag ggccctttct tgctgatctc aaaagcctcc acctttctcc 5820
aggtgcaaat ttacacaaaa tgaaatagtc cagacccaaa tgcttagcat ttttgcttcc 5880
acatctcttt tggaaaatgt gaaaagaaaa ttttttcatg gatttgcaga atgacagatt 5940
tgatagaata tctagagcac ctaccaccca aactctccac attatagatg aagtaaatga 6000
atcttccacg gtaagaaggt gacttaccta ggatcacctt catagcaaga cagtaacata 6060
aaaaggactt gaaactcaca agatctaaac aatgttaaag gctttcattc tgaagactgg 6120
ttctgattga tgagaaggct ggcaaagagc aaaagggcac aggtacacaa aagtgtgata 6180
gaaagaaagt tgagtggcat ttctcagaaa ccttttgagg tttgtcactg tcaccttagt 6240
tgccaagtag gtatgccatc tacgtttgct tctttcctct gttccgcctc ttcaggccgt 6300
cccatcctgg aagtgccaga gagtgtaaca ggaccttgga aaggggatgt gaatcttccc 6360
tgcacctatg accccctgca aggctacacc caagtcttgg tgaagtggct ggtacaacgt 6420
ggctcagacc ctgtcaccat ctttctacgt gactcttctg gagaccatat ccagcaggca 6480
aagtaccagg gccgcctgca tgtgagccac aaggttccag gagatgtatc cctccaattg 6540
agcaccctgg agatggatga ccggagccac tacacgtgtg aagtcacctg gcagactcct 6600
gatggcaacc aagtcgtgag agataagatt actgagctcc gtgtccagaa acgtgagtca 6660
ctatgggggt aggaaagcac tgataatcaa tgaatcaata gtggatgtaa ttctagaaaa 6720
gcctgaaaaa tccagaggcc ttcgtttata cagaggctct ccacaggtat atgtgcttat 6780
cagaggaagt ggacaggcag aggattctta gggtcagcat tcccatagtt aaatttagga 6840
agtgctggga agggttcctg acctgcaaat ctctatccct tcgagtgtcc cagaaatgcc 6900
agtatccatg gactagttac cctccttggg ctctgggctt tacaactcaa aaatgagtac 6960
atttaatttg tagatagatg ctgatagaga agctctgggg aaagggaggc agaggttagc 7020
caggataagt ttgcttgctg gacaatttta caaaagtctg gccctgataa tccacaactg 7080
caggtaatca aaagctctac ttgagcccca gaacaaacta cattaatttt aaaggtcagt 7140
tgatttttac ttccaagtat tccaaaaccc cgggtaatac caaaaagtac ctaccttcaa 7200
aggaagccat tttatttgta ttgccctttc cttcttattt cctccaaagt cagaagcccc 7260
ctttagttcc agttgcagat atatgcatgc ccttacgccc aacaagaatg attcagcctt 7320
ttggtcccat atccttatga ctgcccagag tttcctgtct tgtcttttct ttgcagtctc 7380
tgtctccaag cccacagtga caactggcag cggttatggc ttcacggtgc cccagggaat 7440
gaggattagc cttcaatgcc aggctcgggg ttctcctccc atcagttata tttggtataa 7500
gcaacagact aataaccagg aacccatcaa agtagcaacc ctaagtacct tactcttcaa 7560
gcctgcggtg atagccgact caggctccta tttctgcact gccaagggcc aggttggctc 7620
tgagcagcac agcgacattg tgaagtttgt ggtcaaaggt gagcggccct ctttcctggt 7680
gagcatctta acacacaagc ttgaaacaaa gatacctcaa aggtgccct tatgcaaaag 7740
aagaattggg agaggaggat cccaagcagg caatggttgt acaatcacaa agaaaaaaaa 7800

-continued

```
cttggactgg ggacaacagg gatagagaca ttgcctatca tgccataggt taagtagata   7860
aagacggtaa aggaaagaga gatttactag cacattgtat ttgccagata caaagtacaa   7920
taacttgaca cacattttct cattgaatcc ccacaactgt cccatgagat agttatcatt   7980
actcttactt tacagaagag gaaacagagt cagaaagggg aatctacttg cccatggtct   8040
cacagcaagg aagtataaat ctggatttgt actcagattt catgctcttc ctactatgtc   8100
tgattgtttc tcatggttga atctatatca gatcctgggc accctttgaa agctgttgtt   8160
ttttgtttgt gtgttctgtt tgtttggtta ttgttttgct tgtttgatta ggcttgatct   8220
aatatatcta catgctttct tttaacttcc ctcccccact tcattgtaaa cccaaataca   8280
agttctggtt gaagtatcct ttaagatggg ctcttgttaa tcaagatctg actatttctt   8340
acagcactgt cctgggagca ctacaaacta tgcatataaa gactgtaagc tgaggcttaa   8400
atgaagagtc cagcagtgat atgtccagat gagttttctt agctttcaag agatctcctt   8460
ggaaagaaag acaccccaac aaggttacca ttgcccaaaa catgttggaa actaactgat   8520
tttagggaat tgccctcaga accatctgaa aattattgtc ttctgaggat agttctgtgt   8580
aaggagaggg cgtaaaccta gcccaaatgg cttattacca tttgggctag gagactgatg   8640
ttggtttgag actcttgtgt ttgcctggag gaatttgttt cccaaagtta agctgtagtg   8700
aggatgtgtg tgctgtagat catggtttgt tagttttggg aggaacaaga gtggtccgcc   8760
ctgaaagtta tatgaacagt gtcccagttc tctaagagct gacagtctgg tcaagcagag   8820
agggcagggc gtgaccagaa agcccaagaa tgtatacttc ataaagagac taattgaaca   8880
ttcttgcctt tctgtgagtt acttctcaga ccacctaggc aagaacttgc tcacagtaaa   8940
ccctcctgtt tattccttct cacagtcaat gcttattaca gtgctgttaa gcagtgctcg   9000
ccattgcccc ctactgacag ataggaaaac tgaggctcag ggaagttatt ctcagccttc   9060
cactcttccc tgctctgtga gccaacgtaa tctttcctgg ctacctctac ctgcctccct   9120
gtccacccaa ccttgtcccc tgagtctgac cccctatttc acctctgccc tacggaactc   9180
tcagcccttt caccccttcca cctcactctg cactgttctt tagttctaga atgactctgg   9240
aggccctgct tttgctcatg ttcttggact gctgagcttt gctgacgaac aaaacaaaac   9300
acagatatga attgactcca cttgaatttt atgctctgcg atatgtactg cctgacccca   9360
tgccgtgtgt ctatttgctt atctttgtct cattcctcat agcagctttt cagcacattt   9420
ctaccttatt tcaggccccc agccttgctc ctaaaagata aggtaacttc cttcctctgt   9480
aagaaggtcc agaccctctt catatgtgaa ttttatcaac taccctcctc tctgccttga   9540
tatttcccta tccatttcct cttggctcag agtaaggtat gctttgctcc tctccacaac   9600
aagcccctcc tcctgaactc ttaacatcag ctactccaat gccctgcaat accctttatc   9660
ctctacctaa gccaaataga tatgcatgta taatatatgt atatatgtca gtatgcaagc   9720
ctaatacata catatatata tgttattttt caaaaatctt tctctccatc tgccacctca   9780
tctctcctat gttcactacc aaccttctca cgaaggtagc ttccaccagc tgaacctctc   9840
aattcattca ccacaacata actttgtaat ttggggtcat cattaacctc catatcacca   9900
aatcccaaga cctctccatt catacttttc ctcctcaaca tctgtgtagc agtggatcct   9960
gttggccatt tcttccacct caatattctt ttaatcactg ctattgatga caccaactta  10020
tcttggttct tctaagacct tcctgaatga tccttctgag acacctttgt tggctctttt  10080
ttcattcact ccttaattgt aaatgttctc aaagactcaa ttcttattca tctctgcatg  10140
```

-continued

```
tatttctata ttatcaggag attttattta cttctgtggc ttcaaatatc acctgtagtc  10200
tgatgactct ccaaccataa tattatctgt atttattttt tcctgactgc tagatcccag  10260
tgtctagtta ccttctggac agcttcattt ctaatttcag cgtgttcaaa actgatcgta  10320
ccttttactc accaaacctg ttcctcaaac ctgttagaaa acatagcagt acctttgact  10380
cctccttctc ttttacctcg catcgtcaaa taatcatcaa tattaccaag tgctgtgaat  10440
tcacctactg aatcagatac cttattaggc tctttctttc tcttcctata ccctcatggt  10500
ctcatattct tttttaaaaa acaatttcaa tcatcttcta aatgttctcc ccatgttcat  10560
acattcttac gaagtcatca acttattcaa tatttattga gtatatattt tatgtcacta  10620
gattataaaa ttcaagagtg cagaattcta cctgtctact tcattgctgt ttttcagagc  10680
ccagcaaagt atctggcaca aagaagacac tagacactag atgaatactg tatttgttaa  10740
tgaatgggga aaatatgcta ttgccttacc tttgaaaatc ctaccacact gttgtcagaa  10800
ttatttccaa aaaaaataga ctgaacaatt tttgcttcct ttctcaaaag gaagtaaacc  10860
tttctcaaaa ggtgtaacct tctgttacac cccatggatc tttccaacta aagaacaaag  10920
cccaaaccct tttagtctgt tttcagccta cctatccaga cttatctact aatatgtttc  10980
gccacatcta aaacggagca tgctgtttcc tctgctagca agagggagaa gcttatggtt  11040
ttctcatgtc ttttctgagc aggtacatgg ccctgtgctt gtgtgtggcc tcctagtttc  11100
ccagaactgt gtcagaactc ttcaaaatcc ctatggaaat cttattcctc aaccattttt  11160
aaggctattt tggttagttt tttttgtttt ctcgcctatt atccattgcc tcaggcagct  11220
gtgtgacaaa tgctacccca tccctgggga gaggctctta gcactgggtg accaataaaa  11280
caagtctttt gagtcaggtc tttcagggaa ccaccagaca ggccaaataa tggcaattat  11340
tcaaaaatga agtttgttgg gctcactcca gcacctggaa tggggttgta tgttcaagat  11400
tacctctgag gtagaagggg taaggggact aggagaagtt aaaacagcac aaagcttgct  11460
gttcttacca aaactgggat atttttcttc cataaatcct gtctaaggtg ctgcaaacct  11520
ttggctattt tgcaaaattc taaaaaaaaa aaaaaaaaaa aaaaaaagtt gattacgtca  11580
aattttgcat tatttcactg atgttgttaa agggtaaatt tctggaggtt attatgtcac  11640
cattttcact gatgtcaccc attgccactt tctttatgat acttcccaag tttctctcaa  11700
gagaattaat tactaggtct cagttagaag ttagtaaaaa taaaatatat tttcccatcc  11760
aagttgactg actctctgaa ctctagctac aggttccttc gagatctatt aatcctgggt  11820
taaaaactct gtccttgatt gatgtatgaa agatgaacaa gcaacacagg acttaccagc  11880
atcatgacag aagtgttgag gcaggtccaa gtatggacct gaatggcctt tacttacttc  11940
ctatttccct agggcattaa actattcacc aaagggtacc aggtcccttc aatcggttcc  12000
cttttccttg cagactcctc aaagctactc aagaccaaga ctgaggcacc tacaaccatg  12060
acatacccct tgaaaggtga gttttgctag agtctgagga agtagtagag gttcaaaatg  12120
gtgtcatcgt agccaagaaa ggaatcacaa tgccatggaa tggctaataa acagtcactt  12180
ggttcctcag agagaacata gcagtaaagg aatggaaaca aaagaaaggt aacaatgatg  12240
aatatatact cttttttttgt gaaaacttct gaggcaaaag gaaagagagg gttagaatta  12300
ctcccattgg aaatacaaaa aacaagaaca ctaaattcta ttctgctcct agtttgactt  12360
gctgtgtgac tttgggtaca ttacctcccc tcgatgggaa ttcttctcac tgcccacacc  12420
taacagtaag aaatgaagat gccttatctc atggtactag tggttgataa catggtcagg  12480
taccctggaa agtacagcac aaatggccag ggaaggactc caacctttgc aaccatctcc  12540
```

-continued

```
tatctctcaa ctttttgaaa gaagagagac atctctgacc ctattctcta tattcatagc  12600
aacatctaca gtgaagcagt cctgggactg gaccactgac atggatggct accttggaga  12660
gaccagtgct gggccaggta ggaatattgt caggatttct atcttttctt cttgactcta  12720
agctttgtga ccaaaacttt ccccttatgca cactgttcta cagcattgaa atctgcaaat  12780
cattacctgc tatgtgccaa gcaatggtca agggcactga ggatgggtaa agtgggtagg  12840
atgtagagag agagatacag atccagagat gagcaaagtc agagtgaggt taaggggagt  12900
gataaatgtg ccctttattt agttctctgt tgtcatagta atatgctttc caaacattct  12960
gagcaagaat atggataggg acattatgac atcatgacct caaccaggta aggataatgg  13020
ctgagtgtca ttgcttgagc tcttaaccag ggctcttcaa gccgcttgaa gctgatttct  13080
gattcctcca aagccttgaa aattcccaag tcagggtctc agagattcaa atcccaaata  13140
aatcttttgt gtttcacctg catctgatag tcagttggta tgccttcaca tgactacatt  13200
gactgttgaa ataatagaac actctcacac caattgataa ttagctgctc cccttaaccc  13260
ctgagccctc cattattacc tggggctgcc ttgtcccatt cctcagaact ctctagacca  13320
cccccatggt catgcaacaa aaggtatacc aaggaatctc taagactcca agtctacagt  13380
aggcatctgt tgtgactggt tggaattaaa tagtttgata actatcactc ctggtactca  13440
ttctctgcct gtgtataatt gagagagtgg acttccaaat gctctttgta actctccatt  13500
cctgattgca gagtttttg gctatccctt ggcagcactc aaacctgttt tatgttccac  13560
atttgcattg ccatctttgg cttcaagatt tccatagctc cgttcctctc cgagaagaac  13620
atctactggg agaagagaag ttagaaattg cctcataggg agttggtttg gaaaaatgag  13680
aaaataacct tgggcaaagt tattagatgt tgggtctgcg ccctattttc tctaccaagt  13740
tttttagtac ttgactctct tcaaaagaga atatttcttc gatttgtacc agcttataac  13800
ttgagctctc tcagtcccaa caagacactc tgaggaccac aaatactgga ttcctaggac  13860
acgatatctt agagtctcat gaaaacaagc cagttgcagc aacaaatcct aagtacactg  13920
aggttccttt cctcacgcct ctctatcccc cctgacctag catcttagat tcagaatatt  13980
atagctaaaa gtgctttaga catcatccaa tcttttcatt gaacttatgg ggtaactaag  14040
gcctagtgac agtcaaagtt ttgtctaagg tcactgtatt cattttttcca tggctgctgt  14100
aaaaacttac cccaaaccta gtatcttaaa acagcataaa tatattatct tccacttctg  14160
gaaataagtc tgacacaatt atcactgagc taaaatcaaa atgtcagtca gcaaggctat  14220
gttccctttg gagggtttgg agaagaatta atttccttgt ctttcttttc tggcttctag  14280
aagctaccca cgttctttgg ctcatggccc ccttcctcca ttttcaaaac taacaatgta  14340
gcattctcaa atctctgttc ctttttacta tgtaaactaa catactgaca ggttccagga  14400
atttggatgt gaatatcttt agaggaccat tattctgcct accatagtca tacagaaagt  14460
aaataacaga tctaggactg gaagccaagt ccagttgatt ctttcagctt ttaggcataa  14520
tgggaatatg tgtctcaagt ggctcagtgg aaatatgttt tgagaaagaa ggaagctggg  14580
gacttgacca gagcgtgtga tgggaagaat ctttgtggct agaagtaact gaccagaatc  14640
ttaataaggt atgtagcatt tttggtgaag ctggaaagtc aggatattat tttctttttt  14700
ctaagggaag gtgaaaacct tctgtcttgg ccctatagaa agcatagaca actagctcaa  14760
atgcccaggc caatcagccc accagtgagt ctggaagaac ctgtttacac atggcatctc  14820
tttctcaagt ctttctcatg ggactggagt tttttctctc tggctagcta agaaggttag  14880
```

```
gagaatatgg aaaatgaaaa agaaaaaggc ctggcttagt ctaggctgtt tcttagagtt  14940
tttgtttctg gccttatttt caatcaaata ccacttgatc ttgttttacc ctctaggaaa  15000
gagcctgcct gtctttgcca tcatcctcat catctccttg tgctgtatgg tggtttttac  15060
catggcctat atcatgctct gtcggaagac atcccaacaa ggttagtgat gaatatgaga  15120
aggtggcttt ggctcatttg ttctttctgt cagtatactt gagcctaaat tctgtatcag  15180
gcattgtgtt aggcacttca agaagctccc agcctagttt gggagttaag gttggggtgc  15240
agggaggcag atgttcgagc aaacaatggc ataagactta cagaactaaa tgcactaggc  15300
tttggtactc agtgaagtac agccatcttt ctaacgagtc atcttgtaat gatgcaagag  15360
aaggagaagt cacaatccct ggcctcaagt tgctcacaat ttatttagga gattcaaggt  15420
agaaacatgg aatttatcaa tgacaataca tagcaataga ggctatgagc tcaaaaacta  15480
gagaagacaa ttaatgctaa agggatccag aggagaagag agtaatttaa ggcttgggta  15540
attagcaagg gatttcagaa ggaagaatat cttagaccac attttggagg atgaaaacaa  15600
gttgtaagga gacagtattt caggaagaga gaactacatc agcatagttg ttagggccta  15660
aaagacaact gagagtgggg tcatcaataa agaaaatttc tgtagatggg caacagggaa  15720
gtacagtggg aaatgaaagc ttattcctga ttatagaagg ccttaaatgc caggttaaat  15780
aatttggact ttcttcacta ggccttgcaa gggcactaaa tttaccaaat ttttcaagca  15840
tggaagtggc ataatgacag cacagttgtc agagccattt aaaaactatg aaccaaccga  15900
ggaggaaaaa aattgggatg cttgtttcta aaagaaaaaa atactagctg tctctcaatg  15960
cccagtgcac tagtcatgtt gcctagcatc aatttgtctt attctctgta gtatctctta  16020
ctcccaaata gcctggttac taccatggat ctgatggatt tccatcacca gaagggagcc  16080
ttgagtatct ccttctccca ggtttcaatt ataagctctg gcttttgcca gttagcatgt  16140
ttatcaccat gaggctgaac ttgatagcac atgactacaa accccagggg cactaaaatg  16200
aaagcatttg catatagcct tgatgaggct gggcataagc ggtaaccaca ttaaattgtt  16260
tctctctcaa aaaccttcca tggcttctta tggcccaggg gataaaggtc aaaatgtagc  16320
attctattca aggctctctg tgatgtgggt ctagccaatt ttctcaaccc accacttcct  16380
tatacctagt ctcatttcca aaaattcctc tttcctatct ctgtataagg gagacagcct  16440
cagagcatca atttaattta acataattac tgagcaccta ttgtgtgaca ggtgctgagc  16500
atattaagat gaaaaagaca cgacccttgc ggtacaggtg ctcataggcc aatgggcgag  16560
taagacacag aaatgcaggg ctctaccata aggcagaagt cctgtggctt cccttgttta  16620
ctttgttgtc atttaatgct tgcatttcca gttgcatccc tgaaaaatta taagcaccta  16680
gagggcagta caaagaaata tctgtctttg caccaaccta agcctttgag cctgtacgga  16740
atataggaca ctcctcctcc acagacacta gggggcaatg gtaaccaata ccatggtttt  16800
tcctgggtat atagtggggg tgagtgcatt tgggaatgtc ttgggtcacg gccatcagca  16860
tcaggctaat ccagtccctt cttcctggta tgtggcctga cagtcaagtt tcccacaagg  16920
actctctggg gatccttggg ggagattcct gggtaaagag caagtccagt tctagtgccc  16980
tcccccaacc cataccgaga aactgctcca gcccaatatc ctgagtccaa gatgacaaaa  17040
aggatagtga ccaaatgtgc ttccccttct tttacctgat aaatttgcat ctctgtgttt  17100
caattcacct ccccaatacc tcccagttgt tggaaagcta agacatatta aaatcccctc  17160
ctctgtaccc ttccctcatc ttttgactgg tacccaggat ccatgattga cctttgtcca  17220
cttgccatga aaacttctga catgattcct cctttttttc tagagcatgt ctacgaagca  17280
```

gccaggtaag aaagtctctc ctcttccatt tttgaccccg tccctgccct caattttgat 17340
tactggcagg aaatgtggag gaagggggt gtggcacaga cccaatccta aggccggagg 17400
ccttcagggt caggacatag ctgccttccc tctctcaggc accttctgag gttgttttgg 17460
ccctctgaac acaaaggata atttagatcc atctgccttc tgcttccaga atccctgggt 17520
ggtaggatcc tgataattaa ttggcaagaa ttgaggcaga agggtgggaa accaggacca 17580
cagccccaag tcccttctta tgggtggtgg gctcttgggc catagggcac atgccagaga 17640
ggccaacgac tctggagaaa ccatgagggt ggccatcttc gcaagtggct gctccagtga 17700
tgagccaact tcccagaatc tgggcaacaa ctactctgat gagccctgca taggacagga 17760
gtaccagatc atcgcccaga tcaatggcaa ctacgcccgc ctgctggaca cagttcctct 17820
ggattatgag tttctggcca ctgagggcaa aagtgtctgt taaaaatgcc ccattaggcc 17880
aggatctgct gacataattg cctagtcagt ccttgccttc tgcatggcct tcttccctgc 17940
tacctctctt cctggatagc ccaaagtgtc cgcctaccaa cactggagcc gctgggagtc 18000
actggctttg ccctggaatt tgccagatgc atctcaagta agccagctgc tggatttggc 18060
tctgggccct tctagtatct ctgccggggg cttctggtac tcctctctaa ataccagagg 18120
gaagatgccc atagcactag gacttggtca tcatgcctac agacactatt caactttggc 18180
atcttgccac cagaagaccc gagggaggct cagctctgcc agctcagagg accagctata 18240
tccaggatca tttctctttc ttcagggcca gacagctttt aattgaaatt gttatttcac 18300
aggccagggt tcagttctgc tcctccacta taagtctaat gttctgactc tctcctggtg 18360
ctcaataaat atctaatcat aacagcaa 18388

<210> SEQ ID NO 1108
<211> LENGTH: 34449
<212> TYPE: DNA
<213> ORGANISM: Homo sapiens

<400> SEQUENCE: 1108
tttcagccaa ccagactgga gcagctgcga gtgctacatc ttggctgtct gaagcgattg 60
gctcctctct ggggagtgga gggtgttcag ttattaatga ccgctgagca ggcagcacca 120
tgtcagtgtg acaactgatc gggtgaacga tgcaccacta accaccatgg aaacaaggaa 180
aaataaagcc agctcacagg atctctcttc actggattga gagcctcagc ctgccgactg 240
agaaaaagag ttccaggaaa aagaaggaat cccggctgca gcctcctgcc ttcctttata 300
ttttaaaata gagagataag attgcgtgca tgtgtgcata tctatagtat atattttgta 360
cactttgtta cacagacaca caaatgcacc tatttatacc gggcaagaac acaaccatgt 420
gattatctca accaaggaac tgaggaatcc agcacgcaag gacatcggag gtgggctagc 480
actgaaactg cttttcaagg taagtttaaa atacacatat attttaaaat acgttctatt 540
tcttgtctct tcgatgatca tgtttttaca cctaaatcct cctttgatgt cttcttcttg 600
tctgaattct aagagcattt ttcttttatt gcacttttga gaagaaattc acatgcaaaa 660
cccagctggc tctgtgtgtg cctagctgtg tttgtgagat tctccaacat gcattttact 720
agcttgaatg cccattagag gatgtgagtg ggagagaaaa agcagtgttg gggggaggag 780
aaaaaggagg gagacagaag agaagggaac agtgggggag aagagaggag gagagggaga 840
gagaaggaga tggggaagag agaagacaga gaggagacag agaggagagg agagtcacgg 900
gtgatggggt gcaattttcc tttttcttca cattatttgt agtgaaaagc agatcacaca 960

-continued

```
ttattctctg ttttgaaatc aacccaccaa atggggcatt tttattttgt ctcatccagt   1020
ggatgcaaat taaggcaaat gctgttgtat gttaagagct aaaccactaa gcagagtagc   1080
agaatgagca tatcacaaac agttattgaa tttctgccag gctacatctt acggactggg   1140
gtaaatgact tccctttaat aacatcccct cgctggtctg aagggacagt gcaaatgtct   1200
gattgctaat gcagctggaa ctgccacaca ctaggtgaaa ggatcccatg aaccagaaga   1260
gttctaatct ttggtaatta acaggatcac agcaggatgg ctttaaagta catttcctat   1320
ttaagaaaat tgtttgttct aaccaactgc tatattccct ttgctgttgt tgagctggat   1380
ggcttaattc ggctctaatt tattcatttt taacaatatg tccttgtttc tctgcctcta   1440
atttcagtga aagcaggcta tgaatatgag tagaaccgtc ctaatttagt gaaaagggga   1500
taatgtgaaa acaaaaatag aagtaaaggt tcaaaatatc tacctagaaa atagtgtgct   1560
ctggtaccat aaatattact gatatatttc tcatctttag tttcagaagc aatgcctttg   1620
agacagaatt actctcagta aactctatga gcatccatgt attgatgatt catggaattc   1680
agtgtgggtt aatttttact tccaatcttg taaagggaag ccagctactt agaatatgct   1740
ttcaaacaga caacaccaat tgaggatatt catggaaaca ttcactgccc tctttactgg   1800
gtcctggaaa gacagtaaaa gaaacctagc atttgtattt catcttctgg agctctctcc   1860
tgccttcttt tagttcaact aaccacacag ttaacagagt cagcttcttt gaaactgtgg   1920
gttatttttt tccacaactg tgatttcaga gctattattg gtttcctagt ttgtaatata   1980
agccaaagca aaaagacaat aaccagccac ttagatcctg ccactttccc ataaatgtgt   2040
caaaaaaatg agtcagttta caacatgtaa tataagaagt caattaattc cagtgacctt   2100
tgtaaatgat gacaataaag cagctctgac aatatgccag tggcttcgat tttctctctg   2160
taagatgaac aagtttaaga agagggttcc tgctcagaga aaaatgaaag gtgctgaagc   2220
atcagcttgc aatattggca gctttgctcg ctctgcctca aatgccacat gcaatctata   2280
aaaaaaacca aaatgattta ttacaaaaag gaaaaagtgt tttatttgct tttctgctat   2340
ttattaaaag tgctgctttt gaaacagacc agatctgata ttttgaggta cctcctaagt   2400
tcctaaccaa gaggaaaaga cttgaagtag atactcaacc ctctgatttc aaactcctat   2460
ataatgtagc attgcagtat ttaattcagt ttttcttaga ccttttccag ggaaagtttg   2520
catgccagac acacattctt aaatctaacc cgccttattt taaaattgca atagatgaca   2580
cctaagaaca gtggattcac tctttaacct tagtaaagct cacatacata ttttgtggat   2640
tacagagatc agtaatgtgc ccacttcagt ctgagaaata ccaacactcc aggccccggg   2700
tgttgccact cagtgtgtgc cagtgagttt ggtgatttga tcagcaccta cgaatgccag   2760
atgatggaca tttgtgtatg actggaagat ttacccatag tctccccaaa tcatgtaact   2820
ataccagaaa tagcaccttc ctggcaagac aattcaaagg accatttttt tcagggtgtc   2880
gcttgtcaca ggcaacatgc tgagttagaa tgctgatgag taggtggaat tttttatttg   2940
gaggtggtgg ttgttgttgt taatggctta ataaacggtg ctaccagcct tccaggccag   3000
caatttagtg acctacaaaa aaggtgatca acttatgatg cactaactat atttcactgt   3060
ttctttgttc tttccttttt tgtaacatct tttgctttcg ccatgtgatg ggtttgatgt   3120
ttcactcctc cccccgaatc tgaatttttt tggggtgtaa cattcctgtg taacatggca   3180
ctatggtatt tattacaatc taagttgatc agaaagctct ataaccggag tttcgtttta   3240
aaaaaacact tatgtaagtt aaatgttatt acttaattag cagcccctga aaatgggcag   3300
aggtgaggta tctgttggtg aatctgaagg agatcattaa aagaaagcta atagtagact   3360
```

-continued

```
aaaaaatgag ttcctacttc tagcctcagt aaggatgctc ctctaaaatg atttaaaata   3420
atgtggctcc agccagtctg aagaaacact agacatgtgt acagcacact aaaatgttcc   3480
atgtagacct ggttctgaga gtttagctac ttatgtatca ctctttggta catgaaacta   3540
aataaagcag gtaaactcta ggcaaaacat cagtacatct tgtcagtgct gtcaaagata   3600
aagctctctg atattggcta tgcaatgagt acttaggaaa gcttcactgt ataacaactg   3660
aacatagctc ctgcacagag ctcagggaat tcctctcctc tccttctgat aaagtgatgt   3720
attgttagac atctacgaag tcactagtaa aacatgataa caattatttc tttagccaca   3780
atgtgaaagg aaaggaagtc aaattctaat ataaagacag tagctggtgc cagaggatgg   3840
gaaaaaggaa cagggataaa tcggaacgtt tttctaactt gttgaaagga atggaaggtc   3900
tcaatagatg ctatttagag gtcattaaat acaggattaa caaggaagac ttaatgtcca   3960
tctcaaatct ttctgaagaa gtacagtacc tacagggcca tttactatat ttgcataatt   4020
gtcaagtttg tatacacctg cttgctatta tgttaattca tctttaggcc ataataaggg   4080
aagaattttc tatggtgcca ttaataaaaa cacatgacac agcttcagga gacggggaat   4140
aaagagggga gacatgcttt catagaataa aatttttgaa ctgaaagaga cattagtagc   4200
tagtctaata tgttcatttg ataggtgaaa aacactgagg ctgaaagggt ttgaaatcgt   4260
tataatgtaa tacattatac tttgtattca cccagctatt tattggagag gcctaggtta   4320
gaacccctta caatacttcc tccagaattc cattaaaatt ctgcctcctt ggtctttcaa   4380
aaataatgtt ttctcaaaaa cctcctatgt gcaaaaaatc cccccaaatt cacagatatg   4440
tacaaaaaag agaaatattt attcagataa tcaaatattc taaaaggaaa agccaatatt   4500
caataataga agcaacgatt tattaagtat ataacaccca aatatttcaa acccataatt   4560
catcatttga atatagttta ccatattctg taaagtcata aaaattagag ttttgccctg   4620
tttttaaaac atgttaataa taatactgct atccttcacc tacagagact cagctattga   4680
tcatccacta taagttttaa ggttttccaa gaattctgaa gaggctttcc acatctgttt   4740
ttacttggtt tcactgtaaa taatttaagg cacttaacat gtgccctttt tttatataca   4800
gtgtccactc tcaggatcca tgctttgctt atacatctca ctggaaaaca ataaatatat   4860
tatcaggaca gcaatccctc tccctctctc cctcccctac cccatcccaa cttacttttt   4920
gatttctaga gtcagactga gagctccagt aggcaatgat atctccttaa tatcacaatc   4980
ctattctttt cttttgggca aatttctctg tttttaaatg tgctctccaa attttgctta   5040
acataatagt aattaattga ctcaacttgt aagaaggata caaaatataa acacaataat   5100
tgtgaatatt tgtttaaagc tctaccattt acagagcaat ttttcaacaa ttactttgct   5160
cctcacaaca atctggtgaa gtagggtaga tatgatgatg attaacatct ttaagacagg   5220
agaatgaggt tctgtgaggt tagagacttg ctagcatgtt gaggtgcaag ggtctctgac   5280
tccagagagt agaagaaaat atgggtgcag cactggtccc tggcatttct gaagttagta   5340
ataaatgtta gttccctttt tatggaactt ccactctaga tcttaccctt ccaacaacta   5400
tgtcctttgt accataccac actatatctg gatagattct tgcaaattaa aatctttatt   5460
tcttaattta aatcacagct attgctatgc ctgagttaaa tttaaaaaaa aaaaaacaaa   5520
acaaaaccca caaccaacat ctattcttgg agaaaaagac tgtatgttgt tctacctact   5580
catccatatg tttgtctgac agcattagca ctttgataaa cagacacttg gcaaaggtct   5640
caaaaactgg aaaaaatgag atgagtaaat tatttaggga ttttccaggt tactaaaaat   5700
```

-continued

```
tatgaacaaa gtctccaaag tcacttaaga acccccaatg gatcaagtgt caacataaaa   5760
gcaacttcct tagcatctcc tttctggttt gtcttgggtt gaaaatgaca cactaaataa   5820
gataaaaata ctagttaatt tgaaagtaaa ctggtatatt tgtaaactac taaagtcaaa   5880
atgccagtaa acttacatac attattctgt gagccctttc taggggagat tgtgtctgtc   5940
aaaagtaata tagaccttaa aatgaataaa aatcccttta aaaaatcttc taaagtttgt   6000
catttcacgc tttacttcca ggaggtgaag cattccacag ataatcagct actctattca   6060
gggaaggagt gtaaacatca ccactttttg catgtttgca taaaaaaggc ccactgaatc   6120
agttaaaggt tagtatcaat aggcaacatt ctctatttcc aaaggcctga agctcctggg   6180
atctaattcc ctgaggaaca atggaagagg cactgtttcc caactggtac aaaacaggac   6240
ttcaggaaca gcagaatgtg ttctccaggg attaagcccc ctaacgtgaa gcttgggact   6300
cacaacactt acaagtgaca tgaataatag tagatatttt aactatagaa gacatttaag   6360
agacttcgtt ttcactgtga taaacaggtt tgatttggac ttataacttt tttctaaaat   6420
tatcaaatta ataacgacta taatgaaata gaggcaaata ttttagagga ttcattcctt   6480
ggggtaacat ttgttctata atttatagtc tcataatgtt gagagattaa agcatttaaa   6540
taacattgtc aactaacttt cagcttacct ttcttaagga aaaaaaacaa aaaaatgtta   6600
aaaatagaca tgtatttttc aaacatacaa ttcatgtttt tatgtcatta gactgtttac   6660
tgtatcgcta tatttatatg cctctgaaat atggagtgtt aatggggtct aaatttaatt   6720
ctatttttat caaaactcag tcactcagaa ataccaaaca ctgaacatgt tctacaaaaa   6780
gtattcaaca tctgtagaat acatggaacc acaatgacct ttactgaaat ttcaatagtt   6840
gcaggaaata atttcaatat atatctacac agattatatt ttgatttcta caaaggccaa   6900
ggggttaatg accttaaact gcaggtgccc aaggcattga gaacaaaaaa gatagagcaa   6960
gcgaaaagag aattgtgtct aggtcacaat gctgtagcat tgaaaagaaa gtgcaacaga   7020
acagaatgga aagagcaaaa caaggtgact gccatatatg aaagataaac atactctaag   7080
aacatataaa ctttgaaagc tctattcaca gtcattcttg aatgaaaaat atataaaatg   7140
ccattataag atataaacat catccaagtc aatttgttgt gtgactagct gaactgactc   7200
acttaccaaa cacatagttt atatttgttc ctcttattgt catttattac tcacgtattt   7260
tttacacaaa caccacagtt gttgaaagag tttcataagg tgatgttcag ctaacttttt   7320
aaaatcagtg aggcattttc caaaccattt cctcaatcaa ttactttta atgaggaagc    7380
aaaatttatg taaatatcaa agtctcattt ttatatttag gctataaatt ataccataat   7440
atgctgctgt tgggcaaaat aatcaaagta atgatgaatt aaaacaaatg ttctgacata   7500
aattaatgta agcagagccc ttatacgttc aaaccacatc atctctctta gacaatcctt   7560
tactggctaa aggaatggta ataatactgg cagatctcat ttacaacata caagcatttt   7620
ctgtgccaaa cattatgcta agcacttaac atacattttc tcatttaatc ttcataacga   7680
ccgtactaag taagcgctat gtttaaccca ttttaccaac gtgaaaaata aggcttagag   7740
aagaaaagta acttgccata actaatgaag aacacgaaaa ggaacctagg ttagttagct   7800
cgaaagaaca agcctttgtg catgaggcaa cactgcctcc cgttggtact gcctaaatat   7860
agctagttga tatcgccttc caagagtcag attctctatc aaaatacagt aactctgttt   7920
ctagtttcat atcatgcatt ctgctcatac tagaatatta tacctttgta ggattcttct   7980
tttctttctg agaaaggagt gatgctttaa ttatttatat ctgagttttg ctatccacta   8040
gattaactaa aatgattttt tgtagttcaa ttcacagcta gacctgtgaa ctggcagctt   8100
```

-continued

```
ataacttcct ctatcatcat ttttccatcg agtggaagtc aacatacttc ttcacctgag   8160
gtcatgcagt ataataagtg acacaaaaga aaaatgcaaa acttagctca ttggtctcaa   8220
atttcattat ttataataag ctttccttgt atctagttcc aaattttaga cacttttttc   8280
ccctcatgca ttctctttta aatgatgaag atgaaaatag tctgaataca atttcattgc   8340
tactatgagc atcaattttc aatgaaattc atcaatcttc ttcagtatga ataagctgct   8400
agccctgcaa agttaattga tgaaagctgt aatttgcttt tcaaactgag gatgctgagc   8460
caaacctaaa actttagtag aagcgttcta tattagctgt ttgtaaaact tcagcatttc   8520
ttgctatgtc acctcctgaa agggctatca ggggagtcct tcaacttgac tgtcctacaa   8580
aacaaaatct gaatgtaaaa ttaaagcaaa aatgttgctg aggattcctc cagtgattaa   8640
aaatggagtt tagagagctc acatcaacat acattttcta ttcaaaatga agtttttttt   8700
ttgaaagtta taagcaatta gacaactaaa aaaagaaatt caattttgag gtgataaaag   8760
gttaaagtat tgtgaatcat gaataaccta acatgtaaga aataaagaag gacatgtata   8820
atttaaaatt aaacttttgg ggttttttttc ctgctacttc ttacatacaa caaagacgag   8880
gaagaggagg agaaagagaa agaagaggaa gatgttgggc aacatttatt taacatgctc   8940
cacagcccgg accctgggta agctctttgt acaactcacc tcatttcact ttgattccat   9000
gagggaactg aggcttgaaa tggagaagca tttgcccaac ttcactcatt ggaaaggtcc   9060
tgatttgaac cctgaatgtc tgactctgaa gcccatgtta tggtgtcttc cttagcatgt   9120
atttcttttt tttaaatttc aatagctttt tgggaaacag atggtgtctg gttacatgaa   9180
taaattattt agaggtgatt tctgagattt tggtgcaccc atcacccaag cagtgtacac   9240
tgtacccaat gccttatcac atatttctta gaataagcat aatatattta tccttagaga   9300
agcatttgac tttttatgca gaagcatcta acaacaggct ctttctacag ttttaaactt   9360
ctcagccaag atcaggagta tatatatata ataatatgct taaactttat atataataaa   9420
atatatgtaa tgaaaatata tattaaaata tttataacat atacagattt aaaataaata   9480
caataagtgc atcaaacttt acagttttac cacatggtac aacctgatta gtataatatt   9540
atttaataaa taatataatg ataatgaaca cttaatataa ttcaactaat ctaaaagtat   9600
tacttgtgga ttttctactt aaacattctt attaatctgt tgaaaatgca tagagccaaa   9660
agataaaaat ttaggctctg gctgaactgg attaaggttt ttttgttttt gtaattttag   9720
aagtgtaatg tatgtaaaaa tatcatggtt gaattccagg aggatttatg aacatctaag   9780
atctttatca tttcttaggg aatggaaatc agtaatgaaa taaggaaagt tttattgacc   9840
ataaatatct tgcaaattga acaagtagaa caatgtttta accttattct ttcagccctg   9900
aatgttgctc accagttttg aaaatatttg aaaactttta aatatctttc tatattttgt   9960
aaagatgatg aacatttata agtttaaaat tcccccataa agaatttttc ctgtccagaa  10020
tggtaactcc tcctccttga tcaccacatt ctgcctccac acctgctagc agtatatcga  10080
attctcaacc ccatttaagc atggtgcttt cttttcacat catcatattt agtttttaag  10140
caatctgctg ctctggattt tacttgatat agacttttat gtctttgaaa gaagaaatat  10200
tctaagataa tatcttacca cttattcatt tagacatttc atctcatggt catttaatca  10260
atgaccatga tatagataca tccctagtca ttgaacagaa ccttggcata ctgataagcg  10320
ataatgtcta taagatacaa caagcagaat catatattcg tgtctgtgat gatgtactac  10380
caaactcact tgggtacttt taatgtatga tctcagaatc tgtgagagta acacctaaga  10440
```

-continued

```
atccatactt attttctgca caaagttaca gaattattgg gttaagattc aagtcttttt  10500
cttttgtcca ctgtctacca tttttgttgt agatttagta aaaaaaaaaa ttacttgaga  10560
caatcgttcg aattaataca gaatatacat aggtacaaca ggtacaatag gtatactgtc  10620
ttgtatattt cctgtgaaat atacaagaaa aataaaggtt caataggtat attgtcttgt  10680
gtcttccctg agaagactga gaagagggta tagctaaatg agttaggggt ttgattttaa  10740
gggacctgac tgggacattc aaagtaaata gtctcagtta atatgtaata atgtaaggct  10800
gtggtaaaca tagttcctat ctctactgcc cccaatctaa aaaggtatac catccacagt  10860
catttcttgg cagtcaggtg atatctgtag agtactaggt tatgtatcct taggagaaac  10920
atctaccaaa aatggacaaa actcttctgc ccacatgttc atgaactcta attttcatac  10980
actatatctc actccatatg gaactcaaat gagggccatg cagaaactgc cgccaatatg  11040
attaatgagt gaactctaca ctgcctgtca atttctttaa aaaaaaaaaa tgagtcagaa  11100
tataacaaaa tccctatatt gggatagatt ttacagattt taggtcactt gttcaaagtg  11160
acttacagac ataattagaa ccaaaaccag gtgattcaat ccttacccag tgggtatttc  11220
atagcacatt gactatgatt atagttttaa aaagtttgga ccatatgctc ctgtcaaatc  11280
attctttttt ttaatgcatc atgatgacca aaacttccca aactcaaccc tatagagaaa  11340
ctcagcagtg ccttatctgt gaagggccca tatttgtgga acctcttagc tgctggagtt  11400
tagcagaagc acaattcact gtcatccagt cagttttcaa gatgtctctt tagattgtca  11460
ttttattgac agtaatgtgt tgctgctgct ttacatcaaa catgttaatt acttgagtct  11520
ggagttttga atttttgccc taaagtgatt ttagctgaag cattattttg ttttgtttaa  11580
atcagtcaaa taaaagagag agagaaaaat tactaaatgg aagcccacaa gtataataaa  11640
agaatggaaa ccacagaaat agcaagtttg aagtttcata cctatctaaa aaataaatag  11700
aataatccag cttcttcgtg ctattctatt agaaacttcc actactctgg gacattccat  11760
ctcaaattta aaaagctccg aaaccattct tcactaatcc tctttgctag ggtcataaaa  11820
gacttcataa tatgtataaa ataattacaa tctttgaaat tataaatctc attgtaaact  11880
tattttttta aacgttaatt aaaaccccaa tgtcccaatt tccccttaaa agaccatata  11940
gtataggaca atgagcactc aagcccttga gttgctaaaa tttaaaaatt gctgacaata  12000
acatggtctt ttttaagact acagtgtcca ttgatcatag tgacttcaca gttttcattt  12060
ctctcttatt tgtactctaa ttagcatttt gcgtgagtac taatgaatgt tgttaaattt  12120
taacaatatc tattagactt tgtttcctgc aaaatgtaac tatatctcaa gaaataacaa  12180
ctgcattact ccatcatctc aaaaaacctg tattagcatt tctgcagatt tatggttaat  12240
aattgtactt ctttatctct atctattccg ttgccaacaa gcatacacgt atacatttac  12300
actttcacac acagaccaat attggatttt ttcaaatatt tgccaactgc taatagtttt  12360
taccagttta taaatattta actaagtcta gccacactga tttgcacctg ctttccaagg  12420
atttttttctt cttctaagac atgtcatata actaacatgg taaatagcgt gatacatttt  12480
tagaattatt ttcacagaaa taaccagaaa aatatcgatt aggcaagtaa aattctacaa  12540
ccttttatga taatcagagc caaatgacat ttaagtagtt ctattttgtt ctgtcatttc  12600
tcctgttcca atattttcac ctgtaagttt aagttacagc aaattctaat gagttcttat  12660
ccgtatgatg acttcttaat atgatagtga ttaacattta gtaaccactc tgtatgtgtc  12720
gggtgcagaa gaactttttt atactatgaa cttttaacgc attattttat ttaattttca  12780
caacattcct ttcaagtagg taccattatc actcaccttt cagtagatga ggaaacaatg  12840
```

acatggcagc agcacagaaa gaacgagagt ccatgcctga tcccttaatg actaggctgc 12900
ttctattgaa caccattttg agagtaccag agagcaaaat aaggcatttg tattggcaat 12960
tcaagaaatt ttagggttaa atgtggaaca aaatgggaac actgaaaagt ggtactcctg 13020
taatatgtgt gtgaaatgaa aagttacatt ttcattttca cttccccagc ataacaactc 13080
ttcatatctc tgagtttggg cctatattca ggcaactttt ttgaaaggca aatttgctgg 13140
aggatacctt ccttcattca tgcatgcaca tacctgcctt tactattcgc atcttgagcc 13200
aattttgcag agttggaaat gatgaaactc caggtagggg agagacaaaa gtcatatgat 13260
tttccttctc ccactccctc tgtgtcccaa tttcctgtaa atgtttactt ctgtaatcca 13320
cagttcaaat ttattgtaga gaatgaaaca atttcttttg ttatctgctt tagatttacc 13380
aaactctaca ttttgttcta gaaattgttc tcacttctgt tgataatgct ccatgtttat 13440
atattttgat atgatgtcac tttagtaact aataccatca cttctattga agctgatatc 13500
aattttttaa aaggctgagg ggacattata tgtgaaacta cttagtatgg ttgccagcaa 13560
tagttgtaaa tcatgctaaa taacagaaaa gtctcatcat taatccccct atctagtctt 13620
tttgattcgg ggagcaaatg ctaaagaaaa atttttaaat gtggagaaaa ggaaaattaa 13680
tagcagggat gaaaagtgtg aaggacttgt cacaagcgat gagatgttaa tgtattcaca 13740
ataagctgta agctacactt cctatcaaat taaaaatatg catagaaata cccagcctcg 13800
catctcattg gaagcagggc aaaatctatt tagaacgaga gggtcatggc ttctagaaca 13860
gtggggaaga cagaaaaaga aagcagagag aaggggacag tctctcacac aaaagaggaa 13920
gaaaaacaaa aagaagagat ggggagttcc aaatataatg gctgttacaa gtgatttgag 13980
tctaaaatgt gaatctactt gccagaatgc aaagagcaga gaggcatgac catagaattc 14040
cagaagctcc cagtccagag ctatttccta tttccttact aaaggtctca ttgagacaaa 14100
aatatattct taactctgta gactgtaaat atgtgttttc aaataaaata accacaaaac 14160
ctttgaagtg ccctttaaaa attaatttga ttcttcttca tgaaataaag aattcttatg 14220
tcaataggct gaaaaattac aaaacagatg tcaaataacc ttcattttgc aacaaccttc 14280
tatgaatctg acatctagtt atttcagtta acatcatgta taaaactcag aaactccgaa 14340
attatgcatc caaagaatgg aatactaatt catgacagca tgttgaaaag agcagataga 14400
acaatacacc acaacagtac ataaattgac caaatgagac tgcatacgtt accatcttcc 14460
atgacaacag aaacttactg acggacaatt tacatctggt ttgctccctt attctgcaaa 14520
tcacaaaaat gggttgctgt agcaactgcc acatgcaatt tagctggctg gggggaaaac 14580
acccttagag tactttctaa gaaacaaata caacatgtat ttttgttgtt cctcctatcc 14640
taaattgaac aaatctcctg acaggtctat tttcccatag ctttaaaaat gggcttgctc 14700
tctgttgttt gcatttgtat tatgtgtact aacaatttat gcaaaaggtg aaaagaaaaa 14760
aaaatccata aaaatataaa agaaatagat agagatgcct atatctagtc acatgaatgt 14820
gatagggcca ttgtctttta tagcatcccc actttttatc actgacagct cttttagcca 14880
gtttaactcc actgatgtat gtatcaaatc tacgcatgac actcccagga atacacaaca 14940
tctcaattcc taatgcacca gcaagggcaa gcttattttt ctgaatcaga aacaagagca 15000
agtacaaata ataggcagtt aattttctta gaaacatatt tgtaatatca cagtaacaca 15060
taacatagtc tttttccaag gatacagcag aggaccttag aacatataat accaacattg 15120
gtgcacattg gagcagacaa attagcacct acatgctaaa taaaatggga ggaatactca 15180

-continued

```
tcctttacct acttacttct caattgggaa ctaagagaag aagcaaagta cctggaacac  15240
tcaaagccct gaatgtggaa caattgaagc acaagtcatt gttctcctta tttaatggca  15300
agtttgacaa cttttcaaac tctacagaca ttggtctgat gtgggaaggt caactttttt  15360
gaaggatctt aactatcagc ccttgaaata atagaaatct cttctctctg gaaactcact  15420
ggttttgaga aactctctaa gaaaaacagt ccaattaaaa acaaacaaat aaaatgaaaa  15480
acagatatgt cttctaccat caccattttt gccatgtgga aacttctcat gaacttctca  15540
ctgccccagg cttgagtgaa aggcttgcta ttttgaggtg gagactcaaa tagggcaaga  15600
gttggtgaag tatggctgct aagagatgtg agggacttat aaataatatt aagataacag  15660
gaattaaagt ctcggtgtgt gaaaatactg tatatctagg atgcacataa aaactgccct  15720
tacagatctt gcagggaaaa gtacctgact atactgtata agacttctgc tgtaccattt  15780
aatcatacca aaaaaaatgg aatcaacaca caaatagatt tcttttccac tgttctcaat  15840
ttaaaaataa ttggagaaat gtgtgctttg tttagaagag taaaggaaaa cattcattca  15900
atagtaccat gcagaatgat ttgcttaata gcatttctaa tatgttatgc atgtattcaa  15960
tctacttctt tctatattaa aatgcaaaaa caattactct ggatgtaaat cctagaaaac  16020
aatcaaagtt tctattaaat cagagaagag acagttaagc tgcaatgtga tttgcagatg  16080
ctcatgaata gacaatactt agaatctctc tcactagaat gtgaaaaaga taggtgggag  16140
agattcagaa acttccttct ttccccttc cctctctctc cttccctccc ttcttccttc  16200
tctctttcct ctcccatttt tactttcttt ttagacagac tttgaagaaa agtttttata  16260
taaagtctaa taatttaaat tatatgggca tgtaaaattg ccttatatta caacgccagc  16320
cctacagcag gtagaaaatt cctttcaaca ttctgttgta aacagtttag attcaactga  16380
tcagtcacag gggaatatgg gcagtttcaa cctcttacca cctttgtctc taaaaagaaa  16440
ttctggatag ttctttgtat acttatatta aagccatttc tgttcattaa aaactcaata  16500
taagcatgtt gaagaagggg caatggaaca tgaagcaatg aataaaaaga ttctgtgcat  16560
gtataacaag cattctgtat tttactttat ctgaatagaa ttttagaatc tacatgcttt  16620
aattggggca ctagtaaagt aataatctca aatatgaaat acaatagatg cgtttcatgc  16680
tctgattaaa tgtcaaggcc acagatttgt tatttcagat ctagtgagta ataattttgt  16740
tggctaataa tgaactccca aagatttatt tgcaacattt ggctgttgca acatttcaaa  16800
gctcttggtc aagctgtagt atttccaatt ctgcagataa tattatagac tctagcatgc  16860
aaagcttaaa cttttaagta aattttacta gtttcatgtg tgctgcatag atttagagtt  16920
ctgctgaaat tttgcaccaa aaatatttcc cagtctcaac ttacagcaga tattgtcttg  16980
atttgcatca actttttctt aaccgagtat atatggcttt ctttacaata ctgtttttgt  17040
ttttattgtt gttgttgttg ttttctccta aagtacagtg tcttctgtaa gtgtcacttt  17100
ctagtgcaga ttcttaaccc cagtctgggt ttggagacaa aaacctcaca gattgttgat  17160
gtattccatt tgatcactat cagctggcaa caagcatggt ctggcctgca gccacatcaa  17220
accaattttc tagaggactt ttctcagtac ttaacactca attatattaa tgtttattat  17280
tgctcttttt gttgttgata cagcttttta cattaattct gaaagtctgt ggcactttca  17340
atcattaaga atacatttta acctaaatta catggttttc tatgttctcc aaatacaaat  17400
gtcacaaatt ttaagaaact aatctgtata tattataccc ccactacact gtgctattac  17460
tagagatata atatataaaa atcaattgaa aactatatct caagtaaaaa agatatacga  17520
acaaaacata catatctcca ttagtttcct cacaacagat ttattcgaga tataatgaga  17580
```

-continued gtagacattg gcttagaaga aatttatgat tctttttaaa caatcacaga tttaattata 17640
cccttctaaa gtgggtattg ttacactttt gtaatctcct gaatttaaaa aaaacatatt 17700
tatttctgtt tgccaagctt acatcatcac tcaatagttc atgcatacaa accacatgag 17760
tcaattcagc attcaccaac aaaacaaagg tcacaaatga gtacctcgta cagcaaattt 17820
ttttaaatgt ataataagat ggaaatttat aattaaaagc aactgatatt cattcattca 17880
ttcagtagat atttattgaa caacaatagc aggcaatatt ctagctaggc attggagatc 17940
catagctctg aataaaacgg aaacaacttt aataaagcta acattctagt ggagatgatg 18000
ggaagtaagc aataaacaaa aagcaaataa tttctagcag tcttaaatga tctataaaga 18060
aaacaacatg gtgagaataa gaatgacttt aggggatatt ttaagtaagg tggtccgtaa 18120
ataaggtatt atcaagaaga attaaagacc aaattaaaga acaaacatct agaatgtgta 18180
aaacattttc agtacaattt aacatgttca ttgccagcta catgataaac cattaacttt 18240
ccttccataa ttaagttttt tttttcaagt caggtttcca aggtatgacg gaggcacatc 18300
tcatacaaga gcaagaaaac ccaatcatca tgcttacgaa ctacaaaagc atcttaatta 18360
agttttaaaa gaaagtatca tttaatttca ctgtgcaaag aagacaagtc agcacacaag 18420
tataggctta ctcagtgagt aagacatagg tctagacatg aaggtgtttc attaacaact 18480
agtaaggggg caatcaagta catatatatc tgcgacacaa agctttatta cacagagctc 18540
acaggaagag acctgaaaat ggagtcaagg acctggaata gagttcagga gccatcactg 18600
ataatgcccc ttcaactttc accacctcat gaaatctctc tgagttatca cctgtaaagt 18660
gggtataact gcacatgctg acaggattat taggggaatc agataaggtc atatatgaaa 18720
attgaactga atttgtacat tgtagcacaa tatgactgtg actactatcg ctgttttcat 18780
tgtttgttgc tattgttata tgatggaaaa ctgaagttaa tggaaagggc ccttaaaaag 18840
tcttcagggg ctgggcgcgg tggctcatgc ctgtaattcc agcactttgg gaggccaagg 18900
tgggcggatc acaaggtcag gagttcaaga ccggcctgat caatatggtg aaacactgtg 18960
tctattaaaa ttacaaaagt tagccaggca tgatggatga acacctgtag tccaagctac 19020
tcaggaggct gaggcaggag aatcgcttga acccaggagg tggaggttgc agtaagctga 19080
gatcacgcca ctgcactcca gcctaggcaa cacagtgaga ctctgtctca aaaaataaag 19140
tctttaggat ctgaactata ctaaaatatg caaagataag taaagcatca aagatcctat 19200
ctgttcatgg atattagaca tgaagacatc attagggaaa atgatattct ttttcaaatc 19260
tttgtttctc cacacaattg ataggaatca gtcattaaag aaaacctcaa aactaatatt 19320
tttcaagtcc atattcatta ttatgacaaa gtttaattat gcttctcata tatttagaat 19380
agcttttatt cactgaaata atatcttatc ttccaagaaa acataaacaa taccaggaat 19440
gatcacaaat atagattata tcttactaac cagtgtcatg aattagaatt aacagaaatc 19500
atgaaaaagt tttattcgtt tttcagtttg gatgttgagc tccaagccca aaatggttta 19560
gcataaactt tactacataa ctgtcttgaa gaatatatat aaaaacataa gtataaatat 19620
caaacatata agtatagaat acaaataact taaagttcaa agaatgtttc tacatatatg 19680
aaattaatgt tgagtaattc ttgactgagc aatgtgaact atttctgcag tagacattac 19740
tgatattaat ttaataccag ttatttaatt ataaatttcc ttcacaaaat aattttgtct 19800
tggcatattg gaacagtaaa gttaggtgaa tgtcccagat caaatttaag ggattccaga 19860
tcttaaatca tgtgactgtg aagggaaaat ttcttctcct aactcagatc caataatcta 19920
acactattca ttttatccat aaaaatgtat taaatcctaa cctgtgaagc tgctataaca 19980
taatataaaa ccatttgctt ttctgagcct aaactgatag tctgaaacat aatcctaaat 20040
tatctggaaa gagtttatct actaagaaat tttcccaaac aggtgatttg tcacttagct 20100
ttcacctaat ccacatatga gatgaatacc aggcttctaa gagtgaaatg aatgcaaatt 20160
tataaccctg ttttgaaaga actctttttc tccattaaga tttagaactc cctttggtgc 20220
tctagtcatg tacaaccttg caaaaagacg cttatgtggg catatcgccc atgctcttca 20280
tgggtagcag ttgtaaaaaa aaaaaaaaaa aaaaaaagtt aatgttagca agggcctaca 20340
ttgcccatta acaaaaatta aaatttggta ggcatcacaa attacactgc tttccatccc 20400
cccccaaaaa aaaatggccc gttagtattt ttacttcccc cgcccttaat tttagccctc 20460
tctattcaac acataaggca aaatgtattt catttactat gccactcttt tgggggatct 20520
catatttccc aaatgttcat aacctgatat agactagtcc ttaaatggta tagtagtcaa 20580
atattataaa cacattaaag tagaattcac cataaagctc ttacgaacag aaataatgtg 20640
aatcaactaa tgtccccccc tgcgtcaata gtaattttaa atgaattcaa gggggttgta 20700
ggcaaccaaa ttttgcaaag tcatctacat aaagtagtcc tacataatta gcttcaagta 20760
aagagttatt gtgaggcttc tataaagtta agtgactgaa ctccatcctg ggcgacaaaa 20820
ggagaccttg tctctgaaaa agaaaaaata catgccttta agttaagtta ggtgacagga 20880
aaaaggaaat gcaaaacttt atttatatat tttatttata tatatatata tagtttgttt 20940
tttttttttt tttttttttt gagatggagt cttgctctgt ctcccaggct ggagtgcagt 21000
ggtgcgatct cggctcactg caacctctgc ctcctgggtt ccggtgattc tcctgtctca 21060
gcctcccgag tagctgggtt tacaggcgca tgccaccaca cccggctaat ttttgtattt 21120
ttagtagaga cggagtattt ttagcagaga ctgggtttcg ccatgttggc tggtcttgaa 21180
ctcctgacct caggtatatc cgcctgactt cgcctcccaa agtgctggga ttacaggcat 21240
gagccaccac tcctggccct gaaaatgaaa aactttaacc tgcatatagt gcctttaatt 21300
tccacacagg aactaaatga caaagcttca ctgacctagc atacatcaag aactttaact 21360
ctgtctgtca cttcgtactt cagagtgcca ccaagtcatc tcatattaac catttaacac 21420
gagtgttagg gaaagagctc atgtcctgta cagtaatgaa tttccactca caaaaagatg 21480
cacaaacatg cacacagcca taaatatggc ctccatgtct tggttgaaac tcaaagccat 21540
aattcaggaa gtttttttcaa agcttacagt ggaatgtatg ttgttctatt tttaaaactt 21600
ttttgtatcc tctggacaca aatatagcaa tgttgtttaa agcagattgt caggaattta 21660
agcaggaaac aaaccacaga gcatgaggga aatctgacac acttttgaaa agaaaataga 21720
caaacaatcc catgcttatt atagggaact aaaaatacag cccacatcgc tattatcgtc 21780
ttccttaggt atagtaacag aaaagcacca tccaactctg aactcatggc aggcatcagc 21840
taaccccagc acacccgaaa atgtggtgct ataatttagt ctcttgttta ttgcatttga 21900
aaaaattctt tcaaactgaa ggagctaatt ttatttcctt tctttcaacg tatgttttat 21960
cttctcaatt cttagtaaaa acgtaaaaca ctgatattag tgttgtttta tttaatagca 22020
atgagaacca tattttatta tatgcagaac agaaagtgaa ctacccagaa accttctact 22080
ctgagttcct tcagagtaat gttcccctcc aaaatataat tttaagattt ctgtaataat 22140
attgtaacta aaatgttctt cattctctat ctatactagg tcattggact cttgtccaca 22200
ggcttcctta ccttctttac aaaccagtga ctttctattc tgtcaaactg agttaatcaa 22260
ggaatacaaa tgagttgaaa acctttttgc tgccatcctt ttacagcata tctatgcttc 22320
aaaaccatcc ctcctgagat tgataaaagc atttacttat ggcaatcaat atagaatagt 22380

-continued

```
cttttttttt tgtatacatg tctatcatgt cctcccatgt ataaggccct agagagtagt  22440
gcttgcaaga tcagaaagca taaggcagca tacttgtgcc tgttcataaa atcaactcaa  22500
gctgcaatca cttcatttat ttttttcttt taactatacc agggagatgg acagtcttca  22560
tgtgacataa agaatggaga cttcaaagac aggatatttg gctatcttcc aataaaaaaa  22620
tgacttaaaa attgtttaaa ttatctggat aattacccca aatgttttca tctgaaatgc  22680
aggataattg aaagagggtc tacatgagac acacatttcc caaaccattg tactgcaagg  22740
cacaatgtaa gtctgtctcc tgtcattcaa gcaggggaat ttccaaatct agttggaaat  22800
tcctttgaag ataaaaggat gacatcattt accagtcata ctaccacact aacttctcaa  22860
ataaactgga actaaatcat aagaatgagc ttttagagac caaaacttac gagagaataa  22920
ggaaagcata tttgggcaga cttttcctct caatttatgt gaaatgtgta aaatacaaat  22980
taaggcctaa ttaaatccct ctaaatatct attgatagaa ataaagagtg gacaaaatgg  23040
gaaattttaa tgcataaatt tagtcagtca cattcaaaat tttctgaaca gaactgaagt  23100
ctctcaacat acacatacac ataaatctac acacacacac acacacacac acacacattt  23160
ttgccaggaa aacaatgatt tctcttacaa gtgtatataa attactcctg acatacaaat  23220
gtttaaaatt cttcaaattt ttcatgaatt tgtacagctc ctaaggatct ttttatagac  23280
tacttctgat gtaaatgaaa ttagcacctt gtctatctct atgccactgt ttgacagaca  23340
cataaaacgt gaataagcat gaaaaactaa aaatatcata aaatctctga gtaaatccta  23400
tcggtatcca tccaagtaca ttgtattaag tttgcacaaa gaaatatatt ggctgggcac  23460
agtgacccac acctgtaatc ccagcacttt gtgagttcaa ggagggcaga tcattaggtc  23520
aggagtttga gaccagcctg gccaacatgg tgaaacccca tctgtactaa aaatacaaac  23580
attcgctggg tgtggtggca ggtgcctgta atcccagcca cttgggaggc tgaggcagga  23640
gaattgtttg aacccaggag gtggagggtg cagtgagtga gccgagatcg caccactgcc  23700
ctctagcctg ggcaacaggc gagactccat ctcaaaaaaa aaaaaaaaga aagaaagaaa  23760
aaaaaagaaa tacattgaaa ccattttgag aatatttaag ggttactaca aaaattatat  23820
aataatagaa tttgaaggtg atttttattt tagaaatgaa gtcactaaag gtcacgaggt  23880
ctcctcctaa ctcccgggtc tgcatactta cacaatagcc tactgttaaa gtgctggtaa  23940
ttttacagac aggcatcacc caaatagaga tctctagttt aattataacc tgaagcaaat  24000
tttccatcac tatggaaaac aagatgatta tacttcaatc taagatgagt gaatattaag  24060
gataatgaat aaatgagtgt ttttcccaga gagacctaca tttgggacca tataaatgct  24120
aaataacaag gtaaataaaa gagaggttaa aaaggcaaat caggcaatca aactccattg  24180
gctctcaaac aatattgaat aatgtactgt tatgacatat tgtaaattag aattccccag  24240
tatatggtgt gatgcttata ggaaaaaata taagcatcaa gagacaagtt atgacttaaa  24300
attatcattt gttttactaa tcatgtacaa aagtcaactt cacaaataat gctattaatg  24360
aagtgctcag ttgagcaaaa tcaataatta aatataacta caaatcagaa ttttcataaa  24420
aaatgacagt atcatgacaa gctggtaatt tatgagtata cagaaatgac taccccaata  24480
tgaaatgtgc ctgtgattaa gatttcatcc ccccctctgt aaaagaaaat tataaagaga  24540
gatttctgta ctgtaaacta ccctttctaa attatagctg tactataact agattccaca  24600
aattggacgt attagggtga gacatttgca attatttttt atttttatta tttattttta  24660
tatatttata tatatttctt agacagactc acactctgtc gctcaggcta gagtgcagct  24720
ggcaccatct gggctcactg cagccaccgc ctcccaggtt ccagcgattc tcgtgcctca  24780
```

-continued

```
gcctcccgag tagctgggac tagagatgtg caccaccaac tctagcacac ctggctaatt  24840
tttgtatttt tactagagac tgggtttcac tatgttgacc aggctggtct caaactcctg  24900
gccttaggtg atccacccaa ctcagcctcc caaagggctg ggattacagg catgagccac  24960
cacatccggc cggaattatt gtttaaagaa aactatcccc atgtagcaca agcctcaatt  25020
ctaaaaacaa gagaagaaaa aagataaaac atccaagatt ctctcaaatc tgcccaaagc  25080
atatcttgag actcaggaga gagaattgtg ctatttaagt tactactggt ttctctgaga  25140
gaactttatt acaaggccta tattgtcatc taaaggactc atctgagccc tatatccaga  25200
ggaatggaaa cagcacatga tttgtttatg atctgcatta atgcttgctg ggtaaaaata  25260
aaagttctta aacatgacaa ggacataaaa taaaattgcc cctcctttta aaaaaatcta  25320
tagttatttc tataatgata ataagaggat ttttgccagt ttgaaaatct caaaatatca  25380
gatttgagaa tctgaaaata tcagaatcca ctctaaaacc actctaaaag acagcatcca  25440
ttaaatatat gggtatacat gacatacatt ttactatata aattttgaac aataacaaaa  25500
ataattttc tctaataaac aaatttcttt ataatggcaa tcccacacaa aatctctaca  25560
atttcacagg acattaacaa tcaacttgaa aacaagagta aaaatttagt gcatattttg  25620
tgagaaacta agattcagag agcgatgtga ttactctcac atagcaaaac taggcctaga  25680
aaacagtttt tattttattc cttccacaat actcaactgc cttataattt catctgagtg  25740
aaactttatt atcaaaggaa gagaaacacc caacaataat aacaaaaaag gcagtgcacc  25800
tatacagttg gaggaaacac ctttctgaga agataccaag gtgtgtggtg ctgttttaaa  25860
aataaacatt tgagagaaag tagaacttag tggttaagac tgagctttag aggcaaaatg  25920
aaggaatttg aattcacatc tgaatttaga tgaagtgctc taatcgaggc aatttacttc  25980
ctactggtta gtctgcctta atttaatgat taaagtaact ctctagtttg tttactactg  26040
tgtagataaa aagataaaat agaaataatg gcaggtaact aatttgatag tctttaaaag  26100
ccccataatg actaaaattc actgatccta aatttgttaa tggcatggga ctagagtatt  26160
gaatataaac ttgtaatcaa ttaaaaaaca caaaggttaa aatcagataa gtgagtttac  26220
acacattcaa ttgttagaca cctttggaaa aaatctttga tgttcacaga atagtatcat  26280
gtaagtttgg gatgtgaaag aatcttacaa ctcatgcaac caaatttcta aattatagag  26340
atcaataatc tgaggtacaa gaaagtgagg tatcctgtcc ccagttacaa aatcatccag  26400
taaacctggc ccatgtttct taatgcaaaa caaattttct ttcggtgtat caatttctca  26460
ttgacatcag tttttaagga tagcattcat taagctattc taaataatta ccattatcca  26520
tttcctgaga gttgtcatat aaattcaaat aatttgtttt gaaaaactgg aaaagaaata  26580
tttcccaagg aaaatagaac agtcttttac aaggatgcat ttagtataat tcaacaatac  26640
ctctgggata tggaaccttc aattagaact aaagaaagat caagtcttac aacaagggaa  26700
tatgaagtta gatagtggga gaatagaatt taagttcttt atacaaatga acttagccag  26760
caatttgcta tagaagaaaa ggaaaaactg ggttttaatg tacccatggc aattttttttc  26820
ttcaccaatt tttcaactta agtatcaaaa tgtttctttt cctcacactc tgtagtcttt  26880
ataatacaca taataaagtg caaagaagaa ggcacacttt gttcttaagc tttagcattg  26940
caaaaactca tctaaaagac agtggatttt aaatcttctt actcacatgt cctcactata  27000
ccccagctga tttttcataa gtatcacaaa agaccacaga acattcatgt tgctcctttt  27060
ggaggaacag aattaagcat tctctccttt gtgcatccac agagcattgc acacattttt  27120
attgtaaatc aaatctactg tgcatcattg tcctcagcta tttactcctt tgataactga  27180
```

-continued

```
aaacttggtg agcagatatt ttatcttatt tattgctgac tttccagtgt ctatgataat  27240
gcctgccaaa aagtaggtgt tggatcaata tttcataaat gatgaaaaac agataaagaa  27300
gctaaagaat aaagatctct ttactaagga aaagtagctt tatccataaa agcttctaca  27360
tataattata ccaagaaaca atctgtattt tcacataaag aaatctcaaa ttataagtgt  27420
ccacaggaat tggatatata agatatgaga attcttacaa ttgtttgatt ttaacggcct  27480
aaactaggtt ttaatcccac cccaccattt atttgttgtg tggtatcagg cagatgggtc  27540
tcaataacct tacattaaaa agtggagatt aatgtacctc accaacctat ctcacaagtt  27600
cattaatatt aaattaataa tgaataagaa aaggctttga aaactataaa gcactaagaa  27660
gatactatta ttacttactt attatcctgc aaatagccca tactaaatag catattaatg  27720
aaatatcata atcatttcca cagacttaag aaaaagtcaa tattatgcta aagaaacgat  27780
aaatttctat attctctatt gtgtttccca tactattgct tcctacagac caggagaaac  27840
aacatttgaa tatgctcacc actataaaca ctctcatttg caaaagcttt cagaagaaat  27900
ctaattcaaa atgtggttgt ttctagcata tggctatgta aatgatgaaa taagaaaaca  27960
ttttctaatt aaacacaaat ataaatttta agacacccac caggataatt tcaaaaagtg  28020
gcattatatt aagactcccc cagaaagaat gcctcatctt taatatttcc aaacctctag  28080
ttaacttaaa gaaggatata ggtacctctc tgctctgctg gagaaagcag acctaacgaa  28140
ttaattgaca gaagtaatgg tttctccatt ctcagctaag tgatttatgg aaacatacag  28200
aaatgcaatt ggactttgta cctaggtttt tccttcattc tggacataca ggggcaatag  28260
atttctattt tcattttatt cggaggggta tatgctccca aatgagcatg catacggaat  28320
tgtaaccatc tgtttacttc tgtttcccct ccagactgaa atttactaa agaaatcaac  28380
catatctaag tcatctgttt tccctctagc tattaaccca gtaattggca tgtagaaagt  28440
gctcaataaa tgttgactgg ataaattgaa gaataaagca cagatataat agattaactt  28500
ttctcttaaa gtctaacatt cctttgtatt agcctgaatt ttaatctctg gattttagta  28560
atatatgtaa cacaaatttg atgttagtaa atacttatac acattaaaac agatttactg  28620
aaattagaaa ttaagcagat agaattactt aagtaacatg taaaaggatg catacaggat  28680
tctactaata caattcattt atcagttcat tcaaaacatt tcttgagcac atactacatt  28740
ataatgataa tgcccagaag ataggatgca aagccaggca ggcctcacgc tctcaaggag  28800
gttagtgcct ggtgaaggaa aggatcaagg aaatgcctga cagaaacaag tgctggagcc  28860
atgggaccac tgtgaagggg cagctaagta catgtggagg gaggggttat atgaaagtct  28920
tgtatgaaag acttcccaga ggggagattc ttgaactgag gtttgaaaag acagtaaaac  28980
ataatttaaa acaaagaaag aagtattcca ggcagagtga tgcaaccata gctctaccaa  29040
tagggagaag gttgcctgca ggaaaatggc agacggtgag gtaaacatag aaggatctcc  29100
atatatcaaa tttgcaactt ggtgttggaa atgattatat ttcaaagaca ctggtataga  29160
tttaaaagaa aaatatctag gtctttgtgt tactgattgc attaatccgt tctcatgctg  29220
ctaatagaga catatccaag actgagtaat ttacaaagaa aaagagattt aatggactca  29280
cagctccaca tggctggaaa ggcctcacaa tcatggcaga tggcaaaagg cacatcttac  29340
atttaggcag gcaagagaga atgagactca agcaaaagac atttccccta taaaaacatc  29400
agatctcctg agacttattt cactaccatg agcatggggg aaactgcccc catgatttaa  29460
ttatctccca ccaggtccct cccacaacac atgggaatta tcggagctac aattcaagat  29520
gagatttggg cggggacaca gccaaaccat atcagtgatg taataaaatt gtttttttcat  29580
```

-continued tgttagtaat ggaaggtaag ttattctcag ggaaaaataa aacagccaaa tgttaatctt 29640
gtgaacttta gttacgaatg ataacacaca ggtacatcta cagcaagtta aacttaatct 29700
tctctgaata ctgcaaaact caagtcactt tatgcaaagg agactatgga gagaagtatg 29760
aatgaaaatg ggaaacagct aataccacta catctagctt acttaacatt ttataatttt 29820
tgtctctaaa tcctgtctcc tgggaacctg ttgaatcgca atctaactca tttggttgta 29880
agtgaacagt attattcatt tattggcctt ttatgttgcc tctctaacag gcaaaaaaaa 29940
aaagccatga acagttgaaa gatttaaaag ttgttttcct tttttcccta taactaaatt 30000
tcaaagctaa tgaaaatata acaaataaaa ttacaaggta taaacaagca aagatttgaa 30060
ataacagaaa acttctggaa acacattcat taaaataata aatgtttaac cttttaacga 30120
ttaaatttct cagcctgccc aatgcctagg ccaagaatta tcaaggacat atccttcgcc 30180
cactttttga tggggttgtt tgttttttttc ttgtaaattt gtttgagttc attgtagatt 30240
ctggatatta gctgtctgtc agatgagtag attgcaaaaa ttttctccca ttctgtaggt 30300
tgcctgttcg ctctgatggt agtttctttt gctgtgcaga agctctttag tttaattaga 30360
tcccatttgt caattttggc ttttgttgcc attgcttttg gtgttttaga catggatatg 30420
aacagacaat tctcaaaaga agacatttat gcagccaaaa gacacatgaa aaaatgatca 30480
tcatcactgg ccatcagaga aatgcaaatc aaaaccacaa tgagatacca tctcacacca 30540
gttagaatgg caatcattaa aaagtcagga aacaacagct gctagagagg atgtggagaa 30600
ataggaacac ttttacactg ttggtggggc tgtaaactag ttcaaccatt gtagaagaca 30660
gtgtggcgat tcctcgggga tctagaacta gaaataccat ttgacccagc caacccatta 30720
ctgggtatat acccaaagga ctaaaacatg ctgatataaa gacacatgca cacgtatgtt 30780
tattgcagca gtattcacaa tagcaaagac ttggaaccaa cccaaatgtc caacaatgat 30840
aaactggatt aagaaaatgt ggcaaatata caccatggaa tactatgcag ccataaaaaa 30900
tgatgagttc atgtcctttg tagggacatg gatgaagctg gaaatcatca ttctcagcaa 30960
actatcgcaa ggacaaaaaa accaaacacc acatgttctc actcatagtt gggaactgaa 31020
caatgagaac acatggacac aggaagggga acatcacaca ccggggcctg ttgtggggtg 31080
gggggaggga tagcattagg agatatacct aatgttaaat gacgagttaa tgggtgcagc 31140
acaccaacat ggcacatgta tacatatgta acaaacctgc acgttgtgca catgtaccct 31200
aaaacttaaa gtataataaa aaaaaagaat tatcaaggac agtcatgaaa aagataaagt 31260
caccaaacat actgaagtac ttaaactcta agaatataat ttatacatga aataattata 31320
attaggtaat gaatatcaat tatggtattt ttcatttgta ctaattattg ttctcttttt 31380
tctttcatat ttcattttat tacatttagc atcatgctgc tattcctgca aatactgaag 31440
aagcatggga tttaaatatt ttacttctaa ataaatgaat tactcaatct cctatgacca 31500
tctatacata ctccaccttc aaaaagtaca tcaatattat atcattaagg aaatagtaac 31560
cttctcttct ccaatatgca tgacattttt ggacaatgca attgtggcac tggcacttat 31620
ttcagtgaag aaaaactttg tggttctatg gcattcatca tttgacaaat gcaagcatct 31680
tccttatcaa tcagctccta ttgaacttac tagcactgac tgtggaatcc ttaagggccc 31740
attacatttc tgaagaagaa agctaagatg aaggacatgc cactccgaat tcatgtgcta 31800
cttggcctag ctatcactac actagtacaa gctgtagata aaaaagtgga ttgtccacgg 31860
ttatgtacgt gtgaaatcag gccttggttt acacccagat ccatttatat ggaagcatct 31920
acagtggatt gtaatgattt aggtctttta actttcccag ccagattgcc agctaacaca 31980

-continued

```
cagattcttc tcctacagac taacaatatt gcaaaaattg aatactccac agactttcca  32040
gtaaacctta ctggcctgga tttatctcaa aacaatttat cttcagtcac caatattaat  32100
gtaaaaaaga tgcctcagct cctttctgtg tacctagagg aaaacaaact tactgaactg  32160
cctgaaaaat gtctgtccga actgagcaac ttacaagaac tctatattaa tcacaacttg  32220
ctttctacaa tttcacctgg agcctttatt ggcctacata atcttcttcg acttcatctc  32280
aattcaaata gattgcagat gatcaacagt aagtggtttg atgctcttcc aaatctagag  32340
attctgatga ttggggaaaa tccaattatc agaatcaaag acatgaactt taagcctctt  32400
atcaatcttc gcagcctggt tatagctggt ataaacctca cagaaatacc agataacgcc  32460
ttggttggac tggaaaactt agaaagcatc tctttttacg ataacaggct tattaaagta  32520
ccccatgttg ctcttcaaaa agttgtaaat ctcaaatttt tggatctaaa taaaaatcct  32580
attaatagaa tacgaagggg tgattttagc aatatgctac acttaaaaga gttggggata  32640
aataatatgc ctgagctgat ttccatcgat agtcttgctg tggataacct gccagattta  32700
agaaaaatag aagctactaa caaccctaga ttgtcttaca ttcaccccaa tgcatttttc  32760
agactcccca agctggaatc actcatgctg aacagcaatg ctctcagtgc cctgtaccat  32820
ggtaccattg agtctctgcc aaacctcaag gaaatcagca tacacagtaa ccccatcagg  32880
tgtgactgtg tcatccgttg gatgaacatg aacaaaacca acattcgatt catggagcca  32940
gattcactgt tttgcgtgga cccacctgaa ttccaaggtc agaatgttcg gcaagtgcat  33000
ttcagggaca tgatggaaat ttgtctccct cttatagctc ctgagagctt tccttctaat  33060
ctaaatgtag aagctgggag ctatgtttcc tttcactgta gagctactgc agaaccacag  33120
cctgaaatct actggataac accttctggt caaaaactct tgcctaatac cctgacagac  33180
aagttctatg tccattctga gggaacacta gatataaatg gcgtaactcc caaagaaggg  33240
ggtttatata cttgtatagc aactaaccta gttggcgctg acttgaagtc tgttatgatc  33300
aaagtggatg gatcttttcc acaagataac aatggctctt tgaatattaa aataagagat  33360
attcaggcca attcagtttt ggtgtcctgg aaagcaagtt ctaaaattct caaatctagt  33420
gttaaatgga cagcctttgt caagactgaa aattctcatg ctgcgcaaag tgctcgaata  33480
ccatctgatg tcaaggtata taatcttact catctgaatc catcaactga gtataaaatt  33540
tgtattgata ttcccaccat ctatcagaaa aacagaaaaa aatgtgtaaa tgtcaccacc  33600
aaaggtttgc accctgatca aaaagagtat gaaaagaata ataccacaac acttatggcc  33660
tgtcttggag gccttctggg gattattggt gtgatatgtc ttatcagctg cctctctcca  33720
gaaatgaact gtgatggtgg acacagctat gtgaggaatt acttacagaa accaaccttt  33780
gcattaggtg agctttatcc tcctctgata aatctctggg aagcaggaaa agaaaaaagt  33840
acatcactga aagtaaaagc aactgttata ggtttaccaa caaatatgtc ctaaaaacca  33900
ccaaggaaac ctactccaaa aatgaacaaa aaaaaaaaaa gcgaaagact gcagttgtgc  33960
taaaaacaaa acaaaacaaa caaacaaaca aaaaagtaaa aaaagattac tttcgagaga  34020
gaagtttaag cttcaccaat gctgctcctg accaatggaa atatgtacaa cttcagcatt  34080
ttaagtaact ggcttcaagg ggtactgtgg caaccaaata aaataactcc attttctaaa  34140
actttcatgt aacttttatg tctggactac agttcaagtg gacaaaaaca tttctgtatt  34200
ttttttaagt aaataagagt agttgaactg agcaatacct cctcctgtgt tgtattacac  34260
atattagcca cgagtttttg cagtgaccag ataaacttga attgacacgt ggtgtaataa  34320
aatggacaaa ttctgtagag tagacacagt gagtatgtgg acctctttta taaggaaaaa  34380
```

-continued

```
tacattttgg attaaaatca attgcttctg tcttgttttg tttctaaata aagaataatt  34440

tctgggaaa                                                           34449
```